US009499514B2

(12) United States Patent
Hansen et al.

(10) Patent No.: US 9,499,514 B2
(45) Date of Patent: Nov. 22, 2016

(54) ANTIPROLIFERATIVE COMPOUNDS AND METHODS OF USE THEREOF

(71) Applicant: Celgene Corporation, Summit, NJ (US)

(72) Inventors: Joshua Hansen, La Jolla, CA (US); Matthew Daniel Correa, San Diego, CA (US); Raj Raheja, Poway, CA (US); Antonia Lopez-Girona, San Diego, CA (US); Hon-Wah Man, Princeton, NJ (US); George W. Muller, Rancho Santa Fe, CA (US); Ehab M. Khalil, Whitehouse Station, NJ (US); Kyle MacBeth, San Francisco, CA (US); Brian E. Cathers, San Diego, CA (US); Michael Pourdehnad, San Francisco, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/795,837

(22) Filed: Jul. 9, 2015

(65) Prior Publication Data

US 2016/0009683 A1 Jan. 14, 2016

Related U.S. Application Data

(60) Provisional application No. 62/023,775, filed on Jul. 11, 2014.

(51) Int. Cl.
| | |
|---|---|
| *A61K 31/454* | (2006.01) |
| *C07D 401/14* | (2006.01) |
| *C07D 401/04* | (2006.01) |
| *A61K 31/4545* | (2006.01) |
| *A61K 31/496* | (2006.01) |
| *A61K 31/501* | (2006.01) |
| *A61K 31/506* | (2006.01) |
| *A61K 31/5377* | (2006.01) |
| *A61K 45/06* | (2006.01) |
| *C07D 209/34* | (2006.01) |

(52) U.S. Cl.
CPC ........... *C07D 401/04* (2013.01); *A61K 31/454* (2013.01); *A61K 31/4545* (2013.01); *A61K 31/496* (2013.01); *A61K 31/501* (2013.01); *A61K 31/506* (2013.01); *A61K 31/5377* (2013.01); *A61K 45/06* (2013.01); *C07D 401/14* (2013.01); *C07D 209/34* (2013.01)

(58) Field of Classification Search
CPC ........... A61K 31/454; A61K 31/4045; C07D 209/34; C07D 211/40
USPC .......................................... 514/323; 546/201
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,044,126 A | 8/1977 | Cook et al. |
| 4,328,245 A | 5/1982 | Yu et al. |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 4,810,643 A | 3/1989 | Souza |
| 4,999,291 A | 3/1991 | Souza |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,229,496 A | 7/1993 | Deeley et al. |
| 5,323,907 A | 6/1994 | Kalvelage |
| 5,354,556 A | 10/1994 | Sparks et al. |
| 5,391,485 A | 2/1995 | Deeley et al. |
| 5,393,870 A | 2/1995 | Deeley et al. |
| 5,528,823 A | 6/1996 | Rudy, Jr. et al. |
| 5,580,755 A | 12/1996 | Souza |
| 5,591,767 A | 1/1997 | Mohr et al. |
| 5,639,476 A | 6/1997 | Oshlack et al. |
| 5,674,533 A | 10/1997 | Santus et al. |
| 5,709,874 A | 1/1998 | Hanson et al. |
| 5,733,566 A | 3/1998 | Lewis |

(Continued)

FOREIGN PATENT DOCUMENTS

| | | |
|---|---|---|
| WO | WO 2009/145899 A1 | 12/2009 |
| WO | WO 2010/053732 A1 | 5/2010 |

OTHER PUBLICATIONS

Aklilu et al., "Depletion of normal B cells with rituximab as an adjunct to IL-2 therapy for renal cell carcinoma and melanoma," Annals Oncology, 15:1109-1114 (2004).

(Continued)

*Primary Examiner* — Kamal Saeed
*Assistant Examiner* — Janet L Coppins
(74) *Attorney, Agent, or Firm* — Jones Day

(57) ABSTRACT

Compounds of formula I for treating, preventing or managing cancer are disclosed. Also disclosed are methods of treating, preventing or managing cancer, such as leukemia, comprising administering the compounds. In certain embodiments, the method of treatment comprise administering a compound provided herein in combination with a second agent. Pharmaceutical compositions and single unit dosage forms comprising the compounds are also disclosed.

29 Claims, No Drawings

(56) References Cited

U.S. PATENT DOCUMENTS

| | | | |
|---|---|---|---|
| 5,739,108 A | 4/1998 | Mitchell | |
| 5,759,542 A | 6/1998 | Gurewich | |
| 5,840,674 A | 11/1998 | Yatvin et al. | |
| 5,891,474 A | 4/1999 | Busetti et al. | |
| 5,900,252 A | 5/1999 | Calanchi et al. | |
| 5,922,356 A | 7/1999 | Koseki et al. | |
| 5,972,366 A | 10/1999 | Haynes et al. | |
| 5,972,891 A | 10/1999 | Kamei et al. | |
| 5,980,945 A | 11/1999 | Ruiz | |
| 5,985,307 A | 11/1999 | Hanson et al. | |
| 5,993,855 A | 11/1999 | Yoshimoto et al. | |
| 6,004,534 A | 12/1999 | Langer et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,087,324 A | 7/2000 | Igari et al. | |
| 6,113,943 A | 9/2000 | Okada et al. | |
| 6,120,751 A | 9/2000 | Unger | |
| 6,131,570 A | 10/2000 | Schuster et al. | |
| 6,139,865 A | 10/2000 | Friend et al. | |
| 6,197,350 B1 | 3/2001 | Yamagata et al. | |
| 6,248,363 B1 | 6/2001 | Patel et al. | |
| 6,264,970 B1 | 7/2001 | Hata et al. | |
| 6,267,981 B1 | 7/2001 | Okamoto et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 6,376,461 B1 | 4/2002 | Igari et al. | |
| 6,419,961 B1 | 7/2002 | Igari et al. | |
| 6,589,548 B1 | 7/2003 | Oh et al. | |
| 6,613,358 B2 | 9/2003 | Randolph et al. | |
| 6,699,500 B2 | 3/2004 | Okada et al. | |
| 6,740,634 B1 | 5/2004 | Saikawa et al. | |
| 7,393,862 B2 * | 7/2008 | Zeldis | A61K 31/00 514/315 |
| 7,468,363 B2 | 12/2008 | Zeldis | |
| 7,498,171 B2 | 3/2009 | Hariri et al. | |
| 2008/0051379 A1 | 2/2008 | Lerner et al. | |

OTHER PUBLICATIONS

Anolik et al., "B cell reconstitution after rituximab treatment of lymphoma recapitulates B cell ontogeny," Clin. Immunol., 122:139-145 (2007).
Bedingfield et al., "Structure-activity relationships for a series of phenylglycine derivatives acting at metabotropic glutamate receptors (mGluRs)," Br. J. Pharmac., 116:3323-3329 (1995).
Buchwald et al., "Long-term, continuous intravenous heparin administration by an implantable infusion pump in ambulatory patients with recurrent venous thrombosis," Surgery, 88:507-516 (1980).
Cairns et al., "Regulation of cancer cell metabolism," Nature Rev., 11:85-95 (2011).
Cancer: Principles & Practice of Oncology, Third Edition, J. B. Lippincott Co., Philadelphia, PA, pp. 1843-1847 (1989).
Carstensen, Drug Stability: Principles & Practices, Second Edition, Marcel Dekker, New York, NY, pp. 379-380 (1995).
Cerny et al., "Advances in the treatment of non-Hodgkin's lymphoma," Ann. Oncol., 13 Suppl., 4:211-216 (2002).
Clarke et al., "Changing incidence of non-Hodgkin lymphomas in the United States," Cancer, 94(7):2015-2023 (2002).
Emens et al., "Chemotherapy: friend of foe to cancer vaccines," Curr. Opin. Mol. Ther., 3(1):77-84 (2001).
Foster, "Deuterium isotope effects in the metabolism of drugs and xenobiotics: implications for drug design," Adv. Drug Res., 14:1-40 (1985).
Gatley et al., "Deuterioglucose: alteration of biodistribution by an isotope effect," J. Nucl. Med., 27(3):388-394 (1986).
Goodson, "Medical Applications of Controlled Release," vol. 2, CRC Press, Inc., Boca Raton, FL, pp. 115-138 (1984).
Gordon et al., "The metabolism of the abortifacient terpene, (R)-(+)-pulegone, to a proximate toxin, menthofuran," Drug Metab. Dispos., 15(5):589-594 (1987).
Hoffmann-Osienhof, "IUPAC-IUB commission on biochemical nomenclature abbreviated nomenclature of synthetic polypeptides (polymerized amino acids)", Biochem., 11(5):942-944 (1972).
Jemal et al., "Cancer Statistics," CA Cancer J. Clin., 57:43-66 (2007).
Kim et al., "Use of absolute lymphocyte counts to predict response to chemotherapy and survival in diffuse large B-cell lymphoma," J. Clin. Oncology, ASCO Annual Meeting Proceedings Part I., 25(18S), June 20 Supplement, p. 8082 (2007).
Kushner et al., "Pharmacological uses and perspectives of heavy water and deuterated compounds," Can. J. Physiol. Pharmacol, 77(2):79-88 (1999).
Langer, "New methods of drug delivery," Science, 249(4976):1527-1533 (1990).
Lijinsky et al., "Dose-response studies in carcinogenesis by nitroso-N-methyl-N-(2-phenyl)ethylamine in rats and the effects of deuterium substitution," Food Chem. Toxicol., 20(4):393-399 (1982).
Lijinsky et al., "Dose-response studies with nitrosoheptamethyleneimine and its α-deuterium-labeled derivative in F344 rats," J. Natl. Cancer Instit., 69(5):1127-1133 (1982).
Mangold et al., "Effects of deuterium labeling on azido amino acid mutagenicity in Salmonella typhimurium," Mutat. Res., 308(1):33-42 (1994).
Mardis et al., "Recurring mutations found by sequencing an acute myeloid leukemia genome," N. Engl. J. Med., 361(11):1058-1066 (2009).
Parsons et al., "An integrated genomic analysis of human glioblastoma multiforme," Science, 321:1807-1812 (2008).
Penichet et al., "Antibody-cytokine fusion proteins for the therapy of cancer," J. Immunol. Methods, 284:91-101 (2001).
Roitt et al., Immunology, Third Edition, Mosby, St. Louis, MO, 17.1-17.12 (1993).
Saudek et al., "A preliminary trial of the programmable implantable medication system for insulin delivery," N. Engl. J. Med., 321(9):574-579 (1989).
Sefton, "Implantable pumps," Crit. Rev. Biomed. Eng., 14(3):201-240 (1987).
Shackelford et al., "The LKB1-AMPK pathway: metabolism and growth control in tumour suppression," Nature Rev., 9:563-575 (2009).
Stahnke et al., "Activation of apoptosis pathways in peripheral blood lymphocytes by in vivo chemotherapy," Blood, 98:3066-3073 (2001).
Stockdale, Medicine, vol. 3, Rubenstein and Federman, eds., Chapter 12, Section IV and Section X (1998).
The Merck Manual, 17th Edition, Merck & Company, West Point, PA, pp. 448, 944-952 (1999).
Therasse et al., "New guidelines to evaluate the response to treatment in solid tumors," J. Natl. Cancer Inst., 92(3):205-216 (2000).
Wade, "Deuterium isotope effects on noncovalent interactions between molecules," Chem. Biol. Interact., 117:191-217 (1999).
Zello et al., "Plasma and urine enrichments following infusion of L-[1-13C]phenylalanine and L[ring-2H5]phenylalanine in humans: evidence for an isotope effect in renal tubular reabsorption," Metabolism, 43(4):487-491 (1994).

* cited by examiner

ANTIPROLIFERATIVE COMPOUNDS AND METHODS OF USE THEREOF

1. CROSS REFERENCE TO RELATED APPLICATIONS

This application claims the benefit of the priority of U.S. Provisional Application No. 62/023,775, filed Jul. 11, 2014, the disclosure of which is incorporated herein by reference in its entirety.

2. FIELD

Provided herein are compounds for treating, preventing or managing cancer. Also provided are pharmaceutical compositions comprising the compounds and methods of use of the compounds and compositions. In certain embodiments, the methods encompass treating, preventing or managing cancer, including solid tumors and blood borne tumors using the compounds provided herein.

3. BACKGROUND

Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Lymphoma refers to cancers that originate in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatment of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the US population. Id. Clarke C A, et al., *Cancer* 2002; 94(7):2015-2023.

Diffuse large B-cell lymphoma (DLBCL) accounts for approximately one-third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma. See D. Kim et al., *Journal of Clinical Oncology*, 2007 ASCO Annual Meeting Proceedings Part I. Vol 25, No. 18S (June 20 Supplement), 2007: 8082.

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 (17$^{th}$ ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 (17$^{th}$ ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloblastic leukemia (AML), occurs at all ages and is the more common acute leukemia among adults; it is the form usually associated with irradiation as a causative agent.

Chronic leukemias are described as being lymphocytic (CLL) or myelocytic (CML). The Merck Manual, 949-952 (17th ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome.

In addition to the acute and chronic categorization, neoplasms are also categorized based upon the cells giving rise to such disorder into precursor or peripheral. See e.g., U.S. patent publication no. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, diffuse large B-cell lymphoma and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Solid tumors are abnormal masses of tissue that may, but usually do not contain cysts or liquid areas. Solid tumors may be benign (not cancer), or malignant (cancer). Different types of solid tumors are named for the type of cells that form them. Examples of types solid tumors include, but are not limited to malignant melanoma, adrenal carcinoma, breast carcinoma, renal cell cancer, carcinoma of the pancreas, non-small-cell lung carcinoma (NSCLC) and carcinoma of unknown primary. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

While patients who achieve a complete remission after initial therapy have a good chance for cure, less than 10% of those who do not respond or relapse achieve a cure or a response lasting longer than 3 years. See Cerny T, et al., Ann Oncol 2002; 13 Suppl 4:211-216.

Rituximab is known to deplete normal host B cells. See M. Aklilu et al., Annals of Oncology 15:1109-1114, 2004. The long-term immunologic effects of B cell depletion with rituximab and the characteristics of the reconstituting B cell pool in lymphoma patients are not well defined, despite the widespread usage of this therapy. See Jennifer H. Anolik et al., Clinical Immunology, vol. 122, issue 2, February 2007, pages 139-145.

The approach for patients with relapsed or refractory disease relies heavily on experimental treatments followed by stem cell transplantation, which may not be appropriate for patients with a poor performance status or advanced age. Therefore, a tremendous demand exists for new methods that can be used to treat patients with NHL.

The link between cancer an altered cellular metabolism has been well established. See Cairns, R. A., et al. Nature Rev., 2011, 11:85-95. Understanding tumor cell metabolism and the associated genetic changes thereof may lead to the identification of improved methods of cancer treatment. Id. For example, tumor cell survival and proliferation via increased glucose metabolism has been linked to the PIK3 pathway, whereby mutations in tumor suppressor genes such as PTEN activate tumor cell metabolism. Id. AKT1 (a.k.a., PKB) stimulates glucose metabolism associated with tumor cell growth by various interactions with PFKFB3, ENTPD5, mTOR and TSC2 (a.k.a., tuberin). Id.

Transcription factors HIF1 and HIF2 are largely responsible for cellular response to low oxygen conditions often associated with tumors. Id. Once activated, HIF1 promotes tumor cell capacity to carry out glycolysis. Id. Thus, inhibition of HIF1 may slow or reverse tumor cell metabolism. Activation of HIF1 has been linked to PI3K, tumor suppressor proteins such as VHL, succinate dehydrogenase (SDH) and fumarate hydratase. Id. The oncogenic transcription factor MYC has also been linked to tumor cell metabolism, specifically glycolysis. Id. MYC also promotes cell proliferation by glutamine metabolic pathways. Id.

AMP-activated protein kinase (AMPK) functions as a metabolic check point which tumor cells must overcome in order to proliferate. Id. Several mutations have been identified which suppress AMPK signaling in tumor cells. See Shackelford, D. B. & Shaw, R. J., Nature Rev. Cancer, 2009, 9: 563-575. STK11 has been identified as a tumor suppressor gene related to the role of AMPK. See Cairns, R. A., et al. *Nature Rev.*, 2011, 11:85-95.

The transcription factor p53, a tumor suppressor, also has an important role in the regulation of cellular metabolism. Id. The loss of p53 in tumor cells may be a significant contributor to changes in tumor cell metabolism to the glycolytic pathway. Id. The OCT1 transcription factor, another potential target for chemotherapeutics, may cooperate with p53 in regulating tumor cell metabolism. Id.

Pyruvate kinate M2 (PKM2) promotes changes in cellular metabolism which confer metabolic advantages to cancer cells by supporting cell proliferation. Id. For example, lung cancer cells which express PKM2 over PKM1 have been found to have such an advantage. Id. In the clinic, PKM2 has been identified as being overexpressed in a number of cancer types. Id. Thus PKM2 may be a useful biomarker for the early detection of tumors.

Mutations in isocitrate dehydrogenases IDH1 and IDH2 have been linked to tumorigenesis, specifically, in glioblastoma and acute myeloid leukemia. See Mardis, E. R. et al., *N. Engl. J. Med.*, 2009, 361: 1058-1066; Parsons, D. W. et al., *Science*, 2008, 321: 1807-1812.

The incidence of cancer continues to climb as the general population ages, as new cancers develop, and as susceptible populations (e.g., people infected with AIDS, the elderly or excessively exposed to sunlight) grow. A tremendous demand therefore exists for new methods, treatments and compositions that can be used to treat patients with cancer including but not limited to those with lymphoma, NHL, multiple myeloma, AML, leukemias, and solid tumors.

Accordingly, compounds that can control and/or inhibit unwanted angiogenesis or inhibit the production of certain cytokines, including TNF-α, may be useful in the treatment and prevention of various forms of cancer.

Methods of Treating Cancer

Current cancer therapy may involve surgery, chemotherapy, hormonal therapy and/or radiation treatment to eradicate neoplastic cells in a patient (see, for example, Stockdale, 1998, *Medicine*, vol. 3, Rubenstein and Federman, eds., Chapter 12, Section IV). Recently, cancer therapy could also involve biological therapy or immunotherapy. All of these approaches may pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Certain biological and other therapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A number of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as multidrug resistance. Because of the drug resistance, many cancers prove refractory to standard chemotherapeutic treatment protocols.

There exists a significant need for safe and effective compounds and methods for treating, preventing and managing cancer, including for cancers that are refractory to standard treatments, such as surgery, radiation therapy, chemotherapy and hormonal therapy, while reducing or avoiding the toxicities and/or side effects associated with the conventional therapies.

4. SUMMARY

Provided herein are compounds, pharmaceutical compositions containing the compounds and methods of use thereof in treating cancer, including solid tumors and blood borne tumors. In one embodiment, the compounds for use in the compositions and methods provided herein are of Formula I:

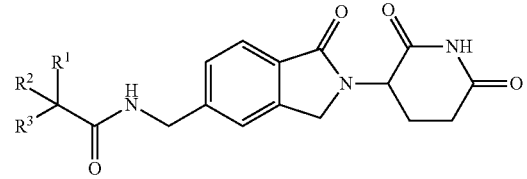

or an enantiomer or a mixture of enantiomers thereof, or a pharmaceutically acceptable salt, solvate, hydrate, co-crystal, clathrate, or polymorph thereof, wherein:

$R^1$ is H, optionally substituted alkyl, cycloalkyl, aryl, heteroaryl or heterocyclyl;

$R^2$ and $R^3$ are each halo; and where the substituents on $R^1$, when present, are one to three groups Q, where each Q is independently alkyl, halo, haloalkyl, alkoxyalkyl, oxo, hydroxyl, alkoxy, cycloalkyl, cycloalkylalkyl, heterocyclyl, heterocyclylalkyl, aryl, heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

each $R^4$ is independently alkylene, alkenylene or a direct bond;

each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 groups $Q^1$, where each $Q^1$ is independently alkyl, haloalkyl or halo;

$R^6$ and $R^7$ are selected as follows:
  i) $R^6$ and $R^7$ are each independently hydrogen or alkyl; or
  ii) $R^6$ and $R^7$ together with the nitrogen atom on which they are substituted form a 5 or 6-membered heterocyclyl or heteroaryl ring, optionally substituted with one or two halo, alkyl or haloalkyl;

$R^8$ is alkyl, haloalkyl, or hydroxyalkyl;
$R^9$ is alkyl or aryl;
J is O or S; and
t is 1 or 2.

Provided herein are compounds, pharmaceutical compositions containing the compounds and methods of use thereof in treating cancer, including solid tumors and blood borne tumors.

In one embodiment, the compounds for use in the compositions and methods provided herein are of Formula I or an enantiomer or a mixture of enantiomers thereof, or a pharmaceutically acceptable salt, solvate, hydrate, co-crystal, clathrate, or polymorph thereof, wherein:

$R^1$ is H, optionally substituted alkyl, cycloalkyl, aryl, heteroaryl or heterocyclyl;
$R^2$ and $R^3$ are each halo; and
where the substituents on $R^1$, when present, are one to three groups Q, where each Q is independently alkyl, halo, haloalkyl, hydroxyl, alkoxy, cycloalkyl, cycloalkylalkyl, —$R^4OR^5$, —$R^4N(R^6)(R^7)$, —$R^4SR^5$, —$R^4OR^4N(R^6)(R^7)$ or —$R^4OR^4C(J)N(R^6)(R^7)$;
each $R^4$ is independently alkylene, alkenylene or a direct bond;
each $R^5$ is independently hydrogen, alkyl, haloalkyl or hydroxyalkyl; and
$R^6$ and $R^7$ are each independently hydrogen or alkyl.

In one embodiment, the compounds for use in the compositions and methods provided herein are of Formula I or an enantiomer or a mixture of enantiomers thereof, or a pharmaceutically acceptable salt, solvate, hydrate, co-crystal, clathrate, or polymorph thereof, wherein:

$R^1$ is optionally substituted cycloalkyl, aryl, heteroaryl or heterocyclyl;
$R^2$ and $R^3$ are each halo; and
where the substituents on $R^1$, when present, are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4N(R^6)(R^7)$, —$R^4SR^5$, —$R^4OR^4N(R^6)(R^7)$ or —$R^4OR^4C(J)N(R^6)(R^7)$;
each $R^4$ is independently alkylene, alkenylene or a direct bond;
each $R^5$ is independently hydrogen, alkyl, haloalkyl or hydroxyalkyl; and $R^6$ and
$R^7$ are each independently hydrogen or alkyl or $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, the compound provided herein is a compound of formula I. In one embodiment, the compound provided herein is a pharmaceutically acceptable salt of the compound of formula I. In one embodiment, the compound provided herein is a solvate of the compound of formula I. In one embodiment, the compound provided herein is a hydrate of compound of formula I. In one embodiment, the compound provided herein is a clathrate of the compound of formula I.

Also provided are pharmaceutical compositions formulated for administration by an appropriate route and means containing effective concentrations of one or more of the compounds provided herein, or an enantiomer or a mixture of enantiomers thereof, or a pharmaceutically acceptable salt, solvate, hydrate, co-crystal, clathrate, or polymorph thereof, and optionally comprising at least one pharmaceutical carrier.

In one embodiment, the pharmaceutical compositions deliver amounts effective for the treatment of cancer, including solid tumors and blood borne tumors. In one embodiment, the pharmaceutical compositions deliver amounts effective for the prevention of cancer, including solid tumors and blood borne tumors. In one embodiment, the pharmaceutical compositions deliver amounts effective for the amelioration of cancer, including solid tumors and blood borne tumors.

Also provided herein are combination therapies using one or more compounds or compositions provided herein, or an enantiomer or a mixture of enantiomers thereof, or a pharmaceutically acceptable salt, solvate, hydrate, co-crystal, clathrate, or polymorph thereof in combination with a therapy e.g., another pharmaceutical agent with activity against cancer or its symptoms. Examples of therapies within the scope of the methods include, but are not limited to, surgery, chemotherapy, radiation therapy, hormonal therapy, biological therapy, immunotherapy, and combinations thereof.

The compounds or compositions provided herein, or pharmaceutically acceptable derivatives thereof, may be administered simultaneously with, prior to, or after administration of one or more of the above therapies. Pharmaceutical compositions containing a compound provided herein and one or more of the above agents are also provided.

In certain embodiments, provided herein are methods of treating, preventing or ameliorating cancer, including solid tumors and blood borne tumors, or one or more symptoms or causes thereof. In certain embodiments, provided herein are methods of preventing cancer, including solid tumors and blood borne tumors, or one or more symptoms or causes thereof. In certain embodiments, provided herein are methods of ameliorating cancer, including solid tumors and blood borne tumors, or one or more symptoms or causes thereof. In certain embodiments, the blood borne tumor is leukemia. In certain embodiments, methods provided herein encompass methods of treating various forms of leukemias such as chronic lymphocytic leukemia, chronic myeloid leukemia, acute lymphocytic leukemia, acute myeloid leukemia and acute myeloblastic leukemia. In certain embodiments, methods provided herein encompass methods of preventing various forms of leukemias such as chronic lymphocytic leukemia, chronic myeloid leukemia, acute lymphocytic leukemia, acute myeloid leukemia and acute myeloblastic leukemia. In certain embodiments, methods provided herein encompass methods of managing various forms of leukemias such as chronic lymphocytic leukemia, chronic myeloid leukemia, acute lymphocytic leukemia, acute myeloid leukemia and acute myeloblastic leukemia. The methods provided herein include treatment of leukemias that are relapsed, refractory or resistant. The methods provided herein include prevention of leukemias that are relapsed, refractory or resistant. The methods provided herein include management of leukemias that are relapsed, refractory or resistant. In one embodiment, methods provided herein encompass methods of treating acute myeloid leukemia. In one embodiment, methods provided herein encompass methods of preventing acute myeloid leukemia. In one embodiment, methods provided herein encompass methods of managing acute myeloid leukemia.

In practicing the methods, effective amounts of the compounds or compositions containing therapeutically effective concentrations of the compounds are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

5. DETAILED DESCRIPTION OF THE INVENTION

Provided herein are compounds of formula I. Provided herein is an enantiomer of compounds of formula I. Provided herein is a mixture of enantiomers of compounds of formula I. Provided herein is a pharmaceutically acceptable salt of a compound of formula I. Provided herein is a pharmaceutically acceptable solvate of a compound of formula I. Provided herein is a pharmaceutically acceptable hydrate of a compound of formula I. Provided herein is a pharmaceutically acceptable co-crystal of a compound of formula I. Provided herein is a pharmaceutically acceptable clathrate of a compound of formula I. Provided herein is a pharmaceutically acceptable polymorph of a compound of formula I. Further provided are methods of treating cancer, including solid tumors blood borne tumors, and pharmaceutical compositions and dosage forms useful for such methods. Further provided are methods of preventing cancer, including solid tumors blood borne tumors, and pharmaceutical compositions and dosage forms useful for such methods. Further provided are methods of ameliorating cancer, including solid tumors blood borne tumors, and pharmaceutical compositions and dosage forms useful for such methods. The compounds, methods and compositions are described in detail in the sections below.

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain group consisting solely of carbon and hydrogen atoms, containing no unsaturation, having from one to ten, one to eight, one to six or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from two to eight carbon atoms, wherein the unsaturation is present only as double bonds and wherein the double bond can exist between any two carbon atoms in the chain, e.g., ethenylene, prop-1-enylene, but-2-enylene and the like. The alkenylene chain may be attached to the rest of the molecule through any two carbons within the chain.

"Alkoxy" refers to the group having the formula —OR wherein R is alkyl or haloalkyl. An "optionally substituted alkoxy" refers to the group having the formula —OR wherein R is an optionally substituted alkyl as defined herein.

"Amino" refers to a radical having the formula —NR'R" wherein R' and R" are each independently hydrogen, alkyl or haloalkyl. An "optionally substituted amino" refers to a radical having the formula —NR'R" wherein one or both of R' and R" are optionally substituted alkyl as defined herein.

"Aryl" refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Cycloalkyl" refers to a stable monovalent monocyclic or bicyclic hydrocarbon group consisting solely of carbon and hydrogen atoms, having from three to ten carbon atoms which is saturated, e.g., cyclopropyl, cyclobutyl, cyclopentyl, cyclohexyl, decalinyl, norbornane, norbornene, adamantyl, bicyclo[2.2.2]octane and the like.

"Halo, "halogen" or "halide" refers to F, Cl, Br or I.

"Haloalkyl" refers to an alkyl group, in certain embodiments, $C_{1-6}$alkyl group in which one or more of the hydrogen atoms are replaced by halogen. Such groups include, but are not limited to, chloromethyl, trifluoromethyl 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethylethyl.

"Heterocycle" or "Heterocyclyl" refers to a stable 3- to 15-membered non-aromatic ring radical which consists of carbon atoms and from one to five heteroatoms selected from a group consisting of nitrogen, oxygen and sulfur. In one embodiment, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated. The heterocyclic ring system may be attached to the main structure at any heteroatom or carbon atom which results in the creation of a stable compound. Exemplary heterocylic radicals include, morpholinyl, piperidinyl, piperazinyl, pyranyl, pyrrolidinyl, oxetanyl, azetidinyl, quinuclidinyl, octahydroquinolizinyl, decahydroquinolizinyl, azabicyclo[3.2.1]octanyl, azabicyclo[2.2.2]octanyl, isoindolinyl, indolinyl and others.

"Heteroaryl" refers to a heterocyclyl group as defined above which is aromatic. The heteroaryl groups include, but are not limited to monocyclyl, bicyclyl and tricyclyl groups, and may be attached to the main structure at any heteroatom or carbon atom which results in the creation of a stable compound. Examples of such heteroaryl groups include, but are not limited to: furanyl, imidazolyl, oxazolyl, isoxazolyl, pyrimidinyl, pyridinyl, pyridazinyl, thiazolyl, thienyl, benzimidazolyl, imidazo[4,5-b]pyridinyl, imidazo[1,2-a]pyridinyl, imidazo[1,2-b]pyridazinyl, imidazo[1,2-a]pyrazinyl and others.

"$IC_{50}$" refers to an amount, concentration or dosage of a particular test compound that achieves a 50% inhibition of a maximal response, such as cell growth or proliferation, measured via any of the in vitro or cell based assay described herein.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

As used herein and unless otherwise indicated, the term "hydrate" means a compound provided herein or a salt thereof, that further includes a stoichiometric or non-stoichiometeric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

Unless stated otherwise specifically described in the specification, it is understood that the substitution can occur on any atom of the alkyl, alkenyl, alkynyl, cycloalkyl, heterocyclyl, aryl or heteroaryl group.

Where the number of any given substituent is not specified (e.g., haloalkyl), there may be one or more substituents present. For example, "haloalkyl" may include one or more of the same or different halogens.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; oxygen (=O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; $B(OH)_2$, or O(alkyl)aminocarbonyl.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

In the description herein, if there is any discrepancy between a chemical name and chemical structure, the structure controls.

As used herein and unless otherwise indicated, the terms "treat," "treating" and "treatment" refer to alleviating or reducing the severity of a symptom associated with the disease or condition being treated.

The term "prevention" includes the inhibition of a symptom of the particular disease or disorder. In some embodiments, patients with familial history of cancer, including solid tumors and blood borne tumors, are candidates for preventive regimens. Generally, the term "preventing" refers to administration of the drug prior to the onset of symptoms, particularly to patients at risk of cancer, including solid tumors and blood borne tumors.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" is an animal, typically a mammal, including a human, such as a human patient.

As used herein, the term "tumor," refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, "hematologic malignancy" refers to cancer of the body's blood-forming and immune system—the bone marrow and lymphatic tissue. Such cancers include leukemias, lymphomas (Non-Hodgkin's Lymphoma), Hodgkin's disease (also called Hodgkin's Lymphoma) and myeloma.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be relapsed, refractory or resistant to conventional therapy.

As used herein, "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of regions of chromosomes 15 and 17.

As used herein, "acute lymphocytic leukemia (ALL)", also known as "acute lymphoblastic leukemia" refers to a malignant disease caused by the abnormal growth and development of early nongranular white blood cells, or lymphocytes.

As used herein, "T-cell leukemia" refers to a disease in which certain cells of the lymphoid system called T lymphocytes or T cells are malignant. T cells are white blood cells that normally can attack virus-infected cells, foreign cells, and cancer cells and produce substances that regulate the immune response.

The term "relapsed" refers to a situation where patients who have had a remission of leukemia after therapy have a return of leukemia cells in the marrow and a decrease in normal blood cells.

The term "refractory or resistant" refers to a circumstance where patients, even after intensive treatment, have residual leukemia cells in their marrow.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of two therapeutic agents (for example, a compound provided herein and another anti-cancer agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "the supportive care agent" refers to any substance that treats, prevents or manages an adverse effect from treatment with the compound of Formula I.

The term "biological therapy" refers to administration of biological therapeutics such as cord blood, stem cells, growth factors and the like.

The term "about," as used herein, unless otherwise indicated, refers to a value that is no more than 10% above or below the value being modified by the term. For example, the term "about 10 mg/m$^2$" means a range of from 9 mg/m$^2$ to 11 mg/m$^2$.

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxorubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, and radiation treatment.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

B. Compounds

In certain embodiments, provided herein are compounds of Formula I:

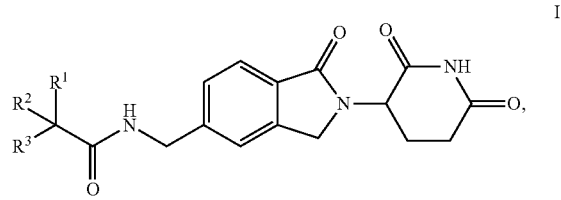

or an enantiomer or a mixture of enantiomers thereof, or a pharmaceutically acceptable salt, solvate, hydrate, co-crystal, clathrate, or polymorph thereof, wherein:

$R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein is a compound of Formula I, wherein:

$R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein is an enantiomer of a compound of Formula I, wherein:

$R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein is a mixture of enantiomers of a compound of Formula I, wherein:

$R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein is a pharmaceutically acceptable salt of a compound of Formula I, wherein:

$R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein is a solvate of a compound of Formula I, wherein:

$R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein is a hydrate of a compound of Formula I, wherein $R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein is a co-crystal of a compound of Formula I, wherein:

$R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein is polymorph of a compound of Formula I, wherein:

$R^1$ is H, optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

J is O or S;

each $R^4$ is independently alkylene, alkenylene or a direct bond;

each $R^5$ is independently hydrogen, alkyl, haloalkyl or hydroxyalkyl; and $R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl.

In certain embodiments, provided herein are compounds of Formula I or an enantiomer or a mixture of enantiomers thereof, or a pharmaceutically acceptable salt, solvate, hydrate, co-crystal, clathrate, or polymorph thereof, wherein:

$R^1$ is optionally substituted alkyl, optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, hydroxyl, alkoxy, cycloalkyl, cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

each $R^4$ is independently alkylene, alkenylene or a direct bond;

each $R^5$ is independently hydrogen, alkyl, haloalkyl or hydroxyalkyl; and $R^6$ and $R^7$ are each independently hydrogen or alkyl.

In certain embodiments, provided herein are compounds of Formula I or an enantiomer or a mixture of enantiomers thereof, or a pharmaceutically acceptable salt, solvate, hydrate, co-crystal, clathrate, or polymorph thereof, wherein:

$R^1$ is optionally substituted cycloalkyl, optionally substituted aryl, optionally substituted heteroaryl or optionally substituted heterocyclyl;

$R^2$ and $R^3$ are each halo;

where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_rR^8$;

each $R^4$ is independently alkylene, alkenylene or a direct bond;

each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl;

$R^8$ is alkyl, haloalkyl, or hydroxyalkyl;
$R^9$ is alkyl or aryl;
J is O or S; and
t is 1 or 2.

In certain embodiments, provided herein are compounds of Formula I or an enantiomer or a mixture of enantiomers thereof, or a pharmaceutically acceptable salt, solvate, hydrate, co-crystal, clathrate, or polymorph thereof, wherein:

$R^1$ is optionally substituted cycloalkyl, optionally substituted aryl, optionally substituted heteroaryl or optionally substituted heterocyclyl;
$R^2$ and $R^3$ are each halo;
where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;
where the substituents on Q, when present are one to three groups $Q^a$, where each $Q^a$ is independently alkyl, halo, haloalkyl, alkoxyalkyl, oxo, hydroxyl or alkoxy;
each $R^4$ is independently alkylene, alkenylene or a direct bond;
each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl;

$R^8$ is alkyl, haloalkyl, or hydroxyalkyl;
$R^9$ is alkyl or aryl;
J is O or S; and
t is 1 or 2.

In certain embodiments, provided herein are compounds of Formula I, wherein:

$R^1$ is optionally substituted cycloalkyl, optionally substituted aryl, optionally substituted heteroaryl or optionally substituted heterocyclyl;
$R^2$ and $R^3$ are each halo;
where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;
where the substituents on Q, when present are one to three groups $Q^a$, where each $Q^a$ is independently alkyl, halo, haloalkyl, alkoxyalkyl, oxo, hydroxyl or alkoxy;
each $R^4$ is independently alkylene, alkenylene or a direct bond;
each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl;

$R^8$ is alkyl, haloalkyl, or hydroxyalkyl;
$R^9$ is alkyl or aryl;
J is O or S; and
t is 1 or 2.

In certain embodiments, provided herein is an enatiomer of a compound of Formula I, wherein:

$R^1$ is optionally substituted cycloalkyl, optionally substituted aryl, optionally substituted heteroaryl or optionally substituted heterocyclyl;
$R^2$ and $R^3$ are each halo;
where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;
where the substituents on Q, when present are one to three groups $Q^a$, where each $Q^a$ is independently alkyl, halo, haloalkyl, alkoxyalkyl, oxo, hydroxyl or alkoxy;
each $R^4$ is independently alkylene, alkenylene or a direct bond;
each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl;

$R^8$ is alkyl, haloalkyl, or hydroxyalkyl;
$R^9$ is alkyl or aryl;
J is O or S; and
t is 1 or 2.

In certain embodiments, provided herein is a mixture of enantiomers of a compound of Formula I, wherein:
- $R^1$ is optionally substituted cycloalkyl, optionally substituted aryl, optionally substituted heteroaryl or optionally substituted heterocyclyl;
- $R^2$ and $R^3$ are each halo;
- where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;
- where the substituents on Q, when present are one to three groups $Q^a$, where each $Q^a$ is independently alkyl, halo, haloalkyl, alkoxyalkyl, oxo, hydroxyl or alkoxy;
- each $R^4$ is independently alkylene, alkenylene or a direct bond;
- each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;
- $R^6$ and $R^7$ are selected as follows:
  i) $R^6$ and $R^7$ are each independently hydrogen or alkyl; or
  ii) $R^6$ and $R^7$ together with the nitrogen atom on which they are substituted form a 5 or 6-membered heterocyclyl or heteroaryl ring, optionally substituted with one or two halo, alkyl or haloalkyl;
- $R^8$ is alkyl, haloalkyl, or hydroxyalkyl;
- $R^9$ is alkyl or aryl;
- J is O or S; and
- t is 1 or 2.

In certain embodiments, provided herein is a pharmaceutically acceptable salt of a compound of Formula I, wherein:
- $R^1$ is optionally substituted cycloalkyl, optionally substituted aryl, optionally substituted heteroaryl or optionally substituted heterocyclyl;
- $R^2$ and $R^3$ are each halo;
- where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;
- where the substituents on Q, when present are one to three groups $Q^a$, where each $Q^a$ is independently alkyl, halo, haloalkyl, alkoxyalkyl, oxo, hydroxyl or alkoxy;
- each $R^4$ is independently alkylene, alkenylene or a direct bond;
- each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;
- $R^6$ and $R^7$ are selected as follows:
  i) $R^6$ and $R^7$ are each independently hydrogen or alkyl; or
  ii) $R^6$ and $R^7$ together with the nitrogen atom on which they are substituted form a 5 or 6-membered heterocyclyl or heteroaryl ring, optionally substituted with one or two halo, alkyl or haloalkyl;
- $R^8$ is alkyl, haloalkyl, or hydroxyalkyl;
- $R^9$ is alkyl or aryl;
- J is O or S; and
- t is 1 or 2.

In certain embodiments, provided herein is a solvate of a compound of Formula I, wherein:
- $R^1$ is optionally substituted cycloalkyl, optionally substituted aryl, optionally substituted heteroaryl or optionally substituted heterocyclyl;
- $R^2$ and $R^3$ are each halo;
- where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;
- where the substituents on Q, when present are one to three groups $Q^a$, where each $Q^a$ is independently alkyl, halo, haloalkyl, alkoxyalkyl, oxo, hydroxyl or alkoxy;
- each $R^4$ is independently alkylene, alkenylene or a direct bond;
- each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;
- $R^6$ and $R^7$ are selected as follows:
  i) $R^6$ and $R^7$ are each independently hydrogen or alkyl; or
  ii) $R^6$ and $R^7$ together with the nitrogen atom on which they are substituted form a 5 or 6-membered heterocyclyl or heteroaryl ring, optionally substituted with one or two halo, alkyl or haloalkyl;
- $R^8$ is alkyl, haloalkyl, or hydroxyalkyl;
- $R^9$ is alkyl or aryl;
- J is O or S; and
- t is 1 or 2.

In certain embodiments, provided herein is a hydrate of a compound of Formula I, wherein:
- $R^1$ is optionally substituted cycloalkyl, optionally substituted aryl, optionally substituted heteroaryl or optionally substituted heterocyclyl;
- $R^2$ and $R^3$ are each halo;
- where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;

where the substituents on Q, when present are one to three groups $Q^a$, where each $Q^a$ is independently alkyl, halo, haloalkyl, alkoxyalkyl, oxo, hydroxyl or alkoxy;

each $R^4$ is independently alkylene, alkenylene or a direct bond;

each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl;

$R^8$ is alkyl, haloalkyl, or hydroxyalkyl;
$R^9$ is alkyl or aryl;
J is O or S; and
t is 1 or 2.

In certain embodiments, provided herein is a clathrate of a compound of Formula I, wherein:
$R^1$ is optionally substituted cycloalkyl, optionally substituted aryl, optionally substituted heteroaryl or optionally substituted heterocyclyl;
$R^2$ and $R^3$ are each halo;
where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;

where the substituents on Q, when present are one to three groups $Q^a$, where each $Q^a$ is independently alkyl, halo, haloalkyl, alkoxyalkyl, oxo, hydroxyl or alkoxy;

each $R^4$ is independently alkylene, alkenylene or a direct bond;

each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl;

$R^8$ is alkyl, haloalkyl, or hydroxyalkyl;
$R^9$ is alkyl or aryl;
J is O or S; and
t is 1 or 2.

In certain embodiments, provided herein is a co-crystal of a compound of Formula I, wherein:
$R^1$ is optionally substituted cycloalkyl, optionally substituted aryl, optionally substituted heteroaryl or optionally substituted heterocyclyl;
$R^2$ and $R^3$ are each halo;
where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;

where the substituents on Q, when present are one to three groups $Q^a$, where each $Q^a$ is independently alkyl, halo, haloalkyl, alkoxyalkyl, oxo, hydroxyl or alkoxy;

each $R^4$ is independently alkylene, alkenylene or a direct bond;

each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl;

$R^8$ is alkyl, haloalkyl, or hydroxyalkyl;
$R^9$ is alkyl or aryl;
J is O or S; and
t is 1 or 2.

In certain embodiments, provided herein is a polymorph of a compound of Formula I, wherein:
$R^1$ is optionally substituted cycloalkyl, optionally substituted aryl, optionally substituted heteroaryl or optionally substituted heterocyclyl;
$R^2$ and $R^3$ are each halo;
where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;

where the substituents on Q, when present are one to three groups $Q^a$, where each $Q^a$ is independently alkyl, halo, haloalkyl, alkoxyalkyl, oxo, hydroxyl or alkoxy;

each $R^4$ is independently alkylene, alkenylene or a direct bond;

each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;

R$^6$ and R$^7$ are selected as follows:
i) R$^6$ and R$^7$ are each independently hydrogen or alkyl; or
ii) R$^6$ and R$^7$ together with the nitrogen atom on which they are substituted form a 5 or 6-membered heterocyclyl or heteroaryl ring, optionally substituted with one or two halo, alkyl or haloalkyl;
R$^8$ is alkyl, haloalkyl, or hydroxyalkyl;
R$^9$ is alkyl or aryl;
J is O or S; and
t is 1 or 2.

In one embodiment, provided herein are compounds of Formula II:

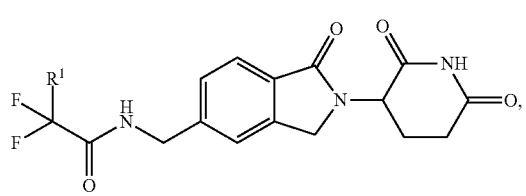

II or an enantiomer or a mixture of enantiomers thereof, or a pharmaceutically acceptable salt, solvate, hydrate, co-crystal, clathrate, or polymorph thereof, wherein:

R$^1$ is optionally substituted cycloalkyl, optionally substituted aryl, optionally substituted heteroaryl or optionally substituted heterocyclyl;

where the substituents on R$^1$, when present, are one to three groups Q, where each Q is independently alkyl, halo, haloalkyl, hydroxyl, alkoxy, optionally substituted cycloalkyl, optionally substituted cycloalkylalkyl, optionally substituted aryl, —R$^4$OR$^5$, —R$^4$SR$^5$, —R$^4$N(R$^6$)(R$^7$), R$^4$OR$^4$N(R$^6$)(R$^7$) or R$^4$OR$^4$C(J)N(R$^6$)(R$^7$);

J is O or S;

each R$^4$ is independently alkylene, alkenylene or a direct bond;

each R$^5$ is independently hydrogen, alkyl, haloalkyl or hydroxyalkyl; and

R$^6$ and R$^7$ are selected as follows:
i) R$^6$ and R$^7$ are each independently hydrogen or alkyl; or
ii) R$^6$ and R$^7$ together with the nitrogen atom on which they are substituted form a 5 or 6-membered heterocyclyl or heteroaryl ring, optionally substituted with one or two halo, alkyl or haloalkyl.

In one embodiment, provided herein is a compound of Formula II, wherein the substituents are as described above.

In one embodiment, provided herein is an enantiomer of a compound of Formula II, wherein the substituents are as described above.

In one embodiment, provided herein is a mixture of enantiomers of a compound of Formula II, wherein the substituents are as described above.

In one embodiment, provided herein is a pharmaceutically acceptable salt of a compound of Formula II, wherein the substituents are as described above.

In one embodiment, provided herein is a solvate of a compound of Formula II, wherein the substituents are as described above.

In one embodiment, provided herein is a hydrate of a compound of Formula II, wherein the substituents are as described above.

In one embodiment, provided herein is a clathrate of a compound of Formula II, wherein the substituents are as described above.

In one embodiment, provided herein is a co-crystal of a compound of Formula II, wherein the substituents are as described above.

In one embodiment, provided herein is a polymorph of a compound of Formula II, wherein the substituents are as described above.

In one embodiment, the compounds have Formula I or Formula II, wherein R$^1$ is optionally substituted aryl;
where the substituents on R$^1$, when present, are one to three groups Q, where each Q is independently alkyl, halo, haloalkyl, hydroxyl, alkoxy, optionally substituted cycloalkyl, optionally substituted cycloalkylalkyl, optionally substituted aryl, —R$^4$OR$^5$, —R$^4$SR$^5$, —R$^4$N(R$^6$)(R$^7$), R$^4$OR$^4$N(R$^6$)(R$^7$) or R$^4$OR$^4$C(J)N(R$^6$)(R$^7$);

each R$^4$ is independently alkylene, alkenylene or a direct bond;

each R$^5$ is independently hydrogen, alkyl, haloalkyl or hydroxyalkyl; and

R$^6$ and R$^7$ are selected as follows:
i) R$^6$ and R$^7$ are each independently hydrogen or alkyl; or
ii) R$^6$ and R$^7$ together with the nitrogen atom on which they are substituted form a 5 or 6-membered heterocyclyl or heteroaryl ring, optionally substituted with one or two halo, alkyl or haloalkyl.

In one embodiment, the compounds have Formula I or Formula II, wherein R$^1$ is optionally substituted aryl, optionally substituted cycloalkyl, optionally substituted heterocyclyl, or optionally substituted heteroaryl, where the substituents on R$^1$, when present, are one to three groups Q, where each Q is independently halo, alkyl, optionally substituted cycloalkyl, optionally substituted aryl, —R$^4$OR$^5$ or —R$^4$N(R$^6$)(R$^7$); each R$^4$ is independently a direct bond or alkylene; each R$^5$ is independently hydrogen, halo, alkyl, alkoxy, haloalkoxy or haloalkyl; and R$^6$ and R$^7$ are selected as follows:
i) R$^6$ and R$^7$ are each independently hydrogen or alkyl; or
ii) R$^6$ and R$^7$ together with the nitrogen atom on which they are substituted form a 5 or 6-membered heterocyclyl or heteroaryl ring, optionally substituted with one or two halo, alkyl or haloalkyl.

In one embodiment, the compounds have Formula I or Formula II, wherein R$^1$ is optionally substituted phenyl, optionally substituted cyclohexyl, optionally substituted piperidinyl, or optionally substituted pyridyl, where the substituents on R$^1$, when present, are one to three groups Q, where each Q is independently halo, alkyl, —R$^4$OR$^5$ or —R$^4$N(R$^6$)(R$^7$); each R$^4$ is independently a direct bond or alkylene; each R$^5$ is independently hydrogen, halo, alkyl, alkoxy, haloalkoxy or haloalkyl; and R$^6$ and R$^7$ are selected as follows:
i) R$^6$ and R$^7$ are each independently hydrogen or alkyl; or
ii) R$^6$ and R$^7$ together with the nitrogen atom on which they are substituted form a 5 or 6-membered heterocyclyl ring.

In one embodiment, the compounds have Formula I or Formula II, wherein R$^1$ is optionally substituted phenyl, optionally substituted cyclohexyl, optionally substituted piperidinyl, or optionally substituted pyridyl, where the substituents on R$^1$, when present, are one to three groups Q, where each Q is independently chloro, bromo, fluoro, methyl, isopropyl, tert butyl, trifluromethyl, methoxy, ethoxy, isopropyloxy, methoxyethoxy, isopropyloxyethoxy, trifluoromethoxy, methylamino, dimethylamino or piperidinyl.

In one embodiment, the compounds have Formula I or Formula II, wherein R$^1$ is optionally substituted aryl, where the substituents on R$^1$, when present, are one to three groups Q, where each Q is independently halo, alkyl, —$R^4OR^5$, —$R^4SR^5$ or $R^4OR^4C(O)N(R^6)(R^7)$; each $R^4$ is independently a direct bond or alkylene; each $R^5$ is independently hydrogen, halo, alkyl or haloalkyl; and $R^6$ and $R^7$ are each independently hydrogen or alkyl.

In one embodiment, the compounds have Formula I or Formula II, wherein $R^1$ is optionally substituted aryl, where the substituents on $R^1$, when present, are one to three groups Q, where each Q is independently fluoro, chloro, methyl, —$R^4OR^5$, —$R^4N(R^6)(R^7)$, —$R^4SR^5$ or $R^4OR^4C(O)N(R^6)(R^7)$; each $R^4$ is independently a direct bond or methylene; each $R^5$ is independently hydrogen, methyl, ethyl or trifluoromethyl; and $R^6$ and $R^7$ are each independently hydrogen or methyl.

In one embodiment, the compounds have Formula I or Formula II, wherein $R^1$ is optionally substituted phenyl, where the substituents on $R^1$, when present, are one to three groups Q, where each Q is independently fluoro, chloro, methyl, tert butyl, —$R^4OR^5$, —$R^4N(R^6)(R^7)$, —$R^4SR^5$ or $R^4OR^4C(O)N(R^6)(R^7)$; each $R^4$ is independently a direct bond or methylene; each $R^5$ is independently hydrogen, methyl, ethyl or trifluoromethyl; and $R^6$ and $R^7$ are each independently hydrogen or methyl.

In one embodiment, provided herein are compounds of Formula III:

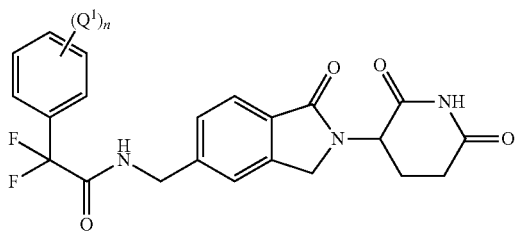

III or an enantiomer or a mixture of enantiomers thereof, or a pharmaceutically acceptable salt, solvate, hydrate, co-crystal, clathrate, or polymorph thereof, wherein:

each $Q^1$ is independently alkyl, halo, haloalkyl, alkoxyalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, halo, alkoxy, haloalkyl or hydroxyalkyl;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl; and n is 0-3.

In one embodiment, provided herein is a compound of Formula III, wherein the substituents are as described above.

In one embodiment, provided herein is an enantiomer of a compound of Formula III, wherein the substituents are as described above.

In one embodiment, provided herein is a mixture of enantiomers of a compound of Formula III, wherein the substituents are as described above.

In one embodiment, provided herein is a pharmaceutically acceptable salt of a compound of Formula III, wherein the substituents are as described above.

In one embodiment, provided herein is a solvate of a compound of Formula III, wherein the substituents are as described above.

In one embodiment, provided herein is a hydrate of a compound of Formula III, wherein the substituents are as described above.

In one embodiment, provided herein is a clathrate of a compound of Formula III, wherein the substituents are as described above.

In one embodiment, provided herein is a co-crystal of a compound of Formula III, wherein the substituents are as described above.

In one embodiment, provided herein is a polymorph of a compound of Formula III, wherein the substituents are as described above.

In one embodiment, provided herein are compounds of Formula III or an enantiomer or a mixture of enantiomers thereof, or a pharmaceutically acceptable salt, solvate, hydrate, co-crystal, clathrate, or polymorph thereof, wherein:

each $Q^1$ is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$;

each $R^4$ is independently alkylene, alkenylene or a direct bond;

each $R^5$ is independently hydrogen, alkyl, haloalkyl or hydroxyalkyl;

$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl; and n is 0-3.

In one embodiment, the compounds herein are of Formula III, where each $Q^1$ is independently hydrogen, Br, Cl, F, methyl, isopropyl, t-butyl, isopropyl, cyclopropyl, —$CF_3$, OH, —$SCH_3$, —$SCF_3$, —$C(CH_3)_2F$, —$OCH_3$, —$OCF_3$, —$OCH_2CH_3$, —$OCH(CH_3)_2$, —$OCH_2CF_3$, —$O(CH_2)_2OCH_3$, —$O(CH_2)_2OCH(CH_3)_2$, —$O(CH_2)_2O(CH_2)_2OCH_3$, —$NHCH_3$, —$N(CH_3)_2$, —$O(CH_2)_2$-morpholinyl, piperidyl, morpholinyl, —$CH_2$-morpholinyl, —$O(CH_2)_2$-4,4-difluoro-1-piperidyl, or p-fluorophenyl.

In one embodiment, provided herein are compounds of Formula IV:

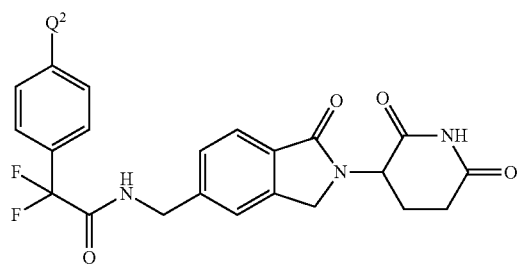

IV or an enantiomer or a mixture of enantiomers thereof, or a pharmaceutically acceptable salt, solvate, hydrate, co-crystal, clathrate, or polymorph thereof, wherein:

Q² is hydrogen, alkyl, halo, haloalkyl, hydroxyl, alkoxy, optionally substituted cycloalkyl, optionally substituted cycloalkylalkyl, optionally substituted aryl, —R⁴OR⁵, —R⁴SR⁵, —R⁴N(R⁶)(R⁷), R⁴OR⁴N(R⁶)(R⁷) or R⁴OR⁴C(J)N(R⁶)(R⁷);

J is O or S;

each R⁴ is independently alkylene, alkenylene or a direct bond;

each R⁵ is independently hydrogen, alkyl, haloalkyl or hydroxyalkyl; and

R⁶ and R⁷ are each independently hydrogen or alkyl.

In one embodiment, provided herein is a compound of Formula IV, wherein the substituents are as described above.

In one embodiment, provided herein is an enantiomer of a compound of Formula IV, wherein the substituents are as described above.

In one embodiment, provided herein is a mixture of enantiomers of a compound of Formula IV, wherein the substituents are as described above.

In one embodiment, provided herein is a pharmaceutically acceptable salt of a compound of Formula IV, wherein the substituents are as described above.

In one embodiment, provided herein is a solvate of a compound of Formula IV, wherein the substituents are as described above.

In one embodiment, provided herein is a hydrate of a compound of Formula IV, wherein the substituents are as described above.

In one embodiment, provided herein is a clathrate of a compound of Formula IV, wherein the substituents are as described above.

In one embodiment, provided herein is a co-crystal of a compound of Formula IV, wherein the substituents are as described above.

In one embodiment, provided herein is a polymorph of a compound of Formula IV, wherein the substituents are as described above.

In one embodiment, the compounds herein are of Formula IV, where Q² is hydrogen, halo, alkyl, optionally substituted aryl, —R⁴OR⁵ or —R⁴N(R⁶)(R⁷); R⁴ is independently a direct bond or alkylene; R⁵ is hydrogen, alkyl or haloalkyl; and R⁶ and R⁷ are each independently hydrogen or alkyl. In some embodiments, Q² is hydrogen, Br, Cl, F, methyl, isopropyl, t-butyl, isopropyl, —OCH₃, —SCH₃, —C(CH₃)₂F, —OCH(CH₃)₂, —O(CH₂)₂OCH₃, or p-fluorophenyl.

In one embodiment, provided herein are compounds of Formula V:

V

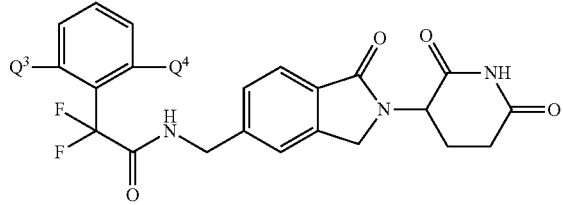

or an enantiomer or a mixture of enantiomers thereof, or a pharmaceutically acceptable salt, solvate, hydrate, co-crystal, clathrate, or polymorph thereof, wherein:

Q³ and Q⁴ are each independently hydrogen, alkyl, halo, haloalkyl, hydroxyl, alkoxy, optionally substituted cycloalkyl, optionally substituted cycloalkylalkyl, —R⁴OR⁵, —R⁴SR⁵, —R⁴N(R⁶)(R⁷), R⁴OR⁴N(R⁶)(R⁷) or R⁴OR⁴C(J)N(R⁶)(R⁷);

J is O or S;

each R⁴ is independently alkylene, alkenylene or a direct bond;

each R⁵ is independently hydrogen, alkyl, haloalkyl, hydroxyalkyl, or alkoxyalkyl; and R⁶ and R⁷ are each independently hydrogen or alkyl.

In one embodiment, provided herein is a compound of Formula V, wherein the substituents are as described above.

In one embodiment, provided herein is an enantiomer of a compound of Formula V, wherein the substituents are as described above.

In one embodiment, provided herein is a mixture of enantiomers of a compound of Formula V, wherein the substituents are as described above.

In one embodiment, provided herein is a pharmaceutically acceptable salt of a compound of Formula V, wherein the substituents are as described above.

In one embodiment, provided herein is a solvate of a compound of Formula V, wherein the substituents are as described above.

In one embodiment, provided herein is a hydrate of a compound of Formula V, wherein the substituents are as described above.

In one embodiment, provided herein is a clathrate of a compound of Formula V, wherein the substituents are as described above.

In one embodiment, provided herein is a co-crystal of a compound of Formula V, wherein the substituents are as described above.

In one embodiment, provided herein is a polymorph of a compound of Formula V, wherein the substituents are as described above.

In one embodiment, the compounds herein are of Formula V, where Q⁴ and Q³ are each independently hydrogen, halo, alkyl, alkoxyalkyl, —R⁴OR⁵, or —R⁴N(R⁶)(R⁷); R⁴ is a direct bond or alkylene; and R⁵ is hydrogen, alkyl or haloalkyl; and R⁶ and R⁷ are each independently hydrogen or alkyl. In some such embodiments, Q⁴ and Q³ are each independently hydrogen, F, methyl, —CF₃, OH, —OCF₃, —OCH₂CH₃, OCH(CH₃)₂, —OCH₂CF₃, or —NHCH₃.

In one embodiment, the compounds herein are of Formula V, where Q⁴ is hydrogen, Q³ is hydrogen, halo, alkyl, alkoxyalkyl, —R⁴N(R⁶)(R⁷), or —R⁴OR⁵; R⁴ is a direct bond or alkylene; R⁵ is hydrogen, alkyl or haloalkyl; and R⁶ and R⁷ are each independently hydrogen or alkyl.

In one embodiment, provided herein are compounds of Formula VI:

VI

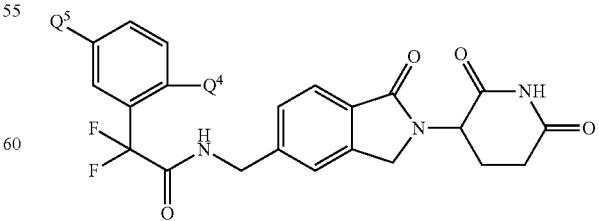

or an enantiomer or a mixture of enantiomers thereof, or a pharmaceutically acceptable salt, solvate, hydrate, co-crystal, clathrate, or polymorph thereof, wherein:

$Q^4$ and $Q^5$ are each independently hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl, alkoxyalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, provided herein is a compound of Formula VI, wherein the substituents are as described above.

In one embodiment, provided herein is an enantiomer of a compound of Formula VI, wherein the substituents are as described above.

In one embodiment, provided herein is a mixture of enantiomers of a compound of Formula VI, wherein the substituents are as described above.

In one embodiment, provided herein is a pharmaceutically acceptable salt of a compound of Formula VI, wherein the substituents are as described above.

In one embodiment, provided herein is a solvate of a compound of Formula VI, wherein the substituents are as described above.

In one embodiment, provided herein is a hydrate of a compound of Formula VI, wherein the substituents are as described above.

In one embodiment, provided herein is a clathrate of a compound of Formula VI, wherein the substituents are as described above.

In one embodiment, provided herein is a co-crystal of a compound of Formula VI, wherein the substituents are as described above.

In one embodiment, provided herein is a polymorph of a compound of Formula VI, wherein the substituents are as described above.

In one embodiment, the compounds herein are of Formula VI, where $Q^4$ and $Q^5$ are each independently hydrogen, halo, alkyl, alkoxyalkyl, —$R^4N(R^6)(R^7)$, or —$R^4OR^5$; $R^4$ is a direct bond or alkylene; $R^5$ is hydrogen, alkyl or haloalkyl; and $R^6$ and $R^7$ together with the nitrogen atom on which they are substituted form a 6-membered heterocyclyl. In some such embodiments, $Q^4$ and $Q^5$ are each independently hydrogen, F, Cl, OH, methyl, —$CF_3$, —$NHCH_3$, —$N(CH_3)_2$, —$OCF_3$, —$OCH_2CH_3$, —$OCH_2CF_3$, —$OCH(CH_3)_2$, —$O(CH_2)_2OCH_3$, —$O(CH_2)_2OCH(CH_3)_2$, —$O(CH_2)_2O(CH_2)_2OCH_3$, $O(CH_2)_2$-morpholinyl, piperidyl, morpholinyl, —$CH_2$-morpholinyl, or —$O(CH_2)_2$-4,4-difluoro-1-piperidyl.

In one embodiment, provided herein are compounds of Formula VII:

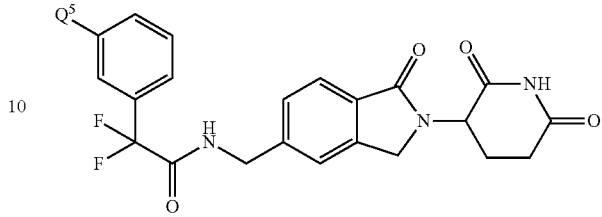

VII or an enantiomer or a mixture of enantiomers thereof, or a pharmaceutically acceptable salt, solvate, hydrate, co-crystal, clathrate, or polymorph thereof, wherein:

$Q^5$ is hydrogen, alkyl, halo, haloalkyl, hydroxyl, alkoxy, optionally substituted cycloalkyl, optionally substituted cycloalkylalkyl, —$R^4OR^5$, —$R^4SR^5$, —$R^4N(R^6)(R^7)$, $R^4OR^4N(R^6)(R^7)$ or $R^4OR^4C(J)N(R^6)(R^7)$;

J is O or S;

each $R^4$ is independently alkylene, alkenylene or a direct bond;

each $R^5$ is independently hydrogen, alkyl, haloalkyl, alkoxyalkyl or hydroxyalkyl; and $R^6$ and $R^7$ are selected as follows:

i) $R^6$ and $R^7$ are each independently hydrogen or alkyl; or ii) $R^6$ and $R^7$ together with the nitrogen atom on which they are substituted form a 5 or 6-membered heterocyclyl or heteroaryl ring, optionally substituted with one or two halo, alkyl or haloalkyl.

In one embodiment, provided herein is a compound of Formula VII, wherein the substituents are as described above.

In one embodiment, provided herein is an enantiomer of a compound of Formula VII, wherein the substituents are as described above.

In one embodiment, provided herein is a mixture of enantiomers of a compound of Formula VII, wherein the substituents are as described above.

In one embodiment, provided herein is a pharmaceutically acceptable salt of a compound of Formula VII, wherein the substituents are as described above.

In one embodiment, provided herein is a solvate of a compound of Formula VII, wherein the substituents are as described above.

In one embodiment, provided herein is a hydrate of a compound of Formula VII, wherein the substituents are as described above.

In one embodiment, provided herein is a clathrate of a compound of Formula VII, wherein the substituents are as described above.

In one embodiment, provided herein is a co-crystal of a compound of Formula VII, wherein the substituents are as described above.

In one embodiment, provided herein is a polymorph of a compound of Formula VII, wherein the substituents are as described above.

In one embodiment, the compounds herein are of Formula VII, where $Q^5$ is hydrogen, halo, alkyl, alkoxyalkyl, —$R^4N(R^6)(R^7)$ or —$R^4OR^5$; $R^4$ is a direct bond or alkylene; and $R^5$ is hydrogen, alkyl or haloalkyl; and $R^6$ and $R^7$ together with the nitrogen atom on which they are substituted form a 6-membered heterocyclyl. In some such embodiments, $Q^5$ is hydrogen, F, Cl, methyl, piperidyl, morpholinyl, —CH$_2$-morpholinyl, —N(CH$_3$)$_2$, —O(CH$_2$)$_2$OCH$_3$, —O(CH$_2$)$_2$OCH(CH$_3$)$_2$, —O(CH$_2$)$_2$O(CH$_2$)$_2$OCH$_3$, or —O(CH$_2$)$_2$-4,4-difluoro-1-piperidyl.

In one embodiment, provided herein are compounds of Formula VIII:

VIII or an enantiomer or a mixture of enantiomers thereof, or a pharmaceutically acceptable salt, solvate, hydrate, co-crystal, clathrate, or polymorph thereof, wherein:

Q$^2$ and Q$^5$ are each independently hydrogen, alkyl, halo, haloalkyl, hydroxyl, alkoxy, optionally substituted cycloalkyl, optionally substituted cycloalkylalkyl, optionally substituted aryl, —R$^4$OR$^5$, —R$^4$SR$^5$, —R$^4$N(R$^6$)(R$^7$), R$^4$OR$^4$N(R$^6$)(R$^7$) or R$^4$OR$^4$C(J)N(R$^6$)(R$^7$);

J is O or S;

each R$^4$ is independently alkylene, alkenylene or a direct bond;

each R$^5$ is independently hydrogen, alkyl, haloalkyl or hydroxyalkyl; and

R$^6$ and R$^7$ are each independently hydrogen or alkyl, or R$^6$ and R$^7$ together with the nitrogen atom on which they are substituted form a 6-membered heterocyclyl.

In one embodiment, provided herein is a compound of Formula VIII, wherein the substituents are as described above.

In one embodiment, provided herein is an enantiomer of a compound of Formula VIII, wherein the substituents are as described above.

In one embodiment, provided herein is a mixture of enantiomers of a compound of Formula VIII, wherein the substituents are as described above.

In one embodiment, provided herein is a pharmaceutically acceptable salt of a compound of Formula VIII, wherein the substituents are as described above.

In one embodiment, provided herein is a solvate of a compound of Formula VIII, wherein the substituents are as described above.

In one embodiment, provided herein is a hydrate of a compound of Formula VIII, wherein the substituents are as described above.

In one embodiment, provided herein is a clathrate of a compound of Formula VIII, wherein the substituents are as described above.

In one embodiment, provided herein is a co-crystal of a compound of Formula VIII, wherein the substituents are as described above.

In one embodiment, provided herein is a polymorph of a compound of Formula VIII, wherein the substituents are as described above.

In one embodiment, the compounds herein are of Formula VIII, where Q$^2$ and Q$^5$ are each independently hydrogen, halo, alkyl, alkoxyalkyl, optionally substituted aryl, or —R$^4$OR$^5$; R$^4$ is a direct bond or alkylene; and R$^5$ is hydrogen, alkyl or haloalkyl. In some such embodiments, Q$^2$ and Q$^5$ are each independently hydrogen, F, Br, Cl, methyl, isopropyl, t-butyl, —C(CH$_3$)$_2$F, p-fluorophenyl, cyclopropyl, —N(CH$_3$)$_2$, —OCH$_3$, —OCH(CH$_3$)$_2$, O(CH$_2$)$_2$OCH$_3$, —O(CH$_2$)$_2$OCH(CH$_3$)$_2$, —O(CH$_2$)$_2$OCH$_3$, —O(CH$_2$)$_2$O(CH$_2$)$_2$OCH$_3$, —OCF$_3$, —O(CH$_2$)$_2$-4,4-difluoro-1-piperidyl, —SCF$_3$, morpholinyl, piperidyl, or CH$_2$-morpholinyl.

In one embodiment, provided herein are compounds of Formula IX:

IX or an enantiomer or a mixture of enantiomers thereof, or a pharmaceutically acceptable salt, solvate, hydrate, co-crystal, clathrate, or polymorph thereof, wherein:

each Q$^1$ is independently alkyl, halo, haloalkyl, alkoxyalkyl, hydroxyl, alkoxy, optionally substituted cycloalkyl; optionally substituted cycloalkylalkyl, optionally substituted heterocyclyl, —R$^4$OR$^5$, —R$^4$OR$^5$—R$^4$OR$^5$, —R$^4$N(R$^6$)(R$^7$), —R$^4$SR$^5$, —R$^4$OR$^4$N(R$^6$)(R$^7$), —R$^4$OR$^4$C(J)N(R$^6$)(R$^7$), —C(J)R$^9$ or R$^4$S(O)$_t$R$^8$;

J is O or S;

each R$^4$ is independently alkylene, alkenylene or a direct bond;

each R$^5$ is independently hydrogen, oxo, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in R$^5$ are each independently optionally substituted with 1-3 Q$^1$ groups selected from alkyl, haloalkyl or halo;

R$^6$ and R$^7$ are each independently hydrogen or alkyl;

R is alkyl, haloalkyl, or hydroxyalkyl;

R$^9$ is alkyl or aryl;

J is O or S;

t is 1 or 2; and n is 0-3.

In one embodiment, provided herein is a compound of Formula IX, wherein the substituents are as described above.

In one embodiment, provided herein is an enantiomer of a compound of Formula IX, wherein the substituents are as described above.

In one embodiment, provided herein is a mixture of enantiomers of a compound of Formula IX, wherein the substituents are as described above.

In one embodiment, provided herein is a pharmaceutically acceptable salt of a compound of Formula IX, wherein the substituents are as described above.

In one embodiment, provided herein is a solvate of a compound of Formula IX, wherein the substituents are as described above.

In one embodiment, provided herein is a hydrate of a compound of Formula IX, wherein the substituents are as described above.

In one embodiment, provided herein is a clathrate of a compound of Formula IX, wherein the substituents are as described above.

In one embodiment, provided herein is a co-crystal of a compound of Formula IX, wherein the substituents are as described above.

In one embodiment, provided herein is a polymorph of a compound of Formula IX, wherein the substituents are as described above.

In one embodiment, the compounds herein are of Formula IX, where each $Q^1$ is independently hydrogen, halo, alkyl, haloalkyl, alkoxyalkyl or haloalkoxyalkyl. In some embodiments, each $Q^1$ is independently fluoro, chloro, bromo, methyl, isopropyl, t-butyl, —$CF_3$, —O—$CH_2CH_3$, —O—$CH(CH_3)_2$, or cyclopropyl.

In one embodiment, the compound provided herein is selected from the group consisting of:

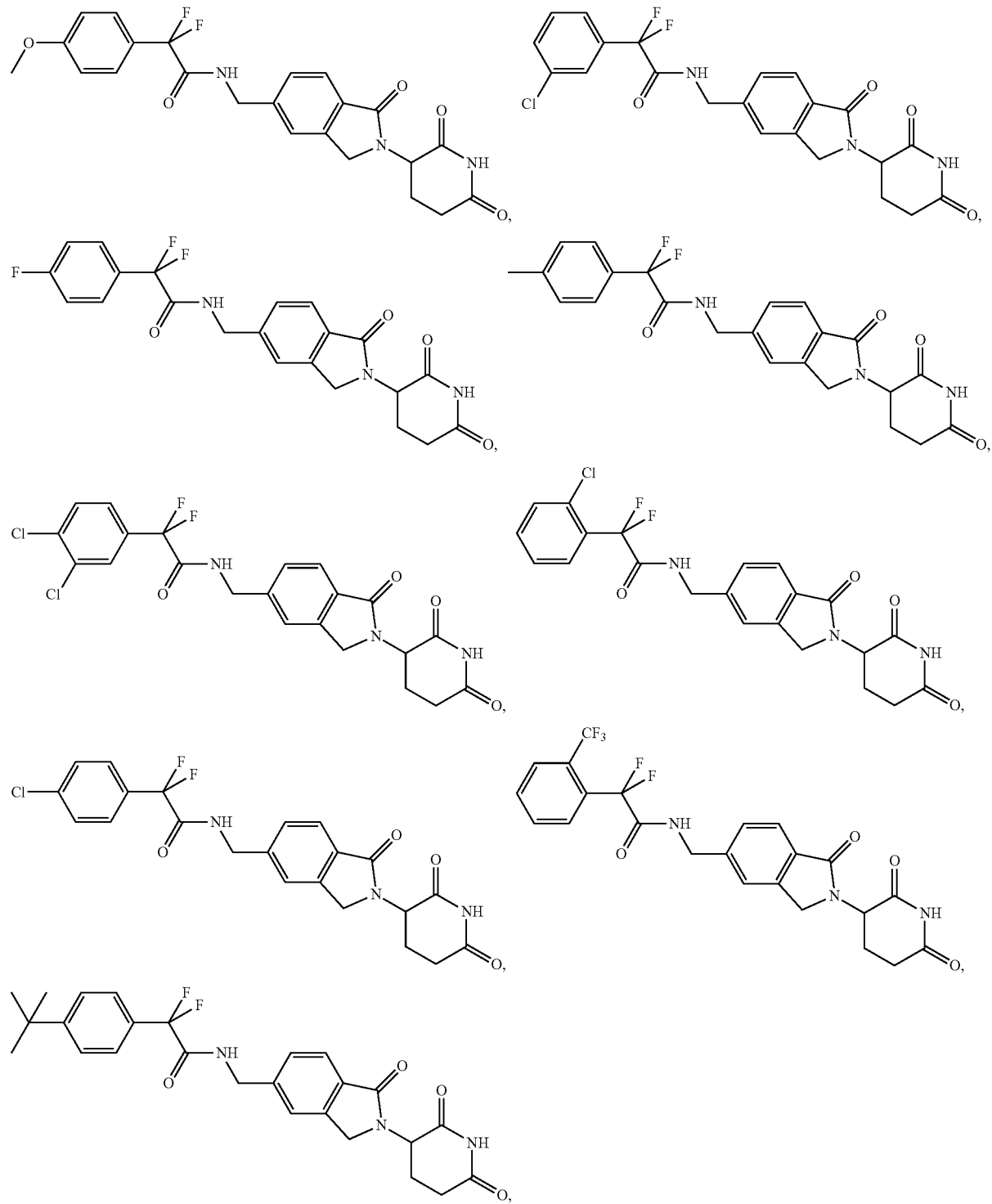

-continued
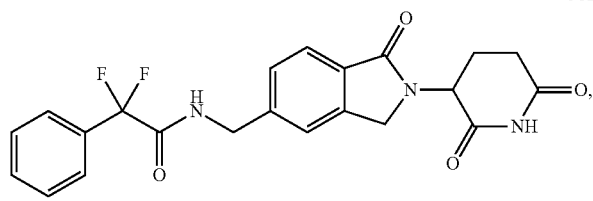
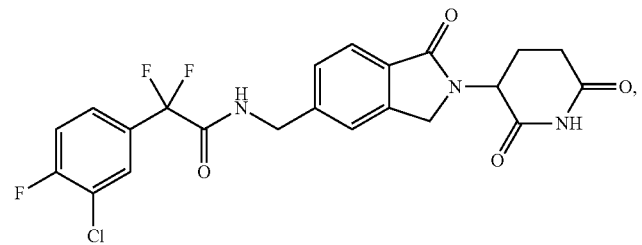
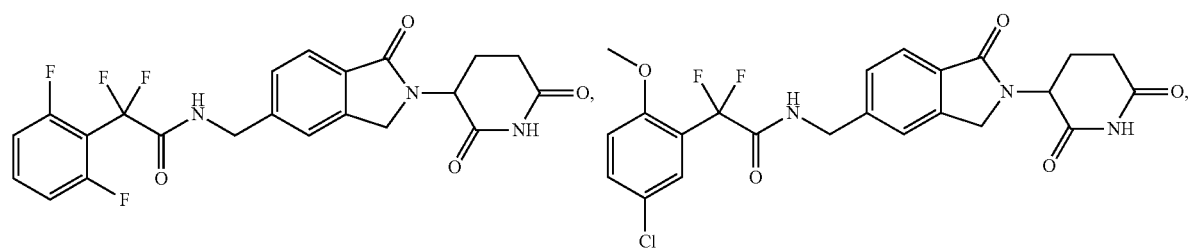
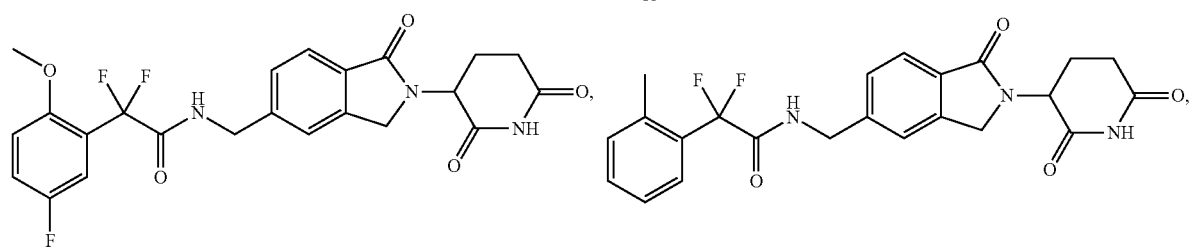
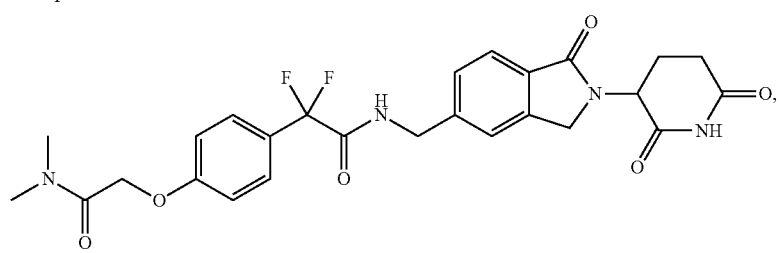
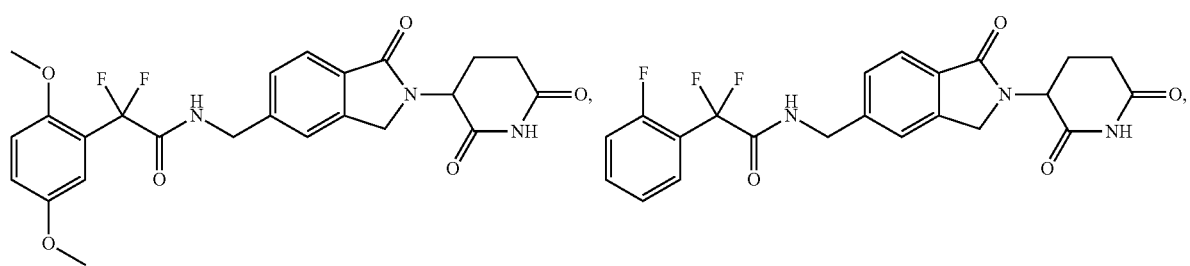
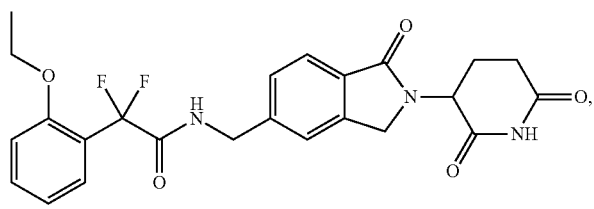

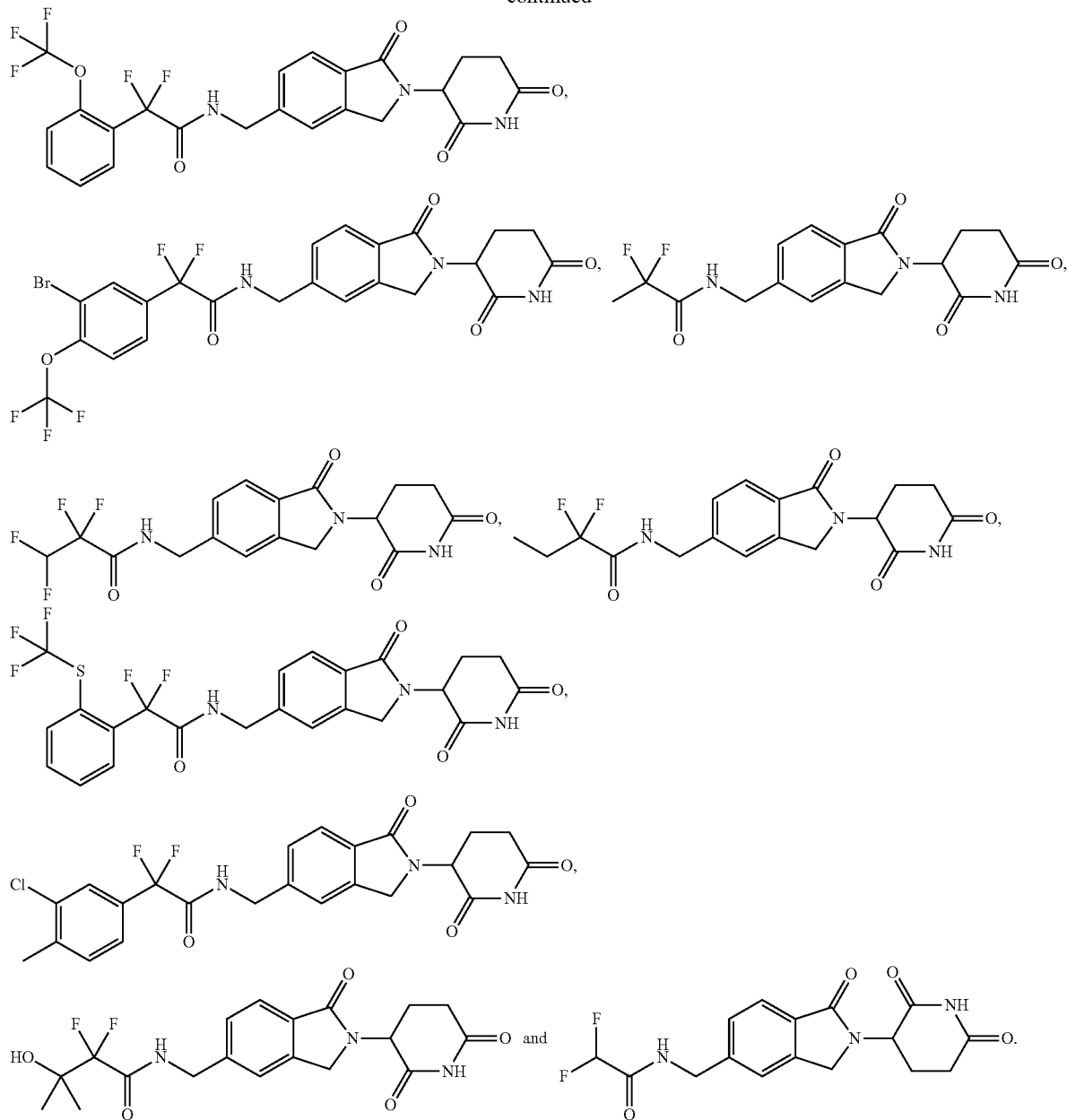

In one embodiment, the compound provided herein is a compound of Table 1.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.,* 20: 393 (1982); Lijinsky et. al., *J. Nat. Cancer Inst.,* 69: 1127 (1982); Mangold et. al., *Mutation Res.* 308: 33 (1994); Gordon et. al., *Drug Metab. Dispos.,* 15: 589 (1987); Zello et. al., *Metabolism,* 43: 487 (1994); Gately et. al., *J. Nucl. Med.,* 27: 388 (1986); Wade D, *Chem. Biol. Interact.* 117: 191 (1999).

Without being limited by any particular theory, iotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. As a result, these drugs often require the administration of multiple or high daily doses.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

C. Methods of Treatment and Prevention

In one embodiment, provided herein is a method of treating and preventing cancer, which comprises administering to a patient a compound provided herein, e.g., the compound of Formula I, or an enantiomer or a mixture of enantiomers thereof, or a pharmaceutically acceptable salt, solvate, hydrate, co-crystal, clathrate, or polymorph thereof.

In another embodiment, provided herein is method of managing cancer, which comprises administering to a patient a compound provided herein, e.g., the compound of Formula I, or an enantiomer or a mixture of enantiomers thereof, or a pharmaceutically acceptable salt, solvate, hydrate, co-crystal, clathrate, or polymorph thereof.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is leukemia.

In one embodiment, methods provided herein encompass treating, preventing or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of a compound of formula I or an enantiomer or a mixture of enantiomers thereof, or a pharmaceutically acceptable salt, solvate, hydrate, co-crystal, clathrate, or polymorph thereof.

In some embodiments, the methods provided herein encompass treating, preventing or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant [M3V]). In one embodiment, the acute myeloid leukemia is myelomonocytic leukemia (M4 or M4 variant with eosinophilia [M4E]). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7). Thus, the methods of treating, preventing or managing acute myeloid leukemia in a subject comprise the step of administering to the subject an amount of a compound provided herein or an enantiomer or a mixture of enantiomers thereof, or a pharmaceutically acceptable salt, solvate, hydrate, co-crystal, clathrate, or polymorph thereof effective to treat, prevent or manage acute myeloid leukemia alone or in combination. In some embodiments, the methods comprise the step of administering to the subject a compound provided herein or an enantiomer or a mixture of enantiomers thereof, or a pharmaceutically acceptable salt, solvate, hydrate, co-crystal, clathrate, or polymorph thereof in combination with a second active agent in amounts effective to treat, prevent or manage acute myeloid leukemia.

In some embodiments, the methods provided herein encompass treating, preventing or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T-cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing or managing acute lymphocytic leukemia in a subject comprise the step of administering to the subject an amount of a compound provided herein or an enantiomer or a mixture of enantiomers thereof, or a pharmaceutically acceptable salt, solvate, hydrate, co-crystal, clathrate, or polymorph thereof effective to treat, prevent or manage acute lymphocytic leukemia alone or in combination with a second active agent. In some embodiments, the methods comprise the step of administering to the subject a compound provided herein or an enantiomer or a mixture of enantiomers thereof, or a pharmaceutically acceptable salt, solvate, hydrate, co-crystal, clathrate, or polymorph thereof in combination with a second active agent in amounts effective to treat, prevent or manage acute lymphocytic leukemia.

In some embodiments, the methods provided herein encompass treating, preventing or managing chronic myelogenous leukemia (CML) in a subject. The methods comprise the step of administering to the subject an amount of a compound provided herein or an enantiomer or a mixture of enantiomers thereof, or a pharmaceutically acceptable salt, solvate, hydrate, co-crystal, clathrate, or polymorph thereof effective to treat, prevent or manage chronic myelogenous leukemia. In some embodiments, the methods comprise the step of administering to the subject a compound provided herein or an enantiomer or a mixture of enantiomers thereof, or a pharmaceutically acceptable salt, solvate, hydrate, co-crystal, clathrate, or polymorph thereof in combination with a second active agent in amounts effective to treat, prevent or manage chronic myelogenous leukemia.

In some embodiments, the methods provided herein encompass treating, preventing or managing chronic lymphocytic leukemia (CLL) in a subject. The methods comprise the step of administering to the subject an amount of a compound provided herein or an enantiomer or a mixture of enantiomers thereof, or a pharmaceutically acceptable salt, solvate, hydrate, co-crystal, clathrate, or polymorph thereof effective to treat, prevent or manage chronic lymphocytic leukemia. In some embodiments, the methods comprise the step of administering to the subject a compound provided herein or an enantiomer or a mixture of enantiomers thereof, or a pharmaceutically acceptable salt, solvate, hydrate, co-crystal, clathrate, or polymorph thereof in combination with a second active agent in amounts effective to treat, prevent or manage chronic lymphocytic leukemia.

In certain embodiments, provided herein are methods of treating, preventing, and/or managing disease in patients with impaired renal function. In certain embodiments, provided herein are method of treating, preventing, and/or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, and/or managing lymphoma, including non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in patients with impaired renal function or a symptom thereof, comprising administering a therapeutically effective amount of the compound of Formula I, or an enantiomer or a mixture of enantiomers thereof, or a pharmaceutically acceptable salt, solvate, hydrate, stereoisomer, tautomer or racemic mixtures thereof to a patient having relapsed/refractory multiple myeloma with impaired renal function.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day. In some such embodiments, the therapeutically or prophylactically effective amount is about 2, about 3, about 4, about 5, about 6 or about 7 mg per day.

In one embodiment, the recommended daily dose range of the compound of Formula I, or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day to patients with leukemia, including AML. In a particular embodiment, the compound can be administered in an amount of about 10 mg/day to patients with leukemia, including AML. In a particular embodiment, the compound can be administered in an amount of about 5 mg/day to patients with leukemia, including AML. In a particular embodiment, the compound can be administered in an amount of about 4 mg/day to patients with leukemia, including AML. In a particular embodiment, the compound can be administered in an amount of about 3 mg/day to patients with leukemia, including AML.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In certain embodiments, the amount of the compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the compound administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25

µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of the compound of Formula I, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has been treated with anticancer therapy prior to the administration of the compound of Formula I, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has developed drug resistance to the anticancer therapy.

The methods provided herein encompass treating a patient regardless of patient's age, although some diseases or disorders are more common in certain age groups.

Depending on the disease to be treated and the subject's condition, the compound of Formula I, or an enantiomer or a mixture of enantiomers thereof; or a pharmaceutically acceptable salt, solvate, hydrate, co-crystal, clathrate, or polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound of Formula I, or an enantiomer or a mixture of enantiomers thereof; or a pharmaceutically acceptable salt, solvate, hydrate, co-crystal, clathrate, or polymorph thereof, may be formulated, alone or together, in suitable dosage unit with pharmaceutically acceptable excipients, carriers, adjuvants and vehicles, appropriate for each route of administration.

In one embodiment, the compound of Formula I, or an enantiomer or a mixture of enantiomers thereof; or a pharmaceutically acceptable salt, solvate, hydrate, co-crystal, clathrate, or polymorph thereof, is administered orally. In another embodiment, the compound of Formula I, or an enantiomer or a mixture of enantiomers thereof; or a pharmaceutically acceptable salt, solvate, hydrate, co-crystal, clathrate, or polymorph thereof, is administered parenterally. In yet another embodiment, the compound of Formula I, or an enantiomer or a mixture of enantiomers thereof; or a pharmaceutically acceptable salt, solvate, hydrate, co-crystal, clathrate, or polymorph thereof, is administered intravenously.

The compound of Formula I, or an enantiomer or a mixture of enantiomers thereof; or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound of Formula I, or an enantiomer or a mixture of enantiomers thereof; or a pharmaceutically acceptable salt, solvate, hydrate, co-crystal, clathrate, or polymorph thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound of Formula I, is administered once or more than once each day, for example, for a period of time. The term "continuous" is intended to mean that a therapeutic compound, such as the compound of Formula I, is administered daily for an uninterrupted period of at least 10 days to 52 weeks. The term "intermittent" or "intermittently" as used herein is intended to mean stopping and starting at either regular or irregular intervals. For example, intermittent administration of the compound of Formula I is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound of Formula I, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound of Formula I, or an enantiomer or a mixture of enantiomers thereof; or a pharmaceutically acceptable salt, solvate, hydrate, co-crystal, clathrate, or polymorph thereof, is administered once a day. In another embodiment, the compound of Formula I, or an enantiomer or a mixture of enantiomers thereof; or a pharmaceutically acceptable salt, solvate, hydrate, co-crystal, clathrate, or polymorph thereof, is administered twice a day. In yet another embodiment, the compound of Formula I, or an enantiomer or a mixture of enantiomers thereof; or a pharmaceutically acceptable salt, solvate, hydrate, co-crystal, clathrate, or polymorph thereof, is administered three times a day. In still another embodiment, the compound of Formula I, or an enantiomer or a mixture of enantiomers thereof; or a pharmaceutically acceptable salt, solvate, hydrate, co-crystal, clathrate, or polymorph thereof, is administered four times a day.

In certain embodiments, the compound of Formula I, or an enantiomer or a mixture of enantiomers thereof; or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, the compound of Formula I, or a pharmaceutically acceptable salt or solvate thereof, is administered once per day for one week, two weeks, three weeks, or four weeks. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for 4 days. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for 5 days. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for 6 days. In one embodiment, the compound of Formula I, or an enantiomer or a mixture of enantiomers thereof; or a pharmaceutically acceptable salt, solvate, hydrate, co-crystal, clathrate, or polymorph thereof, is administered once per day for one week. In another embodiment, the compound of Formula I, or an enantiomer or a mixture of enantiomers thereof; or a pharmaceutically acceptable salt, solvate, hydrate, co-crystal, clathrate, or polymorph thereof, is administered once per day for two weeks. In yet another embodiment, the compound of Formula I, or an enantiomer or a mixture of enantiomers thereof; or a pharmaceutically acceptable salt, solvate, hydrate, co-crystal, clathrate, or polymorph thereof, is administered once per day for three weeks. In still another embodiment, the compound of Formula I, or an enantiomer or a mixture of enantiomers thereof; or a pharmaceutically acceptable salt, solvate, hydrate, co-crystal, clathrate, or polymorph thereof, is administered once per day for four weeks.

C-1. Combination Therapy with a Second Active Agent

The compound of Formula I, or an enantiomer or a mixture of enantiomers thereof; or a pharmaceutically acceptable salt, solvate, hydrate, co-crystal, clathrate, or polymorph thereof, can also be combined or used in combination with other therapeutic agents useful in the treatment and/or prevention of cancer described herein.

In one embodiment, provided herein is a method of treating, preventing, or managing cancer, comprising administering to a patient a compound of Formula I, or an enantiomer or a mixture of enantiomers thereof; or a pharmaceutically acceptable salt, solvate, hydrate, co-crystal, clathrate, or polymorph thereof; in combination with one or more second active agents, and optionally in combination with radiation therapy, blood transfusions, or surgery. Examples of second active agents are disclosed herein (see, e.g., section 5.4).

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, e.g., the compound of Formula I, or an enantiomer or a mixture of enantiomers thereof, or a pharmaceutically acceptable salt, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound of Formula I and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compound of Formula I is independent of the route of administration of a second therapy. In one embodiment, the compound of Formula I is administered orally. In another embodiment, the compound of Formula I is administered intravenously. Thus, in accordance with these embodiments, the compound of Formula I is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, the compound of Formula I and a second therapy are administered by the same mode of administration, orally or by IV. In another embodiment, the compound of Formula I is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound of Formula I provided herein and any optional additional active agents concurrently administered to the patient.

One or more second active ingredients or agents can be used together with the compound of formula I in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393, 870; and 5,229,496; all of which are incorporated herein by reference. Recombinant and mutated forms of G-CSF can be prepared as described in U.S. Pat. Nos. 4,810,643; 4,999, 291; 5,528,823; and 5,580,755; the entireties of which are incorporated herein by reference.

Also provided for use in combination with a compound provided herein or an enantiomer or a mixture of enantiomers thereof, or a pharmaceutically acceptable salt, solvate, hydrate, co-crystal, clathrate, or polymorph thereof are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with a compound provided herein or an enantiomer or a mixture of enantiomers thereof, or a pharmaceutically acceptable salt, solvate, hydrate, co-crystal, clathrate, or polymorph thereof include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. The compounds provided herein or an enantiomer or a mixture of enantiomers thereof, or a pharmaceutically acceptable salt, solvate, hydrate, co-crystal, clathrate, or polymorph thereof can also be combined with, or used in combination with, anti-TNF-α antibodies, and/or anti-EGFR antibodies, such as, for example, Erbitux® or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

Second active agents that are small molecules can also be used to alleviate adverse effects associated with the administration of a compound provided herein or an enantiomer or a mixture of enantiomers thereof, or a pharmaceutically acceptable salt, solvate, hydrate, co-crystal, clathrate, or polymorph thereof. However, like some large molecules, many are believed to be capable of providing a synergistic effect when administered with (e.g., before, after or simultaneously) a compound provided herein or an enantiomer or a mixture of enantiomers thereof, or a pharmaceutically acceptable salt, solvate, hydrate, co-crystal, clathrate, or polymorph thereof. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitor or a TOR kinase inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman;

piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, Ara-C, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments of the methods provided herein, use of a second active agent in combination with a compound provided herein or an enantiomer or a mixture of enantiomers thereof, or a pharmaceutically acceptable salt, solvate, hydrate, co-crystal, clathrate, or polymorph thereof may be modified or delayed during or shortly following administration of a compound provided herein or an enantiomer or a mixture of enantiomers thereof, or a pharmaceutically acceptable salt, solvate, hydrate, co-crystal, clathrate, or polymorph thereof as deemed appropriate by the practitioner of skill in the art. In certain embodiments, subjects being administered a compound provided herein or an enantiomer or a mixture of enantiomers thereof, or a pharmaceutically acceptable salt, solvate, hydrate, co-crystal, clathrate, or polymorph thereof alone or in combination with other therapies may receive supportive care including antiemetics, myeloid growth factors, and transfusions of platelets, when appropriate. In some embodiments, subjects being administered a compound provided herein or an enantiomer or a mixture of enantiomers thereof, or a pharmaceutically acceptable salt, solvate, hydrate, co-crystal, clathrate, or polymorph thereof may be administered a growth factor as a second active agent according to the judgment of the practitioner of skill in the art. In some embodiments, provided is administration of a compound provided herein or an enantiomer or a mixture of enantiomers thereof, or a pharmaceutically acceptable salt, solvate, hydrate, co-crystal, clathrate, or polymorph thereof in combination with erythropoietin or darbepoetin (Aranesp).

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine and cisplatinum to patients with locally advanced or metastatic transitional cell bladder cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with temozolomide to patients with neuroendocrine tumors.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine to patients with recurrent or metastatic head or neck cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with gemcitabine to patients with pancreatic cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with colon cancer in combination with ARISA®, avastatin, taxol, and/or taxotere.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with capecitabine and/or PLX4032 (Plexxikon) to patients with refractory colorectal cancer or patients who fail first line therapy or have poor performance in colon or rectal adenocarcinoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with fluorouracil, leucovorin, and irinotecan to patients with Dukes C & D colorectal cancer or to patients who have been previously treated for metastatic colorectal cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with refractory colorectal cancer in combination with capecitabine, xeloda, and/or CPT-11.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with capecitabine and irinotecan to patients with refractory colorectal cancer or to patients with unresectable or metastatic colorectal carcinoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with interferon alpha or capecitabine to patients with unresectable or metastatic hepatocellular carcinoma; or with cisplatin and thiotepa to patients with primary or metastatic liver cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with pegylated interferon alpha to patients with Kaposi's sarcoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with fludarabine, carboplatin, and/or topotecan to patients with refractory or relapsed or high-risk acute myeloid leukemia.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with liposomal daunorubicin, topotecan and/or cytarabine to patients with unfavorable karotype acute myeloblastic leukemia.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with gemcitabine, abraxane, erlotinib, geftinib, and/or irinotecan to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with carboplatin and irinotecan to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered with doxetaxol to patients with non-small cell lung cancer who have been previously treated with carbo/VP 16 and radiotherapy.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with carboplatin and/or taxotere, or in combination with carboplatin, paclitaxel and/or thoracic radiotherapy to patients with non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with taxotere to patients with stage IIIB or IV non-small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with oblimersen (Genasense®) to patients with small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with ABT-737 (Abbott Laboratories) and/or obatoclax (GX15-070) to patients with lymphoma and other blood cancers.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with taxotere, IL-2, IFN, GM-CSF, PLX4032 (Plexxikon) and/or dacarbazine to patients with various types or stages of melanoma.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered alone or in combination with vinorelbine to patients with malignant mesothelioma, or stage IIIB non-small cell lung cancer with pleural implants or malignant pleural effusion mesothelioma syndrome.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with relapsed or refractory multiple myeloma in combination with doxorubicin (Doxil®), vincristine and/or dexamethasone (Decadron®).

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of renal cell cancer, in combination with capecitabine, IFN, tamoxifen, IL-2, GM-CSF, Celebrex®, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of gynecologic, uterus or soft tissue sarcoma cancer in combination with IFN, a COX-2 inhibitor such as Celebrex®, and/or sulindac.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) or an enantiomer or a mixture of enantiomers thereof, or a pharmaceutically acceptable salt, solvate, hydrate, co-crystal, clathrate, or polymorph thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof, alleviates or reduces adverse effects which are of such severity that it would otherwise limit the amount of anti-cancer drug.

In one embodiment, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with specific agents such as heparin, aspirin, coumadin, or G-CSF to avoid adverse effects that are associated with anti-cancer drugs such as but not limited to neutropenia or thrombocytopenia.

In one embodiment, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering the compound of Formula I, or an enantiomer or a mixture of enantiomers thereof, or a pharmaceutically acceptable salt, solvate, hydrate, co-crystal, clathrate, or polymorph thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that the compound of Formula I may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A compound provided herein, e.g., the compound of Formula I, or an enantiomer or a mixture of enantiomers thereof, or a pharmaceutically acceptable salt, solvate, hydrate, co-crystal, clathrate, or polymorph thereof, and other active ingredient can be administered to a patient prior to, during, or after the occurrence of the adverse effect associated with conventional therapy.

In one embodiment, the compound of Formula I can be administered in an amount ranging from about 0.1 to about 150 mg, from about 1 to about 25 mg, or from about 2 to about 10 mg orally and daily alone, or in combination with a second active agent disclosed herein (see, e.g., section 5.4), prior to, during, or after the use of conventional therapy.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, and doxetaxol are administered to patients with non-small cell lung cancer who were previously treated with carbo/VP 16 and radiotherapy.

C-2. Use with Transplantation Therapy

The compound of Formula I, or an enantiomer or a mixture of enantiomers thereof, or a pharmaceutically acceptable salt, solvate, hydrate, co-crystal, clathrate, or polymorph thereof, provided herein can be used to reduce the risk of Graft Versus Host Disease (GVHD). Therefore, encompassed herein is a method of treating, preventing and/or managing cancer, which comprises administering the compound of Formula I, or an enantiomer or a mixture of enantiomers thereof, or a pharmaceutically acceptable salt, solvate, hydrate, co-crystal, clathrate, or polymorph thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the compound of Formula I, or an enantiomer or a mixture of enantiomers thereof, or a pharmaceutically acceptable salt, solvate, hydrate, co-crystal, clathrate, or polymorph thereof, provided herein and transplantation therapy provides a unique and unexpected synergism. In particular, the compound of Formula I, or an enantiomer or a mixture of enantiomers thereof, or a pharmaceutically acceptable salt, solvate, hydrate, co-crystal, clathrate, or polymorph thereof, exhibits immunomodulatory activity that may provide additive or synergistic effects when given concurrently with transplantation therapy in patients with cancer.

The compound of Formula I, or an enantiomer or a mixture of enantiomers thereof, or a pharmaceutically acceptable salt, solvate, hydrate, co-crystal, clathrate, or polymorph thereof, can work in combination with transplantation therapy reducing complications associated with the invasive procedure of transplantation and risk of GVHD. Encompassed herein is a method of treating, preventing and/or managing cancer which comprises administering to a patient (e.g., a human) the compound of Formula I, or an enantiomer or a mixture of enantiomers thereof, or a pharmaceutically acceptable salt, solvate, hydrate, co-crystal, clathrate, or polymorph thereof, before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, the compound of Formula I, or an enantiomer or a mixture of enantiomers thereof, or a pharmaceutically acceptable salt, solvate, hydrate, co-crystal, clathrate, or polymorph thereof, is administered to patients with multiple myeloma before, during, or after the transplantation of autologous peripheral blood progenitor cell.

In one embodiment, the compound of Formula I, or an enantiomer or a mixture of enantiomers thereof, or a pharmaceutically acceptable salt, solvate, hydrate, co-crystal, clathrate, or polymorph thereof, is administered to patients with NHL (e.g., DLBCL) before, during, or after the transplantation of autologous peripheral blood progenitor cell.

C-3. Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, the compound of Formula I, or an enantiomer or a mixture of enantiomers thereof, or a pharmaceutically acceptable salt, solvate, hydrate, co-crystal, clathrate, or polymorph thereof, provided herein is administered daily in a single or divided doses in a four to six week cycle with a rest period of about a week or two weeks. The cycling method further allows the frequency, number, and length of dosing cycles to be increased. Thus, encompassed herein in certain embodiments is the administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof, for more cycles than are typical when it is administered alone. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered for a greater number of cycles that would typically cause dose-limiting toxicity in a patient to whom a second active ingredient is not also being administered.

In one embodiment, the compound of Formula I, or an enantiomer or a mixture of enantiomers thereof, or a pharmaceutically acceptable salt, solvate, hydrate, co-crystal, clathrate, or polymorph thereof, is administered daily and continuously for three or four weeks at a dose of from about 0.1 to about 150 mg/d followed by a break of one or two weeks.

In another embodiment, the compound of Formula I, or an enantiomer or a mixture of enantiomers thereof, or a pharmaceutically acceptable salt, solvate, hydrate, co-crystal, clathrate, or polymorph thereof, and a second active ingredient are administered orally, with administration of the compound of Formula I occurring 30 to 60 minutes prior to a second active ingredient, during a cycle of four to six weeks. In certain embodiments, the combination of the compound of Formula I, or an enantiomer or a mixture of enantiomers thereof, or a pharmaceutically acceptable salt, solvate, hydrate, co-crystal, clathrate, or polymorph thereof, and a second active ingredient is administered by intravenous infusion over about 90 minutes every cycle. In certain embodiments, one cycle comprises the administration from about 0.1 to about 150 mg/day of the compound of Formula I, or an enantiomer or a mixture of enantiomers thereof, or a pharmaceutically acceptable salt, solvate, hydrate, co-crystal, clathrate, or polymorph thereof, and from about 50 to about 200 mg/m²/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

D. Patient Population

In certain embodiments of the methods provided herein, the subject is an animal, preferably a mammal, more preferably a non-human primate. In particular embodiments, the subject is a human. The subject can be a male or female subject.

Particularly useful subjects for the methods provided herein include human cancer patients, for example, those who have been diagnosed with leukemia, including acute myeloid leukemia, acute lymphocytic leukemia, chronic myelogenous leukemia, and chronic myelogenous leukemia. In certain embodiments, the subject has not been diagnosed with acute promyelocytic leukemia.

In some embodiments, the subject has a higher than normal blast population. In some embodiments, the subject has a blast population of at least 10%. In some embodiments, the subject has a blast population of between 10 and 15%. In some embodiments, the subject has a blast population of at least 15%. In some embodiments, the subject has a blast population of between 15 and 20%. In some embodiments, the subject has a blast population of at least 20%. In some embodiments, the subject has a blast population of about 10-15%, about 15-20%, or about 20-25%. In other embodiments, the subject has a blast population of less than 10%. In the context of the methods described herein, useful subjects having a blast population of less than 10% includes those subjects that, for any reason according to the judgment of the skilled practitioner in the art, are in need of treatment with a compound provided herein, alone or in combination with a second active agent.

In some embodiments, the subject is treated based on the Eastern Cooperative Oncology Group (ECOG) performance status score of the subject for leukemia. ECOG performance status can be scored on a scale of 0 to 5, with 0 denoting asymptomatic; 1 denoting symptomatic but completely ambulant; 2 denoting symptomatic and <50% in bed during the day; 3 denoting symptomatic and >50% in bed, but not bed bound; 4 denoting bed bound; and 5 denoting death. In some embodiments, the subject has an ECOG performance status score of 0 or 1. In some embodiments, the subject has an ECOG performance status score of 0. In some embodiments, the subject has an ECOG performance status score of 1. In other embodiments, the subject has an ECOG performance status score of 2.

In certain embodiments, the methods provided herein encompass the treatment of subjects who have not been previously treated for leukemia. In some embodiments, the subject has not undergone allogeneic bone marrow transplantation. In some embodiments, the subject has not undergone a stem cell transplantation. In some embodiments, the subject has not received hydroxyurea treatment. In some embodiments, the subject has not been treated with any investigational products for leukemia. In some embodiments, the subject has not been treated with systemic glucocorticoids.

In other embodiments, the methods encompass treating subjects who have been previously treated or are currently being treated for leukemia. For example, the subject may have been previously treated or are currently being treated with a standard treatment regimen for leukemia. The subject may have been treated with any standard leukemia treatment regimen known to the practitioner of skill in the art. In certain embodiments, the subject has been previously treated with at least one induction/reinduction or consolidation AML regimen. In some embodiments, the subject has undergone autologous bone marrow transplantation or stem cell transplantation as part of a consolidation regimen. In some embodiments, the bone marrow or stem cell transplantation occurred at least 3 months prior to treatment according to the methods provided herein. In some embodiments, the subject has undergone hydroxyurea treatment. In some embodiments, the hydroxyurea treatment occurred no later than 24 hours prior to treatment according to the methods provided herein. In some embodiments, the subject has undergone prior induction or consolidation therapy with cytarabine (Ara-C). In some embodiments, the subject has undergone treatment with systemic glucocorticosteroids. In some embodiments, the glucocorticosteroid treatment occurred no later 24 hours prior to treatment according to the methods described herein. In other embodiments, the methods encompass treating subjects who have been previously treated for cancer, but are non-responsive to standard therapies.

Also encompassed are methods of treating subjects having relapsed or refractory leukemia. In some embodiments, the subject has been diagnosed with a relapsed or refractory AML subtype, as defined by the World Health Organization (WHO). Relapsed or refractory disease may be de novo AML or secondary AML, e.g., therapy-related AML (t-AML).

In some embodiments, the methods provided herein are used to treat drug resistant leukemias, such as chronic myelogenous leukemia (CML). Thus, treatment with a compound provided herein could provide an alternative for patients who do not respond to other methods of treatment. In some embodiments, such other methods of treatment encompass treatment with Gleevec® (imatinib mesylate). In some embodiments, provided herein are methods of treatment of Philadelphia chromosome positive chronic myelogenous leukemia (Ph+CML). In some embodiments, provided herein are methods of treatment of Gleevec® (imatinib mesylate) resistant Philadelphia chromosome positive chronic myelogenous leukemia (Ph+CML).

Also encompassed are methods of treating a subject regardless of the subject's age, although some diseases or disorders are more common in certain age groups. In some embodiments, the subject is at least 18 years old. In some embodiments, the subject is more than 18, 25, 35, 40, 45, 50, 55, 60, 65, or 70 years old. In other embodiments, the subject is less than 65 years old. In some embodiments, the subject is less than 18 years old. In some embodiments, the subject is less than 18, 15, 12, 10, 9, 8 or 7 years old.

In some embodiments, the methods may find use in subjects at least 50 years of age, although younger subjects could benefit from the method as well. In other embodiments, the subjects are at least 55, at least 60, at least 65, and at least 70 years of age. In another embodiment, the subjects have adverse cytogenetics. "Adverse cytogenetics" is defined as any nondiploid karyotype, or greater than or equal to 3 chromosomal abnormalities. In another embodiment, the subjects are at least 60 years of age and have adverse cytogenetics. In another embodiment, the subjects are 60-65 years of age and have adverse cytogenetics. In another embodiment, the subjects are 65-70 years of age and have adverse cytogenetics.

In certain embodiments, the subject treated has no history of myocardial infarction within three months of treatment according to the methods provided herein. In some embodiments, the subject has no history of cerebrovascular accident or transient ischemic attack within three months of treatment according to the methods provided herein. In some embodiments, the subject has no suffered no thromboembelic event, including deep vein thrombosis or pulmonary embolus, within 28 days of treatment according to the methods provided herein. In other embodiments, the subject has not experienced or is not experiencing uncontrolled disseminated intravascular coagulation.

Because subjects with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual subject with cancer.

It will be appreciated that every suitable combination of the compounds provided herein with one or more of the aforementioned compounds and optionally one or more further pharmacologically active substances is contemplated herein.

E. Formulation of Pharmaceutical Compositions

The pharmaceutical compositions provided herein contain therapeutically effective amounts of one or more of compounds provided herein and a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of cancer, including solid tumors and blood borne tumors.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

In certain embodiments, a therapeutically effective dosage should produce a serum concentration of active ingredient of from about 0.1 ng/mL to about 50-100 µg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1 85% or about 75-95%.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%)

is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

E-1. Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable salt thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

E-2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

E-3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

E-4. Topical Administration

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable salts thereof may be formulated as aerosols for topical application, such as by inhalation (see, e.g., U.S. Pat. Nos. 4,044, 126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds may be formulated for local or topical application, such as for topical application to the skin and mucous membranes, such as in the eye, in the form of gels, creams, and lotions and for application to the eye or for intracistemal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

E-5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

E-6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, CRC Crit. Ref Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

E-7. Targeted Formulations

The compounds provided herein, or pharmaceutically acceptable salts thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

E-8. Articles of Manufacture

The compounds or pharmaceutically acceptable salts can be packaged as articles of manufacture containing packaging material, a compound or pharmaceutically acceptable salt thereof provided herein, which is used for treatment, prevention or amelioration of one or more symptoms or progression of cancer, including solid tumors and blood borne tumors, and a label that indicates that the compound or pharmaceutically acceptable salt thereof is used for treatment, prevention or amelioration of one or more symptoms or progression of cancer, including solid tumors and blood borne tumors.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

F. Evaluation of the Activity of the Compounds

Standard physiological, pharmacological and biochemical procedures are available for testing the compounds to identify those that possess the desired anti-proliferative activity.

Such assays include, for example, biochemical assays such as binding assays, radioactivity incorporation assays, as well as a variety of cell based assays.

G. Preparation of Compounds

The compounds provided herein can be prepared by methods known to one of skill in the art and following procedures similar to those described in the Examples section herein and routine modifications thereof.

An exemplary reaction scheme for the preparation of compounds is illustrated below.

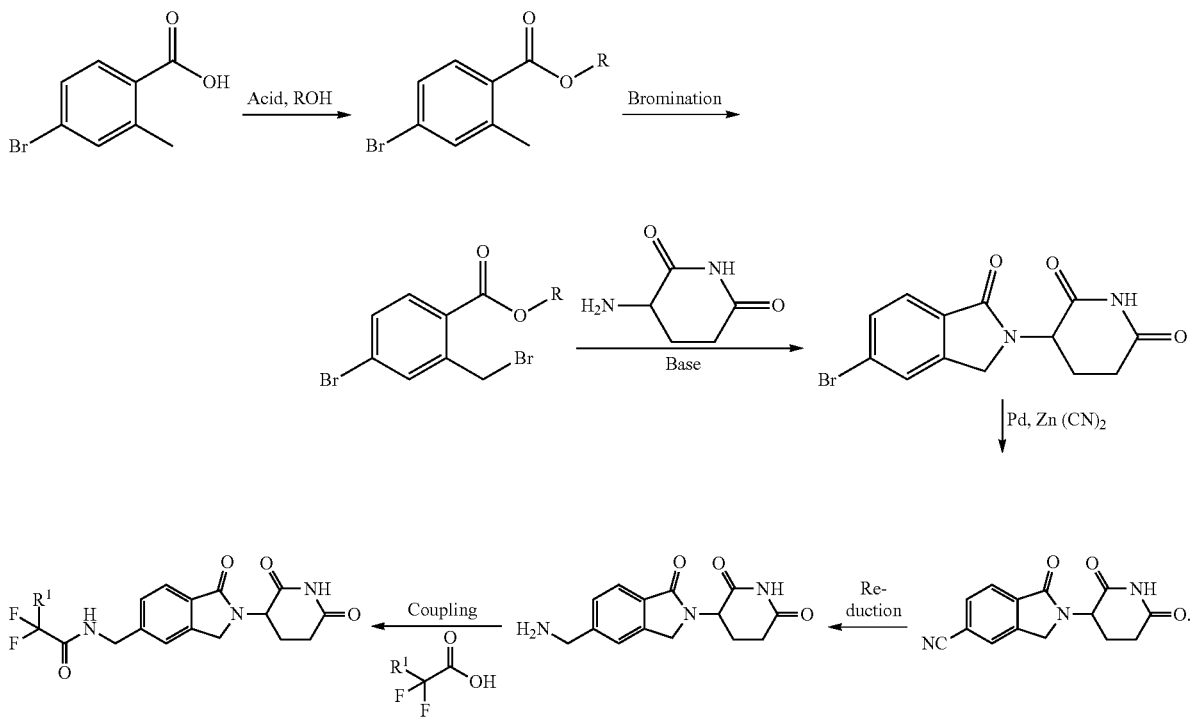

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

6. EXAMPLES

Certain embodiments of the invention are illustrated by the following non-limiting example.

Example 1

Synthesis of N-((2-(2,6-dioxopiperidin-3-yl)-1-oxoisoindolin-5-yl)methyl)-2,2-difluoro-2-(4-methoxyphenyl)acetamide

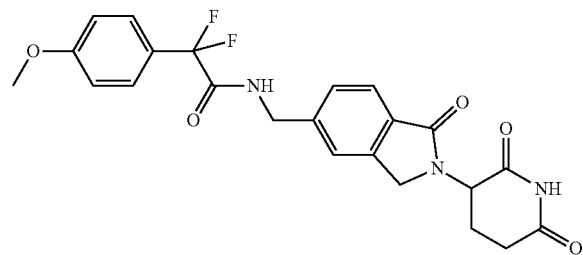 [SMILES: COc1ccc(C(F)(F)C(=O)NCc2ccc3c(c2)CN(C2CCC(=O)NC2=O)C3=O)cc1]

Methyl 4-bromo-2-methylbenzoate

4-Bromo-2-methylbenzoic acid (100 g, 465.02 mmol), concentrated sulfuric acid (52 mL) in methanol (1 L) were combined and heated to 65° C. for 18 h. The reaction was concentrated and the residue diluted with ethyl acetate (500 mL), washed with saturated sodium bicarbonate solution (150 mL), water (200 mL), brine (250 mL) and dried over sodium sulfate. The organic phase was concentrated under reduced pressure and further dried under high vacuum to give methyl 4-bromo-2-methylbenzoate (102 g, 445.27 mmol, 95% yield) as a red liquid. 1H NMR (400 MHz, Chloroform-$d_1$) δ 7.78 (d, J=8.3 Hz, 1H), 7.45-7.30 (m, 2H), 3.88 (s, 3H), 2.57 (s, 3H).

Methyl-4-bromo-2-(bromomethyl)benzoate

Methyl 4-bromo-2-methylbenzoate (102 g, 445.27 mmol), NBS (79.2 g, 445.27 mmol), Azo-isobutyronitrile (2.58 g, 16 mmol) in acetonitrile (600 mL) were combined and refluxed at 85° C. for 18 h. The mixture was concentrated, and to the residue was added dichloromethane (150 mL). The resultant solid was removed by filtration. The filtrate was concentrated and purified by flash column chromatography (0-4% EtOAc in Hexanes). Fractions containing product was concentrated under reduced pressure and further dried under high vacuum to give Methyl-4-bromo-2-(bromomethyl)benzoate (100 g, 324.70 mmol, 72.9% yield) as an off-white solid. 1H NMR (300 MHz, Dimethylsulfoxide-$d_6$) δ 7.88 (d, J=2.2 Hz, 1H), 7.82 (dd, J=8.4, 2.1 Hz, 1H), 7.72-7.64 (m, 1H), 5.00 (s, 2H), 3.88 (s, 3H).

3-(5-Bromo-1-oxoisoindolin-2-yl)piperidine-2,6-dione

Methyl-4-bromo-2-(bromomethyl)benzoate (100 g, 324.70 mmol), 3-Aminopiperidine-2,6-dione.hydrochloride (53.2 g, 324.70 mmol), triethylamine (113.29 mL, 811.75 mmol), and dry dimethylformamide (400 mL) were combined and stirred at room temperature under inert atmosphere for 18 h. The reaction was cooled to 5° C. and diluted with water (400 mL), acetic acid (115 mL), diethylether (300 mL) with continued stirring at room temperature for 2 h. The resultant solid was filtered, washed with ether (100 mL) and further dried under high vacuum to give 3-(5-Bromo-1-oxoisoindolin-2-yl)piperidine-2,6-dione (46 g, 142.35 mmol, 43.8% yield) as a light blue solid. MS (ESI) m/z 325.0 [M+1]$^+$.

2-(2,6-dioxopiperidin-3-yl)-1-oxoisoindoline-5-carbonitrile 3-(5-Bromo-1-oxoisoindolin-2-yl)piperidine-2,6-dione (46 g, 142.35 mmol), 1,1'-Bis(diphenylphosphino)ferrocene (788 mg, 1.423 mmol), zinc cyanide (25 g, 213.52 mmol), zinc acetate (7.83 g, 42.7 mmol) and dry dimethylformamide (360 mL) were combined and degassed before addition of tris(dibenzylideneacetone)dipalladium(0) (0.364 g, 0.398 mmol). The mixtures was evacuated and replaced with argon 3 times, then stirred at 120° C. for 20 h. The mixture was cooled to room temperature, filtered and purified by silica column chromatography (0-5% methanol in dichloromethane). Fractions containing product were combined and solvent removed under reduced pressure and then further dried under high vacuum to give 2-(2,6-dioxopiperidin-3-yl)-1-oxoisoindoline-5-carbonitrile (22 g, 81.78 mmol, 57.2% yield) as a brown solid. MS (ESI) m/z 268.0 [M–H$^+$].

3-(5-(aminomethyl)-1-oxoisoindolin-2-yl)piperidine-2,6-dione 2-(2,6-Dioxopiperidin-3-yl)-1-oxoisoindoline-5-carbonitrile (10 g, 37.13 mmol), methanesulfonic acid (2.6 mL, 40.85 mmol), 10% dry Palladium on carbon (4 g) and dimethylacetamide (320 mL) were combined and shaken in a hydrogenation vessel and kept under 50 Psi at 40° C. for 20 h. The hydrogen atmosphere was evacuated and the mixture was filtered through a celite pad, washed with water (100 mL), and concentrated. To the resulting residue was added 1% methanol-dichloromethane which upon filtration and drying under high vacuum gave 3-(5-(aminomethyl)-1-oxoisoindolin-2-yl)piperidine-2,6-dione (5.6 g, 15.17 mmol, 40% yield) as an off-white solid. MS (ESI) m/z 272.0 [M–1].

N-((2-(2,6-dioxopiperidin-3-yl)-1-oxoisoindolin-5-yl)methyl)-2,2-difluoro-2-(4-methoxyphenyl)acetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2,2-difluoro-2-(4-methoxyphenyl)acetic acid (0.109 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford N-((2-(2,6-dioxopiperidin-3-yl)-1-oxoisoindolin-5-yl)methyl)-2,2-difluoro-2-(4-methoxyphenyl)acetamide (0.080 g, 0.175 mmol, 32.3% yield) as a white solid. $^1$H NMR (500 MHz, DMSO-$d_6$) δ ppm 10.98 (s, 1H) 9.57 (t, J=6.15 Hz, 1H) 7.69 (d, J=7.88 Hz, 1H) 7.48-7.57 (m, 2H) 7.34-7.45 (m, 2H) 7.07 (m, J=8.83 Hz, 2H) 5.11 (dd, J=13.24, 5.36 Hz, 1H) 4.38-4.50 (m, 3H) 4.23-4.36 (m, 1H) 3.81 (s, 3H) 2.85-2.98 (m, 1H) 2.56-2.68 (m, 1H) 2.39 (dd, J=12.93, 4.73 Hz, 1H) 1.95-2.07 (m, 1H). MS (ESI) m/z 458.2 [M+1]$^+$.

Example 2

Synthesis of 2-(3-chlorophenyl)-N-((2-(2,6-dioxopiperidin-3-yl)-1-oxoisoindolin-5-yl)methyl)-2,2-difluoroacetamide

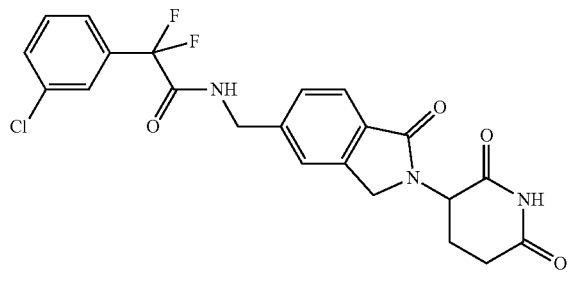 [SMILES: O=C1CCC(N2Cc3cc(CNC(=O)C(F)(F)c4cccc(Cl)c4)ccc3C2=O)C(=O)N1]

2-(3-chlorophenyl)-N-((2-(2,6-dioxopiperidin-3-yl)-1-oxoisoindolin-5-yl)methyl)-2,2-difluoroacetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2-(3-chlorophenyl)-2,2-difluoroacetic acid (0.112 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford 2-(3-chlorophenyl)-N-((2-(2,6-dioxopiperidin-3-yl)-1-oxoisoindolin-5-yl)methyl)-2,2-difluoroacetamide (0.090 g, 0.195 mmol, 36.0% yield) as a white solid. $^1$H NMR (500 MHz, DMSO-d$_6$) δ ppm 10.98 (s, 1H) 9.70 (t, J=5.99 Hz, 1H) 7.53-7.71 (m, 5H) 7.32-7.45 (m, 2H) 5.11 (dd, J=13.40, 5.20 Hz, 1H) 4.39-4.51 (m, 3H) 4.25-4.38 (m, 1H) 2.85-2.99 (m, 1H) 2.55-2.68 (m, 1H) 2.40 (dd, J=13.08, 4.57 Hz, 1H) 1.95-2.05 (m, 1H). MS (ESI) m/z 462.2 [M+1]$^+$.

Example 3

Synthesis of N-((2-(2,6-dioxopiperidin-3-yl)-1-oxoisoindolin-5-yl)methyl)-2,2-difluoro-2-(4-fluorophenyl)acetamide

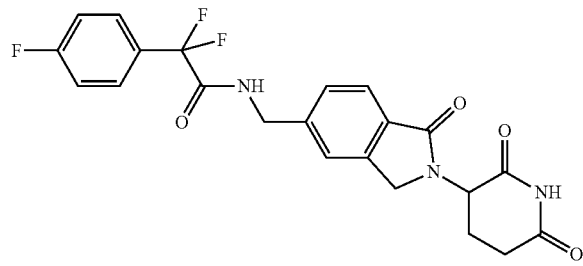 [SMILES: O=C1CCC(N2Cc3cc(CNC(=O)C(F)(F)c4ccc(F)cc4)ccc3C2=O)C(=O)N1]

N-((2-(2,6-dioxopiperidin-3-yl)-1-oxoisoindolin-5-yl)methyl)-2,2-difluoro-2-(4-fluorophenyl)acetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2,2-difluoro-2-(4-fluorophenyl)acetic acid (0.103 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford N-((2-(2,6-dioxopiperidin-3-yl)-1-oxoisoindolin-5-yl)methyl)-2,2-difluoro-2-(4-fluorophenyl)acetamide (0.100 g, 0.225 mmol, 41.5% yield) as a white solid. $^1$H NMR (500 MHz, DMSO-d$_6$) δ ppm 10.98 (br. s., 1H) 9.66 (t, J=5.99 Hz, 1H) 7.58-7.73 (m, 3H) 7.29-7.47 (m, 4H) 5.11 (dd, J=13.40, 5.20 Hz, 1H) 4.38-4.53 (m, 3H) 4.24-4.36 (m, 1H) 2.81-3.00 (m, 1H) 2.56-2.67 (m, 1H) 2.40 (qd, J=13.19, 4.57 Hz, 1H) 1.91-2.07 (m, 1H).

Example 4

Synthesis of N-((2-(2,6-dioxopiperidin-3-yl)-1-oxoisoindolin-5-yl)methyl)-2,2-difluoro-2-(p-tolyl)acetamide

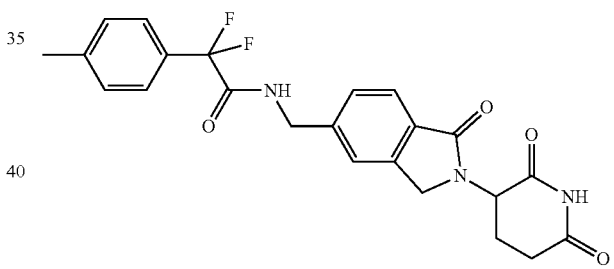

N-((2-(2,6-dioxopiperidin-3-yl)-1-oxoisoindolin-5-yl)methyl)-2,2-difluoro-2-(p-tolyl)acetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2,2-difluoro-2-(p-tolyl)acetic acid (0.101 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford N-((2-(2,6-dioxopiperidin-3-yl)-1-oxoisoindolin-5-yl)methyl)-2,2-difluoro-2-(p-tolyl)acetamide (0.110 g, 0.249 mmol, 46.0% yield) as a white solid. $^1$H NMR (500 MHz, DMSO-d$_6$) δ ppm 10.98 (s, 1H) 9.59 (t, J=6.15 Hz, 1H) 7.68 (d, J=7.88 Hz, 1H) 7.48 (d, J=8.20 Hz, 2H) 7.26-7.43 (m, 4H) 5.11 (dd, J=13.24, 5.04 Hz, 1H) 4.37-4.50 (m, 3H) 4.22-4.34 (m, 1H) 2.84-2.99 (m, 1H) 2.56-2.67 (m, 1H) 2.31-2.45 (m, 4H) 1.93-2.07 (m, 1H). MS (ESI) m/z 442.2 [M+1]$^+$.

Example 5

Synthesis of 2-(3,4-dichlorophenyl)-N-((2-(2,6-dioxopiperidin-3-yl)-1-oxoisoindolin-5-yl)methyl)-2,2-difluoroacetamide

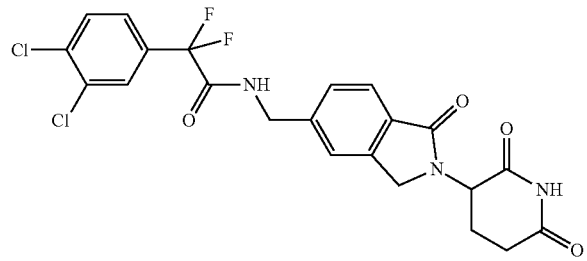 [SMILES: O=C1CCC(N2Cc3cc(CNC(=O)C(F)(F)c4ccc(Cl)c(Cl)c4)ccc3C2=O)C(=O)N1]

2-(3,4-dichlorophenyl)-N-((2-(2,6-dioxopiperidin-3-yl)-1-oxoisoindolin-5-yl)methyl)-2,2-difluoroacetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2-(3,4-dichlorophenyl)-2,2-difluoroacetic acid (0.130 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford 2-(3,4-dichlorophenyl)-N-((2-(2,6-dioxopiperidin-3-yl)-1-oxoisoindolin-5-yl)methyl)-2,2-difluoroacetamide (0.110 g, 0.222 mmol, 40.9% yield) as a white solid. $^1$H NMR (500 MHz, DMSO-$d_6$) δ ppm 10.98 (s, 1H) 9.71 (t, J=5.99 Hz, 1H) 7.79-7.88 (m, 2H) 7.69 (d, J=7.88 Hz, 1H) 7.59 (dd, J=8.51, 2.21 Hz, 1H) 7.43 (s, 1H) 7.38 (d, J=7.88 Hz, 1H) 5.11 (dd, J=13.08, 5.20 Hz, 1H) 4.39-4.51 (m, 3H) 4.26-4.37 (m, 1H) 2.86-2.98 (m, 1H) 2.61 (d, J=18.92 Hz, 1H) 2.39 (dd, J=13.40, 4.89 Hz, 1H) 1.95-2.06 (m, 1H). MS (ESI) m/z 498.0 [M+1]$^+$.

Example 6

Synthesis of 2-(2-chlorophenyl)-N-((2-(2,6-dioxopiperidin-3-yl)-1-oxoisoindolin-5-yl)methyl)-2,2-difluoroacetamide

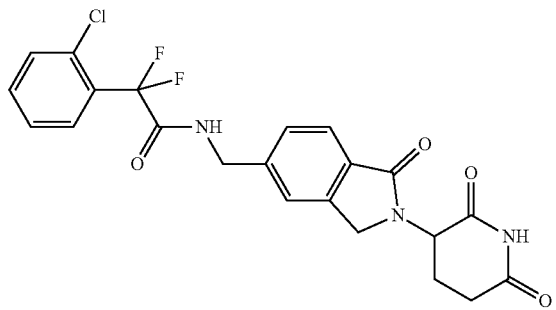 [SMILES: O=C1CCC(N2Cc3cc(CNC(=O)C(F)(F)c4ccccc4Cl)ccc3C2=O)C(=O)N1]

2-(2-chlorophenyl)-N-((2-(2,6-dioxopiperidin-3-yl)-1-oxoisoindolin-5-yl)methyl)-2,2-difluoroacetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2-(2-chlorophenyl)-2,2-difluoroacetic acid (0.112 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford 2-(2-chlorophenyl)-N-((2-(2,6-dioxopiperidin-3-yl)-1-oxoisoindolin-5-yl)methyl)-2,2-difluoroacetamide (0.090 g, 0.195 mmol, 36.0% yield) as a white solid. $^1$H NMR (500 MHz, DMSO-$d_6$) δ ppm 10.98 (s, 1H) 9.68 (t, J=6.31 Hz, 1H) 7.68-7.79 (m, 2H) 7.56-7.63 (m, 2H) 7.49-7.56 (m, 2H) 7.46 (d, J=7.88 Hz, 1H) 5.12 (dd, J=13.24, 5.36 Hz, 1H) 4.40-4.56 (m, 3H) 4.27-4.38 (m, 1H) 2.92 (ddd, J=17.50, 13.71, 5.36 Hz, 1H) 2.61 (d, J=16.71 Hz, 1H) 2.32-2.46 (m, 1H) 1.94-2.10 (m, 1H). MS (ESI) m/z 462.0 [M+1]$^+$.

Example 7

Synthesis of 2-(4-chlorophenyl)-N-((2-(2,6-dioxopiperidin-3-yl)-1-oxoisoindolin-5-yl)methyl)-2,2-difluoroacetamide

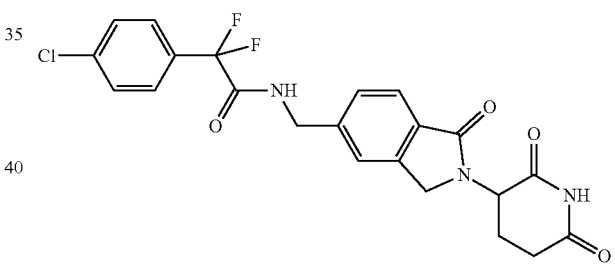

2-(4-chlorophenyl)-N-((2-(2,6-dioxopiperidin-3-yl)-1-oxoisoindolin-5-yl)methyl)-2,2-difluoroacetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2-(4-chlorophenyl)-2,2-difluoroacetic acid (0.112 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford 2-(4-chlorophenyl)-N-((2-(2,6-dioxopiperidin-3-yl)-1-oxoisoindolin-5-yl)methyl)-2,2-difluoroacetamide (0.080 g, 0.173 mmol, 32.0% yield) as a white solid. $^1$H NMR (500 MHz, DMSO-$d_6$) δ ppm 10.98 (s, 1H) 9.68 (t, J=6.15 Hz, 1H) 7.69 (d, J=7.88 Hz, 1H) 7.58-7.66 (m, 4H) 7.33-7.44 (m, 2H) 5.11 (dd, J=13.24, 5.04 Hz, 1H) 4.39-4.50 (m, 3H) 4.24-4.35 (m, 1H) 2.85-2.98 (m, 1H) 2.61 (dd, J=15.29, 2.05 Hz, 1H) 2.39 (dd, J=12.93, 4.73 Hz, 1H) 1.95-2.07 (m, 1H). MS (ESI) m/z 462.0 [M+1]$^+$.

Example 8

Synthesis of N-((2-(2,6-dioxopiperidin-3-yl)-1-oxoisoindolin-5-yl)methyl)-2,2-difluoro-2-(2-(trifluoromethyl)phenyl)acetamide

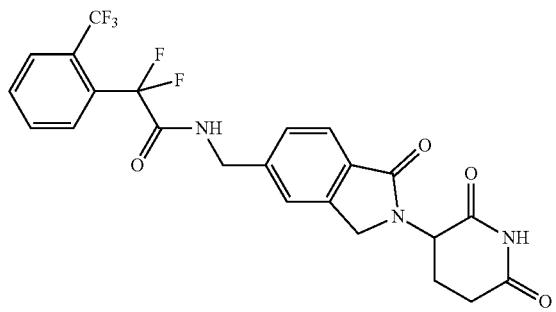 [SMILES: O=C1CCC(N2Cc3cc(CNC(=O)C(F)(F)c4ccccc4C(F)(F)F)ccc3C2=O)C(=O)N1]

N-((2-(2,6-dioxopiperidin-3-yl)-1-oxoisoindolin-5-yl)methyl)-2,2-difluoro-2-(2-(trifluoromethyl)phenyl)acetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2,2-difluoro-2-(2-(trifluoromethyl)phenyl)acetic acid (0.130 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford N-((2-(2,6-dioxopiperidin-3-yl)-1-oxoisoindolin-5-yl)methyl)-2,2-difluoro-2-(2-(trifluoromethyl)phenyl)acetamide (0.080 g, 0.161 mmol, 29.8% yield) as a white solid. $^1$H NMR (500 MHz, DMSO-$d_6$) δ ppm 10.98 (s, 1H) 9.70 (t, J=6.15 Hz, 1H) 7.66-7.81 (m, 3H) 7.47-7.59 (m, 3H) 7.44 (d, J=8.51 Hz, 3H) 5.12 (dd, J=13.40, 5.20 Hz, 1H) 4.40-4.54 (m, 3H) 4.27-4.38 (m, 1H) 2.85-3.00 (m, 1H) 2.57-2.67 (m, 1H) 2.35-2.45 (m, 1H) 1.94-2.07 (m, 1H).

Example 9

Synthesis of 2-(4-(tert-butyl)phenyl)-N-((2-(2,6-dioxopiperidin-3-yl)-1-oxoisoindolin-5-yl)methyl)-2,2-difluoroacetamide

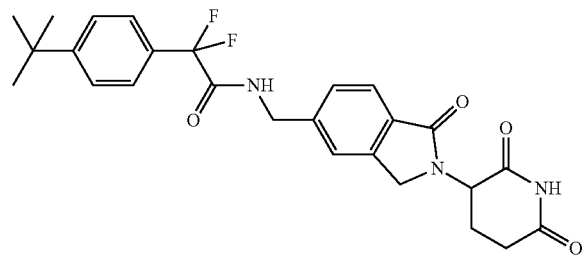 [SMILES: CC(C)(C)c1ccc(C(F)(F)C(=O)NCc2ccc3c(c2)CN(C2CCC(=O)NC2=O)C3=O)cc1]

2-(4-(tert-butyl)phenyl)-N-((2-(2,6-dioxopiperidin-3-yl)-1-oxoisoindolin-5-yl)methyl)-2,2-difluoroacetamide To 3-(5-(aminomethyl)-1-oxoisoindolin-2-yl)piperidine-2,6-dione methanesulfonate (0.200 g, 0.541 mmol) in DMF (3 mL) was added HATU (0.226 g, 0.596 mmol), 2-(4-(tert-butyl)phenyl)-2,2-difluoroacetic acid (0.124 g, 0.541 mmol) followed by N-ethyl-N-isopropylpropan-2-amine (0.262 mL, 1.624 mmol). Let stir at 25° C. for 16 h. Added 30 mL of water and filtered. Rinsed with EtOAc, dried under vacuum to afford 2-(4-(tert-butyl)phenyl)-N-((2-(2,6-dioxopiperidin-3-yl)-1-oxoisoindolin-5-yl)methyl)-2,2-difluoroacetamide (0.095 g, 0.196 mmol, 36.3% yield) as a white solid. $^1$H NMR (500 MHz, DMSO-$d_6$) δ ppm 10.98 (s, 1H) 9.61 (t, J=5.99 Hz, 1H) 7.68 (d, J=7.88 Hz, 1H) 7.49-7.60 (m, 4H) 7.33-7.44 (m, 2H) 5.11 (dd, J=13.24, 5.04 Hz, 1H) 4.37-4.50 (m, 3H) 4.24-4.35 (m, 1H) 2.86-2.98 (m, 1H) 2.57-2.67 (m, 1H) 2.38 (dd, J=13.40, 4.57 Hz, 1H) 1.92-2.06 (m, 1H) 1.22-1.36 (m, 9H). MS (ESI) m/z 484.0 [M+1]$^+$.

Example 10

Synthesis of N-((2-(2,6-dioxopiperidin-3-yl)-1-oxoisoindolin-5-yl)methyl)-2,2-difluoro-2-phenylacetamide

A. N-((2-(2,6-dioxopiperidin-3-yl)-1-oxoisoindolin-5-yl)methyl)-2,2-difluoro-2-phenylacetamide 3-(5-(aminomethyl)-1-oxoisoindolin-2-yl)piperidine-2,6-dione, Mesylic acid (0.050 g, 0.135 mmol) was placed in a vial with N,N-dimethylformamide (1.0 mL), 2,2-difluoro-2-phenylacetic acid (0.023 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoro-2-phenylacetamide (0.039 g, 0.091 mmol, 67.4% yield) as a white solid. $^1$H NMR (400 MHz, DMSO-$d_6$) δ 11.00 (s, 1H), 9.67 (t, J=6.25 Hz, 1H), 7.67 (d, J=7.81 Hz, 1H), 7.50-7.62 (m, 5H), 7.34-7.42 (m, 2H), 5.11 (dd, J=5.08, 13.28 Hz, 1H), 4.38-4.47 (m, 3H), 4.24-4.31 (m, 1H), 2.86-2.97 (m, 1H), 2.55-2.64 (m, 1H), 2.32-2.45 (m, 1H), 1.99 (dtd, J=2.34, 5.25, 12.55 Hz, 1H). MS (ESI) m/z 428.2 [M+1]$^+$.

Example 11

Synthesis of 2-(3-chloro-4-fluorophenyl)-N-((2-(2,6-dioxopiperidin-3-yl)-1-oxoisoindolin-5-yl)methyl)-2,2-difluoroacetamide

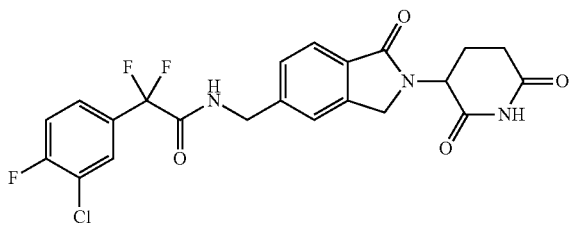 [SMILES: O=C1CCC(N2Cc3cc(CNC(=O)C(F)(F)c4ccc(F)c(Cl)c4)ccc3C2=O)C(=O)N1]

A. 2-(3-chloro-4-fluorophenyl)-N-((2-(2,6-dioxopiperidin-3-yl)-1-oxoisoindolin-5-yl)methyl)-2,2-difluoroacetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2-(3-chloro-4-fluorophenyl)-2,2-difluoroacetic acid (0.030 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give 2-(3-chloro-4-fluorophenyl)-N-((2-(2,6-dioxopiperidin-3-yl)-1-oxoisoindolin-5-yl)methyl)-2,2-difluoroacetamide as a white solid. $^1$H NMR (400 MHz, DMSO-d$_6$) δ 11.01 (s, 1H), 9.72 (t, J=6.05 Hz, 1H), 7.81 (dd, J=1.76, 7.23 Hz, 1H), 7.69 (d, J=7.81 Hz, 1H), 7.58-7.65 (m, 2H), 7.43 (s, 1H), 7.35-7.39 (m, 1H), 5.11 (dd, J=5.08, 13.28 Hz, 1H), 4.40-4.48 (m, 3H), 4.26-4.34 (m, 1H), 2.92 (ddd, J=5.47, 13.77, 17.48 Hz, 1H), 2.56-2.64 (m, 1H), 2.31-2.45 (m, 1H), 1.95-2.04 (m, 1H). MS (ESI) m/z 480.0 [M+1]$^+$.

Example 12

Synthesis of 2-(2,6-difluorophenyl)-N-((2-(2,6-dioxopiperidin-3-yl)-1-oxoisoindolin-5-yl)methyl)-2,2-difluoroacetamide

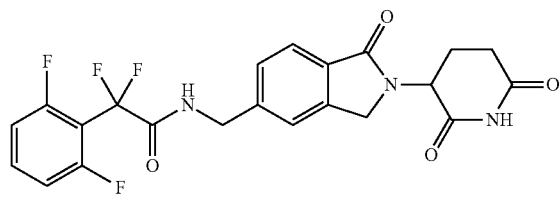 [SMILES: O=C1CCC(N2Cc3cc(CNC(=O)C(F)(F)c4c(F)cccc4F)ccc3C2=O)C(=O)N1]

A. 2-(2,6-difluorophenyl)-N-((2-(2,6-dioxopiperidin-3-yl)-1-oxoisoindolin-5-yl)methyl)-2,2-difluoroacetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2-(2,6-difluorophenyl)-2,2-difluoroacetic acid (0.028 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give 2-(2,6-difluorophenyl)-N-((2-(2,6-dioxopiperidin-3-yl)-1-oxoisoindolin-5-yl)methyl)-2,2-difluoroacetamide (0.039 g, 0.084 mmol, 62.2% yield) as a white solid. $^1$H NMR (500 MHz, DMSO-d$_6$) δ 10.98 (s, 1H), 9.73 (t, J=5.99 Hz, 1H), 7.65-7.73 (m, 2H), 7.49 (s, 1H), 7.43 (d, J=7.88 Hz, 1H), 7.27 (dd, J=8.67, 9.62 Hz, 2H), 5.11 (dd, J=5.20, 13.40 Hz, 1H), 4.50 (d, J=5.99 Hz, 2H), 4.46 (d, J=17.34 Hz, 1H), 4.29-4.35 (m, 1H), 2.91 (ddd, J=5.36, 13.71, 17.50 Hz, 1H), 2.57-2.63 (m, 1H), 2.40 (qd, J=4.57, 13.19 Hz, 1H), 2.01 (dtd, J=2.36, 5.26, 12.65 Hz, 1H). MS (ESI) m/z 464.2 [M+1]$^+$.

Example 13

Synthesis of 2-(5-chloro-2-methoxyphenyl)-N-((2-(2,6-dioxopiperidin-3-yl)-1-oxoisoindolin-5-yl)methyl)-2,2-difluoroacetamide

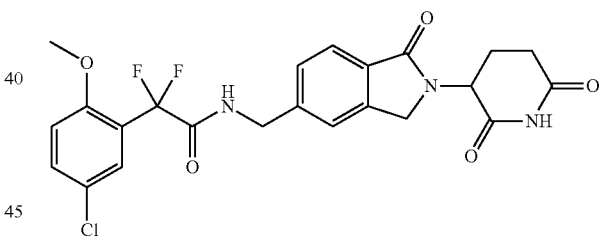

A. 2-(5-chloro-2-methoxyphenyl)-N-((2-(2,6-dioxopiperidin-3-yl)-1-oxoisoindolin-5-yl)methyl)-2,2-difluoroacetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2-(5-chloro-2-methoxyphenyl)-2,2-difluoroacetic acid (0.032 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give 2-(5-chloro-2-methoxyphenyl)-N-((2-(2,6-dioxopiperidin-3-yl)-1-oxoisoindolin-5-yl)methyl)-2,2-difluoroacetamide (0.044 g, 0.089 mmol, 66.1% yield) as a white solid. $^1$H NMR (500 MHz, DMSO-d$_6$) δ 10.97 (s, 1H), 9.41 (t, J=5.99 Hz, 1H), 7.73 (d, J=7.88 Hz, 1H), 7.59 (dd, J=2.84, 8.83 Hz, 1H), 7.53 (d, J=2.52 Hz, 1H), 7.48 (s, 1H), 7.43 (d, J=7.57 Hz, 1H), 7.17 (d, J=8.83 Hz, 1H), 5.11 (dd, J=5.20, 13.40 Hz, 1H), 4.43-4.49 (m, 3H), 4.29-4.35 (m, 1H), 3.68 (s, 3H), 2.91 (ddd, J=5.36, 13.71, 17.50 Hz, 1H), 2.57-2.63 (m, 1H), 2.40 (qd, J=4.26, 13.08 Hz, 1H), 2.00 (dtd, J=2.52, 5.32, 12.69 Hz, 1H). MS (ESI) m/z 492.2 [M+1]$^+$.

Example 14

Synthesis of N-((2-(2,6-dioxopiperidin-3-yl)-1-oxoisoindolin-5-yl)methyl)-2,2-difluoro-2-(5-fluoro-2-methoxyphenyl)acetamide

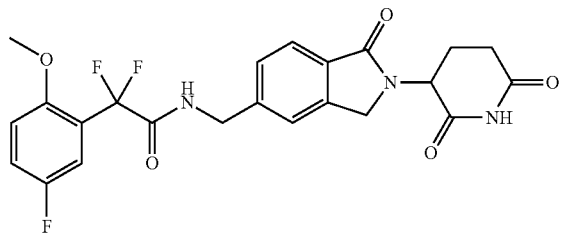 [SMILES: COc1ccc(F)cc1C(F)(F)C(=O)NCc1ccc2c(c1)CN(C1CCC(=O)NC1=O)C2=O]

A. N-((2-(2,6-dioxopiperidin-3-yl)-1-oxoisoindolin-5-yl)methyl)-2,2-difluoro-2-(5-fluoro-2-methoxyphenyl)acetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2,2-difluoro-2-(5-fluoro-2-methoxyphenyl)acetic acid (0.030 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoro-2-(5-fluoro-2-methoxyphenyl)acetamide (0.043 g, 0.090 mmol, 66.8% yield) as a white solid. $^1$H NMR (500 MHz, DMSO-d$_6$) δ 10.97 (s, 1H), 9.40 (t, J=5.99 Hz, 1H), 7.73 (d, J=7.57 Hz, 1H), 7.49 (s, 1H), 7.44 (d, J=7.88 Hz, 1H), 7.36-7.41 (m, 2H), 7.13-7.18 (m, 1H), 5.11 (dd, J=5.20, 13.40 Hz, 1H), 4.43-4.50 (m, 3H), 4.29-4.35 (m, 1H), 3.65 (s, 3H), 2.92 (ddd, J=5.52, 13.64, 17.42 Hz, 1H), 2.57-2.63 (m, 1H), 2.40 (qd, J=4.10, 13.24 Hz, 1H), 2.01 (dtd, J=2.21, 5.34, 12.65 Hz, 1H). MS (ESI) m/z 476.0 [M+1]$^+$.

Example 15

Synthesis of N-((2-(2,6-dioxopiperidin-3-yl)-1-oxoisoindolin-5-yl)methyl)-2,2-difluoro-2-(o-tolyl)acetamide

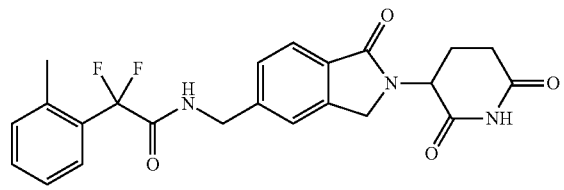

A. N-((2-(2,6-dioxopiperidin-3-yl)-1-oxoisoindolin-5-yl)methyl)-2,2-difluoro-2-(o-tolyl)acetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2,2-difluoro-2-(o-tolyl)acetic acid (0.025 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoro-2-(o-tolyl)acetamide (0.038 g, 0.086 mmol, 63.6% yield) as a white solid. $^1$H NMR (500 MHz, DMSO-d$_6$) δ 10.97 (s, 1H), 9.59 (t, J=5.99 Hz, 1H), 7.69 (d, J=8.20 Hz, 1H), 7.50-7.53 (m, 1H), 7.39-7.46 (m, 3H), 7.28-7.34 (m, 2H), 5.10 (dd, J=5.36, 13.24 Hz, 1H), 4.41-4.49 (m, 3H), 4.27-4.33 (m, 1H), 2.87-2.95 (m, 1H), 2.57-2.63 (m, 1H), 2.39 (qd, J=4.41, 13.24 Hz, 1H), 2.33 (s, 3H), 2.00 (dtd, J=2.21, 5.32, 12.69 Hz, 1H). MS (ESI) m/z 442.2 [M+1]$^+$.

Example 16

Synthesis of 2-(4-(2-(dimethylamino)-2-oxoethoxy)phenyl)-N-((2-(2,6-dioxopiperidin-3-yl)-1-oxoisoindolin-5-yl)methyl)-2,2-difluoroacetamide

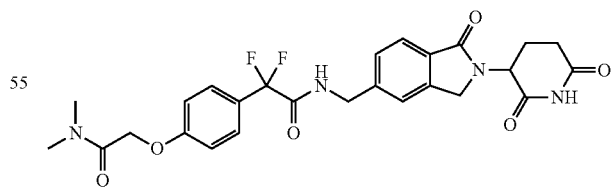

A. 2-(4-(2-(dimethylamino)-2-oxoethoxy)phenyl)-N-((2-(2,6-dioxopiperidin-3-yl)-1-oxoisoindolin-5-yl)methyl)-2,2-difluoroacetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2-(4-(2-(dimethylamino)-2-oxoethoxy)phenyl)-2,2-difluoroacetic acid (0.037 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give 2-(4-(2-(dimethylamino)-2-oxoethoxy)phenyl)-N-((2-(2,6-dioxopiperidin-3-yl)-1-oxoisoindolin-5-yl)methyl)-2,2-difluoroacetamide (0.021 g, 0.040 mmol, 29.4% yield) as a white solid. $^1$H NMR (500 MHz, DMSO-$d_6$) δ 10.97 (s, 1H), 9.56 (t, J=6.15 Hz, 1H), 7.67 (dd, J=0.63, 7.57 Hz, 1H), 7.46-7.50 (m, 2H), 7.35-7.38 (m, 2H), 7.00-7.04 (m, 2H), 5.10 (dd, J=5.20, 13.40 Hz, 1H), 4.89 (s, 2H), 4.39-4.46 (m, 3H), 4.26-4.31 (m, 1H), 2.99 (s, 3H), 2.87-2.95 (m, 1H), 2.84 (s, 3H), 2.57-2.62 (m, 1H), 2.33-2.43 (m, 1H), 2.00 (dtd, J=2.36, 5.18, 12.49 Hz, 1H). MS (ESI) m/z 529.2 [M+1]$^+$.

Example 17

Synthesis of 2-(2,5-dimethoxyphenyl)-N-((2-(2,6-dioxopiperidin-3-yl)-1-oxoisoindolin-5-yl)methyl)-2,2-difluoroacetamide

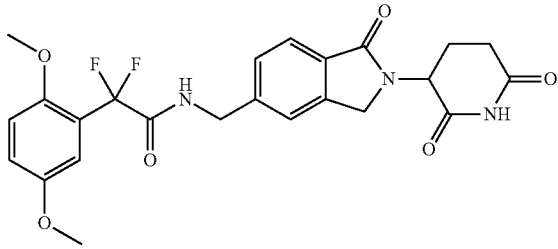 [SMILES: COc1ccc(OC)c(C(F)(F)C(=O)NCc2ccc3c(c2)CN(C2CCC(=O)NC2=O)C3=O)c1]

A. 2-(2,5-dimethoxyphenyl)-N-((2-(2,6-dioxopiperidin-3-yl)-1-oxoisoindolin-5-yl)methyl)-2,2-difluoroacetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2-(2,5-dimethoxyphenyl)-2,2-difluoroacetic acid (0.031 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give 2-(2,5-dimethoxyphenyl)-N-((2-(2,6-dioxopiperidin-3-yl)-1-oxoisoindolin-5-yl)methyl)-2,2-difluoroacetamide (0.043 g, 0.088 mmol, 65.2% yield) as a white solid. $^1$H NMR (500 MHz, DMSO-$d_6$) δ 10.97 (s, 1H), 9.33 (t, J=5.99 Hz, 1H), 7.72 (d, J=7.88 Hz, 1H), 7.49 (s, 1H), 7.42-7.46 (m, 1H), 7.04-7.10 (m, 3H), 5.11 (dd, J=5.20, 13.40 Hz, 1H), 4.43-4.49 (m, 3H), 4.29-4.35 (m, 1H), 3.75 (s, 3H), 3.61 (s, 3H), 2.91 (ddd, J=5.52, 13.56, 17.50 Hz, 1H), 2.57-2.64 (m, 1H), 2.40 (qd, J=4.73, 13.24 Hz, 1H), 2.00 (dtd, J=2.36, 5.30, 12.57 Hz, 1H). MS (ESI) m/z 488.2 [M+1]$^+$.

Example 18

Synthesis of N-((2-(2,6-dioxopiperidin-3-yl)-1-oxoisoindolin-5-yl)methyl)-2,2-difluoro-2-(2-fluorophenyl)acetamide

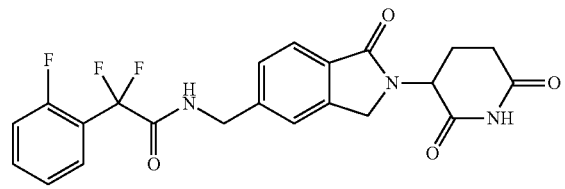

A. N-((2-(2,6-dioxopiperidin-3-yl)-1-oxoisoindolin-5-yl)methyl)-2,2-difluoro-2-(2-fluorophenyl)acetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2,2-difluoro-2-(2-fluorophenyl)acetic acid (0.026 g, 0.135 mmol), diisopropylethylamine (0.071 mL, 0.406 mmol), and 1-[Bis(dimethylamino)methylene]-1H-1,2,3-triazolo[4,5-b] pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoro-2-(2-fluorophenyl)acetamide (0.030 g, 0.067 mmol, 49.8% yield) as a white solid. $^1$H NMR (500 MHz, DMSO-$d_6$) δ 10.97 (s, 1H), 9.69 (t, J=6.15 Hz, 1H), 7.70 (d, J=8.20 Hz, 1H), 7.61-7.67 (m, 2H), 7.47 (s, 1H), 7.40-7.44 (m, 1H), 7.34-7.40 (m, 2H), 5.11 (dd, J=5.20, 13.40 Hz, 1H), 4.50 (d, J=6.31 Hz, 2H), 4.45 (d, J=17.34 Hz, 1H), 4.29-4.34 (m, 1H), 2.91 (ddd, J=5.52, 13.64, 17.42 Hz, 1H), 2.57-2.63 (m, 1H), 2.40 (qd, J=4.73, 13.24 Hz, 1H), 2.01 (dtd, J=2.36, 5.26, 12.65 Hz, 1H). MS (ESI) m/z 446.2 [M+1]$^+$.

Example 19

Synthesis of N-((2-(2,6-dioxopiperidin-3-yl)-1-oxoisoindolin-5-yl)methyl)-2-(2-ethoxyphenyl)-2,2-difluoroacetamide

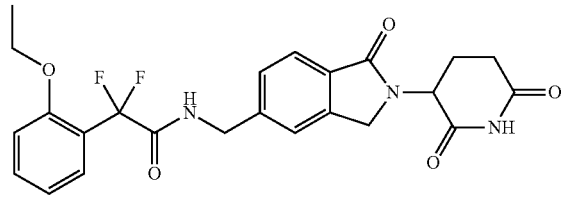 [SMILES: CCOc1ccccc1C(F)(F)C(=O)NCc1ccc2c(c1)CN(C1CCC(=O)NC1=O)C2=O]

A. N-((2-(2,6-dioxopiperidin-3-yl)-1-oxoisoindolin-5-yl)methyl)-2-(2-ethoxyphenyl)-2,2-difluoroacetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2-(2-ethoxyphenyl)-2,2-difluoroacetic acid (0.029 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2-(2-ethoxyphenyl)-2,2-difluoroacetamide (0.045 g, 0.095 mmol, 70.5% yield) as a white solid. $^1$H NMR (500 MHz, DMSO-$d_6$) δ 10.97 (s, 1H), 9.31 (t, J=6.15 Hz, 1H), 7.70 (d, J=7.88 Hz, 1H), 7.55 (dd, J=1.58, 7.57 Hz, 1H), 7.47-7.52 (m, 2H), 7.45 (d, J=8.51 Hz, 1H), 7.11 (d, J=8.20 Hz, 1H), 7.05 (td, J=0.79, 7.49 Hz, 1H), 5.11 (dd, J=5.20, 13.40 Hz, 1H), 4.42-4.48 (m, 3H), 4.28-4.34 (m, 1H), 3.99 (q, J=6.94 Hz, 2H), 2.87-2.96 (m, 1H), 2.57-2.63 (m, 1H), 2.40 (qd, J=4.41, 13.24 Hz, 1H), 2.00 (dtd, J=2.21, 5.08, 12.53 Hz, 1H), 1.13 (t, J=6.94 Hz, 3H). MS (ESI) m/z 472.2 [M+1]$^+$.

Example 20

Synthesis of N-((2-(2,6-dioxopiperidin-3-yl)-1-oxoisoindolin-5-yl)methyl)-2,2-difluoro-2-(2-(trifluoromethoxy)phenyl)acetamide

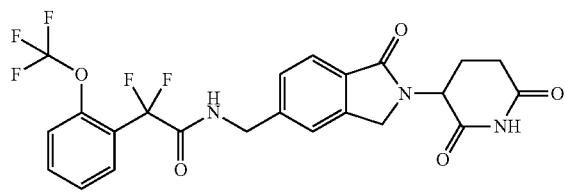 [SMILES: O=C1CCC(N2Cc3cc(CNC(=O)C(F)(F)c4ccccc4OC(F)(F)F)ccc3C2=O)C(=O)N1]

A. N-((2-(2,6-dioxopiperidin-3-yl)-1-oxoisoindolin-5-yl)methyl)-2,2-difluoro-2-(2-(trifluoromethoxy)phenyl)acetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2,2-difluoro-2-(2-(trifluoromethoxy)phenyl)acetic acid (0.035 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2-(2-difluoro-2-(2-(trifluoromethoxy)phenyl)acetamide (0.047 g, 0.092 mmol, 67.9% yield) as a white solid. $^1$H NMR (500 MHz, DMSO-$d_6$) δ 10.97 (s, 1H), 9.69 (t, J=5.83 Hz, 1H), 7.77 (dd, J=1.58, 7.88 Hz, 1H), 7.68-7.74 (m, 2H), 7.48-7.56 (m, 3H), 7.43 (d, J=7.88 Hz, 1H), 5.11 (dd, J=5.04, 13.24 Hz, 1H), 4.49 (d, J=6.31 Hz, 2H), 4.44 (d, J=17.34 Hz, 1H), 4.28-4.33 (m, 1H), 2.91 (ddd, J=5.36, 13.79, 17.42 Hz, 1H), 2.57-2.63 (m, 1H), 2.40 (qd, J=4.26, 13.19 Hz, 1H), 2.00 (dtd, J=2.36, 5.26, 12.65 Hz, 1H). MS (ESI) m/z 512.2 [M+1]$^+$.

Example 21

Synthesis of 2-(3-bromo-4-(trifluoromethoxy)phenyl)-N-((2-(2,6-dioxopiperidin-3-yl)-1-oxoisoindolin-5-yl)methyl)-2,2-difluoroacetamide

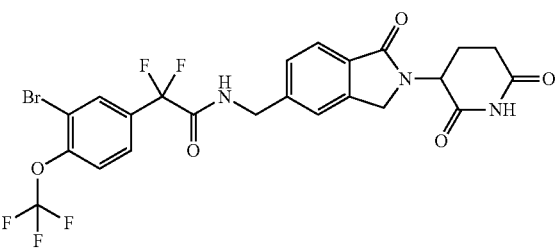 [SMILES: O=C1CCC(N2Cc3cc(CNC(=O)C(F)(F)c4ccc(OC(F)(F)F)c(Br)c4)ccc3C2=O)C(=O)N1]

A. 2-(3-bromo-4-(trifluoromethoxy)phenyl)-N-((2-(2,6-dioxopiperidin-3-yl)-1-oxoisoindolin-5-yl)methyl)-2,2-difluoroacetamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2-(3-bromo-4-(trifluoromethoxy)phenyl)-2,2-difluoroacetic acid (0.045 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give 2-(3-bromo-4-(trifluoromethoxy)phenyl)-N-((2-(2,6-dioxopiperidin-3-yl)-1-oxoisoindolin-5-yl)methyl)-2,2-difluoroacetamide (0.048 g, 0.081 mmol, 60.1% yield) as a white solid. $^1$H NMR (500 MHz, DMSO-$d_6$) δ 10.99 (s, 1H), 9.75 (t, J=6.15 Hz, 1H), 8.01 (d, J=1.89 Hz, 1H), 7.73-7.78 (m, 2H), 7.69 (d, J=7.57 Hz, 1H), 7.45 (s, 1H), 7.38 (d, J=7.88 Hz, 1H), 5.11 (dd, J=5.04, 13.24 Hz, 1H), 4.41-4.49 (m, 3H), 4.28-4.34 (m, 1H), 2.92 (ddd, J=5.36, 13.71, 17.50 Hz, 1H), 2.58-2.64 (m, 1H), 2.39 (qd, J=4.41, 13.24 Hz, 1H), 2.01 (dtd, J=2.21, 5.20, 12.61 Hz, 1H). MS (ESI) m/z 592.0 [M+2]$^+$.

Example 22

Synthesis of N-((2-(2,6-dioxopiperidin-3-yl)-1-oxoisoindolin-5-yl)methyl)-2,2-difluoropropanamide

A. N-((2-(2,6-dioxopiperidin-3-yl)-1-oxoisoindolin-5-yl)methyl)-2,2-difluoropropanamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2,2-difluoropropanoic acid (0.015 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoropropanamide (0.016 g, 0.044 mmol, 32.4% yield) as a white solid. $^1$H NMR (500 MHz, DMSO-$d_6$) δ 10.98 (s, 1H), 9.36 (t, J=5.99 Hz, 1H), 7.71 (d, J=7.88 Hz, 1H), 7.49 (s, 1H), 7.42 (d, J=7.88 Hz, 1H), 5.12 (dd, J=5.20, 13.40 Hz, 1H), 4.43-4.49 (m, 3H), 4.30-4.35 (m, 1H), 2.92 (ddd, J=5.52, 13.64, 17.42 Hz, 1H), 2.58-2.64 (m, 1H), 2.40 (qd, J=4.57, 13.19 Hz, 1H), 2.01 (dtd, J=2.21, 5.16, 12.69 Hz, 1H), 1.74-1.84 (m, 3H). MS (ESI) m/z 366.2 [M+1]$^+$.

Example 23

Synthesis of N-((2-(2,6-dioxopiperidin-3-yl)-1-oxoisoindolin-5-yl)methyl)-2,2,3,3-tetrafluoropropanamide

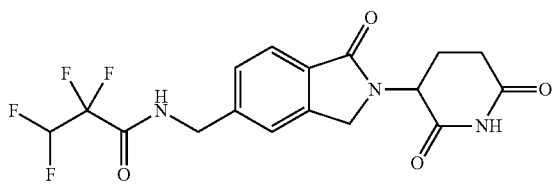 [SMILES: O=C1CCC(N2Cc3cc(CNC(=O)C(F)(F)C(F)F)ccc3C2=O)C(=O)N1]

A. N-((2-(2,6-dioxopiperidin-3-yl)-1-oxoisoindolin-5-yl)methyl)-2,2,3,3-tetrafluoropropanamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2,2,3,3-tetrafluoropropanoic acid (0.020 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2,3,3-tetrafluoropropanamide (0.013 g, 0.032 mmol, 23.93% yield) as a white solid. $^1$H NMR (500 MHz, DMSO-$d_6$) δ 10.97 (s, 1H), 9.92 (t, J=5.99 Hz, 1H), 7.71 (d, J=7.88 Hz, 1H), 7.47 (s, 1H), 7.41 (d, J=7.88 Hz, 1H), 6.64-6.89 (m, 1H), 5.11 (dd, J=5.04, 13.24 Hz, 1H), 4.50 (d, J=6.31 Hz, 2H), 4.46 (d, J=17.34 Hz, 1H), 4.29-4.34 (m, 1H), 2.87-2.95 (m, 1H), 2.57-2.63 (m, 1H), 2.39 (qd, J=4.73, 13.24 Hz, 1H), 2.00 (dtd, J=2.21, 5.24, 12.53 Hz, 1H). MS (ESI) m/z 402.0 [M+1]$^+$.

Example 24

Synthesis of N-((2-(2,6-dioxopiperidin-3-yl)-1-oxoisoindolin-5-yl)methyl)-2,2-difluorobutanamide

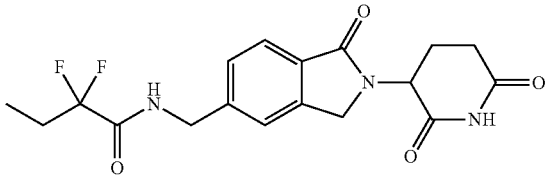 [SMILES: CCC(F)(F)C(=O)NCc1ccc2c(c1)CN(C1CCC(=O)NC1=O)C2=O]

A. N-((2-(2,6-dioxopiperidin-3-yl)-1-oxoisoindolin-5-yl)methyl)-2,2-difluorobutanamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2,2-difluorobutanoic acid (0.017 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluorobutanamide (0.027 g, 0.071 mmol, 52.6% yield) as a white solid. $^1$H NMR (500 MHz, DMSO-$d_6$) δ 10.97 (s, 1H), 9.37 (t, J=5.99 Hz, 1H), 7.70 (d, J=7.88 Hz, 1H), 7.47 (s, 1H), 7.41 (d, J=7.88 Hz, 1H), 5.10 (dd, J=5.20, 13.40 Hz, 1H), 4.42-4.48 (m, 3H), 4.28-4.34 (m, 1H), 2.91 (ddd, J=5.36, 13.64, 17.58 Hz, 1H), 2.57-2.63 (m, 1H), 2.39 (qd, J=4.57, 13.29 Hz, 1H), 1.97-2.14 (m, 3H), 0.92 (t, J=7.41 Hz, 3H). MS (ESI) m/z 380.2 [M+1]$^+$.

Example 25

Synthesis of N-((2-(2,6-dioxopiperidin-3-yl)-1-oxoisoindolin-5-yl)methyl)-2,2-difluoro-3-hydroxy-3-methylbutanamide

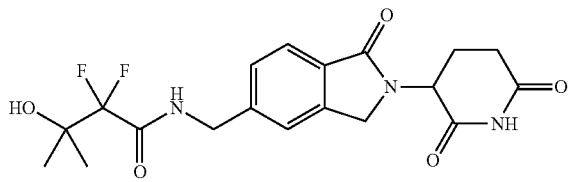 [SMILES: CC(C)(O)C(F)(F)C(=O)NCc1ccc2c(c1)CN(C1CCC(=O)NC1=O)C2=O]

A. N-((2-(2,6-dioxopiperidin-3-yl)-1-oxoisoindolin-5-yl)methyl)-2,2-difluoro-3-hydroxy-3-methylbutanamide 3-(5-(aminomethyl)-1-oxoisoindolin-2-yl)piperidine-2,6-dione, Mesylic acid (0.050 g, 0.135 mmol) was placed in a vial with N,N-Dimethylformamide (1.0 mL), 2,2-difluoro-3-hydroxy-3-methylbutanoic acid (0.021 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at room temperature for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoro-3-hydroxy-3-methylbutanamide (0.049 g, 0.120 mmol, 88% yield) as a white solid. $^1$H NMR (500 MHz, DMSO-$d_6$) δ 10.97 (s, 1H), 9.07 (t, J=5.99 Hz, 1H), 7.68 (d, J=8.20 Hz, 1H), 7.50 (s, 1H), 7.43 (d, J=7.25 Hz, 1H), 5.46 (br. s., 1H), 5.10 (dd, J=5.04, 13.24 Hz, 1H), 4.41-4.46 (m, 3H), 4.27-4.33 (m, 1H), 2.86-2.96 (m, 1H), 2.57-2.63 (m, 1H), 2.39 (qd, J=4.57, 13.19 Hz, 1H), 2.00 (dtd, J=2.36, 5.26, 12.65 Hz, 1H), 1.24 (s, 6H). MS (ESI) m/z 410.2 [M+1]$^+$.

Example 26

2-(3-chloro-4-methylphenyl)-N-((2-(2,6-dioxopiperidin-3-yl)-1-oxoisoindolin-5-yl)methyl)-2,2-difluoroacetamide

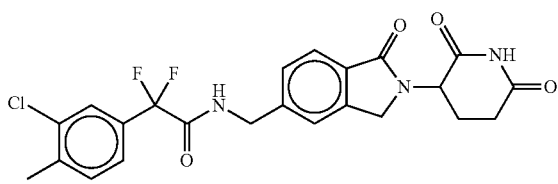

A. 1-(3-chloro-4-methylphenyl)ethanone

To a stirred solution of 3-chloro-4-methylbenzonitrile (3 g, 19.86 mmol) in benzene (25 mL) was added methyl magnesium iodide (6.6 mL, 19.86 mmol, 3M in diethyl ether) at room temperature and stirred at 80° C. for 8 h. Then the reaction mixture was cooled to room temperature and added 6N hydrochloric acid (25 mL) and stirred at 80° C. for 6 h. The reaction mixture was cooled to room temperature and extracted with ethyl acetate (3×50 mL). The combined organic layers were washed with water (2×20 mL), brine (20 mL), dried over sodium sulphate and concentrated to afford 1-(3-chloro-4-methylphenyl)ethanone (2 g, 11.90 mmol, 60% yield) as off-white solid. $^1$H NMR (400 MHz, DMSO-$d_6$) δ 7.93 (d, J=1.8 Hz, 1H), 7.82 (dd, J=7.8, 1.8 Hz, 1H), 7.51 (dd, J=7.7, 1.0 Hz, 1H), 2.57 (s, 3H), 2.40 (s, 3H).

B. Ethyl 2-(3-chloro-4-methylphenyl)-2-oxoacetate

To a stirred solution of 1-(3-chloro-4-methylphenyl) ethanone (500 mg, 2.97 mmol) in pyridine (5 mL) was added selenium dioxide (660 mg, 5.95 mmol) and stirred for 12 h at 100° C. The reaction mixture was diluted with dichloromethane (20 mL) and filtered through Celite pad. To the filtrate was added ethyl chloroformate (2 mL) at 0° C. and stirred at room temperature for 2 h. The reaction mixture was acidified with 1N aqueous hydrochloric acid (up to pH-4) and extracted with ethyl acetate (3×10 mL). The combined organic layers were washed with water (2×5 mL), brine (5 mL), dried over sodium sulphate and concentrated to afford ethyl 2-(3-chloro-4-methylphenyl)-2-oxoacetate (300 mg, 1.32 mmol, 45%) as a brown liquid. $^1$H NMR (300 MHz, DMSO-$d_6$) δ 7.99 (dd, J=5.5, 1.7 Hz, 1H), 7.86 (dd, J=7.9, 1.8 Hz, 1H), 7.59 (dd, J=11.6, 7.9 Hz, 1H), 4.42 (q, J=7.1 Hz, 2H), 2.44 (s, 3H), 1.33 (t, J=7.1 Hz, 3H).

C. Ethyl 2-(3-chloro-4-methylphenyl)-2,2-difluoroacetate

To ethyl 2-(3-chloro-4-methylphenyl)-2-oxoacetate (300 mg, 1.32 mmol) was added diethyl amino sulfur trifluoride (2 mL) and stirred for 12 h at room temperature. The reaction mixture was neutralized with aqueous saturated sodium bicarbonate (up to pH-8) and extracted with ethyl acetate (3×10 mL). The combined organic layers were washed with water (2×5 mL), brine (10 mL), dried over sodium sulphate and was concentrated to afford ethyl 2-(3-chloro-4-methylphenyl)-2,2-difluoroacetate (200 mg, 0.804 mmol, 61%) as a brown liquid. $^1$H NMR (400 MHz, DMSO-$d_6$) δ 7.63-7.52 (m, 2H), 7.47 (dd, J=7.9, 1.9 Hz, 1H), 4.32 (q, J=7.1 Hz, 2H), 2.39 (s, 3H), 1.23 (t, J=7.1 Hz, 4H).

D. 2-(3-chloro-4-methylphenyl)-2,2-difluoroacetic acid

To a cold (0° C.) stirred solution of ethyl 2-(3-chloro-4-methylphenyl)-2,2-difluoroacetate (200 mg, 0.806 mmol) in methanol/tetrahydrofuran/water (10 mL, 1:1:1) was added lithium hydroxide monohydrate (169 mg, 4.03 mmol) and stirred at room temperature for 2 h. The reaction mixture was concentrated and the residue was neutralized with 10% aqueous hydrochloric acid (10 mL) and extracted with ethyl acetate (2×15 mL). The combined organic layers were washed with brine (20 mL), dried over sodium sulphate and concentrated to afford 2-(3-chloro-4-methylphenyl)-2,2-difluoroacetic acid (150 mg, 0.68 mmol, 84% yield) as a brown semi solid. ¹H NMR (300 MHz, DMSO-d₆) δ 7.61-7.50 (m, 2H), 7.45 (dd, J=8.0, 1.8 Hz, 1H), 2.39 (s, 3H).

E. 2-(3-Chloro-4-methylphenyl)-N-((2-(2,6-dioxopiperidin-3-yl)-1-oxoisoindolin-5-yl)methyl)-2,2-difluoroacetamide To a cold (0° C.) stirred solution of 3-(5-(amino methyl)-1-oxoisoindolin-2-yl)piperidine-2,6-dione methane sulfonate (200 mg, 0.619 mmol) in N,N-dimethylformamide (20 mL) was added 2-(3-chloro-4-methylphenyl)-2,2-difluoroacetic acid (150 mg, 0.68 mmol) followed by N,N-diisopropylethylamine (240 mg, 1.85 mmol), 1-[Bis(dimethylamino)methylene]-1H-1,2,3-triazolo[4,5-b]pyridinium 3-oxid hexafluorophosphate (352 mg, 0.92 mmol) and stirred at room temperature for 12 h. The reaction mixture was diluted with water (100 mL) and extracted with ethyl acetate (2×10 mL) and the combined organic layers were washed with brine (20 mL), dried over sodium sulphate and concentrated under vacuum. The product was purified by Reveleris C-18 reversed phase column using 70% acetonitrile in aqueous formic acid (0.1%) to give 2-(3-chloro-4-methylphenyl)-N-((2-(2,6-dioxopiperidin-3-yl)-1-oxoisoindolin-5-yl)methyl)-2,2-difluoroacetamide (40 mg, 0.08 mmol, 14% yield) as an off white solid. MS (ESI) m/z 476.18 [M+1]⁺. ¹H NMR (300 MHz, DMSO-d₆) δ 10.98 (s, 1H), 9.66 (t, J=6.0 Hz, 1H), 7.68 (d, J=7.9 Hz, 1H), 7.61-7.50 (m, 2H), 7.49-7.33 (m, 3H), 5.10 (dd, J=13.3, 5.0 Hz, 1H), 4.51-4.12 (m, 4H), 2.98-2.83 (m, 1H), 2.65-2.55 (m, 1H), 2.46-2.27 (m, 4H), 2.06-1.93 (m, 1H).

Example 27

N-((2-(2,6-dioxopiperidin-3-yl)-1-oxoisoindolin-5-yl)methyl)-2,2-difluoro-2-(4-(trifluoromethylthio)phenyl)acetamide

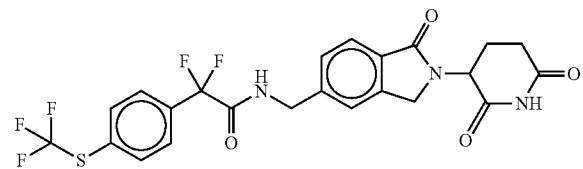

A. 1-(4-(Trifluoromethylthio)phenyl)ethanone

In a stirred and evacuated round bottom flask were taken potassium phosphate (19.38 g, 91.44 mmol), molecular sieves (5 g, 4 Å), sulphur-8 (2.92 g, 91.44 mmol), silver carbonate (16.80 g, 60.96 mmol), (4-acetylphenyl)boronic acid (5 g, 30.48 mmol), copper (1) thiocyanate (370 mg, 3.04 mmol) and 1,10-phenanthroline (1.09 g, 6.09). Trimethyl (trifluoromethyl)silane (21.67 g, 152.43 mmol) in dry N,N-dimethylformamide (50 mL) was added to the round bottom flask and stirred for 12 h at room temperature. The reaction mixture was filtered through Celite pad, cold water (20 mL) was added and extracted with ethyl acetate (3×50 mL). The combined organic layers were washed with water (2×10 mL), brine (10 mL), dried over sodium sulphate and concentrated. The resultant residue was purified by column chromatography (100-200 silica) using 10% ethyl acetate in pet.ether to afford 1-(4-(trifluoromethylthio)phenyl)ethanone (2.8 g, 13.20 mmol, 45%) as a light yellow liquid. ¹H NMR (400 MHz, CDCl₃) δ 8.03-7.89 (m, 2H), 7.75 (d, J=7.9 Hz, 2H), 2.80-2.42 (m, 3H).

B. Ethyl 2-oxo-2-(4-(trifluoromethylthio)phenyl)acetate

To a stirred solution of 1-(4-(trifluoromethylthio)phenyl) ethanone (2.5 g, 11.79 mmol) in pyridine (50 mL) was added selenium dioxide (2.61 g, 23.58 mmol) and stirred for 4 h at 100° C. The reaction mixture was diluted with dichloromethane (50 mL) and filtered through Celite pad. To the filtrate was added dichloromethane (30 mL) followed by ethyl chloroformate (5 mL) at 0° C. and stirred for 2 h. The pH of the reaction mixture was adjusted to pH-4 with 1N aqueous hydrochloric acid and extracted with ethyl acetate (3×50 mL). The combined organic layers were washed with water (2×10 mL), brine (10 mL), dried over sodium sulphate and concentrated. The resultant residue was purified by column chromatography (100-200 silica) using 10% ethyl acetate in pet.ether to afford ethyl 2-oxo-2-(4-(trifluoromethylthio)phenyl)acetate (2.0 g, 7.19 mmol, 62%) as a liquid. ¹H NMR (400 MHz, CDCl₃) δ 8.12-8.04 (m, 2H), 7.84-7.72 (m, 2H), 4.61-4.33 (m, 2H), 1.49-1.34 (m, 3H).

C. Ethyl 2,2-difluoro-2-(4-(trifluoromethylthio)phenyl)acetate

To ethyl 2-oxo-2-(4-(trifluoromethylthio)phenyl)acetate (2.0 g, 7.19 mmol) was added diethyl amino sulfur trifluoride (1.4 mL, 10.79 mmol) and stirred for 12 h at room temperature. The reaction mixture was neutralized with aqueous saturated sodium bicarbonate (up to pH-8) and extracted with ethyl acetate (3×50 mL). The combined organic layer was washed with water (2×10 mL), brine (10 mL), dried over sodium sulphate and concentrated to afford ethyl 2,2-difluoro-2-(4-(trifluoromethylthio)phenyl)acetate (2.0 g, 6.66 mmol, 95%) as a liquid. ¹H NMR (400 MHz, CDCl₃) δ 7.75 (d, J=8.2 Hz, 2H), 4.32 (q, J=7.1 Hz, 2H), 1.32 (t, J=7.1 Hz, 3H).

D. 2,2-Difluoro-2-(4-(trifluoromethylthio)phenyl)acetic acid

To a stirred cold (0° C.) solution of ethyl 2,2-difluoro-2-(4-(trifluoromethylthio)phenyl)acetate (1.5 g, 5.0 mmol) in aqueous methanol (10 mL, 80%) was added sodium hydroxide (0.4 g, 10.0 mmol) and stirred at room temperature for 6 h. The reaction mixture was concentrated and the residue was neutralized with 10% aqueous hydrochloric acid (10 mL) and extracted with ethyl acetate (2×20 mL). The combined organic layers were washed with brine (20 mL), dried over sodium sulphate and concentrated to afford 2,2-difluoro-2-(4-(trifluoromethylthio)phenyl)acetic acid (1 g, 3.67 mmol, 73% yield) as an brown solid. MS (ESI) m/z 271.22 [M−1]⁺.

E. N-((2-(2,6-Dioxopiperidin-3-yl)-1-oxoisoindolin-5-yl)methyl)-2,2-difluoro-2-(4-(trifluoromethylthio) phenyl)acetamide To a cold (0° C.) stirred solution of 3-(5-(amino methyl)-1-oxoisoindolin-2-yl)piperidine-2,6-dione methane sulfonate (500 mg, 1.61 mmol) in N,N-dimethylformamide (20 mL) was added 2,2-difluoro-2-(4-(trifluoromethylthio)phenyl)acetic acid (520 mg, 1.94 mmol), N,N-diisopropylethylamine (0.86 mL, 4.8 mmol) followed by 1-[Bis(dimethylamino)methylene]-1H-1,2,3-triazolo[4,5-b]pyridinium 3-oxid hexafluorophosphate (920 mg, 2.4 mmol) and stirred at room temperature for 12 h. The reaction mixture was diluted with water (100 mL) and the solid precipitated was filtered, dried under vacuum and purified by Reveleris C-18 reversed phase column using 70% acetonitrile in aqueous formic acid (0.1%) to give N-((2-(2,6-dioxopiperidin-3-yl)-1-oxoisoindolin-5-yl)methyl)-2,2-difluoro-2-(4-(trifluoromethylthio)phenyl)acetamide (60 mg, 0.11 mmol, 7% yield) as an off white solid. MS (ESI) m/z 528.07 [M+1]$^+$. $^1$H NMR (400 MHz, DMSO-d$_6$) δ 10.98 (s, 1H), 9.76 (t, J=6.1 Hz, 1H), 7.91 (d, J=8.1 Hz, 2H), 7.81-7.61 (m, 3H), 7.53-7.21 (m, 2H), 5.10 (dd, J=13.4, 5.1 Hz, 1H), 4.57-4.10 (m, 4H), 2.85-2.93 (m, 1H), 2.72-2.56 (m, 1H), 2.42-2.26 (m, 1H), 2.10-1.94 (m, 1H).

Example 28

2-(3-Chloro-4-methoxyphenyl)-N-((2-(2,6-dioxopiperidin-3-yl)-1-oxoisoindolin-5-yl)methyl)-2,2-difluoroacetamide

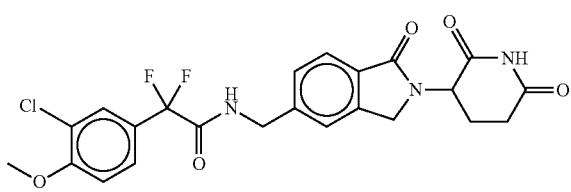

A. Ethyl 2-(3-chloro-4-methoxyphenyl)-2-oxoacetate

To a stirred solution of 1-(3-chloro-4-methoxyphenyl) ethanone (2 g, 10.83 mmol) in pyridine (15 mL) was added selenium dioxide (3 g, 27.08 mmol) at room temperature. The reaction mixture was stirred at 100° C. for 16 h. The reaction mixture was filtered through a Celite pad and washed with dichloromethane (30 mL). Ethyl chloroformate (6 mL) was added to the filtrate at 0° C. and stirred at room temperature for 4 h. The reaction mixture was quenched with ice water and extracted with dichloromethane (3×25 mL). The combined organic layers were washed with 1N hydrochloride solution (20 mL) and brine (20 mL), dried over sodium sulfate, filtered and concentrated to afford ethyl 2-(3-chloro-4-methoxyphenyl)-2-oxoacetate (1.45 g, 5.98 mmol, 55% yield) as a colourless liquid. MS (ESI) m/z 242.1 [M]$^+$.

B. Ethyl 2-(3-chloro-4-methoxyphenyl)-2,2-difluoroacetate

Ethyl 2-(3-chloro-4-methoxyphenyl)-2-oxoacetate (1.45 g, 5.99 mmol) was added in portion into diethylaminosulfur trifluoride (2.35 mL) at 0° C. and stirred at room temperature for 16 h. The reaction mixture was quenched with aqueous sodium bicarbonate solution and extracted with ethyl acetate (3×20 mL). The combined organic layers were washed with brine (20 mL), dried over sodium sulphate, filtered and concentrated. Obtained crude was purified by flash column chromatography (100-200 silica gel, 10% ethyl acetate in pet ether) to afford ethyl 2-(3-chloro-4-methoxyphenyl)-2,2-difluoroacetate (1 g, 3.78 mmol, 63% yield) as a colourless liquid. MS (ESI) m/z 264.1 [M]$^+$.

C. 2-(3-Chloro-4-methoxyphenyl)-2,2-difluoroacetic acid

To a stirred solution of ethyl 2-(3-chloro-4-methoxyphenyl)-2,2-difluoroacetate (1 g, 3.78 mmol) in tetrahydrofuran:ethanol:water (15 mL, 1:1:1) was added lithium hydroxide monohydrate (480 mg, 11.36 mmol) and stirred at room temperature for 16 h. The reaction mixture was concentrated under reduced pressure and the resultant residue was dissolved in water (20 mL) and washed with ethyl acetate (2×15 mL). Aqueous layer was acidified with 1N hydrochloride solution and extracted with ethyl acetate (3×15 mL). The combined organic layer was washed with brine (15 mL), dried over sodium sulphate, filtered and concentrated to afford 2-(3-chloro-4-methoxyphenyl)-2,2-difluoroacetic acid (550 mg, 2.32 mmol, 61% yield) as semi-solid compound. $^1$H NMR (300 MHz, DMSO-d$_6$) δ 7.57-7.52 (m, 2H), 7.29 (d, J=8.7 Hz, 1H), 3.92 (s, 3H).

D. 2-(3-Chloro-4-methoxyphenyl)-N-((2-(2,6-dioxopiperidin-3-yl)-1-oxoisoindolin-5-yl)methyl)-2,2-difluoroacetamide To a stirred solution of 3-(5-(aminomethyl)-1-oxoisoindolin-2-yl)piperidine-2,6-dione hydrochloride (300 mg, 0.97 mmol) in dry N,N-dimethylformamide (6 mL) was added 2-(3-chloro-4-methoxyphenyl)-2,2-difluoroacetic acid (252 mg, 1.07 mmol) followed by 1-[Bis(dimethylamino)methylene]-1H-1,2,3-triazolo[4,5-b]pyridinium 3-oxid hexafluorophosphate (442 mg, 1.16 mmol) and diisopropylethylamine (375 mg, 2.91 mmol) at 0° C. and stirred at room temperature for 16 h. The reaction mixture was concentrated under reduced pressure and obtained residue was dissolved in water (15 mL) and extracted with ethyl acetate (3×15 mL). The combined organic layer was washed with brine (10 mL), dried over sodium sulfate, filtered and concentrated. The resultant residue was purified by Reveleris C-18 reversed phase Grace column chromatography (45-55% acetonitrile in aqueous 0.1% formic acid) to afford 2-(3-Chloro-4-methoxyphenyl)-N-((2-(2,6-dioxopiperidin-3-yl)-1-oxoisoindolin-5-yl)methyl)-2,2-difluoro acetamide (58 mg, 11.7 mmol, 12% yield) as an off-white solid. MS (ESI) m/z 492.47 [M+1]$^+$. $^1$H NMR (300 MHz, DMSO-d6) δ 10.98 (s, 1H), 9.62 (t, 1H), 7.68 (d, J=7.8 Hz, 1H), 7.60 (d, J=2.3 Hz, 1H), 7.53 (d, J=8.7 Hz, 1H), 7.41 (s, 1H), 7.37 (d, J=8.0 Hz, 1H), 7.29 (d, J=8.7 Hz, 1H), 5.10 (dd, J=13.2, 5.1 Hz, 1H), 4.45 (d, J=5.4 Hz, 2H), 4.42 (d, J=17.9 Hz, 1H), 4.28 (d, J=17.9 Hz, 1H), 3.91 (s, 3H), 2.96-2.86 (m, 1H), 2.64-2.55 (m, 1H), 2.47-2.25 (m, 1H), 2.08-1.94 (m, 1H).

Example 29

N-((2-(2,6-Dioxopiperidin-3-yl)-1-oxoisoindolin-5-yl)methyl)-2,2-difluoro-2-(m-tolyl)acetamide

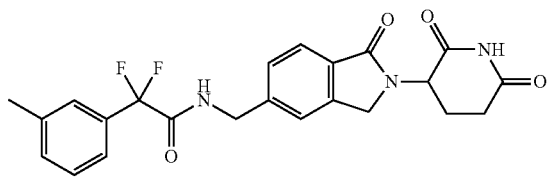 [SMILES: Cc1cccc(C(F)(F)C(=O)NCc2ccc3c(c2)CN(C2CCC(=O)NC2=O)C3=O)c1]

A. Ethyl 2-oxo-2-m-tolylacetate

To a stirred solution of 1-m-tolylethanone (3.0 g, 22.37 mmol) in pyridine (50 mL) was added selenium dioxide (4.96 g, 44.74 mmol) and stirred for 16 h at 100° C. The reaction mixture was diluted with dichloromethane (50 mL) and filtered through Celite pad. To the filtrate was added ethyl chloroformate (6 mL) at 0° C. and stirred for 2 h. The reaction mixture was neutralized with 1N aqueous hydrochloric acid (up to pH-4) and extracted with ethyl acetate (2×100 mL). The combined organic layers were washed with water (2×100 mL), brine (100 mL) and dried over sodium sulphate and concentrated. The resultant residue was purified by column chromatography (100-200 silica) using 10% ethyl acetate in pet.ether to afford ethyl 2-oxo-2-m-tolylacetate (2.0 g, 10.41 mmol, 46.6%) as a liquid. GC-MS (ESI) m/z 192.2.

B. Ethyl 2,2-difluoro-2-m-tolylacetate

To a stirred solution of ethyl 2-oxo-2-m-tolylacetate (2.0 g, 10.41 mmol) was reacted with diethyl amino sulfur trifluoride (3.41 mL, 26.02 mmol) and stirred for 12 h at room temperature. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated to afford ethyl 2,2-difluoro-2-m-tolylacetate (1.2 g, 5.60 mmol, 52.4%) as a liquid. GC-MS (ESI) m/z 214.1.

C. 2,2-Difluoro-2-m-tolylacetic acid

To a cold (0° C.) stirred solution of ethyl 2,2-difluoro-2-m-tolylacetate (1.2 g, 7.47 mmol) in tetrahydrofuran-methanol-water solvent mixture (45 mL, 1:1:1), was added lithium hydroxide (1.85 g, 44.84 mmol) and stirred at room temperature for 2 h. The reaction mixture was concentrated and the residue was neutralized with 10% aqueous hydrochloric acid (10 mL) and extracted with ethyl acetate (2×20 mL). The combined organic layers were washed with brine (20 mL), dried over sodium sulphate and concentrated to afford 2,2-difluoro-2-m-tolylacetic acid (900 mg, 4.83 mmol, 86.5% yield) as a brown solid. MS (ESI) m/z 185.21 [M−1]⁻.

D. N-((2-(2,6-Dioxopiperidin-3-yl)-1-oxoisoindolin-5-yl)methyl)-2,2-difluoro-2-(m-tolyl)acetamide To a cold (0° C.) stirred solution of 2,2-difluoro-2-m-tolylacetic acid (216.6 mg, 0.970 mmol) in pyridine (10 mL) was added phosphorus trichloride (0.3 mL, 2.912 mmol) and stirred at 0° C.-5° C. for 1 h. (300 mg, 2.40 mmol) was added to the reaction mixture at 0° C. and continued stirring at room temperature for 1 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The crude product was purified by Reveleris C-18 reversed phase Grace column chromatography using 45% acetonitrile in aqueous formic acid (0.1%) to afford N-((2-(2,6-dioxopiperidin-3-yl)-1-oxoisoindolin-5-yl)methyl)-2,2-difluoro-2-(m-tolyl)acetamide (63 mg, 0.147 mmol, 14.7% yield) as an off white solid. MS (ESI) m/z 442.25 [M+1]⁺. ¹H NMR (300 MHz, DMSO-d₆) δ 10.98 (s, 1H), 9.61 (t, J=6.1 Hz, 1H), 7.68 (d, J=7.8 Hz, 1H), 7.48-7.32 (m, 6H), 5.10 (dd, J=13.3, 5.0 Hz, 1H), 4.49-4.22 (m, 4H), 2.98-2.82 (m, 1H), 2.64-2.53 (m, 1H), 2.45-2.24 (m, 4H), 2.05-1.93 (m, 1H).

Example 30

N-((2-(2,6-Dioxopiperidin-3-yl)-1-oxoisoindolin-5-yl)methyl)-2,2-difluoro-2-(4-isopropoxyphenyl)acetamide

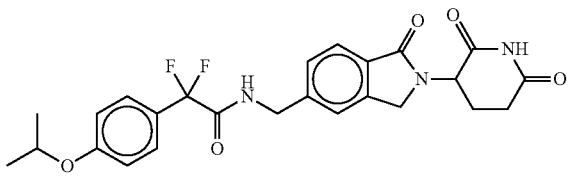

A. 1-(4-Isopropoxyphenyl)ethanone

To a stirred solution of 1-(4-hydroxyphenyl)ethanone (2.5 g, 18.38 mmol) in N,N-dimethylformamide was added potassium carbonate (6.34 g, 45.95 mmol) followed by isopropyl iodide (4.59 g, 27.57 mmol) at 0° C. and then heated at 100° C. for 16 h. The reaction mixture was quenched with ice water and extracted with ethyl acetate (3×25 mL). The combined organic layers were washed with brine (25 mL), dried over sodium sulphate, filtered, concentrated. Obtained crude compound was purified by flash column chromatography (100-200 silica gel, 20% ethyl acetate/pet ether) to afford 1-(4-isopropoxyphenyl)ethanone (2 g, 11.23 mmol, 61% yield) as a liquid. MS (ESI) m/z 179.13 [M+H]⁺.

B. Ethyl 2-(4-isopropoxyphenyl)-2-oxoacetate

To a stirred solution of 1-(4-isopropoxyphenyl)ethanone (3 g, 16.85 mmol) in pyridine (15 mL) was added selenium dioxide (4.67 g, 42.1 mmol) at room temperature and stirred at 100° C. for 16 h. The reaction mixture was filtered through a Celite pad and washed with dichloromethane (30 mL). Filtrate was cooled to 0° C., treated with ethyl chloroformate (6 mL) and stirred at room temperature for 4 h. The reaction mixture was quenched with ice water and extracted with dichloromethane (3×30 mL). The combined organic layers were washed with 1N hydrochloride solution (30 mL), brine (30 mL), dried over sodium sulphate, filtered and concentrated to afford ethyl 2-(4-isopropoxyphenyl)-2-oxoacetate (3 g, 12.76 mmol, 75% yield) as a colourless liquid. MS (ESI) m/z 236.2 [M]⁺.

C. Ethyl 2,2-difluoro-2-(4-isopropoxyphenyl)acetate

To ethyl 2-(4-isopropoxyphenyl)-2-oxoacetate (3 g, 12.76 mmol) was added diethylaminosulfur trifluoride (4.9 mL) at 0° C. and stirred at room temperature for 16 h. The reaction mixture was quenched with aqueous sodium bicarbonate solution and extracted with ethyl acetate (3×30 mL). The combined organic layer was washed with brine (30 mL), dried over sodium sulphate, filtered and concentrated. Obtained crude was purified by flash column chromatography (100-200 silica gel, 10% ethyl acetate/pet ether) to afford ethyl 2,2-difluoro-2-(4-isopropoxyphenyl)acetate (2 g, 7.75 mmol, 61% yield) as a colourless liquid. MS (ESI) m/z 258.2 [M+H]⁺.

D. 2,2-Difluoro-2-(4-isopropoxyphenyl)acetic acid

To a stirred solution of ethyl 2,2-difluoro-2-(4-isopropoxyphenyl)acetate (2 g, 7.75 mmol) in tetrahydrofuran:ethanol:water (20 mL, 1:1:1) was added lithium hydroxide monohydrate (1.6 g, 38.75 mmol) and stirred at room temperature for 16 h. The reaction mixture was concentrated under reduced pressure and the resultant residue was dissolved in water (20 mL) and washed with ethyl acetate (2×20 mL). Aqueous layer was acidified with 1N hydrochloride solution and extracted with ethyl acetate (3×20 mL). The combined organic layer was washed with brine (20 mL), dried over sodium sulphate, filtered and concentrated to afford 2,2-difluoro-2-(4-isopropoxyphenyl)acetic acid (1.2 g, 5.21 mmol, 67% yield) as semi-solid compound. ¹H NMR (300 MHz, DMSO-d₆) δ 7.47 (d, J=8.7 Hz, 2H), 7.03 (d, J=9 Hz, 2H), 4.71-4.63 (m, 1H), 1.28 (d, J=6 Hz, 6H).

E. N-((2-(2,6-Dioxopiperidin-3-yl)-1-oxoisoindolin-5-yl)methyl)-2,2-difluoro-2-(4-isopropoxyphenyl) acetamide To an ice cold solution of 2,2-difluoro-2-(4-isopropoxyphenyl)acetic acid (267 mg, 1.16 mmol) in pyridine (6 mL) was added phosphoryl chloride (0.27 mL, 2.91 mmol) dropwise and stirred at 0-5° C. for 1 h. Then, 3-(5-(aminomethyl)-1-oxoisoindolin-2-yl)piperidine-2,6-dione hydrochloride (300 mg, 0.97 mmol) was added into the reaction mixture and stirred at room temperature for 30 min. The reaction mixture was neutralized with aqueous saturated sodium bicarbonate (up to pH-8) and extracted with ethyl acetate (3×15 mL). The combined organic layer was washed with water (15 mL), brine (15 mL), dried over sodium sulphate, filtered and concentrated. The resultant residue was purified by Reveleris C-18 reversed phase column chromatography (45-55% acetonitrile in aqueous formic acid 0.1%) to afford N-((2-(2,6-dioxopiperidin-3-yl)-1-oxoisoindolin-5-yl)methyl)-2,2-difluoro-2-(4-isopropoxyphenyl) acetamide (27 mg, 0.05 mmol, 6% yield) as an off-white solid. MS (ESI) m/z 486.09 [M+1]⁺. ¹H NMR (400 MHz, DMSO-d₆) δ 10.98 (s, 1H), 9.56 (t, J=6.3 Hz, 1H), 7.67 (d, J=7.7 Hz, 1H), 7.48 (d, J=8.4 Hz, 2H), 7.43-7.33 (m, 2H), 7.03 (d, J=8.4 Hz, 2H), 5.10 (dd, J=13.3, 5.2 Hz, 1H), 4.74-4.62 (m, 1H), 4.49-4.27 (m, 4H), 3.02-2.83 (m, 1H), 2.69-2.58 (m, 1H), 2.39-2.28 (m, 1H), 2.05-1.95 (m, 1H), 1.27 (d, J=6.0 Hz, 6H).

Example 31

2-(3,4-Difluorophenyl)-N-((2-(2,6-dioxopiperidin-3-yl)-1-oxoisoindolin-5-yl)methyl)-2,2-difluoroacetamide

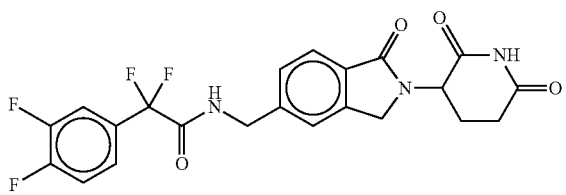

A. Ethyl 2-(3,4-difluorophenyl)-2-oxoacetate

To a stirred solution of 1-(3,4-difluorophenyl)ethanone (1 g, 6.4 mmol) in pyridine (15 mL) was added selenium dioxide (1.7 g, 16.01 mmol) at room temperature. The reaction mixture was stirred at 100° C. for 16 h. The reaction mixture was filtered through Celite pad and washed with dichloromethane (30 mL). ethyl chloroformate (4 mL) was added to the filtrate at 0° C. and stirred at room temperature for 4 h. The reaction mixture was quenched with ice water and extracted with dichloromethane (3×25 mL). The combined organic layers were washed with 1N hydrochloride solution (20 mL), brine (20 mL), dried over sodium sulfate, filtered and concentrated to afford ethyl 2-(3,4-difluorophenyl)-2-oxoacetate (750 mg, 3.50 mmol, 55% yield) as a colourless liquid. MS (ESI) m/z 214.1 [M]⁺.

B. Ethyl 2-(3,4-difluorophenyl)-2,2-difluoroacetate

Ethyl 2-(3,4-difluorophenyl)-2-oxoacetate (750 mg, 3.5 mmol) was added to diethylamino sulfur trifluoride (1.37 mL) under nitrogen atmosphere at 0° C. and stirred at room temperature for 16 h. The reaction mixture was quenched with aqueous sodium bicarbonate solution and extracted with ethyl acetate (3×20 mL). The combined organic layer was washed with brine (20 mL), dried over sodium sulfate, filtered and concentrated. Obtained crude was purified by flash column chromatography (100-200 silica gel, 10% ethyl acetate in pet ether) to afford ethyl 2-(3,4-difluorophenyl)-2,2-difluoroacetate (520 mg, 2.20 mmol, 63% yield) as a colourless liquid. MS (ESI) m/z 236.1 [M]⁺.

C. 2-(3,4-Difluorophenyl)-2,2-difluoroacetic acid

To a stirred solution of ethyl 2-(3,4-difluorophenyl)-2,2-difluoroacetate (500 mg, 2.11 mmol) in tetrahydrofuran:ethanol:water (15 mL, 1:1:1) was added lithium hydroxide monohydrate (267 mg, 6.35 mmol) and stirred at room temperature for 16 h. The volatiles were removed under reduced pressure and obtained crude was dissolved in water (15 mL) and washed with ethyl acetate (2×10 mL). Aqueous layer was acidified with 1N hydrochloride solution and extracted with ethyl acetate (3×15 mL). The combined organic layer was washed with brine (10 mL) dried over sodium sulfate, filtered and concentrated to afford 2-(3,4-difluorophenyl)-2,2-difluoroacetic acid (300 mg, 1.44 mmol, 68% yield) as semi-solid compound. MS (ESI) m/z 208.1 [M]⁺.

D. 2-(3,4-Difluorophenyl)-N-((2-(2,6-dioxopiperidin-3-yl)-1-oxoisoindolin-5-yl)methyl)-2,2-difluoroacetamide To a stirred solution of 3-(5-(aminomethyl)-1-oxoisoindolin-2-yl)piperidine-2,6-dione hydrochloride (300 mg, 0.97 mmol) in dry N,N-dimethylformamide (6 mL) was added 2-(3,4-difluorophenyl)-2,2-difluoroacetic acid (222 mg, 1.07 mmol) followed by 1-[Bis(dimethylamino)methylene]-1H-1,2,3-triazolo[4,5-b]pyridinium 3-oxid hexafluorophosphate (442 mg, 1.16 mmol) and diisopropylethylamine (0.5 mL, 2.91 mmol) at 0° C. and stirred at room temperature for 16 h. The reaction mixture was concentrated under reduced pressure and the obtained crude was dissolved in water (10 mL) and extracted with ethyl acetate (3×10 mL). The combined organic layers were washed with brine (10 mL), dried over sodium sulfate, filtered and concentrated. The crude compound was purified by Reveleris C-18 reversed phase Grace column chromatography (45-55% acetonitrile in 0.1% aqueous formic acid to afford 2-(3,4-difluorophenyl)-N-((2-(2,6-dioxopiperidin-3-yl)-1-oxoisoindolin-5-yl)methyl)-2,2-difluoro acetamide (75 mg, 0.16 mmol, 17% yield) as an off-white solid. MS (ESI) m/z 463.99 [M+1]$^+$. $^1$H NMR (300 MHz, DMSO-d$_6$) δ 10.98 (s, 1H), 9.69 (t, J=5.9 Hz, 1H), 7.72-7.62 (m, 2H), 7.61 (d, J=8.4 Hz, 1H), 7.51-7.44 (m, 1H), 7.43 (s, 1H), 7.37 (d, J=7.8 Hz, 1H), 5.10 (dd, J=13.3, 5.0 Hz, 1H), 4.46 (d, J=5.4 Hz, 2H), 4.43 (d, J=17.4 Hz, 1H), 4.29 (d, J=17.1 Hz, 1H), 2.98-2.87 (m, 1H), 2.65-2.56 (m, 1H), 2.45-2.29 (m, 1H), 2.08-1.90 (m, 1H).

Example 32

N-((2-(2,6-Dioxopiperidin-3-yl)-1-oxoisoindolin-5-yl)methyl)-2,2-difluoro-2-(3-fluorophenyl)acetamide

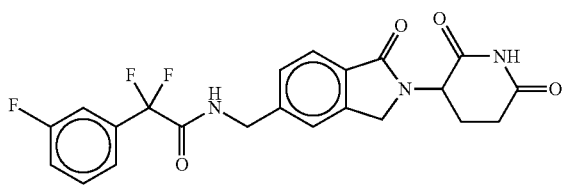

A. Ethyl 2-(3-fluorophenyl)-2-oxoacetate

To a stirred solution of 1-(3-fluorophenyl)ethanone (2 g, 14.48 mmol) in pyridine (15 mL) was added selenium dioxide (4.01 g, 36.19 mmol) at room temperature. The reaction mixture was stirred at 100° C. for 16 h. The reaction mixture was filtered through Celite pad and washed with dichloromethane (30 mL). Ethyl chloroformate (6 mL) was added to the filtrate at 0° C. and stirred at room temperature for 4 h. The reaction mixture was quenched with ice water and extracted with dichloromethane (3×25 mL). The combined organic layers were washed with 1N hydrochloride solution (20 mL), brine (20 mL), dried over sodium sulfate, filtered and concentrated to afford ethyl 2-(3-fluorophenyl)-2-oxoacetate (1.5 g, 7.65 mmol, 53% yield) as a colourless liquid. MS (ESI) m/z 196.1 [M]$^+$.

B. Ethyl 2,2-difluoro-2-(3-fluorophenyl)acetate

Ethyl 2-(3-fluorophenyl)-2-oxoacetate (1.5 g, 7.65 mmol) was added to diethylaminosulfur trifluoride (3 mL) at 0° C. and stirred at room temperature for 16 h. The reaction mixture was quenched with aqueous sodium bicarbonate solution and extracted with ethyl acetate (3×20 mL). The combined organic layers were washed with brine (20 mL), dried over sodium sulfate, filtered and concentrated. Obtained crude was purified by flash column chromatography (100-200 silica gel, 10% ethyl acetate in pet ether) to afford ethyl 2,2-difluoro-2-(3-fluorophenyl)acetate (850 mg, 3.89 mmol, 90% yield) as a colourless liquid. MS (ESI) m/z 218.1 [M]$^+$.

C. 2,2-Difluoro-2-(3-fluorophenyl)acetic acid

To a stirred solution of ethyl 2,2-difluoro-2-(3-fluorophenyl)acetate (850 mg, 3.89 mmol) in tetrahydrofuran:ethanol:water (15 mL, 1:1:1) was added lithium hydroxide monohydrate (491 mg, 11.69 mmol) and stirred at room temperature for 16 h. The reaction mixture was concentrated under reduced pressure and obtained crude was dissolved in water (15 mL) and washed with ethyl acetate (2×10 mL). The aqueous layer was acidified with 1N hydrochloride solution and extracted with ethyl acetate (3×15 mL). The combined organic layers were washed with brine (10 mL) dried over sodium sulfate, filtered and concentrated to afford 2,2-difluoro-2-(3-fluorophenyl)acetic acid (500 mg, 2.63 mmol, 67% yield) as semi-solid compound. MS (ESI) m/z 190.1 [M]$^+$.

D. N-((2-(2,6-Dioxopiperidin-3-yl)-1-oxoisoindolin-5-yl)methyl)-2,2-difluoro-2-(3-fluorophenyl)acetamide To a stirred solution of 3-(5-(aminomethyl)-1-oxoisoindolin-2-yl)piperidine-2,6-dione hydrochloride (203 mg, 1.07 mmol) in dry N,N-dimethylformamide. (6 mL) was added 2,2-difluoro-2-(3-fluorophenyl)acetic acid (300 mg, 0.97 mmol) followed by 1-[Bis(dimethylamino)methylene]-1H-1,2,3-triazolo[4,5-b]pyridinium 3-oxid hexafluorophosphate (442 mg, 1.16 mmol) and N,N-diisopropylethylamine (375 mg, 2.91 mmol) at 0° C. and stirred at room temperature for 16 h. The reaction mixture was concentrated under reduced pressure and obtained crude was dissolved in water (10 mL) and extracted with ethyl acetate (3×10 mL). The combined organic layers were washed with brine (10 mL), dried over sodium sulphate, filtered and concentrated. Obtained crude compound was purified by Reveleris C-18 reversed phase column chromatography (45-55% acetonitrile in 0.1% aqueous formic acid to afford N-((2-(2,6-dioxopiperidin-3-yl)-1-oxoisoindolin-5-yl)methyl)-2,2-difluoro-2-(3-fluorophenyl)acetamide (45 mg, 0.1 mmol, 10% yield) as an off-white solid. MS (ESI) m/z 446.04 [M+1]$^+$. $^1$H NMR (300 MHz, DMSO-d$_6$) δ 10.98 (s, 1H), 9.68 (t, J=5.9 Hz, 1H), 7.67 (d, J=8.1 Hz, 1H), 7.60 (dd, J=13.5, 7.8 Hz, 1H), 7.47-7.41 (m, 4H), 7.36 (d, J=8.1 Hz, 1H), 5.10 (dd, J=13.3, 5.0 Hz, 1H), 4.46 (d, J=5.7 Hz, 2H), 4.42 (d, J=15.0 Hz, 1H), 4.28 (d, J=17.4 Hz, 1H), 2.96-2.86 (m, 1H), 2.65-2.54 (m, 1H), 2.46-2.28 (m, 1H), 2.05-1.92 (m, 1H).

Example 33

N-((2-(2,6-dioxopiperidin-3-yl)-1-oxoisoindolin-5-yl)methyl)-2,2-difluoro-2-(3-(trifluoromethyl)pyridin-2-yl)acetamide

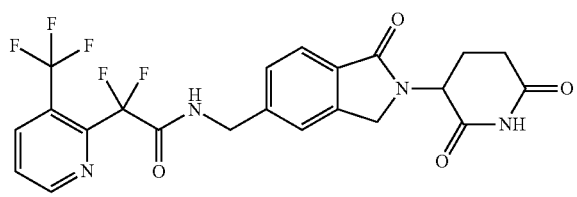 [SMILES: O=C1CCC(N2Cc3cc(CNC(=O)C(F)(F)c4ncccc4C(F)(F)F)ccc3C2=O)C(=O)N1]

A. N-((2-(2,6-dioxopiperidin-3-yl)-1-oxoisoindolin-5-yl)methyl)-2,2-difluoro-2-(3-(trifluoromethyl)pyridin-2-yl)acetamide 3-(5-(Aminomethyl)-1-oxoisoindolin-2-yl)piperidine-2,6-dione, mesylic acid (0.050 g, 0.135 mmol) was placed in a vial with N,N-dimethylformamide (1.0 mL), 2,2-difluoro-2-(3-(trifluoromethyl)pyridin-2-yl)acetic acid (0.033 g, 0.135 mmol), diisopropylethylamine (0.071 mL, 0.406 mmol), and 1-[Bis(dimethylamino)methylene]-1H-1,2,3-triazolo[4,5-b]pyridinium 3-oxid hexafluorophosphate (0.057 g, 0.149 mmol). The reaction mixture was stirred at RT for 18 h. The reaction mixture was taken up in dimethylsulfoxide and purified using reverse-phase semi preparative HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoro-2-(3-(trifluoromethyl)pyridin-2-yl)acetamide (0.033 g, 0.066 mmol, 49.1% yield) as a white solid. $^1$H NMR (500 MHz, DMSO-d$_6$) δ 10.98 (s, 1H), 9.59 (t, J=6.15 Hz, 1H), 8.99 (d, J=4.73 Hz, 1H), 8.47 (dd, J=1.26, 8.20 Hz, 1H), 7.88 (dd, J=4.73, 8.20 Hz, 1H), 7.74 (d, J=7.57 Hz, 1H), 7.60 (s, 1H), 7.51 (dd, J=0.63, 7.88 Hz, 1H), 5.12 (dd, J=5.20, 13.40 Hz, 1H), 4.55 (d, J=6.31 Hz, 2H), 4.49 (d, J=17.34 Hz, 1H), 4.32-4.37 (m, 1H), 2.88-2.97 (m, 1H), 2.58-2.64 (m, 1H), 2.36-2.46 (m, 1H), 2.02 (dtd, J=2.21, 5.16, 12.69 Hz, 1H). MS (ESI) m/z 497.4 [M+1]$^+$.

Example 34

N-((2-(2,6-dioxopiperidin-3-yl)-1-oxoisoindolin-5-yl)methyl)-2,2-difluoro-2-(4-isopropylphenyl)acetamide

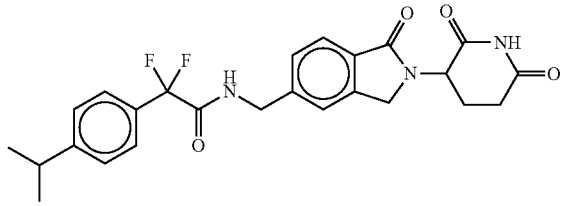

A. Ethyl 2-(4-isopropylphenyl)-2-oxoacetate

To a stirred solution of 1-(4-isopropylphenyl)ethanone (2.0 g, 12.33 mmol) in pyridine (25 mL) was added selenium dioxide (3.42 g, 30.82 mmol) and stirred for 16 h at 100° C. The reaction mixture was diluted with dichloromethane (50 mL) and filtered through Celite pad. To the filtrate was added ethyl chloroformate (6 mL) at 0° C. and stirred for 2 h. The reaction mixture was diluted with water (50 mL) and extracted with dichloromethane (3×100 mL). The combined organic layers were washed with water (2×50 mL), brine (50 mL), dried over sodium sulphate and concentrated to afford ethyl 2-(4-isopropylphenyl)-2-oxoacetate (2.0 g, 9.09 mmol, 74% yield). MS (ESI) m/z 221.29 [M+1]$^+$.

B. Ethyl 2,2-difluoro-2-(4-isopropylphenyl)acetate

To ethyl 2-(4-isopropylphenyl)-2-oxoacetate (1.0 g, 4.27 mmol) was added diethyl amino sulfur trifluoride (3 mL) at 0° C. and stirred at room temperature for 16 h. The reaction mixture was neutralized with aqueous saturated sodium bicarbonate (up to pH-8) and extracted with ethyl acetate (3×50 mL). The combined organic layers were washed with water (2×25 mL), brine (25 mL), dried over sodium sulphate and concentrated to afford ethyl 2,2-difluoro-2-(4-isopropylphenyl)acetate (1.0 g, 4.13 mmol, 91% yield). GCMS (m/z) 242.2 [M]$^+$.

C. 2,2-Difluoro-2-(4-isopropylphenyl)acetic acid

To a stirred solution of ethyl 2,2-difluoro-2-(4-isopropylphenyl)acetate (1.0 g, 4.13 mmol) in tetrahydrofuran:methanol:water (30 mL, 1:1:1) was added lithium hydroxide (868 mg, 20.66 mmol) and stirred at room temperature for 4 h. The reaction mixture was concentrated and the residue was neutralized with saturated potassium bisulphate (20 mL) and extracted with ethyl acetate (2×25 mL). The combined organic layers were washed with brine (25 mL), dried over sodium sulphate and concentrated to afford 2,2-difluoro-2-(4-isopropylphenyl)acetic acid (700 mg, 3.27 mmol, 79% yield) as an brown liquid. MS (ESI) m/z 213.33 [M−1]$^+$.

D. N-((2-(2,6-dioxopiperidin-3-yl)-1-oxoisoindolin-5-yl)methyl)-2,2-difluoro-2-(4-isopropylphenyl)acetamide To a cold (0° C.) stirred solution of 2,2-difluoro-2-(4-isopropylphenyl)acetic acid (200 mg, 0.93 mmol) in pyridine (20 mL) was added phosphoryl chloride (429 mg, 2.80 mmol) dropwise and stirred at 0-5° C. for 1 h. To this reaction mixture was then added 3-(5-(aminomethyl)-1-oxoisoindolin-2-yl)piperidine-2,6-dione hydrochloride (290 mg, 0.93 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 50-55% acetonitrile in aqueous formic acid (0.1%) to afford N-((2-(2,6-dioxopiperidin-3-yl)-1-oxoisoindolin-5-yl)methyl)-2,2-difluoro-2-(4-isopropylphenyl)acetamide (85 mg, 0.18 mmol, 19% yield) as a pale yellow solid. MS (ESI) m/z 470.21 [M+1]$^+$. $^1$H NMR (300 MHz, DMSO-d$_6$) δ 10.99 (s, 1H), 9.60 (t, J=6.1 Hz, 1H), 7.67 (d, J=8.1 Hz, 1H), 7.57-7.47 (m, 2H), 7.45-7.30 (m, 4H), 5.10 (dd, J=5.1, 13.2 Hz, 1H), 4.48-4.22 (m, 4H), 3.02-2.84 (m, 2H), 2.74-2.54 (m, 1H), 2.46-2.30 (m, 1H), 2.05-1.93 (m, 1H), 1.3-1.12 (m, 6H).

Example 35

2-(2,4-Dichlorophenyl)-N-((2-(2,6-dioxopiperidin-3-yl)-1-oxoisoindolin-5-yl)methyl)-2,2-difluoroacetamide

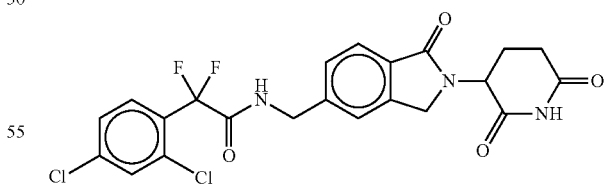

A. Ethyl 2-(2,4-dichlorophenyl)-2-oxoacetate

To a stirred solution of 1-(2,4-dichlorophenyl)ethanone (3.0 g, 15.87 mmol) in pyridine (20 mL) was added selenium dioxide (3.5 g, 31.74 mmol) and stirred at 100° C. for 16 h. The reaction mixture was diluted with dichloromethane (30 mL) and filtered through Celite pad. To the filtrate was added ethyl chloroformate (6 mL) at 0° C. and stirred at room temperature for 3 h. The reaction mixture was neutralized with 1N aqueous hydrochloric acid (up to pH-4) and extracted with ethyl acetate (2×100 mL). The combined organic layers were washed with water (2×50 mL), brine (50 mL), dried over sodium sulphate and concentrated to afford ethyl 2-(2,4-dichlorophenyl)-2-oxoacetate (3.0 g, 12.19 mmol, 76% yield). $^{1}$H NMR complies. $^{1}$H NMR (400 MHz, DMSO-d$_6$) δ 7.88-7.82 (m, 2H), 7.65 (d, J=8.4 Hz, 1H), 4.37 (q, J=7.0 Hz, 2H), 1.30 (t, J=7.0 Hz, 3H), B. Ethyl 2-(2,4-dichlorophenyl)-2,2-difluoroacetate A solution of ethyl 2-(2,4-dichlorophenyl)-2-oxoacetate (1.0 g, 4.58 mmol) and diethyl amino sulfur trifluoride (3.7 g, 22.89 mmol) was stirred at room temperature for 16 h. The reaction mixture was neutralized with aqueous saturated sodium bicarbonate (up to pH-8) and extracted with ethyl acetate (3×50 mL). The combined organic layers were washed with water (2×30 mL), brine (30 mL), dried over sodium sulphate and concentrated to afford ethyl 2-(2,4-dichlorophenyl)-2,2-difluoroacetate (1.0 g, 3.73 mmol, 92% yield). GCMS (m/z) 268 [M]$^+$.

C. 2-(2,4-Dichlorophenyl)-2,2-difluoroacetic acid

To a stirred solution of ethyl 2-(2,4-dichlorophenyl)-2,2-difluoroacetate (1.0 g, 3.73 mmol) in tetrahydrofuran:methanol:water mixture (30 mL, 1:1:1) was added lithium hydroxide monohydrate (940.2 mg, 22.38 mmol) and stirred at room temperature for 2 h. The reaction mixture was concentrated and the residue was neutralized with 10% aqueous hydrochloric acid (10 mL) and extracted with ethyl acetate (2×50 mL). The combined organic layers were washed with brine (20 mL), dried over sodium sulphate and concentrated to afford 2-(2,4-dichlorophenyl)-2,2-difluoroacetic acid (800 mg, 3.33 mmol, 89% yield). MS (ESI) m/z 241 [M+2]$^+$.

D. 2-(2,4-Dichlorophenyl)-N-((2-(2,6-dioxopiperidin-3-yl)-1-oxoisoindolin-5-yl)methyl)-2,2-difluoroacetamide To a cold (0° C.) stirred solution of 2-(2,4-dichlorophenyl)-2,2-difluoroacetic acid (279.6 mg, 1.165 mmol) in pyridine (10 mL) was added phosphoryl chloride (0.3 mL, 2.91 mmol) and stirred at 0-5° C. for 30 min. To this reaction mixture was then added 3-(5-(aminomethyl)-1-oxoisoindolin-2-yl)piperidine-2,6-dione hydrochloride (300 mg, 0.97 mmol) and stirred at room temperature for 1 h. The reaction mixture was neutralized with aqueous saturated sodium bicarbonate (up to pH-8) and extracted with ethyl acetate (2×25 mL). The combined organic layers were washed with water (25 mL), brine (25 mL), dried over sodium sulphate and concentrated. The resultant residue was purified by Reveleris C-18 reversed phase Grace column chromatography using 50-55% acetonitrile in aqueous formic acid (0.1%) to afford 2-(2,4-Dichlorophenyl)-N-((2-(2,6-dioxopiperidin-3-yl)-1-oxoisoindolin-5-yl)methyl)-2,2-difluoroacetamide (60 mg, 0.12 mmol, 12% yield) as an off white solid. MS (ESI) m/z 496.03 [M+1]$^+$. $^{1}$H NMR (300 MHz, DMSO-d$_6$) δ 10.99 (m, 1H), 9.70 (t, J=6.3 Hz, 1H), 7.84-7.65 (m, 3H), 7.66-7.57 (d, J=8.4 Hz, 1H), 7.50 (s, 1H), 7.44 (d, J=8.0 Hz, 1H), 5.11 (dd, J=5.1, 13.2 Hz, 1H), 4.49 (br d, J=5.5 Hz, 2H), 4.43 (s, 1H), 4.34 (s, 1H), 4.28 (s, 1H), 2.99-2.84 (m, 1H), 2.60-2.57 (m, 1H), 2.44-2.31 (m, 1H), 2.05-1.94 (m, 1H).

Example 36

N-((2-(2,6-dioxopiperidin-3-yl)-1-oxoisoindolin-5-yl)methyl)-2,2-difluoro-2-(2-methoxyphenyl)acetamide

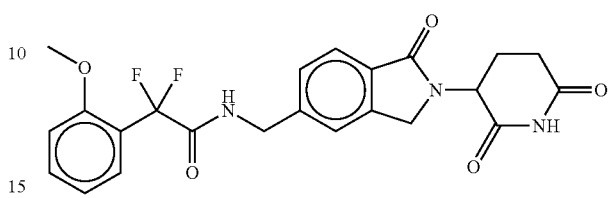

A. Ethyl 2-(2-methoxyphenyl)-2-oxoacetate

To a stirred solution of 1-(2-methoxyphenyl)ethanone (2.0 g, 13.32 mmol) in pyridine (25 mL) was added selenium dioxide (3.7 g, 33.29 mmol) and stirred for 16 h at 100° C. The reaction mixture was diluted with dichloromethane (50 mL) and filtered through Celite pad. To the filtrate was added ethyl chloroformate (6 mL) at 0° C. and stirred for 2 h. The reaction mixture was diluted with water (30 mL) and extracted with ethyl acetate (3×100 mL). The combined organic layers were washed with water (2×50 mL), brine (50 mL), dried over sodium sulphate and concentrated to afford ethyl 2-(2-methoxyphenyl)-2-oxoacetate (2.0 g, 9.62 mmol, 72% yield). GCMS (m/z) 208.2 [M]$^+$.

B. Ethyl 2,2-difluoro-2-(2-methoxyphenyl)acetate

To ethyl 2-(2-methoxyphenyl)-2-oxoacetate (1.0 g, 4.81 mmol) was added diethyl amino sulfur trifluoride (3 mL) at 0° C. and stirred at room temperature for 16 h. The reaction mixture was neutralized with aqueous saturated sodium bicarbonate (up to pH-8) and extracted with ethyl acetate (3×50 mL). The combined organic layers were washed with water (2×25 mL), brine (25 mL), dried over sodium sulphate and concentrated to afford ethyl 2,2-difluoro-2-(2-methoxyphenyl)acetate (1.0 g, 4.35 mmol, 90% yield). GCMS (m/z) 230.2 [M$^+$].

C. 2,2-Difluoro-2-(2-methoxyphenyl)acetic acid

To a stirred solution of ethyl 2,2-difluoro-2-(2-methoxyphenyl)acetate (1.0 g, 4.35 mmol) in tetrahydrofuran:methanol:water mixture (30 mL, 1:1:1) was added lithium hydroxide monohydrate (913 mg, 21.74 mmol) and stirred at room temperature for 4 h. The reaction mixture was concentrated and the residue was neutralized with saturated potassium bisulphate (20 mL) and extracted with ethyl acetate (2×25 mL). The combined organic layers were washed with brine (25 mL), dried over sodium sulphate and concentrated to afford 2,2-difluoro-2-(2-methoxyphenyl)acetic acid (700 mg, 3.46 mmol, 79% yield). MS (ESI) m/z 201.29 [M−1]$^+$.

D. N-((2-(2,6-dioxopiperidin-3-yl)-1-oxoisoindolin-5-yl)methyl)-2,2-difluoro-2-(2-methoxyphenyl)acetamide To a cold (0° C.) stirred solution of 2,2-difluoro-2-(2-methoxyphenyl)acetic acid (200 mg, 0.99 mmol) in pyridine (20 mL) was added phosphoryl chloride (454 mg, 0.99 mmol) dropwise and stirred at 0-5° C. for 1 h and then added 3-(5-(aminomethyl)-1-oxoisoindolin-2-yl)piperidine-2,6-dione hydrochloride (306 mg, 0.99 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 50-55% acetonitrile in aqueous formic acid (0.1%) to give N-((2-(2,6-dioxopiperidin-3-yl)-1-oxoisoindolin-5-yl)methyl)-2,2-difluoro-2-(2-methoxyphenyl)acetamide (80 mg, 0.17 mmol, 17% yield) as an off white solid. MS (ESI) m/z 458.15 [M+1]$^+$. $^1$H NMR (300 MHz, DMSO-d$_6$) δ 10.99 (s, 1H), 9.37 (t, J=5.9 Hz, 1H), 7.73 (d, J=7.7 Hz, 1H), 7.59-7.41 (m, 4H), 7.17-7.03 (m, 2H), 5.11 (dd, J=5.0, 13.0 Hz, 1H), 4.53-4.26 (m, 4H), 3.66 (s, 3H), 3.01-2.85 (m, 1H), 2.74-2.54 (m, 1H), 2.45-2.29 (m, 1H), 2.09-1.90 (m, 1H)

Example 37

2-(4-Cyclopropylphenyl)-N-((2-(2,6-dioxopiperidin-3-yl)-1-oxoisoindolin-5-yl)methyl)-2,2-difluoroacetamide

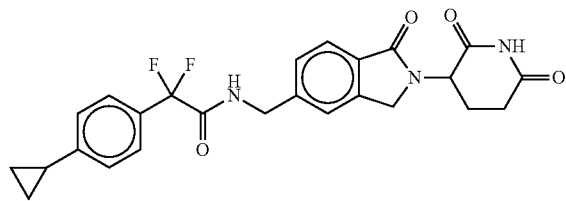

A. 1-(4-Cyclopropylphenyl)ethanone

To a stirred and degassed solution of 1-(4-bromophenyl) ethanone (1 g, 5.02 mmol) in water: 1,4-dioxane (1:10, 50 mL) was added cyclopropylboronic acid (519 mg, 6.02 mmol) followed by potassium phosphate (3.2 g, 15.07 mmol), [1,1'-bis(diphenylphosphino)ferrocene]dichloropalladium (II) dichloromethane complex (205 mg, 0.25 mmol). The reaction mixture was degassed for 10 min and heated at 100° C. for 8 h. The reaction mixture was cooled to room temperature and filtered through the Celite pad. To the filtrate was added cold water (50 mL) and extracted with ethyl acetate (3×50 mL). The combined organic layers were washed with water (2×50 mL), brine (50 mL), dried over sodium sulphate and concentrated. The resultant residue was purified by column chromatography (100-200 silica) using 20% ethyl acetate in pet ether to afford 1-(4-cyclopropylphenyl)ethanone (700 mg, 4.37 mmol, 87% yield). GCMS (m/z) 160.2 [M]$^+$.

B. Ethyl 2-(4-cyclopropylphenyl)-2-oxoacetate

To a stirred solution of 1-(4-cyclopropylphenyl)ethanone (700 mg, 4.37 mmol) in pyridine (10 mL) was added selenium dioxide (1.2 g, 10.93 mmol) and stirred at 100° C. for 16 h. The reaction mixture was diluted with dichloromethane (20 mL) and filtered through Celite pad. To the filtrate was added ethyl chloroformate (2 mL) at 0° C. and stirred at room temperature for 3 h. The reaction mixture was neutralized with 1N aqueous hydrochloric acid (up to pH-4) and extracted with ethyl acetate (2×60 mL). The combined organic layers were washed with water (2×30 mL), brine (30 mL), dried over sodium sulphate and concentrated to afford ethyl 2-(4-cyclopropylphenyl)-2-oxoacetate (890 mg, 4.08 mmol, 93% yield). GCMS (m/z) 218.2 [M]$^+$ C. Ethyl 2-(4-cyclopropylphenyl)-2,2-difluoroacetate A solution of ethyl 2-(4-cyclopropylphenyl)-2-oxoacetate (890 mg, 4.08 mmol) and diethyl amino sulfur trifluoride (3.7 g, 22.89 mmol) was stirred at room temperature for 16 h. The reaction mixture was neutralized with aqueous saturated sodium bicarbonate (up to pH-8) and extracted with ethyl acetate (3×50 mL). The combined organic layers were washed with water (2×30 mL), brine (30 mL), dried over sodium sulphate and concentrated to afford ethyl 2-(4-cyclopropylphenyl)-2,2-difluoroacetate (920 mg, 3.83 mmol, 94% yield). GCMS (m/z) 240.2 [M]$^+$ D. 2-(4-Cyclopropylphenyl)-2,2-difluoroacetic acid To a stirred solution of ethyl 2-(4-cyclopropylphenyl)-2,2-difluoroacetate (920 mg, 3.83 mmol) in tetrahydrofuran-methanol-water (30 mL, 1:1:1) was added lithium hydroxide monohydrate (483 mg, 11.49 mmol) and stirred at room temperature for 2 h. The reaction mixture was concentrated and the residue was neutralized with 10% aqueous hydrochloric acid (10 mL) and extracted with ethyl acetate (2×50 mL). The combined organic layers were washed with brine (20 mL), dried over sodium sulphate and concentrated to afford 2-(4-cyclopropylphenyl)-2,2-difluoroacetic acid (750 mg, 3.53 mmol, 92% yield). GCMS (m/z) 212.1 [M]$^+$.

E. 2-(4-Cyclopropylphenyl)-N-((2-(2,6-dioxopiperidin-3-yl)-1-oxoisoindolin-5-yl)methyl)-2,2-difluoroacetamide To a cold (0° C.) stirred solution of 2-(4-cyclopropylphenyl)-2,2-difluoroacetic acid (200 mg, 0.943 mmol) in pyridine (10 mL) was added phosphoryl chloride (0.4 mL, 2.830 mmol) and stirred at 0-5° C. for 30 min. To this reaction mixture was then added 3-(5-(aminomethyl)-1-oxoisoindolin-2-yl)piperidine-2,6-dione hydrochloride (359 mg, 1.16 mmol) and stirred at room temperature for 1 h. The reaction mixture was neutralized with aqueous saturated sodium bicarbonate (up to pH-8) and extracted with ethyl acetate (2×25 mL). The combined organic layers were washed with water (25 mL), brine (25 mL), dried over sodium sulphate and concentrated. The resultant residue was purified by Reveleris C-18 reversed phase column chromatography using 40-45% acetonitrile in aqueous formic acid (0.1%) to afford 2-(4-cyclopropylphenyl)-N-((2-(2,6-dioxopiperidin-3-yl)-1-oxoisoindolin-5-yl)methyl)-2,2-difluoroacetamide (90 mg, 0.192 mmol, 20.0% yield) as an off white solid. MS (ESI) m/z 468.13 [M+1]$^+$. $^1$H NMR (300 MHz, DMSO-d$_6$) δ 10.99 (s, 1H), 9.58 (t, J=5.9 Hz, 1H), 7.67 (d, J=8.1 Hz, 1H), 7.44 (d, J=8.1 Hz, 2H), 7.39-7.31 (m, 2H), 7.21 (d, J=8.1 Hz, 2H), 5.10 (dd, J=5.1, 13.2 Hz, 1H), 4.49-4.21 (m, 4H), 3.00-2.81 (m, 1H), 2.67-2.56 (m, 1H), 2.45-2.29 (m, 1H), 2.07-1.92 (m, 2H), 1.04-0.97 (m, 2H), 0.55-0.77 (m, 2H).

Example 38

2-(4-Chloro-2-fluorophenyl)-N-((2-(2,6-dioxopiperidin-3-yl)-1-oxoisoindolin-5-yl)methyl)-2,2-difluoroacetamide

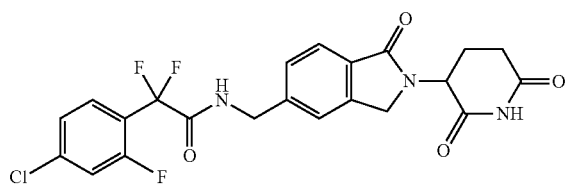 [SMILES: O=C1CCC(N2Cc3cc(CNC(=O)C(F)(F)c4ccc(Cl)cc4F)ccc3C2=O)C(=O)N1]

A. Ethyl 2-(4-chloro-2-fluorophenyl)-2-oxoacetate

To a stirred solution of 1-(4-chloro-2-fluorophenyl)ethanone (2.0 g, 11.588 mmol) in pyridine (30 mL) was added selenium dioxide (2.57 g, 23.176 mmol) and stirred for 16 h at 100° C. The reaction mixture was diluted with dichloromethane (30 mL) and filtered through Celite pad. To the filtrate was added ethyl chloroformate (4 mL) at 0° C. and stirred for 2 h. To the reaction mixture was added water (30 mL) and extracted with ethyl acetate (3×50 mL). The combined organic layers were washed with water (2×20 mL), brine (20 mL), dried over sodium sulphate and concentrated. The resultant residue was purified by column chromatography (100-200 silica) using 5-10% ethyl acetate in petroleum ether to afford ethyl 2-(4-chloro-2-fluorophenyl)-2-oxoacetate (1.71 g, 7.434 mmol, 64% yield) as a colourless liquid. MS (ESI) m/z. 230.1.

B. Ethyl 2-(4-chloro-2-fluorophenyl)-2,2-difluoroacetate

Ethyl 2-(4-chloro-2-fluorophenyl)-2-oxoacetate (1.71 g, 7.434 mmol) was reacted with diethylaminosulfur trifluoride (2.45 mL, 18.585 mmol) and stirred for 12 h at room temperature. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated to afford ethyl 2-(4-chloro-2-fluorophenyl)-2,2-difluoroacetate (1.0 g, 4.087 mmol, 55% yield) as a colorless liquid. MS (ESI) m/z. 252.1.

C. 2-(4-Chloro-2-fluorophenyl)-2,2-difluoroacetic acid

To a cold (0° C.) stirred solution of ethyl 2-(4-chloro-2-methylphenyl)-2,2-difluoroacetate (1.0 g, 4.087 mmol) in tetrahydrofuran:ethanol:water mixture (30 mL, 1:1:1) was added lithium hydroxide monohydrate (0.85 g, 20.436 mmol) and stirred at room temperature for 6 h. The reaction mixture was concentrated and the residue was neutralized with 10% aqueous hydrochloric acid (10 mL) and extracted with ethyl acetate (2×20 mL). The combined organic layers were washed with brine (20 mL), dried over sodium sulphate and concentrated to 2-(4-chloro-2-fluorophenyl)-2,2-difluoroacetic acid (550 mg, 2.455 mmol, 62% yield) as an brown solid. MS (ESI) m/z. 224.0.

D. 2-(4-Chloro-2-fluorophenyl)-N-((2-(2,6-dioxopiperidin-3-yl)-1-oxoisoindolin-5-yl)methyl)-2,2-difluoroacetamide To a cold (0° C.) stirred solution of 2-(4-chloro-2-fluorophenyl)-2,2-difluoroacetic acid (217 mg, 0.968 mmol) in pyridine was added phosphorus oxychloride (0.27 mL, 2.906 mmol) dropwise and stirred at 0-5° C. for 1 h. To this reaction mixture was added 3-(5-(aminomethyl)-1-oxoisoindolin-2-yl)piperidine-2,6-dione hydrochloride (300 mg, 0.968 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The resultant residue was purified by Reveleris C-18 reversed phase column chromatography using 40-55% acetonitrile in aqueous formic acid (0.1%) to give 2-(4-chloro-2-fluorophenyl)-N-((2-(2,6-dioxopiperidin-3-yl)-1-oxoisoindolin-5-yl)methyl)-2,2-difluoroacetamide (59 mg, 0.123 mmol, 12% yield) as an off white solid. MS (ESI) m/z 480.07 [M+1]+. $^1$H NMR (300 MHz, DMSO-$d_6$) δ 10.99 (s, 1H), 9.74 (s, 1H), 7.69 (dd, J=11.1, 7.8 Hz, 3H), 7.55-7.29 (m, 3H), 5.16-5.09 (dd, J=5.1 Hz, 1H), 4.52-4.27 (m, 4H), 3.00-2.84 (m, 1H), 2.66-2.55 (m, 1H), 2.41-2.30 (m, 1H), 2.04-1.94 (m, 1H).

Example 39

2-(4-Chloro-3-fluorophenyl)-N-((2-(2,6-dioxopiperidin-3-yl)-1-oxoisoindolin-5-yl)methyl)-2,2-difluoroacetamide

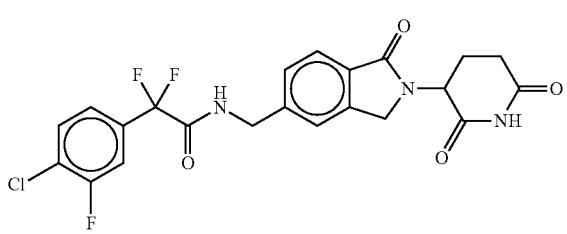

A. Ethyl 2-(4-chloro-3-fluorophenyl)-2-oxoacetate

To a stirred solution of 1-(4-chloro-3-fluorophenyl)ethanone (2.0 g, 11.62 mmol) in pyridine (20 mL) was added selenium dioxide (2.5 g, 23.25 mmol) and stirred at 100° C. for 16 h. The reaction mixture was diluted with dichloromethane (30 mL) and filtered through Celite pad. To the filtrate was added ethyl chloroformate (6 mL) at 0° C. and stirred at room temperature for 3 h. The reaction mixture was neutralized with 1N aqueous hydrochloric acid (up to pH-4) and extracted with ethyl acetate (2×100 mL). The combined organic layers were washed with water (2×50 mL), brine (50 mL), dried over sodium sulphate and concentrated to afford ethyl 2-(4-chloro-3-fluorophenyl)-2-oxoacetate (2.0 g, 8.69 mmol, 75% yield). GCMS (m/z) 230 [M]+.

B. Ethyl 2-(4-chloro-3-fluorophenyl)-2,2-difluoroacetate

A solution of ethyl 2-(4-chloro-3-fluorophenyl)-2-oxoacetate (1.0 g, 4.34 mmol) and diethyl amino sulfur trifluoride (3.7 g, 22.89 mmol) was stirred at room temperature for 16 h. The reaction mixture was neutralized with aqueous saturated sodium bicarbonate (up to pH-8) and extracted with ethyl acetate (3×50 mL). The combined organic layers were washed with water (2×30 mL), brine (30 mL), dried over sodium sulphate and concentrated to afford ethyl 2-(4-chloro-3-fluorophenyl)-2,2-difluoroacetate (900 mg, 3.57 mmol, 82% yield). GCMS (m/z) 252.1 [M]⁺.

C. 2-(4-Chloro-3-fluorophenyl)-2,2-difluoroacetic acid

To a stirred solution of ethyl 2-(4-chloro-3-fluorophenyl)-2,2-difluoroacetate (800 mg, 3.17 mmol) in tetrahydrofuran:methanol:water mixture (20 mL, 1:1:1) was added lithium hydroxide monohydrate (798 mg, 19.04 mmol) and stirred at room temperature for 2 h. The reaction mixture was concentrated and the residue was neutralized with 10% aqueous hydrochloric acid (10 mL) and extracted with ethyl acetate (2×50 mL). The combined organic layers were washed with brine (20 mL), dried over sodium sulphate and concentrated to afford 2-(4-chloro-3-fluorophenyl)-2,2-difluoroacetic acid (600 mg, 2.67 mmol, 84% yield. MS (ESI) m/z 223.1 [M-1]⁺.

D. 2-(4-Chloro-3-fluorophenyl)-N-((2-(2,6-dioxopiperidin-3-yl)-1-oxoisoindolin-5-yl)methyl)-2,2-difluoroacetamide To a cold (0° C.) stirred solution of 2-(4-chloro-3-fluorophenyl)-2,2-difluoroacetic acid (261 mg, 1.165 mmol) in pyridine (10 mL) was added phosphoryl chloride (0.3 mL, 2.91 mmol) and stirred at 0-5° C. for 30 min. To this reaction mixture was then added 3-(5-(aminomethyl)-1-oxoisoindolin-2-yl)piperidine-2,6-dione hydrochloride (300 mg, 0.97 mmol) and stirred at room temperature for 1 h. The reaction mixture was neutralized with aqueous saturated sodium bicarbonate (up to pH-8) and extracted with ethyl acetate (2×25 mL). The combined organic layers were washed with water (25 mL), brine (25 mL), dried over sodium sulphate and concentrated. The resultant residue was purified by Reveleris C-18 reversed phase Grace column chromatography using 50-55% acetonitrile in aqueous formic acid (0.1%) to afford 2-(4-Chloro-3-fluorophenyl)-N-((2-(2,6-dioxopiperidin-3-yl)-1-oxoisoindolin-5-yl)methyl)-2,2-difluoroacetamide (50 mg, 0.10 mmol, 11% yield) as an off white solid. MS (ESI) m/z 480.05 [M+1]⁺. ¹H NMR (300 MHz, DMSO-d₆) δ 10.99 (s, 1H), 9.70 (br s, 1H), 7.81 (br t, J=7.9 Hz, 1H), 7.71-7.60 (m, 2H), 7.49-7.32 (m, 3H), 5.10 (br dd, J=5.1, 13.2 Hz, 1H), 4.49-4.38 (m, 3H), 4.34-4.25 (m, 1H), 2.99-2.83 (m, 1H), 2.63-2.56 (br s, 1H), 2.44-2.26 (m, 1H), 2.06-1.94 (m, 1H).

Example 40

N-((2-(2,6-Dioxopiperidin-3-yl)-1-oxoisoindolin-5-yl)methyl)-2,2-difluoro-2-(3-fluoro-2-methylphenyl)acetamide

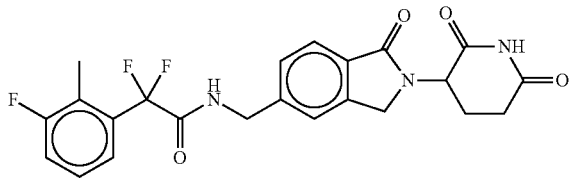

A. 1-(3-Fluoro-2-methylphenyl)ethanone

To a stirred solution of 3-fluoro-2-methylbenzonitrile (3 g, 22.22 mmol) in benzene (20 mL) was added methyl magnesium iodide (9.0 mL, 26.64 mmol, 3M in diethyl ether) at 0° C. and stirred at 80° C. for 8 h. Then the reaction mixture was cooled to room temperature, added 6N hydrochloric acid (25 mL) and stirred at heated 80° C. for 8 h. The reaction mixture was cooled to room temperature and extracted with ethyl acetate (3×100 mL). The combined organic layers were washed with water (2×100 mL), brine (100 mL), dried over sodium sulphate and concentrated to afford 1-(3-fluoro-2-methylphenyl)ethanone (920 mg, 6.05 mmol, 27% yield). GCMS (m/z) 152.2 [M]⁺

B. Ethyl 2-(3-fluoro-2-methylphenyl)-2-oxoacetate

To a stirred solution of 1-(3-fluoro-2-methylphenyl)ethanone (900 mg, 5.91 mmol) in pyridine (25 mL) was added selenium dioxide (1.7 g, 14.79 mmol) and stirred for 12 h at 100° C. The reaction mixture was diluted with dichloromethane (20 mL) and filtered through Celite pad. To the filtrate was added ethyl chloroformate (3 mL) at 0° C. and stirred at room temperature for 2 h. The reaction mixture was neutralized with 1N aqueous hydrochloric acid (up to pH-4) and extracted with ethyl acetate (3×50 mL). The combined organic layers were washed with water (2×50 mL), brine (50 mL), dried over sodium sulphate and concentrated to afford ethyl 2-(3-fluoro-2-methylphenyl)-2-oxoacetate (1.2 g, 5.71 mmol, 96%). GCMS (m/z) 210.2 [M]⁺

C. Ethyl 2,2-difluoro-2-(3-fluoro-2-methylphenyl)acetate

A solution of ethyl 2-(3-fluoro-2-methylphenyl)-2-oxoacetate (1.2 g, 5.71 mmol) and diethyl amino sulfur trifluoride (4.3 g, 26.67 mmol) were stirred at room temperature for 16 h. The reaction mixture was neutralized with aqueous saturated sodium bicarbonate (up to pH-8) and extracted with ethyl acetate (3×50 mL). The combined organic layer was washed with water (2×50 mL), brine (50 mL), dried over sodium sulphate and concentrated to afford ethyl 2,2-difluoro-2-(3-fluoro-2-methylphenyl)acetate (1.0 g, 4.31 mmol, 76%) as a brown liquid. GCMS (m/z) 232.2 [M]⁺

D. 2,2-Difluoro-2-(3-fluoro-2-methylphenyl)acetic acid

To a cold (0° C.) stirred solution of ethyl 2,2-difluoro-2-(3-fluoro-2-methylphenyl)acetate (1.0 g, 4.31 mmol) in methanol:tetrahydrofuran:water (1:1:1, 30 mL) was added lithium hydroxide monohydrate (543 mg, 12.93 mmol) and stirred at room temperature for 2 h. The reaction mixture was concentrated and the residue was neutralized with 10% aqueous hydrochloric acid (10 mL) and extracted with ethyl acetate (2×50 mL). The combined organic layers were washed with brine (50 mL), dried over sodium sulphate and concentrated to afford 2,2-difluoro-2-(3-fluoro-2-methylphenyl)acetic acid (800 mg, 3.92 mmol, 91% yield). GCMS (m/z) 204.1 [M]⁺

E. N-((2-(2,6-dioxopiperidin-3-yl)-1-oxoisoindolin-5-yl)methyl)-2,2-difluoro-2-(3-fluoro-2-methylphenyl)acetamide To a cold (0° C.) stirred solution of 2,2-difluoro-2-(3-fluoro-2-methylphenyl)acetic acid (200 mg, 0.98 mmol) in pyridine (10 mL) was added phosphoryl chloride (0.3 mL, 2.94 mmol) dropwise and stirred at 0-5° C. for 30 min. To this reaction mixture was then added 3-(5-(aminomethyl)-1-oxoisoindolin-2-yl)piperidine-2,6-dione hydrochloride (303 mg, 0.98 mmol) and stirred at room temperature for 1 h. The reaction mixture was neutralized with aqueous saturated sodium bicarbonate (up to pH-8) and extracted with ethyl acetate (2×25 mL). The combined organic layers were washed with water (25 mL), brine (25 mL), dried over sodium sulphate and concentrated. The resultant residue was purified by Reveleris C-18 reversed phase column chromatography using 40-45% acetonitrile in aqueous formic acid (0.1%) to afford N-((2-(2,6-dioxopiperidin-3-yl)-1-oxoisoindolin-5-yl)methyl)-2,2-difluoro-2-(3-fluoro-2-methylphenyl)acetamide (80 mg, 0.17 mmol, 18.0% yield) as an off white solid. MS (ESI) m/z 460.10 [M+1]$^+$. $^1$H NMR (300 MHz, DMSO-d$_6$) δ 10.98 (s, 1H), 9.68 (t, J=5.9 Hz, 1H), 7.70 (d, J=8.1 Hz, 1H), 7.49-7.31 (m, 5H), 5.10 (dd, J=4.8, 13.2 Hz, 1H), 4.52-4.22 (m, 4H), 3.00-2.82 (m, 1H), 2.67-2.54 (m, 1H), 2.46-2.30 (m, 1H), 2.21 (br s, 3H), 2.09-1.92 (m, 1H).

Example 41

2-(3-Chloro-2-methylphenyl)-N-((2-(2,6-dioxopiperidin-3-yl)-1-oxoisoindolin-5-yl)methyl)-2,2-difluoroacetamide

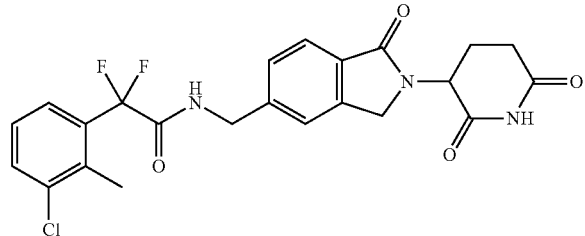 [SMILES: Cc1c(Cl)cccc1C(F)(F)C(=O)NCc1ccc2c(c1)CN(C1CCC(=O)NC1=O)C2=O]

A. 1-(3-Chloro-2-methylphenyl)ethanone

To a stirred solution of 3-chloro-2-methylbenzonitrile (2.0 g, 13.245 mmol) in benzene (30 mL) was added methyl magnesium iodide (3M) in diethyl ether solution (5.3 mL, 15.89 mmol) at 0° C. and stirred for 16 h at 75° C. The reaction mixture was treated with 6N aqueous hydrochloric acid solution (20 mL) at 0° C. and stirred for 4 h at 75° C. The reaction mixture was quenched with water (50 mL) and extracted with ethyl acetate (3×50 mL). The combined organic layers were washed with water (2×20 mL), brine (20 mL), dried over sodium sulphate and concentrated. The obtained residue was purified by column chromatography (100-200 silica) using 5-8% ethyl acetate in petroleum ether to afford 1-(4-chloro-2-methylphenyl)ethanone (1.4 g, 8.333 mmol, 63% yield) as a colorless liquid. GCMS (ESI) m/z. 168.1.

B. Ethyl 2-(3-chloro-2-methylphenyl)-2-oxoacetate

To a stirred solution of 1-(4-chloro-2-methylphenyl)ethanone (1.4 g, 8.333 mmol) in pyridine (30 mL) at 0° C., was added selenium dioxide (1.85 g, 16.666 mmol) and stirred for 16 h at 100° C. The reaction mixture was diluted with dichloromethane (30 mL) and filtered through Celite pad. To the filtrate was added ethyl chloroformate (3 mL) at 0° C. and stirred for 2 h. The reaction mixture quenched with water and extracted with ethyl acetate (3×50 mL). The combined organic layers were washed with water (2×20 mL), brine (20 mL), dried over sodium sulphate and concentrated. The resultant residue was purified by column chromatography (100-200 silica) using 5-10% ethyl acetate in pet. ether to give ethyl 2-(3-chloro-2-methylphenyl)-2-oxoacetate (1.1 g, 4.867 mmol, 58.5% yield) as a colorless liquid. GCMS (ESI) m/z. 226.1.

C. Ethyl 2-(3-chloro-2-methylphenyl)-2,2-difluoroacetate

To ethyl 2-(3-chloro-2-methylphenyl)-2-oxoacetate (1.1 g, 4.867 mmol) was added diethyl amino sulfur trifluoride (1.6 mL, 12.168 mmol) and stirred for 12 h at room temperature. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated to afford ethyl 2-(3-chloro-2-methylphenyl)-2,2-difluoroacetate (710 mg, 2.862 mmol, 58% yield) as a colourless liquid. GCMS (ESI) m/z. 248.1.

D. 2-(3-Chloro-2-methylphenyl)-2,2-difluoroacetic acid

To a cold (0° C.) stirred solution of ethyl 2-(3-chloro-2-methylphenyl)-2,2-difluoroacetate (710 mg, 2.862 mmol) in tetrahydrofuran:ethanol:water mixture (30 mL, 1:1:1) was added lithium hydroxide (0.6 g, 14.314 mmol) and stirred at room temperature for 6 h. The reaction mixture was concentrated and the residue was neutralized with 10% aqueous hydrochloric acid (10 mL) and extracted with ethyl acetate (2×30 mL). The combined organic layers were washed with brine (20 mL), dried over sodium sulphate and concentrated to afford 2-(3-chloro-2-methylphenyl)-2,2-difluoroacetic acid (382 g, 1.736 mmol, 60% yield) as an solid. MS (ESI) m/z 219.17 [M−1]$^−$.

E. 2-(3-Chloro-2-methylphenyl)-N-((2-(2,6-dioxopiperidin-3-yl)-1-oxoisoindolin-5-yl)methyl)-2,2-difluoroacetamide To a cold (0° C.) stirred solution of 2-(3-chloro-2-methylphenyl)-2,2-difluoroacetic acid (213 mg, 0.968 mmol) in pyridine was added phosphorus oxychloride (0.27 mL, 2.906 mmol) dropwise and stirred at 0-5° C. for 1 h and then added 3-(5-(aminomethyl)-1-oxoisoindolin-2-yl)piperidine-2,6-dione hydrochloride (300 mg, 0.968 mmol) and stirred at room temperature for 30 min. The reaction mixture was neutralized with aqueous saturated sodium bicarbonate (up to pH-8) and extracted with ethyl acetate (3×50 mL). The combined organic layer was washed with water (2×10 mL), brine (10 mL) and dried over sodium sulphate and concentrated. The resultant residue was purified by Reveleris C-18 reversed phase column chromatography using 40-55% acetonitrile in aqueous formic acid (0.1%) to afford 2-(3-chloro-2-methylphenyl)-N-((2-(2,6-dioxopiperidin-3-yl)-1-oxoisoindolin-5-yl)methyl)-2,2-difluoroacetamide (62 mg, 0.130 mmol, 13% yield) as white solid. MS (ESI) m/z 476.07 [M+1]$^+$. $^1$H NMR (300 MHz, DMSO-d$_6$) δ 10.98 (s, 1H), 9.68 (s, 1H), 7.68 (dd, J=15.3, 7.9 Hz, 2H), 7.55 (d, J=7.3 Hz, 1H), 7.46 (s, 1H), 7.44-7.34 (m, 2H), 5.11 (dd, J=13.3, 5.0 Hz, 1H), 4.52-4.27 (m, 4H), 3.00-2.84 (m, 1H), 2.66-2.55 (m, 1H), 2.43-2.30 (m, 4H), 2.04-1.94 (m, 1H).

Example 42

N-((2-(2,6-dioxopiperidin-3-yl)-1-oxoisoindolin-5-yl)methyl)-2,2-difluoro-2-(4-fluoro-2-(trifluoromethyl)phenyl)acetamide

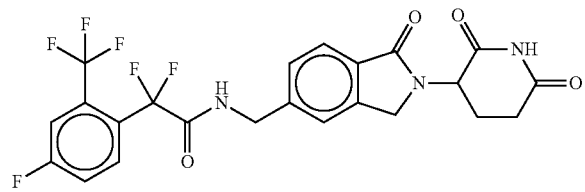

A. Ethyl 2,2-difluoro-2-(4-fluoro-2-(trifluoromethyl)phenyl)acetate

To a stirred solution of 4-fluoro-1-iodo-2-(trifluoromethyl)benzene (500 mg, 1.72 mmol) in dimethylsulfoxide (5.2 mL) was added copper (329 mg, 5.17 mmol) and ethyl 2-bromo-2,2-difluoroacetate (418 mg, 2.07 mmol) at room temperature and stirred at 55° C. for 16 h. The reaction mixture was neutralized with aqueous saturated ammonium chloride solution and extracted with ethyl acetate (3×25 mL). The combined organic layers were washed with water (2×25 mL), brine (25 mL), dried over sodium sulphate and concentrated to afford ethyl 2,2-difluoro-2-(4-fluoro-2-(trifluoromethyl)phenyl)acetate (300 mg, 1.05 mmol, 61%). 1H NMR (400 MHz, CDCl$_3$) δ 7.87-7.83 (m, 1H), 7.51-7.48 (m, 1H), 7.39-7.34 (m, 1H), 4.35-4.30 (m, 2H), 1.30 (t, J=5.1 Hz, 3H).

B. 2,2-Difluoro-2-(4-fluoro-2-(trifluoromethyl)phenyl)acetic acid

To a stirred solution of ethyl 2,2-difluoro-2-(4-fluoro-2-(trifluoromethyl)phenyl)acetate (300 mg, 1.05 mmol) in tetrahydrofuran:methanol:water mixture (15 mL, 1:1:1) was added lithium hydroxide (132 mg, 3.15 mmol) and stirred at room temperature for 4 h. The reaction mixture was concentrated and the residue was neutralized with saturated potassium bisulphate (20 mL) and extracted with ethyl acetate (2×25 mL). The combined organic layers were washed with brine (25 mL), dried over sodium sulphate and concentrated to afford 2,2-difluoro-2-(4-fluoro-2-(trifluoromethyl)phenyl)acetic acid (220 mg, 0.85 mmol, 81% yield). MS (ESI) m/z 257.1[M−1]$^+$.

C. N-((2-(2,6-dioxopiperidin-3-yl)-1-oxoisoindolin-5-yl)methyl)-2,2-difluoro-2-(4-fluoro-2-(trifluoromethyl)phenyl)acetamide To a cold (0° C.) stirred solution of 2,2-difluoro-2-(4-fluoro-2-(trifluoromethyl)phenyl)acetic acid (200 mg, 0.78 mmol) in pyridine (20 mL) was added phosphoryl chloride (356 mg, 2.32 mmol) dropwise and stirred at 0-5° C. for 1 h and then added 3-(5-(aminomethyl)-1-oxoisoindolin-2-yl)piperidine-2,6-dione hydrochloride (302 mg, 0.78 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 55-60% acetonitrile in aqueous formic acid (0.1%) to afford N-((2-(2,6-dioxopiperidin-3-yl)-1-oxoisoindolin-5-yl)methyl)-2,2-difluoro-2-(4-fluoro-2-(trifluoromethyl)phenyl)acetamide (75 mg, 0.17 mmol, 21% yield) as a white solid. MS (ESI) m/z 514.07 [M+1]$^+$. $^1$H NMR (300 MHz, DMSO-d$_6$) δ=10.98 (s, 1H), 9.73-9.62 (m, 1H), 7.96-7.82 (m, 2H), 7.78-7.67 (m, 2H), 7.49-7.37 (m, 2H), 5.11 (dd, J=4.8, 13.2 Hz, 1H), 4.53-4.26 (m, 4H), 3.00-2.82 (m, 1H), 2.77-2.54 (m, 1H), 2.44-2.23 (m, 1H), 2.08-1.93 (m, 1H)

Example 43

2-(4-Chloro-2-methylphenyl)-N-((2-(2,6-dioxopiperidin-3-yl)-1-oxoisoindolin-5-yl)methyl)-2,2-difluoroacetamide

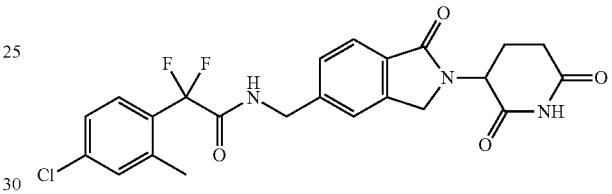

A. 1-(4-Chloro-2-methylphenyl)ethanone

To a stirred solution of 4-chloro-2-methylbenzonitrile (2.0 g, 13.193 mmol) in benzene (30 mL) was added methyl magnesium iodide (3M) in diethyl ether solution (5.27 mL, 15.83 mmol) at 0° C. and stirred for 16 h at 75° C. The reaction mixture was cooled to 0° C. and quenched with 6N hydrochloric acid solution (20 mL) and continued to stir at 75° C. for 4 h. The reaction mixture was quenched with water and extracted with ethyl acetate (3×50 mL). The combined organic layers were washed with water (2×20 mL), brine (20 mL), dried over sodium sulphate and concentrated. The obtained residue was purified by column chromatography (100-200 silica) using 5-10% ethyl acetate in petroleum ether to afford 1-(4-chloro-2-methylphenyl)ethanone (1.5 g, 8.928 mmol, 67% yield) as a colorless liquid. GCMS (ESI) m/z. 168.1.

B. Ethyl 2-(4-chloro-2-methylphenyl)-2-oxoacetate

To a stirred solution of 1-(4-chloro-2-methylphenyl)ethanone (1.5 g, 8.928 mmol) in pyridine (30 mL) was added selenium dioxide (2 g, 17.857 mmol) and stirred for 16 h at 100° C. The reaction mixture was cooled to room temperature, diluted with dichloromethane (30 mL) and filtered through Celite pad. To the filtrate was added ethyl chloroformate (3 mL) at 0° C. and stirred for 2 h. The reaction mixture was quenched with water and extracted with ethyl acetate (3×50 mL). The combined organic layers were washed with water (2×20 mL), brine (20 mL), dried over sodium sulphate and concentrated. The obtained residue was purified by column chromatography (100-200 silica) using 5-10% ethyl acetate in pet. ether to afford ethyl 2-(4-chloro-2-methylphenyl)-2-oxoacetate (1.1 g, 4.867 mmol, 54% yield) as a colorless liquid. MS (ESI) m/z. 226.2.

C. Ethyl 2-(4-chloro-2-methylphenyl)-2,2-difluoroacetate

To ethyl 2-(4-chloro-2-methylphenyl)-2-oxoacetate (1.1 g, 4.867 mmol) was added diethylaminosulfur trifluoride (1.6 mL, 12.168 mmol) and stirred for 12 h at room temperature. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated to afford ethyl 2-(4-chloro-2-methylphenyl)-2,2-difluoroacetate (692 mg, 2.790 mmol, 57% yield) as a colorless liquid. GCMS (ESI) m/z. 248.1.

D. 2-(4-Chloro-2-methylphenyl)-2,2-difluoroacetic acid

To a cold (0° C.) stirred solution of ethyl 2-(4-chloro-2-methylphenyl)-2,2-difluoroacetate (692 mg, 2.790 mmol) in tetrahydrofuran:ethanol:water mixture (30 mL, 1:1:1) was added lithium hydroxide (585 mg, 13.951 mmol) and stirred at room temperature for 6 h. The reaction mixture was concentrated and the residue was neutralized with 10% aqueous hydrochloric acid (10 mL) and extracted with ethyl acetate (2×20 mL). The combined organic layers were washed with brine (20 mL), dried over sodium sulphate and concentrated to afford 2-(4-chloro-2-methylphenyl)-2,2-difluoroacetic acid (446 g, 2.027 mmol, 72% yield) as an brown liquid. MS (ESI) m/z 219.29 [M−1]⁻.

E. 2-(4-Chloro-2-methylphenyl)-N-((2-(2,6-dioxopiperidin-3-yl)-1-oxoisoindolin-5-yl)methyl)-2,2-difluoroacetamide To a cold (0° C.) stirred solution of 2-(4-chloro-2-methylphenyl)-2,2-difluoroacetic acid (213 mg, 0.968 mmol) in pyridine was added phosphorus oxychloride (0.27 mL, 2.906 mmol) dropwise and stirred at 0-5° C. for 1 h and then added 3-(5-(aminomethyl)-1-oxoisoindolin-2-yl)piperidine-2,6-dione hydrochloride (300 mg, 0.968 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The obtained residue was purified by Reveleris C-18 reversed phase column chromatography using 40-60% acetonitrile in aqueous formic acid (0.1%) to afford 2-(4-chloro-2-methylphenyl)-N-((2-(2,6-dioxopiperidin-3-yl)-1-oxoisoindolin-5-yl)methyl)-2,2-difluoroacetamide (90 mg, 0.189 mmol, 19.5% yield) as an off white solid. MS (ESI) m/z 476.09 [M+1]⁺. ¹H NMR (300 MHz, DMSO-d₆) δ 10.99 (s, 1H), 9.65 (t, J=5.9 Hz, 1H), 7.70 (d, J=7.8 Hz, 1H), 7.54 (d, J=8.3 Hz, 1H), 7.50-7.31 (m, 4H), 5.11 (dd, J=13.2, 5.1 Hz, 1H), 4.52-4.25 (m, 4H), 3.00-2.85 (m, 1H), 2.65-2.55 (m, 1H), 2.45-2.31 (m, 4H), 2.08-1.94 (m, 1H).

Example 44

N-((2-(2,6-Dioxopiperidin-3-yl)-1-oxoisoindolin-5-yl)methyl)-2,2-difluoro-2-(4-fluoro-2-methylphenyl)acetamide

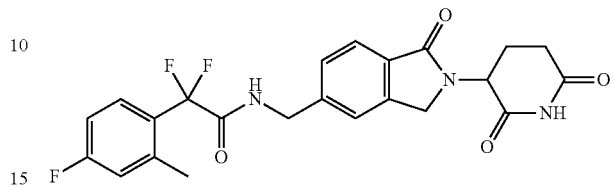

A. 1-(4-Fluoro-2-methylphenyl)ethanone

To a stirred solution of 4-fluoro-2-methylbenzonitrile (2.0 g, 14.803 mmol) in benzene (30 mL) was added methyl magnesium iodide (3M) in diethyl ether solution (5.92 mL, 17.764 mmol) at 0° C. and stirred for 16 h at 75° C. The reaction mixture was cooled to 0° C. and quenched with 6N hydrochloric acid solution (20 mL) and continued to stir at 75° C. for 4 h. The reaction mixture was quenched with water and extracted with ethyl acetate (3×50 mL). The combined organic layers were washed with water (2×20 mL), brine (20 mL), dried over sodium sulphate and concentrated. The residue obtained was purified by column chromatography (100-200 silica) using 5-10% ethyl acetate in petroleum ether to afford 1-(4-fluoro-2-methylphenyl)ethanone (1.6 g, 10.526 mmol, 71% yield) as a colourless liquid. GCMS (ESI) m/z. 152.2.

B. Ethyl 2-(4-fluoro-2-methylphenyl)-2-oxoacetate

To a stirred solution of 1-(4-fluoro-2-methylphenyl)ethanone (1.6 g, 10.526 mmol) in pyridine (30 mL) was added selenium dioxide (2.3 g, 21.052 mmol) and stirred for 16 h at 100° C. The reaction mixture was cooled to room temperature, diluted with dichloromethane (30 mL) and filtered through Celite pad. To the filtrate was added ethyl chloroformate (3.2 mL) at 0° C. and stirred for 2 h. The reaction mixture was quenched with water and extracted with ethyl acetate (3×50 mL). The combined organic layers were washed with water (2×20 mL), brine (20 mL), dried over sodium sulphate and concentrated. Obtained residue was purified by column chromatography (100-200 silica) using 5-10% ethyl acetate in petether to afford ethyl 2-(4-fluoro-2-methylphenyl)-2-oxoacetate (1.37 g, 6.523 mmol, 62% yield) as a colourless liquid. GCMS (ESI) m/z. 210.1.

C. Ethyl 2,2-difluoro-2-(4-fluoro-2-methylphenyl)acetate

To ethyl 2-(4-chloro-2-methylphenyl)-2-oxoacetate (1.37 g, 6.523 mmol) was added diethylaminosulfur trifluoride (2.1 mL, 16.307 mmol) and stirred for 12 h at room temperature. The reaction mixture was neutralized with aqueous saturated sodium bicarbonate (up to pH-8) and extracted with ethyl acetate (3×50 mL). The combined organic layers were washed with water (2×20 mL), brine (20 mL), dried over sodium sulphate and concentrated to afford ethyl 2,2-difluoro-2-(4-fluoro-2-methylphenyl)acetate (860 mg, 3.706 mmol, 57% yield) as a colourless liquid. GCMS (ESI) m/z. 232.2.

D. 2,2-Difluoro-2-(4-fluoro-2-methylphenyl)acetic acid

To a cold (0° C.) stirred solution of ethyl 2-(4-chloro-2-methylphenyl)-2,2-difluoroacetate (860 mg, 3.706 mmol) in tetrahydrofuran:ethanol:water mixture (30 mL, 1:1:1) was added lithium hydroxide monohydrate (933 mg, 22.241 mmol) and stirred at room temperature for 6 h. The reaction mixture was concentrated and the residue was neutralized with 10% aqueous hydrochloric acid (10 mL) and extracted with ethyl acetate (2×20 mL). The combined organic layers were washed with brine (20 mL), dried over sodium sulphate and concentrated to afford 2,2-difluoro-2-(4-fluoro-2-methylphenyl)acetic acid (684 g, 2.948 mmol, 72% yield) as an brown liquid. LCMS (ESI) m/z 203.37 [M−1]$^{−ve}$.

E. N-((2-(2,6-Dioxopiperidin-3-yl)-1-oxoisoindolin-5-yl)methyl)-2,2-difluoro-2-(4-fluoro-2-methylphenyl)acetamide To a cold (0° C.) stirred solution of 2,2-difluoro-2-(4-fluoro-2-methylphenyl)acetic acid (197 mg, 0.968 mmol) in pyridine was added phosphorus oxychloride (0.27 mL, 2.906 mmol) dropwise and stirred at 0-5° C. for 1 h. To this reaction mixture was then added 3-(5-(aminomethyl)-1-oxoisoindolin-2-yl)piperidine-2,6-dione hydrochloride (300 mg, 0.968 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The residue obtained was purified by Reveleris C-18 reversed phase column chromatography using 50-60% acetonitrile in aqueous formic acid (0.1%) to afford N-((2-(2,6-Dioxopiperidin-3-yl)-1-oxoisoindolin-5-yl)methyl)-2,2-difluoro-2-(4-fluoro-2-methylphenyl)acetamide (79 mg, 0.172 mmol, 18% yield) as an off white solid. MS (ESI) m/z 460.10 [M+1]$^{+}$. $^{1}$H NMR (300 MHz, DMSO-d$_{6}$) δ 10.99 (s, 1H), 9.63 (t, J=6.0 Hz, 1H), 7.70 (d, J=7.8 Hz, 1H), 7.56 (dd, J=8.7, 5.8 Hz, 1H), 7.46 (s, 1H), 7.40 (d, J=7.6 Hz, 1H), 7.25-7.11 (m, 2H), 5.11 (dd, J=13.3, 5.0 Hz, 1H), 4.50-4.27 (m, 4H), 2.98-2.86 (m, 1H), 2.68-2.55 (m, 1H), 2.46-2.28 (m, 4H), 2.08-1.94 (m, 1H).

Example 45

2-(4-Chloro-2-(trifluoromethyl)phenyl)-N-((2-(2,6-dioxopiperidin-3-yl)-1-oxoisoindolin-5-yl)methyl)-2,2-difluoroacetamide

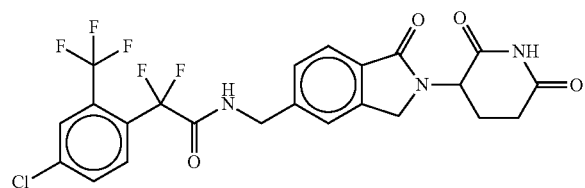

A. Ethyl 2-(4-chloro-2-(trifluoromethyl)phenyl)-2,2-difluoroacetate

To a stirred solution of 4-chloro-1-iodo-2-(trifluoromethyl)benzene (1.0 g, 3.26 mmol) in dimethylsulfoxide (15 mL) was added copper (539 mg, 8.48 mmol) and ethyl 2-bromo-2,2-difluoroacetate (994 mg, 4.89 mmol) at room temperature and stirred at 55° C. for 16 h. The reaction mixture was neutralized with aqueous saturated ammonium chloride solution and extracted with ethyl acetate (2×100 mL). The combined organic layers were washed with water (2×100 mL), brine (100 mL), dried over sodium sulphate and concentrated to afford ethyl 2-(4-chloro-2-(trifluoromethyl)phenyl)-2,2-difluoroacetate (900 mg, 2.98 mmol, 91%). GCMS (m/z) 302.0 [M]$^{+}$.

B. 2-(4-Chloro-2-(trifluoromethyl)phenyl)-2,2-difluoroacetic acid

To a stirred solution of ethyl 2-(4-chloro-2-(trifluoromethyl)phenyl)-2,2-difluoroacetate (900 mg, 2.98 mmol) in tetrahydrofuran:methanol:water (15 mL, 1:1:1) was added lithium hydroxide (375 mg, 8.94 mmol) and stirred at room temperature for 4 h. The reaction mixture was concentrated and the residue was neutralized with saturated potassium hydrogen sulphate (20 mL) and extracted with ethyl acetate (2×100 mL). The combined organic layers were washed with brine (100 mL), dried over sodium sulphate and concentrated to afford 2-(4-chloro-2-(trifluoromethyl)phenyl)-2,2-difluoroacetic acid (700 mg, 2.55 mmol, 86% yield). GCMS (m/z) 274.1 [M]$^{+}$.

C. 2-(4-Chloro-2-(trifluoromethyl)phenyl)-N-((2-(2,6-dioxopiperidin-3-yl)-1-oxoisoindolin-5-yl)methyl)-2,2-difluoroacetamide To a cold (0° C.) stirred solution of 2-(4-chloro-2-(trifluoromethyl)phenyl)-2,2-difluoroacetic acid (200 mg, 0.72 mmol) in pyridine (10 mL) was added phosphoryl chloride (336 mg, 2.18 mmol) dropwise and stirred at 0-5° C. for 1 h. and then added 3-(5-(aminomethyl)-1-oxoisoindolin-2-yl)piperidine-2,6-dione hydrochloride (226 mg, 0.72 mmol) and stirred at room temperature for 1 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 80-90% acetonitrile in aqueous formic acid (0.1%) to afford 2-(4-chloro-2-(trifluoromethyl)phenyl)-N-((2-(2,6-dioxopiperidin-3-yl)-1-oxoisoindolin-5-yl)methyl)-2,2-difluoroacetamide (80 mg, 0.11 mmol, 21% yield) as an off-white solid. LCMS (ESI) m/z 530.05 [M+1]$^{+}$. $^{1}$H NMR (300 MHz, DMSO-d$_{6}$) δ 10.98 (s, 1H), 9.70 (br t, J=5.9 Hz, 1H), 8.03 (s, 1H), 7.97 (br d, J=8.4 Hz, 1H), 7.85 (d, J=9 Hz, 1H), 7.70 (d, J=7.7 Hz, 1H), 7.47 (s, 1H), 7.41 (br d, J=7.7 Hz, 1H), 5.11 (br dd, J=4.8, 13.2 Hz, 1H), 4.53-4.25 (m, 4H), 3.01-2.82 (m, 1H), 2.67-2.54 (m, 1H), 2.48-2.30 (m, 1H), 2.08-1.94 (m, 1H)

Example 46

2-Cyclohexyl-N-((2-(2,6-dioxopiperidin-3-yl)-1-oxoisoindolin-5-yl)methyl)-2,2-difluoroacetamide

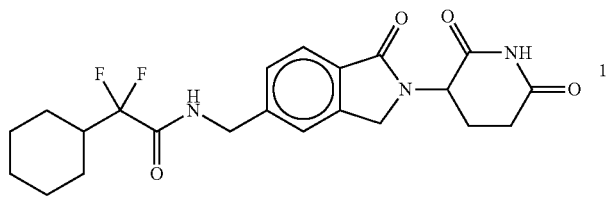

A. Ethyl 2-cyclohexyl-2,2-difluoroacetate

Ethyl-2-cyclohexyl-2-oxoacetate (1 g, 5.43 mmol) was added into diethylamino sulfur trifluoride (2.5 mL) at 0° C. and stirred at room temperature for 16 h. The reaction mixture was quenched with aqueous sodium bicarbonate solution and extracted with ethyl acetate (3×20 mL). The combined organic layers were washed with brine (20 mL), dried over sodium sulphate, filtered and solvent was evaporated. Obtained crude was purified by column chromatography (100-200 silica gel, 10% ethyl acetate in pet ether) to afford ethyl 2-cyclohexyl-2,2-difluoroacetate (900 mg, 4.36 mmol, 80% yield) as a colourless liquid. $^1$H NMR (300 MHz, CDCl$_3$) 4.32 (q, J=6.9 Hz, 2H), 2.06-2.04 (m, 1H), 1.80-1.60 (m, 6H), 1.37-1.30 (m, 4H), 1.26-1.19 (m, 3H).

B. 2-Cyclohexyl-2,2-difluoroacetic acid

To a stirred solution of ethyl 2-cyclohexyl-2,2-difluoroacetate (900 mg, 4.36 mmol) in mixture of tetrahydrofuran:ethanol:water (15 mL, 1:1:1), was added lithium hydroxide monohydrate (550 mg, 13.10 mmol) and stirred at room temperature for 16 h. The volatiles were evaporated under reduced pressure and the resultant residue was dissolved in water (15 mL) and washed with ethyl acetate (2×15 mL). Aqueous layer was acidified with 1N hydrochloride aqueous solution and extracted with ethyl acetate (3×20 mL). The combined organic layers were washed with brine (20 mL), dried over sodium sulphate, filtered and solvent was evaporated to afford 2-cyclohexyl-2,2-difluoroacetic acid (550 mg, 3.08 mmol, 70% yield) as semi-solid compound. MS (ESI) m/z 178 [M]$^+$.

C. 2-Cyclohexyl-N-((2-(2,6-dioxopiperidin-3-yl)-1-oxoisoindolin-5-yl)methyl)-2,2-difluoroacetamide To an ice cold solution of 2-cyclohexyl-2,2-difluoroacetic acid (207 mg, 1.16 mmol) in pyridine (6 mL) was added phosphorus oxychloride (0.27 mL, 2.9 mmol) dropwise and stirred at 0-5° C. for 1 h. Then, the reaction mixture was treated with 3-(5-(aminomethyl)-1-oxoisoindolin-2-yl)piperidine-2,6-dione hydrochloride (300 mg, 0.97 mmol) and stirred at room temperature for 2 h. The reaction mixture was basified with aqueous saturated sodium bicarbonate solution and extracted with ethyl acetate (3×15 mL). The combined organic layers were washed with water (15 mL), brine (15 mL), dried over sodium sulphate, filtered and solvent was evaporated. The resultant residue was purified by Reveleris C-18 reversed phase column chromatography (50-55% acetonitrile in 0.1% aqueous formic acid) to afford 2-cyclohexyl-N-((2-(2,6-dioxopiperidin-3-yl)-1-oxoisoindolin-5-yl)methyl)-2,2-di fluoro acetamide (53 mg, 0.122 mmol, 12% yield) as white solid. MS (ESI) m/z 434.07 [M+1]$^+$. $^1$H NMR (300 MHz, DMSO-d$_6$) δ 10.99 (s, 1H), 9.35 (t, J=6.0 Hz, 1H), 7.70 (d, J=7.8 Hz, 1H), 7.47 (s, 1H), 7.41 (d, J=7.8 Hz, 1H), 5.11 (dd, J=13.2, 5.4 Hz, 1H), 4.45 (d, J=16.8 Hz, 1H), 4.44 (d, J=6.6 Hz, 2H), 4.31 (d, J=17.7 Hz, 1H), 2.93-2.85 (m, 1H), 2.63-2.56 (m, 1H), 2.45-2.36 (m, 1H), 2.10-1.97 (m, 2H), 1.74-1.64 (m, 5H), 1.23-1.08 (m, 5H).

Example 47

2-(4-Chloro-2-(trifluoromethoxy)phenyl)-N-((2-(2,6-dioxopiperidin-3-yl)-1-oxoisoindolin-5-yl)methyl)-2,2-difluoroacetamide

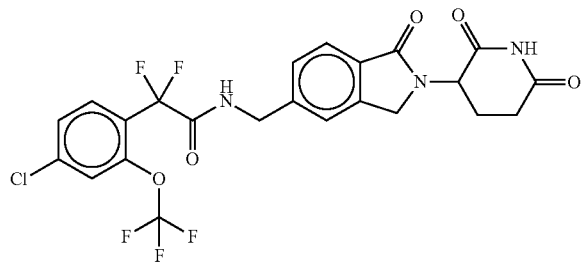

A. 4-Chloro-1-iodo-2-(trifluoromethoxy)benzene

To a solution of 4-chloro-2-(trifluoromethoxy)aniline (2 g, 10.025 mmol) in 66% aqueous sulfuric acid (10 mL) was added a solution of sodium nitrite (760 mg, 11.027 mmol) in water (2 mL) at 0° C. and stirred at 0° C. for 20 min. Then a solution of urea (90 mg, 1.5 mmol) in water (1 mL) was added at 0° C. and stirred at same temperature for 10 min. Then a solution of potassium iodide (3.49 g, 21.052 mmol) in water (5 mL) was added at 0° C. and stirred at 50° C. for 2 h. To the reaction mixture was added ethyl acetate (300 mL) and washed with water (2×100 mL), brine (100 mL) and dried over sodium sulphate, and concentrated. The resultant residue was purified by silica gel (100-200) chromatography using pentane as eluent to afford the 4-chloro-1-iodo-2-(trifluoromethoxy)benzene (2.1 g, 6.52 mmol, 69% yield) as a colorless syrup. $^1$H NMR (400 MHz, CDCl$_3$) δ (ppm) 7.79 (d, J=8.8 Hz, 1H), 7.32-7.26 (m, 1H), 7.05 (dd, J=2.4, 8.3 Hz, 1H).

B. Ethyl 2-(4-chloro-2-(trifluoromethoxy)phenyl)-2,2-difluoroacetate

To a stirred solution of 4-fluoro-1-iodo-2-(trifluoromethyl)benzene (2.1 g, 6.525 mmol) in dimethyl sulfoxide (10 mL) was added copper powder (1.03 g, 16.31 mmol) and ethyl 2-bromo-2,2-difluoroacetate (1.25 mL, 9.78 mmol) at room temperature and stirred at 60° C. for 16 h. The reaction mixture was neutralized with aqueous saturated ammonium chloride solution and extracted with ethyl acetate (3×50 mL). The combined organic layers were washed with water (2×50 mL), brine (25 mL), dried over sodium sulphate and concentrated. The resultant residue was purified by silica gel (100-200) chromatography using 5% diethyl ether in pentane as eluent to afford ethyl 2-(4-chloro-2-(trifluoromethoxy)phenyl)-2,2-difluoroacetate (1.8 g, 5.66 mmol, 87%). 1H NMR (300 MHz, CDCl$_3$) δ (ppm) 7.70 (d, J=8.4 Hz, 1H), 7.44-7.32 (m, 2H), 4.34 (q, J=7.3 Hz, 2H), 1.32 (t, J=7.1 Hz, 3H).

C. 2-(4-Chloro-2-(trifluoromethoxy)phenyl)-2,2-difluoroacetic acid

To a stirred solution of 2-(4-chloro-2-(trifluoromethoxy)phenyl)-2,2-difluoroacetate (1.8 g, 6.14 mmol) in tetrahydrofuran:methanol:water mixture (15 mL, 1:1:1) was added lithium hydroxide monohydrate (774 mg, 18.42 mmol) and stirred at room temperature for 2 h. The reaction mixture was concentrated and the residue was neutralized with saturated potassium bisulphate (20 mL) and extracted with ethyl acetate (2×50 mL). The combined organic layers were washed with brine (25 mL), dried over sodium sulphate and concentrated to afford 2-(4-chloro-2-(trifluoromethoxy)phenyl)-2,2-difluoroacetic acid (1.2 g, 4.137 mmol, 73% yield). MS (ESI) m/z 289.14[M−1]$^+$.

D. 2-(4-Chloro-2-(trifluoromethoxy)phenyl)-N-((2-(2,6-dioxopiperidin-3-yl)-1-oxoisoindolin-5-yl)methyl)-2,2-difluoroacetamide To a cold (0° C.) stirred solution of 3-(5-(aminomethyl)-1-oxoisoindolin-2-yl)piperidine-2,6-dione hydrochloride (300 mg, 0.97 mmol) and 2-(4-chloro-2-(trifluoromethoxy)phenyl)-2,2-difluoroacetic acid (280 mg, 0.97 mmol) in N,N-dimethylformamide (10 mL) was added N,N-diisopropylethylamine (375 mg, 2.91 mmol) followed by 1-[Bis(dimethylamino)methylene]-1H-1,2,3-triazolo[4,5-b]pyridinium 3-oxid hexafluorophosphate (480 mg, 1.26 mmol) and continued stirring at room temperature for 16 h. The reaction mixture was diluted with water (100 mL) and the solid obtained was filtered, washed with diethyl ether (20 mL), dried and purified using silica gel chromatography (3% methanol in chloroform) to afford 2-(4-chloro-2-(trifluoromethoxy)phenyl)-N-((2-(2,6-dioxopiperidin-3-yl)-1-oxoisoindolin-5-yl)methyl)-2,2-difluoroacetamide (70 mg, 0.128 mmol, 13% yield) as a white solid. MS (ESI) m/z 545.97 (M+1)$^+$. $^1$H NMR (300 MHz, DMSO-d$_6$) δ (ppm) 10.95 (br s, 1H), 9.72 (br t, J=5.7 Hz, 1H), 7.79 (d, J=9.2 Hz, 1H), 7.71-7.61 (m, 3H), 7.46 (s, 1H), 7.41 (d, J=8.1 Hz, 1H), 5.10 (br dd, J=5.1, 13.2 Hz, 1H), 4.50-4.25 (m, 4H), 2.99-2.80 (m, 1H), 2.68-2.53 (m, 1H), 2.47-2.30 (m, 2H), 2.04-1.92 (m, 1H).

Example 48

N-((2-(2,6-Dioxopiperidin-3-yl)-1-oxoisoindolin-5-yl)methyl)-2,2-difluoro-2-(3-(2-methoxyethoxy)phenyl)acetamide

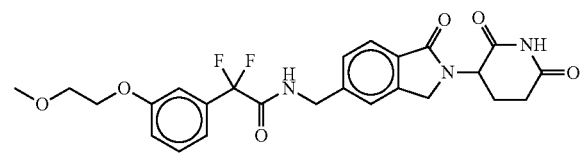

A. 1-Iodo-3-(2-methoxyethoxy)benzene

To a stirred solution of 3-iodophenol (2 g, 9.09 mmol) in N,N-dimethylformamide (20 mL) was added potassium carbonate (3.13 g, 22.72 mmol) followed by 1-bromo-2-methoxyethane (1.51 g, 10.90 mmol) at RT and stirred at 70° C. for 16 h. The reaction mixture was quenched with ice water (30 mL) and extracted with ethyl acetate (3×20 mL). The combined organic layers were washed with water (20 mL), brine (20 mL), dried over sodium sulfate, filtered and concentrated. Obtained crude was purified by column chromatography (100-200 silica gel) using 15% ethyl acetate in pet ether was used as eluent to afford 1-iodo-3-(2-methoxyethoxy)benzene (1.3 g, 4.69 mmol, 52% yield) as colorless liquid. MS (ESI) m/z 279.04 [M+1]$^+$.

B. Ethyl 2,2-difluoro-2-(3-(2-methoxyethoxy)phenyl)acetate

To a stirred solution of 1-iodo-3-(2-methoxyethoxy)benzene (1 g, 3.6 mmol) in dimethylsulfoxide (15 mL) was added ethyl 2-bromo-2,2-difluoroacetate (0.69 mL, 5.41 mmol) and copper (0.59 g, 9.36 mmol) at 0° C. and stirred at 60° C. for 5 h. The reaction mixture was quenched with ice water and filtered through celite pad; filtrate was extracted with ethyl acetate (3×20 mL). The combined organic layers were washed with water (15 mL), brine (15 mL), dried over sodium sulfate, filtered and concentrated to afford ethyl 2,2-difluoro-2-(3-(2-methoxyethoxy)phenyl)acetate (0.60 g, 2.19 mmol, 61%) as a brown liquid. MS (ESI) m/z 274.1 [M]$^+$.

C. 2,2-Difluoro-2-(3-(2-methoxyethoxy)phenyl)acetic acid

To a cold (0° C.) stirred solution of ethyl 2,2-difluoro-2-(3-(2-methoxyethoxy)phenyl)acetate (800 mg, 2.93 mmol) in methanol:tetrahydrofuran:water mixture (15 mL, 1:1:1) was added lithium hydroxide monohydrate (370 mg, 8.79 mmol) and stirred at room temperature for 5 h. The reaction mixture was concentrated and obtained crude was diluted with water (10 mL) and washed with ethyl acetate (2×10 mL). Aqueous layer was acidified with 2N aqueous hydrochloric acid (10 mL) and extracted with ethyl acetate (3×15 mL). The combined organic layers were washed with brine (15 mL), dried over sodium sulfate, filtered; filtrate was concentrated to afford 2,2-difluoro-2-(3-(2-methoxyethoxy)phenyl)acetic acid (600 mg, 3.47 mmol, 83% yield) as a brown semi solid. $^1$H NMR (300 MHz, DMSO-d$_6$) δ 7.37-7.33 (m, 1H), 7.22-7.15 (m, 2H), 7.05-7.03 (m, 1H), 4.84 (brs, 1H), 4.14 (s, 3H), 3.86-3.77 (m, 4H).

D. N-((2-(2,6-Dioxopiperidin-3-yl)-1-oxoisoindolin-5-yl)methyl)-2,2-difluoro-2-(3-(2-methoxyethoxy)phenyl)acetamide To a cold (0° C.) stirred solution of 2,2-difluoro-2-(3-(2-methoxyethoxy)phenyl)acetic acid (285 mg, 1.16 mmol) in pyridine (3 mL) was added phosphoryl chloride (0.27 mL, 2.91 mmol) dropwise and stirred at 0-5° C. for 1 h and then added 3-(5-(aminomethyl)-1-oxoisoindolin-2-yl)piperidine-2,6-dione hydrochloride (300 mg, 0.97 mmol) and stirred at room temperature for 30 min. The reaction mixture was basified with aqueous saturated sodium bicarbonate (up to pH-8) and extracted with ethyl acetate (3×15 mL). The combined organic layers were washed with water (15 mL), brine (15 mL), dried over sodium sulfate and filtered, concentrated. The resultant residue was purified by Reveleris C-18 reversed phase column chromatography using 50-55% acetonitrile in aqueous formic acid (0.1%) afford N-((2-(2,6-dioxopiperidin-3-yl)-1-oxoisoindolin-5-yl) methyl)-2,2-difluoro-2-(3-(2-methoxyethoxy)phenyl)acetamide (48 mg, 0.09 mmol, 9% yield) as an off-white solid. MS (ESI) m/z 501.96 [M+1]+. 1H NMR (300 MHz, DMSO-d6) δ 10.98 (s, 1H), 9.54 (t, J=5.8 Hz, 1H), 7.67 (d, J=8.1 Hz, 1H), 7.47-7.35 (m, 3H), 7.16-7.11 (m, 3H), 5.12 (dd, J=13.2, 5.1 Hz, 1H), 4.45-4.27 (m, 4H), 4.11 (t, J=4.2 Hz, 2H), 3.65 (t, J=4.5 Hz, 2H), 3.30 (s, 3H), 2.91-2.80 (m, 1H), 2.63-2.57 (m, 1H), 2.44-2.36 (m, 1H), 2.08-2.05 (m, 1H).

Example 49

N-((2-(2,6-Dioxopiperidin-3-yl)-1-oxoisoindolin-5-yl)methyl)-2,2-difluoro-2-(3-(2-hydroxyethoxy)phenyl)acetamide

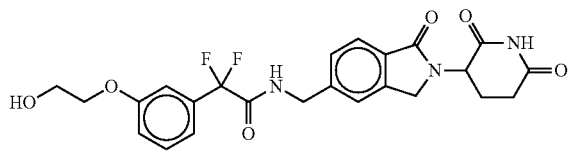

A. (2-Bromoethoxy)(tert-butyl)dimethylsilane

To a stirred solution of 2-bromoethanol (10 g, 80 mmol) in dichloromethane (100 mL) was added tert-butylchlorodimethylsilane (14.5 g, 96.77 mmol) and imidazole (10 g, 161.2 mmol) at 0° C. and stirred at room temperature for 12 h. The reaction mixture was quenched with aqueous sodium bicarbonate solution (40 mL) and extracted with ethyl acetate (3×50 mL). The combined organic layers were washed with water (40 mL), brine (40 mL), dried over sodium sulfate and concentrated to afford (2-bromoethoxy)(tert-butyl)dimethylsilane (8 g, 33.61 mmol, 42% yield) as colorless liquid.

B.
Tert-butyl(2-(3-iodophenoxy)ethoxy)dimethylsilane

To a stirred solution of (2-bromoethoxy)(tert-butyl)dimethylsilane (5.19 g, 21.8 mmol) in N,N-dimethylformamide (20 mL) was added potassium carbonate (6.27 g, 45.45 mmol), tetrabutyl ammonium iodide (1.34 g, 3.63 mmol) followed by 3-iodophenol (4 g, 18.18 mmol) at RT and stirred at 70° C. for 16 h. The reaction mixture was quenched with ice water (20 mL) and extracted with ethyl acetate (3×50 mL). The combined organic layers were washed with water (40 mL), brine (40 mL), dried over sodium sulfate, filtered and concentrated. Obtained crude was purified by column chromatography (100-200 silica gel, 15% ethyl acetate in pet ether) to afford tert-butyl(2-(3-iodophenoxy) ethoxy)dimethylsilane (3.5 g, 9.25 mmol, 43% yield) as colorless liquid. 1H NMR (300 MHz, CDCl3) δ 7.28-7.26 (m, 2H), 6.98 (t, J=8.4 Hz, 1H), 6.89-6.86 (m, 1H), 4.02-3.94 (m, 4H), 0.90 (s, 9H), 0.07 (s, 6H).

C. Methyl
2,2-difluoro-2-(3-(2-hydroxyethoxy)phenyl)acetate

To a stirred solution of tert-butyl(2-(3-iodophenoxy) ethoxy)dimethylsilane (1 g, 2.64 mmol) in dimethylsulfoxide (20 mL) was added ethyl 2-bromo-2,2-difluoroacetate (0.8 g, 3.97 mmol) and copper (0.43 g, 6.87 mmol) at 0° C. and stirred at 60° C. for 5 h. The reaction mixture was quenched with ice water and filtered through a Celite pad. The filtrate was extracted with ethyl acetate (3×20 mL) and the combined organic layers were washed with water (15 mL), brine (15 mL), dried over sodium sulfate, filtered and concentrated to afford methyl 2,2-difluoro-2-(3-(2-hydroxyethoxy)phenyl)acetate (0.2 g, 0.77 mmol, 29%) as a brown liquid. MS (ESI) m/z 260.2 [M]+.

D.
2,2-Difluoro-2-(3-(2-hydroxyethoxy)phenyl)acetic acid

To an ice cold solution of methyl 2,2-difluoro-2-(3-(2-hydroxyethoxy)phenyl)acetate (200 mg, 0.77 mmol) in methanol:tetrahydrofuran:water mixture (15 mL, 1:1:1) was added lithium hydroxide monohydrate (97 mg, 2.31 mmol) and stirred at room temperature for 5 h. The volatiles were removed under reduced pressure and resultant residue was diluted with water (6 mL) and washed with ethyl acetate (2×5 mL). Aqueous layer was acidified with 2N aqueous hydrochloric acid (5 mL) and extracted with ethyl acetate (3×5 mL). The combined organic layers were washed with brine (5 mL), dried over sodium sulfate, concentrated to afford 2,2-difluoro-2-(3-(2-hydroxyethoxy)phenyl)acetic acid (150 mg, 0.65 mmol, 84% yield) as a brown semi solid. 1H NMR (300 MHz, CDCl3) δ 7.49-7.43 (m, 1H), 7.19-7.05 (m, 3H), 4.05-3.99 (m, 2H), 3.85 (brs, 1H), 3.73-3.70 (m, 2H).

E. N-((2-(2,6-Dioxopiperidin-3-yl)-1-oxoisoindolin-5-yl)methyl)-2,2-difluoro-2-(3-(2-hydroxyethoxy) phenyl)acetamide To an ice cold solution of 3-(5-(aminomethyl)-1-oxoisoindolin-2-yl)piperidine-2,6-dione hydrochloride (300 mg, 0.97 mmol) and 2,2-difluoro-2-(3-(2-hydroxyethoxy) phenyl)acetic acid (225 mg, 0.97 mmol) in N,N-dimethylformamide (10 mL) was added N,N-diisopropylethylamine (0.52 mL, 2.91 mmol) followed by 1-[Bis(dimethylamino) methylene]-1H-1,2,3-triazolo[4,5-b]pyridinium 3-oxid hexafluorophosphate (479 mg, 1.26 mmol) and stirred at room temperature for 4 h. The reaction mixture was diluted with ice water (15 mL) and extracted with ethyl acetate (3×15 mL). The combined organic layers were washed with brine (15 mL), dried over sodium sulfate, filtered, concentrated and obtained crude was purified by Reveleris C-18 reversed phase column (50% acetonitrile in 0.1% aqueous formic acid) to afford N-((2-(2,6-dioxopiperidin-3-yl)-1-oxoisoindolin-5-yl)methyl)-2,2-difluoro-2-(3-(2-hydroxy ethoxy)phenyl)acetamide (61 mg, 0.16 mmol, 16% yield) as an off-white solid. MS (ESI) m/z 488.08 [M+1]+. 1H NMR (300 MHz, DMSO-d6) δ 10.99 (s, 1H), 9.56 (s, 1H), 7.67 (d, J=7.8 Hz, 1H), 7.47-7.35 (m, 3H), 7.15-7.12 (m, 3H), 5.10 (dd, J=12.6, 4.5 Hz, 1H), 4.88 (t, J=5.7 Hz, 1H), 4.45-4.27 (m, 4H), 4.11 (t, J=4.8 Hz, 2H), 3.71 (q, J=4.8 Hz, 2H), 2.91-2.87 (m, 1H), 2.62-2.56 (m, 1H), 2.41-2.35 (m, 1H), 2.02-1.97 (m, 1H).

Example 50

N-((2-(2,6-dioxopiperidin-3-yl)-1-oxoisoindolin-5-yl)methyl)-2,2-difluoro-2-(4-(2-methoxyethoxy)phenyl)acetamide

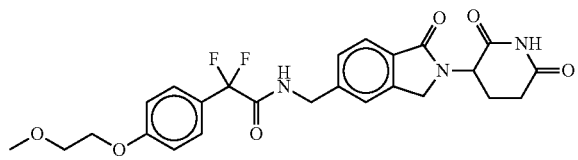

A. 1-Iodo-4-(2-methoxyethoxy)benzene

To a stirred solution of 4-iodophenol (2 g, 9.09 mmol) in N,N-dimethylformamide (25 mL) was added 1-bromo-2-methoxyethane (1.5 g, 10.90 mmol) tetrabutyl ammonium iodide (670 mg, 1.818 mmol) and potassium carbonate (3.13 g, 22.72 mmol) at rt and stirred at 70° C. for 16 h. The reaction mixture was quenched with ice cold water (40 mL) and extracted with ethyl acetate (3×50 mL). The combined organic layers were washed with water (2×10 mL), brine (10 mL), dried over sodium sulphate and concentrated to afford 1-iodo-4-(2-methoxyethoxy)benzene (600 mg, 2.15 mmol, 24% yield) as colorless liquid. MS (ESI) m/z 277.9 [M+1]$^+$.

B. Ethyl 2,2-Difluoro-2-(4-(2-methoxyethoxy)phenyl)acetate

To a stirred solution of 1-iodo-4-(2-methoxyethoxy)benzene (500 mg, 1.798 mmol) in dimethylsulfoxide (5 mL) was reacted with ethyl 2-bromo-2,2-difluoroacetate (0.34 mL, 2.69 mmol), copper (297 mg, 4.67 mmol) and stirred for 12 h at 50° C. The reaction mixture was neutralized with aqueous saturated ammonium chloride solution and extracted with ethyl acetate (3×50 mL). The combined organic layers were washed with water (2×10 mL), brine (10 mL), dried over sodiumsulphate concentrated to afford ethyl 2,2-difluoro-2-(4-(2-methoxyethoxy)phenyl)acetate (120 mg, 0.437 mmol, 24%) as a brown liquid. GCMS (m/z) 274 [M]+

C. 2,2-Difluoro-2-(4-(2-methoxyethoxy)phenyl)acetic acid

To a cold (0° C.) stirred solution of ethyl ethyl 2,2-difluoro-2-(4-(2-methoxyethoxy)phenyl)acetate (1 g, 3.64 mmol) in ethanol/tetrahydrofuran/water mixture (15 mL, 1:1:1) was added lithium hydroxide monohydrate (460 mg, 10.94 mmol) and stirred at room temperature for 12 h. The reaction mixture was concentrated and the residue was neutralized with 10% aqueous hydrochloric acid (10 mL) and extracted with ethyl acetate (2×20 mL). The combined organic layer was washed with brine (10 mL), dried over sodium sulphate and concentrated to afford 2,2-difluoro-2-(4-(2-methoxyethoxy)phenyl)acetic acid (600 mg, 2.43 mmol, 66% yield) as a brown semi solid. Without further purification crude compound used for next step.

D. N-((2-(2,6-dioxopiperidin-3-yl)-1-oxoisoindolin-5-yl)methyl)-2,2-difluoro-2-(4-(2-hydroxyethoxy)phenyl)acetamide To a cold (0° C.) stirred solution of 2,2-difluoro-2-(4-(2-methoxyethoxy)phenyl)acetic acid (573 mg, 2.33 mmol) in pyridine was added phosphorus oxychloride (0.54 mL, 5.82 mmol) dropwise and stirred at 0-5° C. for 1 h and then added 3-(5-(aminomethyl)-1-oxoisoindolin-2-yl)piperidine-2,6-dione hydrochloride (600 mg, 1.94 mmol) and stirred at room temperature for 30 min. The reaction mixture was neutralized with aqueous saturated sodium bicarbonate (up to pH-8) and extracted with ethyl acetate (3×50 mL). The combined organic layer was washed with water (2×20 mL), brine (20 mL) and dried over sodium sulphate and concentrated. The resultant residue was purified by Reveleris C-18 reversed phase column chromatography using 40-55% acetonitrile in aqueous formic acid (0.1%) to afford N-((2-(2,6-dioxopiperidin-3-yl)-1-oxoisoindolin-5-yl)methyl)-2,2-difluoro-2-(4-(2-methoxyethoxy)phenyl)acetamide (40 mg, 0.079 mmol, 4% yield) as a white solid. MS (ESI) m/z 502.08 [M+1]$^+$. $^1$H NMR (300 MHz, DMSO-d$_6$): δ 10.98 (s, 1H), 9.57 (br t, J=6.1 Hz, 1H), 7.68 (d, J=7.7 Hz, 1H), 7.50 (d, J=8.8 Hz, 2H), 7.42-7.32 (m, 2H), 7.07 (d, J=8.8 Hz, 2H), 5.10 (dd, J=13.2, 5.1 Hz, 1H), 4.44-4.25 (m, 4H), 4.20-4.10 (m, 2H), 3.78-3.60 (m, 2H), 3.25 (s, 3H), 3.00-2.83 (m, 1H), 2.66-2.56 (m, 1H), 2.45-2.32 (m, 1H), 2.05-1.94 (m, 1H).

Example 51

N-((2-(2,6-Dioxopiperidin-3-yl)-1-oxoisoindolin-5-yl)methyl)-2,2-difluoro-2-(3-(2-hydroxyethyl)phenyl)acetamide

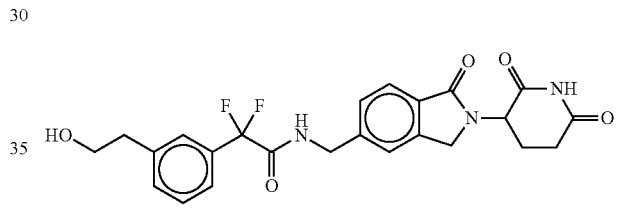

A. 2-(3-Iodophenyl)ethanol

To a stirred solution of 2-(3-iodophenyl)acetic acid (1 g, 3.81 mmol) in tetrahydrofuran (20 mL) was added borane dimethyl sulfide complex (1 mL, 11.45 mmol) at 0° C. and stirred at room temperature for 16 h. The reaction mixture was quenched with 4N hydrochloride acid (15 mL) and extracted with ethyl acetate (3×15 mL). The combined organic layers were washed with water (15 mL), brine (15 mL), dried over sodium sulfate, filtered and concentrated to afford 2-(3-iodophenyl)ethanol (0.9 g, 3.63 mmol, 95% yield) as colorless liquid. $^1$H NMR (300 MHz, DMSO-d$_6$) δ 7.61 (s, 1H), 7.55 (d, J=7.8 Hz, 1H), 7.25 (d, J=7.8 Hz, 1H), 7.08 (dd, J=7.8, 7.5 Hz, 1H), 3.59 (t, J=6.6 Hz, 2H), 2.67 (t, J=6.0 Hz, 2H).

B. 3-Iodophenethyl acetate

To a stirred solution of 2-(3-iodophenyl)ethanol (900 mg, 3.62 mmol) in pyridine (15 mL) was added acetic anhydride (1.11 g, 10.88 mmol) at 0° C. and stirred at 80° C. for 2 h. The reaction mixture was quenched with 1N aqueous hydrochloride (10 mL) at room temperature and extracted with ethyl acetate (3×15 mL). The combined organic layers were washed with water (15 mL), brine (15 mL), dried over sodium sulfate and concentrated to afford 3-iodophenethyl acetate (700 mg, 2.41 mmol, 66% yield) as colorless liquid. $^1$H NMR (400 MHz, DMSO-d$_6$) δ 7.66 (s, 1H), 7.59 (d, J=5.7 Hz, 1H), 7.28 (d, J=6.5 Hz, 1H), 7.11 (dd, J=8.0 Hz, 7.8 Hz, 1H), 4.20 (t, J=6.8 Hz, 2H), 2.85 (t, J=6.8 Hz, 2H), 1.97 (s, 3H).

C. Ethyl 2-(3-(2-acetoxyethyl)phenyl)-2,2-difluoroacetate

To a stirred solution of 3-iodophenethyl acetate (1 g, 3.46 mmol) in dimethyl sulfoxide (20 mL) was added ethyl 2-bromo-2,2-difluoroacetate (1.05 g, 5.19 mmol) followed by copper powder (0.57 g, 8.99 mmol) at room temperature and stirred at 50° C. for 16 h. The reaction mixture was neutralized with aqueous saturated ammonium chloride solution and extracted with ethyl acetate (3×15 mL). The combined organic layers were washed with water (15 mL), brine (15 mL), dried over sodium sulfate and concentrated to afford ethyl 2-(3-(2-acetoxyethyl)phenyl)-2,2-difluoroacetate (550 mg, 1.92 mmol, 55%) as a brown liquid. $^1$H NMR (400 MHz, DMSO-$d_6$) δ 7.49-7.46 (m, 2H), 7.41-7.34 (m, 2H), 4.31-4.27 (m, 4H), 2.98 (t, J=7.2 Hz, 2H), 2.03 (s, 3H), 1.31 (t, J=6.8 Hz, 3H).

D. 2,2-Difluoro-2-(3-(2-hydroxyethyl)phenyl)acetic acid

To an ice cold solution of ethyl 2-(3-(2-acetoxyethyl) phenyl)-2,2-difluoroacetate (0.8 g, 2.77 mmol) in ethanol/tetrahydrofuran/water mixture (15 mL, 1:1:1) was added lithium hydroxide monohydrate (349 mg, 8.3 mmol) and stirred at room temperature for 16 h. The volatiles were removed and the residue was diluted with water (10 mL), washed with ethyl acetate (2×10 mL). Aqueous layer acidified with 2N aqueous hydrochloric acid (10 mL) and extracted with ethyl acetate (3×15 mL). The combined organic layers were washed with brine (15 mL), dried over sodium sulfate, filtered and concentrated to afford 2,2-difluoro-2-(3-(2-hydroxy ethyl)phenyl)acetic acid (450 mg, 2.08 mmol, 75% yield) as a brown semi solid. $^1$H NMR (300 MHz, DMSO-$d_6$) δ 7.56-7.39 (m, 4H), 3.62 (t, J=6.6 Hz, 2H), 2.78 (t, J=6.6 Hz, 2H), 1.91 (s, 1H).

E. N-((2-(2,6-Dioxopiperidin-3-yl)-1-oxoisoindolin-5-yl)methyl)-2,2-difluoro-2-(3-(2-hydroxyethyl)phenyl)acetamide To an ice cold solution of 3-(5-(aminomethyl)-1-oxoisoindolin-2-yl)piperidine-2,6-dione hydrochloride (300 mg, 0.97 mmol) and 2,2-difluoro-2-(3-(2-hydroxyethyl)phenyl)acetic acid (209 mg, 0.97 mmol) in N,N-dimethylformamide (10 mL) was added N,N-diisopropylethylamine (0.52 mL, 2.91 mmol) followed by 1-[Bis(dimethylamino) methylene]-1H-1,2,3-triazolo[4,5-b]pyridinium 3-oxid hexafluorophosphate (479 mg, 1.26 mmol) and stirred at room temperature for 16 h. The reaction mixture was diluted with water (15 mL) and extracted with ethyl acetate (3×15 mL). The combined organic layers were washed with brine (15 mL), dried over sodium sulphate, filtered and concentrated. The obtained crude product was purified by Reveleris C-18 reversed phase column (50% acetonitrile in 0.1% aqueous formic acid to afford N-((2-(2,6-dioxopiperidin-3-yl)-1-oxoisoindolin-5-yl)methyl)-2,2-difluoro-2-(3-(2-hydroxyethyl)phenyl)acetamide (50 mg, 0.10 mmol, 11% yield) as an off-white solid. MS (ESI) m/z 472.11 [M+1]$^+$. $^1$H NMR (300 MHz, DMSO-$d_6$) δ 10.98 (s, 1H), 9.61 (t, J=6.3 Hz, 1H), 7.67 (d, J=8.1 Hz, 1H), 7.43-7.41 (m, 5H), 7.36 (d, J=8.1 Hz, 1H), 6.67 (t, J=5.1 Hz, 1H), 5.10 (dd, J=13.8, 5.1 Hz, 1H), 4.45 (d, J=6.0 Hz, 2H), 4.43 (t, J=15.3 Hz, 1H), 4.28 (d, J=17.7 Hz, 1H), 3.61 (q, J=5.1 Hz, 2H), 2.96-2.83 (m, 1H), 2.75 (t, J=6.9 Hz, 2H), 2.67-2.54 (m, 1H), 2.46-2.30 (m, 1H), 2.04-1.92 (m, 1H).

Example 52

2-(3-(Dimethylamino)phenyl)-N-((2-(2,6-dioxopiperidin-3-yl)-1-oxoisoindolin-5-yl)methyl)-2,2-difluoroacetamide

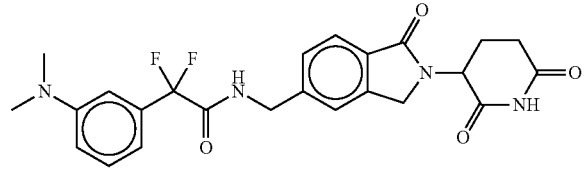

A. 3-Iodo-N,N-dimethylaniline

To a stirred solution of 3-iodoaniline (300 mg, 1.36 mmol) in ethanol (10 mL) was added formaldehyde (82 mg, 2.73 mmol), molecular sieves (1 g) and acetic acid (2 mL) at 0° C., stirred at room temperature for 8 h. The reaction mixture was cooled at 0° C. and treated with sodium cyano borohydride (200 g, 2.73 mmol) and stirred at room temperature for 16 h. The reaction mixture was filtered through a Celite pad and the filtrate was diluted with water (10 mL) and basified with aqueous sodium bicarbonate solution and extracted with ethyl acetate (3×10 mL). Combined organic layers were washed with water (10 mL) and brine (10 mL), dried over sodium sulfate, filtered and concentrated under reduced pressure to give crude compound. Obtained crude was purified by silica gel column chromatography (30% ethyl acetate in pet ether) to afford 3-iodo-N,N-dimethylaniline (210 mg, 0.85 mmol, 74% yield) as a liquid. $^1$H NMR (300 MHz, CDCl$_3$) δ 7.03-6.89 (m, 3H), 6.67-6.64 (m, 1H), 2.92 (s, 6H).

B. Ethyl 2-(3-(dimethylamino)phenyl)-2,2-difluoroacetate

To a stirred solution of 3-iodo-N,N-dimethylaniline (250 mg, 1.01 mmol) in dimethylsulfoxide (10 mL) was added ethyl 2-bromo-2,2-difluoroacetate (0.19 mL, 1.52 mmol) followed by copper powder (167 mg, 2.63 mmol) at RT and stirred at 55° C. for 5 h. The reaction mixture was diluted with water and filtered through a Celite pad. The filtrate was basified with aqueous saturated sodium bicarbonate solution and extracted with ethyl acetate (3×10 mL). The combined organic layers were washed with water (10 mL), brine (10 mL), dried over sodium sulfate, filtered, concentrated to afford ethyl 2-(3-(dimethylamino)phenyl)-2,2-difluoroacetate (80 mg, 6.99 mmol, 33%) as a brown liquid. MS (ESI) m/z 243.2 [M]$^+$

C. 2-(3-(Dimethylamino)phenyl)-2,2-difluoroacetic acid

To an ice cold solution of ethyl 2-(3-(dimethylamino) phenyl)-2,2-difluoroacetate (500 mg, 2.06 mmol) in methanol/tetrahydrofuran/water mixture (15 mL, 1:1:1) was added lithium hydroxide monohydrate (260 mg, 6.17 mmol) and stirred at room temperature for 4 h. The reaction mixture was concentrated and the resultant residue was diluted with water (10 mL) and washed with ethyl acetate (2×10 mL). Aqueous layer acidified with aqueous potassium bi sulfate (10 mL) and extracted with ethyl acetate (3×10 mL). The combined organic layers were washed with brine (10 mL), dried over sodium sulfate, filtered and concentrated to afford 2-(3-(dimethylamino)phenyl)-2,2-difluoroacetic acid (400 mg, 1.86 mmol, 91% yield) as a brown semi solid $^1$H NMR (300 MHz, DMSO-$d_6$) δ 7.64-7.55 (m, 3H), 7.38-7.32 (m, 1H), 2.56 (s, 6H).

D. 2-(3-(Dimethylamino)phenyl)-N-((2-(2,6-dioxopiperidin-3-yl)-1-oxoisoindolin-5-yl)methyl)-2,2-difluoroacetamide To an ice cold solution of 3-(5-(aminomethyl)-1-oxoisoindolin-2-yl)piperidine-2,6-dione hydrochloride (300 mg, 0.97 mmol) and 2-(3-(dimethylamino)phenyl)-2,2-difluoroacetic acid (208 mg, 0.97 mmol) in N,N-dimethylformamide (10 mL) was added N,N-diisopropylethylamine (0.52 mL, 2.91 mmol) followed by 1-[Bis(dimethylamino)methylene]-1H-1,2,3-triazolo[4,5-b]pyridinium 3-oxid hexafluorophosphate (479 mg, 1.26 mmol) and stirred at room temperature for 16 h. The reaction mixture was diluted with water (15 mL) and extracted with ethyl acetate (3×15 mL). The combined organic layers were washed with brine (15 mL), dried over sodium sulfate, filtered and concentrated. The obtained crude was purified by Reveleris C-18 reversed phase column (50% acetonitrile in 0.1% aqueous formic acid) to afford 2-(3-(dimethylamino)phenyl)-N-((2-(2,6-dioxopiperidin-3-yl)-1-oxoisoindolin-5-yl)methyl)-2,2-difluoroacetamide (63 mg, 0.13 mmol, 13% yield) as an off-white solid. MS (ESI) m/z 470.8 [M+1]$^+$. $^1$H NMR (300 MHz, DMSO-$d_6$) δ 10.98 (s, 1H), 9.21 (t, J=5.8 Hz, 1H), 7.72 (d, J=7.8 Hz, 1H), 7.62 (d, J=7.5 Hz, 1H), 7.57-7.48 (m, 4H), 7.32 (dd, J=8.4, 6.9 Hz, 1H), 5.11 (dd, J=13.2, 4.8 Hz, 1H), 4.48 (d, J=6.6 Hz, 2H), 4.46 (d, J=16.5 Hz, 1H), 4.32 (d, J=17.4 Hz, 1H), 2.98-2.86 (m, 1H), 2.73-2.57 (m, 1H), 2.51-2.33 (m, 1H), 2.34 (s, 6H), 2.07-1.98 (m, 1H).

Example 53

N-((2-(2,6-Dioxopiperidin-3-yl)-1-oxoisoindolin-5-yl)methyl)-2,2-difluoro-2-(3-(piperidin-1-yl)phenyl) acetamide

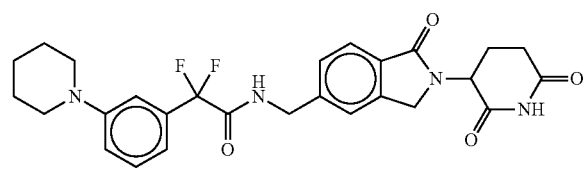

A. 1-(3-Iodophenyl)piperidine

To a stirred solution of 3-iodoaniline (5 g, 22.83 mmol) in toluene (50 mL) was added N,N-diisopropylethylamine (20 mL, 114.1 mmol) followed by 1,5-dibromopentane (4.06 mL, 29.68 mmol) at 0° C. and stirred at 100° C. for 16 h. The reaction mixture was basified aqueous saturated sodium bicarbonate solution and extracted with ethyl acetate (3×40 mL). The combined organic layers were washed with water (40 mL), brine (40 mL), dried over sodium sulfate, filtered; filtrate and concentrated. The obtained crude was purified by flash column chromatography (25% ethyl acetate in pet ether) to afford 1-(3-iodophenyl)piperidine (2.8 g, 9.75 mmol, 43% yield) as a colorless liquid. MS (ESI) m/z 287.90 [M+1]$^+$.

B. Ethyl 2,2-difluoro-2-(3-(piperidin-1-yl)phenyl)acetate

To a stirred solution of 1-(3-iodophenyl)piperidine (500 mg, 1.74 mmol) in dimethyl sulfoxide (5 mL) was added ethyl 2-bromo-2,2-difluoroacetate (690 mg, 2.61 mmol) followed by copper powder (290 mg, 4.53 mmol) at room temperature and stirred at 55° C. for 16 h. The reaction mixture was diluted with water and filtered through a Celite pad. The filtrate was extracted with ethyl acetate (3×10 mL) and the combined organic layers were washed with water (10 mL), brine (10 mL), dried over sodium sulfate, filtered and concentrated. The resultant crude product was purified by flash column chromatography (25% ethyl acetate in pet ether) to afford ethyl 2,2-difluoro-2-(3-(piperidin-1-yl)phenyl)acetate (200 mg, 0.71 mmol, 41% yield) as a colorless liquid. MS (ESI) m/z 283.2 [M]$^+$.

C. 2,2-Difluoro-2-(3-(piperidin-1-yl)phenyl)acetic acid

To a stirred solution of ethyl 2,2-difluoro-2-(3-(piperidin-1-yl)phenyl)acetate (250 mg, 0.88 mmol) in mixture of tetrahydrofuran:methanol:water (5 mL, 1:1:1) was added lithium hydroxide monohydrate (110 mg, 2.65 mmol) and stirred at room temperature for 16 h. The reaction mixture was concentrated under reduced pressure and the obtained residue was dissolved in water (10 mL) and washed with ethyl acetate (2×10 mL). Aqueous layer was acidified with aqueous potassium bi sulfate and extracted with ethyl acetate (3×10 mL). The combined organic layers were washed with brine (10 mL), dried over sodium sulfate, filtered and concentrated to afford 2,2-difluoro-2-(3-(piperidin-1-yl)phenyl)acetic acid (200 mg, 0.78 mmol, 88% yield) as semi-solid compound. $^1$H NMR (300 MHz, CDCl$_3$) δ 8.27 (d, J=9.3 Hz, 1H), 7.89 (s, 1H), 7.70 (d, J=7.5 Hz, 1H), 7.49 (dd, J=7.8 Hz, 7.6 Hz, 1H), 4.28 (brs, 1H), 3.49-3.39 (m, 4H), 2.12-2.08 (m, 4H), 1.69-1.65 (m, 2H).

D. N-((2-(2,6-Dioxopiperidin-3-yl)-1-oxoisoindolin-5-yl)methyl)-2,2-difluoro-2-(3-(piperidin-1-yl)phenyl)acetamide To an ice cold solution of 2,2-difluoro-2-(3-(piperidin-1-yl)phenyl)acetic acid (206 mg, 0.81 mmol) in pyridine (6 mL) was added phosphorus oxychloride (371 mg, 2.43 mmol) drop wise and stirred at 0-5° C. for 1 h. Then, 3-(5-(aminomethyl)-1-oxoisoindolin-2-yl)piperidine-2,6-dione hydrochloride (250 mg, 0.81 mmol) was added into the reaction mixture and stirred at room temperature for 2 h. The reaction mixture was basified with aqueous saturated sodium bicarbonate and extracted with ethyl acetate (3×15 mL). The combined organic layers were washed with water (15 mL), brine (15 mL), dried over sodium sulfate, filtered and concentrated. The resultant residue was purified by Reveleris C-18 reversed phase column chromatography (50-55% acetonitrile in 0.1% aqueous formic acid to afford N-((2-(2,6-dioxopiperidin-3-yl)-1-oxoisoindolin-5-yl) methyl)-2,2-difluoro-2-(3-(piperidin-1-yl)phenyl)acetamide (62 mg, 0.12 mmol, 15% yield) as white solid. MS (ESI) m/z 510.81 [M+1]$^+$. $^1$H NMR (300 MHz, DMSO-$d_6$) δ 10.99 (s, 1H), 9.57 (t, J=5.7 Hz, 1H), 7.66 (d, J=7.5 Hz, 1H), 7.39 (s, 1H), 7.35 (d, J=5.1 Hz, 1H), 7.30 (d, J=8.1 Hz, 1H), 7.08 (d, J=8.7 Hz, 1H), 7.00 (s, 1H), 6.92 (d, J=7.5 Hz, 1H), 5.10 (dd, J=13.2, 4.8 Hz, 1H), 4.45 (d, J=6.0 Hz, 2H), 4.41 (d, J=17.7 Hz, 1H), 4.27 (d, J=17.4 Hz, 1H), 3.31-3.11 (m, 4H), 2.98-2.86 (m, 1H), 2.63-2.57 (m, 1H), 2.40-2.27 (m, 2H), 2.01-1.97 (m, 1H), 1.57-1.54 (m, 5H).

Example 54

N-((2-(2,6-Dioxopiperidin-3-yl)-1-oxoisoindolin-5-yl)methyl)-2,2-difluoro-2-(3-morpholinophenyl) acetamide

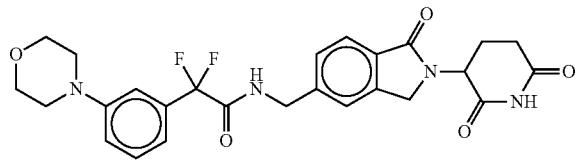

A. 2,2'-Oxybis(ethane-2,1-diyl)dimethanesulfonate

To a stirred solution of 2,2'-oxydiethanol (2.0 g, 18.86 mmol) in dichloromethane (20 mL) was added methane sulfonylchloride (2.1 g, 47.16 mmol), triethylamine (13 mL, 94.33 mmol) at 0° C. and stirred at room temperature for 2 h. The reaction mixture was quenched with water (100 mL) and extracted with dichloromethane (2×100 mL). The combined organic layers were washed with brine (50 mL), dried over sodium sulphate and concentrated to afford 2,2'-oxybis(ethane-2,1-diyl)dimethanesulfonate (4.0 g, 15.26 mmol, 81% yield). GC MS (m/z) 263.1.

B. 4-(3-Iodophenyl)morpholine

To a stirred solution of 3-iodo aniline (1.0 g, 4.56 mmol) in toluene (20 mL) was added 2,2'-Oxybis(ethane-2,1-diyl) dimethanesulfonate (2.1 g, 9.13 mmol), diisopropylethylamine (4 mL, 22.82 mmol) and stirred under reflux for 16 h. The reaction mixture was quenched with water (100 mL) and extracted with ethyl acetate (2×100 mL). The combined organic layers were washed with brine (50 mL), dried over sodium sulphate and concentrated to give 4-(3-iodophenyl) morpholine (1.2 g, 4.15 mmol, 91% yield). LCMS (ESI) m/z 290.16[M+1]$^+$.

C. Ethyl 2,2-difluoro-2-(3-morpholinophenyl)acetate

To a stirred solution of 4-(3-iodophenyl)morpholine (1.2 g, 4.15 mmol) in dimethylsulfoxide (50 mL) was added ethyl 2-bromo-2,2-difluoroacetate (0.6 mL, 4.98 mmol), copper (686 mg, 10.79 mmol) and stirred for 6 h at 55° C. The reaction mixture was neutralized with aqueous saturated ammonium chloride solution and extracted with ethyl acetate (3×100 mL). The combined organic layers were washed with water (2×50 mL), brine (50 mL), dried over sodium sulphate and concentrated to afford ethyl 2,2-difluoro-2-(3-morpholinophenyl)acetate (700 mg, 2.45 mmol, 59% yield). GC MS (m/z) 285.2.

D. 2,2-Difluoro-2-(3-morpholinophenyl)acetic acid

To a cold (0° C.) stirred solution of ethyl 2,2-difluoro-2-(3-morpholinophenyl)acetate (700 mg, 2.45 mmol) in tetrahydrofuran-methanol-water (20 mL, 1:1:1) was added lithium hydroxide monohydrate (309 mg, 7.36 mmol) and stirred at room temperature for 2 h. The reaction mixture was concentrated and the residue was neutralized with 10% aqueous potassium bisulphate (5 mL) and extracted with ethyl acetate (2×50 mL). The combined organic layers were washed with brine (20 mL), dried over sodium sulphate and concentrated to afford 2,2-difluoro-2-(3-morpholinophenyl) acetic acid (550 mg, 2.14 mmol, 87% yield). LCMS (ESI) m/z 258.12[M+1]$^+$.

E. N-((2-(2,6-dioxopiperidin-3-yl)-1-oxoisoindolin-5-yl)methyl)-2,2-difluoro-2-(3-morpholinophenyl) acetamide To a cold (0° C.) stirred solution of 2,2-difluoro-2-(3-morpholinophenyl)acetic acid (300 mg, 1.16 mmol) in pyridine (5 mL) was added phosphoryl chloride (0.4 mL, 3.50 mmol) and stirred at 0-5° C. for 1 h. To this reaction mixture was added 3-(5-(aminomethyl)-1-oxoisoindolin-2-yl)piperidine-2,6-dione hydrochloride (361 mg, 1.16 mmol) and stirred at room temperature for 1 h. The reaction mixture was neutralized with aqueous saturated sodium bicarbonate (up to pH-8) and extracted with ethyl acetate (2×25 mL). The combined organic layers were washed with water (15 mL), brine (15 mL), dried over sodium sulphate and concentrated. The resultant residue was purified by Reveleris C-18 reversed phase column chromatography using 40-45% acetonitrile in aqueous formic acid (0.1%) to afford N-((2-(2,6-dioxopiperidin-3-yl)-1-oxoisoindolin-5-yl)methyl)-2,2-difluoro-2-(3-morpholinophenyl) acetamide (80 mg, 0.15 mmol, 13% yield) as an off white solid. LCMS (ESI) m/z 512.95 [M+1]$^+$. $^1$H NMR (400 MHz, DMSO-d$_6$) δ=10.98 (s, 1H), 9.58 (br t, J=6.1 Hz, 1H), 7.67 (d, J=7.8 Hz, 1H), 7.52-7.31 (m, 2H), 7.11 (br d, J=8.3 Hz, 1H), 7.07-6.95 (m, 1H), 5.10 (dd, J=4.9, 13.2 Hz, 1H), 4.51-4.26 (m, 4H), 3.77-3.66 (m, 4H), 3.14-3.03 (m, 4H), 2.98-2.84 (m, 1H), 2.66-2.55 (m, 1H), 2.45-2.30 (m, 1H), 2.06-1.94 (m, 1H)

Example 55

N-((2-(2,6-Dioxopiperidin-3-yl)-1-oxoisoindolin-5-yl)methyl)-2,2-difluoro-2-(4-fluoro-2-isopropoxyphenyl)acetamide

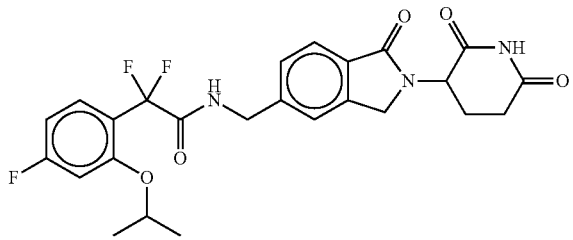

A. 1-(4-Fluoro-2-isopropoxycyclohexyl)ethanone

To a stirred solution of 1-(4-fluoro-2-hydroxyphenyl) ethanone (3 g, 19.48 mmol) in N,N-dimethylformamide (15 mL) was added 2-bromopropane (5.94 g, 48.76 mmol) potassium carbonate (8.06 g 58.44 mmol) and stirred for 16 h at 90° C. The reaction mixture was diluted with ethyl acetate (30 mL) and extracted with ethyl acetate (2×100 mL). The combined organic layers were washed with water (2×50 mL), brine (50 mL) and dried over sodium sulphate and was concentrated to afford 1-(4-fluoro-2-isopropoxyphenyl)ethanone (2.5 g, 12.75 mmol, 65% yield) as a brown liquid. MS (ESI) m/z 197.33 [M]$^+$

B. Ethyl 2-(4-fluoro-2-isopropoxyphenyl)-2-oxoacetate

To a stirred solution of 1-(4-fluoro-2-isopropoxyphenyl)ethanone (2.0 g, 10.20 mmol) in pyridine (15 mL) was added selenium dioxide (2.83 g, 25.51 mmol) and stirred for 16 h at 100° C. The reaction mixture was diluted with dichloromethane (30 mL) and filtered through Celite pad. The filtrate was treated with ethyl chloroformate (6 mL) at 0° C. and stirred at room temperature for 3 h. The reaction mixture was neutralized with 1N aqueous hydrochloric acid (up to pH-4) and extracted with ethyl acetate (2×100 mL). The combined organic layers were washed with water (2×50 mL), brine (50 mL) and dried over sodium sulphate and concentrated. The crude was purified with column chromatography using 100-200 mesh silica gel eluting 10% ethylacetate in hexanes to afford ethyl 2-(4-fluoro-2-isopropoxyphenyl)-2-oxoacetate (800 g, 3.14 mmol, 32% yield) as a brown liquid. MS (ESI) m/z 255.33 [M]$^+$

C. Ethyl 2,2-difluoro-2-(4-fluoro-2-isopropoxyphenyl)acetate

To a stirred solution of ethyl 2-(4-fluoro-2-isopropoxyphenyl)-2-oxoacetate (450 mg, 1.77 mmol) was added diethyl amino sulfur trifluoride (714 mg, 4.42 mmol) and stirred at room temperature for 16 h. The reaction mixture was basified with aqueous saturated sodium bicarbonate to pH-8 and extracted with ethyl acetate (3×50 mL). The combined organic layers were washed with water (2×30 mL), brine (30 mL), dried over sodium sulphate and concentrated to afford ethyl 2,2-difluoro-2-(4-fluoro-2-isopropoxyphenyl)acetate (200 mg, 0.724 mmol, 40% yield) as a brown liquid. GC-MS (ESI) m/z 276 [M]$^+$

D. 2,2-Difluoro-2-(4-fluoro-2-isopropoxyphenyl)acetic acid

To a stirred solution of ethyl 2,2-difluoro-2-(4-fluoro-2-isopropoxyphenyl)acetate (350 mg, 1.26 mmol) in tetrahydrofuran/Methanol/Water mixture (30 mL, 1:1:1) was added lithium hydroxide monohydrate (160 mg, 3.80 mmol) and stirred at room temperature for 4 h. The reaction mixture was concentrated; the residue obtained was neutralized with 10% aqueous hydrochloric acid (10 mL) and extracted with ethyl acetate (2×50 mL). The combined organic layers were washed with brine (20 mL), dried over sodium sulphate and concentrated to afford 2,2-difluoro-2-(4-fluoro-2-isopropoxyphenyl)acetic acid (200 mg, 0.806 mmol, 63% yield) as a brown semi solid. GC-MS (ESI) m/z 224.0 [M]$^+$; $^1$H NMR (300 MHz, CDCl$_3$) δ ppm 7.62 (dd, J=8.4, 2.1 Hz, 1H), 7.19 (brs, 1H), 6.72 (ddd, J=10.8, 8.4, 2.1 Hz, 1H), 6.65 (brd, J=10.5 Hz, 1H), 4.58 (sep, J=5.7 Hz, 1H), 1.33 (d, J=6.3 Hz, 6H).

E. N-((2-(2,6-Dioxopiperidin-3-yl)-1-oxoisoindolin-5-yl)methyl)-2,2-difluoro-2-(4-fluoro-2-isopropoxyphenyl)acetamide To an ice cold solution of 2,2-difluoro-2-(4-fluoro-2-isopropoxyphenyl)acetic acid (289 mg, 1.165 mmol) in pyridine (10 mL) was added POCl$_3$ (446 mg, 2.91 mmol) and stirring at 0-5° C. for 1 h. The reaction mixture was then treated with 3-(5-(aminomethyl)-1-oxoisoindolin-2-yl)piperidine-2,6-dione hydrochloride (300 mg, 0.970 mmol) and stirred at 0-30° C. for 1 h. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The crude product was purified by Reveleris C-18 reversed phase column (45-55% acetonitrile in 0.1% aqueous formic acid) to afford N-((2-(2,6-dioxopiperidin-3-yl)-1-oxoisoindolin-5-yl)methyl)-2,2-difluoro-2-(4-fluoro-2-isopropoxyphenyl)acetamide (35 mg, 0.069 mmol, 7% yield) as an off white solid. MS (ESI) m/z 503.95 [M+1]$^+$. $^1$H NMR (300 MHz, DMSO-d$_6$) δ ppm 10.98 (s, 1H), 9.32 (t, J=5.7 Hz, 1H), 7.70 (d, J=7.70 Hz, 1H), 7.60-7.50 (m, 2H), 7.46 (br d, J=7.7 Hz, 1H), 7.08 (br d, J=11.0 Hz, 1H), 6.85 (dd, J=8.7, 6.3 Hz, 1H), 5.11 (dd, J=13.6, 4.77 Hz, 1H), 4.68 (sep, J=6.3 Hz, 1H), 4.53-4.23 (m, 3H), 3.00-2.81 (m, 1H), 2.68-2.49 (m, 1H), 2.44-2.30 (m, 1H), 2.07-1.93 (m, 1H), 1.11 (dd, J=4.5 Hz, 0.2 Hz, 6H).

Example 56

N-((2-(2,6-dioxopiperidin-3-yl)-1-oxoisoindolin-5-yl)methyl)-2,2-difluoro-2-(2-(2,2,2-trifluoroethoxy)phenyl)acetamide

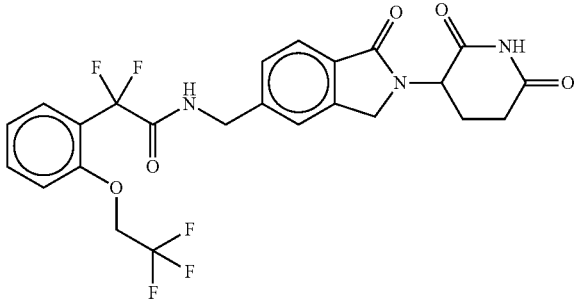

A. 1-Iodo-2-(2,2,2-trifluoroethoxy)benzene

To a stirred solution of 2-iodophenol (2 g, 9.09 mmol) in N,N-dimethylformamide (30 mL) was added 1,1,1-trifluoro-2-iodoethane (1.34 mL, 13.63 mmol), followed by potassium carbonate (3.76 g 2.72 mmol) and stirred at 50° C. for 16 h. The reaction mixture was diluted with ice water (40 mL) and extracted with ethyl acetate (3×40 mL). The combined organic layers were washed with water (40 mL), brine (40 mL), dried over sodium sulfate, filtered and concentrated to afford 1-iodo-2-(2,2,2-trifluoroethoxy)benzene (1.6 g, 5.46 mmol, 58% yield) as a colorless liquid. MS (ESI) m/z 302.0 [M]$^+$.

B. Ethyl 2,2-difluoro-2-(2-(2,2,2-trifluoroethoxy)phenyl)acetate

To a stirred solution of 1-iodo-2-(2,2,2-trifluoroethoxy)benzene (1.5 g, 5.63 mmol) in dimethylsulfoxide (20 mL) was added ethyl 2-bromo-2,2-difluoroacetate (1.1 mL, 8.44 mmol) followed by copper (0.92 g, 14.63 mmol) at RT and stirred at 55° C. for 6 h. The reaction mixture was basified with aqueous saturated sodium bicarbonate solution and extracted with ethyl acetate (3×20 mL). The combined organic layers were washed with water (20 mL), brine (20 mL), dried over sodium sulfate, filtered and concentrated. The obtained crude was purified by silica gel column chromatography (20% ethyl acetate in pet ether) to afford ethyl 2,2-difluoro-2-(2-(2,2,2-trifluoroethoxy)phenyl)acetate (410 mg, 1.37 mmol, 24%) as a colorless liquid. MS (ESI) m/z 298.1 [M]+.

C. 2,2-Difluoro-2-(2-(2,2,2-trifluoroethoxy)phenyl) acetic acid

To a stirred solution of ethyl 2,2-difluoro-2-(2-(2,2,2-trifluoroethoxy)phenyl)acetate (400 mg, 1.34 mmol) in tetrahydrofuran:methanol:water (15 mL, 1:1:1) was added lithium hydroxide monohydrate (169 mg, 4.02 mmol) and stirred at room temperature for 4 h. The volatiles were removed under reduced pressure and obtained crude was dissolved in water (15 mL) and washed with ethyl acetate (2×10 mL). Aqueous layer was acidified with 1N hydrochloride aqueous solution and extracted with ethyl acetate (3×10 mL). The combined organic layers were washed with brine (15 mL), dried over sodium sulfate, filtered and solvent was concentrated to afford 2,2-difluoro-2-(2-(2,2,2-trifluoroethoxy)phenyl)acetic acid (270 mg, 1 mmol, 59% yield) as semi-solid compound. $^1$H NMR (400 MHz, CDCl$_3$) δ 7.72 (d, J=6.3 Hz, 1H), 7.51 (t, J=8.4 Hz, 1H), 7.19 (t, J=7.8 Hz, 1H), 6.93 (d, J=8.4 Hz, 1H), 6.68 (brs, 1H), 4.38 (q, J=8.1 Hz, 1H).

D. N-((2-(2,6-Dioxopiperidin-3-yl)-1-oxoisoindolin-5-yl)methyl)-2,2-difluoro-2-(2-(2,2,2-trifluoroethoxy)phenyl)acetamide To an ice cold solution of 2,2'-difluoro-2-(2-(2,2,2-trifluoroethoxy)phenyl)acetic acid (262 mg, 1.16 mmol) in pyridine (6 mL) was added phosphorus oxychloride (0.27 mL, 2.9 mmol) drop wise and stirred at 0-5° C. for 1 h and then added 3-(5-(aminomethyl)-1-oxoisoindolin-2-yl)piperidine-2,6-dione hydrochloride (300 mg, 0.97 mmol) and stirred at room temperature for 2 h. The reaction mixture was basified with aqueous saturated sodium bicarbonate solution and extracted with ethyl acetate (3×15 mL). The combined organic layers were washed with water (15 mL), brine (15 mL), dried over sodium sulfate, filtered and concentrated. The resultant residue was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl)methyl)-2,2-difluoro-2-(2-(2,2,2-trifluoroethoxy)phenyl)acetamide (60 mg, 0.11 mmol, 11% yield) as white solid. MS (ESI) m/z 525.89 [M+1]+. $^1$H NMR (300 MHz, DMSO-d$_6$) δ 10.98 (s, 1H), 9.42 (t, J=5.4 Hz, 1H), 7.70 (d, J=7.5 Hz, 1H), 7.63-7.52 (m, 2H), 7.49 (s, 1H), 7.43 (d, J=8.1 Hz, 1H), 7.26 (d, J=8.1 Hz, 1H), 7.18 (dd, J=7.7, 7.6 Hz, 1H), 5.11 (dd, J=13.2, 4.8 Hz, 1H), 4.75 (q, J=8.7 Hz, 2H), 4.46 (d, J=17.1 Hz, 1H), 4.45 (d, J=6.0 Hz, 2H), 4.31 (d, J=17.4 Hz, 1H), 2.92-2.86 (m, 1H), 2.63-2.57 (m, 1H), 2.42-2.37 (m, 1H), 2.02-1.98 (m, 1H).

Example 57

N-((2-(2,6-Dioxopiperidin-3-yl)-1-oxoisoindolin-5-yl)methyl)-2-(2-ethoxy-4-fluorophenyl)-2,2-difluoroacetamide

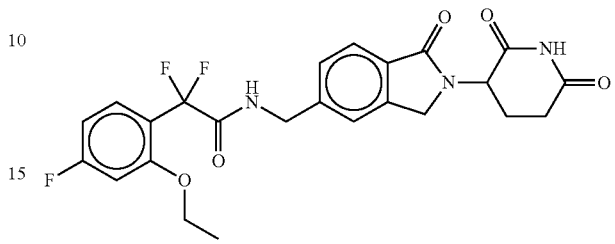

A. 1-(2-Ethoxy-4-fluorophenyl)ethanone

To a stirred solution of 1-(4-fluoro-2-hydroxyphenyl)ethanone (3 g, 19.48 mmol) in N,N-dimethylformamide (15 mL) was added bromoethane (5.30 g, 48.76 mmol) potassium carbonate (8.06 g 58.44 mmol) and stirred for 16 h at 100° C. The reaction mixture was diluted with ethylacetate (30 mL) and extracted with ethyl acetate (2×100 mL). The combined organic layers were washed with water (2×50 mL), brine (50 mL), dried over sodium sulphate and concentrated to afford 1-(2-ethoxy-4-fluorophenyl)ethanone (2.6 g, 14.28 mmol, 74% yield) as a brown liquid. MS (ESI) m/z 183.17 [M]+

B. Ethyl 2-(2-ethoxy-4-fluorophenyl)-2-oxoacetate

To a stirred solution of 1-(2-ethoxy-4-fluorophenyl)ethanone (1.0 g, 5.49 mmol) in pyridine (15 mL) was added selenium dioxide (1.52 g, 13.73 mmol) and stirred for 16 h at 100° C. The reaction mixture was diluted with dichloromethane (30 mL) and filtered through Celite pad. To the filtrate was added ethyl chloroformate (3 mL) at 0° C. and stirred at room temperature for 3 h. The reaction mixture was neutralized with 1N aqueous hydrochloric acid (up to pH-4) and extracted with ethyl acetate (2×100 mL). The combined organic layers were washed with water (2×50 mL), brine (50 mL), dried over sodium sulphate and concentrated. The crude was purified with column chromatography using 100-200 mesh silica gel eluting 10% ethylacetate-pet ether to afford ethyl 2-(2-ethoxy-4-fluorophenyl)-2-oxoacetate (880 g, 3.66 mmol, 67% yield) as a brown liquid. MS (ESI) m/z 241.14 [M]+

C. Ethyl 2-(2-ethoxy-4-fluorophenyl)-2,2-difluoroacetate

To a stirred solution of ethyl 2-(2-ethoxy-4-fluorophenyl)-2-oxoacetate (800 mg, 3.33 mmol) was added diethyl amino sulfur trifluoride (1.34 g, 8.33 mmol) and stirred for 16 h at room temperature. The reaction mixture was neutralized with aqueous saturated sodium bicarbonate (up to pH-8) and extracted with ethyl acetate (3×50 mL). The combined organic layers were washed with water (2×30 mL), brine (30 mL), dried over sodium sulphate and concentrated to afford ethyl 2-(2-ethoxy-4-fluorophenyl)-2,2-difluoroacetate (450 mg, 1.71 mmol, 51% yield) as a brown liquid. GC-MS (ESI) m/z 262 [M]+

D. 2-(2-Ethoxy-4-fluorophenyl)-2,2-difluoroacetic acid

To a stirred solution of ethyl 2-(2-ethoxy-4-fluorophenyl)-2,2-difluoroacetate (1 g, 3.81 mmol) in tetrahydrofuran/Methanol/Water mixture (30 mL, 1:1:1) was added lithium hydroxide monohydrate (480 mg, 11.45 mmol) and stirred at room temperature for 4 h. The reaction mixture was concentrated and the residue was neutralized with 10% aqueous hydrochloric acid (10 mL) and extracted with ethyl acetate (2×50 mL). The combined organic layers were washed with brine (20 mL), dried over sodium sulphate and concentrated to afford 2-(2-ethoxy-4-fluorophenyl)-2,2-difluoroacetic acid (600 mg, 2.56 mmol, 67% yield) as a brown semi solid. The crude compound used for next step without further purification.

E. N-((2-(2,6-dioxopiperidin-3-yl)-1-oxoisoindolin-5-yl)methyl)-2-(2-ethoxy-4-fluorophenyl)-2,2-difluoroacetamide To a cold (0° C.) stirred solution of 2-(2-ethoxy-4-fluorophenyl)-2,2-difluoroacetic acid (181 mg, 0.776 mmol) in pyridine (10 mL) was added phosphoryl chloride (294 mg, 1.93 mmol) and stirred at 0° C.-5° C. for 1 h. To this reaction mixture was then added 3-(5-(aminomethyl)-1-oxoisoindolin-2-yl)piperidine-2,6-dione hydrochloride (200 mg, 0.647 mmol) at 0° C. and allowed to warm room temperature stirring over a period of 1 h. The reaction mixture was neutralized with saturated aqueous sodium bicarbonate (up to pH-8) and extracted with ethyl acetate (3×50 mL). The combined organic layers were washed with water (2×10 mL), brine (10 mL), dried over sodium sulphate and concentrated. The crude product was purified by Releveris C-18 reversed phase column using 45-55% acetonitrile in aqueous formic acid (0.1%) to afford N-((2-(2,6-dioxopiperidin-3-yl)-1-oxoisoindolin-5-yl)methyl)-2-(2-ethoxy-4-fluorophenyl)-2,2-difluoroacetamide (80 mg, 0.163 mmol, 25% yield) as an off white solid. MS (ESI) m/z 489.95 [M+1]$^+$. $^1$H NMR (300 MHz, DMSO-$d_6$) δ 10.98 (s, 1H), 9.35 (br t, J=5.8 Hz, 1H), 7.71 (d, J=7.7 Hz, 1H), 7.59 (dd, J=8.6, 6.8 Hz, 1H), 7.50 (s, 1H), 7.44 (d, J=7.7 Hz, 1H), 7.05 (br d, J=11.0 Hz, 1H), 6.88 (td, J=8.5, 2.4 Hz, 1H), 5.11 (dd, J=13.3, 5.3 Hz, 1H), 4.50-4.26 (m, 4H), 4.00 (q, J=6.9 Hz, 2H), 3.00-2.85 (m, 1H), 2.67-2.55 (m, 1H), 2.44-2.31 (m, 1H), 2.06-1.95 (m, 1H), 1.11 (t, J=6.9 Hz, 3H).

Example 58

N-((2-(2,6-Dioxopiperidin-3-yl)-1-oxoisoindolin-5-yl)methyl)-2,2-difluoro-2-(2-isopropoxyphenyl)acetamide

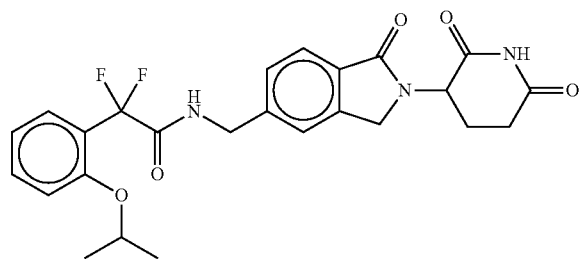

A. 1-Iodo-2-isopropoxybenzene

To a stirred solution of 2-iodophenol (2 g, 9.09 mmol) in N,N-dimethylformamide (20 mL) was added 2-bromopropane (3.38 mL, 36.3 mmol) followed by potassium carbonate (3.76 g, 27.27 mmol) and stirred at 90° C. for 16 h. The reaction mixture was diluted with ice water (25 mL) and extracted with ethyl acetate (3×20 mL). The combined organic layers were washed with water (20 mL), brine (20 mL), dried over sodium sulfate, filtered and concentrated to afford 1-iodo-2-isopropoxybenzene (2.0 g, 7.63 mmol, 84% yield) as a colorless liquid. MS (ESI) m/z 262.21 [M]$^+$.

B. Ethyl 2,2-difluoro-2-(2-isopropoxyphenyl)acetate

To a stirred solution of 1-iodo-2-isopropoxybenzene (2 g, 7.6 mmol) in dimethylsulfoxide (20 mL) was added ethyl 2-bromo-2,2-difluoroacetate (1.5 mL, 11.45 mmol) followed by copper (1.26 g, 19.84 mmol) at RT and stirred at 55° C. for 6 h. The reaction mixture was basified with aqueous saturated sodium bicarbonate solution and extracted with ethyl acetate (3×20 mL). The combined organic layers were washed with water (20 mL), brine (20 mL), dried over sodium sulfate, filtered and concentrated. The obtained crude product was purified by flash chromatography (20% ethyl acetate in pet ether) to afford ethyl 2,2-difluoro-2-(2-isopropoxyphenyl)acetate (1.3 g, 5.03 mmol, 66%) as a colorless liquid. MS (ESI) m/z 259.23 [M+1]$^+$.

C. 2,2-Difluoro-2-(2-isopropoxyphenyl)acetic acid

To a stirred solution of ethyl 2,2-difluoro-2-(2-isopropoxyphenyl)acetate (1 g, 3.87 mmol) in tetrahydrofuran:methanol:water (15 mL, 1:1:1) was added lithium hydroxide monohydrate (0.49 g, 11.62 mmol) and stirred at room temperature for 4 h. The volatiles were removed under reduced pressure and obtained crude was dissolved in water (15 mL), washed with ethyl acetate (2×10 mL). Aqueous layer was acidified with 1N hydrochloride aqueous solution and extracted with ethyl acetate (3×15 mL). The combined organic layers were washed with brine (15 mL), dried over sodium sulfate, filtered and concentrated to afford 2,2-difluoro-2-(2-isopropoxyphenyl)acetic acid (600 mg, 2.60 mmol, 67% yield) as semi-solid compound. $^1$H NMR (300 MHz, CDCl$_3$) δ 8.75 (brs, 1H), 7.65 (d, J=7.2 Hz, 1H), 7.44 (dd, J=8.0, 7.6 Hz, 1H), 7.03 (dd, J=8.0, 7.2 Hz, 1H), 6.94 (d, J=8.4 Hz, 1H), 4.66 (Sep, J=6.0 Hz, 1H), 1.32 (d, J=6.0 Hz, 6H).

D. N-((2-(2,6-Dioxopiperidin-3-yl)-1-oxoisoindolin-5-yl)methyl)-2,2-difluoro-2-(2-isopropoxyphenyl)acetamide To an ice cold solution of 2,2-difluoro-2-(2-isopropoxyphenyl)acetic acid (267 mg, 1.16 mmol) in pyridine (6 mL) was added phosphorus oxychloride (0.27 mL, 2.9 mmol) in drop wise and stirred at 0-5° C. for 1 h. Then, 3-(5-(aminomethyl)-1-oxoisoindolin-2-yl)piperidine-2,6-dione hydrochloride (300 mg, 0.97 mmol) was added and stirred at room temperature for 2 h. The reaction mixture was basified with aqueous saturated sodium bicarbonate solution and extracted with ethyl acetate (3×15 mL). The combined organic layers were washed with water (15 mL), brine (15 mL), dried over sodium sulfate, filtered and concentrated. The resultant residue was purified by Releveris C-18 reversed phase column chromatography (50-55% acetonitrile in 0.1% aqueous formic acid) to afford N-((2-(2,6- dioxopiperidin-3-yl)-1-oxoisoindolin-5-yl)methyl)-2,2-difluoro-2-(2-isopropoxyphenyl)acetamide (40 mg, 0.08 mmol, 8% yield) as white solid. MS (ESI) m/z 485.98 [M+1]⁺. ¹H NMR (300 MHz, DMSO-$d_6$) δ 10.99 (s, 1H), 9.26 (t, J=5.8 Hz, 1H), 7.70 (d, J=7.8 Hz, 1H), 7.55-7.45 (m, 4H), 7.12 (d, J=8.4 Hz, 1H), 7.02 (dd, J=7.2, 7.0 Hz, 1H), 5.11 (dd, J=13.2, 5.1 Hz, 1H), 4.46 (Sep, J=6.0 Hz, 1H), 4.45 (d, J=6.3 Hz, 2H), 4.44 (d, J=17.2, 1H), 4.31 (d, J=17.4 Hz, 1H), 2.98-2.86 (m, 1H), 2.57-2.49 (m, 1H), 2.43-2.30 (m, 1H), 2.04-1.94 (m, 1H), 1.13 (d, J=6.0 Hz, 3H), 1.12 (d, J=6.0 Hz, 3H).

Example 59

N-((2-(2,6-Dioxopiperidin-3-yl)-1-oxoisoindolin-5-yl)methyl)-2,2-difluoro-2-(2-fluoro-4-isopropoxyphenyl)acetamide

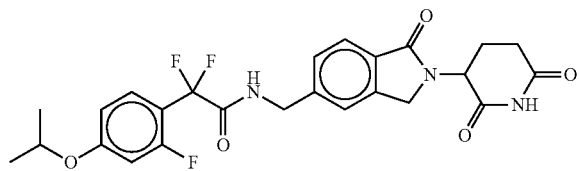

A. 1-(2-Fluoro-4-isopropoxyphenyl)ethanone

To a stirred solution of 1-(2-fluoro-4-hydroxyphenyl)ethanone (300 mg, 1.95 mmol) in N,N-dimethylformamide (3 mL) was added isopropyl iodide (397 mg, 2.33 mmol) followed by potassium carbonate (672 mg, 4.87 mmol) and stirred at 90° C. for 16 h. The reaction mixture was diluted with ice water (20 mL) and extracted with ethyl acetate (3×10 mL). The combined organic layers were washed with water (10 mL), brine (10 mL), dried over sodium sulfate, filtered and concentrated to afford 1-(2-fluoro-4-isopropoxyphenyl)ethanone (300 mg, 1.53 mmol, 79% yield) as a colorless liquid. MS (ESI) m/z 197.2 [M+1]⁺.

B. Ethyl 2-(2-fluoro-4-isopropoxyphenyl)-2-oxoacetate

To a stirred solution of 1-(2-fluoro-4-isopropoxyphenyl)ethanone (300 mg, 1.63 mmol) in pyridine (3 mL) was added selenium dioxide (452 mg, 3.38 mmol) at room temperature. The reaction mixture was stirred at 100° C. for 16 h. The reaction mixture was filtered through a Celite pad and washed thoroughly with dichloromethane (10 mL). Ethyl chloroformate (0.64 mL) was added to the filtrate at 0° C. and stirred at room temperature for 4 h. The reaction mixture was quenched with ice water and extracted with dichloromethane (3×10 mL). The combined organic layers were washed with 1N hydrochloride solution (10 mL), brine (10 mL), dried over sodium sulfate, filtered and concentrated to afford ethyl 2-(2-fluoro-4-isopropoxyphenyl)-2-oxoacetate (200 mg, 0.787 mmol, 48% yield) as a colorless liquid. MS (ESI) m/z 255.28 [M+1]⁺.

C. Ethyl 2,2-difluoro-2-(2-fluoro-4-isopropoxyphenyl)acetate

Ethyl 2-(2-fluoro-4-isopropoxyphenyl)-2-oxoacetate (200 mg, 0.787 mmol) was added into diethylamino sulfur trifluoride (0.4 mL) at 0° C. and stirred at room temperature for 16 h. The reaction mixture was quenched with aqueous sodium bicarbonate solution and extracted with ethyl acetate (3×10 mL). The combined organic layers were washed with brine (10 mL), dried over sodium sulfate, filtered and concentrated. Obtained crude product was purified by flash column chromatography (100-200 silica gel, 10% ethyl acetate in pet ether) to afford ethyl 2,2-difluoro-2-(2-fluoro-4-isopropoxyphenyl)acetate (200 mg, 0.72 mmol, 92% yield) as a colourless liquid. MS (ESI) m/z 276.1 [M+1]⁺.

D. 2,2-Difluoro-2-(2-fluoro-4-isopropoxyphenyl)acetic acid

To a stirred solution of ethyl 2,2-difluoro-2-(2-fluoro-4-isopropoxyphenyl)acetate (200 mg, 0.72 mmol) in mixture of tetrahydrofuran:methanol:water (10 mL, 1:1:1) was added lithium hydroxide monohydrate (91 mg, 2.17 mmol) and stirred at room temperature for 16 h. The reaction mixture was concentrated under reduced pressure and the resultant residue was dissolved in water (10 mL) and washed with ethyl acetate (2×10 mL). The aqueous layer was acidified with 1N hydrochloride aqueous solution and extracted with ethyl acetate (3×10 mL). The combined organic layers were washed with brine (10 mL), dried over sodium sulfate, filtered and concentrated to afford 2,2-difluoro-2-(2-fluoro-4-isopropoxyphenyl)acetic acid (160 mg, 0.65 mmol, 89% yield) as semi-solid compound.

E. N-((2-(2,6-Dioxopiperidin-3-yl)-1-oxoisoindolin-5-yl)methyl)-2,2-difluoro-2-(2-fluoro-4-isopropoxyphenyl)acetamide To an ice cold solution of 2,2-difluoro-2-(2-fluoro-4-isopropoxyphenyl)acetic acid (289 mg, 1.16 mmol) in pyridine (9 mL) was added phosphorus oxychloride (0.27 mL, 2.9 mmol) in drop wise and stirred at 0-5° C. for 1 h. Then, 3-(5-(aminomethyl)-1-oxoisoindolin-2-yl) piperidine-2,6-dione hydrochloride (300 mg, 0.97 mmol) was added into the reaction mixture and stirred at room temperature for 1 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant crude product was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl)methyl)-2,2-difluoro-2-(2-fluoro-4-isopropoxyphenyl)acetamide (60 mg, 0.12 mmol, 12% yield) as white solid. MS (ESI) m/z 503.99 [M+1]⁺. ¹H NMR (400 MHz, DMSO-$d_6$) δ 10.99 (s, 1H), 9.59 (d, J=7.2 Hz, 1H), 7.70 (d, J=7.6 Hz, 1H), 7.48 (dd, J=8.8, 8.7 Hz, 1H), 7.47 (s, 1H), 7.41 (d, J=8.0 Hz, 1H), 6.96 (dd, J=13.2, 2.0 Hz, 1H), 6.87 (dd, J=8.3, 2.0 Hz, 1H), 5.11 (dd, J=13.2, 5.2 Hz, 1H), 4.71 (sep, J=6.0 Hz, 1H), 4.48 (d, J=6.4 Hz, 2H), 4.45 (d, J=17.2 Hz, 1H), 4.31 (d, J=18.0 Hz, 1H), 2.95-2.87 (m, 1H), 2.62-2.58 (m, 1H), 2.41-2.37 (m, 1H), 2.02-1.99 (m, 1H), 1.28 (d, J=5.6 Hz, 6H).

Example 60

N-((2-(2,6-dioxopiperidin-3-yl)-1-oxoisoindolin-5-yl)methyl)-2,2-difluoro-2-(3-(morpholinomethyl)phenyl)acetamide

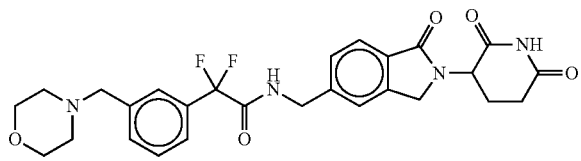

A. Ethyl 2,2-difluoro-2-(3-(morpholinomethyl)phenyl)acetate

To a stirred solution of ethyl 2,2-difluoro-2-(3-formyl-phenyl)acetate (1.2 g, 5.26 mmol) in ethanol (25 mL) was added morpholine (0.91 g, 10.52 mmol), acetic acid (0.63 mL, 10.52 mmol) and stirred at 0° C. for 1 h and then added sodium cyanoborohydride (0.661 g 10.52 mmol) and stirred at room temperature for 3 h. The reaction mixture was quenched with water (50 mL) and extracted with ethyl acetate (3×50 mL). The combined organic layers were washed with water (2×20 mL), brine (30 mL), dried over sodium sulphate and concentrated to afford ethyl 2,2-difluoro-2-(3-(morpholinomethyl)phenyl)acetate (0.8 g, 2.67 mmol, 51% yield) as brown liquid. LCMS (ESI) m/z 300.0.

B. 2,2-Difluoro-2-(3-(morpholinomethyl)phenyl)acetic acid

To a cold (0° C.) stirred solution of ethyl 2,2-difluoro-2-(3-(morpholinomethyl)phenyl)acetate (0.8 g, 2.67 mmol) in methanol/tetrahydrofuran/water mixture (15 mL, 1:1:1) was added lithium hydroxide monohydrate (337 mg, 8.02 mmol) and stirred at room temperature for 2 h. The reaction mixture was concentrated and the residue was neutralized with 10% aqueous potassium bisulphate (20 mL) and extracted with ethyl acetate (2×40 mL). The combined organic layers were washed with brine (20 mL), dried over sodium sulphate and concentrated to afford 2,2-difluoro-2-(3-(morpholinomethyl)phenyl)acetic acid (600 mg, 2.21 mmol, 82% yield) as a brown solid. LCMS (ESI) m/z 272.

C. N-((2-(2,6-Dioxopiperidin-3-yl)-1-oxoisoindolin-5-yl)methyl)-2,2-difluoro-2-(3-(morpholinomethyl)phenyl)acetamide To a cold (0° C.) stirred solution of 2,2-difluoro-2-(3-(morpholinomethyl)phenyl)acetic acid (290 mg, 1.06 mmol) and 3-(5-(aminomethyl)-1-oxoisoindolin-2-yl)piperidine-2,6-dione hydrochloride (300 mg, 0.970 mmol) in N,N-dimethylformamide (20 mL) was added N,N-diisopropylethylamine (0.6 mL, 3.33 mmol) followed by 1-[Bis(dimethylamino)methylene]-1H-1,2,3-triazolo[4,5-b]pyridinium 3-oxid hexafluorophosphate (553.3 mg, 1.45 mmol) and stirred at room temperature for 4 h. The reaction mixture was diluted with water (50 mL) and extracted with ethyl acetate (2×40 mL). The combined organic layers were washed with brine (30 mL), dried over sodium sulphate, concentrated and dried under vacuum. The product was purified by Reveleris C-18 reversed phase column using 40% acetonitrile in aqueous formic acid (0.1%) to afford N-((2-(2,6-dioxopiperidin-3-yl)-1-oxoisoindolin-5-yl)methyl)-2,2-difluoro-2-(3-(morpholinomethyl)phenyl) acetamide (40 mg, 0.06 mmol, 8% yield) as an off-white solid. LCMS (ESI) m/z 526.7 [M+1]+. 1H NMR (300 MHz, TFA-d4) δ=8.03-7.92 (m, 2H), 7.83 (br s, 1H), 7.72 (br s, 2H), 7.64-7.54 (m, 2H), 5.64-5.0 (m, 1H), 4.80 (br s, 2H), 4.73 (br s, 2H), 4.6 (br s, 2H), 4.4 (s, 2H), 4.08 (t, J=11.7 Hz, 2H), 3.73 (d, J=11.7 Hz, 1H), 3.51 (d, J=12.1 Hz, 1H), 3.33-3.04 (m, 2H), 2.92-2.61 (m, 1H), 2.53 (s, 1H).

Example 61

N-((2-(2,6-Dioxopiperidin-3-yl)-1-oxoisoindolin-5-yl)methyl)-2,2-difluoro-2-(4-fluoro-2-(2,2,2-trifluoroethoxy)phenyl)acetamide

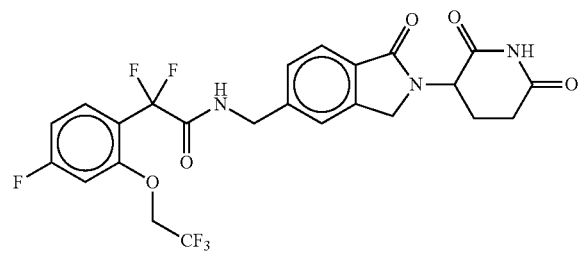

A. 1-(4-Fluoro-2-(2,2,2-trifluoroethoxy)phenyl)ethanone

To a stirred solution of 1-(4-fluoro-2-hydroxyphenyl)ethanone (1 g, 6.48 mmol) in N,N-dimethylformamide (20 mL) was added 1,1,1-trifluoro-2-iodoethane (0.64 mL, 6.48 mmol) followed by potassium carbonate (2.68 g, 19.46 mmol) and stirred at 90° C. for 16 h. The reaction mixture was diluted with ice water (30 mL) and extracted with ethyl acetate (3×20 mL). The combined organic layers were washed with water (20 mL), brine (20 mL), dried over sodium sulfate, filtered and solvent was concentrated to afford 1-(4-fluoro-2-(2,2,2-trifluoroethoxy)phenyl)ethanone (325 mg, 1.36 mmol, 20% yield) as a colorless liquid. 1H NMR (400 MHz, CDCl3) δ 7.90 (dd, J=6.8, 6.8 Hz, 1H), 6.85-6.81 (m, 1H), 6.61 (dd, J=2.0, 2.4 Hz, 1H), 4.42-4.38 (m, 2H), 2.61 (s, 3H).

B. Ethyl 2-(4-fluoro-2-(2,2,2-trifluoroethoxy)phenyl)-2-oxoacetate

To a stirred solution of 1-(4-fluoro-2-(2,2,2-trifluoroethoxy)phenyl)ethanone (320 mg, 1.35 mmol) in pyridine (10 mL) was added selenium dioxide (376 mg, 3.38 mmol) at room temperature. The reaction mixture was stirred at 100° C. for 16 h. The reaction mixture was filtered through celite pad and washed with dichloromethane (10 mL). Ethyl chloroformate (0.64 mL) was added to the filtrate at 0° C. and stirred at room temperature for 4 h. The reaction mixture was quenched with ice water and extracted with dichloromethane (3×10 mL). The combined organic layers were washed with 1N hydrochloride solution (15 mL), brine (10 mL), dried over sodium sulfate, filtered and concentrated to afford ethyl 2-(4-fluoro-2-(2,2,2-trifluoroethoxy)phenyl)-2-oxoacetate (300 mg, 1.02 mmol, 75% yield) as a colorless liquid. 1H NMR (400 MHz, CDCl3) δ 7.99-7.95 (m, 1H), 6.94-6.89 (m, 1H), 6.66 (dd, J=2.4, 9.6 Hz, 1H), 4.42-4.35 (m, 4H), 1.38 (t, J=7.6 Hz, 3H).

C. Ethyl 2,2-difluoro-2-(4-fluoro-2-(2,2,2-trifluoroethoxy)phenyl)acetate

Ethyl 2-(4-fluoro-2-(2,2,2-trifluoroethoxy)phenyl)-2-oxoacetate (300 mg, 1.02 mmol) was added into Diethylamino sulfur trifluoride (DAST, 0.9 mL) at 0° C. and stirred at room temperature for 16 h. The reaction mixture was quenched with aqueous sodium bicarbonate solution and extracted with ethyl acetate (3×10 mL). The combined organic layers were washed with brine (10 mL), dried over sodium sulfate, filtered and concentrated. Obtained crude was purified by column chromatography (100-200 silica gel, 10% ethyl acetate in pet ether) to afford ethyl 2,2-difluoro-2-(4-fluoro-2-(2,2,2-trifluoroethoxy)phenyl)acetate (250 mg, 0.79 mmol, 77% yield) as a colourless liquid. $^1$H NMR (300 MHz, CDCl$_3$) δ 7.71-7.66 (m, 1H), 6.91-6.85 (m, 1H), 6.66 (d, J=9.6 Hz, 1H), 4.39-4.28 (m, 4H), 1.33 (t, J=4.2 Hz, 3H).

D. 2,2-Difluoro-2-(4-fluoro-2-(2,2,2-trifluoroethoxy)phenyl)acetic acid

To a stirred solution of ethyl 2,2-difluoro-2-(4-fluoro-2-(2,2,2-trifluoro ethoxy)phenyl)acetate (390 mg, 1.23 mmol) in tetrahydrofuran:methanol:water (12 mL, 1:1:1) was added lithium hydroxide monohydrate (155 mg, 3.70 mmol) and stirred at room temperature for 16 h. The reaction mixture was concentrated under reduced pressure and obtained crude was dissolved in water (10 mL) and washed with ethyl acetate (2×10 mL). Aqueous layer was acidified with 1N hydrochloride aqueous solution and extracted with ethyl acetate (3×10 mL). The combined organic layers were washed with brine (10 mL), dried over sodium sulfate, filtered and solvent was concentrated to afford 2,2-difluoro-2-(4-fluoro-2-(2,2,2-trifluoroethoxy)phenyl)acetic acid (280 mg, 0.98 mmol, 79% yield) as semi-solid compound. $^1$H NMR (400 MHz, CDCl$_3$) δ 7.72-7.69 (m, 1H), 6.91-6.87 (m, 1H), 6.66 (d, J=9.2 Hz, 1H), 6.57 (brs, 1H), 4.39-4.34 (m, 2H).

E. N-((2-(2,6-Dioxopiperidin-3-yl)-1-oxoisoindolin-5-yl)methyl)-2,2-difluoro-2-(4-fluoro-2-(2,2,2-trifluoroethoxy)phenyl)acetamide To an ice cold solution of 2,2-difluoro-2-(4-fluoro-2-(2,2,2-trifluoroethoxy)phenyl)acetic acid (280 mg, 0.97 mmol) in pyridine (9 mL) was added phosphorus oxychloride (0.27 mL, 2.9 mmol) drop wise and stirred at 0-5° C. for 1 h. Then, 3-(5-(aminomethyl)-1-oxoisoindolin-2-yl)piperidine-2,6-dione hydrochloride (300 mg, 0.97 mmol) was added into the reaction mixture and stirred at room temperature for 1 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to give N-((2-(2,6-dioxopiperidin-3-yl)-1-oxoisoindolin-5-yl)methyl)-2,2-difluoro-2-(4-fluoro-2-(2,2,2-trifluoroethoxy)phenyl)acetamide (45 mg, 0.08 mmol, 8% yield) as white solid. MS (ESI) m/z 544.03 [M+1]$^+$. $^1$H NMR (300 MHz, DMSO-d$_6$) δ 10.99 (s, 1H), 9.44 (t, J=5.7 Hz, 1H), 7.70 (d, J=7.8 Hz, 1H), 7.64 (dd, J=9.0, 6.6 Hz, 1H), 8.49 (s, 1H), 7.42 (d, J=8.1 Hz, 1H), 7.26 (dd, J=11.1, 0.6 Hz, 1H), 7.02 (ddd, J=10.8, 8.7, 2.4 Hz, 1H), 5.11 (dd, J=13.2, 5.1 Hz, 1H), 4.81 (q, J=8.7 Hz, 2H), 4.45 (d, J=7.2 Hz, 2H), 4.44 (d, J=16.2 Hz, 1H), 4.31 (d, J=17.1 Hz, 1H), 2.93-2.90 (m, 1H), 2.63-2.54 (m, 1H), 2.45-2.36 (m, 1H), 2.01-1.98 (m, 1H).

Example 62

N-((2-(2,6-Dioxopiperidin-3-yl)-1-oxoisoindolin-5-yl)methyl)-2,2-difluoro-2-(4-isopropoxy-2-methylphenyl)acetamide

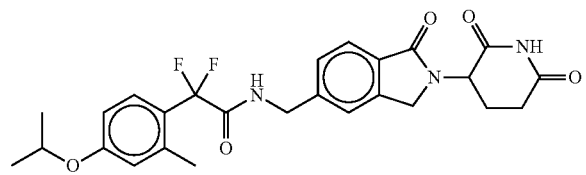

A. 1-(4-Isopropoxy-2-methylphenyl)ethanone

To a stirred solution of 1-(4-hydroxy-2-methylphenyl)ethanone (2.0 g, 13.333 mmol) in N,N-dimethylformamide (20 mL) was added potassium carbonate (5.5 g, 49.0 mmol) followed by isopropyl iodide (2 mL, 20.0 mmol) and stirred at 80° C. for 4 h. The reaction mixture was filtered and water (20 mL) was added and extracted with ethyl acetate (2×40 mL). The combined organic layers were washed with brine (30 mL), dried over sodium sulphate and concentrated. The resultant residue was purified by column chromatography (100-200 silica) using 0-10% ethyl acetate in hexanes to afford 1-(4-isopropoxy-2-methylphenyl)ethanone (1.58 g, 8.229 mmol, 62% yield). MS (ESI) m/z 193.48[M+1]$^+$.

B. Ethyl 2-(4-isopropoxy-2-methylphenyl)-2-oxoacetate

To a stirred solution of 1-(4-isopropoxy-2-methylphenyl)ethanone (1.58 g, 8.229 mmol) in pyridine (30 mL) was added selenium dioxide (1.82 g, 16.46 mmol) and stirred for 16 h at 100° C. The reaction mixture was diluted with dichloromethane (40 mL) and filtered through Celite pad. To the filtrate was added ethyl chloroformate (3 mL) at 0° C. and stirred for 2 h. The reaction mixture was neutralized with 1N aqueous hydrochloric acid (up to pH-4) and extracted with ethyl acetate (3×50 mL). The combined organic layers were washed with water (2×10 mL), brine (10 mL), dried over sodium sulphate and concentrated. The resultant residue was purified by column chromatography (100-200 silica) using 10% ethyl acetate in pet ether to afford ethyl 2-(4-isopropoxy-2-methylphenyl)-2-oxoacetate (1.0 g, 4.01 mmol, 49%) as a colorless liquid. MS (ESI) m/z 251.40 [M+1]$^+$.

C. Ethyl 2,2-difluoro-2-(4-isopropoxy-2-methylphenyl)acetate

To a stirred solution of ethyl 2-(4-isopropoxy-2-methylphenyl)-2-oxoacetate (1.0 g, 4.01 mmol) was reacted with diethyl amino sulfur trifluoride (1.32 mL, 10.025 mmol) and stirred for 12 h at room temperature. The reaction mixture was neutralized with aqueous saturated sodium bicarbonate (up to pH-8) and extracted with ethyl acetate (3×50 mL). The combined organic layer was washed with water (2×10 mL), brine (10 mL), dried over sodium sulphate and concentrated to afford ethyl 2,2-difluoro-2-(4-isopropoxy-2-methylphenyl)acetate (990 mg, 3.639 mmol, 91%) as a liquid. GC-MS (m/z) 272.2 [M]$^+$.

D. 2,2-Difluoro-2-(4-isopropoxy-2-methylphenyl)acetic acid

To a cold (0° C.) stirred solution of ethyl 2,2-difluoro-2-(4-isopropoxy-2-methylphenyl)acetate (990 mg, 3.694 mmol) in tetrahydrofuran:methanol:water mixture (1:1:1, 10 mL) was added lithium hydroxide (916 mg, 21.838 mmol) and stirred at room temperature for 2 h. The reaction mixture was concentrated and the residue was neutralized with 10% aqueous hydrochloric acid (10 mL) and extracted with ethyl acetate (2×20 mL). The combined organic layers were washed with brine (20 mL), dried over sodium sulphate and concentrated to afford 2,2-difluoro-2-(4-isopropoxy-2-methylphenyl)acetic acid (719 mg, 2.618 mmol, 81% yield) as an brown solid. $^1$H NMR (400 MHz, CDCl$_3$) δ ppm 9.59 (br s, 1H) 7.49 (d, J=8.80 Hz, 1H) 6.58-6.85 (m, 2H) 4.41-4.67 (m, 1H) 2.41 (s, 3H) 1.34 (m, 6H).

E. N-((2-(2,6-Dioxopiperidin-3-yl)-1-oxoisoindolin-5-yl)methyl)-2,2-difluoro-2-(4-isopropoxy-2-methylphenyl)acetamide To a stirred solution of 2,2-difluoro-2-(4-isopropoxy-2-methylphenyl)acetic acid (236 mg, 0.968 mmol) in pyridine (25 mL) was added phosphoryl chloride (0.3 mL, 2.16 mmol) dropwise and stirred at 0-5° C. for 1 h and then added 3-(5-(aminomethyl)-1-oxoisoindolin-2-yl)piperidine-2,6-dione hydrochloride (300 mg, 0.968 mmol) and stirred at room temperature for 1 h. The reaction mixture was neutralized with aqueous saturated sodium bicarbonate (up to pH-8) and extracted with ethyl acetate (3×50 mL). The combined organic layer was washed with water (2×50 mL), brine (50 mL), dried over sodium sulphate and concentrated. The resultant residue was purified by Reveleris C-18 reversed phase Grace column chromatography using 40-50% acetonitrile in aqueous formic acid (0.1%) to afford N-((2-(2,6-dioxopiperidin-3-yl)-1-oxoisoindolin-5-yl)methyl)-2,2-difluoro-2-(4-isopropoxy-2-methylphenyl)acetamide (79 mg, 0.158 mmol, 16% yield) as an off white solid. MS (ESI) m/z 500.2329 [M+1]$^+$. $^1$H NMR (300 MHz, DMSO-d$_6$) δ ppm 10.98 (s, 1H), 9.51 (br t, J=6.05 Hz, 1H), 7.69 (d, J=7.70 Hz, 1H), 7.51-7.28 (m, 3H), 6.83 (s, 2H), 5.11 (br dd, J=13.20, 5.14 Hz, 1H), 4.66 (dt, J=12.10, 6.05 Hz, 1H), 4.51-4.25 (m, 4H), 2.99-2.82 (m, 1H), 2.67-2.54 (m, 1H), 2.46-2.30 (m, 1H), 2.28 (s, 3H), 2.07-1.95 (m, 1H), 1.26 (m, 6H).

Example 63

N-((2-(2,6-Dioxopiperidin-3-yl)-1-oxoisoindolin-5-yl)methyl)-2,2-difluoro-2-(4-isopropoxy-3-methylphenyl)acetamide

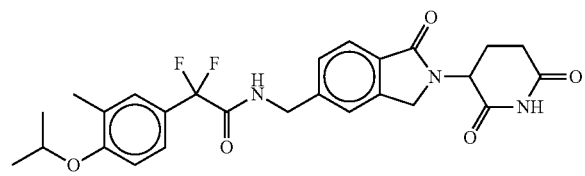

A. 1-(4-Isopropoxy-3-methylphenyl)ethanone

To a stirred solution of 1-(4-hydroxy-3-methylphenyl)ethanone (3.0 g, 19.97 mmol) in N,N-dimethyl formamide (20 mL) was added potassium carbonate (8.3 g, 59.91 mmol), isopropyl iodide (4.0 g, 23.96 mmol) at room temperature and stirred at 100° C. for 4 h. The reaction mixture was quenched with water (150 mL) and extracted with ethyl acetate (2×100 mL). The combined organic layers were washed with water (2×100 mL), brine (100 mL), dried over sodium sulphate and concentrated to afford 1-(4-isopropoxy-3-methylphenyl)ethanone (3.2 g, 16.66 mmol, 84% yield). LCMS (ESI) m/z 193.3 [M+1]$^+$.

B. Ethyl 2-(4-isopropoxy-3-methylphenyl)-2-oxoacetate

To a stirred solution of 1-(4-isopropoxy-3-methylphenyl)ethanone (3.2 g, 16.66 mmol) in pyridine (15 mL) was added selenium dioxide (4.6 g, 41.66 mmol) and stirred at 100° C. for 16 h. The reaction mixture was diluted with dichloromethane (30 mL) and filtered through Celite pad. To the filtrate was added ethyl chloroformate (9 mL) at 0° C. and stirred at room temperature for 3 h. The reaction mixture was neutralized with 1N aqueous hydrochloric acid (up to pH-4) and extracted with ethyl acetate (2×100 mL). The combined organic layers were washed with water (2×50 mL), brine (50 mL), dried over sodium sulphate and concentrated to afford ethyl 2-(4-isopropoxy-3-methylphenyl)-2-oxoacetate (2.5 g, 10.0 mmol, 60% yield). LCMS (ESI) m/z 251.28 [M+1]$^+$.

C. Ethyl 2,2-difluoro-2-(4-isopropoxy-3-methylphenyl)acetate

To a stirred solution of ethyl 2-(4-isopropoxy-3-methylphenyl)-2-oxoacetate (500 mg, 2.00 mmol) was reacted with diethyl amino sulfur trifluoride (2.5 g, 15.26 mmol) and stirred at room temperature for 16 h. The reaction mixture was neutralized with aqueous saturated sodium bicarbonate (up to pH-8) and extracted with ethyl acetate (3×50 mL). The combined organic layers were washed with water (2×30 mL), brine (30 mL) and dried over sodium sulphate and was concentrated to give ethyl 2,2-difluoro-2-(4-isopropoxy-3-methylphenyl)acetate (450 mg, 1.65 mmol, 83% yield). GCMS (m/z) 272.2 [M]$^+$.

D. 2,2-Difluoro-2-(4-isopropoxy-3-methylphenyl)acetic acid

To a stirred solution of ethyl 2,2-difluoro-2-(4-isopropoxy-3-methylphenyl)acetate (450 mg, 1.65 mmol) in tetrahydrofuran-methanol-water (20 mL, 1:1:1) was added lithium hydroxide monohydrate (208 mg, 4.96 mmol) and stirred at room temperature for 2 h. The reaction mixture was concentrated and the residue was neutralized with 10% aqueous hydrochloric acid (5 mL) and extracted with ethyl acetate (2×50 mL). The combined organic layers were washed with brine (20 mL), dried over sodium sulphate and concentrated to give 2,2-difluoro-2-(4-isopropoxy-3-methylphenyl)acetic acid (200 mg, 0.81 mmol, 50% yield). LCMS (ESI) m/z 243.34 [M−1]$^+$.

E. N-((2-(2,6-Dioxopiperidin-3-yl)-1-oxoisoindolin-5-yl)methyl)-2,2-difluoro-2-(4-isopropoxy-3-methylphenyl)acetamide To a cold (0° C.) stirred solution of 2,2-difluoro-2-(4-isopropoxy-3-methylphenyl)acetic acid (200 mg, 0.81 mmol) in pyridine (5 mL) was added phosphoryl chloride (0.3 mL, 2.45 mmol) and stirred at 0-5° C. for 1 h. Then added 3-(5-(amino methyl)-1-oxoisoindolin-2-yl)piperidine-2,6-dione hydrochloride (253 mg, 0.81 mmol) and stirred at room temperature for 1 h. The reaction mixture was neutralized with aqueous saturated sodium bicarbonate (up to pH-8) and extracted with ethyl acetate (2×25 mL). The combined organic layers were washed with water (25 mL), brine (25 mL), dried over sodium sulphate and concentrated. The resultant residue was purified by Reveleris C-18 reversed phase column chromatography using 40-45% acetonitrile in aqueous formic acid (0.1%) to afford N-((2-(2,6-dioxopiperidin-3-yl)-1-oxoisoindolin-5-yl)methyl)-2,2-difluoro-2-(4-isopropoxy-3-methylphenyl)acetamide (90 mg, 0.18 mmol, 22.0% yield) as an off white solid. LCMS (ESI) m/z 500.57 [M+1]$^+$. $^1$H NMR (400 MHz, DMSO-d$_6$) δ=10.98 (s, 1H), 9.52 (br t, J=6.1 Hz, 1H), 7.68 (d, J=7.8 Hz, 1H), 7.44-7.26 (m, 2H), 7.06 (d, J=8.3 Hz, 1H), 5.11 (dd, J=4.9, 13.2 Hz, 1H), 4.72-4.60 (m, 1H), 4.50-4.20 (m, 4H), 3.00-2.83 (m, 1H), 2.67-2.54 (m, 1H), 2.44-2.29 (m, 1H), 2.14 (s, 3H), 2.05-1.95 (m, 1H), 1.29 (d, J=6.4 Hz, 6H).

Example 64

N-((2-(2,6-Dioxopiperidin-3-yl)-1-oxoisoindolin-5-yl)methyl)-2,2-difluoro-2-(3-fluoro-4-isopropoxyphenyl)acetamide

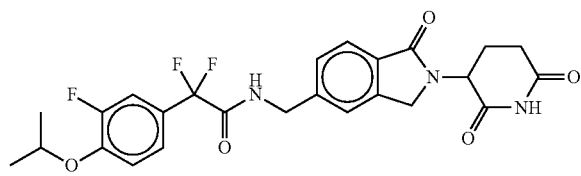

A. 1-(3-Fluoro-4-isopropoxyphenyl)ethanone

To a stirred solution of 1-(3-fluoro-4-hydroxyphenyl) ethanone (3.0 g, 19.46 mmol) in N,N-dimethylformamide (20 mL) was added potassium carbonate (8.0 g, 58.38 mmol), isopropyl iodide (3.9 g, 23.35 mmol) at room temperature and stirred at 100° C. for 4 h. The reaction mixture was quenched with water (150 mL) and extracted with ethyl acetate (2×100 mL). The combined organic layers were washed with water (2×100 mL), brine (100 mL), dried over sodium sulphate and concentrated to afford 1-(3-fluoro-4-isopropoxyphenyl)ethanone (3.1 g, 15.81 mmol, 81% yield). LCMS (ESI) m/z 197.3 [M+1]$^+$.

B. Ethyl 2-(3-fluoro-4-isopropoxyphenyl)-2-oxoacetate

To a stirred solution of 1-(3-fluoro-4-isopropoxyphenyl) ethanone (3.1 g, 15.81 mmol) in pyridine (15 mL) was added selenium dioxide (4.6 g, 39.54 mmol) and stirred at 100° C. for 16 h. The reaction mixture was diluted with dichloromethane (30 mL) and filtered through Celite pad. To the filtrate was added ethyl chloroformate (9 mL) at 0° C. and stirred at room temperature for 3 h. The reaction mixture was neutralized with 1N aqueous hydrochloric acid (up to pH-4) and extracted with ethyl acetate (2×100 mL). The combined organic layers were washed with water (2×50 mL), brine (50 mL), dried over sodium sulphate and concentrated to afford ethyl 2-(3-fluoro-4-isopropoxyphenyl)-2-oxoacetate (2.5 g, 9.84 mmol, 62% yield). LCMS (ESI) m/z 255.28 [M+1]$^+$.

C. Ethyl 2,2-difluoro-2-(3-fluoro-4-isopropoxyphenyl)acetate

To a stirred solution of ethyl 2-(3-fluoro-4-isopropoxyphenyl)-2-oxoacetate (1.2 g, 4.72 mmol) was added diethyl amino sulfur trifluoride (3.1 g, 19.23 mmol) and stirred at room temperature for 16 h. The reaction mixture was neutralized with aqueous saturated sodium bicarbonate (up to pH-8) and extracted with ethyl acetate (3×100 mL). The combined organic layers were washed with water (2×50 mL), brine (50 mL), dried over sodium sulphate and concentrated to afford ethyl 2,2-difluoro-2-(3-fluoro-4-isopropoxyphenyl)acetate (900 mg, 3.26 mmol, 69% yield). GCMS (m/z) 276.2 [M]$^+$.

D. 2,2-Difluoro-2-(3-fluoro-4-isopropoxyphenyl)acetic acid

To a stirred solution of ethyl 2,2-difluoro-2-(3-fluoro-4-isopropoxyphenyl)acetate (900 mg, 3.26 mmol) in tetrahydrofuran-methanol-water (20 mL, 1:1:1) was added lithium hydroxide monohydrate (410 mg, 9.78 mmol) and stirred at room temperature for 2 h. The reaction mixture was concentrated and the residue was neutralized with 10% aqueous hydrochloric acid (5 mL) and extracted with ethyl acetate (2×50 mL). The combined organic layers were washed with brine (20 mL), dried over sodium sulphate and concentrated to afford 2,2-difluoro-2-(3-fluoro-4-isopropoxyphenyl)acetic acid (700 mg, 2.82 mmol, 87% yield). LCMS (ESI) m/z 247.52 [M-1]$^+$.

E. N-((2-(2,6-Dioxopiperidin-3-yl)-1-oxoisoindolin-5-yl)methyl)-2,2-difluoro-2-(3-fluoro-4-isopropoxyphenyl)acetamide To a cold (0° C.) stirred solution of 2,2-difluoro-2-(3-fluoro-4-isopropoxyphenyl)acetic acid (300 mg, 1.20 mmol) in pyridine (10 mL) was added phosphoryl chloride (0.4 mL, 3.62 mmol) and stirred at 0-5° C. for 1 h. Then added 3-(5-(amino methyl)-1-oxoisoindolin-2-yl)piperidine-2,6-dione hydrochloride (374 mg, 1.20 mmol) and stirred at room temperature for 1 h. The reaction mixture was neutralized with aqueous saturated sodium bicarbonate (up to pH-8) and extracted with ethyl acetate (2×25 mL). The combined organic layers were washed with water (25 mL), brine (25 mL), dried over sodium sulphate and concentrated. The resultant residue was purified by Reveleris C-18 reversed phase column chromatography using 35-40% acetonitrile in aqueous formic acid (0.1%) to afford N-((2-(2,6-dioxopiperidin-3-yl)-1-oxoisoindolin-5-yl)methyl)-2,2-difluoro-2-(3-fluoro-4-isopropoxyphenyl) acetamide (80 mg, 0.15 mmol, 13.0% yield) as an off white solid. LCMS (ESI) m/z 504.56 [M+1]$^+$. $^1$H NMR (400 MHz, DMSO-d$_6$) δ=10.98 (s, 1H), 9.60 (br t, J=6.1 Hz, 1H), 7.68 (d, J=7.8 Hz, 1H), 7.45-7.26 (m, 5H), 5.10 (dd, J=5.1, 13.5 Hz, 1H), 4.73 (m, 1H), 4.50-4.23 (m, 4H), 2.98-2.85 (m, 1H), 2.67-2.55 (m, 1H), 2.45-2.30 (m, 1H), 2.04-1.95 (m, 1H), 1.30 (d, J=5.9 Hz, 6H).

Example 65

2-(3-Chloro-4-isopropoxyphenyl)-N-((2-(2,6-dioxopiperidin-3-yl)-1-oxoisoindolin-5-yl)methyl)-2,2-difluoroacetamide

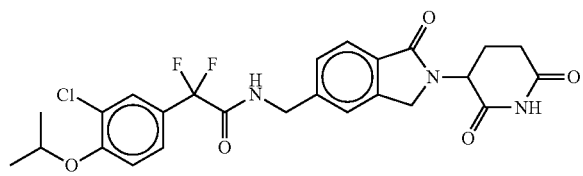

A. 1-(3-Chloro-4-isopropoxyphenyl)ethanone

To a stirred solution of 1-(3-chloro-4-hydroxyphenyl)ethanone (2.5 g, 14.62 mmol) in N,N-dimethylformamide (30 mL) was added 2-iodopropane (2.98 g, 17.54 mmol) followed by potassium carbonate (5.04 g, 36.55 mmol) and stirred at 90° C. for 16 h. The reaction mixture was diluted with ice water (40 mL) and extracted with ethyl acetate (3×30 mL). The combined organic layers were washed with water (30 mL), brine (30 mL), dried over sodium sulfate, filtered and concentrated to afford 1-(3-chloro-4-isopropoxyphenyl)ethanone (2.3 g, 10.84 mmol, 74% yield) as a colorless liquid. MS (ESI) m/z 213.23 [M]$^+$.

B. Ethyl 2-(3-chloro-4-isopropoxyphenyl)-2-oxoacetate

To a stirred solution of 1-(3-chloro-4-isopropoxyphenyl)ethanone (2 g, 8.26 mmol) in pyridine (30 mL) was added selenium dioxide (2.69 g, 24.79 mmol) at room temperature. The reaction mixture was stirred at 100° C. for 16 h. The reaction mixture was filtered through a Celite pad and washed with dichloromethane (30 mL). Ethyl chloroformate (6 mL) was added to the filtrate at 0° C. and stirred at room temperature for 4 h. The reaction mixture was quenched with ice water and extracted with dichloromethane (3×30 mL). The combined organic layers were washed with 1N hydrochloride solution (30 mL), brine (30 mL), dried over sodium sulfate, filtered and concentrated to afford ethyl 2-(3-chloro-4-isopropoxyphenyl)-2-oxoacetate (1.8 g, 6.66 mmol, 80% yield) as a colourless liquid. $^1$H NMR (400 MHz, CDCl$_3$) δ 8.08 (d, J=2.0 Hz, 1H), 7.92 (dd, J=8.8, 2.8 Hz, 1H), 7.00 (d, J=8.8 Hz, 1H), 4.71 (sep, J=6.2 Hz, 1H), 4.44 (q, J=6.8 Hz, 2H), 1.44 (d, J=6.5 Hz, 6H), 1.38 (t, J=7.2 Hz, 3H).

C. Ethyl 2-(3-chloro-4-isopropoxyphenyl)-2,2-difluoroacetate

Diethylamino sulfur trifluoride (1.47 mL) was added into ethyl 2-(3-chloro-4-isopropoxyphenyl)-2-oxoacetate (1 g, 3.7 mmol) at 0° C. and stirred at room temperature for 16 h. The reaction mixture was quenched with aqueous sodium bicarbonate solution and extracted with ethyl acetate (3×15 mL). The combined organic layers were washed with brine (15 mL), dried over sodium sulfate, filtered and concentrated. Obtained crude was purified by column chromatography (100-200 silica gel, 10% ethyl acetate in pet ether) to afford ethyl 2-(3-chloro-4-isopropoxyphenyl)-2,2-difluoroacetate (900 mg, 3.08 mmol, 89% yield) as a colourless liquid. MS (ESI) m/z 293.1 [M+1]$^+$.

D. 2-(3-Chloro-4-isopropoxyphenyl)-2,2-difluoroacetic acid

To a stirred solution of ethyl 2-(3-chloro-4-isopropoxyphenyl)-2,2-difluoroacetate (0.45 g, 1.54 mmol) in tetrahydrofuran:methanol:water (15 mL, 1:1:1) was added lithium hydroxide monohydrate (195 mg, 4.54 mmol) and stirred at room temperature for 16 h. The volatiles were removed under reduced pressure and the obtained residue was dissolved in water (10 mL), washed with ethyl acetate (2×10 mL). Aqueous layer was acidified with 1N hydrochloride solution and extracted with ethyl acetate (3×10 mL). The combined organic layers were washed with brine (10 mL), dried over sodium sulfate, filtered and concentrated to afford 2-(3-chloro-4-isopropoxyphenyl)-2,2-difluoroacetic acid (300 mg, 1.13 mmol, 74% yield) as semi-solid compound. $^1$H NMR (400 MHz, CDCl$_3$) δ 8.41 (brs, 1H), 7.65 (d, J=2.1 Hz, 1H), 7.47 (dd, J=8.7, 2.1 Hz, 1H), 6.97 (dd, J=5.1, 8.7 Hz, 1H), 4.62 (sep, J=5.7 Hz, 1H), 1.40 (d, J=6.3 Hz, 6H).

E. 2-(3-Chloro-4-isopropoxyphenyl)-N-((2-(2,6-dioxopiperidin-3-yl)-1-oxoisoindolin-5-yl)methyl)-2,2-difluoroacetamide To an ice cold solution of 2-(3-chloro-4-isopropoxyphenyl)-2,2-difluoroacetic acid (235 mg, 0.89 mmol) in pyridine (6 mL) was added phosphorus oxychloride (0.23 mL, 2.43 mmol) in dropwise and stirred at 0-5° C. for 1 h. Then, 3-(5-(aminomethyl)-1-oxoisoindolin-2-yl)piperidine-2,6-dione hydrochloride (250 mg, 0.81 mmol) was added and stirred at room temperature for 2 h. The reaction mixture was basified with aqueous saturated sodium bicarbonate solution and extracted with ethyl acetate (3×15 mL). The combined organic layers were washed with water (15 mL), brine (15 mL), dried over sodium sulfate, filtered and concentrated. The resultant residue was purified by Reveleris C-18 reversed phase column chromatography (50-55% acetonitrile in 0.1% aqueous formic acid) to give 2-(3-chloro-4-isopropoxyphenyl)-N-((2-(2,6-dioxopiperidin-3-yl)-1-oxoisoindolin-5-yl)methyl)-2,2-difluoro acetamide (60 mg, 0.11 mmol, 14% yield) as white solid. MS (ESI) m/z 520.01 [M+1]$^+$. $^1$H NMR (300 MHz, DMSO-d$_6$) δ 10.98 (s, 1H), 9.62 (t, J=5.7 Hz, 1H), 7.68 (d, J=7.8 Hz, 1H), 7.59 (d, J=2.4 Hz, 1H), 7.49 (dd, J=8.7, 2.1 Hz, 1H), 7.41 (s, 1H), 7.37 (d, J=8.1 Hz, 1H), 7.31 (d, J=8.7 Hz, 1H), 5.11 (dd, J=13.2, 5.4 Hz, 1H), 4.76 (sep, J=6.3 Hz, 1H), 4.45 (d, J=5.7 Hz, 2H), 4.42 (d, J=18.0 Hz, 1H), 4.28 (d, J=17.7 Hz, 1H), 2.93-2.87 (m, 1H), 2.63-2.57 (m, 1H), 2.40-2.30 (m, 1H), 2.04-1.94 (m, 1H), 1.31 (d, J=5.7 Hz, 6H).

Example 66

N-((2-(2,6-Dioxopiperidin-3-yl)-1-oxoisoindolin-5-yl)methyl)-2,2-difluoro-2-(2-methyl-4-(trifluoromethoxy)phenyl)acetamide

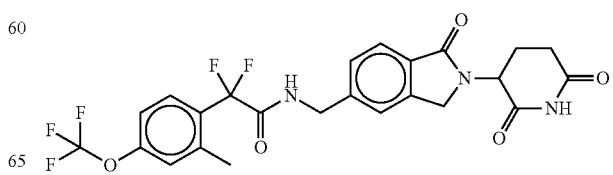

A. Ethyl 2,2-difluoro-2-(2-methyl-4-(trifluoromethoxy)phenyl)acetate

To a stirred solution of 1-iodo-2-methyl-4-(trifluoromethoxy)benzene (1.0 g, 3.31 mmol) in dimethylsulfoxide (13 mL) was added copper (546 mg, 8.60 mmol) and ethyl 2-bromo-2,2-difluoroacetate (0.638 mL 4.96 mmol) at room temperature and stirred at 55° C. for 2 h. The reaction mixture was neutralized with aqueous saturated ammonium chloride (50 mL) solution and extracted with ethyl acetate (2×100 mL). The combined organic layers were washed with water (2×100 mL), brine (100 mL), dried over sodium sulphate and concentrated to afford ethyl 2,2-difluoro-2-(2-methyl-4-(trifluoromethoxy)phenyl)acetate (900 mg, 3.02 mmol, 91%). $^1$H NMR (400 MHz, CDCl$_3$) δ 7.65-7.58 (d, 1H), 7.18-7.02 (m, 2H), 4.41-4.25 (m, 2H), 2.43 (s, 3H), 1.36-1.29 (m, 3H). (Ethyl acetate traces indicated along with the product in the $^1$H NMR)

B. 2,2-Difluoro-2-(2-methyl-4-(trifluoromethoxy)phenyl)acetic acid

To a stirred solution of ethyl 2,2-difluoro-2-(2-methyl-4-(trifluoromethoxy)phenyl)acetate (900 mg, 3.020 mmol) in tetrahydrofuran:methanol:water mixture (30 mL, 1:1:1) was added lithium hydroxide monohydrate (634 mg, 15.106 mmol) and stirred at room temperature for 4 h. The reaction mixture was concentrated and the residue was neutralized with saturated potassium bisulphate (25 mL) and extracted with ethyl acetate (2×50 mL). The combined organic layers were washed with brine (50 mL), dried over sodium sulphate and concentrated to afford 2,2-difluoro-2-(2-methyl-4-(trifluoromethoxy)phenyl)acetic acid (450 mg, 1.66 mmol, 55% yield). $^1$H NMR (400 MHz, CDCl$_3$) δ 7.65-7.49 (d, J=9.2 Hz, 1H), 7.20-7.16 (m, 2H), 2.18 (s, 3H).

C. N-((2-(2,6-Dioxopiperidin-3-yl)-1-oxoisoindolin-5-yl)methyl)-2,2-difluoro-2-(2-methyl-4-(trifluoromethoxy)phenyl)acetamide To a cold (0° C.) stirred solution of 2,2-difluoro-2-(2-methyl-4-(trifluoromethoxy)phenyl)acetic acid (261 mg, 0.968 mmol) in pyridine was added phosphoryl chloride (0.27 mL, 2.906 mmol) drop wise and stirred at 0-5° C. for 1 h. To this reaction mixture was then added 3-(5-(aminomethyl)-1-oxoisoindolin-2-yl)piperidine-2,6-dione hydrochloride (300 mg, 0.968 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The resultant residue was purified by Reveleris C-18 reversed phase column chromatography using 40-60% acetonitrile in aqueous formic acid (0.1%) to afford N-((2-(2,6-dioxopiperidin-3-yl)-1-oxoisoindolin-5-yl)methyl)-2,2-difluoro-2-(2-methyl-4-(trifluoromethoxy)phenyl)acetamide (60 mg, 0.114 mmol, 11% yield) as an off white solid. MS (ESI) m/z 526.52 [M+1]$^+$. $^1$H NMR (300 MHz, DMSO-d$_6$) δ 10.99 (s, 1H), 9.65 (t, J=5.9 Hz, 1H), 7.73-7.63 (m, 2H), 7.46 (s, 1H), 7.43-7.38 (d, J=8.0 Hz, 1H), 7.38-7.32 (m, 2H), 5.10 (dd, J=13.2, 5.1 Hz, 1H), 4.52-4.28 (m, 4H), 2.96-2.85 (m, 1H), 2.68-2.53 (m, 1H), 2.47-2.31 (m, 4H), 2.08-1.94 (m, 1H).

Example 67

N-((2-(2,6-Dioxopiperidin-3-yl)-1-oxoisoindolin-5-yl)methyl)-2,2-difluoro-2-(2-fluoro-4-(trifluoromethoxy)phenyl)acetamide

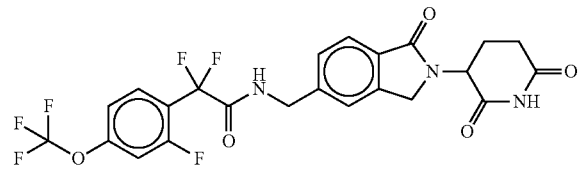

A. 2-Fluoro-1-iodo-4-(trifluoromethoxy)benzene

To a stirred solution of 1-bromo-2-fluoro-4-(trifluoromethoxy)benzene (500 mg, 1.93 mmol) in 1,4-dioxane (10 mL) was added sodium iodide (579 mg, 3.86 mmol), copper iodide (18 mg, 0.09 mmol) and trans-N,N'-dimethylcyclohexane-1,2-diamine (30 mg, 0.11 mmol) at room temperature, then heated at 110° C. for 16 h. The reaction mixture was quenched with water (10 mL) and extracted with ethyl acetate (3×10 mL). The combined organic layers were washed with water (10 mL), brine (10 mL), dried over sodium sulfate, filtered and concentrated to afford 2-fluoro-1-iodo-4-(trifluoromethoxy)benzene (400 mg, 1.3 mmol, 68% yield) as brown liquid. $^1$H NMR (300 MHz, CDCl$_3$) δ 7.78 (dd, J=8.4, 6.9 Hz, 1H), 6.98 (dd, J=8.1, 1.5 Hz, 1H), 6.84 (d, J=8.3 Hz, 1H).

B. Ethyl 2,2-difluoro-2-(2-fluoro-4-(trifluoromethoxy)phenyl)acetate

To a stirred solution of 2-fluoro-1-iodo-4-(trifluoromethoxy)benzene (1 g, 3.27 mmol) in dimethylsulfoxide (20 mL) was added ethyl 2-bromo-2,2-difluoroacetate (0.6 mL, 4.9 mmol) followed by copper (0.54 g, 8.49 mmol) at RT and stirred at 60° C. for 6 h. The reaction mixture was basified with aqueous saturated sodium bicarbonate solution and extracted with ethyl acetate (3×15 mL). The combined organic layers were washed with water (15 mL), brine (15 mL), dried over sodium sulfate, filtered and concentrated. The obtained crude product was purified by flash chromatography (20% ethyl acetate in pet ether) to afford ethyl 2,2-difluoro-2-(2-fluoro-4-(trifluoromethoxy)phenyl)acetate (800 mg, 2.64 mmol, 81% yield) as a colorless liquid. MS (ESI) m/z 302.1 [M]$^+$.

C. 2,2-Difluoro-2-(2-fluoro-4-(trifluoromethoxy)phenyl)acetic acid

To a stirred solution of ethyl 2,2-difluoro-2-(2-fluoro-4-(trifluoromethoxy)phenyl)acetate (800 mg, 2.64 mmol) in mixture of tetrahydrofuran:methanol:water (15 mL, 1:1:1) was added lithium hydroxide monohydrate (333 mg, 7.94 mmol) and stirred at room temperature for 4 h. The volatiles were removed under reduced pressure and the obtained crude was dissolved in water (15 mL) and washed with ethyl acetate (2×10 mL). Aqueous layer was acidified with 1N hydrochloride aqueous solution and extracted with ethyl acetate (3×10 mL). The combined organic layers were washed with brine (15 mL), dried over sodium sulfate, filtered and concentrated to afford 2,2-difluoro-2-(2-fluoro- 4-(trifluoromethoxy)phenyl)acetic acid (450 mg, 1.64 mmol, 62% yield) as semi-solid compound. MS (ESI) m/z 298.1 [M]⁺. ¹H NMR (400 MHz, CDCl₃) δ 7.70 (dd, J=9.6 Hz, 1.6 Hz, 1H), 7.14 (d, J=7.9 Hz, 1H), 7.06 (dd, J=7.8 Hz, 1.8 Hz, 1H), 5.02 (brs, 1H).

D. N-((2-(2,6-Dioxopiperidin-3-yl)-1-oxoisoindolin-5-yl)methyl)-2,2-difluoro-2-(2-fluoro-4-(trifluoromethoxy)phenyl)acetamide To an ice cold stirred solution of 2,2-difluoro-2-(2-fluoro-4-(trifluoromethoxy)phenyl)acetic acid (274 mg, 1.55 mmol) in pyridine (6 mL) was added phosphorus oxychloride (0.36 mL, 3.87 mmol) dropwise and stirred at 0-5° C. for 1 h. Then, the reaction mixture was treated with 3-(5-(aminomethyl)-1-oxoisoindolin-2-yl)piperidine-2,6-dione hydrochloride (400 mg, 1.29 mmol) and stirred at room temperature for 2 h. The reaction mixture was basified with aqueous saturated sodium bicarbonate solution and extracted with ethyl acetate (3×15 mL). The combined organic layers were washed with water (15 mL), brine (15 mL), dried over sodium sulfate, filtered and concentrated. The resultant residue was purified by Reveleris C-18 reversed phase column chromatography (50-55% acetonitrile in 0.1% aqueous formic acid to afford N-((2-(2,6-dioxopiperidin-3-yl)-1-oxoisoindolin-5-yl)methyl)-2,2-difluoro-2-(2-fluoro-4-(trifluoromethoxy)phenyl)acetamide (60 mg, 0.11 mmol, 9% yield) as white solid. MS (ESI) m/z 529.6 [M+1]⁺. ¹H NMR (300 MHz, DMSO-d₆) δ 10.99 (s, 1H), 9.76 (t, J=5.8 Hz, 1H), 7.82 (dd, J=8.4, 8.3 Hz, 1H), 7.70 (d, J=7.5 Hz, 1H), 7.63 (d, J=11.4 Hz, 1H), 7.48 (s, 1H), 7.43-7.40 (m, 2H), 5.11 (dd, J=12.9, 4.8 Hz, 1H), 4.50 (d, J=6.3 Hz, 2H), 4.46 (t, J=17.7 Hz, 1H), 4.31 (d, J=17.4, 1H), 2.90-2.63 (m, 1H), 2.63-2.56 (m, 1H), 2.42-2.27 (m, 1H), 2.02-1.98 (m, 1H).

Example 68

2-(5-Chloropyridin-2-yl)-N-((2-(2,6-dioxopiperidin-3-yl)-1-oxoisoindolin-5-yl)methyl)-2,2-difluoroacetamide

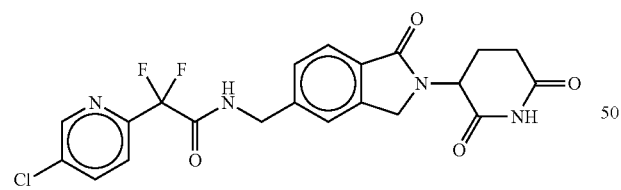

A. Ethyl 2-(5-chloropyridin-2-yl)-2,2-difluoroacetate

To a stirred solution of 5-chloro-2-iodopyridine (1.0 g, 4.18 mmol) in dimethylsulfoxide (11 mL) was added copper (690 mg, 10.86 mmol) and ethyl 2-bromo-2,2-difluoroacetate (1.01 g, 5.01 mmol) at room temperature and stirred at 55° C. for 6 h. The reaction mixture was neutralized with saturated aqueous ammonium chloride solution and extracted with ethyl acetate (2×50 mL). The combined organic layers were washed with water (2×50 mL), brine (50 mL), dried over sodium sulphate and concentrated to afford ethyl 2-(5-chloropyridin-2-yl)-2,2-difluoroacetate (700 mg, 2.98 mmol, 70%). GCMS (m/z) 235.1 [M]⁺.

B. 2-(5-Chloropyridin-2-yl)-2,2-difluoroacetic acid

To a stirred solution of ethyl 2-(5-chloropyridin-2-yl)-2,2-difluoroacetate (800 mg, 3.40 mmol) in tetrahydrofuran:methanol:water mixture (30 mL, 1:1:1) was added lithium hydroxide monohydrate (429 mg, 10.21 mmol) and stirred at room temperature for 4 h. The reaction mixture was concentrated and the residue was neutralized with saturated potassium bisulphate (20 mL) and extracted with ethyl acetate (2×25 mL). The combined organic layers were washed with brine (25 mL), dried over sodium sulphate and concentrated to afford 2-(5-chloropyridin-2-yl)-2,2-difluoroacetic acid (400 mg, 1.94 mmol, 57% yield). MS (ESI) m/z 208.30 [M+1]⁺.

C. 2-(5-Chloropyridin-2-yl)-N-((2-(2,6-dioxopiperidin-3-yl)-1-oxoisoindolin-5-yl)methyl)-2,2-difluoroacetamide To a cold (0° C.) stirred solution of 2-(5-chloropyridin-2-yl)-2,2-difluoroacetic acid (200 mg, 0.96 mmol) in pyridine (20 mL) was added phosphoryl chloride (443 mg, 2.89 mmol) dropwise and stirred at 0-5° C. for 30 min. To this reaction mixture was then added 3-(5-(aminomethyl)-1-oxoisoindolin-2-yl)piperidine-2,6-dione hydrochloride (300 mg, 0.96 mmol) and stirred at room temperature for 1 h. The reaction mixture was neutralized with saturated aqueous sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 40-45% acetonitrile in aqueous formic acid (0.1%) to afford 2-(5-chloropyridin-2-yl)-N-((2-(2,6-dioxopiperidin-3-yl)-1-oxoisoindolin-5-yl)methyl)-2,2-difluoroacetamide (65 mg, 0.14 mmol, 14% yield) as an off-white solid. MS (ESI) m/z 462.69 [M+1]⁺. ¹H NMR (300 MHz, DMSO-d₆) δ=10.99 (s, 1H), 9.69 (t, J=5.9 Hz, 1H), 8.81 (d, J=2.2 Hz, 1H), 8.19 (dd, J=2.6, 8.4 Hz, 1H), 7.85 (d, J=8.4 Hz, 1H), 7.72 (d, J=8.1 Hz, 1H), 7.50 (s, 1H), 7.44 (d, J=7.7 Hz, 1H), 5.11 (dd, J=5.0, 13.0 Hz, 1H), 4.56-4.27 (m, 4H), 3.00-2.84 (m, 1H), 2.74-2.55 (m, 1H), 2.45-2.22 (m, 1H), 2.09-1.91 (m, 1H).

Example 69

N-((2-(2,6-Dioxopiperidin-3-yl)-1-oxoisoindolin-5-yl)methyl)-2,2-difluoro-2-(5-fluoropyridin-2-yl)acetamide

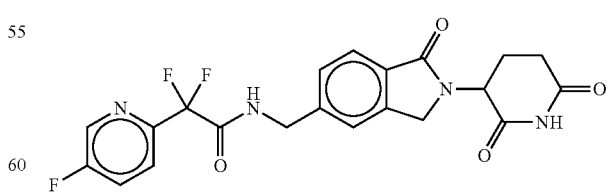

A. 5-Fluoro-2-iodopyridine

To a stirred solution of 2-bromo-5-fluoropyridine (2.5 g, 14.2 mmol) in 1,4-dioxane (10 mL) was added sodium iodide (4.26 g, 28.4 mmol), copper iodide (135 mg, 0.71 mmol) followed by trans-N,N-dimethylcyclohexane-1,2-diamine (0.24 mL, 1.56 mmol) at room temperature and stirred at 110° C. for 16 h. The reaction mixture was quenched with water (30 mL) and extracted with ethyl acetate (3×25 mL). The combined organic layers were washed with water (25 mL), brine (25 mL), dried over sodium sulfate, filtered and concentrated to afford 5-fluoro-2-iodopyridine (2.2 g, 9.86 mmol, 71% yield) as brown liquid. LCMS (m/z) 224.3 [M⁺].

B. Ethyl 2,2-difluoro-2-(5-fluoropyridin-2-yl)acetate

To a stirred solution of 5-fluoro-2-iodopyridine (300 mg, 1.34 mmol) in dimethylsulfoxide (3.4 mL) was added ethyl 2-bromo-2,2-difluoroacetate (409 mg, 2.02 mmol) followed by copper (22 mg, 3.49 mmol) at RT and stirred at 60° C. for 6 h. The reaction mixture was basified with aqueous saturated sodium bicarbonate solution and extracted with ethyl acetate (3×10 mL). The combined organic layers were washed with water (10 mL), brine (10 mL), dried over sodium sulfate, filtered and concentrated. The obtained crude was purified by silica gel column chromatography (20% ethyl acetate in pet ether) to afford ethyl 2,2-difluoro-2-(5-fluoropyridin-2-yl)acetate (200 mg, 0.72 mmol, 54% yield) as a colorless liquid. MS (ESI) m/z 278 [M]⁺.

C. 2,2-Difluoro-2-(5-fluoropyridin-2-yl)acetic acid

To a stirred solution of ethyl 2,2-difluoro-2-(5-fluoropyridin-2-yl)acetate (250 mg, 1.14 mmol) in mixture of tetrahydrofuran:methanol:water (10 mL, 1:1:1) was added lithium hydroxide monohydrate (144 mg, 3.42 mmol) and stirred at room temperature for 4 h. The volatiles were removed under reduced pressure and the obtained crude was dissolved in water (10 mL), washed with ethyl acetate (2×10 mL). Aqueous layer was acidified with 1N hydrochloride aqueous solution and extracted with ethyl acetate (3×10 mL). The combined organic layers were washed with brine (10 mL), dried over sodium sulfate, filtered and concentrated to afford 2,2-difluoro-2-(5-fluoropyridin-2-yl)acetic acid (150 mg, 0.78 mmol, 69% yield) as semi-solid compound. ¹H NMR (400 MHz, CDCl₃) δ 8.56 (s, 1H), 8.37 (brs, 1H), 7.84 (dd, J=8.8 Hz, 4.4 Hz, 1H), 7.64 (ddd, J=10.8 Hz, 8.8 Hz, 2.4 Hz, 1H).

D. N-((2-(2,6-Dioxopiperidin-3-yl)-1-oxoisoindolin-5-yl)methyl)-2,2-difluoro-2-(5-fluoropyridin-2-yl) acetamide To an ice cold solution of 2,2-difluoro-2-(5-fluoropyridin-2-yl)acetic acid (221 mg, 1.16 mmol) in pyridine (6 mL) was added phosphorus oxychloride (0.27 mL, 2.91 mmol) dropwise and stirred at 0-5° C. for 1 h. Then, 3-(5-(aminomethyl)-1-oxoisoindolin-2-yl)piperidine-2,6-dione hydrochloride (300 mg, 0.97 mmol) was added and stirred at room temperature for 2 h. The reaction mixture was basified with aqueous saturated sodium bicarbonate solution and extracted with ethyl acetate (3×15 mL). The combined organic layers were washed with water (15 mL), brine (15 mL), dried over sodium sulfate, filtered and concentrated. The resultant residue was purified by Reveleris C-18 reversed phase column chromatography (50-55% acetonitrile in 0.1% aqueous formic acid to afford N-((2-(2,6-dioxopiperidin-3-yl)-1-oxoisoindolin-5-yl)methyl)-2,2-difluoro-2-(5-fluoro pyridin-2-yl)acetamide (60 mg, 0.11 mmol, 14% yield) as white solid. MS (ESI) m/z 446.7 [M+1]⁺. ¹H NMR (300 MHz, DMSO-d₆) δ 10.98 (s, 1H), 9.67 (t, J=5.7 Hz, 1H), 8.76 (d, J=2.4 Hz, 1H), 8.01-7.89 (m, 2H), 7.71 (d, J=7.8 Hz, 1H), 7.52 (s, 1H), 7.45 (d, J=8.1 Hz, 1H), 5.11 (dd, J=13.5, 5.1 Hz, 1H), 4.50 (d, J=5.4 Hz, 2H), 4.47 (d, J=17.4 Hz, 1H), 4.32 (d, J=17.1 Hz, 1H), 2.98-2.84 (m, 1H), 2.66-2.58 (m, 1H), 2.43-2.30 (m, 1H), 2.02-1.94 (m, 1H).

Example 70

2-(2,4-Difluorophenyl)-N-((2-(2,6-dioxopiperidin-3-yl)-1-oxoisoindolin-5-yl)methyl)-2,2-difluoroacetamide

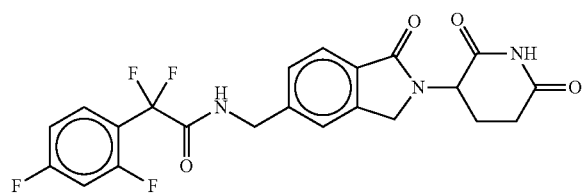

A. Ethyl 2-(2,4-difluorophenyl)-2,2-difluoroacetate

To a stirred solution of 2,4-difluoro-1-iodobenzene (800 mg, 3.33 mmol) in dimethyl sulfoxide (10 mL) was added ethyl 2-bromo-2,2-difluoroacetate (1.01 g, 4.99 mmol), copper (550 mg, 8.65 mmol) and stirred at 55° C. for 6 h. The reaction mixture was neutralized with aqueous saturated ammonium chloride solution and extracted with ethyl acetate (3×50 mL). The combined organic layers were washed with water (2×50 mL), brine (50 mL), dried over sodium sulphate and concentrated to afford ethyl 2-(2,4-difluorophenyl)-2,2-difluoroacetate (400 mg, 1.69 mmol, 51%) as a brown liquid. GCMS: 236.1[M]⁺.

B. 2-(2,4-Difluorophenyl)-2,2-difluoroacetic acid

To a stirred solution of ethyl 2-(2,4-difluorophenyl)-2,2-difluoroacetate (400 mg, 1.69 mmol) in ethanol:tetrahydrofuran:water (10 mL, 1:1:1) was added lithium hydroxide (214 mg, 5.08 mmol) and stirred at room temperature for 4 h. The reaction mixture was concentrated and the residue was neutralized with sat.potassium hydrozensulphate (20 mL) and extracted with ethyl acetate (2×50 mL). The combined organic layer was washed with brine (25 mL), dried over sodium sulphate and concentrated to give 2-(2, 4-difluorophenyl)-2,2-difluoroacetic acid (250 mg, 1.20 mmol, 71% yield). MS (ESI) m/z 207.43 [M−1]⁺

C. 2-(2,4-Difluorophenyl)-N-((2-(2,6-dioxopiperidin-3-yl)-1-oxoisoindolin-5-yl)methyl)-2,2-difluoroacetamide To a stirred cold (0° C.) solution of 3-(5-(aminomethyl)-1-oxoisoindolin-2-yl)piperidine-2,6-dione hydrochloride (300 mg, 0.97 mmol) in N,N-dimethylformamide (10 mL) was added 2-(2,4-difluorophenyl)-2,2-difluoroacetic acid (202 mg, 0.97 mmol) followed by diisopropylethylamine (0.52 mL, 2.91 mmol), 1-[Bis(dimethylamino)methylene]-1H-1,2,3-triazolo[4,5-b]pyridinium 3-oxid hexafluorophosphate (480 mg, 1.26 mmol) and stirred at room temperature for 16 h. The reaction mixture was diluted with water (100 mL) and the solid obtained was filtered, washed with diethyl ether (20 mL), dried and purified by column chromatography (100-200 silica) using 4% methanol in dichloromethane as eluent to afford 2-(2,4-difluorophenyl)-N-((2-(2,6-dioxopiperidin-3-yl)-1-oxoisoindolin-5-yl)methyl)-2,2-difluoroacetamide (60 mg, 0.129 mmol, 13% yield) as an off white solid. MS (ESI) m/z 463.68 [M+1]$^+$. H NMR (400 MHz, DMSO-$d_6$) δ=10.98 (s, 1H), 9.72 (br t, J=5.9 Hz, 1H), 7.78-7.65 (m, 2H), 7.55-7.34 (m, 3H), 7.29-7.18 (m, 1H), 5.11 (br dd, J=5.1, 13.2 Hz, 1H), 4.56-4.16 (m, 4H), 3.08-2.80 (m, 1H), 2.75-2.59 (m, 1H), 2.44-2.32 (m, 1H), 2.06-1.92 (m, 1H).

Example 71

2-(4-Bromophenyl)-N-((2-(2,6-dioxopiperidin-3-yl)-1-oxoisoindolin-5-yl)methyl)-2,2-difluoroacetamide

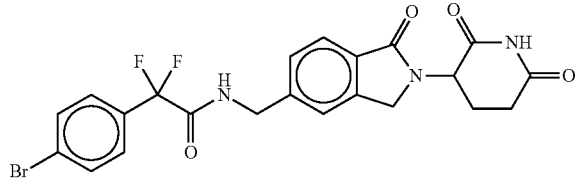

A. Ethyl 2-(4-bromophenyl)-2,2-difluoroacetate

To a stirred solution of 1-bromo-4-iodobenzene (300 mg, 2.81 mmol) in dimethyl sulfoxide (3 mL) was added ethyl 2-bromo-2,2-difluoroacetate (324 mg, 1.6 mmol) followed by copper powder (175 mg, 2.75 mmol) at room temperature and stirred at 55° C. for 6 h. The reaction mixture was basified with aqueous sodium bicarbonate solution and extracted with ethyl acetate (3×10 mL). The combined organic layers were washed with water (10 mL), brine (10 mL), dried over sodium sulfate, filtered and concentrated. The obtained crude was purified by silica gel column chromatography (20% ethyl acetate in pet ether) to afford ethyl 2-(4-bromophenyl)-2,2-difluoroacetate (200 mg, 0.72 mmol, 25% yield) as a colorless liquid. GCMS (ESI) m/z 278.1 [M]$^+$ B. 2-(4-Bromophenyl)-2,2-difluoroacetic acid To a stirred solution of ethyl 2-(4-bromophenyl)-2,2-difluoroacetate (200 mg, 0.72 mmol) in mixture of tetrahydrofuran:methanol:water (15 mL, 1:1:1) was added lithium hydroxide monohydrate (90 mg, 2.15 mmol) and stirred at room temperature for 4 h. The volatiles were removed under reduced pressure and obtained residue was dissolved in water (15 mL), washed with ethyl acetate (2×10 mL). Aqueous layer was acidified with 1N hydrochloride aqueous solution and extracted with ethyl acetate (3×10 mL). The combined organic layers were washed with brine (10 mL), dried over sodium sulfate, filtered and solvent was concentrated to afford 2-(4-bromophenyl)-2,2-difluoroacetic acid (150 mg, 0.60 mmol, 84% yield) as semi-solid compound. MS (ESI) m/z 251.43 [M−H]$^+$ C. 2-(4-Bromophenyl)-N-((2-(2,6-dioxopiperidin-3-yl)-1-oxoisoindolin-5-yl)methyl)-2,2-difluoroacetamide To an ice cold solution of 2-(4-bromophenyl)-2,2-difluoroacetic acid (291 mg, 1.16 mmol) in pyridine (6 mL) was added phosphorus oxychloride (0.27 mL, 2.9 mmol) in dropwise and stirred at 0-5° C. for 1 h. Then, 3-(5-(aminomethyl)-1-oxoisoindolin-2-yl)piperidine-2,6-dione hydrochloride (300 mg, 0.97 mmol) was added into the reaction mixture and stirred at room temperature for 2 h. The reaction mixture was basified with aqueous saturated sodium bicarbonate solution and extracted with ethyl acetate (3×15 mL). The combined organic layers were washed with water (15 mL), brine (15 mL), dried over sodium sulfate, filtered and concentrated. The resultant residue was purified by Reveleris C-18 reversed phase column chromatography (50-55% 0.1% acetonitrile in aqueous formic acid) to afford 2-(4-bromophenyl)-N-((2-(2,6-dioxopiperidin-3-yl)-1-oxoisoindolin-5-yl)methyl)-2,2-difluoroacetamide (50 mg, 0.098 mmol, 10% yield) as white solid. MS (ESI) m/z 505.6 [M+1]$^+$. $^1$H NMR (300 MHz, DMSO-$d_6$) δ 10.99 (s, 1H), 9.68 (t, J=5.8 Hz, 1H), 7.77 (d, J=8.4 Hz, 2H), 7.68 (d, J=7.8 Hz, 1H), 7.54 (d, J=8.7 Hz, 2H), 7.39 (s, 1H), 7.36 (d, J=8.1 Hz, 1H), 5.10 (dd, J=13.2, 4.8 Hz, 1H), 4.45 (d, J=6.0 Hz, 2H), 4.43 (d, J=18.1 Hz, 1H), 4.28 (d, J=17.4 Hz, 1H), 2.96-2.86 (m, 1H), 2.63-2.49 (m, 1H), 2.41-2.30 (m, 1H), 2.07-1.94 (m, 1H).

Example 72

N-((2-(2,6-Dioxopiperidin-3-yl)-1-oxoisoindolin-5-yl)methyl)-2,2-difluoro-2-(2-(2-methoxyethoxy)phenyl)acetamide

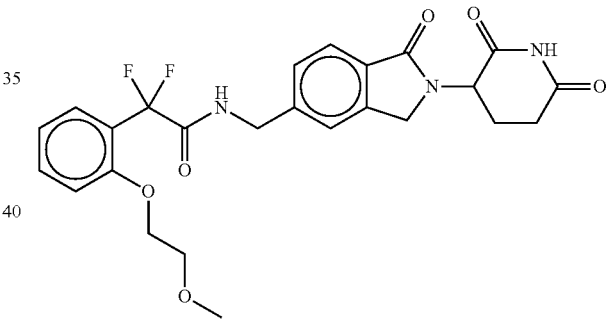

A. 1-Iodo-2-(2-methoxyethoxy)benzene

To a stirred solution of 2-iodophenol (1 g, 4.54 mmol) in N,N-dimethylformamide (10 mL) was added potassium carbonate (1.88 g, 13.64 mmol) followed by potassium iodide (0.07 g, 0.45 mmol) and 1-bromo-2-methoxyethane (0.46 mL, 4.99 mmol) at room temperature and stirred at 70° C. for 16 h. The reaction mixture was quenched with water (15 mL) and extracted with ethyl acetate (3×15 mL). The combined organic layers were washed with water (15 mL), brine (15 mL), dried over sodium sulfate, filtered and concentrated to afford 1-iodo-2-(2-methoxy ethoxy)benzene (0.8 g, 2.87 mmol, 84% yield) as colorless liquid. GCMS (m/z) 278.1 [M$^+$].

B. Ethyl 2,2-difluoro-2-(2-(2-methoxyethoxy)phenyl)acetate

To a stirred solution of 1-iodo-2-(2-methoxyethoxy)benzene (800 mg, 2.87 mmol) in dimethyl sulfoxide (15 mL) was added ethyl 2-bromo-2,2-difluoroacetate (0.42 mL, 4.31 mmol) followed by copper powder (470 mg, 7.46 mmol) at RT and stirred at 60° C. for 6 h. The reaction mixture was quenched with water and filtered through a Celite pad. The filtrate was basified with aqueous saturated sodium bicarbonate solution and extracted with ethyl acetate (3×15 mL). The combined organic layers were washed with water (15 mL), brine (15 mL), dried over sodium sulfate, filtered and concentrated. The obtained crude was purified by flash column chromatography (20% ethyl acetate in pet ether) to afford ethyl 2,2-difluoro-2-(2-(2-methoxyethoxy)phenyl)acetate (460 mg, 1.37 mmol, 24% yield) as a colorless liquid. MS (ESI) m/z 274.2 [M]⁺.

C. 2,2-Difluoro-2-(2-(2-methoxyethoxy)phenyl)acetic acid

To a stirred solution of ethyl 2,2-difluoro-2-(2-(2-methoxyethoxy)phenyl)acetate (450 mg, 1.64 mmol) in tetrahydrofuran:methanol:water mixture (15 mL, 1:1:1) was added lithium hydroxide monohydrate (206 mg, 4.92 mmol) and stirred at room temperature for 4 h. The volatiles were removed under reduced pressure and the obtained crude was dissolved in water (10 mL), washed with ethyl acetate (2×10 mL). Aqueous layer was acidified with 1N hydrochloride aqueous solution and extracted with ethyl acetate (3×10 mL). The combined organic layers were washed with brine (10 mL), dried over sodium sulfate, filtered and concentrated to afford 2,2-difluoro-2-(2-(2-methoxyethoxy)phenyl)acetic acid (290 mg, 1.17 mmol, 72% yield) as semi-solid compound. MS (ESI) m/z 247.28 [M+H]⁺.

D. N-((2-(2,6-Dioxopiperidin-3-yl)-1-oxoisoindolin-5-yl)methyl)-2,2-difluoro-2-(2-(2-methoxyethoxy)phenyl)acetamide To an ice cold solution of 2,2-difluoro-2-(2-(2-methoxyethoxy)phenyl)acetic acid (262 mg, 1.07 mmol) in pyridine (9 mL) was added phosphorus oxychloride (0.27 mL, 2.9 mmol) in dropwise and stirred at 0-5° C. for 1 h. Then, the reaction mixture was treated with 3-(5-(aminomethyl)-1-oxoisoindolin-2-yl)piperidine-2,6-dione hydrochloride (300 mg, 0.97 mmol) and stirred at room temperature for 2 h. The reaction mixture was basified with aqueous saturated sodium bicarbonate solution and extracted with ethyl acetate (3×15 mL). The combined organic layers were washed with water (15 mL), brine (15 mL), dried over sodium sulfate, filtered and solvent was concentrated. The resultant residue was purified by Reveleris C-18 reversed phase column chromatography (50-55% acetonitrile in 0.1% aqueous formic acid to afford N-((2-(2,6-dioxopiperidin-3-yl)-1-oxoisoindolin-5-yl)methyl)-2,2-difluoro-2-(2-(2-methoxyethoxy)phenyl)acetamide (60 mg, 0.12 mmol, 12% yield) as white solid. MS (ESI) m/z 502.34 [M+1]⁺. ¹H NMR (300 MHz, DMSO-d₆) δ 10.99 (s, 1H), 9.23 (t, J=5.6 Hz, 1H), 7.71 (d, J=8.1 Hz, 1H), 7.55 (dd, J=9.6, 1.5 Hz, 1H), 7.52-7.48 (m, 2H), 7.45 (d, J=8.1 Hz, 1H), 7.15 (d, J=8.4 Hz, 1H), 7.07 (dd, J=7.8, 7.2 Hz, 1H), 5.11 (dd, J=13.5, 5.1 Hz, 1H), 4.47 (d, J=6.3 Hz, 2H), 4.45 (d, J=15.9 Hz, 1H), 4.31 (d, J=17.4 Hz, 1H), 4.05 (t, J=4.8 Hz, 2H), 3.45 (t, J=5.1 Hz, 2H), 3.24 (s, 3H), 2.96-2.86 (m, 1H), 2.66-2.57 (m, 1H), 2.45-2.30 (m, 1H), 2.04-1.94 (m, 1H).

Example 73

N-((2-(2,6-dioxopiperidin-3-yl)-1-oxoisoindolin-5-yl)methyl)-2,2-difluoro-2-(1-hydroxycyclohexyl)acetamide

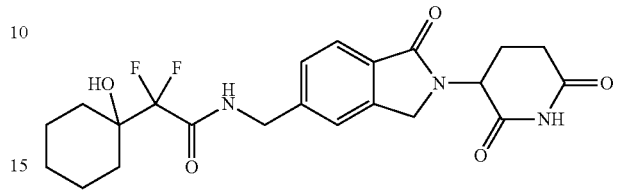

A. N-((2-(2,6-dioxopiperidin-3-yl)-1-oxoisoindolin-5-yl)methyl)-2,2-difluoro-2-(1-hydroxycyclohexyl)acetamide 3-(5-(Aminomethyl)-1-oxoisoindolin-2-yl)piperidine-2,6-dione, Mesylic acid (0.050 g, 0.135 mmol) (0.050 g, 0.113 mmol) was placed in a vial with 2,2-difluoro-2-(1-hydroxycyclohexyl)acetic acid (0.026 g, 0.135 mmol), diisopropylethylamine (0.071 mL, 0.406 mmol), 1-[Bis(dimethylamino)methylene]-1H-1,2,3-triazolo[4,5-b]pyridinium 3-oxid hexafluorophosphate (0.057 g, 0.149 mmol) and N,N-dimethylformamide (1.0 mL). The reaction mixture was stirred at 40° C. for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoro-2-(1-hydroxycyclohexyl)acetamide (0.041 g, 0.091 mmol, 67.4% yield) as a white solid. ¹H NMR (500 MHz, DMSO-d₆) δ 10.97 (s, 1H), 9.04 (t, J=6.15 Hz, 1H), 7.68 (d, J=7.88 Hz, 1H), 7.50 (s, 1H), 7.43 (d, J=7.88 Hz, 1H), 5.19 (s, 1H), 5.10 (dd, J=5.04, 13.24 Hz, 1H), 4.40-4.47 (m, 3H), 4.27-4.34 (m, 1H), 2.86-2.96 (m, 1H), 2.57-2.63 (m, 1H), 2.40 (qd, J=4.57, 13.19 Hz, 1H), 2.00 (dtd, J=2.05, 5.28, 12.61 Hz, 1H), 1.70 (d, J=12.30 Hz, 2H), 1.45-1.61 (m, 5H), 1.34-1.43 (m, 2H), 1.00-1.13 (m, 1H). MS (ESI) m/z 450.2 [M+1]⁺.

Example 74

N-((2-(2,6-dioxopiperidin-3-yl)-1-oxoisoindolin-5-yl)methyl)-2,2-difluoro-2-(1-hydroxycyclopentyl)acetamide

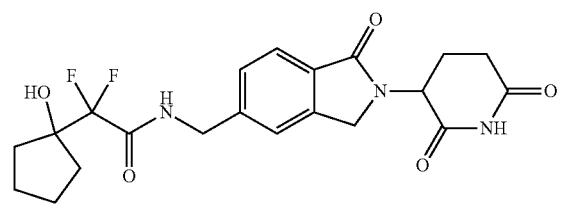 [SMILES: O=C1CCC(N2Cc3cc(CNC(=O)C(F)(F)C4(O)CCCC4)ccc3C2=O)C(=O)N1]

A. N-((2-(2,6-dioxopiperidin-3-yl)-1-oxoisoindolin-5-yl)methyl)-2,2-difluoro-2-(1-hydroxycyclopentyl)acetamide 3-(5-(Aminomethyl)-1-oxoisoindolin-2-yl)piperidine-2,6-dione, Mesylic acid (0.050 g, 0.135 mmol) (0.050 g, 0.113 mmol) was placed in a vial with 2,2-difluoro-2-(1-hydroxycyclopentyl)acetic acid (0.024 g, 0.135 mmol), diisopropylethylamine (0.071 mL, 0.406 mmol), 1-[Bis(dimethylamino)methylene]-1H-1,2,3-triazolo[4,5-b]pyridinium 3-oxid hexafluorophosphate (0.057 g, 0.149 mmol) and N,N-Dimethylformamide (1.0 mL). The reaction mixture was stirred at 40° C. for 18 h. The reaction mixture was taken up in dimethylsulfoxide and purified using reverse-phase semi preparatory HPLC (5-100% acetonitrile+0.1% formic acid in water+0.1% formic acid, over 20 min). Fractions containing desired product were combined and volatile organics were removed under reduced pressure to give N-((2-(2,6-dioxopiperidin-3-yl)-1-oxoisoindolin-5-yl)methyl)-2,2-difluoro-2-(1-hydroxycyclopentyl)acetamide (0.044 g, 0.101 mmol, 74.7% yield) as a white solid. $^1$H NMR (500 MHz, DMSO-$d_6$) δ 10.97 (s, 1H), 9.10 (t, J=6.15 Hz, 1H), 7.68 (d, J=7.57 Hz, 1H), 7.49 (s, 1H), 7.43 (d, J=7.88 Hz, 1H), 5.35 (s, 1H), 5.10 (dd, J=5.20, 13.40 Hz, 1H), 4.40-4.49 (m, 3H), 4.27-4.33 (m, 1H), 2.91 (ddd, J=5.36, 13.79, 17.42 Hz, 1H), 2.57-2.63 (m, 1H), 2.39 (qd, J=4.57, 13.29 Hz, 1H), 2.00 (dtd, J=2.36, 5.26, 12.65 Hz, 1H), 1.88-1.96 (m, 2H), 1.62-1.76 (m, 4H), 1.52-1.60 (m, 2H). MS (ESI) m/z 436.2 [M+1]$^+$.

Example 75

N-((2-(2,6-dioxopiperidin-3-yl)-1-oxoisoindolin-5-yl)methyl)-2,2-difluoro-2-(3-methyl-4-(trifluoromethoxy)phenyl)acetamide

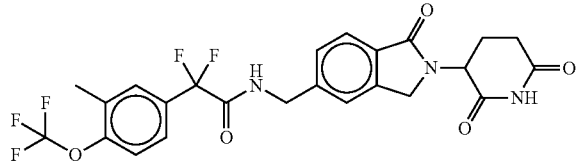

A. 4-Iodo-2-methyl-1-(trifluoromethoxy)benzene

To a stirred solution of 4-bromo-2-methyl-1-(trifluoromethoxy)benzene (1 g, 3.92 mmol) in 1,4-dioxane (10 mL) was added sodium iodide (1.17 g, 7.84 mmol), copper iodide (37.3 mg, 0.19 mmol), trans-N,N'-dimethylcyclohexane-1,2-diamine (61.3 mg, 0.43 mmol) at room temperature and stirred at 110° C. for 16 h. The reaction mixture was quenched with water (50 mL) and extracted with ethyl acetate (3×50 mL). The combined organic layer was washed with water (2×50 mL), brine (50 mL), dried over sodium sulphate and concentrated to afford 4-iodo-2-methyl-1-(trifluoromethoxy)benzene (1.0 g, 3.31 mmol, 84%) as brown liquid. GCMS (m/z) 302[M$^+$].

B. Ethyl 2,2-difluoro-2-(3-methyl-4-(trifluoromethoxy)phenyl)acetate

To a stirred solution of 4-iodo-2-methyl-1-(trifluoromethoxy)benzene (1.0 g, 3.31 mmol) in dimethylsulfoxide (10 mL) was reacted with ethyl 2-bromo-2,2-difluoroacetate (802 mm, 3.97 mmol), copper (547 mg, 8.61 mmol) and stirred at 55° C. for 6 h. The reaction mixture was neutralized with aqueous saturated ammonium chloride solution and extracted with ethyl acetate (3×50 mL). The combined organic layer was washed with water (2×50 mL), brine (50 mL) and dried over sodium sulphate and was concentrated to afford ethyl 2,2-difluoro-2-(3-methyl-4-(trifluoromethoxy)phenyl)acetate (700 mg, 2.35 mmol, 70%) as a brown liquid. GCMS (m/z) 298.1[M]$^+$.

C. 2,2-Difluoro-2-(3-methyl-4-(trifluoromethoxy)phenyl)acetic acid

To a stirred solution of ethyl 2,2-difluoro-2-(3-methyl-4-(trifluoromethoxy)phenyl)acetate (700 mg, 2.35 mmol) in ethanol:tetrahydrofuran:water (15 mL, 1:1:1) was added lithium hydroxide (296 mg, 7.05 mmol) and stirred at room temperature for 4 h. The reaction mixture was concentrated and the residue was neutralized with saturated potassium bisulphate (20 mL) and extracted with ethyl acetate (2×25 mL). The combined organic layer was washed with brine (25 mL), dried over sodium sulphate and concentrated to afford 2,2-difluoro-2-(3-methyl-4-(trifluoromethoxy)phenyl)acetic acid (400 mg, 1.48 mmol, 63% yield). MS (ESI) m/z 269.45 [M−1]$^+$.

D. N-((2-(2,6-Dioxopiperidin-3-yl)-1-oxoisoindolin-5-yl)methyl)-2,2-difluoro-2-(3-methyl-4-(trifluoromethoxy)phenyl)acetamide To a cold (0° C.) stirred solution of 2,2-difluoro-2-(3-methyl-4-(trifluoromethoxy)phenyl) acetic acid (200 mg, 0.74 mmol) in pyridine (20 mL) was added phosphoryl chloride (340 mg, 2.22 mmol) dropwise and stirred at 0-5° C. for 1 h and then added 3-(5-(aminomethyl)-1-oxoisoindolin-2-yl)piperidine-2,6-dione hydrochloride (229 mg, 0.74 mmol) and stirred at room temperature for 30 min. The reaction mixture was neutralized with aqueous saturated sodium bicarbonate (up to pH-8) and extracted with ethyl acetate (3×50 mL). The combined organic layer was washed with water (2×50 mL), brine (50 mL), dried over sodium sulphate and concentrated. The resultant residue was purified by Reveleris C-18 reversed phase column chromatography using 40-50% acetonitrile in aqueous formic acid (0.1%) to afford N-((2-(2,6-dioxopiperidin-3-yl)-1-oxoisoindolin-5-yl)methyl)-2,2-difluoro-2-(3-methyl-4-(trifluoromethoxy)phenyl)acetamide (80 mg, 0.15 mmol, 20% yield) as a white solid. MS (ESI) m/z 526.26 [M+1]$^+$. $^1$H NMR (400 MHz, DMS)-$d_6$) δ=10.98 (s, 1H), 9.68 (t, J=6.1 Hz, 1H), 7.68 (d, J=7.9 Hz, 1H), 7.62 (s, 1H), 7.57-7.47 (m, 2H), 7.42 (s, 1H), 7.37 (d, J=7.9 Hz, 1H), 5.10 (dd, J=5.2, 13.4 Hz, 1H), 4.49-4.25 (m, 4H), 2.98-2.85 (m, 1H), 2.69-2.55 (m, 1H), 2.44-2.34 (m, 1H), 2.33 (s, 3H), 2.05-1.94 (m, 1H).

Example 76

N-((2-(2,6-dioxopiperidin-3-yl)-1-oxoisoindolin-5-yl)methyl)-2-(3-ethoxypyridin-2-yl)-2,2-difluoroacetamide

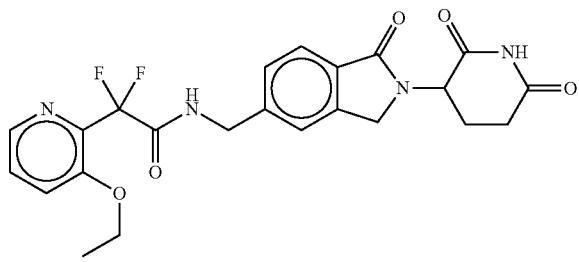

A. 3-Ethoxy-2-iodopyridine

To a stirred solution of 2-iodopyridin-3-ol (1 g, 4.52 mmol) in N,N-dimethyl formamide (20 mL) was added potassium carbonate (0.936 g, 6.78 mmol) at room temperature, and stirred for 10 min. To this reaction mixture was added ethyl iodide (1.41 g, 9.04 mmol) at room temperature and stirred for 2 h at 80° C. The reaction mixture was quenched with water (50 mL) and extracted with ethyl acetate (2×100 mL). The combined organic layers were washed with water (2×100 mL), brine (100 mL), dried over sodium sulphate and concentrated. The resultant residue was purified by column chromatography (silica-gel 100-200) 100% hexane as eluent to afford 3-ethoxy-2-iodopyridine (1 g, 4.0 mmol, 88.8% yield) as brown liquid. LCMS (ESI) m/z 251.1 [M]+.

B. Ethyl 2-(3-ethoxypyridin-2-yl)-2,2-difluoroacetate

To a stirred solution of 3-ethoxy-2-iodopyridine (1.0 g, 4.01 mmol) in dimethyl sulfoxide (20 mL) was added ethyl 2-bromo-2,2-difluoroacetate (1.6 mL, 8.03 mmol), copper (0.66 g, 10.44 mmol) and stirred at 55° C. for 16 h. The reaction mixture was neutralized with aqueous saturated ammonium chloride solution and extracted with ethyl acetate (3×100 mL). The combined organic layers were washed with water (2×100 mL), brine (10 mL), dried over sodium sulphate and concentrated to afford ethyl 2-(3-ethoxypyridin-2-yl)-2,2-difluoroacetate (800 mg, 3.26 mmol, 81%) as a brown liquid. LCMS (ESI) m/z 246.1 [M]+.

C. 2-(3-Ethoxypyridin-2-yl)-2,2-difluoroacetic acid

To a cold (0° C.) stirred solution of ethyl 2-(3-ethoxypyridin-2-yl)-2,2-difluoroacetate (800 mg, 3.26 mmol) in Methanol:tetrahydrofuran:water (9 mL, 1:1:1) was added lithium hydroxide monohydrate (410 mg, 9.78 mmol) and stirred at room temperature for 2 h. The reaction mixture was concentrated, the residue was neutralized with 10% aqueous potassium bisulphate (10 mL) and extracted with ethyl acetate (2×50 mL). The combined organic layers were washed with brine (20 mL), dried over sodium sulphate and concentrated to afford 2-(3-ethoxypyridin-2-yl)-2,2-difluoroacetic acid (500 mg, 2.13 mmol, 88% yield) as a brown semi solid. The reaction mixture was taken to the next step without further purification.

D. N-((2-(2,6-Dioxopiperidin-3-yl)-1-oxoisoindolin-5-yl)methyl)-2-(3-ethoxypyridin-2-yl)-2,2-difluoroacetamide To a cold (0° C.) stirred solution of 2-(3-ethoxypyridin-2-yl)-2,2-difluoroacetic acid (252 mg, 1.16 mmol) in pyridine (20 mL) was added phosphoryl chloride (446.4 mg, 2.91 mmol) drop wise and stirred at 0-5° C. for 30 min. To this reaction mixture was then added 3-(5-(aminomethyl)-1-oxoisoindolin-2-yl)piperidine-2,6-dione hydrochloride (300 mg, 0.97 mmol) and stirred at room temperature for 2 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase Grace column chromatography using 45-50% acetonitrile in aqueous formic acid (0.1%) to afford N-((2-(2,6-dioxopiperidin-3-yl)-1-oxoisoindolin-5-yl)methyl)-2-(3-ethoxypyridin-2-yl)-2,2-difluoroacetamide (60 mg, 0.12 mmol, 13% yield) as an off-white solid. LCMS (ESI) m/z 473.29 [M+1]+. $^1$H NMR (400 MHz, DMSO-$d_6$) δ=10.98 (s, 1H), 9.41 (br t, J=6.3 Hz, 1H), 8.22 (dd, J=1.1, 4.4 Hz, 1H), 7.72 (d, J=7.9 Hz, 1H), 7.66-7.61 (m, 1H), 7.59-7.53 (m, 2H), 7.48 (d, J=7.9 Hz, 1H), 5.12 (dd, J=5.6, 13.2 Hz, 1H), 4.53-4.27 (m, 4H), 4.08 (q, J=7.2, 2H), 2.99-2.86 (m, 1H), 2.70-2.56 (m, 1H), 2.47-2.32 (m, 1H), 2.05-1.96 (m, 1H), 1.19 (t, J=7.2 Hz, 3H).

Example 77

N-((2-(2,6-Dioxopiperidin-3-yl)-1-oxoisoindolin-5-yl)methyl)-2,2-difluoro-2-(3-methylpyridin-2-yl)acetamide

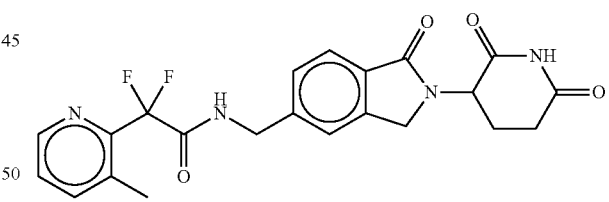

A. Ethyl 2,2-difluoro-2-(3-methylpyridin-2-yl)acetate

To a stirred solution of 2-iodo-3-methylpyridine (0.7 g, 3.19 mmol) in dimethyl sulfoxide (20 mL) was added ethyl 2-bromo-2,2-difluoroacetate (0.8 mL, 6.39 mmol), copper (0.52 g, 8.29 mmol) and stirred for 16 h at 50° C. The reaction mixture was neutralized with aqueous saturated ammonium chloride solution and extracted with ethyl acetate (3×50 mL). The combined organic layers were washed with water (2×10 mL), brine (10 mL) and dried over sodium sulphate and was concentrated to afford ethyl 2,2-difluoro-2-(3-methylpyridin-2-yl)acetate (500 mg, 2.32 mmol, 73%) as a brown liquid. GCMS (m/z) 215.2.

B. 2,2-Difluoro-2-(3-methylpyridin-2-yl)acetic acid

To a cold (0° C.) stirred solution of ethyl 2,2-difluoro-2-(3-methylpyridin-2-yl)acetate (500 mg, 2.32 mmol) in methanol/tetrahydrofuran/water mixture (9 mL, 1:1:1) was added lithium hydroxide monohydrate (327 mg, 6.97 mmol) and stirred at room temperature for 2 h. The reaction mixture was concentrated and the residue was neutralized with 10% aqueous potassium bisulphate (10 mL) and extracted with ethyl acetate (2×30 mL). The combined organic layers were washed with brine (10 mL), dried over sodium sulphate and concentrated to afford 2,2-difluoro-2-(3-methylpyridin-2-yl) acetic acid (400 mg, 2.13 mmol, 88% yield) as a brown semi solid. MS (ESI) m/z 188.31.

C. N-((2-(2,6-Dioxopiperidin-3-yl)-1-oxoisoindolin-5-yl)methyl)-2,2-difluoro-2-(3-methylpyridin-2-yl) acetamide To a cold (0° C.) stirred solution of 2,2-difluoro-2-(3-methylpyridin-2-yl)acetic acid (300 mg, 1.60 mmol) in pyridine (20 mL) was added phosphoryl chloride (735 mg, 4.80 mmol) dropwise and stirred at 0-5° C. for 30 min. To the reaction mixture was then added 3-(5-(aminomethyl)-1-oxoisoindolin-2-yl)piperidine-2,6-dione hydrochloride (395 mg, 1.60 mmol) and stirred at room temperature for 2 h. The reaction mixture was neutralized with aqueous saturated sodium bicarbonate (up to pH-8) and extracted with ethyl acetate (3×50 mL). The combined organic layers were washed with water (2×50 mL), brine (50 mL) and dried over sodium sulphate and concentrated. The resultant residue was purified by Reveleris C-18 reversed phase column chromatography using 45-50% acetonitrile in aqueous formic acid (0.1%) to afford N-((2-(2,6-dioxopiperidin-3-yl)-1-oxoisoindolin-5-yl)methyl)-2,2-difluoro-2-(3-methylpyridin-2-yl)acetamide (40 mg, 0.09 mmol, 7% yield) as an off-white solid. MS (ESI) m/z 443.30 [M+1]$^+$. $^1$H NMR (300 MHz, DMSO-d$_6$) δ 10.99 (s, 1H), 9.45 (br t, J=6.1 Hz, 1H), 8.51 (br d, J=3.9 Hz, 1H), 7.84 (br d, J=7.8 Hz, 1H), 7.72 (d, J=7.8 Hz, 1H), 7.63 (s, 1H), 7.51 (br d, J=7.8 Hz, 2H), 5.19-5.03 (m, 1H), 4.58-4.28 (m, 4H), 2.92-2.85 (m, 1H), 2.68-2.54 (m, 1H), 2.45-2.30 (m, 4H), 2.10-1.92 (m, 1H).

Example 78

N-((2-(2,6-Dioxopiperidin-3-yl)-1-oxoisoindolin-5-yl)methyl)-2,2-difluoro-2-(5-methylpyridin-2-yl) acetamide

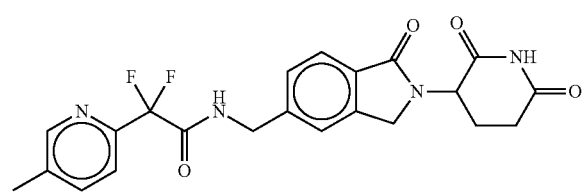

A. 2-Iodo-5-methylpyridine

To a stirred solution of 2-bromo-5-methylpyridine (2 g, 11.63 mmol) in 1,4-dioxane (30 mL) was added sodium iodide (3.4 g, 23.24 mmol), copper iodide (110 mg, 0.58 mmol), trans-N,N'-dimethylcyclohexane-1,2-diamine (180 mg, 1.26 mmol) at room temperature and stirred at 110° C. for 16 h in sealed tube. The reaction mixture was quenched with water (30 mL) and extracted with ethyl acetate (3×30 mL). The combined organic layers were washed with water (2×20 mL), brine (20 mL), dried over sodium sulphate and concentrated to afford 2-iodo-5-methylpyridine (1.3 g, 5.93 mmol, 52% yield) as brown liquid. $^1$H NMR (300 MHz, CDCl$_3$) δ 8.2 (s, 1H), 7.6-7.56 (d, J=8.1 Hz, 1H), 7.18-7.12 (m, 1H), 2.3-2.25 (s, 1H).

B. Ethyl 2,2-difluoro-2-(5-methylpyridin-2-yl)acetate

To a stirred solution of 2-iodo-5-methylpyridine (1 g, 4.56 mmol) in dimethyl sulfoxide (20 mL) was added ethyl 2-bromo-2,2-difluoroacetate (1.2 mL, 9.13 mmol), copper (0.75 g, 11.85 mmol) and stirred for 16 h at 50° C. The reaction mixture was neutralized with aqueous saturated ammonium chloride solution and extracted with ethyl acetate (3×50 mL). The combined organic layers were washed with water (2×10 mL), brine (10 mL), dried over sodium sulphate and concentrated to afford ethyl ethyl 2,2-difluoro-2-(5-methylpyridin-2-yl)acetate (600 mg, 2.72 mmol, 60%) as a brown liquid. GCMS (m/z) 215.0

C. 2,2-Difluoro-2-(5-methylpyridin-2-yl)acetic acid

To a cold (0° C.) stirred solution of ethyl 2,2-difluoro-2-(5-methylpyridin-2-yl)acetate (500 mg, 2.32 mmol) in methanol/tetrahydrofuran/water mixture (9 mL, 1:1:1) was added lithium hydroxide monohydrate (327 mg, 6.97 mmol) and stirred at room temperature for 2 h. The reaction mixture was concentrated and the residue was neutralized with 10% aqueous potassium bisulphate (10 mL) and extracted with ethyl acetate (2×30 mL). The combined organic layers were washed with brine (10 mL), dried over sodium sulphate and concentrated to afford 2,2-difluoro-2-(5-methylpyridin-2-yl) acetic acid (350 mg, 1.87 mmol, 87% yield) as a brown semi solid. MS (ESI) m/z 188.39.

D. N-((2-(2,6-Dioxopiperidin-3-yl)-1-oxoisoindolin-5-yl)methyl)-2,2-difluoro-2-(5-methylpyridin-2-yl) acetamide To a cold (0° C.) stirred solution of 2,2-difluoro-2-(5-methylpyridin-2-yl)acetic acid (180 mg, 0.97 mmol) in pyridine (20 mL) was added phosphoryl chloride (0.2 mL, 2.91 mmol) dropwise and stirred at 0-5° C. for 30 min. To this reaction mixture was then added 3-(5-(aminomethyl)-1-oxoisoindolin-2-yl)piperidine-2,6-dione hydrochloride (300 mg, 0.97 mmol) and stirred at room temperature for 2 h. The reaction mixture was neutralized with aqueous saturated sodium bicarbonate (up to pH-8) and extracted with ethyl acetate (3×50 mL). The combined organic layers were washed with water (2×50 mL), brine (50 mL) and dried over sodium sulphate and concentrated. The resultant residue was purified by Reveleris C-18 reversed phase column chromatography using 45-50% acetonitrile in aqueous formic acid (0.1%) to afford N-((2-(2,6-dioxopiperidin-3-yl)-1-oxoisoindolin-5-yl)methyl)-2,2-difluoro-2-(5-methylpyridin-2-yl)acetamide (64 mg, 0.14 mmol, 13% yield) as an off-white solid. MS (ESI) m/z 443.30 [M+1]$^+$. $^1$H NMR (300 MHz, DMSO-d$_6$) δ 10.99 (s, 1H), 9.60 (br t, J=5.9 Hz, 1H), 8.55 (bs, 1H), 7.88-7.98 (m, 1H), 7.69-7.63 (t, J=8.6 Hz, 2H), 7.52 (s, 1H), 7.49-7.40 (m, 1H), 5.11 (dd, J=5.1, 13.5 Hz, 1H), 4.59-4.21 (m, 4H), 2.98-2.85 (m, 1H), 2.68-2.53 (m, 1H), 2.45-2.39 (m, 4H), 2.06-1.97 (m, 1H).

Example 79

N-((2-(2,6-Dioxopiperidin-3-yl)-1-oxoisoindolin-5-yl)methyl)-2-(2-ethoxy-6-fluorophenyl)-2,2-difluoroacetamide

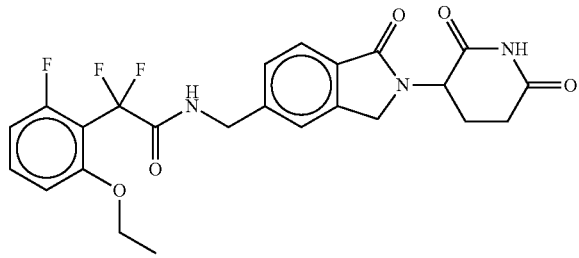

A. 1-Ethoxy-3-fluoro-2-iodobenzene

To a stirred solution of 2-bromo-1-ethoxy-3-fluorobenzene (1 g, 4.58 mmol) in 1,4-dioxane (30 mL) was added sodium iodide (1.37 g, 9.17 mmol), copper iodide (43.6 mg, 0.22 mmol), trans-N,N'-dimethylcyclohexane-1,2-diamine (71.2 mg, 0.504 mmol) at room temperature and stirred at 110° C. for 16 h in sealed tube. The reaction mixture was quenched with water (100 mL) and extracted with ethyl acetate (3×100 mL). The combined organic layers were washed with water (2×50 mL), brine (50 mL), dried over sodium sulphate and concentrated to afford 1-ethoxy-3-fluoro-2-iodobenzene (1 g, 5.93 mmol, 52% yield) as brown liquid. GC-MS (ESI) m/z 266.

B. Ethyl 2-(2-ethoxy-6-fluorophenyl)-2,2-difluoroacetate

To a stirred solution of 1-ethoxy-3-fluoro-2-iodobenzene (1 g, 3.17 mmol) in dimethyl sulfoxide (20 mL) was added ethyl 2-bromo-2,2-difluoroacetate (1.53 g, 7.54 mmol), copper (0.62 g, 9.80 mmol) and stirred for 16 h at 50° C. The reaction mixture was neutralized with aqueous saturated ammonium chloride solution and extracted with ethyl acetate (3×50 mL). The combined organic layers were washed with water (2×20 mL), brine (20 mL), dried over sodium sulphate and concentrated to afford ethyl 2-(2-ethoxy-6-fluorophenyl)-2,2-difluoroacetate (800 mg, 3.05 mmol, 81%) as a brown liquid. GC-MS (ESI) m/z 262.2

C. 2-(2-Ethoxy-6-fluorophenyl)-2,2-difluoroacetic acid

To a cold (0° C.) stirred solution of and was concentrated to give ethyl 2-(2-ethoxy-6-fluorophenyl)-2,2-difluoroacetate (500 mg, 2.32 mmol) in ethanol/tetrahydrofuran/water mixture (9 mL, 1:1:1) was added lithium hydroxide monohydrate (327 mg, 6.97 mmol) and stirred at room temperature for 2 h. The reaction mixture was concentrated and the residue was neutralized with 10% aqueous potassium bisulphate (10 mL) and extracted with ethyl acetate (2×30 mL). The combined organic layers were washed with brine (10 mL), dried over sodium sulphate and concentrated to afford 2-(2-Ethoxy-6-fluorophenyl)-2,2-difluoroacetic acid (400 mg, 1.70 mmol, 56% yield) as a brown semi solid. LCMS (ESI) m/z 233.4 [M−1]⁻.

D. N-((2-(2,6-Dioxopiperidin-3-yl)-1-oxoisoindolin-5-yl)methyl)-2,2-difluoro-2-(5-methylpyridin-2-yl)acetamide To a cold (0° C.) stirred solution of 2,2-difluoro-2-(5-methylpyridin-2-yl)acetic acid (272 mg, 1.16 mmol) in pyridine (20 mL) was added phosphoryl chloride (0.3 mL, 2.91 mmol) dropwise and stirred at 0-5° C. for 30 min. To this reaction mixture was then added 3-(5-(aminomethyl)-1-oxoisoindolin-2-yl)piperidine-2,6-dione hydrochloride (300 mg, 0.97 mmol) and stirred at room temperature for 2 h. The reaction mixture was neutralized with aqueous saturated sodium bicarbonate (up to pH-8) and extracted with ethyl acetate (3×50 mL). The combined organic layers were washed with water (2×50 mL), brine (50 mL) and dried over sodium sulphate and concentrated. The resultant residue was purified by Reveleris C-18 reversed phase Grace column chromatography using 45-50% acetonitrile in aqueous formic acid (0.1%) to afford N-((2-(2,6-dioxopiperidin-3-yl)-1-oxoisoindolin-5-yl)methyl)-2,2-difluoro-2-(5-methylpyridin-2-yl)acetamide (60 mg, 0.12 mmol, 12% yield) as an off-white solid. LCMS (ESI) m/z 490.3 [M+1]⁺. ¹H NMR (400 MHz, DMSO-d₆) δ=10.98 (s, 1H), 9.36 (br t, J=6.1 Hz, 1H), 7.71 (d, J=7.6 Hz, 1H), 7.54-7.47 (m, 3H), 7.45 (d, J=7.6 Hz, 1H), 7.00-6.84 (m, 1H), 5.11 (br dd, J=5.0, 13.3 Hz, 1H), 4.52-4.27 (m, 4H), 3.99 (q, J=7.0 Hz, 1H), 3.04-2.82 (m, 1H), 2.71-2.54 (m, 1H), 2.46-2.28 (m, 1H), 2.04-1.94 (m, 1H), 1.14 (t, J=7.0 Hz, 1H).

Example 80

N-((2-(2,6-Dioxopiperidin-3-yl)-1-oxoisoindolin-5-yl)methyl)-2,2-difluoro-2-(4'-fluorobiphenyl-4-yl)acetamide

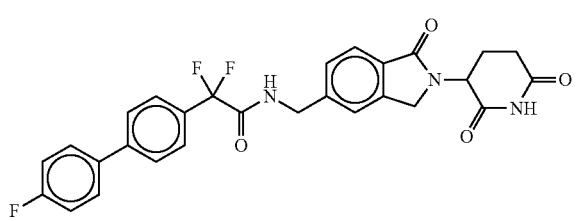

A. 1-(4'-Fluorobiphenyl-4-yl)ethanone

To a solution of 1-(4-bromophenyl)ethanone (2 g, 10.05 mmol) in toluene/ethanol ((10 mL, 2:1) was added 4-fluorophenylboronic acid (1.68 g, 12.06 mmol) followed by potassium carbonate (3.46 g, 25.12 mmol) and degassed for 10 min. The reaction mixture was further charged with tetrakis(triphenylphosphine)palladium(0) (1.16 mg, 1.005 mmol) and degassed for additional 10 min and heated at 80° C. in a sealed tube for 6 h. The reaction mixture was cooled to room temperature, filtered through the celite pad. The filtrate was diluted with cold water and extracted with ethyl acetate (3×10 mL). The combined organic layers were washed with water (10 mL), brine (10 mL), dried over sodium sulfate, filtered and concentrated. The obtained residue was purified by column chromatography (100-200 silica gel, 30% ethyl acetate in hexane) to afford 1-(4'-fluorobiphenyl-4-yl)ethanone (1 g, 4.67 mmol, 48% yield) as an off-white solid. MS (ESI) m/z 215.27 [M+1]⁺.

B. Ethyl 2-(4'-fluorobiphenyl-4-yl)-2-oxoacetate

To a stirred solution of 1-(4'-fluorobiphenyl-4-yl)ethanone (1.5 g, 7.009 mmol) in pyridine (10 mL) was added selenium dioxide (1.94 g, 17.52 mmol) at room temperature. The reaction mixture was stirred at 100° C. for 16 h. The reaction mixture was filtered through celite pad and washed with dichloromethane (15 mL). Ethyl chloroformate (15 mL) was added to the filtrate at 0° C. and stirred at room temperature for 4 h. The reaction mixture was quenched with ice water and extracted with dichloromethane (3×10 mL). The combined organic layers were washed with 1N hydrochloride (15 mL), brine (10 mL), dried over sodium sulfate, filtered and concentrated to afford ethyl 2-(4'-fluorobiphenyl-4-yl)-2-oxoacetate (900 mg, 3.308 mmol, 47% yield) as a colorless liquid. MS (ESI) m/z 273.51 [M+1]$^+$.

C. Ethyl 2,2-difluoro-2-(4'-fluorobiphenyl-4-yl)acetate

Ethyl 2-(4'-fluorobiphenyl-4-yl)-2-oxoacetate (1 g, 3.676 mmol) was added in portion into diethylaminosulfur trifluoride (1.4 mL) at 0° C. and stirred at room temperature for 16 h. The reaction mixture was quenched with aqueous sodium bicarbonate and extracted with ethyl acetate (3×10 mL). The combined organic layers were washed with brine (10 mL), dried over sodium sulfate, filtered and concentrated. The obtained crude was purified by column chromatography [using (100-200) silica gel, 10% ethyl acetate in pet ether] to afford ethyl 2,2-difluoro-2-(4'-fluorobiphenyl-4-yl)acetate (800 mg, 2.72 mmol, 80% yield) as a colorless liquid. GCMS (ESI) m/z 294 [M+1]$^+$.

D. 2,2-Difluoro-2-(4'-fluorobiphenyl-4-yl)acetic acid

To a stirred solution of ethyl 2,2-difluoro-2-(4'-fluorobiphenyl-4-yl)acetate (900 mg, 3.06 mmol) in tetrahydrofuran:methanol:water mixture (12 mL, 1:1:1) was added lithium hydroxide monohydrate (385 mg, 9.18 mmol) and stirred at room temperature for 4 h. The reaction mixture was concentrated under reduced pressure and the residue obtained was dissolved in water (10 mL), washed with ethyl acetate (2×10 mL). The aqueous layer was acidified with 1N hydrochloride aqueous solution and extracted with ethyl acetate (3×10 mL). The combined organic layers were washed with brine (10 mL), dried over sodium sulfate, filtered and concentrated to afford 2,2-difluoro-2-(4'-fluorobiphenyl-4-yl)acetic acid (400 mg, 2.91 mmol, 44% yield) as semi-solid compound. The crude was used to next step without purification.

E. N-((2-(2,6-Dioxopiperidin-3-yl)-1-oxoisoindolin-5-yl)methyl)-2,2-difluoro-2-(4'-fluorobiphenyl-4-yl)acetamide To an ice cold solution of 2,2-difluoro-2-(4'-fluorobiphenyl-4-yl)acetic acid (266 mg, 1.16 mmol) in pyridine (15 mL) was added phosphorus oxychloride (445 mL, 2.91 mmol) drop wise and stirred at 0-5° C. for 1 h. Then, 3-(5-(aminomethyl)-1-oxoisoindolin-2-yl)piperidine-2,6-dione hydrochloride (300 mg, 0.97 mmol) was added into the reaction mixture and stirred at room temperature for 1 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl)methyl)-2,2-difluoro-2-(4'-fluorobiphenyl-4-yl) acetamide (60 mg, 0.114 mmol, 11% yield) as white solid. MS (ESI) m/z 522.46 [M+1]$^+$. $^1$H NMR (300 MHz, DMSO-d$_6$) δ ppm 10.98 (s, 1H), 9.68 (t, J=5.8 Hz, 1H), 7.86-7.72 (m, 4H), 7.72-7.62 (m, 3H), 7.43-7.28 (m, 4H), 5.09 (dd, J=13.2, 5.1 Hz, 1H), 4.47 (d, J=5.7 Hz, 2H), 4.38 (d, J=17.1 Hz, 1H), 4.24 (d, J=17.1 Hz, 1H), 3.00-2.81 (m, 1H), 2.64-2.53 (m, 1H), 2.38-2.20 (m, 1H), 2.03-1.90 (m, 1H).

Example 81

N-((2-(2,6-Dioxopiperidin-3-yl)-1-oxoisoindolin-5-yl)methyl)-2-(2-ethoxy-5-fluorophenyl)-2,2-difluoroacetamide

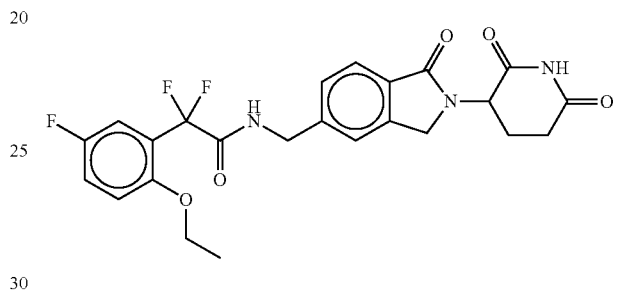

A. 1-(2-Ethoxy-5-fluorophenyl)ethanone

To a stirred solution of 1-(5-fluoro-2-hydroxyphenyl)ethanone (500 mg, 3.24 mmol) in N,N-dimethylformamide (15 mL) was added ethyl bromide (607 mg, 3.89 mmol) followed by potassium carbonate (1.11 g, 8.10 mmol) and stirred at 90° C. for 16 h. The reaction mixture was diluted with ice water (15 mL) and extracted with ethyl acetate (3×10 mL). The combined organic layers were washed with water (10 mL), brine (10 mL), dried over sodium sulfate, filtered and concentrated to afford 1-(2-ethoxy-5-fluorophenyl)ethanone (350 mg, 1.36 mmol, 20% yield) as a colorless liquid. MS (ESI) m/z 183.34 [M+1]$^+$.

B. Ethyl 2-(2-ethoxy-5-fluorophenyl)-2-oxoacetate

To a stirred solution of 1-(2-ethoxy-5-fluorophenyl)ethanone (2 g, 10.99 mmol) in pyridine (10 mL) was added selenium dioxide (3.05 g, 27.47 mmol) at room temperature heated at 100° C. for 16 h. The reaction mixture was filtered through a Celite pad and washed with dichloromethane (15 mL). 4 mL of ethyl chloroformate was added to the filtrate at 0° C. and stirred at room temperature for 4 h. The reaction mixture was quenched with ice water and extracted with dichloromethane (3×30 mL). The combined organic layers were washed with 1N hydrochloride solution (30 mL), brine (30 mL), dried over sodium sulfate, filtered and concentrated to afford ethyl 2-(2-ethoxy-5-fluorophenyl)-2-oxoacetate (1.7 g, 7.08 mmol, 75% yield) as a colorless liquid. Without further purification used for next step.

C. Ethyl 2-(2-ethoxy-5-fluorophenyl)-2,2-difluoroacetate

Ethyl 2-(2-ethoxy-5-fluorophenyl)-2-oxoacetate (1 g, 4.16 mmol) was added into diethylamino sulfur trifluoride (2 mL) at 0° C. and stirred at room temperature for 16 h. The reaction mixture was quenched with aqueous sodium bicarbonate solution and extracted with ethyl acetate (3×10 mL). The combined organic layers were washed with brine (10 mL), dried over sodium sulfate, filtered and concentrated. Obtained crude was purified by column chromatography (100-200 silica gel, 10% ethyl acetate in pet ether) to afford ethyl 2-(2-ethoxy-5-fluorophenyl)-2,2-difluoroacetate (800 mg, 3.05 mmol, 73% yield) as a colourless liquid. MS (ESI) m/z 262.2 [M]+.

D. 2-(2-Ethoxy-5-fluorophenyl)-2,2-difluoroacetic acid

To a stirred solution of ethyl 2-(2-ethoxy-5-fluorophenyl)-2,2-difluoroacetate (600 mg, 2.29 mmol) in mixture of tetrahydrofuran:methanol:water (12 mL, 1:1:1) was added lithium hydroxide monohydrate (288 mg, 6.87 mmol) and stirred at room temperature for 16 h. The volatiles were removed under reduced pressure and obtained residue was dissolved in water (10 mL) and washed with ethyl acetate (2×10 mL). Aqueous layer was acidified with 1N hydrochloride aqueous solution and extracted with ethyl acetate (3×10 mL). The combined organic layers were washed with brine (10 mL), dried over sodium sulfate, filtered and solvent was concentrated to afford 2-(2-ethoxy-5-fluorophenyl)-2,2-difluoroacetic acid (310 mg, 1.32 mmol, 87% yield) as semi-solid compound. $^1$H NMR (400 MHz, CDCl$_3$) δ 7.38 (dd, J=8.8, 3.2 Hz, 1H), 7.16 (ddd, J=11.2, 8.8, 3.2 Hz, 1H), 6.91 (dd, J=9.2, 4.4 Hz, 1H), 4.08 (q, J=7.2 Hz, 2H), 2.68 (brs, 1H), 1.39 (t, J=6.8 Hz, 3H).

E. N-((2-(2,6-Dioxopiperidin-3-yl)-1-oxoisoindolin-5-yl)methyl)-2-(2-ethoxy-5-fluorophenyl)-2,2-difluoroacetamide To an ice cold solution of 2-(2-ethoxy-5-fluorophenyl)-2,2-difluoroacetic acid (151 mg, 0.65 mmol) in pyridine (9 mL) was added phosphorus oxychloride (0.18 mL, 1.94 mmol) in drop wise and stirred at 0-5° C. for 1 h. Then, 3-(5-(aminomethyl)-1-oxoisoindolin-2-yl)piperidine-2,6-dione hydrochloride (200 mg, 0.65 mmol) was added into the reaction mixture and stirred at room temperature for 1 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to give N-((2-(2,6-dioxopiperidin-3-yl)-1-oxoisoindolin-5-yl)methyl)-2-(2-ethoxy-5-fluorophenyl)-2,2-difluoro acetamide (55 mg, 0.11 mmol, 17% yield) as white solid. MS (ESI) m/z 490.1 [M+1]+. $^1$H NMR (300 MHz, DMSO-d$_6$) δ 10.98 (s, 1H), 9.38 (t, J=5.6 Hz, 1H), 7.70 (d, J=7.5 Hz, 1H), 7.50 (s, 1H), 7.44 (d, J=8.4 Hz, 1H), 7.39-7.34 (m, 2H), 7.19-7.11 (m, 1H), 5.11 (dd, J=13.2, 5.1 Hz, 1H), 4.47 (d, J=6.6 Hz, 2H), 4.45 (d, J=16.5 Hz, 1H), 4.31 (d, J=17.7 Hz, 1H), 3.97 (q, J=6.9 Hz, 2H), 2.96-2.85 (m, 1H), 2.67-2.55 (m, 1H), 2.45-2.30 (m, 1H), 2.04-1.94 (m, 1H), 1.11 (t, J=7.2 Hz, 3H).

Example 82

2-Cyclopentyl-N-((2-(2,6-dioxopiperidin-3-yl)-1-oxoisoindolin-5-yl)methyl)-2,2-difluoroacetamide

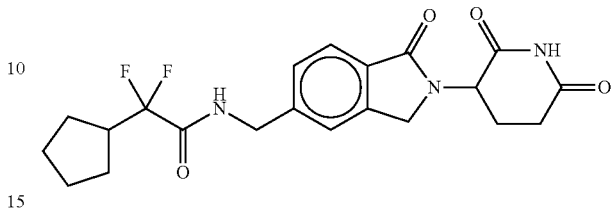

A. Ethyl 2,2-difluoro-2-(1-hydroxycyclopentyl)acetate

To a stirred solution of cyclopentanone (1 g, 11.90 mmol) in tetrahydrofuran (20 mL) was added anhydrous cerium(III) chloride (0.06 g, 0.24 mmol) followed by activated zinc dust (0.93 g, 14.28 mmol) and ethyl 2-bromo-2,2-difluoroacetate (2.01 mL, 15.47 mmol) at 0° C. and stirred at room temperature for 16 h. The reaction mixture was diluted with water (20 mL) and extracted with ethyl acetate (3×20 mL). The combined organic layers were washed with water (20 mL), brine (20 mL), dried over sodium sulfate, filtered and solvent was concentrated and obtained crude was purified by silica gel column chromatography (30% ethyl acetate in pet ether) to afford ethyl 2,2-difluoro-2-(1-hydroxycyclopentyl) acetate (0.55 g, 2.40 mmol, 22% yield) as a colorless liquid. $^1$H NMR (300 MHz, DMSO-d$_6$) δ 5.48 (s, 1H), 4.27 (q, J=6.9 Hz, 2H), 1.87-1.81 (m, 2H), 1.75-1.57 (m, 6H), 1.26 (t, J=6.9 Hz, 3H).

B. Ethyl 2-cyclopentenyl-2,2-difluoroacetate

To a stirred solution of ethyl 2,2-difluoro-2-(1-hydroxycyclopentyl)acetate (50 mg, 0.24 mmol) in pyridine (1.7 mL) was added thionyl chloride (0.17 mL, 2.40 mmol) at 0° C. and stirred at room temperature for 16 h. The reaction mixture was diluted with water (4 mL) and basified with aqueous sodium bicarbonate solution and extracted with ethyl acetate (3×4 mL). The combined organic layers were washed with water (4 mL), brine (4 mL), dried over sodium sulfate, filtered and concentrated. The obtained crude product was purified by silica gel column chromatography (30% ethyl acetate in pet ether) to afford ethyl 2-cyclopentenyl-2,2-difluoroacetate (25 mg, 0.13 mmol, 45% yield) as a colorless liquid. MS (ESI) m/z 190.1 [M]+.

C. Ethyl 2-cyclopentyl-2,2-difluoroacetate

To a stirred solution of ethyl 2-cyclopentenyl-2,2-difluoroacetate (100 mg, 0.52 mmol) in ethyl acetate (10 mL) was added slurry of 10% palladium hydroxide (30 mg) in ethyl acetate under nitrogen stream and stirred under hydrogen balloon pressure at room temperature for 4 h. The hydrogen atmosphere was evacuated and reaction mixture was filtered through a Celite pad, filtrate was concentrated to afford ethyl 2-cyclopentyl-2,2-difluoroacetate (60 mg, 0.31 mmol, 59% yield) as a colorless liquid. $^1$H NMR (300 MHz, CDCl$_3$) δ 4.32 (q, J=7.2 Hz, 2H), 2.67-2.57 (m, 1H), 1.79-1.55 (m, 8H), 1.35 (t, J=6.9 Hz, 3H).

D. 2-Cyclopentyl-2,2-difluoroacetic acid

To a stirred solution of ethyl 2-cyclopentyl-2,2-difluoroacetate (450 mg, 2.34 mmol) in tetrahydrofuran:methanol:water mixture (15 mL, 1:1:1) was added lithium hydroxide monohydrate (295 mg, 7.03 mmol) and stirred at room temperature for 4 h. The volatiles were removed under reduced pressure and the resultant residue was dissolved in water (10 mL) and washed with ethyl acetate (2×10 mL). Aqueous layer was acidified with 1N hydrochloride aqueous solution and extracted with ethyl acetate (3×10 mL). The combined organic layers were washed with brine (10 mL), dried over sodium sulfate, filtered and concentrated to afford 2-cyclopentyl-2,2-difluoroacetic acid (280 mg, 1.70 mmol, 72% yield) as semi-solid compound. $^1$H NMR (300 MHz, DMSO-$d_6$) δ 8.68 (brs, 1H), 2.69-2.59 (m, 1H), 1.84-1.59 (m, 8H).

E. 2-Cyclopentyl-N-((2-(2,6-dioxopiperidin-3-yl)-1-oxoisoindolin-5-yl)methyl)-2,2-difluoroacetamide To an ice cold solution of 2-cyclopentyl-2,2-difluoroacetic acid (159 mg, 0.97 mmol) in pyridine (9 mL) was added phosphorus oxychloride (0.27 mL, 2.9 mmol) drop wise and stirred at 0-5° C. for 1 h. Then, 3-(5-(aminomethyl)-1-oxoisoindolin-2-yl)piperidine-2,6-dione hydrochloride (300 mg, 0.97 mmol) was added into the reaction mixture and stirred at room temperature for 2 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to afford 2-cyclopentyl-N-((2-(2,6-dioxopiperidin-3-yl)-1-oxoisoindolin-5-yl)methyl)-2,2-difluoroacetamide (50 mg, 0.12 mmol, 12% yield) as white solid. MS (ESI) m/z 420.17 [M+1]$^+$. $^1$H NMR (300 MHz, DMSO-$d_6$) δ 10.98 (s, 1H), 9.36 (t, J=6.3 Hz, 1H), 7.70 (d, J=7.8 Hz, 1H), 7.47 (s, 1H), 7.40 (d, J=8.1 Hz, 1H), 5.11 (dd, J=13.5, 5.1 Hz, 1H), 4.46 (d, J=17.1 Hz, 1H), 4.44 (d, J=6.0 Hz, 2H), 4.31 (d, J=17.7 Hz, 1H), 2.92-2.87 (m, 1H), 2.73-2.57 (m, 2H), 2.40-2.36 (m, 1H), 2.02-1.98 (m, 1H), 1.70-1.53 (m, 8H).

Example 83

N-((2-(2,6-Dioxopiperidin-3-yl)-1-oxoisoindolin-5-yl)methyl)-2,2-difluoro-2-(3-methyl-4-(trifluoromethoxy)phenyl)acetamide

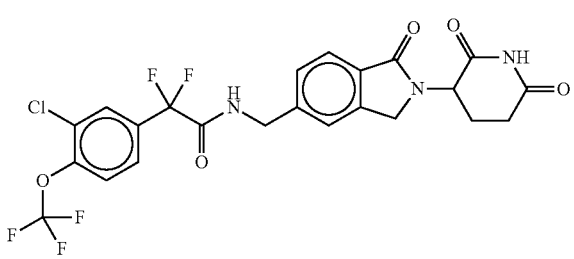

A. 2-Chloro-4-iodo-1-(trifluoromethoxy)benzene

To a cold (0° C.) stirred solution of 3-chloro-4-(trifluoromethoxy)aniline (2.5 g, 11.79 mmol) in aq H$_2$SO$_4$ (10 mL) was added sodium nitrite (894 mg, 12.96 mmol) urea (106 mg, 1.768 mmol) and potassium iodide (4.1 g, 24.75 mmol) at 0° C. and stirred at 50° C. for 2 h. The reaction mixture was quenched with aqueous sodium bicarbonate solution (40 mL) and extracted with ethyl acetate (3×50 mL). The combined organic layers were washed with water (2×10 mL), brine (10 mL), dried over sodium sulphate and concentrated to afford 2-chloro-4-iodo-1-(trifluoromethoxy)benzene and crude (2 g, 6.23 mmol, 52% yield) as colorless liquid which was used to next step without any purification.

B. Ethyl 2-(3-chloro-4-(trifluoromethoxy)phenyl)-2,2-difluoroacetate

To a stirred solution of 2-chloro-4-iodo-1-(trifluoromethoxy)benzene (1.5 g, 4.56 mmol) in dimethylsulfoxide (12 mL) was reacted with ethyl 2-bromo-2,2-difluoroacetate (138 g 6.84 mmol), copper (753 mg, 11.85 mmol) and stirred for 6 h at 55° C. The reaction mixture was neutralized with aqueous saturated ammonium chloride solution and extracted with ethyl acetate (3×50 mL). The combined organic layers were washed with water (2×10 mL), brine (10 mL), dried over sodium sulphate and concentrated to afford ethyl 2-(3-chloro-4-(trifluoromethoxy)phenyl)-2,2-difluoroacetate (1.1 g, 3.45 mmol, 78% yield) as a brown liquid. MS (ESI) m/z 318 [M+1]$^+$.

C. 2-(3-Chloro-4-(trifluoromethoxy)phenyl)-2,2-difluoroacetic acid

To a cold (0° C.) stirred solution of ethyl 2-(3-chloro-4-(trifluoromethoxy)phenyl)-2,2-difluoroacetate (2 g, 6.289 mmol) in methanol/tetrahydrofuran/water mixture (10 mL, 1:1:1) was added lithium hydroxide monohydrate (792 mg, 18.86 mmol) and stirred at room temperature for 16 h. The reaction mixture was concentrated and the residue was neutralized with 10% aqueous hydrochloric acid (10 mL) in 1,4-dioxane and extracted with ethyl acetate (2×30 mL). The combined organic layers were washed with brine (10 mL), dried over sodium sulphate and concentrated to afford 2-(3-chloro-4-(trifluoromethoxy)phenyl)-2,2-difluoroacetic acid and crude (800 mg, 2.75 mmol, 44% yield) as a brown semi solid which was used to next step without any purification

D. 2-(3-Chloro-4-(trifluoromethoxy)phenyl)-N-((2-(2,6-dioxopiperidin-3-yl)-1-oxoisoindolin-5-yl)methyl)-2,2-difluoroacetamide To a cold (0° C.) stirred solution of 3-(5-(aminomethyl)-1-oxoisoindolin-2-yl)piperidine-2,6-dione hydrochloride (250 mg, 0.809 mmol) and 2-(3-chloro-4-(trifluoromethoxy)phenyl)-2,2-difluoroacetic acid (234 mg, 0.970 mmol) in N,N-dimethylformamide (10 mL) was added N,N-diisopropylethylamine (0.4 mL, 2.42 mmol) followed by 1-[Bis(dimethylamino)methylene]-1H-1,2,3-triazolo[4,5-b]pyridinium 3-oxid hexafluorophosphate (614 mg, 1.61 mmol) and stirred at room temperature for 16 h. The reaction mixture was diluted with water (30 mL) and extracted with ethyl acetate (2×40 mL). The combined organic layers were washed with brine (20 mL), dried over sodium sulphate and concentrated dried under vacuum. The product was purified by Reveleris C-18 reversed phase column using 60% acetonitrile in aqueous formic acid (0.1%) to afford N-((2-

(2,6-dioxopiperidin-3-yl)-1-oxoisoindolin-5-yl)methyl)-2,2-difluoro-2-(2-(2-hydroxyethoxy)phenyl)acetamide (35 mg, 0.064 mmol, 8% yield) as an off-white solid. MS (ESI) m/z 546.26 [M+1]$^+$. $^1$H NMR (300 MHz, DMSO-d$_6$) δ 10.98 (s, 1H), 9.75 (br t, J=5.9 Hz, 1H), 7.92-7.90 (m, 1H), 7.82-7.64 (m, 3H), 7.47-7.34 (m, 2H), 5.10 (dd, J=13.2, 5.1 Hz, 1H), 4.51-4.24 (m, 4H), 2.99-2.84 (m, 1H), 2.67-2.55 (m, 1H), 2.45-2.25 (m, 1H), 2.05-1.93 (m, 1H).

Example 84

N-((2-(2,6-dioxopiperidin-3-yl)-1-oxoisoindolin-5-yl)methyl)-2,2-difluoro-2-(4-methoxy-2-(trifluoromethyl)phenyl)acetamide

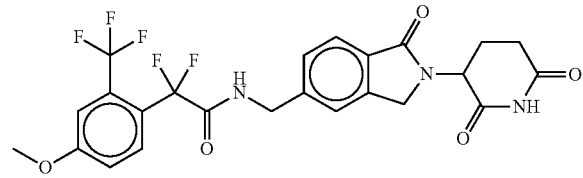

A. 1-Bromo-4-methoxy-2-(trifluoromethyl)benzene

To a stirred solution of 4-bromo-3-(trifluoromethyl)phenol (2 g, 8.29 mmol) in N,N-dimethyl formamide (20 mL) was added portion wise sodium hydride (398 mg, 16.59 mmol) at 0° C., and stirred for 30 min at room temperature. To this reaction mass was added methyl iodide (671 mg, 10.78 mmol) at 0° C. and stirred at room temperature for 1 h. The reaction mixture was quenched with water (50 mL) and extracted with ethyl acetate (2×200 mL). The combined organic layers were washed with water (2×100 mL), brine (100 mL), dried over sodium sulphate and concentrated. The resultant residue was purified by column chromatography (silica-gel 100-200) 100% hexane as a eluent to afford 1-bromo-4-methoxy-2-(trifluoromethyl)benzene (1.2 g, 4.72 mmol, 57% yield) as an off-white solid. MS (ESI) m/z 254.1 [M]$^+$.

B. 1-Iodo-4-methoxy-2-(trifluoromethyl)benzene

To a stirred solution of 1-bromo-4-methoxy-2-(trifluoromethyl)benzene (1 g, 3.93 mmol) in 1,4-dioxane (10 mL) was added sodium iodide (1.76 g, 11.79 mmol), copper iodide (150 mg, 0.786 mmol) followed by trans-N,N'-dimethylcyclohexane-1,2-diamine (168 mg, 1.18 mmol) at room temperature and stirred at 110° C. for 2 h in microwave. The reaction mixture was quenched with water (20 mL) and extracted with ethyl acetate (3×200 mL). The combined organic layers were washed with water (2×50 mL), brine (50 mL), dried over sodium sulphate and concentrated to afforde 1-iodo-4-methoxy-2-(trifluoromethyl)benzene (800 g, 2.65 mmol, 68% yield) as brown liquid. MS (ESI) m/z 302.0 [M]$^+$.

C. Ethyl 2,2-difluoro-2-(4-methoxy-2-(trifluoromethyl)phenyl)acetate

To a stirred solution of 1-iodo-4-methoxy-2-(trifluoromethyl)benzene (800 mg, 2.65 mmol) in dimethyl sulfoxide (20 mL) was added ethyl 2-iodo-2,2-difluoroacetate (0.62 mL, 3.97 mmol), copper (438 g, 6.89 mmol) and stirred for 16 h at room temperature. The reaction mixture was neutralized with aqueous saturated ammonium chloride solution and extracted with ethyl acetate (3×50 mL). The combined organic layers were washed with water (2×10 mL), brine (10 mL), dried over sodium sulphate and concentrated to afford ethyl 2,2-difluoro-2-(4-methoxy-2-(trifluoromethyl)phenyl)acetate (600 mg, 2.01 mmol, 76%) as a brown liquid. MS (ESI) m/z 298.1 [M]$^+$.

D. 2,2-Difluoro-2-(4-methoxy-2-(trifluoromethyl)phenyl)acetic acid

To a cold (0° C.) stirred solution of ethyl 2,2-difluoro-2-(4-methoxy-2-(trifluoromethyl)phenyl)acetate (600 mg, 2.01 mmol) in methanol/tetrahydrofuran/water (9 mL, 1:1:1) was added lithium hydroxide monohydrate (253 mg, 6.03 mmol) and stirred at room temperature for 4 h. The reaction mixture was concentrated and the residue was neutralized with 10% aqueous potassium bisulphate (10 mL) and extracted with ethyl acetate (2×30 mL). The combined organic layers were washed with brine (10 mL), dried over sodium sulphate and concentrated to afford 2,2-difluoro-2-(4-methoxy-2-(trifluoromethyl)phenyl)acetic acid (450 mg, 1.66 mmol, 83% yield) as a brown semi solid. MS (ESI) m/z 269.30 [M−1]$^+$.

E. N-((2-(2,6-dioxopiperidin-3-yl)-1-oxoisoindolin-5-yl)methyl)-2,2-difluoro-2-(4-methoxy-2-(trifluoromethyl)phenyl)acetamide To a cold (0° C.) stirred solution of 2,2-difluoro-2-(4-methoxy-2-(trifluoromethyl)phenyl)acetic acid (314 mg, 1.16 mmol) in pyridine (20 mL) was added phosphoryl chloride (0.7 mL, 2.91 mmol) dropwise and stirred at 0-5° C. for 30 min. To this, 3-(5-(aminomethyl)-1-oxoisoindolin-2-yl)piperidine-2,6-dione hydrochloride (300 mg, 0.97 mmol) was added and stirred at room temperature for 1 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 50-55% acetonitrile in aqueous formic acid (0.1%) to afford N-((2-(2,6-dioxopiperidin-3-yl)-1-oxoisoindolin-5-yl)methyl)-2,2-difluoro-2-(4-methoxy-2-(trifluoromethyl)phenyl)acetamide (35 mg, 0.07 mmol, 7% yield) as an off-white solid. MS (ESI) m/z 526.21 [M+1]$^+$. $^1$H NMR (300 MHz, DMSO-d$_6$) δ ppm 10.97 (br s, 1H), 9.59 (br t, J=5.87 Hz, 1H), 7.81-7.60 (m, 2H), 7.56-7.20 (m, 4H), 5.11 (br dd, J=13.39, 4.95 Hz, 1H), 4.56-4.14 (m, 4H), 3.89 (s, 3H), 3.02-2.85 (m, 1H), 2.67-2.55 (m, 1H), 2.46-2.30 (m, 1H), 2.06-1.94 (m, 1H).

Example 85

N-((2-(2,6-Dioxopiperidin-3-yl)-1-oxoisoindolin-5-yl)methyl)-2,2-difluoro-2-(2-(2-hydroxyethoxy)phenyl)acetamide

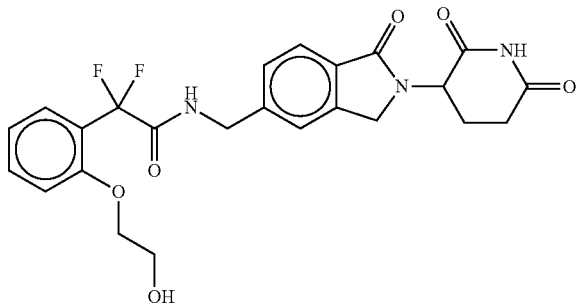

A. (2-Bromoethoxy)(tert-butyl)dimethylsilane

To a stirred solution of 2-bromoethanol (10 g, 80 mmol) in dichloromethane (100 mL) was added tert-butylchlorodimethylsilane (14.5 g, 96.77 mmol) and imidazole (10 g, 161.2 mmol) at 0° C. and stirred at room temperature for 16 h. The reaction mixture was quenched with aqueous sodium bicarbonate solution (40 mL) and extracted with ethyl acetate (3×50 mL). The combined organic layers were washed with water (2×10 mL), brine (10 mL), dried over sodium sulphate and concentrated to afford (2-bromoethoxy)(tert-butyl)dimethylsilane (8 g, 33.61 mmol, 42% yield) as colorless liquid.

B. Tert-butyl(2-(2-iodophenoxy)ethoxy)dimethylsilane

To a stirred solution of 2-iodophenol (3 g, 13.6 mmol) in N,N-dimethylformamide (20 mL) was added (2-bromoethoxy)(tert-butyl)dimethylsilane (3.89 g, 16.36 mmol), tert-butyl ammonium iodide (1 g 2.72 mmol) and potassium carbonate (4.69 g 34 mmol) at 0° C. and stirred at 80° C. for 16 h. The reaction mixture was quenched with water (40 mL) and extracted with ethyl acetate (3×50 mL). The combined organic layers were washed with water (2×10 mL), brine (10 mL), dried over sodium sulphate and concentrated to afford tert-butyl(2-(2-iodophenoxy)ethoxy)dimethylsilane (2.5 g, 6.613 mmol, 49% yield) as colorless liquid.

C. Ethyl 2,2-difluoro-2-(2-(2-hydroxyethoxy)phenyl)acetate

To a stirred solution of tert-butyl(2-(2-iodophenoxy)ethoxy)dimethylsilane (3 g, 7.936 mmol) in dimethyl sulfoxide (20 mL) was added ethyl 2-bromo-2,2-difluoroacetate (2.41 g 11.90 mmol), copper powder (1.3. g, 20.63 mmol) and stirred at 50° C. for 6 h. The reaction mixture was neutralized with aqueous saturated ammonium chloride solution and extracted with ethyl acetate (3×50 mL). The combined organic layers were washed with water (2×10 mL), brine (10 mL), dried over sodium sulphate and concentrated to afford ethyl 2,2-difluoro-2-(2-(2-hydroxyethoxy)phenyl)acetate (900 mg, 3.406 mmol, 45%) as a brown liquid.

D. 2,2-Difluoro-2-(2-(2-hydroxyethoxy)phenyl)acetic acid

To an ice cold solution of ethyl 2,2-difluoro-2-(2-(2-hydroxyethoxy)phenyl)acetate (1.2 g, 3.20 mmol) in ethanol/tetrahydrofuran/water mixture (15 mL, 1:1:1) was added lithium hydroxide monohydrate (404 mg, 9.62 mmol) and stirred at room temperature for 6 h. The reaction mixture was concentrated and the resultant residue was neutralized with 10% aqueous hydrochloric acid in 1,4-dioxane (10 mL) and extracted with ethyl acetate (2×30 mL). The combined organic layer was washed with brine (10 mL), dried over sodium sulphate and concentrated to afford 2,2-difluoro-2-(2-(2-hydroxyethoxy)phenyl)acetic acid (650 mg, 2.82 mmol, 65% yield) as a brown semi solid. $^1$H NMR (300 MHz, DMSO-$d_6$) δ 7.68 (d, J=7.2 Hz, 1H), 7.46 (dd, J=8.1 Hz, 7.8 Hz, 1H), 7.09 (dd, J=8.0, 7.8 Hz, 1H), 6.91 (d, J=8.4 Hz, 1H), 6.38 (brs, 1H), 4.12 (t, J=5.4 Hz, 2H), 3.99 (t, J=3.9 Hz, 2H).

E. N-((2-(2,6-Dioxopiperidin-3-yl)-1-oxoisoindolin-5-yl)methyl)-2,2-difluoro-2-(2-(2-hydroxyethoxy)phenyl)acetamide To an ice cold solution of 3-(5-(aminomethyl)-1-oxoisoindolin-2-yl)piperidine-2,6-dione hydrochloride (300 mg, 0.970 mmol) and 2,2-difluoro-2-(2-(2-hydroxyethoxy)phenyl)acetic acid (225 mg, 0.970 mmol) in N,N-dimethylformamide (10 mL) was added N,N-diisopropylethylamine (0.5 mL, 2.91 mmol) followed by 1-[Bis(dimethylamino)methylene]-1H-1,2,3-triazolo[4,5-b]pyridinium 3-oxid hexafluorophosphate (737 mg, 1.94 mmol) and stirred at room temperature for 12 h. The reaction mixture was diluted with water (30 mL) and extracted with ethyl acetate (2×40 mL). The combined organic layers were washed with brine (20 mL), dried over sodium sulphate and concentrated dried under vacuum. The product was purified by Reveleris C-18 reversed phase column (60% acetonitrile in 0.1% aqueous formic acid) to afford N-((2-(2,6-dioxopiperidin-3-yl)-1-oxoisoindolin-5-yl)methyl)-2,2-difluoro-2-(2-(2-hydroxyethoxy)phenyl)acetamide (40 mg, 0.082 mmol, 8% yield) as an off-white solid. MS (ESI) m/z 488.12. $^1$H NMR (300 MHz, DMSO-$d_6$): δ=10.98 (s, 1H), 9.29 (t, J=5.7 Hz, 1H), 7.70 (d, J=7.7 Hz, 1H), 7.60-7.39 (m, 4H), 7.16 (br d, J=8.1 Hz, 1H), 7.10-7.01 (m, 1H), 5.11 (dd, J=13.0, 5.0 Hz, 1H), 4.72 (t, J=5.5 Hz, 1H), 4.51-4.27 (m, 4H), 3.98 (t, J=5.3 Hz, 1H), 3.60 (q, J=5.3 Hz, 1H), 3.00-2.82 (m, 1H), 2.63-2.54 (m, 1H), 2.45-2.32 (m, 1H), 2.06-1.94 (m, 1H).

Example 86

2-(4-Chloro-2-ethoxyphenyl)-N-((2-(2,6-dioxopiperidin-3-yl)-1-oxoisoindolin-5-yl)methyl)-2,2-difluoroacetamide

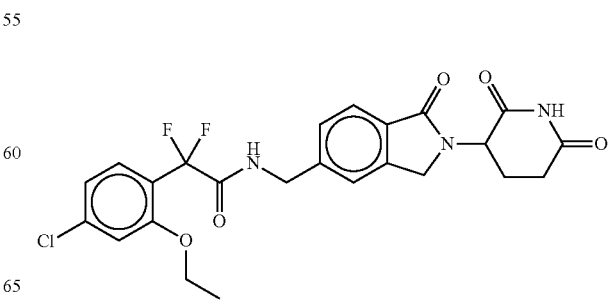

A. 1-(4-Chloro-2-ethoxyphenyl)ethanone

To a stirred solution of 1-(4-chloro-2-hydroxyphenyl)ethanone (2 g, 11.76 mmol) in N,N-dimethylformamide (15 mL) was added ethyl iodide (2.8 mL, 29.4 mmol) followed by potassium carbonate (4.87 g, 35.29 mmol) and stirred at 90° C. for 16 h. The reaction mixture was diluted with ice water (20 mL) and extracted with ethyl acetate (3×20 mL). The combined organic layers were washed with water (20 mL), brine (20 mL), dried over sodium sulfate, filtered and concentrated to afford 1-(4-chloro-2-ethoxyphenyl)ethanone (1.7 g, 8.58 mmol, 73% yield) as a colorless liquid. MS (ESI) m/z 199.41 [M+1]$^+$.

B. Ethyl 2-(4-chloro-2-ethoxyphenyl)-2-oxoacetate

To a stirred solution of 1-(4-chloro-2-ethoxyphenyl)ethanone (1.7 g, 8.58 mmol) in pyridine (10 mL) was added selenium dioxide (2.38 g, 21.46 mmol) at room temperature and stirred at 100° C. for 16 h. The reaction mixture was filtered through a Celite pad and washed with dichloromethane (15 mL). Ethyl chloroformate (3.4 mL) was added to the filtrate at 0° C. and stirred at room temperature for 4 h. The reaction mixture was quenched with ice water and extracted with dichloromethane (3×20 mL). The combined organic layers were washed with 1N hydrochloride solution (20 mL), brine (20 mL), dried over sodium sulfate, filtered and concentrated to afford ethyl 2-(4-chloro-2-ethoxyphenyl)-2-oxoacetate (1.2 g, 4.68 mmol, 54% yield) as a colorless liquid. MS (ESI) m/z 256.1 [M]$^+$.

C. Ethyl 2-(4-chloro-2-ethoxyphenyl)-2,2-difluoroacetate

Ethyl 2-(4-chloro-2-ethoxyphenyl)-2-oxoacetate (1 g, 3.9 mmol) was added into diethylamino sulfur trifluoride (1.89 g, 11.72 mmol) at 0° C. and stirred at room temperature for 16 h. The reaction mixture was quenched with aqueous sodium bicarbonate solution and extracted with ethyl acetate (3×15 mL). The combined organic layers were washed with brine (15 mL), dried over sodium sulfate, filtered and concentrated. Obtained crude was purified by flash chromatography (100-200 silica gel, 10% ethyl acetate in pet ether) to afford ethyl 2-(4-chloro-2-ethoxyphenyl)-2,2-difluoroacetate (570 mg, 2.05 mmol, 52% yield) as a colourless liquid. $^1$H NMR (400 MHz, CDCl$_3$) δ 7.56 (d, J=8.4 Hz, 1H), 7.03 (dd, J=8.4, 1.6 Hz, 1H), 6.91 (s, 1H), 4.31 (q, J=7.6 Hz, 2H), 4.05 (q, J=6.8 Hz, 2H), 1.37 (t, J=7.2 Hz, 3H), 1.31 (t, J=7.2 Hz, 3H).

D. 2-(4-Chloro-2-ethoxyphenyl)-2,2-difluoroacetic acid

To a stirred solution of ethyl 2-(4-chloro-2-ethoxyphenyl)-2,2-difluoroacetate (470 mg, 1.69 mmol) in tetrahydrofuran:methanol:water (12 mL, 1:1:1) was added lithium hydroxide monohydrate (213 mg, 5.07 mmol) and stirred at room temperature for 16 h. The volatiles were removed under reduced pressure and obtained crude was dissolved in water (10 mL) and washed with ethyl acetate (2×10 mL). Aqueous layer was acidified with 1N hydrochloride aqueous solution and extracted with ethyl acetate (3×10 mL). The combined organic layers were washed with brine (10 mL), dried over sodium sulfate, filtered and solvent was concentrated to afford 2-(4-chloro-2-ethoxyphenyl)-2,2-difluoroacetic acid (260 mg, 1.04 mmol, 61% yield) as semi-solid compound. $^1$H NMR (300 MHz, CDCl$_3$) δ 7.58 (d, J=8.7 Hz, 1H), 7.05 (d, J=8.1 Hz, 1H), 6.94 (s, 1H), 4.09 (q, J=7.2 Hz, 2H), 1.39 (t, J=6.9 Hz, 3H).

E. 2-(4-Chloro-2-ethoxyphenyl)-N-((2-(2,6-dioxopiperidin-3-yl)-1-oxoisoindolin-5-yl)methyl)-2,2-difluoroacetamide To an ice cold solution of 2-(4 chloro-2-ethoxyphenyl)-2,2-difluoroacetic acid (178 mg, 0.71 mmol) in pyridine (9 mL) was added phosphorus oxychloride (0.18 mL, 1.94 mmol) in drop wise and stirred at 0-5° C. for 1 h. Then, 3-(5-(aminomethyl)-1-oxoisoindolin-2-yl)piperidine-2,6-dione hydrochloride (200 mg, 0.64 mmol) was added into the reaction mixture and stirred at room temperature for 1 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to give 2-(4-chloro-2-ethoxyphenyl)-N-((2-(2,6-dioxopiperidin-3-yl)-1-oxoisoindolin-5-yl)methyl)-2,2-difluoroacetamide (58 mg, 0.11 mmol, 18% yield) as white solid. MS (ESI) m/z 506.1 [M+1]$^+$. $^1$H NMR (300 MHz, DMSO-d$_6$) δ 10.98 (s, 1H), 9.38 (t, J=5.6 Hz, 1H), 7.71 (d, J=7.8 Hz, 1H), 7.56 (d, J=8.1 Hz, 1H), 7.50 (s, 1H), 7.44 (d, J=7.5 Hz, 1H), 7.22 (s, 1H), 7.12 (dd, J=7.8, 1.8 Hz, 1H), 5.11 (dd, J=13.2, 5.1 Hz, 1H), 4.46 (d, J=17.2 Hz, 1H), 4.46 (d, J=5.7 Hz, 2H), 4.31 (d, J=17.4, 1H), 4.03 (q, J=6.9 Hz, 2H), 2.98-2.85 (m, 1H), 2.67-2.55 (m, 1H), 2.43-2.30 (m, 1H), 2.04-1.93 (m, 1H), 1.11 (t, J=6.9 Hz, 3H).

Example 87

N-((2-(2,6-Dioxopiperidin-3-yl)-1-oxoisoindolin-5-yl)methyl)-2,2-difluoro-2-(2-hydroxyphenyl)acetamide

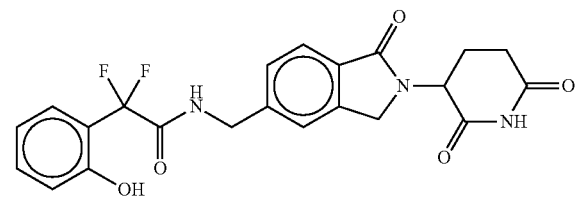

A. 1-Iodo-2-(methoxymethoxy)benzene

To a stirred solution of 2-iodophenol (3 g, 13.63 mmol) in dichloro methane (30 mL) was added diisopropyl ethyl amine (7.2 mL, 40.89 mmol) followed by chloro methyl methyl ether (1.63 g, 20.45 mmol) at 0° C. and stirred at room temperature for 16 h. The reaction mixture was quenched with ice water (30 mL) and extracted with dichloro methane (3×30 mL). The combined organic layers were washed with water (30 mL), brine (30 mL), dried over sodium sulfate, filtered and concentrated. The resultant crude product was purified by silica gel column chromatography (20% ethyl acetate in pet ether) to afford 1-iodo-2-(methoxymethoxy)benzene (2.5 g, 9.61 mmol, 72% yield) as a brown liquid. $^1$H NMR (400 MHz, CDCl$_3$) δ 7.78 (dd, J=8.0, 1.6 Hz, 1H), 7.28 (ddd, J=8.5, 7.4, 1.6 Hz, 1H), 7.07 (dd, J=8.4, 1.6 Hz, 1H), 6.76 (ddd, J=8.8, 7.2, 0.8 Hz, 1H), 5.24 (s, 2H), 3.52 (s, 3H).

B. Ethyl 2,2-difluoro-2-(2-(methoxymethoxy)phenyl)acetate

To a stirred solution of 1-iodo-2-(methoxymethoxy)benzene (3 g, 8.24 mmol) in dimethylsulfoxide (11.5 mL) was added ethyl 2-bromo-2,2-difluoroacetate (2.67 g, 13.18 mmol) followed by copper powder (1.31 g, 20.6 mmol) at 0° C. and stirred at 60° C. for 5 h. The reaction mixture was quenched with ice water (30 mL) and filtered through a Celite pad. The filtrate was extracted with ethyl acetate (3×30 mL) and the combined organic layers were washed with water (30 mL), brine (30 mL), dried over sodium sulfate, filtered and concentrated. The obtained crude product was purified by flash chromatography (20% ethyl acetate in pet ether to afford ethyl 2,2-difluoro-2-(2-(methoxymethoxy)phenyl)acetate (1.3 g, 5.0 mmol, 62% yield) as a colorless liquid. MS (ESI) m/z 260.2 [M]$^+$.

C. 2,2-Difluoro-2-(2-(methoxymethoxy)phenyl)acetic acid

To a stirred solution of ethyl 2,2-difluoro-2-(2-(methoxymethoxy)phenyl)acetate (2 g, 7.69 mmol) in mixture of methanol:tetrahydrofuran:water (20 mL, 1:1:1) at 0° C. was added lithium hydroxide monohydrate (970 mg, 23.07 mmol) and stirred at room temperature for 4 h. The volatiles were removed under reduced pressure and the obtained crude was diluted with water (20 mL) and washed with ethyl acetate (2×15 mL). Aqueous layer was acidified with aqueous potassium bisulfate solution and extracted with ethyl acetate (3×20 mL). The combined organic layers were washed with brine (20 mL), dried over sodium sulfate, filtered and concentrated to afford 2,2-difluoro-2-(2-(methoxymethoxy)phenyl)acetic acid (1.2 g, 4.87 mmol, 63% yield) as a brown semi solid. MS (ESI) m/z 246.3 [M]$^+$.

D. N-((2-(2,6-Dioxopiperidin-3-yl)-1-oxoisoindolin-5-yl)methyl)-2,2-difluoro-2-(2-hydroxyphenyl)acetamide To an ice cold solution of 2,2-difluoro-2-(2-(methoxymethoxy)phenyl)acetic acid (258 mg, 1.16 mmol) in pyridine (9 mL) was added phosphorus oxychloride (0.27 mL, 2.9 mmol) drop wise and stirred at 0-5° C. for 1 h. Then, 3-(5-(aminomethyl)-1-oxoisoindolin-2-yl)piperidine-2,6-dione hydrochloride (300 mg, 0.97 mmol) was added into the reaction mixture and stirred at room temperature for 1 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl)methyl)-2,2-difluoro-2-(2-hydroxyphenyl) acetamide (33 mg, 0.07 mmol, 8% yield) as white solid. MS (ESI) m/z 444.35 [M+1]$^+$. $^1$H NMR (300 MHz, DMSO-d$_6$) δ 11.00 (s, 1H), 10.24 (bs, 1H), 9.38 (bs, 1H), 7.68 (d, J=7.8 Hz, 1H), 7.51 (s, 1H), 7.47-7.44 (m, 2H), 7.34 (dd, J=7.8, 7.5 Hz, 1H), 6.91-6.87 (m, 2H), 5.11 (dd, J=13.5, 5.1 Hz, 1H), 4.48 (d, J=4.5 Hz, 2H), 4.46 (d, J=18.0 Hz, 1H), 4.32 (d, J=17.4 Hz, 1H), 2.96-2.86 (m, 1H), 2.58-2.49 (m, 1H), 2.42-2.27 (m, 1H), 2.07-1.98 (m, 1H).

Example 88

N-((2-(2,6-Dioxopiperidin-3-yl)-1-oxoisoindolin-5-yl)methyl)-2,2-difluoro-2-(2-(methylamino)phenyl) acetamide

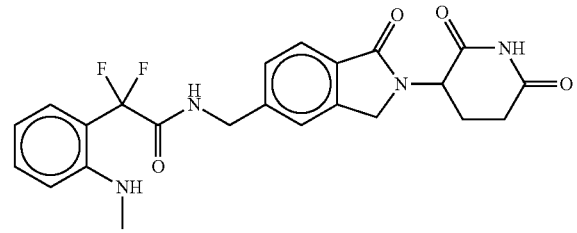

A. Benzyl 2-iodophenylcarbamate

To a stirred solution of 2-iodoaniline (3 g, 13.69 mmol) in 4N sodium aqueous hydroxide (3 mL), water (10 mL) was added benzyl chloroformate (2.79 g, 16.43 mmol) at 0° C. and stirred at room temperature for 3 h. The reaction mixture was diluted with water (30 mL) and extracted with ethyl acetate (3×30 mL). The combined organic layers were washed with water (30 mL), brine (30 mL), dried over sodium sulfate and concentrated to afford benzyl 2-iodophenylcarbamate (3 g, 8.49 mmol, 62% yield) as a colorless liquid.
$^1$H NMR (400 MHz, CDCl$_3$) δ 8.08 (d, J=8.8 Hz, 1H), 7.76 (dd, J=11.8 Hz, 1.8 Hz, 1H), 7.48-7.32 (m, 6H), 7.02 (brs, 1H), 6.79 (ddd, J=8.0, 7.7, 1.8 Hz, 1H), 5.23 (s, 2H).

B. Benzyl 2-iodophenyl(methyl)carbamate

To a stirred solution of benzyl 2-iodophenylcarbamate (1.5 g, 4.24 mmol) in N,N-dimethylformamide (15 mL) was added cesium carbonate (4.13 g, 12.72 mmol) followed by iodo methane (0.9 g, 6.37 mmol) at 0° C. and stirred at 60° C. for 5 h. The reaction mixture was diluted with water (25 mL) and extracted with ethyl acetate (3×25 mL). The combined organic layers were washed with water (25 mL), brine (25 mL), dried over sodium sulfate, filtered and concentrated. The obtained crude was purified by silica gel column chromatography using 30% ethyl acetate in pet ether to afford benzyl 2-iodophenyl(methyl)carbamate (1.2 g, 3.26 mmol, 80% yield) as a colorless liquid. MS (ESI) m/z 368.01 [M+1]$^+$

C. Ethyl 2-(2-((benzyloxycarbonyl)(methyl)amino) phenyl)-2,2-difluoroacetate To a stirred solution of benzyl 2-iodophenyl(methyl) carbamate (1 g, 2.72 mmol) in dimethylsulfoxide (20 mL) was added ethyl 2-bromo-2,2-difluoroacetate (0.83 g, 4.08 mmol) followed by copper (0.45 g, 7.08 mmol) at 0° C. and stirred at 60° C. for 5 h. The reaction mixture was quenched with ice water and filtered through a Celite pad. The filtrate was extracted with ethyl acetate (3×15 mL) and the combined organic layers were washed with water (15 mL), brine (15 mL), dried over sodium sulfate, filtered and concentrated. The obtained crude was purified by flash chromatography (20% ethyl acetate in pet ether to afford ethyl 2-(2-((benzyloxycarbonyl)(methyl)amino)phenyl)-2,2-difluoroacetate (0.72 g, 1.98 mmol, 73% yield) as a colorless liquid. MS (ESI) m/z 363.1 [M]$^+$.

D. 2-(2-((Benzyloxycarbonyl)(methyl)amino)phenyl)-2,2-difluoroacetic acid

To a cold (0° C.) stirred solution of ethyl 2-(2-((benzyloxycarbonyl)(methyl)amino)phenyl)-2,2-difluoroacetate (700 mg, 1.9 mmol) in mixture of methanol:tetrahydrofuran:water mixture (15 mL, 1:1:1) was added lithium hydroxide monohydrate (242 mg, 5.78 mmol) and stirred at room temperature for 4 h. The volatiles were removed under reduced pressure and the obtained residue was dissolved in water (10 mL), washed with ethyl acetate (2×10 mL). Aqueous layer was acidified with aqueous potassium bisulfate solution and extracted with ethyl acetate (3×15 mL). The combined organic layers were washed with brine (15 mL), dried over sodium sulfate, filtered and concentrated to afford 2-(2-((benzyloxycarbonyl)(methyl)amino)phenyl)-2,2-difluoroacetic acid (620 mg, 1.85 mmol, 97% yield) as a semi solid. MS (ESI) m/z 336.4 [M+1]$^+$.

E. Benzyl 2-(2-((2-(2,6-dioxopiperidin-3-yl)-1-oxoisoindolin-5-yl)methylamino)-1,1-difluoro-2-oxoethyl)phenyl(methyl)carbamate To an ice cold solution of 2-(2-((benzyloxycarbonyl)(methyl)amino)phenyl)-2,2-difluoroacetic acid (325 mg, 0.97 mmol) in pyridine (9 mL) was added phosphorus oxychloride (0.27 mL, 2.9 mmol) in drop wise and stirred at 0-5° C. for 1 h. Then, 3-(5-(aminomethyl)-1-oxoisoindolin-2-yl)piperidine-2,6-dione hydrochloride (300 mg, 0.97 mmol) was added into the reaction mixture and stirred at room temperature for 2 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to afford benzyl 2-(2-((2-(2,6-dioxopiperidin-3-yl)-1-oxoisoindolin-5-yl)methylamino)-1,1-difluoro-2-oxoethyl)phenyl(methyl)carbamate (150 mg, 0.25 mmol, 26% yield) as white solid. MS (ESI) m/z 591.62 [M+1]$^+$.

F. N-((2-(2,6-Dioxopiperidin-3-yl)-1-oxoisoindolin-5-yl)methyl)-2,2-difluoro-2-(2-(methylamino)phenyl)acetamide To a stirred solution of benzyl 2-(2-((2-(2,6-dioxopiperidin-3-yl)-1-oxoisoindolin-5-yl)methylamino)-1,1-difluoro-2-oxoethyl)phenyl(methyl)carbamate (0.1 g, 0.169 mmol) in methanol (15 mL) was added a slurry of 10% palladium hydroxide (10 mg) in methanol under nitrogen stream and stirred under 60 psi hydrogen pressure at room temperature for 6 h. The hydrogen atmosphere was evacuated and reaction mixture was filtered through a Celite pad and the filtrate was concentrated. The resultant residue was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl)methyl)-2,2-difluoro-2-(2-(methyl amino)phenyl)acetamide (62 mg, 0.13 mmol, 80% yield) as a white solid. MS (ESI) m/z 457.23 [M+H]$^+$. $^1$H NMR (300 MHz, DMSO-d$_6$) δ 10.98 (s, 1H), 9.56 (t, J=6.0 Hz, 1H), 7.67 (d, J=8.7 Hz, 1H), 7.42 (s, 1H), 7.39-7.28 (m, 3H), 6.70-6.65 (m, 2H), 5.43 (q, J=4.2 Hz, 1H), 5.10 (dd, J=13.5, 5.1 Hz, 1H), 4.47 (d, J=6.0 Hz, 2H), 4.42 (d, J=17.9 Hz, 1H), 4.28 (d, J=17.1 Hz, 1H), 2.91-2.85 (m, 1H), 2.74 (d, J=4.8 Hz, 3H), 2.62-2.50 (m, 1H), 2.43-2.34 (m, 1H), 2.01-1.99 (m, 1H).

Example 89

N-((2-(2,6-Dioxopiperidin-3-yl)-1-oxoisoindolin-5-yl)methyl)-2,2-difluoro-2-(4-isopropoxy-2-(trifluoromethyl)phenyl)acetamide

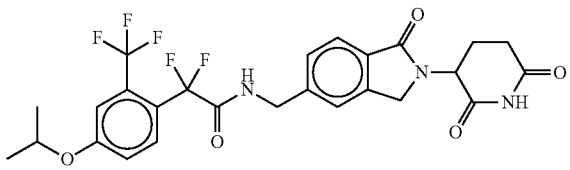

A. 1-Bromo-4-isopropoxy-2-(trifluoromethyl)benzene

To a stirred solution of 4-bromo-3-(trifluoromethyl)phenol (5 g, 20.83 mmol) in N,N-dimethylformamide (20 mL) was added potassium carbonate (8.6 g, 62.49 mmol) followed by isopropyl iodide (3.1 mL, 31.24 mmol) and stirred at 80° C. for 4 h. The reaction mixture was filtered and water (50 mL) was added and extracted with ethyl acetate (2×60 mL). The combined organic layers were washed with brine (50 mL), dried over sodium sulphate and concentrated. The resultant residue was purified by column chromatography (100-200 silica) using 0-10% ethyl acetate in hexanes to afford 1-bromo-4-isopropoxy-2-(trifluoromethyl)benzene (3.5 g, 12.41 mmol, 59% yield). LCMS (ESI) m/z 284.38 [M+2]$^+$.

B. 1-Iodo-4-isopropoxy-2-(trifluoromethyl)benzene

To a stirred solution of 1-bromo-4-isopropoxy-2-(trifluoromethyl)benzene (3.5 g, 12.41 mmol) in 1,4-dioxane (30 mL) was added sodium iodide (5.58 g, 37.23 mmol), copper iodide (471 mg, 2.48 mmol), trans-N,N'-dimethylcyclohexane-1,2-diamine (529 mg, 3.72 mmol) at room temperature and stirred at 110° C. for 16 h in sealed tube. The reaction mixture was quenched with water (20 mL) and extracted with ethyl acetate (3×300 mL). The combined organic layers were washed with water (2×50 mL), brine (50 mL), dried over sodium sulphate and concentrated to afford 1-iodo-4-isopropoxy-2-(trifluoromethyl)benzene (3 g, 9.09 mmol, 73% yield) as brown liquid. MS (ESI) m/z 331.0 [M]$^+$.

C. Ethyl 2,2-difluoro-2-(2-methyl-4-(trifluoromethoxy)phenyl)acetate

To a stirred solution of 1-iodo-4-isopropoxy-2-(trifluoromethyl)benzene (3 g, 9.09 mmol) in dimethyl sulfoxide (25 mL) was added copper (1.5 g, 23.63 mmol) and ethyl 2-ido-2,2-difluoroacetate (2.005 mL, 13.63 mmol) at room temperature and stirred at 55° C. for 2 h. The reaction mixture was neutralized with aqueous saturated ammonium chloride (50 mL) solution and extracted with ethyl acetate

193

(2×100 mL). The combined organic layers were washed with water (2×100 mL), brine (100 mL), dried over sodium sulphate and concentrated to afford ethyl 2,2-difluoro-2-(4-isopropoxy-2-(trifluoromethyl)phenyl)acetate (2.5 g, 7.66 mmol, 84%). GCMS (ESI) m/z 326.2.

D. 2,2-Difluoro-2-(4-isopropoxy-2-(trifluoromethyl)phenyl)acetic acid

To a cold (0° C.) stirred solution of ethyl ethyl 2,2-difluoro-2-(4-isopropoxy-2-(trifluoromethyl)phenyl)acetate (2.5 g, 7.66 mmol) in tetrahydrofuran:Methanol:water (30 mL, 1:1:1) was added lithium hydroxide (1.6 g, 38.34 mmol) and stirred at room temperature for 6 h. The reaction mixture was concentrated and the residue was neutralized with 10% aqueous hydrochloric acid (10 mL) and extracted with ethyl acetate (2×20 mL). The combined organic layer was washed with brine (20 mL), dried over sodium sulphate and concentrated to afford 2,2-difluoro-2-(4-isopropoxy-2-(trifluoromethyl)phenyl)acetic acid (1.8 g, 6.04 mmol, 78% yield) as a brown liquid. The crude was taken to the next step without further purification.

E. N-((2-(2,6-dioxopiperidin-3-yl)-1-oxoisoindolin-5-yl)methyl)-2,2-difluoro-2-(4-isopropoxy-2-(trifluoromethyl)phenyl)acetamide To a cold (0° C.) stirred solution of 2,2-difluoro-2-(4-isopropoxy-2-(trifluoromethyl)phenyl)acetic acid (380 mg, 1.165 mmol) in pyridine was added POCl$_3$ (0.27 mL, 2.91 mmol) dropwise and stirred at 0-5° C. for 1 h and then added 3-(5-(aminomethyl)-1-oxoisoindolin-2-yl)piperidine-2,6-dione hydrochloride (300 mg, 0.968 mmol) and continued stirring at room temperature for 30 min. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The resultant residue was purified by Reveleris C-18 reversed phase column chromatography using 40-60% acetonitrile in aqueous formic acid (0.1%) to give N-((2-(2,6-dioxopiperidin-3-yl)-1-oxoisoindolin-5-yl)methyl)-2,2-difluoro-2-(4-isopropoxy-2-(trifluoromethyl)phenyl)acetamide (48 mg, 0.086 mmol, 10% yield) as an off white solid. MS (ESI) m/z 554.03 [M+1]$^+$. $^1$H NMR (300 MHz, DMSO-d$_6$) δ 10.99 (s, 1H), 9.58 (t, J=5.6 Hz, 1H), 7.73-7.64 (m, 2H), 7.47 (s, 1H), 7.41 (d, J=7.6 Hz, 1H), 7.36 (d, J=8.8 Hz, 1H), 7.32-7.28 (m, 1H), 5.11 (dd, J=13.2, 5.1 Hz, 1H), 5.00-4.25 (m, 4H), 3.00-2.85 (m, 1H), 2.69-2.55 (m, 1H), 2.44-2.35 (m, J=2.0 Hz, 1H), 2.05-1.95 (m, 1H), 1.35-1.25 (m, 6H).

Example 90

N-((2-(2,6-Dioxopiperidin-3-yl)-1-oxoisoindolin-5-yl)methyl)-2,2-difluoro-2-(4-methylcyclohexyl)acetamide

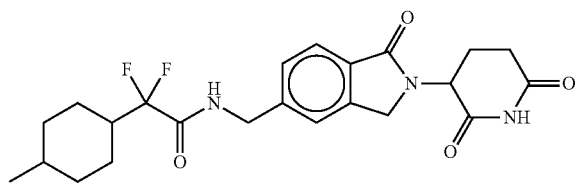

194

A. Ethyl 2,2-difluoro-2-(1-hydroxy-4-methylcyclohexyl)acetate

To a stirred solution of 4-methylcyclohexanone (1 g, 8.92 mmol) in tetrahydrofuran (20 mL) was added catalytic amount of anhydrous cerium(III) chloride (0.22 g, 0.89 mmol), followed by activated zinc dust (0.75 g, 11.6 mmol) and ethyl 2-bromo-2,2-difluoroacetate (1.13 mL, 11.6 mmol) at 0° C. and stirred at room temperature for 16 h. The reaction mixture was diluted with water (20 mL) and extracted with ethyl acetate (3×15 mL). The combined organic layers were washed with water (15 mL), brine (15 mL), dried over sodium sulfate, filtered and concentrated. The obtained crude was purified by silica gel column chromatography (30% ethyl acetate in pet ether) to afford ethyl 2,2-difluoro-2-(1-hydroxy-4-methylcyclohexyl)acetate (0.9 g, 3.81 mmol, 41% yield) as a colorless liquid. $^1$H NMR (400 MHz, DMSO-d$_6$) δ 5.33 (d, J=13.2 Hz, 1H), 4.27 (q, J=7.2 Hz, 2H), 2.37 (dt, J=13.3, 7.8 Hz, 1H), 2.18-2.13 (m, 1H), 1.94-1.86 (m, 1H), 1.78-1.70 (m, 4H), 1.48-1.39 (m, 2H), 1.26 (t, J=7.3 Hz, 3H), 0.91 (dt, J=18.8, 5.6 Hz, 3H).

B. Ethyl 2,2-difluoro-2-(4-methylcyclohex-1-enyl)acetate

To a stirred solution of ethyl 2,2-difluoro-2-(1-hydroxy-4-methylcyclohexyl)acetate (1.8 g, 7.62 mmol) in pyridine (18 mL), was added thionyl chloride (9 mL, 76.27 mmol) at 0° C. and stirred at room temperature for 16 h. The reaction mixture was diluted with water (20 mL) and basified with aqueous sodium bicarbonate solution and extracted with ethyl acetate (3×20 mL). The combined organic layers were washed with water (20 mL), brine (20 mL), dried over sodium sulfate, filtered and concentrated. The obtained crude product was purified by silica gel column chromatography using 20% ethyl acetate in pet ether to afford ethyl 2,2-difluoro-2-(4-methylcyclohex-1-enyl)acetate (1 g, 4.23 mmol, 62% yield) as a colorless liquid. MS (ESI) m/z 218.2 [M]$^+$.

C. Ethyl 2,2-difluoro-2-(4-methylcyclohexyl)acetate

To a stirred solution of ethyl 2,2-difluoro-2-(4-methylcyclohex-1-enyl)acetate (700 mg, 3.21 mmol) in ethyl acetate (15 mL) was added a slurry of 10% palladium hydroxide (200 mg) in ethyl acetate under nitrogen stream and stirred under hydrogen balloon pressure at room temperature for 4 h. The hydrogen atmosphere was evacuated and reaction mixture was filtered through a Celite pad, filtrate was concentrated to afford ethyl 2,2-difluoro-2-(4-methylcyclohexyl)acetate (500 mg, 1.3 mmol, 37% yield) as a colorless liquid. MS (ESI) m/z 220.2 [M]$^+$.

D. 2,2-Difluoro-2-(4-methylcyclohexyl)acetic acid

To a stirred solution of ethyl 2,2-difluoro-2-(4-methylcyclohexyl)acetate (500 mg, 2.27 mmol) in mixture of tetrahydrofuran:methanol:water (15 mL, 1:1:1) was added lithium hydroxide monohydrate (286 mg, 6.81 mmol) and stirred at room temperature for 4 h. The volatiles were removed under reduced pressure and the obtained residue was dissolved in water (10 mL) and washed with ethyl acetate (2×10 mL). Aqueous layer was acidified with 1N hydrochloride and extracted with ethyl acetate (3×10 mL). The combined organic layers were washed with brine (10 mL), dried over sodium sulfate, filtered and solvent was concentrated to afford 2,2-difluoro-2-(4-methylcyclohexyl) acetic acid (280 mg, 1.45 mmol, 64% yield) as semi-solid compound. $^1$H NMR (300 MHz, CDCl$_3$) δ 8.26 (brs, 1H), 2.04-2.02 (m, 1H), 1.85-1.78 (m, 3H), 1.60-1.52 (m, 2H), 1.36-1.24 (m, 2H), 1.01-0.87 (m, 2H), 0.90 (d, J=6.3 Hz, 3H).

E. N-((2-(2,6-Dioxopiperidin-3-yl)-1-oxoisoindolin-5-yl)methyl)-2,2-difluoro-2-(4-methylcyclohexyl) acetamide To an ice cold solution of 2,2-difluoro-2-(4-methylcyclohexyl)acetic acid (186 mg, 0.97 mmol) in pyridine (9 mL) was added phosphorus oxychloride (0.27 mL, 2.9 mmol) drop wise and stirred at 0-5° C. for 1 h. Then, 3-(5-(aminomethyl)-1-oxoisoindolin-2-yl)piperidine-2,6-dione hydrochloride (300 mg, 0.97 mmol) was added into the reaction mixture and stirred at room temperature for 2 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl)methyl)-2,2-difluoro-2-(4-methylcyclohexyl)acetamide (45 mg, 0.1 mmol, 10% yield) as white solid. MS (ESI) m/z 448.19 [M+1]$^+$. $^1$H NMR (300 MHz, DMSO-d$_6$) δ 10.98 (s, 1H), 9.35 (t, J=6.0 Hz, 1H), 7.70 (d, J=7.5 Hz, 1H), 7.47 (s, 1H), 7.41 (d, J=8.1 Hz, 1H), 5.11 (dd, J=13.2, 5.4 Hz, 1H), 4.45 (d, J=16.5 Hz, 1H), 4.44 (d, J=6.6 Hz, 2H), 4.31 (d, J=17.4 Hz, 1H), 2.92-2.87 (m, 1H), 2.63-2.57 (m, 1H), 2.41-2.36 (m, 1H), 2.02-1.98 (m, 2H), 1.68-1.65 (m, 3H), 1.48-1.42 (m, 3H), 1.24-1.15 (m, 2H), 0.99-0.86 (m, 1H), 0.87 (dd, J=6.9, 6.3 Hz, 3H).

Example 91

N-((2-(2,6-Dioxopiperidin-3-yl)-1-oxoisoindolin-5-yl)methyl)-2,2-difluoro-2-(3-(2-isopropoxyethoxy) phenyl)acetamide

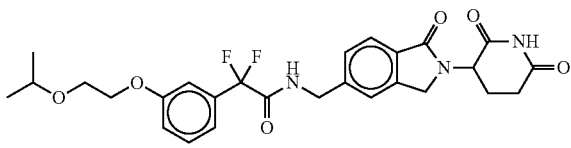

A. Ethyl 2,2-difluoro-2-(3-(2-isopropoxyethoxy) phenyl)acetate

To a stirred solution of ethyl 2,2-difluoro-2-(3-hydroxyphenyl)acetate (200 mg, 0.92 mmol) in tetrahydrofuran (10 mL) was added diisopropyl azodicarboxylate (373 mg, 1.85 mmol) followed by triphenylphosphine (485 mg, 1.85 mmol) and 2-isopropoxyethanol (96.2 mg, 0.92 mmol) at 0° C. and stirred at room temperature for 16 h. The reaction mixture was quenched with ice water and extracted with ethyl acetate (3×10 mL). The combined organic layers were washed with water (10 mL), brine (10 mL), dried over sodium sulfate, filtered and concentrated. The obtained crude was purified by flash chromatography (20% ethyl acetate in pet ether) to afford ethyl 2,2-difluoro-2-(3-(2-isopropoxyethoxy)phenyl)acetate (100 mg, 0.33 mmol, 36% yield) as a colorless liquid. GCMS (ESI) m/z 302.6 [M]$^+$.

B. 2,2-Difluoro-2-(3-(2-isopropoxyethoxy)phenyl) acetic acid

To an ice cold stirred solution of ethyl 2,2-difluoro-2-(3-(2-isopropoxy ethoxy)phenyl)acetate (210 mg, 0.69 mmol) in mixture of methanol:tetrahydrofuran:water (10 mL, 1:1:1) was added lithium hydroxide monohydrate (87 mg, 2.086 mmol) and stirred at room temperature for 4 h. The volatiles were removed under reduced pressure and the obtained residue was dissolved in water (10 mL), washed with ethyl acetate (2×6 mL). Aqueous layer was acidified with aqueous potassium bisulfate solution and extracted with ethyl acetate (3×10 mL). The combined organic layers were washed with brine (10 mL), dried over sodium sulfate, filtered and concentrated to afford 2,2-difluoro-2-(3-(2-isopropoxyethoxy)phenyl)acetic acid (180 mg, 0.65 mmol, 95% yield) as a semi solid. $^1$H NMR (300 MHz, CDCl$_3$) δ 7.29 (dd, J=8.2, 7.5 Hz, 1H), 7.18 (d, J=7.8 Hz, 1H), 7.11 (s, 1H), 6.99 (d, J=7.5 Hz, 1H), 4.11 (t, J=5.4 Hz, 2H), 3.82 (t, J=5.1 Hz, 2H), 3.75 (sep, J=6.0 Hz, 1H), 1.23 (d, J=5.7 Hz, 6H).

C. N-((2-(2,6-Dioxopiperidin-3-yl)-1-oxoisoindolin-5-yl)methyl)-2,2-difluoro-2-(3-(2-isopropoxyethoxy) phenyl)acetamide To an ice cold solution of 2,2-difluoro-2-(3-(2-isopropoxyethoxy)phenyl)acetic acid (221 mg, 0.81 mmol) in pyridine (9 mL) was added phosphorus oxychloride (371 mg, 2.47 mmol) in drop wise and stirred at 0-5° C. for 1 h. Then, 3-(5-(aminomethyl)-1-oxoisoindolin-2-yl)piperidine-2,6-dione hydrochloride (250 mg, 0.81 mmol) was added into the reaction mixture and stirred at room temperature for 1 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl) methyl)-2,2-difluoro-2-(3-(2-isopropoxy ethoxy)phenyl)acetamide (62 mg, 0.116 mmol, 15% yield) as white solid. MS (ESI) m/z 529.9 [M+1]$^+$. $^1$H NMR (300 MHz, DMSO-d$_6$) δ 10.98 (s, 1H), 9.60 (t, J=6.0 Hz, 1H), 7.67 (d, J=7.5 Hz, 1H), 7.45 (d, J=8.1 Hz, 1H), 7.40 (s, 1H), 7.36 (d, J=7.5 Hz, 1H), 7.15-7.12 (m, 3H), 5.10 (dd, J=13.5, 5.1 Hz, 1H), 4.45 (d, J=5.7 Hz, 2H), 4.42 (d, J=18.0 Hz, 1H), 4.27 (d, J=17.4 Hz, 1H), 4.08 (t, J=4.5 Hz, 2H), 3.69 (t, J=4.8 Hz, 2H), 3.62 (sep, J=5.7 Hz, 1H), 2.98-2.87 (m, 1H), 2.66-2.56 (m, 1H), 2.45-2.30 (m, 1H), 2.04-1.94 (m, 1H), 1.09 (d, J=6.3 Hz, 6H).

Example 92

N-((2-(2,6-dioxopiperidin-3-yl)-1-oxoisoindolin-5-yl)methyl)-2,2-difluoro-2-(3-hydroxyphenyl)acetamide

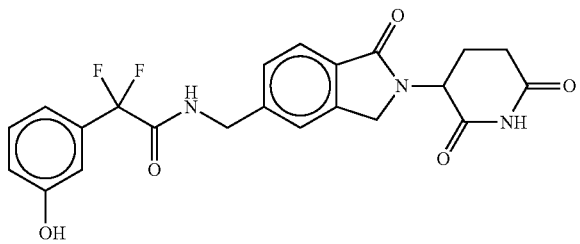

A. 1-Iodo-3-(methoxymethoxy)benzene

To a stirred solution of 3-iodophenol (1 g, 4.54 mmol) in dichloromethane (10 mL) was added N,N-diisopropyl ethyl amine (2.4 mL, 13.63 mmol) followed by chloro methyl methyl ether (0.5 mL, 6.81 mmol) at 0° C. and stirred at room temperature for 2 h. The reaction mixture was quenched with ice water and extracted with dichloromethane (2×100 mL). The combined organic layers were washed with water (50 mL), brine (50 mL), dried over sodium sulfate, filtered and concentrated to afford 1-iodo-3-(methoxymethoxy)benzene (1.0 g, 3.78 mmol, 83% yield). GC MS (m/z) 264.0 [M]$^+$.

B. Ethyl 2,2-difluoro-2-(3-(methoxymethoxy)phenyl)acetate

To a stirred solution of 1-iodo-3-(methoxymethoxy)benzene (800 mg, 3.03 mmol) in dimethylsulfoxide (10 mL) was added ethyl 2-bromo-2,2-difluoroacetate (738 mg, 3.97 mmol) followed by copper (501 mg, 7.88 mmol) and stirred at 55° C. for 5 h. The reaction mixture was quenched with aqueous ammonium chloride solution and was extracted with ethyl acetate (3×50 mL). The combined organic layers were washed with water (50 mL), brine (50 mL), dried over sodium sulfate, filtered and concentrated to afford ethyl 2,2-difluoro-2-(3-(methoxymethoxy)phenyl)acetate (700 mg, 2.69 mmol, 89% yield). GC MS (m/z) 260.2 [M]$^+$.

C. 2,2-Difluoro-2-(3-(methoxymethoxy)phenyl)acetic acid

To a stirred solution of ethyl 2,2-difluoro-2-(3-(methoxymethoxy)phenyl)acetate (700 mg, 2.69 mmol) in methanol-tetrahydrofuran-water mixture (15 mL, 1:1:1) was added lithium hydroxide monohydrate (339 mg, 8.07 mmol) and stirred at room temperature for 2 h. The reaction mixture was diluted with water (50 mL) and acidified with aqueous potassium bisulfate solution and extracted with ethyl acetate (3×50 mL). The combined organic layers were washed with brine (50 mL), dried over sodium sulfate, filtered and concentrated to afford 2,2-difluoro-2-(3-(methoxymethoxy)phenyl)acetic acid (400 mg, 1.72 mmol, 64% yield). LCMS (ESI) m/z 231.31 [M−1]$^-$.

D. N-((2-(2,6-dioxopiperidin-3-yl)-1-oxoisoindolin-5-yl)methyl)-2,2-difluoro-2-(3-(methoxymethoxy)phenyl)acetamide To a cold (0° C.) stirred solution of 2,2-difluoro-2-(3-(methoxymethoxy)phenyl)acetic acid (300 mg, 1.29 mmol) in pyridine (5 mL) was added phosphoryl chloride (0.4 mL, 3.87 mmol) dropwise and stirred at 0-5° C. for 1 h, and then added 3-(5-(aminomethyl)-1-oxoisoindolin-2-yl)piperidine-2,6-dione hydrochloride (400 mg, 1.29 mmol) and stirred at room temperature for 1 h. The reaction mixture was neutralized with aqueous saturated sodium bicarbonate (up to pH-8) and extracted with ethyl acetate (3×50 mL). The combined organic layers were washed with water (2×30 mL), brine (30 mL), dried over sodium sulphate and concentrated to afford N-((2-(2,6-dioxopiperidin-3-yl)-1-oxoisoindolin-5-yl)methyl)-2,2-difluoro-2-(3-(methoxymethoxy)phenyl)acetamide (250 mg, 0.51 mmol, 40% yield). LCMS (ESI) m/z 488.39 [M+1]$^+$.

E. N-((2-(2,6-dioxopiperidin-3-yl)-1-oxoisoindolin-5-yl)methyl)-2,2-difluoro-2-(3-hydroxyphenyl)acetamide To a cold (0° C.) stirred solution of N-((2-(2,6-dioxopiperidin-3-yl)-1-oxoisoindolin-5-yl)methyl)-2,2-difluoro-2-(3-(methoxymethoxy)phenyl)acetamide (250 mg, 0.51 mmol) in 1,4-dioxane (5 mL) was added 1,4-dioxane.HCl (2.0 mL) dropwise and stirred at room temperature for 1 h. The reaction mixture was neutralized with aqueous saturated sodium bicarbonate (up to pH-8) and extracted with ethyl acetate (3×50 mL). The combined organic layer was washed with water (2×30 mL), brine (30 mL) and dried over sodium sulphate and was concentrated. The resultant residue was purified by Reveleris C-18 reversed phase column chromatography using 45-50% acetonitrile in aqueous formic acid (0.1%) to afford N-((2-(2,6-dioxopiperidin-3-yl)-1-oxoisoindolin-5-yl)methyl)-2,2-difluoro-2-(3-hydroxyphenyl)acetamide (75 mg, 0.16 mmol, 33.0% yield) as an off-white solid. LCMS (ESI) m/z 444.13 [M+1]$^+$. $^1$H NMR (300 MHz, dmso) δ=10.98 (s, 1H), 9.87 (s, 1H), 9.62-9.53 (m, 1H), 7.67 (d, J=7.7 Hz, 1H), 7.42-7.27 (m, 4H), 7.02-6.68 (m, 3H), 5.10 (br dd, J=5.0, 13.4 Hz, 1H), 4.50-4.22 (m, 4H), 2.96-2.82 (m, 1H), 2.68-2.54 (m, 1H), 2.44-2.30 (m, 1H), 2.05-1.93 (m, 1H).

Example 93

N-((2-(2,6-Dioxopiperidin-3-yl)-1-oxoisoindolin-5-yl)methyl)-2,2-difluoro-2-(3-((4-methylpiperazin-1-yl)methyl)phenyl)acetamide

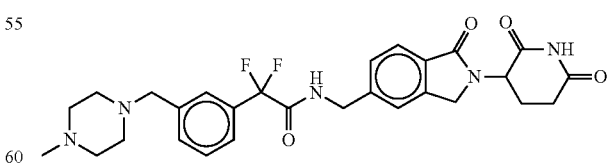

A. Ethyl 2,2-difluoro-2-(3-formylphenyl)acetate

To a stirred solution of 4-iodobenzaldehyde (5 g, 21.55 mmol) in dimethylsulfoxide (50 mL) was added ethyl 2-bromo-2,2-difluoroacetate (6.0 mL, 43.11 mmol), copper (4.0 g, 56.03 mmol) and stirred for 4 h at 55° C. The reaction mixture was neutralized with aqueous saturated ammonium chloride solution and extracted with ethyl acetate (3×100 mL). The combined organic layers were washed with water (2×50 mL), brine (50 mL), dried over sodium sulphate and concentrated to afford ethyl 2,2-difluoro-2-(3-formylphenyl)acetate (3.5 g, 15.35 mmol, 71%). GC MS (m/z) 228.2.

B. Ethyl 2,2-difluoro-2-(3-((4-methylpiperazin-1-yl)methyl)phenyl)acetate

To a stirred solution of ethyl 2,2-difluoro-2-(3-formylphenyl)acetate (1.0 g, 4.38 mmol) in ethanol (25 mL) was added 1-methylpiperazine (878 mg, 8.77 mmol), acetic acid (526 mg, 8.77 mmol) and stirred at 0° C. for 1 h. To this reaction mixture was then added sodium cyanoborohydride (551 mg, 8.77 mmol) and stirred at room temperature for 3 h. The reaction mixture was quenched with water (100 mL) and extracted with ethyl acetate (3×100 mL). The combined organic layers were washed with water (2×100 mL), brine (100 mL), dried over sodium sulphate and concentrated to afford ethyl 2,2-difluoro-2-(3-((4-methylpiperazin-1-yl)methyl)phenyl)acetate (1.0 g, 3.20 mmol, 74% yield). LCMS (ESI) m/z 313.53[M+1]$^+$ C. 2,2-Difluoro-2-(3-((4-methylpiperazin-1-yl)methyl)phenyl)acetic acid To a cold (0° C.) stirred solution of ethyl 2,2-difluoro-2-(3-((4-methylpiperazin-1-yl)methyl)phenyl)acetate (1.0 g, 3.20 mmol) in tetrahydrofuran:methanol:water mixture (1:1:1, 30 mL) was added lithium hydroxide monohydrate (403 mg, 5.01 mmol) and stirred at room temperature for 2 h. The reaction mixture was concentrated and the residue was neutralized with 10% aqueous potassium bisulphate (10 mL) and extracted with ethyl acetate (2×50 mL). The combined organic layers were washed with brine (20 mL), dried over sodium sulphate and concentrated to give 2,2-difluoro-2-(3-((4-methylpiperazin-1-yl)methyl)phenyl)acetic acid (750 mg, 2.64 mmol, 82% yield). LCMS (ESI) m/z 284.9[M+1]$^+$.

D. N-((2-(2,6-Dioxopiperidin-3-yl)-1-oxoisoindolin-5-yl)methyl)-2,2-difluoro-2-(3-((4-methylpiperazin-1-yl)methyl)phenyl)acetamide To a cold (0° C.) stirred solution of 2,2-difluoro-2-(3-((4-methylpiperazin-1-yl)methyl)phenyl)acetic acid (350 mg, 1.23 mmol) in pyridine (5 mL) was added phosphoryl chloride (0.3 mL, 3.69 mmol) and stirred at 0-5° C. for 1 h. Then added 3-(5-(aminomethyl)-1-oxoisoindolin-2-yl)piperidine-2,6-dione hydrochloride (381 mg, 1.23 mmol) and stirred at room temperature for 1 h. The reaction mixture was neutralized with aqueous saturated sodium bicarbonate (up to pH-8) and extracted with ethyl acetate (2×25 mL). The combined organic layers were washed with water (15 mL), brine (15 mL), dried over sodium sulphate and concentrated. The resultant residue was purified by Reveleris C-18 reversed phase column chromatography using 45-50% acetonitrile in aqueous formic acid (0.1%) to afford N-((2-(2,6-dioxopiperidin-3-yl)-1-oxoisoindolin-5-yl)methyl)-2,2-difluoro-2-(3-((4-methylpiperazin-1-yl)methyl)phenyl)acetamide (40 mg, 0.26 mmol, 6% yield) as a pale yellow solid. LCMS (ESI) m/z 540.40 [M+1]$^+$. $^1$H NMR (300 MHz, DMSO-d$_6$) δ 10.99 (s, 1H), 9.67 (t, J=5.8 Hz, 1H), 7.87 (br s, 2H), 7.67-7.55 (m, 3H), 7.45-7.33 (m, 2H), 5.10 (dd, J=4.9, 13.3 Hz, 1H), 4.48-4.24 (m, 6H), 3.65-3.03 (m, 8H), 3.01-2.82 (m, 4H), 2.66-2.54 (m, 1H), 2.48-2.30 (m, 1H), 2.29-1.82 (m, 1H).

Example 94

N-((2-(2,6-dioxopiperidin-3-yl)-1-oxoisoindolin-5-yl)methyl)-2,2-difluoro-2-(4-methyl-2-(trifluoromethyl)phenyl)acetamide

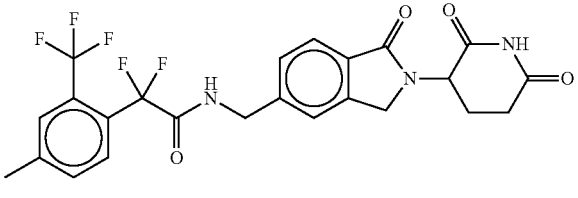

A. 1-Iodo-4-methyl-2-(trifluoromethyl)benzene

To a stirred solution of 1-bromo-4-methyl-2-(trifluoromethyl)benzene (1.0 g, 4.18 mmol) in 1,4-dioxane (10 mL) was added sodium iodide (1.3 g, 8.36 mmol), copper iodide (40 mg, 0.20 mmol), trans-N,N'-dimethylcyclohexane-1,2-diamine (66 mg, 0.46 mmol) at room temperature and stirred at 110° C. for 16 h in sealed tube. The reaction mixture was quenched with water (100 mL) and extracted with ethyl acetate (3×100 mL). The combined organic layers were washed with water (2×50 mL), brine (50 mL), dried over sodium sulphate and concentrated to give 1-Iodo-4-methyl-2-(trifluoromethyl)benzene (900 mg, 3.14 mmol, 75% yield). GCMS (m/z) 286.

B. Ethyl 2,2-difluoro-2-(4-methyl-2-(trifluoromethyl)phenyl)acetate

To a stirred solution of 1-iodo-4-methyl-2-(trifluoromethyl)benzene (900 mg, 3.14 mmol) in dimethylsulfoxide (10 mL) was added ethyl 2-bromo-2,2-difluoroacetate (1.3 g, 6.29 mmol), copper (520 mg, 8.18 mmol) and stirred at 55° C. for 16 h. The reaction mixture was neutralized with aqueous saturated ammonium chloride solution and extracted with ethyl acetate (3×50 mL). The combined organic layers were washed with water (2×50 mL), brine (50 mL), dried over sodium sulphate and concentrated to afford ethyl 2,2-difluoro-2-(4-methyl-2-(trifluoromethyl)phenyl)acetate (800 mg, 2.83 mmol, 90%). GCMS (m/z) 282.1.

C. 2,2-Difluoro-2-(4-methyl-2-(trifluoromethyl)phenyl)acetic acid

To a cold (0° C.) stirred solution of ethyl 2,2-difluoro-2-(4-methyl-2-(trifluoromethyl)phenyl)acetate (800 mg, 2.83 mmol) in tetrahydrofuran-Methanol-water (15 mL, 1:1:1) was added lithium hydroxide monohydrate (357 mg, 8.51 mmol) and stirred at room temperature for 2 h. The reaction mixture was concentrated and the residue was neutralized with 10% aqueous potassium bisulphate (10 mL) and extracted with ethyl acetate (2×50 mL). The combined organic layers were washed with brine (30 mL), dried over sodium sulphate and concentrated to afford 2,2-difluoro-2-(4-methyl-2-(trifluoromethyl)phenyl)acetic acid (400 mg, 1.57 mmol, 56% yield). LCMS (ESI) m/z 253.32 [M−1]$^−$.

D. N-((2-(2,6-dioxopiperidin-3-yl)-1-oxoisoindolin-5-yl)methyl)-2,2-difluoro-2-(4-methyl-2-(trifluoromethyl)phenyl)acetamide To a cold (0° C.) stirred solution of 2,2-difluoro-2-(4-methyl-2-(trifluoromethyl)phenyl)acetic acid (400 mg, 1.57 mmol) in pyridine (5 mL) was added phosphoryl chloride (0.4 mL, 4.72 mmol) drop wise and stirred at 0-5° C. for 1 h. To this reaction mixture was added 3-(5-(aminomethyl)-1-oxoisoindolin-2-yl)piperidine-2,6-dione hydrochloride (487 mg, 1.57 mmol) and stirred at room temperature for 1 h. The reaction mixture was neutralized with aqueous saturated sodium bicarbonate (up to pH-8) and extracted with ethyl acetate (3×50 mL). The combined organic layers were washed with water (2×30 mL), brine (30 mL), dried over sodium sulphate and concentrated. The resultant residue was purified by Reveleris C-18 reversed phase column chromatography using 45-50% acetonitrile in aqueous formic acid (0.1%) to afford N-((2-(2,6-dioxopiperidin-3-yl)-1-oxoisoindolin-5-yl)methyl)-2,2-difluoro-2-(4-methyl-2-(trifluoromethyl)phenyl)acetamide (50 mg, 0.09 mmol, 6.0% yield) as an off-white solid. LCMS (ESI) m/z 510.28 [M+1]$^+$. $^1$H NMR (400 MHz, DMSO-d$_6$) δ=10.98 (s, 1H), 9.62 (br t, J=6.1 Hz, 1H), 7.78-7.60 (m, 4H), 7.75 (s, 1H), 7.41 (d, J=7.6 Hz, 1H), 5.11 (dd, J=5.1, 13.5 Hz, 1H), 4.51-4.21 (m, 4H), 2.98-2.85 (m, 1H), 2.65-2.54 (m, 1H), 2.47-2.31 (m, 4H), 2.04-1.96 (m, 1H).

Example 95

N-((2-(2,6-Dioxopiperidin-3-yl)-1-oxoisoindolin-5-yl)methyl)-2,2-difluoro-2-(3-(2-(2-methoxyethoxy)ethoxy)phenyl)acetamide

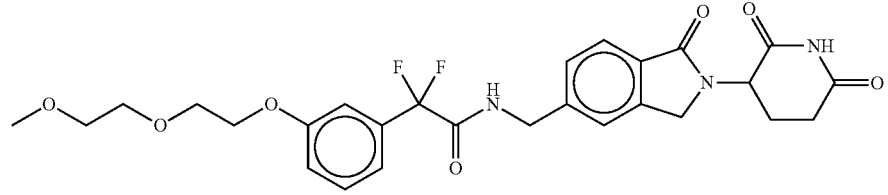

A. 1-Iodo-3-(methoxymethoxy)benzene

To a stirred solution of 3-iodophenol (1 g, 4.54 mmol) in dichloromethane (10 mL) was added N,N-diisopropylethylamine (2.4 mL, 13.63 mmol) followed by chloro methyl methyl ether (0.5 mL, 6.81 mmol) at 0° C. and stirred at room temperature for 2 h. The reaction mixture was quenched with ice water and extracted with dichloromethane (3×15 mL). The combined organic layers were washed with water (15 mL), brine (15 mL), dried over sodium sulfate, filtered and concentrated to afford 1-iodo-3-(methoxymethoxy)benzene (1.0 g, 3.78 mmol, 83% yield). MS (ESI) m/z 264.0 [M]$^+$.

B. Ethyl 2,2-difluoro-2-(3-(methoxymethoxy)phenyl)acetate

To a stirred solution of 1-iodo-3-(methoxymethoxy)benzene (800 mg, 3.03 mmol) in dimethyl sulfoxide (10 mL) was added ethyl 2-bromo-2,2-difluoroacetate (738 mg, 3.97 mmol) followed by copper (501 mg, 7.88 mmol) and stirred at 55° C. for 5 h. The reaction mixture was quenched with aqueous ammonium chloride solution and was extracted with ethyl acetate (3×15 mL). The combined organic layers were washed with water (15 mL), brine (15 mL), dried over sodium sulfate, filtered and concentrated to afford ethyl 2,2-difluoro-2-(3-(methoxymethoxy)phenyl)acetate (700 mg, 2.69 mmol, 89% yield). MS (ESI) m/z 260.2 [M]$^+$.

C. Ethyl 2,2-difluoro-2-(3-hydroxyphenyl)acetate

To an ice cold solution of ethyl 2,2-difluoro-2-(3-(methoxymethoxy)phenyl)acetate (1 g, 3.84 mmol) in 1,4-dioxane (5 mL) was added 1,4-dioxane.HCl (5 mL) at 0° C. and stirred at room temperature for 3 h. The volatiles were removed under reduced pressure and obtained crude was purified by flash column chromatography (20% ethyl acetate in pet ether) to afford ethyl 2,2-difluoro-2-(3-hydroxyphenyl)acetate (0.7 g, 3.24 mmol, 84% yield) as colorless liquid. MS (ESI) m/z 216.1 [M]$^+$.

D. Ethyl 2,2-difluoro-2-(3-(2-(2-methoxyethoxy)ethoxy)phenyl)acetate

To a stirred solution of ethyl 2,2-difluoro-2-(3-hydroxyphenyl)acetate (1 g, 4.63 mmol) in tetrahydrofuran (10 mL) were sequentially added diisopropyl azodicarboxylate (1.87 g, 9.26 mmol), triphenylphosphine (2.42 g, 9.26 mmol) and 2-(2-methoxyethoxy)ethanol (0.55 g, 4.63 mmol) at 0° C. and stirred at room temperature for 16 h. The reaction mixture was quenched with ice water and extracted with ethyl acetate (3×15 mL). The combined organic layers were washed with water (15 mL), brine (15 mL), dried over sodium sulfate, filtered and concentrated. The obtained crude was purified by flash column chromatography (20% ethyl acetate in pet ether) to afford ethyl 2,2-difluoro-2-(3-(2-(2-methoxyethoxy)ethoxy)phenyl)acetate (0.5 g, 1.57 mmol, 34% yield) as a colorless liquid. GCMS (ESI) m/z 318.6 [M]$^+$.

E. 2,2-Difluoro-2-(3-(2-(2-methoxyethoxy)ethoxy)phenyl)acetic acid

To an ice cold solution of ethyl 2,2-difluoro-2-(3-(2-(2-methoxyethoxy) ethoxy)phenyl)acetate (500 mg, 1.57 mmol) in mixture of methanol:tetrahydrofuran:water (15 mL, 1:1:1) was added lithium hydroxide monohydrate (198 mg, 4.71 mmol) and stirred at room temperature for 4 h. The volatiles were removed under reduced pressure and the obtained crude product was dissolved in water (10 mL), washed with ethyl acetate (2×8 mL). Then, the aqueous layer was acidified with aqueous potassium bisulfate solution and extracted with ethyl acetate (3×10 mL). The combined organic layers were washed with brine (10 mL), dried over sodium sulfate, filtered and concentrated to afford 2,2- difluoro-2-(3-(2-(2-methoxyethoxy)ethoxy)phenyl)acetic acid (300 mg, 0.65 mmol, 84% yield) as a semi solid. MS (ESI) m/z 289.36 [M–1]+.

F. N-((2-(2,6-Dioxopiperidin-3-yl)-1-oxoisoindolin-5-yl)methyl)-2,2-difluoro-2-(3-(2-(2-methoxyethoxy)ethoxy)phenyl)acetamide To an ice cold solution of 2,2-difluoro-2-(3-(2-(2-methoxyethoxy)ethoxy)phenyl)acetic acid (375 mg, 1.29 mmol) in pyridine (9 mL) was added phosphorus oxychloride (593 mg, 3.88 mmol) in drop wise and stirred at 0-5° C. for 1 h. Then, 3-(5-(aminomethyl)-1-oxoisoindolin-2-yl)piperidine-2,6-dione hydrochloride (400 mg, 1.29 mmol) was added into the reaction mixture and stirred at room temperature for 2 h. The reaction mixture was basified with aqueous saturated sodium bicarbonate solution and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl)methyl)-2,2-difluoro-2-(3-(2-(2-methoxyethoxy)ethoxy)phenyl)acetamide (46 mg, 0.08 mmol, 7% yield) as white solid. MS (ESI) m/z 546.06 [M+1]+. 1H NMR (300 MHz, DMSO-d6) δ 10.99 (bs, 1H), 9.60 (t, J=6.3 Hz, 1H), 7.67 (d, J=7.5 Hz, 1H), 7.44 (dd, J=8.1, 7.8 Hz, 1H), 7.40 (s, 1H), 7.37 (d, J=7.8 Hz, 1H), 7.16-7.12 (m, 3H), 5.10 (dd, J=13.2, 5.1 Hz, 1H), 4.45 (d, J=5.7 Hz, 2H), 4.41 (d, J=18.2 Hz, 1H), 4.27 (d, J=17.7 Hz, 1H), 4.11 (t, J=4.2 Hz, 2H), 3.73 (t, J=4.5 Hz, 2H), 3.58 (t, J=4.5 Hz, 2H), 3.45 (t, J=5.1 Hz, 2H), 3.24 (s, 3H), 2.98-2.83 (m, 1H), 2.67-2.53 (m, 1H), 2.44-2.30 (m, 1H), 2.05-1.94 (m, 1H).

Example 96

2-(3-(2-(Dimethylamino)ethoxy)phenyl)-N-((2-(2,6-dioxopiperidin-3-yl)-1-oxoisoindolin-5-yl)methyl)-2,2-difluoroacetamide hydrochloride

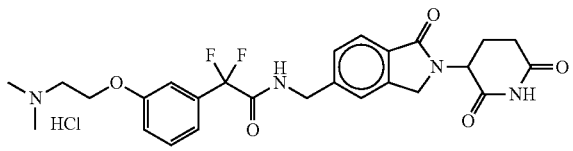

A. 2-(3-Iodophenoxy)-N,N-dimethylethanamine

To a stirred solution of 3-iodophenol (2 g, 9.09 mmol) in acetone (20 mL) was added 2-chloro-N,N-dimethylethanamine hydrochloride (1.57 g, 10.90 mmol), potassium carbonate (5.07 g, 36.36 mmol) and stirred for 16 h at 55° C. The reaction mixture was quenched with water (50 mL) and extracted with ethyl acetate (2×100 mL). The combined organic layers were washed with water (2×100 mL), brine (100 mL), dried over sodium sulphate and concentrated. The resultant residue was purified by column chromatography (silica-gel 100-200) 100% hexane as a eluent to afford 2-(3-Iodophenoxy)-N,N-dimethylethanamine (1.5 g, 5.22 mmol, 57% yield) as brown liquid. MS (ESI) m/z 291[M]+.

B. Ethyl 2-(3-(2-(dimethylamino)ethoxy)phenyl)-2,2-difluoroacetate

To a stirred solution of 2-(3-Iodophenoxy)-N,N-dimethylethanamine (1.5 g, 5.22 mmol) in dimethyl sulfoxide (20 mL) was added ethyl 2-bromo-2,2-difluoroacetate (1.36 mL, 10.45 mmol) followed by copper (0.86 g, 13.58 mmol) and stirred for 16 h at 50° C. The reaction mixture was neutralized with aqueous saturated ammonium chloride solution and extracted with ethyl acetate (3×100 mL). The combined organic layers were washed with water (2×100 mL), brine (10 mL), dried over sodium sulphate and concentrated to afford ethyl 2-(3-(2-(dimethylamino)ethoxy)phenyl)-2,2-difluoroacetate (1.5 g crude) as a brown liquid. MS (ESI) m/z 288.4[M]+.

C. 2-(3-(2-(Dimethylamino)ethoxy)phenyl)-2,2-difluoroacetic acid

To a cold (0° C.) stirred solution of ethyl 2-(3-(2-(dimethylamino)ethoxy)phenyl)-2,2-difluoroacetate (1.0 g, 3.48 mmol) in methanol/tetrahydrofuran/water (20 mL, 1:1:1) was added lithium hydroxide monohydrate (438.4 mg, 10.44 mmol) and stirred at room temperature for 2 h. The reaction mixture was concentrated and the residue was neutralized with 10% aqueous potassium bisulphate (10 mL) and extracted with ethyl acetate (2×50 mL). The combined organic layers were washed with brine (20 mL), dried over sodium sulphate and concentrated to afford 2-(3-(2-(dimethylamino)ethoxy)phenyl)-2,2-difluoroacetic acid (600 mg) as a brown semi solid which was taken to the next step without further purification.

D. 2-(3-(2-(Dimethylamino)ethoxy)phenyl)-N-((2-(2,6-dioxopiperidin-3-yl)-1-oxoisoindolin-5-yl)methyl)-2,2-difluoroacetamide hydrochloride To a cold (0° C.) stirred solution of 2-(3-ethoxypyridin-2-yl)-2,2-difluoroacetic acid (252 mg, 1.16 mmol) in pyridine (20 mL) was added phosphoryl chloride (446.4 mg, 2.91 mmol) dropwise and stirred at 0-5° C. for 30 min. and then added 3-(5-(aminomethyl)-1-oxoisoindolin-2-yl)piperidine-2,6-dione hydrochloride (300 mg, 0.97 mmol) and stirred at room temperature for 2 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 45-50% acetonitrile in aqueous formic acid (0.1%) to afford 2-(3-(2-(dimethylamino)ethoxy)phenyl)-N-((2-(2,6-dioxopiperidin-3-yl)-1-oxoisoindolin-5-yl)methyl)-2,2-difluoroacetamide hydrochloride (50 mg, 0.07 mmol, 7.5% yield) as an off-white solid. MS (ESI) m/z 515.13 [M+1 1H NMR (400 MHz, DMSO-d6) δ ppm 10.99 (s, 1H), 10.31 (br s, 1H), 9.68 (br t, J=5.9 Hz, 1H), 7.68 (d, J=7.8 Hz, 1H), 7.50 (t, J=7.8 Hz, 1H), 7.43-7.33 (m, 3H), 7.26-7.13 (m, 3H), 5.11 (dd, J=4.9, 13.2 Hz, 1H), 4.50-4.34 (m, 4H), 4.33-4.23 (m, 2H), 3.00-2.87 (m, 1H), 2.83-2.70 (br s, 2H), 2.67-2.55 (m, 1H), 2.45-2.25 (m, 7H), 2.05-1.94 (m, 1H).

Example 97

N-((2-(2,6-dioxopiperidin-3-yl)-1-oxoisoindolin-5-yl)methyl)-2,2-difluoro-2-(5-isopropylpyridin-2-yl)acetamide

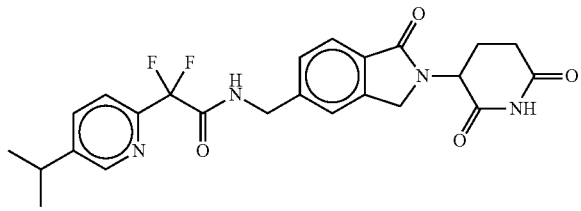

A. 5-(Prop-1-en-2-yl)pyridin-2-amine

To a stirred and degassed solution of 5-bromopyridin-2-amine (3.5 g, 20.34 mmol) in 1,4-dioxane.water (1:1, 40 mL) was added potassium phosphate (12.94 g, 61.04 mmol), and continued degassing for 10 min. Then, 4,4,5,5-tetramethyl-2-(prop-1-en-2-yl)-1,3,2-dioxaborolane (5.21 g, 30.51 mmol) followed by [1,1'-bis(diphenylphosphino)ferrocene]dichloropalladium(II) (1.47 mg, 2.014 mmol) was added, degassed 10 min with stirring and heated to 100° C. for 2 h. The reaction mixture was cooled to room temperature, filtered through the Celite pad. To the filtrate was added cold water and extracted with ethyl acetate (3×200 mL). The organic layers were washed with water (2×100 mL), brine (100 mL), dried over sodium sulphate and concentrated. The resultant residue was purified by silicagel (100-200 mesh) column chromatography using 40% of ethylacetate in petroleum ether to afford 5-(prop-1-en-2-yl)pyridin-2-amine (2.5 g, 18.65 mmol, 91% yield) as brown colored solid. MS (ESI) m/z 135.18 [M+1]$^+$.

B. 5-Isopropylpyridin-2-amine

To slurry of 20% palladium hydroxide (1 g) in ethyl acetate (50 mL) was added 5-(prop-1-en-2-yl)pyridin-2-amine (2.5 g, 18.65 mmol) and stirred at room temperature for 2 h under hydrogen balloon (1 atm). The reaction mixture was filtered through Celite pad, dried over sodium sulphate and concentrated to afford the 5-isopropylpyridin-2-amine (2 g, 14.70 mmol, 79% yield) as a brown liquid. MS (ESI) m/z 137.15 [M+1]$^+$.

C. 2-Bromo-5-isopropylpyridine

To a cold (0° C.) stirred solution of 5-isopropylpyridin-2-amine (2 g, 14.70 mmol) in 47% aqueous hydrobromic acid (20 mL) was added a solution of sodium nitrite (2.63 g, 38.23 mmol, in 5 mL water) and stirred at the same temperature for 30 min. To this reaction mixture bromine (2.27 mL, 44.1 mmol) was drop wise at −5° C. and stirred at room temperature for 4 h. The reaction mixture was neutralized with aqueous sodium hydroxide solution and extracted with dichloromethane (2×50 mL). The combined organic layers were washed with saturated aqueous sodium thiosulphate solution (100 mL), brine (50 mL), dried over sodium sulphate and concentrated to afford 2-bromo-5-isopropylpyridine (1.8 g, 9.04 mmol, 62% yield) as a brown colored liquid. MS (ESI) (m/z) 200.23 [M+1]$^+$.

D. 2-Iodo-5-isopropylpyridine

To a stirred solution of 2-bromo-5-isopropylpyridine (1.8 g, 9.04 mmol) in acetonitrile (20 mL) was added potassium iodide (3.75 g, 22.61 mmol) and acetyl chloride (1.42 g, 18.08 mmol) at room temperature and stirred at 85° C. for 16 h. The reaction mixture was neutralized with aqueous sodium bicarbonate solution and extracted with dichloromethane (2×50 mL). The combined organic layers were washed with saturated aqueous sodium thiosulphate solution (100 mL) brine (50 mL) and dried over sodium sulphate and concentrated. The resultant residue was purified by Silicagel (100-200 mesh) column chromatography using 5% of ethylacetate in pet.ether as eluent to afford 2-bromo-5-isopropylpyridine (850 mg, 3.44 mmol, 39% yield). MS (ESI) (m/z) 248.24 [M+1]$^+$.

E. Ethyl 2,2-difluoro-2-(5-isopropylpyridin-2-yl)acetate

To a stirred solution of 2-iodo-5-isopropylpyridine (800 mg, 3.23 mmol) in dimethyl sulfoxide (15 mL) was added ethyl 2-bromo-2,2-difluoroacetate (0.62 mL, 4.845 mmol) followed by copper (534 g, 8.39 mmol) and stirred for 16 h at 50° C. The reaction mixture was neutralized with aqueous saturated ammonium chloride solution and extracted with ethyl acetate (2×100 mL). The combined organic layers were washed with water (2×50 mL), brine (50 mL), dried over sodium sulphate and concentrated to afford ethyl 2,2-difluoro-2-(5-isopropylpyridin-2-yl)acetate (650 mg, 2.67 mmol, 82%) as a brown liquid. MS (ESI) m/z 244.28 [M+1]$^+$.

F. Ethyl 2,2-difluoro-2-(5-isopropylpyridin-2-yl)acetic acid

To a cold (0° C.) stirred solution of ethyl 2,2-difluoro-2-(5-isopropylpyridin-2-yl)acetate (600 mg, 2.46 mmol) in methanol/tetrahydrofuran/water mixture (9 mL, 1:1:1) was added lithium hydroxide monohydrate (310 mg, 7.40 mmol) and stirred at room temperature for 2 h. The reaction mixture was concentrated and the residue was neutralized with 10% aqueous potassium bisulphate (10 mL) and extracted with ethyl acetate (2×50 mL). The combined organic layers were washed with brine (20 mL), dried over sodium sulphate and concentrated to afford ethyl 2,2-difluoro-2-(5-isopropylpyridin-2-yl)acetic acid (450 mg, 2.09 mmol, 85% yield) as a brown semi solid. MS (ESI) m/z 216.30 [M−1]$^+$.

G. N-((2-(2,6-dioxopiperidin-3-yl)-1-oxoisoindolin-5-yl)methyl)-2,2-difluoro-2-(5-isopropylpyridin-2-yl)acetamide To a cold (0° C.) stirred solution of ethyl 2,2-difluoro-2-(5-isopropylpyridin-2-yl)acetic acid (333 mg, 1.54 mmol) in pyridine (10 mL) was added phosphoryl chloride (0.4 mL, 3.87 mmol) drop wise and stirred at 0-5° C. for 30 min. To this was added 3-(5-(aminomethyl)-1-oxoisoindolin-2-yl)piperidine-2,6-dione hydrochloride (400 mg, 1.29 mmol) and stirred at room temperature for 2 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by column chromatography using 3-4% of methanol in dichloromethane as a eluent to afford N-((2-(2,6-dioxopiperidin-3-yl)-1- oxoisoindolin-5-yl)methyl)-2,2-difluoro-2-(5-isopropylpyridin-2-yl)acetamide (65 mg, 0.138 mmol, 11% yield) as an off-white solid. MS (ESI) m/z 471.10 [M+1]⁺. ¹H NMR (300 MHz, DMSO-d₆) δ ppm 10.99 (s, 1H), 9.61 (br t, J=6.05 Hz, 1H), 8.62 (s, 1H), 7.91 (dd, J=8.07, 1.83 Hz, 1H), 7.71 (d, J=8.07 Hz, 2H), 7.52 (s, 1H), 7.46 (br d, J=7.70 Hz, 1H), 5.11 (br dd, J=13.57, 5.14 Hz, 1H), 4.55-4.27 (m, 4H), 3.10-3.00 (m, 1H), 2.95-2.85 (m, 1H), 2.75-2.67-2.54 (m, 1H), 2.44-2.30 (m, 1H), 2.07-1.93 (m, 1H), 1.30-1.20 (m, 6H).

Example 98

N-((2-(2,6-dioxopiperidin-3-yl)-1-oxoisoindolin-5-yl)methyl)-2,2-difluoro-2-(3-(2-(methylsulfonyl)ethoxy)phenyl)acetamide

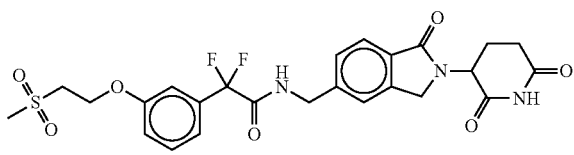

A. (2-(3-Iodophenoxy)ethyl)(methyl)sulfane

To a stirred solution of 3-iodophenol (5 g, 22.72 mmol) in tetrahydrofuran (60 mL) was added diisopropyl azodicarboxylate (8.9 mL, 45.45 mmol) followed by triphenylphosphine (11.9 g, 45.45 mmol) and 2-(methylthio)ethanol (1.97 mL, 22.72 mmol) at 0° C. and stirred at room temperature for 3 h. The reaction mixture was quenched with ice water (50 mL) and extracted with ethyl acetate (3×50 mL). The combined organic layers were washed with water (50 mL), brine (50 mL), dried over sodium sulfate, filtered and concentrated. The obtained crude was purified by flash chromatography (1% ethyl acetate in pet ether) to afford (2-(3-Iodophenoxy)ethyl)(methyl)sulfane (2.5 g, 8.503 mmol, 37% yield) as a colorless liquid. ¹H NMR (300 MHz, DMSO-d₆) δ (ppm) 7.33-7.24 (m, 1H), 7.04-6.95 (m, 1H), 6.90-6.83 (m, 1H), 4.12 (t, J=6.8 Hz, 1H), 2.87 (t, J=6.8 Hz, 1H), 2.21 (s, 1H).

B. 1-Iodo-3-(2-(methylsulfonyl)ethoxy)benzene

To a stirred solution of (2-(3-Iodophenoxy)ethyl)(methyl)sulfane (2.5 g, 8.503 mmol) in dichloromethane (25 mL) was added m-chloroperbenzoic acid (4.4 g, 25.5 mmol) at 0° C. and stirred at room temperature for 3 h. The reaction mixture was basified with aq.NaHCO₃ (200 mL) and extracted with dichloromethane (3×50 mL), washed with brine (50 mL) and dried over sodium sulphate, organic phase was concentrated. Obtained residue was purified by column chromatography (100-200 silica) using 5% ethyl acetate in hexanes to give the 1-iodo-3-(2-(methylsulfonyl)ethoxy)benzene (1.2 g, 3.68 mmol, 43% yield) as an off white solid. MS (ESI) m/z 349.26 [M+Na]⁺.

C. Ethyl 2,2-difluoro-2-(3-(2-(methylsulfonyl)ethoxy)phenyl)acetate

To a stirred solution of 1-iodo-3-(2-(methylsulfonyl)ethoxy)benzene (1.2 g, 3.68 mmol) in dimethyl sulfoxide (12 mL) was added copper (708 mg, 11.04 mmol) and ethyl 2-iodo-2,2-difluoroacetate (1.1 g, 4.42 mmol) at room temperature and stirred at room temperature for 16 h. To the reaction mixture was added aqueous saturated ammonium chloride (50 mL) solution and extracted with ethyl acetate (2×100 mL). The combined organic layers were washed with water (2×100 mL), brine (100 mL), dried over sodium sulphate and concentrated to afford ethyl 2,2-difluoro-2-(3-(2-(methylsulfonyl)ethoxy)phenyl)acetate (720 mg, 2.23 mmol, 61% yield). MS (ESI) m/z 345.4 [M+Na]⁺.

D. 2,2-Difluoro-2-(3-(2-(methylsulfonyl)ethoxy)phenyl)acetic acid

To a stirred solution of ethyl 2,2-difluoro-2-(3-(2-(methylsulfonyl)ethoxy)phenyl)acetate (720 mg, 2.23 mmol) in 1,4-dioxane (30 mL) was added 4M aqueous hydrochloric acid (15 mL) at room temperature and stirred at room temperature for 16 h. The reaction mixture was extracted with ethyl acetate (3×50 mL), washed with brine (50 mL) and dried over sodium sulphate, organic phase was concentrated to give the 2,2-difluoro-2-(3-(2-(methylsulfonyl)ethoxy)phenyl)acetic acid (550 mg, 1.87 mmol, 84% yield) as an off white solid. MS (ESI) m/z 293.21 [M+H]⁺.

E. N-((2-(2,6-dioxopiperidin-3-yl)-1-oxoisoindolin-5-yl)methyl)-2,2-difluoro-2-(3-(2-(methylsulfonyl)ethoxy)phenyl)acetamide To a cold (0° C.) stirred solution of 2,2-difluoro-2-(3-(2-(methylsulfonyl)ethoxy)phenyl)acetic acid (250 mg, 0.85 mmol) in pyridine (10 mL) was added phosphoryl chloride (0.2 mL, 2.55 mmol) drop wise and stirred at 0° C. for 1 h and then added 3-(5-(aminomethyl)-1-oxoisoindolin-2-yl)piperidine-2,6-dione hydrochloride (394 mg, 1.02 mmol) and stirred at room temperature for 1 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 50-55% acetonitrile in aqueous formic acid (0.1%) to give N-((2-(2,6-dioxopiperidin-3-yl)-1-oxoisoindolin-5-yl)methyl)-2,2-difluoro-2-(3-(2-(methylsulfonyl)ethoxy)phenyl)acetamide (50 mg, 0.091 mmol, 11% yield) as a white solid. MS (ESI) m/z 549.81 [M+1]⁺. ¹H NMR (300 MHz, DMSO-d₆) δ (ppm) 10.98 (s, 1H), 9.63 (br t, J=5.9 Hz, 1H), 7.68 (d, J=7.8 Hz, 1H), 7.52-7.44 (m, 1H), 7.41-7.34 (m, 2H), 7.23-7.13 (m, 3H), 5.10 (dd, J=5.1, 13.5 Hz, 1H), 4.45 (br d, J=6.4 Hz, 2H), 4.40-4.22 (m, 4H), 3.64 (t, J=5.4 Hz, 1H), 2.97-2.84 (m, 1H), 2.63-2.57 (m, 1H), 2.44-2.33 (m, 1H), 2.04-1.95 (m, 1H).

Example 99

N-((2-(2,6-Dioxopiperidin-3-yl)-1-oxoisoindolin-5-yl)methyl)-2,2-difluoro-2-(3-(3-(methylsulfonyl)propyl)phenyl)acetamide

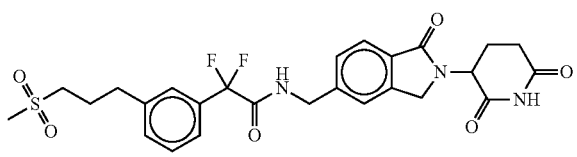

A. Ethyl 2,2-difluoro-2-(3-formylphenyl)acetate

To a stirred solution of 3-iodobenzaldehyde (4 g, 17.24 mmol) in dimethylsulfoxide (20 mL) was added ethyl 2-bromo-2,2-difluoroacetate (5.25 g, 25.86 mmol) followed by copper powder (2.84 g, 44.82 mmol) at room temperature and stirred at 60° C. for 5 h. The reaction mixture was basified with aqueous saturated sodium bicarbonate solution and extracted with ethyl acetate (3×40 mL). The combined organic layers were washed with water (40 mL), brine (40 mL), dried over sodium sulfate, filtered and solvent was concentrated and obtained crude was purified by flash column chromatography (20% ethyl acetate in pet ether) to afford ethyl 2,2-difluoro-2-(3-formylphenyl)acetate (2.3 g, 8.27 mmol, 58%) as a colorless liquid. MS (ESI) m/z 228.1 $[M]^+$.

B. Ethyl 2,2-difluoro-2-(3-vinylphenyl)acetate

To a stirred solution of methyltriphenylphosphonium bromide (1.58 g, 4.4 mmol) in tetrahydrofuran/diethyl ether mixture (30 mL, 2:1), was added n-butyl lithium (1 mL, 2.49 mmol) at −78° C. and stirred the same temperature for 30 min. Then, ethyl 2,2-difluoro-2-(3-formylphenyl)acetate (0.5 g, 2.27 mmol) was added into the reaction mixture at −78° C. and stirred at 0° C. for 3 h. The reaction mixture was quenched with aqueous saturated ammonium chloride solution and extracted with ethyl acetate (3×20 mL). The combined organic layers were washed with water (20 mL), brine (20 mL), dried over sodium sulfate, filtered and solvent was concentrated and obtained crude was purified by flash column chromatography (20% ethyl acetate in pet ether) to afford ethyl 2,2-difluoro-2-(3-vinylphenyl)acetate (0.32 g, 1.41 mmol, 64% yield) as a colorless liquid. $^1$H NMR (400 MHz, CDCl$_3$) δ 7.63 (s, 1H), 7.53-7.48 (m, 2H), 7.42 (d, J=7.6 Hz, 1H), 6.73 (dd, J=17.6, 10.4 Hz, 1H), 5.81 (d, J=17.6 Hz, 1H), 5.33 (d, J=10.8 Hz, 1H), 4.30 (q, J=7.2 Hz, 2H), 1.31 (t, J=7.2 Hz, 3H).

C. 3-(Methylsulfonyl)prop-1-ene

To a stirred solution of allyl(methyl)sulfane (5 g, 56.81 mmol) in dichloromethane (50 mL) was added meta-chloroperoxybenzoic acid (19.65 g, 113.63 mmol) at 0° C. and stirred at room temperature for 16 h. The reaction mixture was basified with saturated sodium bicarbonate solution and extracted with dichloro methane (3×50 mL). The combined organic layers were washed with water (40 mL), brine (40 mL), dried over sodium sulfate, filtered and concentrated. The obtained crude was purified by flash column chromatography (20% ethyl acetate in pet ether) to afford 3-(methylsulfonyl)prop-1-ene (2.5 g, 20.83 mmol, 36% yield) as a white solid. $^1$H NMR (400 MHz, CDCl$_3$) δ 5.98 (ddt, J=17.2, 14.8, 7.2 Hz, 1H), 5.48 (dd, J=17.2, 1.2 Hz, 2H), 3.74 (d, J=7.6 Hz, 2H), 2.88 (s, 3H).

D. (E)-Ethyl 2,2-difluoro-2-(3-(3-(methylsulfonyl)prop-1-enyl)phenyl)acetate To a stirred solution of ethyl 2,2-difluoro-2-(3-vinylphenyl)acetate (100 mg, 0.44 mmol) in dichloromethane (10 mL) was added 3-(methylsulfonyl)prop-1-ene (265 mg, 2.21 mmol) followed by Grubbs' II generation catalyst (19 mg, 0.02 mmol) at room temperature and refluxed at 40° C. for 16 h. The volatiles were remove under reduced pressure and obtained residue was purified by flash column chromatography (30% ethyl acetate in pet ether) to afford (E)-ethyl 2,2-difluoro-2-(3-(3-(methylsulfonyl)prop-1-enyl)phenyl)acetate (60 mg, 0.18 mmol, 42% yield) as a colorless liquid. $^1$H NMR (300 MHz, CDCl$_3$) δ 7.64 (s, 1H), 7.59-7.42 (m, 3H), 6.76 (d, J=16.2 Hz, 1H), 6.41-6.31 (m, 1H), 4.31 (q, J=6.9 Hz, 2H), 3.91 (d, J=7.2 Hz, 2H), 2.92 (s, 3H), 1.31 (t, J=6.9 Hz, 3H).

E. Ethyl 2,2-difluoro-2-(3-(3-(methylsulfonyl)propyl)phenyl)acetate

To a stirred solution of (E)-ethyl 2,2-difluoro-2-(3-(3-(methylsulfonyl)prop-1-enyl)phenyl)acetate (220 mg, 0.69 mmol) in ethyl acetate (10 mL) was added slurry of 10% palladium hydroxide (50 mg) in ethyl acetate under nitrogen stream. The reaction mixture was stirred under hydrogen balloon pressure at room temperature for 16 h. The hydrogen atmosphere was evacuated and reaction mixture was filtered through a Celite pad, filtrated and concentrated obtained residue was purified by flash column chromatography (20% ethyl acetate in pet ether) to afford ethyl 2,2-difluoro-2-(3-(3-(methylsulfonyl)propyl)phenyl)acetate (120 mg, 0.37 mmol, 54% yield) as a colorless liquid. $^1$H NMR (300 MHz, CDCl$_3$) δ 7.48 (d, J=7.8 Hz, 1H), 7.43 (s, 1H), 7.39 (d, J=7.5 Hz, 1H), 7.32 (dd, J=8.1, 7.9 Hz, 1H), 4.31 (q, J=6.9 Hz, 2H), 2.99 (t, J=7.5 Hz, 2H), 2.89 (s, 3H), 2.66 (t, J=7.5 Hz, 2H), 2.23-2.15 (m, 2H), 1.32 (t, J=6.9 Hz, 3H).

F. 2,2-Difluoro-2-(3-(3-(methylsulfonyl)propyl)phenyl)acetic acid

To a stirred solution of ethyl 2,2-difluoro-2-(3-(3-(methylsulfonyl)propyl)phenyl)acetate (150 mg, 0.47 mmol) in tetrahydrofuran:methanol:water mixture (10 mL, 1:1:1) was added lithium hydroxide monohydrate (59 mg, 1.41 mmol) and stirred at room temperature for 4 h. The volatiles were removed under reduced pressure and the obtained crude product was dissolved in water (15 mL), washed with ethyl acetate (2×6 mL). The aqueous layer was acidified with 1N hydrochloride aqueous solution and extracted with ethyl acetate (3×8 mL). The combined organic layers were washed with brine (8 mL), dried over sodium sulfate, filtered and concentrated to afford 2,2-difluoro-2-(3-(3-(methylsulfonyl)propyl)phenyl)acetic acid (130 mg, 0.44 mmol, 94% yield) as semi-solid compound. $^1$H NMR (300 MHz, DMSO-d$_6$) δ 7.50-7.41 (m, 4H), 3.32 (brs, 1H), 3.12-3.09 (m, 2H), 3.04 (s, 3H), 2.78 (t, J=7.8 Hz, 2H), 2.04-1.96 (m, 2H).

G. N-((2-(2,6-Dioxopiperidin-3-yl)-1-oxoisoindolin-5-yl)methyl)-2,2-difluoro-2-(3-(3-(methylsulfonyl)propyl)phenyl)acetamide To an ice cold solution of 3-(5-(aminomethyl)-1-oxoisoindolin-2-yl)piperidine-2,6-dione hydrochloride (180 mg, 0.58 mmol) and 2,2-difluoro-2-(3-(3-(methylsulfonyl)propyl)phenyl)acetic acid (136 mg, 0.46 mmol) in N,N-dimethylformamide (10 mL) was added N,N-diisopropylethylamine (0.3 mL, 1.74 mmol) followed by 1-[Bis(dimethylamino)methylene]-1H-1,2,3-triazolo[4,5-b]pyridinium 3-oxid hexafluorophosphate (442 mg, 1.16 mmol) and stirred at room temperature for 4 h. The reaction mixture was diluted with water (15 mL) and extracted with ethyl acetate (3×10 mL). The combined organic layers were washed with brine (10 mL), dried over sodium sulphate, filtered and concentrated. The obtained crude product was purified by Reveleris C-18 reversed phase column (50% acetonitrile in 0.1% aqueous formic acid) to afford N-((2-(2,6-dioxopiperidin-3-yl)-1-oxoisoindolin-5-yl)methyl)-2,2-difluoro-2-(3-(3-(methylsulfonyl)propyl)phenyl)acetamide (40 mg, 0.07 mmol, 12% yield) as an off-white solid. MS (ESI) m/z 472.11 [M+1]$^+$. $^1$H NMR (300 MHz, DMSO-d$_6$) δ 10.98 (s, 1H), 9.63 (t, J=5.6 Hz, 1H), 7.68 (d, J=7.8 Hz, 1H), 7.44-7.36 (m, 6H), 5.10 (dd, J=13.2, 5.1 Hz, 1H), 4.45 (d, J=5.1 Hz, 2H), 4.42 (d, J=17.9 Hz, 1H), 4.28 (d, J=17.7, 1H), 3.11 (t, J=8.1 Hz, 2H), 2.96 (s, 3H), 2.91-2.85 (m, 1H), 2.76 (t, J=7.8 Hz, 2H), 2.67-2.55 (m, 1H), 2.45-2.30 (m, 1H), 2.06-1.92 (m, 3H).

Example 100

N-((2-(2,6-Dioxopiperidin-3-yl)-1-oxoisoindolin-5-yl)methyl)-2,2-difluoro-2-(4-(2-fluoropropan-2-yl)phenyl)acetamide

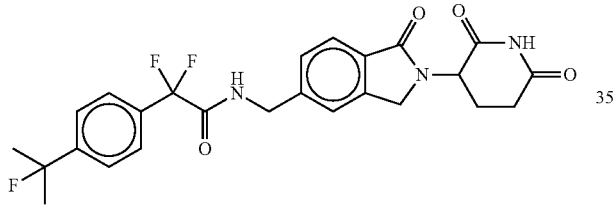

A. N-((2-(2,6-Dioxopiperidin-3-yl)-1-oxoisoindolin-5-yl)methyl)-2,2-difluoro-2-(4-(2-fluoropropan-2-yl)phenyl)acetamide To a cold (0° C.) stirred solution of N-((2-(2,6-dioxopiperidin-3-yl)-1-oxoisoindolin-5-yl)methyl)-2,2-difluoro-2-(4-(2-hydroxypropan-2-yl)phenyl)acetamide (170 mg, 0.35 mmol) in dichloromethane (20 mL) was added diethylaminosulfur trifluoride (0.06 mL, 0.52 mmol) and stirred at room temperature for 2 h. The reaction mixture was diluted with saturated sodium bicarbonate solution (20 mL) and extracted with ethyl acetate (2×25 mL). The combined organic layer was washed with brine (20 mL), dried over sodium sulphate and concentrated. The product was purified by Reveleris C-18 reversed phase column using 65% acetonitrile in aqueous formic acid (0.1%) to afford N-((2-(2,6-dioxopiperidin-3-yl)-1-oxoisoindolin-5-yl)methyl)-2,2-difluoro-2-(4-(2-fluoropropan-2-yl)phenyl)acetamide (70 mg, 0.16 mmol, 41% yield) as an off-white solid. MS (ESI) m/z 486.23 [M+1]$^+$. $^1$H NMR (400 MHz, DMSO-d$_6$) δ 10.98 (s, 1H), 9.65 (br t, J=6.1 Hz, 1H), 7.68 (d, J=7.8 Hz, 1H), 7.64-7.54 (m, 1H), 7.40-7.38 (m, 4H), 7.37-7.32 (d, J=8.3 Hz, 2H), 5.10 (br dd, J=5.1, 13.4 Hz, 1H), 4.54-4.38 (m, 3H), 4.31-4.23 (m, 1H), 2.99-2.84 (m, 1H), 2.69-2.55 (m, 1H), 2.43-2.29 (m, 1H), 2.05-1.93 (m, 1H), 1.69 (s, 3H), 1.63 (s, 3H).

Example 101

2-(1-Benzyl-6-oxo-1,6-dihydropyridin-3-yl)-N-((2-(2,6-dioxopiperidin-3-yl)-1-oxoisoindolin-5-yl)methyl)-2,2-difluoroacetamide

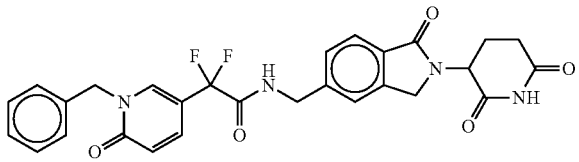

A. 1-Benzyl-5-iodopyridin-2(1H)-one

To a stirred solution of 5-iodopyridin-2-ol (5 g, 22.62 mmol) in dry N,N-dimethylformamide (50 mL) was added potassium carbonate (9.36 g, 67.86 mmol) followed by benzylbromide (2.95 mL, 24.88 mmol) at room temperature and stirred at 70° C. for 4 h. The reaction mixture was quenched with water (100 mL) and extracted with ethyl acetate (2×100 mL). The combined organic layers were washed with brine (50 mL), dried over sodium sulphate and concentrated. The resultant residue was purified by column chromatography (100-200 silica) using 30% ethylacetate in hexanes as eluent to afford 1-benzyl-5-iodopyridin-2(1H)-one (4.5 g, 14.46 mmol, 64% yield) as an off white solid. MS (ESI) m/z 311.98 [M+1]$^+$.

B. 5-Acetyl-1-benzylpyridin-2(1H)-one

To a stirred solution of 1-benzyl-5-iodopyridin-2(1H)-one (1.2 g, 3.858 mmol) in N,N-dimethylformamide (12 mL) was added 1-(vinyloxy)butane (1.93 g, 19.29 mmol) followed by 3M aqueous potassium carbonate (2.4 mL, 11.57 mmol), Pd(OAc)$_2$ (400 mg, 0.192 mmol) was added followed by 1,3-bis(diphenylphosphino) propane (477 mg, 1.157 mmol) and stirred at 80° C. for 3 h. The reaction mixture was cooled to room temperature and 1N aqueous hydrochloric acid (12 mL) was added and stirred at 40° C. for 2 h. The reaction mixture was cooled to room temperature and water (40 mL) was added and extracted with ethyl acetate (3×50 mL), washed with water (2×50 mL), brine (50 mL) and dried over sodium sulphate, organic phase was concentrated. Obtained residue was purified by column chromatography (100-200 silica) using 30% ethyl acetate in hexanes to give the 5-acetyl-1-benzylpyridin-2(1H)-one (700 mg, 3.08 mmol, 80% yield) as yellow syrup. MS (ESI) m/z 228.24 [M+H]$^+$.

C. Ethyl 2-(1-benzyl-6-oxo-1,6-dihydropyridin-3-yl)-2-oxoacetate

To a stirred solution of 5-acetyl-1-benzylpyridin-2(1H)-one (700 mg, 3.08 mmol) in pyridine (7 mL) was added selenium dioxide (855 mg, 7.709 mmol) and stirred at 100° C. for 3 h. The reaction mixture was diluted with dichloromethane (14 mL) and filtered through celite pad. To the filtrate was added ethylchloroformate (2.1 mL) at 0° C. and stirred at room temperature for 16 h. The reaction mixture was neutralized with 1N aqueous hydrochloric acid (up to pH-4) and extracted with ethyl acetate (2×50 mL). The combined organic layer was washed with water (2×50 mL), brine (50 mL) and dried over sodium sulphate and was concentrated to give ethyl 2-(1-benzyl-6-oxo-1,6-dihydropyridin-3-yl)-2-oxoacetate (500 mg, 1.75 mmol, 57% yield) as yellow syrup. MS (ESI) m/z 286.12 [M+H]⁺.

D. Ethyl 2-(1-benzyl-6-oxo-1,6-dihydropyridin-3-yl)-2,2-difluoroacetate

To ethyl 2-(1-benzyl-6-oxo-1,6-dihydropyridin-3-yl)-2-oxoacetate (500 mg, 1.75 mmol) was added diethyl amino sulfur trifluoride (1.5 mL) at 0° C. and stirred at room temperature for 16 h. The reaction mixture was neutralized with aqueous saturated sodium bicarbonate (up to pH-8) and extracted with ethyl acetate (3×50 mL). The combined organic layers were washed with water (2×25 mL), brine (25 mL), dried over sodium sulphate and concentrated to afford ethyl 2-(1-benzyl-6-oxo-1,6-dihydropyridin-3-yl)-2,2-difluoroacetate (450 mg, 1.46 mmol, 84% yield). MS (ESI) m/z 265.07 [M+1]⁺.

E. 2-(1-Benzyl-6-oxo-1,6-dihydropyridin-3-yl)-2,2-difluoroacetic acid

To a stirred solution of ethyl 2-(1-benzyl-6-oxo-1,6-dihydropyridin-3-yl)-2,2-difluoroacetate (400 mg, 1.302 mmol) in tetrahydrofuran:methanol:water mixture (10 mL, 1:1:1) was added lithium hydroxide monohydrate (112 mg, 3.906 mmol) and stirred at room temperature for 2 h. The reaction mixture was concentrated and the residue was neutralized with saturated potassium bisulphate (20 mL) and extracted with ethyl acetate (2×25 mL). The combined organic layers were washed with brine (25 mL), dried over sodium sulphate and concentrated to afford 2-(1-benzyl-6-oxo-1,6-dihydropyridin-3-yl)-2,2-difluoroacetic acid (350 mg, 1.254 mmol, 96% yield). MS (ESI) m/z 280.32 [M+1]⁺.

F. 2-(1-Benzyl-6-oxo-1,6-dihydropyridin-3-yl)-N-((2-(2,6-dioxopiperidin-3-yl)-1-oxoisoindolin-5-yl)methyl)-2,2-difluoroacetamide To a cold (0° C.) stirred solution of 2-(1-benzyl-6-oxo-1,6-dihydropyridin-3-yl)-2,2-difluoroacetic acid (279 mg, 1.294 mmol) in pyridine (10 mL) was added phosphoryl chloride (0.36 mL, 3.894 mmol) drop wise and stirred at 0° C. for 1 h and then added 3-(5-(aminomethyl)-1-oxoisoindolin-2-yl)piperidine-2,6-dione hydrochloride (400 mg, 1.294 mmol) and stirred at room temperature for 1 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by Reveleris C-18 reversed phase column chromatography using 50-55% acetonitrile in aqueous formic acid (0.1%) to afford 2-(1-benzyl-6-oxo-1,6-dihydropyridin-3-yl)-N-((2-(2,6-dioxopiperidin-3-yl)-1-oxoisoindolin-5-yl)methyl)-2,2-difluoroacetamide (80 mg, 0.148 mmol, 11% yield) as an off white solid. MS (ESI) m/z 535.09 [M+1]⁺. ¹H NMR (300 MHz, DMSO-d₆) δ (ppm) 10.99 (s, 1H), 9.62 (br t, J=5.9 Hz, 1H), 8.18 (br s, 1H), 7.68 (d, J=7.8 Hz, 1H), 7.56 (dd, J=2.7, 9.5 Hz, 1H), 7.44 (s, 1H), 7.40-7.24 (m, 6H), 5.16 (s, 1H), 5.10 (br dd, J=4.9, 13.2 Hz, 1H), 4.46 (br d, J=5.9 Hz, 1H), 4.41 (br d, J=17.6 Hz, 1H), 4.27 (br d, J=17.6 Hz, 1H), 2.97-2.85 (m, 1H), 2.69-2.56 (m, 1H), 2.43-2.30 (m, 1H), 2.02-1.98 (m, 1H).

Example 102

N-((2-(2,6-Dioxopiperidin-3-yl)-1-oxoisoindolin-5-yl)methyl)-2,2-difluoro-2-(5-methoxypyridin-2-yl)acetamide

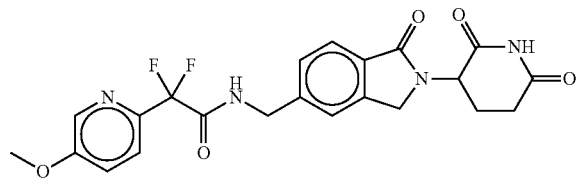

A. 2-Iodo-5-methoxypyridine

To a stirred solution of 2-bromo-5-methoxypyridine (2 g, 10.63 mmol) in 1,4-dioxane (20 mL) was added sodium iodide (3.3 g, 21.27 mmol), copper iodide (100 mg, 0.53 mmol), trans-N,N'-dimethylcyclohexane-1,2-diamine (150 mg, 1.16 mmol) at room temperature and stirred at 110° C. for 16 h in sealed tube. The reaction mixture was quenched with water (20 mL) and extracted with ethyl acetate (3×20 mL). The combined organic layers were washed with water (2×10 mL), brine (10 mL), dried over sodium sulphate and concentrated to afford 2-iodo-5-methoxypyridine (1.1 g, 4.46 mmol, 47% yield) as brown liquid. GCMS (m/z) 235.0 [M]⁺.

B. Ethyl 2,2-difluoro-2-(5-methoxypyridin-2-yl)acetate

To a stirred solution of 2-iodo-5-methoxypyridine (1 g, 4.32 mmol) in dimethyl sulfoxide (20 mL) was added ethyl 2-bromo-2,2-difluoroacetate (1.1 mL, 8.65 mmol), copper (0.73 g, 11.20 mmol) and stirred for 16 h at 50° C. The reaction mixture was neutralized with aqueous saturated ammonium chloride solution and extracted with ethyl acetate (3×50 mL). The combined organic layers were washed with water (2×10 mL), brine (10 mL), dried over sodium sulphate and concentrated to afford ethyl 2,2-difluoro-2-(5-methoxypyridin-2-yl)acetate (700 mg, 3.03 mmol, 71%) as a brown liquid. GCMS (m/z) 231.1.

C. 2,2-Difluoro-2-(5-methoxypyridin-2-yl)acetic acid

To a cold (0° C.) stirred solution of ethyl 2,2-difluoro-2-(5-methoxypyridin-2-yl)acetate (600 mg, 2.59 mmol) in ethanol/tetrahydrofuran/water mixture (9 mL, 1:1:1) was added lithium hydroxide monohydrate (327 mg, 7.79 mmol) and stirred at room temperature for 2 h. The reaction mixture was concentrated and the residue was neutralized with 10% aqueous potassium bisulphate (10 mL) and extracted with ethyl acetate (2×30 mL). The combined organic layers were washed with brine (10 mL), dried over sodium sulphate and concentrated to afford 2,2-difluoro-2-(5-methoxypyridin-2-yl)acetic acid (450 mg, 2.21 mmol, 85% yield) as a brown semi solid. MS (ESI) m/z 204.23 [M+1]⁺.

D. N-((2-(2,6-Dioxopiperidin-3-yl)-1-oxoisoindolin-5-yl)methyl)-2,2-difluoro-2-(5-methoxypyridin-2-yl)acetamide To a cold (0° C.) stirred solution of 2,2-difluoro-2-(5-methoxypyridin-2-yl)acetic acid (300 mg, 1.47 mmol) and 3-(5-(aminomethyl)-1-oxoisoindolin-2-yl)piperidine-2,6-dione hydrochloride (360 mg, 1.18 mmol) in N,N-dimethylformamide (20 mL) was added N,N-diisopropylethylamine (0.8 mL, 2.20 mmol) followed by 1-[Bis(dimethylamino)methylene]-1H-1,2,3-triazolo[4,5-b]pyridinium 3-oxid hexafluorophosphate (670 mg, 4.41 mmol) and stirred at room temperature for 16 h. The reaction mixture was diluted with water (70 mL) and extracted with ethyl acetate (2×20 mL). The combined organic layers were washed with brine (30 mL), dried over sodium sulphate and concentrated. The resultant residue was purified by Reveleris C-18 reversed phase column using 57% acetonitrile in aqueous formic acid (0.1%) to afford N-((2-(2,6-dioxopiperidin-3-yl)-1-oxoisoindolin-5-yl)methyl)-2,2-difluoro-2-(5-methoxypyridin-2-yl)acetamide (58 mg, 0.12 mmol, 8% yield) as an off-white solid. MS (ESI) m/z 459.20 [M+1]$^+$. $^1$H NMR (300 MHz, DMSO-d$_6$) δ 10.99 (s, 1H), 9.61-9.53 (m, 1H), 8.41 (br d, J=2.9 Hz, 1H), 7.72 (dd, J=8.3, 11.2 Hz, 2H), 7.57 (dd, J=2.9, 8.8 Hz, 1H), 7.52 (s, 1H), 7.45 (br d, J=8.3 Hz, 1H), 5.11 (br dd, J=4.9, 13.2 Hz, 1H), 4.53-4.27 (m, 4H), 3.89 (s, 3H) 2.98-2.85 (m, 1H), 2.69-2.56 (m, 1H), 2.44-2.31 (m, 1H), 2.06-1.95 (m, 1H).

Example 103

N-((2-(2,6-Dioxopiperidin-3-yl)-1-oxoisoindolin-5-yl)methyl)-2,2-difluoro-2-(1-methyl-6-oxo-1,6-dihydropyridin-3-yl)acetamide

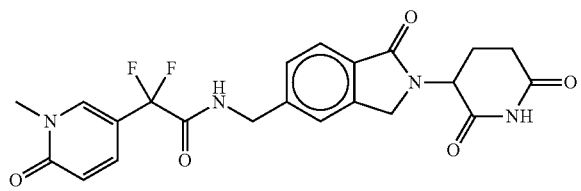

A. 6-Hydroxy-N-methoxy-N-methylnicotinamide

To a stirred solution of 6-hydroxynicotinic acid (10 g, 45.24 mmol) in tetrahydrofuran (100 mL) was added EDC.HCl (13.01 g, 67.87 mmol), HOBT (10.39 g, 67.87 mmol), N,O-dimethyl hydroxylamine HCl (5.29 g, 67.87 mmol), N,N-diisopropylethylamine (31.55 mL, 180.99 mmol) sequentially and stirred at room temperature for 16 h. The reaction mixture was diluted with water (100 mL) and extracted with ethyl acetate (3×500 mL). The combined organic layers were washed with brine (50 mL), dried over sodium sulphate and concentrated. The resultant residue was purified by column chromatography (100-200 silica) using 5% methanol:dichloromethane to afford 6-hydroxy-N-methoxy-N-methylnicotinamide (8 g, 43.95 mmol, 96% yield). LCMS (ESI) m/z 183.0 [M+1]$^+$.

B. N-Methoxy-N,1-dimethyl-6-oxo-1,6-dihydropyridine-3-carboxamide

To a stirred solution of 6-hydroxy-N-methoxy-N-methylnicotinamide (8 g, 43.95 mmol) in N,N-dimethylformamide was added methyl iodide (3.01 mL, 48.35 mmol), potassium carbonate (18.19 g, 131.86 mmol) at room temperature and stirred for 3 h. The reaction mixture was diluted with water (100 mL) and extracted with ethyl acetate (3×500 mL). The combined organic layers were washed with brine (50 mL), dried over sodium sulphate and concentrated. The resultant residue was purified by column chromatography (100-200 silica) using 4% methanol:dichloromethane to afford N-methoxy-N, 1-dimethyl-6-oxo-1,6-dihydropyridine-3-carboxamide (6 g, 30.61 mmol, 69% yield). LCMS (ESI) m/z 197.29 [M+1]$^+$.

C. 5-Acetyl-1-methylpyridin-2(1H)-one

To a stirred solution of N-methoxy-N, 1-dimethyl-6-oxo-1,6-dihydropyridine-3-carboxamide (6 g, 30.61 mmol) in dry tetrahydrofuran (50 mL) was added methyl lithium 1.6 M in diethyl ether (2.67 mL), at 0° C. for 3 h. The reaction mixture was quenched with saturated ammonium chloride solution and extracted with ethyl acetate (2×500 mL). The combined organic layers were washed with brine (50 mL), dried over sodium sulphate and concentrated The resultant residue was purified by column chromatography (100-200 silica) using 7-10% methanol:dichloromethane to afford 5-acetyl-1-methylpyridin-2(1H)-one (4 g, 26.49 mmol, 86% yield). MS (ESI) m/z 152.14 [M+1]$^+$.

D. Ethyl 2-(1-methyl-6-oxo-1,6-dihydropyridin-3-yl)-2-oxoacetate

To a stirred solution of 5-acetyl-1-methylpyridin-2(1H)-one (4 g, 26.49 mmol) in pyridine (50 mL) was added selenium dioxide (7.35 g, 66.22 mmol) and stirred for 16 h at 100° C. The reaction mixture was diluted with dichloromethane (50 mL) and filtered through Celite pad. To the filtrate was added ethyl chloroformate (12 mL) at 0° C. and stirred for 2 h. To the resultant reaction mixture was added water (30 mL) and extracted with ethyl acetate (3×100 mL). The combined organic layers were washed with water (2×100 mL), brine (100 mL), dried over sodium sulphate and concentrated. The resultant residue was purified by column chromatography (100-200 silica) using 15-20% ethyl acetate in pet ether to afford ethyl 2-(1-methyl-6-oxo-1,6-dihydropyridin-3-yl)-2-oxoacetate (2 g, 9.56 mmol, 36% yield). LCMS (ESI) m/z 210.29 [M+1]$^+$.

E. Ethyl 2,2-difluoro-2-(1-methyl-6-oxo-1,6-dihydropyridin-3-yl)acetate

To ethyl 2-(1-methyl-6-oxo-1,6-dihydropyridin-3-yl)-2-oxoacetate (2 g, 9.56 mmol) was added diethylaminosulfur trifluoride (3.2 mL, 23.92 mmol) and stirred for 12 h at room temperature. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated to afford ethyl 2,2-difluoro-2-(1-methyl-6-oxo-1,6-dihydropyridin-3-yl)acetate (1 g, 4.32 mmol, 45%) as a liquid. LCMS (ESI) m/z 232.33[M+1]$^+$.

F. 2,2-Difluoro-2-(1-methyl-6-oxo-1,6-dihydropyridin-3-yl)acetic acid

To a cold (0° C.) stirred solution of ethyl 2,2-difluoro-2-(1-methyl-6-oxo-1,6-dihydropyridin-3-yl)acetate (1 g, 4.32 mmol) in tetrahydrofuran:Methanol:water mixture (30 mL, 1:1:1) was added lithium hydroxide (0.909 g, 21.64 mmol) and stirred at room temperature for 6 h. The reaction mixture was concentrated and the residue was neutralized with 10% aqueous hydrochloric acid (10 mL) and extracted with ethyl acetate (2×20 mL). The combined organic layers were washed with brine (20 mL), dried over sodium sulphate and concentrated to afford 2,2-difluoro-2-(1-methyl-6-oxo-1,6-dihydropyridin-3-yl)acetic acid (500 g, 2.46 mmol, 56% yield) as off white solid. LCMS (ESI) m/z 204.35 [M+1]+.

G. N-((2-(2,6-Dioxopiperidin-3-yl)-1-oxoisoindolin-5-yl)methyl)-2,2-difluoro-2-(1-methyl-6-oxo-1,6-dihydropyridin-3-yl)acetamide To a cold (0° C.) stirred solution of 2,2-difluoro-2-(1-methyl-6-oxo-1,6-dihydropyridin-3-yl)acetic acid (196.6 mg, 0.968 mmol) in pyridine was added phosphoryl chloride (0.27 mL, 2.906 mmol) dropwise and stirred at 0-5° C. for 1 h. To this reaction mixture was added 3-(5-(aminomethyl)-1-oxoisoindolin-2-yl)piperidine-2,6-dione hydrochloride (300 mg, 0.968 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The resultant residue was purified by Reveleris C-18 reversed phase Grace column chromatography using 40-60% acetonitrile in aqueous formic acid (0.1%) to afford N-((2-(2,6-dioxopiperidin-3-yl)-1-oxoisoindolin-5-yl)methyl)-2,2-difluoro-2-(1-methyl-6-oxo-1,6-dihydropyridin-3-yl)acetamide (60 mg, 0.131 mmol, 13% yield) as an off white solid. MS (ESI) m/z 459.16 [M+1]+. 1H NMR (300 MHz, DMSO-d6) δ ppm 10.98 (s, 1H), 9.58 (br t, J=5.85 Hz, 1H), 8.05 (s, 1H), 7.70 (d, J=7.68 Hz, 1H), 7.58-7.35 (m, 3H), 6.49 (d, J=9.50 Hz, 1H), 5.11 (dd, J=13.16, 5.12 Hz, 1H), 4.5-4.35 (m, 3H), 4.35-4.25 (d, 1H), 3.53-3.45 (s, 3H), 2.98-2.82 (m, 1H), 2.67-2.52 (m, 1H), 2.45-2.30 (m, 1H), 2.05-1.95 (m, 1H).

Example 104

2-(5-Tert-butylpyridin-2-yl)-N-((2-(2,6-dioxopiperidin-3-yl)-1-oxoisoindolin-5-yl)methyl)-2,2-difluoroacetamide

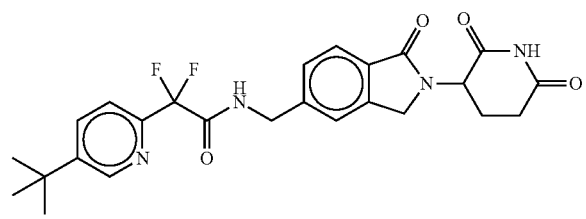

A. tert-Butyl 5-bromopyridin-2-ylcarbamate

To a cold (0° C.) stirred solution of 5-bromopyridin-2-amine (20 g, 116.30 mmol) in dichloromethane (200 mL) was added triethylamine (34 mL, 255.87 mmol), di-tert-butyl dicarbonate (35 mL, 151.19 mmol) followed by 4-dimethylaminopyridine (1.4 g, 11.63 mmol) and stirred at room temperature for 2 h. The reaction mixture was quenched with water and extracted with dichloromethane (2×200 mL). The combined organic layers were washed with water (200 mL), brine (200 mL), dried over sodium sulfate and concentrated. The resultant residue was purified by column chromatography with 5% ethyl acetate in pet ether as eluent to afford tert-butyl 5-bromopyridin-2-ylcarbamate (25.0 g, 91.91 mmol, 79% yield). LCMS (ESI) m/z 219.08 [M+1]+.

B. tert-Butyl 5-tert-butylpyridin-2-ylcarbamate

To a cold (−78° C.) stirred solution of copper cyanide (33 g, 367.64 mmol) in dry tetrahydrofuran (1200 mL) was added tert-butyl magnesium chloride (2.0M in tetrahydrofuran) (362 mL, 735.29 mmol) slowly and stir for 1 h. To this reaction mixture was added tert-butyl 5-bromopyridin-2-ylcarbamate (25.0 g, 91.91 mmol) at −78° C., stirred for 2 h and allowed to stir at room temperature for 16 h. The reaction mixture was quenched with aqueous ammonium chloride solution and extracted with ethyl acetate (3×200 mL). The combined organic layers were washed with water (200 mL), brine (200 mL), dried over sodium sulfate and concentrated. The resultant residue was purified by column chromatography with the eluent of 10% ethyl acetate in pet ether to afford tert-butyl 5-tert-butylpyridin-2-ylcarbamate (15.0 g, 60.00 mmol, 65% yield). LCMS (ESI) m/z 251.48 [M+1]+.

C. 2-Bromo-5-tert-butylpyridine

To a cold (0° C.) stirred solution of tert-butyl 5-tert-butylpyridin-2-ylcarbamate (13.0 g, 52.00 mmol) in aqueous hydrobromic acid (150 mL) was added sodium nitrite (9.3 g, 135.2 mmol) slowly and stir for 15 min. To this reaction mixture was added liquid bromine (8.0 mL, 156.00 mmol) and stirred at room temperature for 4 h. The reaction mixture was quenched with aqueous sodium hydroxide solution and was extracted with ethyl acetate (3×150 mL). The combined organic layers were washed with water (100 mL), brine (100 mL), dried over sodium sulfate and concentrated. The resultant residue was purified by column chromatography with the eluent of 5% ethyl acetate in pet ether to afford 2-bromo-5-tert-butylpyridine (3.2 g, 15.02 mmol, 29% yield). LCMS (ESI) m/z 214.11 [M+1]+.

D. 5-tert-Butyl-2-iodopyridine

To a stirred solution of 2-bromo-5-tert-butylpyridine (3.2 g, 15.02 mmol) in 1,4-dioxane (10 mL) was added sodium iodide (4.5 g, 30.04 mmol), copper iodide (145 mg, 0.75 mmol), trans-N,N'-dimethylcyclohexane-1,2-diamine (235 mg, 1.65 mmol) at room temperature and stirred at 100° C. for 16 h in sealed tube. The reaction mixture was quenched with water (100 mL) and extracted with ethyl acetate (3×100 mL). The combined organic layers were washed with water (2×50 mL), brine (50 mL), dried over sodium sulphate and concentrated to afford 5-tert-butyl-2-iodopyridine (3.5 g, 13.40 mmol, 89% yield). GCMS (m/z) 261.0.

E. Ethyl 2-(5-tert-butylpyridin-2-yl)-2,2-difluoroacetate

To a stirred solution of 5-tert-butyl-2-iodopyridine (3.5 g, 13.40 mmol) in dimethylsulfoxide (30 mL) was added ethyl 2-bromo-2,2-difluoroacetate (5.4 g, 26.81 mmol) followed by copper (2.2 g, 34.86 mmol) and stirred at 55° C. for 5 h. The reaction mixture was quenched with aqueous ammonium chloride solution and was extracted with ethyl acetate (3×100 mL). The combined organic layers were washed with water (100 mL), brine (100 mL), dried over sodium sulfate, filtered and concentrated to afford ethyl 2-(5-tertbutylpyridin-2-yl)-2,2-difluoroacetate (2.8 g, 10.89 mmol, 81% yield). LCMS (ESI) m/z 258.17 [M+1]⁺.

F. 2-(5-tert-Butylpyridin-2-yl)-2,2-difluoroacetic acid

To a stirred solution of ethyl 2-(5-tert-butylpyridin-2-yl)-2,2-difluoroacetate (2.8 g, 10.89 mmol) in methanol-tetrahydrofuran-water mixture (15 mL, 1:1:1) was added lithium hydroxide monohydrate (1.4 g, 32.68 mmol) and stirred at room temperature for 2 h. The reaction mixture was diluted with water (50 mL) and acidified with aqueous potassium bisulfate solution and extracted with ethyl acetate (3×50 mL). The combined organic layers were washed with brine (50 mL), dried over sodium sulfate, filtered was concentrated to afford 2-(5-tert-butylpyridin-2-yl)-2,2-difluoroacetic acid (2.0 g, 8.73 mmol, 80% yield). LCMS (ESI) m/z 230.32 [M+1]⁺.

G. 2-(5-Tert-butylpyridin-2-yl)-N-((2-(2,6-dioxopiperidin-3-yl)-1-oxoisoindolin-5-yl)methyl)-2,2-difluoroacetamide To a cold (0° C.) stirred solution of 2-(5-tert-butylpyridin-2-yl)-2,2-difluoroacetic acid (2.0 g, 8.73 mmol (300 mg, 1.31 mmol) in pyridine (5 mL) was added phosphoryl chloride (0.4 mL, 3.87 mmol) dropwise and stirred at 0-5° C. for 1 h, and then added 3-(5-(aminomethyl)-1-oxoisoindolin-2-yl)piperidine-2,6-dione hydrochloride (404 mg, 1.31 mmol) and stirred at room temperature for 1 h. The reaction mixture was neutralized with aqueous saturated sodium bicarbonate (up to pH-8) and extracted with ethyl acetate (3×50 mL). The combined organic layers were washed with water (2×30 mL), brine (30 mL) and dried over sodium sulphate and was concentrated to afford 2-(5-tert-butylpyridin-2-yl)-N-((2-(2,6-dioxopiperidin-3-yl)-1-oxoisoindolin-5-yl)methyl)-2,2-difluoroacetamide (75 mg, 0.15 mmol, 12% yield) as an off white solid. LCMS (ESI) m/z 485.17 [M+1]⁺. ¹H NMR (400 MHz, DMSO-d₆) δ=10.98 (br s, 1H), 9.62 (br t, J=6.1 Hz, 1H), 8.78 (d, J=2.4 Hz, 1H), 8.02 (dd, J=2.4, 8.3 Hz, 1H), 7.71 (dd, J=2.2, 8.1 Hz, 1H), 7.52 (s, 1H), 7.46 (d, J=7.8 Hz, 1H), 5.11 (dd, J=4.9, 13.2 Hz, 1H), 4.53-4.28 (m, 4H), 2.99-2.84 (m, 1H), 2.69-2.55 (m, 1H), 2.45-2.30 (m, 1H), 2.06-1.94 (m, 1H), 1.35 (s, 9H).

Example 105

2-(5-Cyclopropylpyridin-2-yl)-N-((2-(2,6-dioxopiperidin-3-yl)-1-oxoisoindolin-5-yl)methyl)-2,2-difluoroacetamide

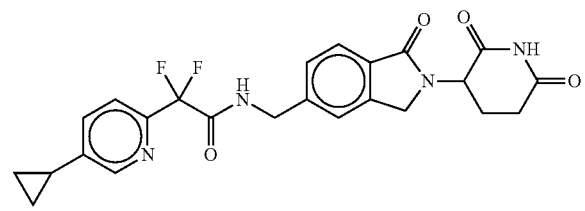

A. 5-Cyclopropylpyridin-2-amine

To a stirred and degassed solution of 5-bromopyridin-2-amine (5 g, 28.90 mmol) in 10% water:toluene mixture (100 mL) was added cyclopropylboronic acid (3.73 g, 43.35 mmol) followed by potassium phosphate (12.25 g, 57.80 mmol), tricyclohexylphosphine (794 mg, 2.89 mmol) and continued degassing for 10 min. Then, palladium(II) acetate (650 mg, 2.89 mmol) was added, degassed for additional 10 min and heated at 110° C. for 3 h. The reaction mixture was cooled to room temperature and filtered through the Celite pad. To the filtrate was added cold water (100 mL) and extracted with ethyl acetate (3×100 mL). The combined organic layers were washed with water (2×100 mL), brine (100 mL), dried over sodium sulphate and concentrated to afford 5-cyclopropylpyridin-2-amine (3.0 g, 22.39 mmol, 77% yield). GCMS (m/z) 134.1 [M]⁺.

B. 2-Bromo-5-cyclopropylpyridine

To a cold (0° C.) stirred solution of 5-cyclopropylpyridin-2-amine (3.0 g, 22.39 mmol) in 47% aqueous hydrobromic acid (25 mL) was added a solution of sodium nitrite (4.0 g, 58.21 mmol) and stirred at the same temperature for 30 min. To this reaction mixture was then added bromine (10.75 g, 67.16 mmol) and stirred at room temperature for 2 h. The reaction mixture poured into water (100 mL) and extracted with ethyl acetate (3×100 mL). The combined organic layers were washed with brine (100 mL), dried over sodium sulphate and concentrated. The resultant residue was purified by combi-column chromatography, using 15-20% ethyl acetate in pet ether to afford 2-bromo-5-cyclopropylpyridine (1.2 g, 6.09 mmol, 27% yield). GCMS (m/z) 197.0 [M]⁺.

C. 5-Cyclopropyl-2-iodopyridine

To a stirred solution of 2-bromo-5-cyclopropylpyridine (1.2 g, 6.09 mmol) in 1,4-dioxane (25 mL) was added sodium iodide (1.83 g, 12.18 mmol), copper iodide (58 mg, 0.30 mmol), trans-N,N'-dimethylcyclohexane-1,2-diamine (95 mg, 0.67 mmol) at room temperature and stirred at 110° C. for 16 h. The reaction mixture was quenched with water (100 mL) and extracted with ethyl acetate (3×100 mL). The combined organic layers were washed with water (2×100 mL), brine (100 mL), dried over sodium sulphate and concentrated to afford 5-cyclopropyl-2-iodopyridine (1.2 g, 4.90 mmol, 81%). GCMS (m/z) 245.0[M]⁺.

D. Ethyl 2-(5-cyclopropylpyridin-2-yl)-2,2-difluoroacetate

To a stirred solution of 5-cyclopropyl-2-iodopyridine (1.2 g, 4.90 mmol) in dimethyl sulfoxide (12 mL) was added copper (809 mg, 12.73 mmol) and ethyl 2-bromo-2,2-difluoroacetate (1.48 g, 7.35 mmol) at room temperature and stirred at 55° C. for 2 h. To the reaction mixture was added aqueous saturated ammonium chloride (50 mL) solution and extracted with ethyl acetate (2×100 mL). The combined organic layers were washed with water (2×100 mL), brine (100 mL), dried over sodium sulphate and concentrated to afford ethyl 2-(5-cyclopropylpyridin-2-yl)-2,2-difluoroacetate (1.0 g, 4.15 mmol, 85%). ¹H NMR (400 MHz, CDCl₃) δ 8.44 (br s, 1H), 7.61 (br s, 1H), 7.43 (d, J=8.0 Hz, 1H), 4.42-4.30 (m, 2H), 2.04-1.91 (m, 1H), 1.40-1.24 (m, 3H), 1.12-1.09 (m, 2H), 0.84-0.77 (m, 2H).

E. 2-(5-Cyclopropylpyridin-2-yl)-2,2-difluoroacetic acid

To a stirred solution of ethyl 2-(5-cyclopropylpyridin-2-yl)-2,2-difluoroacetate (1.0 g, 4.15 mmol) in tetrahydrofuran:methanol:water mixture (30 mL, 1:1:1) was added lithium hydroxide monohydrate (523 mg, 12.45 mmol) and stirred at room temperature for 4 h. The reaction mixture was concentrated and the residue was neutralized with saturated potassium bisulphate (25 mL) and extracted with ethyl acetate (2×50 mL). The combined organic layers were washed with brine (50 mL), dried over sodium sulphate and concentrated to afford 2-(5-cyclopropylpyridin-2-yl)-2,2-difluoroacetic acid (500 mg, 2.35 mmol, 50% yield). MS (ESI) m/z 214.3 [M–1]$^{-ve}$.

F. 2-(5-Cyclopropylpyridin-2-yl)-N-((2-(2,6-dioxopiperidin-3-yl)-1-oxoisoindolin-5-yl)methyl)-2,2-difluoroacetamide To a cold (0° C.) stirred solution of 2-(5-cyclopropylpyridin-2-yl)-2,2-difluoroacetic acid (300 mg, 1.41 mmol) in pyridine (20 mL) was added phosphoryl chloride (646 mg, 4.22 mmol) dropwise and stirred at 0-5° C. for 30 min. To this reaction mixture was then added 3-(5-(aminomethyl)-1-oxoisoindolin-2-yl)piperidine-2,6-dione hydrochloride (435 mg, 1.41 mmol) and stirred at room temperature for 1 h. The reaction mixture was neutralized with aqueous saturated sodium bicarbonate (up to pH-8) and extracted with ethyl acetate (2×100 mL). The combined organic layers were washed with water (100 mL), brine (100 mL), dried over sodium sulphate and concentrated. The resultant residue was purified by Reveleris C-18 reversed phase column chromatography using 60-65% acetonitrile in aqueous formic acid (0.1%) to afford 2-(5-cyclopropylpyridin-2-yl)-N-((2-(2,6-dioxopiperidin-3-yl)-1-oxoisoindolin-5-yl)methyl)-2,2-difluoroacetamide (140 mg, 0.30 mmol, 21% yield) as an off-white solid. MS (ESI) m/z 469.06 [M+1]$^+$. $^1$H NMR (400 MHz, DMSO-d$_6$) δ 10.99 (s, 1H), 9.58 (t, J=6.1 Hz, 1H), 8.53 (s, 1H), 7.71 (d, J=7.8 Hz, 1H), 7.66-7.60 (m, 2H), 7.51 (s, 1H), 7.46 (d, J=8.3 Hz, 1H), 5.11 (dd, J=4.9, 13.2 Hz, 1H), 4.56-4.28 (m, 4H), 3.08-2.85 (m, 1H), 2.67-2.56 (m, 1H), 2.45-2.32 (m, 1H), 2.10-1.96 (m, 2H), 1.13-1.03 (m, 2H), 0.89-0.79 (m, 2H).

Example 106

N-((2-(2,6-Dioxopiperidin-3-yl)-1-oxoisoindolin-5-yl)methyl)-2,2-difluoro-2-(5-isopropoxypyridin-2-yl)acetamide

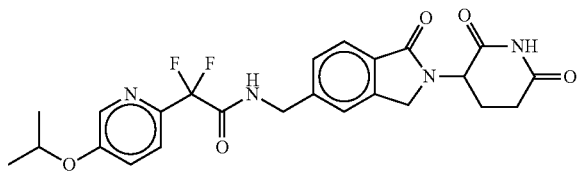

A. 2-Bromo-5-isopropoxypyridine

To a stirred solution of 6-bromopyridin-3-ol (2 g, 11.49 mmol) in N,N-dimethylformamide (20 mL) was added 2-iodopropane (1.4 mL, 13.79 mmol), potassium carbonate (4.7 g, 34.47 mmol) and stirred at 80° C. for 6 h. The reaction mixture was quenched with water and extracted with ethyl acetate (3×50 mL). The combined organic layers were washed with water (2×20 mL), brine (20 mL), dried over sodium sulphate and concentrated to afford 2-bromo-5-isopropoxypyridine (1.4 g, 6.48 mmol, 58%) as a pale yellow solid. MS (ESI) m/z 216.20

B. 2-Iodo-5-isopropoxypyridine

To a stirred solution of 2-bromo-5-isopropoxypyridine (1.4 g, 6.48 mmol) in 1,4-dioxane (30 mL) in a sealed tube, was added sodium iodide (1.9 g, 12.96 mmol), copper iodide (61 mg, 0.32 mmol), trans-N,N'-dimethylcyclohexane-1,2-diamine (101 mg, 0.71 mmol) at room temperature and stirred at 110° C. for 16 h. The reaction mixture was quenched with water (30 mL) and extracted with ethyl acetate (3×30 mL). The combined organic layers were washed with water (2×20 mL), brine (20 mL), dried over sodium sulphate and concentrated to afford 2-iodo-5-isopropoxypyridine (1 g, 3.83 mmol, 58% yield) as brown solid. GCMS (m/z) 263.0.

C. Ethyl 2,2-difluoro-2-(5-isopropoxypyridin-2-yl)acetate

To a stirred solution of 2-iodo-5-isopropoxypyridine (1 g, 3.80 mmol) in dimethyl sulfoxide (10 mL) was added ethyl 2-bromo-2,2-difluoroacetate (1 mL, 7.60 mmol), copper (0.6 g, 10.09 mmol) and stirred for 16 h at 50° C. The reaction mixture was neutralized with aqueous saturated ammonium chloride solution and extracted with ethyl acetate (3×40 mL). The combined organic layers were washed with water (2×20 mL), brine (20 mL), dried over sodium sulphate and concentrated to afford ethyl 2,2-difluoro-2-(5-isopropoxypyridin-2-yl)acetate (500 mg, 2.30 mmol, 60%) as a brown liquid. MS (m/z) 259.1.

D. 2,2-Difluoro-2-(5-isopropoxypyridin-2-yl)acetic acid

To a cold (0° C.) stirred solution of 2,2-difluoro-2-(5-isopropoxypyridin-2-yl)acetate (500 mg, 2.32 mmol) in methanol/tetrahydrofuran/water mixture (9 mL, 1:1:1) was added lithium hydroxide monohydrate (280 mg, 6.91 mmol) and stirred at room temperature for 2 h. The reaction mixture was concentrated and the residue was neutralized with 10% aqueous potassium bisulphate (10 mL) and extracted with ethyl acetate (2×30 mL). The combined organic layers were washed with brine (10 mL), dried over sodium sulphate, concentrated to afford 2,2-difluoro-2-(5-isopropoxypyridin-2-yl)acetic acid (350 mg, 1.51 mmol, 79% yield) as a brown semi solid. MS (ESI) m/z 232.24

E. N-((2-(2,6-Dioxopiperidin-3-yl)-1-oxoisoindolin-5-yl)methyl)-2,2-difluoro-2-(5-isopropoxypyridin-2-yl)acetamide To a cold (0° C.) stirred solution of 3-(6-((methylamino)methyl)-1-oxoisoindolin-2-yl)piperidine-2,6-dione hydrochloride (400 mg, 1.29 mmol) and 2,2-difluoro-2-(5-isopropoxypyridin-2-yl)acetic acid (300 mg, 1.29 mmol) in N,N-dimethylformamide (20 mL) was added N,N-diisopropylethylamine (0.7 mL, 3.86 mmol) followed by 1-[Bis(dimethylamino)methylene]-1H-1,2,3-triazolo[4,5-b]pyridinium 3-oxid hexafluorophosphate (735 mg, 1.93 mmol) and stirred at room temperature for 16 h. The reaction mixture was diluted with water (70 mL) and extracted with ethyl acetate (2×40 mL). The combined organic layers were washed with brine (30 mL), dried over sodium sulphate and concentrated. The resultant residue was purified by Reveleris C-18 reversed phase column using 58% acetonitrile in aqueous formic acid (0.1%) to afford N-((2-(2,6-dioxopiperidin-3-yl)-1-oxoisoindolin-5-yl)methyl)-2,2-difluoro-2-(5-isopropoxy pyridin-2-yl)acetamide (70 mg, 0.14 mmol, 11% yield) as an off white solid. MS (ESI) m/z 487.20 [M+1]⁺. ¹H NMR (300 MHz, DMSO-d₆) δ 10.99 (s, 1H), 9.55 (br t, J=6.1 Hz, 1H), 8.36 (d, J=2.6 Hz, 1H), 7.76-7.66 (m, 2H), 7.60-7.50 (m, 2H), 7.45 (d, J=8.1 Hz, 1H), 5.11 (dd, J=4.8, 13.2 Hz, 1H), 4.80-4.75 (m, 1H), 4.65-4.26 (m, 4H), 3.02-2.83 (m, 1H), 2.75-2.54 (m, 1H), 2.46-2.305 (m, 1H), 2.06-1.94 (m, 1H), 1.31 (m, 6H).

Example 107

2-(5-Bromopyridin-2-yl)-N-((2-(2,6-dioxopiperidin-3-yl)-1-oxoisoindolin-5-yl)methyl)-2,2-difluoroacetamide

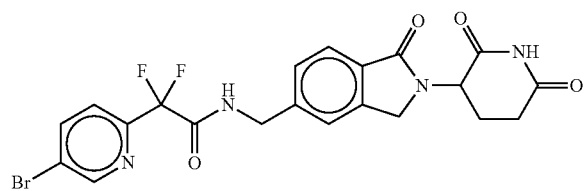

A. Ethyl 2-(5-bromopyridin-2-yl)-2,2-difluoroacetate

To a stirred solution of 5-bromo-2-iodopyridine (3 g, 10.56 mmol) in dimethylsulfoxide (20 mL) was added ethyl 2-bromo-2,2-difluoroacetate (3.13 g, 15.84 mmol) followed by copper powder (1.74 g, 27.46 mmol) at room temperature and stirred at 55° C. for 6 h. The reaction mixture was basified with aqueous saturated sodium bicarbonate solution and extracted with ethyl acetate (3×20 mL). The combined organic layers were washed with water (20 mL), brine (20 mL), dried over sodium sulfate and concentrated. The obtained crude was purified by silica gel column chromatography (20% ethyl acetate in pet ether) to afford ethyl 2-(5-bromopyridin-2-yl)-2,2-difluoroacetate (1.5 g, 5.35 mmol, 60%) as a colorless liquid. MS (ESI) m/z 280.2 [M+1]⁺.

B. 2-(5-Bromopyridin-2-yl)-2,2-difluoroacetic acid

To a stirred solution of ethyl 2-(5-bromopyridin-2-yl)-2,2-difluoroacetate (1.5 g, 5.37 mmol) in mixture of tetrahydrofuran:methanol:water (15 mL, 1:1:1) was added lithium hydroxide monohydrate (677 mg, 16.13 mmol) and stirred at room temperature for 4 h. The volatiles were removed under reduced pressure and the resultant crude product was dissolved in water (15 mL), washed with ethyl acetate (2×10 mL). Aqueous layer was acidified with 1N hydrochloride aqueous solution and extracted with ethyl acetate (3×15 mL). The combined organic layers were washed with brine (15 mL), dried over sodium sulfate and concentrated to afford 2-(5-bromopyridin-2-yl)-2,2-difluoroacetic acid (900 mg, 3.57 mmol, 69% yield) as semi-solid compound. MS (ESI) m/z 252.2 [M+H]⁺.

C. 2-(5-Bromopyridin-2-yl)-N-((2-(2,6-dioxopiperidin-3-yl)-1-oxoisoindolin-5-yl)methyl)-2,2-difluoroacetamide To a cold solution of 2-(5-bromopyridin-2-yl)-2,2-difluoroacetic acid (243 mg, 0.97 mmol) in pyridine (6 mL) was added phosphorus oxychloride (1.8 mL, 2.9 mmol) in drop wise and stirred at 0-5° C. for 1 h. Then, 3-(5-(aminomethyl)-1-oxoisoindolin-2-yl)piperidine-2,6-dione hydrochloride (300 mg, 0.97 mmol) was added and stirred at room temperature for 2 h. The reaction mixture was basified with saturated sodium bicarbonate solution and extracted with ethyl acetate (3×15 mL). The combined organic layers were washed with water (15 mL), brine (15 mL), dried over sodium sulfate, filtered and concentrated. The resultant residue was purified by Reveleris C-18 reversed phase column chromatography (50-55% acetonitrile in 0.1% aqueous formic acid (to afford 2-(5-bromopyridin-2-yl)-N-((2-(2,6-dioxopiperidin-3-yl)-1-oxoisoindolin-5-yl)methyl)-2,2-difluoroacetamide (33 mg, 0.065 mmol, 7% yield) as white solid. MS (ESI) m/z 507.8 [M+1]⁺. ¹H NMR (400 MHz, DMSO-d₆) δ 10.99 (s, 1H), 9.68 (t, J=4.5 Hz, 1H), 8.89 (d, J=1.6 Hz, 1H), 8.31 (dd, J=8.4, 2.4 Hz, 1H), 7.78 (d, J=8.4 Hz, 1H), 7.72 (d, J=8.0 Hz, 1H), 7.49 (s, 1H), 7.44 (d, J=8.0 Hz, 1H), 5.11 (dd, J=13.2, 5.2 Hz, 1H), 4.50 (d, J=6.4 Hz, 2H), 4.46 (d, J=17.9 Hz, 1H), 4.32 (d, J=17.6 Hz, 1H), 2.95-2.87 (m, 1H), 2.66-2.55 (m, 1H), 2.45-2.30 (m, 1H), 2.05-1.96 (m, 1H).

Example 108

N-((2-(2,6-dioxopiperidin-3-yl)-1-oxoisoindolin-5-yl)methyl)-2,2-difluoro-2-(4-fluoro-2-(trifluoromethoxy)phenyl)acetamide

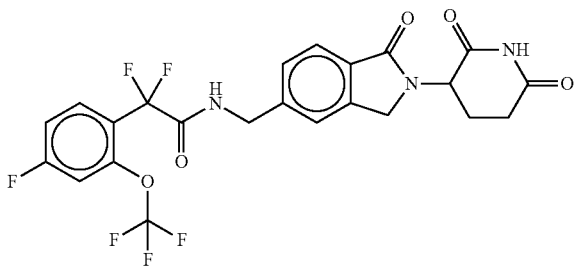

A. (2-Fluoro-6-(trifluoromethoxy)phenyl)trimethylsilane

To a cold (−78° C.) stirred solution of 1-fluoro-3-(trifluoromethoxy)benzene (2.0 g, 11.11 mmol) and TMEDA (1.3 mL, 11.11 mmol) in dry tetrahydrofuran (20 mL) was added sec-butyl lithium (1.4M in cyclohexane, 8 mL) and stirred for 2 h. To this reaction mixture was added trimethylsilyl chloride (1.81 g, 16.66 mmol) at −78° C. and stirred for 1 h at room temperature. The reaction mixture was quenched with aqueous ammonium chloride solution and extracted with diethylether (2×50 mL). The combined organic layers were washed with water (50 mL), brine (50 mL), dried over sodium sulfate and concentrated to afford (2-fluoro-6-(trifluoromethoxy)phenyl)trimethylsilane (1.8 g, 7.14 mmol, 64% yield). ¹H NMR (400 MHz, CDCl₃) δ (ppm) 7.35 (dt, J=6.6, 8.2 Hz, 1H), 7.05-7.00 (m, 1H), 6.92 (t, J=8.3 Hz, 1H), 0.41-0.33 (m, 9H).

B. (6-Fluoro-3-iodo-2-(trifluoromethoxy)phenyl)trimethylsilane

To a cold (−78° C.) stirred solution of 2,2,6,6-tetramethylpiperidine (897 mg, 6.34 mmol) in dry tetrahydrofuran (20 mL) was added n-butyl lithium (2.5M in n-hexane, 2.5 mL, 6.34 mmol) slowly, followed by (2-fluoro-6-(trifluoromethoxy)phenyl)trimethylsilane (1.6 g, 6.34 mmol) in tetrahydrofuran (5 mL) and stirred for 2 h at same temperature. Iodine (2.4 g, 9.52 mmol) in dry tetrahydrofuran (10 mL) was added to this reaction mixture at −78° C. and allowed to stir at 0° C. for 1 h. The reaction mixture was quenched with aqueous ammonium chloride solution and extracted with diethyl ether (2×50 mL). The combined organic layers were washed with water (50 mL), brine (50 mL), dried over sodium sulfate and concentrated to afford (6-fluoro-3-iodo-2-(trifluoromethoxy)phenyl)trimethylsilane (2.0 g, 5.29 mmol, 84% yield). GCMS (m/z) 378.1.

C. Ethyl 2,2-difluoro-2-(4-fluoro-2-(trifluoromethoxy)phenyl)acetate

To a stirred solution of (6-fluoro-3-iodo-2-(trifluoromethoxy)phenyl)trimethylsilane (2.0 g, 5.29 mmol) in dimethyl sulfoxide (30 mL) in sealed tube was added ethyl 2-bromo-2,2-difluoroacetate (2.1 g, 10.58 mmol) followed by copper (874 mg, 13.76 mmol) and stirred at 55° C. for 16 h. The reaction mixture was quenched with aqueous ammonium chloride solution and extracted with ethyl acetate (3×100 mL). The combined organic layers were washed with water (100 mL), brine (50 mL), dried over sodium sulfate, filtered and concentrated to afford ethyl 2,2-difluoro-2-(4-fluoro-2-(trifluoromethoxy)phenyl)acetate (1.5 g, 4.96 mmol, 94% yield). GCMS (m/z) 302.1.

D. 2,2-Difluoro-2-(4-fluoro-2-(trifluoromethoxy)phenyl)acetic acid

To a stirred solution of ethyl 2,2-difluoro-2-(4-fluoro-2-(trifluoromethoxy)phenyl)acetate (1.5 g, 4.96 mmol) in methanol:tetrahydrofuran:water mixture (15 mL, 1:1:1) was added lithium hydroxide monohydrate (1.4 g, 14.90 mmol) and stirred at room temperature for 2 h. The reaction mixture was diluted with water (50 mL), acidified with aqueous potassium bisulfate solution and extracted with ethyl acetate (3×50 mL). The combined organic layers were washed with brine (50 mL), dried over sodium sulfate, filtered was concentrated to afford 2,2-difluoro-2-(4-fluoro-2-(trifluoromethoxy)phenyl)acetic acid (1.0 g, 3.64 mmol, 73% yield). LCMS (ESI) m/z 273.26 [M−1]⁻.

E. N-((2-(2,6-dioxopiperidin-3-yl)-1-oxoisoindolin-5-yl)methyl)-2,2-difluoro-2-(4-fluoro-2-(trifluoromethoxy)phenyl)acetamide To a cold (0° C.) stirred solution of 2,2-difluoro-2-(4-fluoro-2-(trifluoromethoxy)phenyl)acetic acid (300 mg, 1.09 mmol) in pyridine (5 mL) was added phosphoryl chloride (0.3 mL, 3.28 mmol) dropwise and stirred at 0-5° C. for 1 h. 3-(5-(aminomethyl)-1-oxoisoindolin-2-yl)piperidine-2,6-dione hydrochloride (338 mg, 1.09 mmol) was added to this reaction mixture and stirred at room temperature for 1 h. The reaction mixture was neutralized with aqueous saturated sodium bicarbonate (up to pH-8) and extracted with ethyl acetate (3×50 mL). The combined organic layers were washed with water (2×30 mL), brine (30 mL) and dried over sodium sulphate and was concentrated to afford N-((2-(2,6-dioxopiperidin-3-yl)-1-oxoisoindolin-5-yl)methyl)-2,2-difluoro-2-(4-fluoro-2-(trifluoromethoxy)phenyl)acetamide (37 mg, 0.06 mmol, 6% yield) as an off white solid. LCMS (ESI) m/z 530.07 [M+1]⁺. ¹H NMR (300 MHz, DMSO-d₆) δ (ppm) 10.98 (s, 1H), 9.78 (br t, J=5.9 Hz, 1H), 7.82 (t, J=8.6 Hz, 1H), 7.71 (d, J=8.1 Hz, 1H), 7.63 (br d, J=11.4 Hz, 1H), 7.51-7.38 (m, 3H), 5.11 (br dd, J=5.1, 13.2 Hz, 1H), 4.56-4.40 (m, 3H), 4.31 (d, J=17.6 Hz, 1H), 3.00-2.83 (m, 1H), 2.66-2.54 (m, 1H), 2.44-2.30 (m, 1H), 2.08-1.93 (m, 1H).

Example 109

N-((2-(2,6-Dioxopiperidin-3-yl)-1-oxoisoindolin-5-yl)methyl)-2,2-difluoro-2-(4-fluorocyclohexyl)acetamide

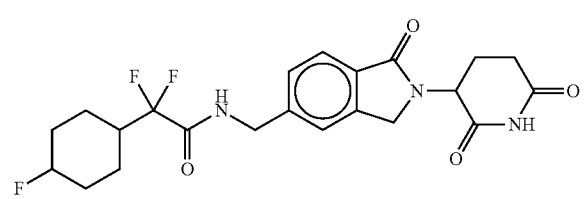

A. 8-Fluoro-1,4-dioxaspiro[4.5]dec-7-ene

To a stirred solution of 1,4-dioxaspiro[4.5]decan-8-one (12 g, 76.92 mmol) in pyridine (120 mL) was added diethylamino sulfur trifluoride (37 g, 230 mmol) at 0° C. and stirred at room temperature for 48 h. The reaction mixture was quenched with aqueous sodium bicarbonate solution and extracted with ethyl acetate (3×100 mL). The combined organic layers were washed with brine (100 mL), dried over sodium sulfate, filtered and concentrated. Obtained crude was purified by column chromatography (100-200 silica gel, 10% ethyl acetate in pet ether) to afford 8-fluoro-1,4-dioxaspiro[4.5]dec-7-ene (6.5 g, 41 mmol, 54% yield) as a colourless liquid. MS (ESI) m/z 158.1 [M]⁺.

B. 8-Fluoro-1,4-dioxaspiro[4.5]decane

To a stirred solution of 8-fluoro-1,4-dioxaspiro[4.5]dec-7-ene (1 g, 3.53 mmol) in ethyl acetate (15 mL) was added a slurry of 10% palladium on charcoal (200 mg) in ethyl acetate under nitrogen stream. The reaction mixture was stirred at room temperature for 4 h under hydrogen atmosphere. The hydrogen atmosphere was evacuated and the reaction mixture was filtered through a Celite pad, filtrate was concentrated to afford to afford 8-fluoro-1,4-dioxaspiro[4.5]decane (500 mg, 1.3 mmol, 37% yield) as a colorless liquid. MS (ESI) m/z 160.1 [M]⁺.

C. 4-Fluorocyclohexanone

To a stirred solution of 8-fluoro-1,4-dioxaspiro[4.5]decane (3.5 g, 21.87 mmol) in tetrahydrofuran (20 mL) was added 20 mL of 4N aqueous hydrochloric acid at 0° C. and stirred at room temperature for 6 h. The reaction mixture was diluted with water (10 mL) and basified with aqueous sodium bicarbonate solution and extracted with ethyl acetate (3×30 mL). The combined organic layers were washed with water (30 mL), brine (30 mL), dried over sodium sulfate and concentrated to afford 4-fluorocyclohexanone (1.2 g, 10.34 mmol, 48% yield) as a colorless liquid. MS (ESI) m/z 116.1 [M]⁺

D. Ethyl 2,2-difluoro-2-(4-fluoro-1-hydroxycyclohexyl)acetate

To a stirred solution of 4-fluorocyclohexanone (1.6 g, 13.7 mmol) in tetrahydrofuran (20 mL) was added cerium(III) chloride heptahydrate (340 mg 1.37 mmol) followed by zinc (1.07 g, 16.55 mmol) and ethyl 2-bromo-2,2-difluoroacetate (3.35 g, 16.55 mmol) at 0° C. and stirred at room temperature for 16 h. The reaction mixture was diluted with water (20 mL) and extracted with ethyl acetate (3×20 mL). The combined organic layers were washed with brine (20 mL), dried over sodium sulfate, filtered and concentrated. The obtained crude product was purified by flash chromatography (30% ethyl acetate in pet ether) to afford ethyl 2,2-difluoro-2-(4-fluoro-1-hydroxycyclohexyl)acetate (1.1 g, 4.58 mmol, 34% yield) as a colorless liquid. $^1$H NMR (300 MHz, DMSO-$d_6$) δ 5.60 (s, 1H), 4.83 (dt, J=49.2, 2.7 Hz, 1H), 4.29 (q, J=7.2 Hz, 2H), 1.82-1.64 (m, 8H), 1.26 (t, J=7.0 Hz, 3H).

E. Ethyl 2,2-difluoro-2-(4-fluorocyclohex-1-enyl)acetate

To a stirred solution of ethyl 2,2-difluoro-2-(4-fluoro-1-hydroxycyclohexyl)acetate (0.75 g, 3.12 mmol) in pyridine (22.6 mL) was added thionyl chloride (3.72 g, 31.25 mmol) at 0° C. and stirred at room temperature for 16 h. The reaction mixture was diluted with water (10 mL), basified with aqueous sodium bicarbonate solution and extracted with ethyl acetate (3×15 mL). The combined organic layers were washed with water (15 mL), brine (15 mL), dried over sodium sulfate, filtered and concentrated. The obtained crude was purified by silica gel column chromatography (5% ethyl acetate in pet ether) to afford ethyl 2,2-difluoro-2-(4-fluorocyclohex-1-enyl)acetate (0.3 g, 1.35 mmol, 43% yield) as a colorless liquid. MS (ESI) m/z 221.9 [M]$^+$.

F. Ethyl 2,2-difluoro-2-(4-fluorocyclohexyl)acetate

To a stirred solution of ethyl 2,2-difluoro-2-(4-fluorocyclohex-1-enyl)acetate (200 mg, 0.9 mmol) in ethyl acetate (10 mL) was added a slurry of 10% platinum oxide (20 mg) in ethyl acetate under nitrogen stream. The reaction mixture was stirred under 60 psi hydrogen pressure at room temperature for 16 h. The hydrogen atmosphere was evacuated and reaction mixture was filtered through a Celite pad, filtrated and concentrated to afford ethyl 2,2-difluoro-2-(4-fluorocyclohexyl)acetate (100 mg, 0.44 mmol, 50% yield) as a colourless liquid. $^1$H NMR (300 MHz, CDCl$_3$) δ 4.83 (dt, J=49.2, 2.7 Hz, 1H), 4.34 (q, J=7.2 Hz, 2H), 2.16-1.98 (m, 4H), 1.70-1.57 (m, 4H), 1.51-1.41 (m, 1H), 1.26 (t, J=6.6 Hz, 3H).

G. 2,2-Difluoro-2-(4-fluorocyclohexyl)acetic acid

To a stirred solution of ethyl 2,2-difluoro-2-(4-fluorocyclohexyl)acetate (100 mg, 0.446 mmol) in mixture of tetrahydrofuran:methanol:water (6 mL, 1:1:1) was added lithium hydroxide monohydrate (56 mg, 1.34 mmol) and stirred at room temperature for 4 h. The volatiles were removed under reduced pressure and the obtained crude was dissolved in water (5 mL), washed with ethyl acetate (2×5 mL). Aqueous layer was acidified with 1N hydrochloride aqueous solution and extracted with ethyl acetate (3×5 mL). The combined organic layers were washed with brine (5 mL), dried over sodium sulfate, filtered and concentrated to afford 2,2-difluoro-2-(4-fluorocyclohexyl)acetic acid (50 mg, 0.255 mmol, 59% yield) as semi-solid compound. $^1$H NMR (300 MHz, CDCl$_3$) δ 4.82 (dt, J=42.2, 6.6 Hz, 1H), 2.18-1.20 (m, 10H).

H. N-((2-(2,6-Dioxopiperidin-3-yl)-1-oxoisoindolin-5-yl)methyl)-2,2-difluoro-2-(4-fluorocyclohexyl)acetamide To an ice cold solution of 2,2-difluoro-2-(4-fluorocyclohexyl)acetic acid (190 mg, 0.97 mmol) in pyridine (9 mL) was added phosphorus oxychloride (445 mg, 2.91 mmol) drop wise and stirred at 0-5° C. for 1 h. Then, 3-(5-(aminomethyl)-1-oxoisoindolin-2-yl)piperidine-2,6-dione hydrochloride was added into the reaction mixture and stirred at room temperature for 2 h. The reaction mixture was basified with aqueous saturated sodium bicarbonate and extracted with ethyl acetate (3×15 mL). The combined organic layers were washed with brine (15 mL), dried over sodium sulfate, filtered and concentrated. The resultant residue was purified by Reveleris C-18 reversed phase column chromatography (50-55% acetonitrile in 0.1% aqueous formic acid) to afford N-((2-(2,6-dioxopiperidin-3-yl)-1-oxoisoindolin-5-yl)methyl)-2,2-difluoro-2-(4-fluorocyclohexyl)acetamide (33 mg, 0.073 mmol, 7% yield) as white solid. MS (ESI) m/z 452.15 [M+1]$^+$. $^1$H NMR (300 MHz, DMSO-$d_6$) δ 10.98 (s, 1H), 9.56 (t, J=5.6 Hz, 1H), 7.70 (d, J=8.1 Hz, 1H), 7.47 (s, 1H), 7.41 (d, J=8.1 Hz, 1H), 5.11 (dd, J=13.2, 5.4 Hz, 1H), 4.84 (d, J=48.6 Hz, 1H), 4.45 (d, J=17.1 Hz, 1H), 4.44 (d, J=6.3 Hz, 2H), 4.31 (d, J=17.4 Hz, 1H), 2.96-2.72 (m, 1H), 2.62-2.51 (m, 1H), 2.40-2.21 (m, 2H), 2.07-1.90 (m, 4H), 1.62-1.41 (m, 6H).

Example 110

N-((2-(2,6-dioxopiperidin-3-yl)-1-oxoisoindolin-5-yl)methyl)-2,2-difluoro-2-(4-(methylsulfonyl)phenyl)acetamide

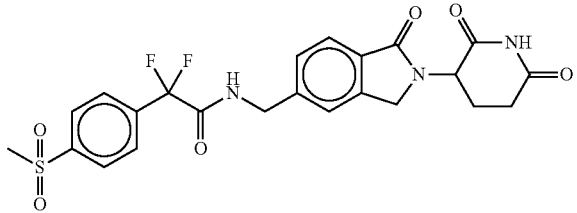

A. 1-Iodo-4-(methylsulfonyl)benzene

To a stirred solution of 1-bromo-4-(methylsulfonyl)benzene (2 g, 8.506 mmol) in 1,4-dioxane (15 mL) was added sodium iodide (2.55 g, 17.01 mmol), copper iodide (80 mg, 0.42 mmol), trans-N,N'-dimethylcyclohexane-1,2-diamine (133 mg, 0.93 mmol) at room temperature and stirred at 110° C. for 16 h in sealtube. The reaction mixture was quenched with water (50 mL) and extracted with ethyl acetate (3×200 mL). The combined organic layers were washed with water (2×50 mL), brine (50 mL), dried over sodium sulphate and concentrated to afford 1-iodo-3-(methylsulfonyl)benzene (1.8 g, 6.38 mmol, 75% yield) as a brown solid. LCMS (ESI) m/z 283.16 [M+H]$^+$.

B. Ethyl 2,2-difluoro-2-(4-(methylsulfonyl)phenyl)acetate

To a stirred solution of 1-iodo-4-(methylsulfonyl)benzene (500 mg, 1.77 mmol) in dimethyl sulfoxide (5 mL) was added ethyl 2-iodo-2,2-difluoroacetate (0.32 mL, 2.313 mmol), copper (107 mg, 1.68 mmol) and stirred for 16 h at room temperature. The reaction mixture was neutralized with aqueous saturated ammonium chloride solution and extracted with ethyl acetate (2×100 mL). The combined organic layers were washed with water (2×50 mL), brine (50 mL), dried over sodium sulphate and concentrated. The resultant residue was purified by silica-gel (100-200 mesh, 20% ethyl acetate in hexanes) to afford to afford ethyl 2,2-difluoro-2-(4-(methylsulfonyl)phenyl)acetate (250 mg, 0.899 mmol, 50%) as an off-white solid. MS (ESI) m/z 279.26 [M+1]$^+$.

C. 2,2-Difluoro-2-(4-(methylsulfonyl)phenyl)acetic acid

To a cold (0° C.) stirred solution of ethyl 2,2-difluoro-2-(4-(methylsulfonyl)phenyl)acetate (250 mg, 0.899 mmol) in methanol/tetrahydrofuran/water (6 mL, 1:1:1) was added lithium hydroxide monohydrate (75 mg, 0.798 mmol) and stirred at room temperature for 2 h. The reaction mixture was concentrated and the residue was neutralized with 10% aqueous potassium bisulphate (10 mL) and extracted with ethyl acetate (3×50 mL). The combined organic layers were washed with brine (50 mL), dried over sodium sulphate and concentrated to afford 2,2-difluoro-2-(4-(methylsulfonyl) phenyl)acetic acid (180 mg, 0.72 mmol, 80% yield) as a gummy solid. MS (ESI) m/z 249.26 [M–1]$^+$.

D. N-((2-(2,6-dioxopiperidin-3-yl)-1-oxoisoindolin-5-yl)methyl)-2,2-difluoro-2-(4-(methylsulfonyl)phenyl)acetamide To a cold (0° C.) stirred solution of 2 2,2-difluoro-2-(4-(methylsulfonyl)phenyl)acetic acid (194 mg, 0.776 mmol) in pyridine (10 mL) was added phosphoryl chloride (0.18 mL, 1.94 mmol) drop wise and stirred at 0-5° C. for 30 min. To this, 3-(5-(aminomethyl)-1-oxoisoindolin-2-yl)piperidine-2,6-dione hydrochloride (200 mg, 0.64 mmol) was added and stirred at room temperature for 2 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by grace column chromatography using 52% ACN in 0.1% aqueous formic acid solution as a eluent to afford N-((2-(2,6-dioxopiperidin-3-yl)-1-oxoisoindolin-5-yl)methyl)-2,2-difluoro-2-(4-(methylsulfonyl)phenyl)acetamide (70 mg, 0.138 mmol, 21% yield) as an off-white solid. MS (ESI) m/z 506.06 [M+1]$^+$. $^1$H NMR (400 MHz, DMSO-d$_6$) δ 10.98 (s, 1H), 9.78 (br t, J=6.1 Hz, 1H), 8.11 (d, J=8.3 Hz, 2H), 7.88 (d, J=8.3 Hz, 2H), 7.69 (d, J=7.8 Hz, 1H), 7.42-7.34 (m, 2H), 5.10 (dd, J=4.9, 13.2 Hz, 1H), 4.53-4.37 (m, 3H), 4.28 (d, J=17.2 Hz, 1H), 3.29 (s, 3H), 2.98-2.87 (m, 1H), 2.68-2.55 (m, 1H), 2.46-2.31 (m, 1H), 2.06-1.94 (m, 1H).

Example 111

N-((2-(2,6-dioxopiperidin-3-yl)-1-oxoisoindolin-5-yl)methyl)-2,2-difluoro-2-(3-(methylsulfonyl)phenyl)acetamide

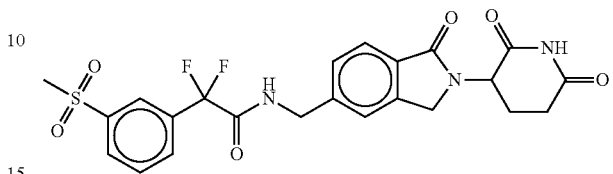

A. 1-Iodo-3-(methylsulfonyl)benzene

To a stirred solution of 1-bromo-3-(methylsulfonyl)benzene (1 g, 4.25 mmol) in 1,4-dioxane (15 mL) was added sodium iodide (1.92 g, 12.76 mmol), copper iodide (81 mg, 0.425 mmol), trans-N,N'-dimethylcyclohexane-1,2-diamine (90 mg, 0.63 mmol) at room temperature and stirred at 110° C. for 16 h in sealtube. The reaction mixture was quenched with water (50 mL) and extracted with ethyl acetate (3×200 mL). The combined organic layers were washed with water (2×50 mL), brine (50 mL), dried over sodium sulphate and concentrated to afford 1-iodo-3-(methylsulfonyl)benzene (900 g, 3.19 mmol, 75% yield) as a brown solid. LCMS (ESI) m/z 282.85 [M+H]$^+$.

B. Ethyl 2,2-difluoro-2-(3-(methylsulfonyl)phenyl)acetate

To a stirred solution of 1-Iodo-3-(methylsulfonyl)benzene (900 mg, 3.19 mmol) in dimethylsulfoxide (15 mL) was added ethyl 2-iodo-2,2-difluoroacetate (0.56 mL, 4.147 mmol), copper (527 mg, 8.29 mmol) and stirred for 16 h at room temperature. The reaction mixture was neutralized with aqueous saturated ammonium chloride solution and extracted with ethyl acetate (2×100 mL). The combined organic layers were washed with water (2×50 mL), brine (50 mL), dried over sodium sulphate and concentrated. The resultant residue was purified by silica-gel (100-200 mesh, 12% ethyl acetate in hexane) to afford ethyl 2,2-difluoro-2-(3-(methylsulfonyl)phenyl)acetate (850 mg, 3.05 mmol, 95%) as an off-white solid. MS (ESI) m/z 320.32 [M+1]$^+$ (ACN (+41) adduct)

C. 2,2-Difluoro-2-(3-(methylsulfonyl)phenyl)acetic acid

To a cold (0° C.) stirred solution of ethyl 2,2-difluoro-2-(3-(methylsulfonyl)phenyl)acetate (800 mg, 2.87 mmol) in methanol/tetrahydrofuran/water (10 mL, 1:1:1) was added lithium hydroxide monohydrate (361 mg, 8.61 mmol) and stirred at room temperature for 2 h. The reaction mixture was concentrated and the residue was neutralized with 10% aqueous potassium bisulphate (20 mL) and extracted with ethyl acetate (3×50 mL). The combined organic layers were washed with brine (50 mL), dried over sodium sulphate and concentrated to afford 2,2-difluoro-2-(3-(methylsulfonyl) phenyl)acetic acid (650 mg, 1.74 mmol, 70% yield) as an gummy solid. MS (ESI) m/z 251.07 [M+1]$^+$.

D. N-((2-(2,6-dioxopiperidin-3-yl)-1-oxoisoindolin-5-yl)methyl)-2,2-difluoro-2-(3-(methylsulfonyl)phenyl)acetamide To a cold (0° C.) stirred solution of 2 2,2-difluoro-2-(3-(methylsulfonyl)phenyl)acetic acid (291 mg, 1.16 mmol) in pyridine (10 mL) was added phosphoryl chloride (0.27 mL, 2.91 mmol) dropwise and stirred at 0-5° C. for 30 min. To this reaction mixture was then added 3-(5-(aminomethyl)-1-oxoisoindolin-2-yl)piperidine-2,6-dione hydrochloride (300 mg, 0.97 mmol) and stirred at room temperature for 2 h. The reaction mixture was neutralized with aqueous saturated sodium bicarbonate (up to pH-8) and extracted with ethyl acetate (3×50 mL). The combined organic layers were washed with water (2×50 mL), brine (50 mL), dried over sodium sulphate and concentrated. The resultant residue was purified by grace column chromatography using 52% of ACN-0.1% formic acid in water as a eluent to afford N-((2-(2,6-dioxopiperidin-3-yl)-1-oxoisoindolin-5-yl)methyl)-2,2-difluoro-2-(3-(methylsulfonyl)phenyl)acetamide (72 mg, 0.142 mmol, 15% yield) as an off-white solid. MS (ESI) m/z 506.01 [M+1]$^+$. $^1$H NMR (300 MHz, DMSO-d$_6$) δ ppm 10.98 (s, 1H) 9.80 (br t, J=5.85 Hz, 1H), 8.12-8.09 (m, 2H), 7.96 (d, J=8.4 Hz, 1H), 7.90-7.80 (m, 1H), 7.67 (d, J=7.68 Hz, 1H), 7.41 (s, 1H), 7.36 (d, J=7.8 Hz, 1H), 5.10 (dd, J=13.16, 5.12 Hz, 1H), 4.54-4.20 (m, 4H), 3.30 (d, J=8.04 Hz, 3H), 3.01-2.79 (m, 1H), 2.67-2.55 (m, 1H), 2.47-2.30 (m, 1H), 2.06-1.92 (m, 1H).

Example 112

2-(2-Aminopyrimidin-5-yl)-N-((2-(2,6-dioxopiperidin-3-yl)-1-oxoisoindolin-5-yl)methyl)-2,2-difluoroacetamide

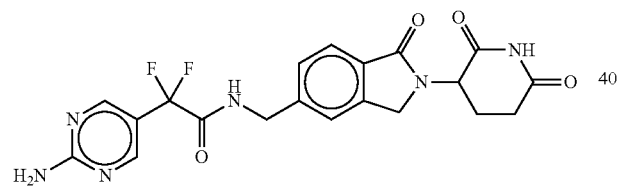

A. Ethyl 2-(2-aminopyrimidin-5-yl)-2,2-difluoroacetate

To a stirred solution of 5-iodopyrimidin-2-amine (1 g, 4.52 mmol) in dimethylsulfoxide (20 mL) was reacted with ethyl 2-bromo-2,2-difluoroacetate (1.1 mL, 9.04 mmol), copper (0.75 g, 11.76 mmol) and stirred for 16 h at 50° C. The reaction mixture was neutralized with aqueous saturated ammonium chloride solution and extracted with ethyl acetate (3×50 mL). The combined organic layer was washed with water (2×10 mL), brine (10 mL) and dried over sodium sulphate and was concentrated to give ethyl 2-(2-aminopyrimidin-5-yl)-2,2-difluoroacetate (600 mg, 2.76 mmol, 61%) as a brown liquid. GCMS (m/z) 217.1.

B. 2-(2-Aminopyrimidin-5-yl)-2,2-difluoroacetic acid

To a cold (0° C.) stirred solution of ethyl 2-(2-aminopyrimidin-5-yl)-2,2-difluoroacetate (500 mg, 2.30 mmol) in ethanol/tetrahydrofuran/water (12 mL, 1:1:1) was added lithium hydroxide monohydrate (290 mg, 6.91 mmol) and stirred at room temperature for 2 h. The reaction mixture was concentrated and the residue was neutralized with 10% aqueous potassium bisulphate (10 mL) and extracted with ethyl acetate (2×30 mL). The combined organic layer was washed with brine (10 mL), dried over sodium sulphate and concentrated to afford 2-(2-aminopyrimidin-5-yl)-2,2-difluoroacetic acid (300 mg, 1.58 mmol, 69% yield) as a brown semi solid. MS (ESI) m/z 190.22. [M+1]$^+$.

C. 2-(2-Aminopyrimidin-5-yl)-N-((2-(2,6-dioxopiperidin-3-yl)-1-oxoisoindolin-5-yl)methyl)-2,2-difluoroacetamide To a cold (0° C.) stirred solution of 2-(2-aminopyrimidin-5-yl)-2,2-difluoroacetic acid (800 mg, 4.23 mmol) and 3-(5-(aminomethyl)-1-oxoisoindolin-2-yl)piperidine-2,6-dione hydrochloride (915 mg, 2.96 mmol) in N,N-dimethylformamide (30 mL) was added N,N-diisopropylethylamine (2.3 mL, 12.69 mmol) followed by 1-[Bis(dimethylamino)methylene]-1H-1,2,3-triazolo[4,5-b]pyridinium 3-oxid hexafluorophosphate (2.4 g, 6.34 mmol) and stirring at room temperature for 16 h. The reaction mixture was diluted with water (70 mL) and and extracted with ethyl acetate (2×20 mL) and the combined organic layer was washed with brine (30 mL), dried over sodium sulphate and concentrated dried under vacuum. The product was purified by Reveleris C-18 reversed phase column using 40% acetonitrile in aqueous formic acid (0.1%) to afford 2-(2-aminopyrimidin-5-yl)-N-((2-(2,6-dioxopiperidin-3-yl)-1-oxoisoindolin-5-yl)methyl)-2,2-difluoroacetamide (45 mg, 1.01 mmol, 15% yield) as an off-white solid. MS (ESI) m/z 445.44 [M+1]$^+$. $^1$H NMR (300 MHz, DMSO-d$_6$) δ 10.96 (s, 1H), 9.59 (br t, J=5.8 Hz, 1H), 8.36 (s, 2H), 7.67 (d, J=7.7 Hz, 1H), 7.43 (s, 1H), 7.37 (d, J=8.0 Hz, 1H), 7.26 (s, 2H), 5.10 (dd, J=5.2, 13.4 Hz, 1H), 4.65-4.24 (m, 4H), 3.02-2.83 (m, 1H), 2.67-2.54 (m, 1H), 2.46-2.30 (m, 1H), 2.01-1.95 (m, 1H).

Example 113

N-((2-(2,6-Dioxopiperidin-3-yl)-1-oxoisoindolin-5-yl)methyl)-2,2-difluoro-2-(5-(trifluoromethylthio)pyridin-2-yl)acetamide

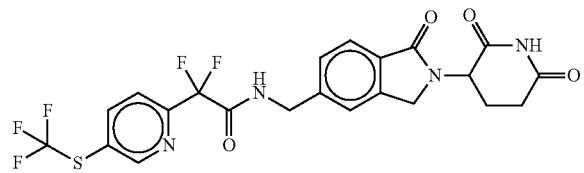

A. tert-Butyl 6-bromopyridin-3-ylcarbamate

To a stirred solution of 6-bromopyridin-3-amine (7 g, 40.46 mmol) in dichloromethane (70 mL) was added di-tert-butyl dicarbonate (10.58 mL, 48.55 mmol) followed by 4-dimethylaminopyridine (0.99 g, 8.09 mmol), triethyl amine (0.99 g, 8.09 mmol) at 0° C. and stirred at room temperature for 6 h. The reaction mixture was diluted with water (50 mL) and extracted with dichloromethane (3×50 mL). The combined organic layers were washed with brine (50 mL), dried over sodium sulfate, filtered and concentrated. The obtained crude was purified by silica gel column chromatography (5% ethyl acetate/pet-ether) to afford tert-butyl 6-bromopyridin-3-ylcarbamate (6 g, 22.05 mmol, 54% yield) as a colorless liquid. MS (ESI) m/z 273.22 [M+1]⁺.

B. Ethyl 2-(5-(tert-butoxycarbonylamino)pyridin-2-yl)-2,2-difluoroacetate

To a stirred solution of tert-butyl 6-bromopyridin-3-ylcarbamate (6 g, 16.08 mmol) in dimethyl sulfoxide (40 mL) was added ethyl 2-bromo-2,2-difluoroacetate (4.89 mL, 24.12 mmol) followed by copper powder (2.65 g, 41.73 mmol) at room temperature and stirred at 60° C. for 6 h. The reaction mixture was diluted with water and filtered through a Celite pad. Filtrate was extracted with ethyl acetate (3×50 mL) and the combined organic layers were washed with brine (50 mL), dried over sodium sulfate, filtered and concentrated. The obtained crude was purified by silica gel column chromatography (5% ethyl acetate/pet-ether) to afford ethyl 2-(5-(tert-butoxycarbonylamino)pyridin-2-yl)-2,2-difluoroacetate (4 g, 12.65 mmol, 57% yield) as a colorless liquid. $^1$H NMR (300 MHz, CDCl$_3$) δ 8.42 (d, J=2.1 Hz, 1H), 8.16 (d, J=6.9 Hz, 1H), 7.66 (d, J=9.0 Hz, 1H), 6.67 (bs, 1H), 4.36 (q, J=7.1 Hz, 2H), 1.53 (s, 9H), 1.32 (t, J=7.2 Hz, 3H).

C. Ethyl 2,2-difluoro-2-(5-thiocyanatopyridin-2-yl)acetate

A stirred solution of ethyl 2-(5-(tert-butoxycarbonylamino)pyridin-2-yl)-2,2-difluoroacetate (4 g, 12.65 mmol) in 6N HCl (80 mL) at 0° C. and stirred at room temperature for 30 min. Then, sodium nitrite (0.87 g, 12.65 mmol) was added into the reaction mixture followed by copper(I) thiocyanate (0.77 g, 6.32 mmol), potassium thiocyanate (0.99 g, 8.09 mmol) at −5° C. and stirred at room temperature for 1 h. The reaction mixture was poured into saturated aqueous sodium bicarbonate solution and extracted with ethyl acetate (3×40 mL). The combined organic layers were washed with brine (40 mL), dried over sodium sulfate, filtered and concentrated. The obtained crude was purified by silica gel column chromatography (5% ethyl acetate/pet-ether) to afford ethyl 2,2-difluoro-2-(5-thiocyanatopyridin-2-yl)acetate (0.7 g, 2.71 mmol, 21% yield) as a colourless liquid. MS (ESI) m/z 259.23 [M+1]⁺.

D. Ethyl 2,2-difluoro-2-(5-(trifluoromethylthio)pyridin-2-yl)acetate

To a stirred solution of ethyl 2,2-difluoro-2-(5-thiocyanatopyridin-2-yl)acetate (700 mg, 2.71 mmol) in tetrahydrofuran (10 mL) was added trifluoromethyltrimethylsilane (770 mg, 5.42 mmol) followed by tetra-n-butylammonium fluoride (1.08 mL, 1.08 mmol) at 0° C. and stirred at room temperature for 16 h. The reaction mixture was quenched with aqueous sodium bicarbonate solution and extracted with ethyl acetate (3×10 mL). The combined organic layers were washed with brine (10 mL), dried over sodium sulfate, filtered and concentrated. The obtained crude was purified by flash column chromatography (100-200 silica gel, 2% ethyl acetate/pet-ether) to afford ethyl 2,2-difluoro-2-(5-(trifluoromethylthio)pyridin-2-yl)acetate (170 mg, 0.56 mmol, 21% yield) as a colourless liquid. MS (ESI) m/z 302.27 [M+1]⁺.

E. 2,2-Difluoro-2-(5-(trifluoromethylthio)pyridin-2-yl)acetic acid

To a stirred solution of ethyl 2,2-difluoro-2-(5-(trifluoromethylthio)pyridin-2-yl)acetate (170 mg, 0.56 mmol) in tetrahydrofuran:ethanol:water (5 mL, 1:1:1) was added lithium hydroxide monohydrate (71 mg, 1.69 mmol) and stirred at room temperature for 4 h. The volatiles were removed under reduced pressure and obtained crude was dissolved in water (5 mL) and washed with ethyl acetate (2×4 mL). The aqueous layer was acidified with aqueous potassium bisulphate solution and extracted with ethyl acetate (3×5 mL). The combined organic layers were washed with brine (5 mL), dried over sodium sulfate, filtered and concentrated to afford 2,2-difluoro-2-(5-(trifluoromethylthio)pyridin-2-yl)acetic acid (140 mg, 0.51 mmol, 91% yield) as a semi-solid compound. MS (ESI) m/z 274.18 [M+1]⁺.

F. N-((2-(2,6-Dioxopiperidin-3-yl)-1-oxoisoindolin-5-yl)methyl)-2,2-difluoro-2-(5-(trifluoromethylthio)pyridin-2-yl)acetamide To an ice cold solution of 2,2-difluoro-2-(5-(trifluoromethylthio)pyridin-2-yl)acetic acid (220 mg, 0.81 mmol) in pyridine (5 mL) was added phosphorus oxychloride (371 mg, 2.42 mmol) drop wise and stirred at 0-5° C. for 1 h. Then, 3-(5-(aminomethyl)-1-oxoisoindolin-2-yl)piperidine-2,6-dione hydrochloride (250 mg, 0.81 mmol) was added into the reaction mixture and stirred at room temperature for 1 h. The reaction mixture was neutralized with aqueous saturated sodium bicarbonate and extracted with ethyl acetate (3×10 mL). The combined organic layers were washed with brine (10 mL), dried over sodium sulphate, filtered and concentrated. The resultant residue was purified by Reveleris C-18 reversed phase column chromatography (50-55% acetonitrile/0.1% aqueous formic acid) to afford N-((2-(2,6-dioxopiperidin-3-yl)-1-oxoisoindolin-5-yl)methyl)-2,2-difluoro-2-(5-(trifluoromethylthio)pyridine-2-yl)acetamide (45 mg, 0.08 mmol, 10% yield) as an off-white solid. MS (ESI) m/z 529.03 [M+1]⁺. $^1$H NMR (300 MHz, DMSO-d$_6$) δ 10.99 (s, 1H), 9.77 (t, J=5.4 Hz, 1H), 9.01 (s, 1H), 8.44 (dd, J=7.8, 0.8 Hz, 1H), 7.98 (d, J=8.4 Hz, 1H), 7.71 (d, J=7.5 Hz, 1H), 7.50 (s, 1H), 7.44 (d, J=7.5 Hz, 1H), 5.11 (dd, J=12.9, 5.1 Hz, 1H), 4.51 (d, J=6.3 Hz, 2H), 4.46 (d, J=17.9 Hz, 1H), 4.31 (d, J=17.6 Hz, 1H), 2.92-2.88 (m, 1H), 2.63-2.57 (m, 1H), 2.41-2.36 (m, 1H), 2.02-2.00 (m, 1H).

Example 114

N-((2-(2,6-Dioxopiperidin-3-yl)-1-oxoisoindolin-5-yl)methyl)-2,2-difluoro-2-(3-(2-(methylamino)ethoxy)phenyl)acetamide hydrochloride

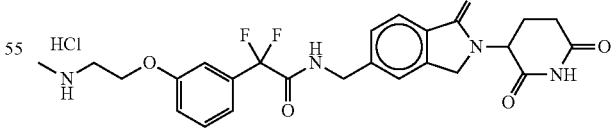

A. Ethyl 2-(3-(2-(tert-butoxycarbonyl(methyl)amino)ethoxy)phenyl)-2,2-difluoroacetate To a stirred solution of ethyl 2,2-difluoro-2-(3-hydroxyphenyl)acetate (2 g, 9.25 mmol) in tetrahydrofuran (20 mL) was added tert-butyl 2-hydroxyethyl(methyl)carbamate (2.43 g 13.88 mmol), N,N-diisopropyl azodicarboxylate (1.87 g 9.25 mmol) followed by triphenyl phosphine (2.4 g, 9.25 mmol) at room temperature and stirred at 50-55° C. for 16 h. The reaction mass was directly concentrated. The resultant residue was purified by column chromatography (silica-gel 100-200) 30% ethylacetate-hexanes as a eluent to afford ethyl 2-(3-(2-(tert-butoxycarbonyl(methyl)amino) ethoxy)phenyl)-2,2-difluoroacetate (1 g, 4.0 mmol, 29% yield) as brown liquid. MS (ESI) m/z 274.2 [M−100]⁺.

B. 2-(3-(2-(tert-Butoxycarbonyl(methyl)amino) ethoxy)phenyl)-2,2-difluoroacetic acid To a cold (0° C.) stirred solution of ethyl 2-(3-(2-(tert-butoxycarbonyl(methyl)amino)ethoxy)phenyl)-2,2-difluoroacetate (1.0 g, 2.67 mmol) in Methanol/Tetrahydrofuran/water (15 mL, 1:1:1) was added lithium hydroxide monohydrate (224.5 mg, 5.64 mmol) and stirred at room temperature for 2 h. The reaction mixture was concentrated and the residue was neutralized with 10% aqueous potassium bisulphate (10 mL) and extracted with ethyl acetate (2×50 mL). The combined organic layer was washed with brine (20 mL), dried over sodium sulphate and concentrated to give ethyl 2-(3-(2-(tert-butoxycarbonyl(methyl)amino) ethoxy)phenyl)-2,2-difluoroacetic acid (600 mg, 1.73 mmol, 65% yield) as a brown semi solid. MS (ESI) m/z 343.8 [M−1]⁺.

C. tert-Butyl 2-(3-(2-((2-(2,6-dioxopiperidin-3-yl)-1-oxoisoindolin-5-yl)methylamino)-1,1-difluoro-2-oxoethyl)phenoxy)ethyl(methyl)carbamate To a solution of ethyl 2-(3-(2-(tert-butoxycarbonyl (methyl)amino)ethoxy)phenyl)-2,2-difluoroacetic acid (447.8 mg, 1.44 mmol) in N,N-dimethylformamide (20 mL) was added (3-(5-(aminomethyl)-1-oxoisoindolin-2-yl)piperidine-2,6-dione hydrochloride (500 mg, 1.44 mmol) was added sub sequentially diisopropylethylamine (561.8 mg, 4.34 mmol) and 1-[Bis(dimethylamino)methylene]-1H-1,2,3-triazolo[4,5-b]pyridinium 3-oxid hexafluorophosphate (825.9 g, 2.17 mmol) at room temperature and reaction was continued to room for 2 h. The reaction mixture was poured in ice cold water (40 mL) to observed off-white solid. The resultant residue was purified by Reveleris C-18 reverse phase column chromatography using 45-50% acetonitrile in aqueous formic acid (0.1%) to give tert-butyl 2-(3-(2-((2-(2,6-dioxopiperidin-3-yl)-1-oxoisoindolin-5-yl)methylamino)-1,1-difluoro-2-oxoethyl)phenoxy)ethyl(methyl)carbamate (200 mg, 0.33 mmol, 20% yield) as an off-white solid. MS (ESI) m/z 501 [M−100]⁺ (De Boc mass).

D. N-((2-(2,6-dioxopiperidin-3-yl)-1-oxoisoindolin-5-yl)methyl)-2,2-difluoro-2-(3-(2-(methylamino) ethoxy)phenyl)acetamide hydrochloride To tert-butyl 2-(3-(2-((2-(2,6-dioxopiperidin-3-yl)-1-oxoisoindolin-5-yl)methylamino)-1,1-difluoro-2-oxoethyl) phenoxy)ethyl(methyl)carbamate (160 mg, 0.26 mmol), 4M hydrochloric acid in dioxane was (5 mL) was added and stirred at room temperature for 4 h. The solution was distilled off under reduced pressure and washed with diethylether to afford 3-(5-(aminomethyl)-1-oxoisoindolin-2-yl) piperidine-2,6-dione hydrochloride (60 mg, 0.11 mmol, 42% yield) as an off white solid. MS (ESI) m/z 501.59 [M+1]⁺. ¹H NMR (400 MHz, DMSO-d₆) δ ppm 10.99 (s, 1H), 9.87-9.58 (m, 1H), 8.98 (br s, 2H), 7.68 (d, J=7.8 Hz, 1H), 7.53-7.46 (m, 1H), 7.44-7.40 (m, 1H), 7.39-7.34 (m, 1H), 7.46-7.32 (m, 1H), 7.24-7.16 (m, 3H), 5.11 (dd, J=5.1, 13.5 Hz, 1H), 4.48-4.39 (m, 3H), 4.33-4.24 (m, 3H), 3.40-3.25 (m, 2H), 2.97-2.85 (m, 1H), 2.67-2.55 (m, 4H), 2.39 (dq, J=4.4, 13.2 Hz, 4H), 2.05-1.94 (m, 1H).

Example 115

N-((2-(2,6-Dioxopiperidin-3-yl)-1-oxoisoindolin-5-yl)methyl)-2,2-difluoro-2-(1-methyl-6-oxo-1,6-dihydropyridazin-3-yl)acetamide

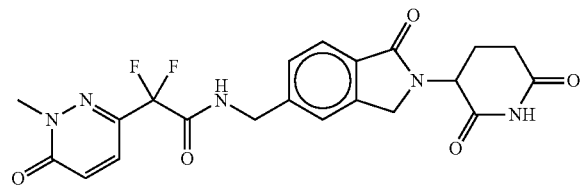

A. 1-tert-Butyl 3-ethyl 2-(6-chloropyridazin-3-yl)malonate

1-Tert-butyl ethyl malonate (26.6 mL, 140.54 mmol) was added drop wise to a suspension of sodium hydride (12.9 g, 324.32 mmol) in dioxane at 10° C. The reaction was stirred at 10° C. for 1 h and then allowed to warm to room temperature. 3,6-dichloropyridazine (20 g, 135.13 mmol) was then added portion wise to the reaction at 25° C. and refluxed for 2 hr. The reaction mixture was diluted with ice cold water (500 mL) extracted with ethyl acetate (5×500 mL). The combined organic layers were washed with brine (50 mL), dried over sodium sulphate and concentrated. The resultant residue was purified by column chromatography (100-200 silica) using 6% EtoAc:Hexene to afford 1-tert-butyl 3-ethyl 2-(6-chloropyridazin-3-yl)malonate (16 g, 53.33 mmol, 39% yield). LCMS (ESI) m/z 301.31 [M+1]⁺.

B. 1-tert-Butyl 3-ethyl 2-(6-chloropyridazin-3-yl)-2-fluoromalonate

To a solution of 1-tert-butyl 3-ethyl 2-(6-chloropyridazin-3-yl)malonate (16 g, 53.33 mmol) in tetrahydrofuran (200 mL) was added sodium hydride (2.31 g, 58.133 mmol) at 0° C. and stirred for 15 min. A cloudy solution of SelectFluor (20.5 g, 58.13 mmol) in dry N,N-dimethylformamide (40 mL) was added drop wise at 0° C. over a period of 20 min and then the reaction was allowed to stir at room temperature for 2 h. The reaction was quenched with ammonium chloride (200 mL) and extracted with ethyl acetate (5×500 mL). The combined organic layers were washed with brine (50 mL), dried over sodium sulphate and concentrated. The resultant residue was purified by column chromatography (100-200 silica) using 5% EtoAc:Hexene to afford 1-tert-butyl 3-ethyl 2-(6-chloropyridazin-3-yl)-2-fluoromalonate (11 g, 34.59 mmol, 64% yield). LCMS (ESI) m/z 219.27 [M+1]⁺.

C. Ethyl 2-(6-chloropyridazin-3-yl)-2-fluoroacetate

A solution of 1-tert-butyl 3-ethyl 2-(6-chloropyridazin-3-yl)-2-fluoromalonate (11 g, 34.54 mmol) in trifluoroacetic acid:dichloromethane mixture (1:1, 60 mL) was stirred at 25° C. for 2 h and then concentrated to dryness over rotary evaporator. The resulting residue was dissolved in ethyl acetate (100 mL), washed with saturated aqueous sodium bicarbonate solution, dried over sodium sulphate and then concentrated to dryness to afford ethyl 2-(6-chloropyridazin-3-yl)-2-fluoroacetate (6 g, 27.52 mmol 79% yield), LCMS (ESI) m/z 219.06 [M+1]+. The material was taken to the next step without further purification.

D. Ethyl 2-fluoro-2-(6-hydroxypyridazin-3-yl)acetate

To a stirred solution of ethyl 2-(6-chloropyridazin-3-yl)-2-fluoroacetate (6 g, 27.52 mmol) in acetic acid (20 mL) was added sodium acetate (22.56 g, 275.52 mmol) and stirred for 16 h at 100° C. The reaction mixture was diluted with ice cold water (500 mL) extracted with ethyl acetate (5×500 mL). The combined organic layers were washed with brine (50 mL), dried over sodium sulphate and concentrated. The resultant residue was purified by column chromatography (100-200 silica) using 30% ethyl acetate in hexanes to afford ethyl 2-fluoro-2-(6-hydroxypyridazin-3-yl)acetate (4 g, 20.00 mmol, 72% yield). LCMS (ESI) m/z 201.22 [M+1]+.

E. Ethyl 2-fluoro-2-(1-methyl-6-oxo-1,6-dihydropyridazin-3-yl)acetate

To a stirred solution of ethyl 2-fluoro-2-(6-hydroxypyridazin-3-yl)acetate (4 g, 20.00 mmol) in N,N-dimethylformamide (20 mL) was added methyl iodide (1.86 mL, 30.00 mmol), potassium carbonate (8.28 g, 60.00 mmol) at room temperature and stirred for 3 h. The reaction mixture was diluted with water (50 mL) and extracted with ethyl acetate (3×100 mL). The combined organic layers were washed with brine (50 mL), dried over sodium sulphate and concentrated. The resultant residue was purified by column chromatography (100-200 silica) using 40% ethyl acetate in hexanes to afford ethyl 2-fluoro-2-(1-methyl-6-oxo-1,6-dihydropyridazin-3-yl)acetate (3 g, 14.01 mmol, 70% yield). LCMS (ESI) m/z 215.66 [M+1]+.

F. Ethyl 2,2-difluoro-2-(1-methyl-6-oxo-1,6-dihydropyridazin-3-yl)acetate

To a solution of ethyl 2-fluoro-2-(1-methyl-6-oxo-1,6-dihydropyridazin-3-yl)acetate (3 g 14.01 mmol) in dry tetrahydrofuran (30 mL) was added lithium hexamethyldisilazide (14 mL, 16.82 mmol) drop wise at −78° C. and stirred for 15 minutes. To this, a suspension of SelectFluor (5.9 g, 16.8 mmol) in dry N,N-dimethylformamide (10 mL) was added drop wise over a period of 10 min. Upon completion addition, the reaction was allowed to warm to room temperature over a period of 30 min. The reaction was quenched with saturated ammonium chloride (50 mL) and the organic fractions were distilled off. The residue obtained was diluted with ice cold water (500 mL) and extracted with ethyl acetate (5×500 mL). The combined organic layers were washed with brine (50 mL), dried over sodium sulphate and concentrated. The resultant residue was purified by Combi-Flash column chromatography (100-200 silica) using 42% ethyl acetate in hexanes to afford ethyl 2,2-difluoro-2-(1-methyl-6-oxo-1,6-dihydropyridazin-3-yl)acetate (1.2 g, 5.17 mmol, 36% yield). LCMS (ESI) m/z 233.33 [M+1]+.

G. 2,2-Difluoro-2-(1-methyl-6-oxo-1,6-dihydropyridazin-3-yl)acetic acid

To a cold (0° C.) stirred solution of ethyl 2,2-difluoro-2-(1-methyl-6-oxo-1,6-dihydropyridazin-3-yl)acetate (1.2 g, 5.17 mmol) in tetrahydrofuran:Methanol:water mixture (30 mL, 1:1:1) was added lithium hydroxide monohydrate (1.08 g, 25.86 mmol) and stirred at room temperature for 6 h. The reaction mixture was concentrated and the residue was neutralized with 10% aqueous hydrochloric acid and extracted with ethyl acetate (2×50 mL). The combined organic layers were washed with brine (20 mL), dried over sodium sulphate and concentrated to afford 2,2-difluoro-2-(1-methyl-6-oxo-1,6-dihydropyridazin-3-yl)acetic acid (700 mg, 3.43 mmol, 66% yield) as an off white solid. LCMS (ESI) m/z 205.31 [M+1]+.

H. N-((2-(2,6-Dioxopiperidin-3-yl)-1-oxoisoindolin-5-yl)methyl)-2,2-difluoro-2-(1-methyl-6-oxo-1,6-dihydropyridazin-3-yl)acetamide To a cold (0° C.) stirred solution of 2,2-difluoro-2-(1-methyl-6-oxo-1,6-dihydropyridazin-3-yl)acetic acid (197.6 mg, 0.968 mmol) in pyridine was added phosphoryl chloride (0.27 mL, 2.906 mmol) dropwise and stirred at 0-5° C. for 1 h. To this reaction mixture was added 3-(5-(aminomethyl)-1-oxoisoindolin-2-yl)piperidine-2,6-dione hydrochloride (300 mg, 0.968 mmol) and continued stirring at room temperature for 30 min. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The resultant residue was purified by Reveleris C-18 reversed phase column chromatography using 40-60% acetonitrile in aqueous formic acid (0.1%) to afford N-((2-(2,6-dioxopiperidin-3-yl)-1-oxoisoindolin-5-yl)methyl)-2,2-difluoro-2-(1-methyl-6-oxo-1,6-dihydropyridazin-3-yl)acetamide (70 mg, 0.152 mmol, 15% yield) as an off white solid. MS (ESI) m/z 460.52 [M+1]+. 1H NMR (300 MHz, DMSO-d6) δ=10.98 (s, 1H), 9.68 (br t, J=5.8 Hz, 1H), 7.79-7.69 (m, 2H), 7.51 (s, 1H), 7.45 (d, J=7.7 Hz, 1H), 7.12 (d, J=9.5 Hz, 1H), 5.11 (dd, J=4.9, 13.3 Hz, 1H), 4.58-4.27 (m, 4H), 3.66 (s, 3H), 2.99-2.83 (m, 1H), 2.67-2.56 (m, 1H), 2.45-2.29 (m, 1H), 2.08-1.93 (m, 1H).

Example 116

2-(2-aminopyrimidin-4-yl)-N-((2-(2,6-dioxopiperidin-3-yl)-1-oxoisoindolin-5-yl)methyl)-2,2-difluoroacetamide

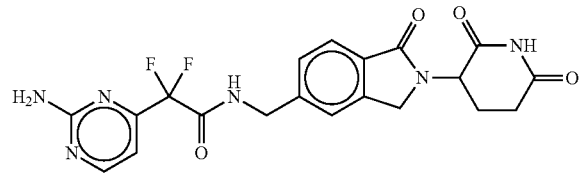

A. 4-Iodopyrimidin-2-amine

To an ice cold solution of 4-chloropyrimidin-2-amine (5 g, 38.5 mmol) in hydroiodic acid (100 mL) was added sodium iodide (17.2 g, 115.7 mmol) at 0° C. and stirred at room temperature for 2 h. The reaction mixture was quenched cautiously with aqueous sodium bicarbonate solution at 0° C. and extracted with dichloromethane (3×150 mL). The combined organic layers were washed water (150 mL), brine (150 mL), dried over sodium sulphate, filtered and concentrated to afford 4-iodopyrimidine-2-amine (1.55 g, 7.01 mmol, 18% yield) as a colourless liquid. MS (ESI) m/z 222 [M+H]+.

B. Ethyl 2-(2-aminopyrimidin-4-yl)-2,2-difluoroacetate

To a stirred solution of 4-iodopyrimidine-2-amine (5 g, 22.60 mmol) in dimethyl sulfoxide (10 mL) was added ethyl 2-bromo-2,2-difluoroacetate (4.53 mL, 33.92 mmol) followed by copper powder (3.7 g, 58.75 mmol) and stirred at 50° C. for 4 h. The reaction mixture was neutralized with aqueous saturated ammonium chloride solution and extracted with ethyl acetate (3×150 mL). The combined organic layers were washed with water (2×50 mL), brine (50 mL), dried over sodium sulphate and concentrated to afford Ethyl 2-(2-aminopyrimidin-4-yl)-2,2-difluoroacetate (1.4 mg, 6.45 mmol, 28%) as a brown liquid. MS (ESI) m/z 218 [M+H]+.

C. 2-(2-aminopyrimidin-4-yl)-2,2-difluoroacetic acid

To a cold (0° C.) stirred solution of ethyl 2-(2-aminopyrimidin-4-yl)-2,2-difluoroacetate (700 mg, 3.22 mmol) in tetrahydrofuran was added 1N hydrochloric acid and stirred at room temperature for 12 h. The reaction mixture was concentrated and the obtained residue was co-distilled with toluene to afford 2-(2-aminopyrimidin-4-yl)-2,2-difluoroacetic acid (550 mg, 2.91 mmol, 82% yield) as a white solid. MS (ESI) m/z 188 [M−H]+.

D. 2-(2-aminopyrimidin-4-yl)-N-((2-(2,6-dioxopiperidin-3-yl)-1-oxoisoindolin-5-yl)methyl)-2,2-difluoroacetamide To a cold (0° C.) solution of 3-(6-((methylamino)methyl)-1-oxoisoindolin-2-yl)piperidine-2,6-dione.hydrochloride (683 mg, 2.21 mmol) and 2-(2-aminopyrimidin-4-yl)-2,2-difluoroacetic acid (500 mg, 2.21 mmol) in N,N-dimethylformamide (10 mL) was added N,N-diisopropylethylamine (1.15 mL, 6.63 mmol) followed by 1-[Bis(dimethylamino)methylene]-1H-1,2,3-triazolo[4,5-b]pyridinium 3-oxid hexafluorophosphate (1 g, 2.65 mmol) and stirred at room temperature for 16 h. The reaction mixture was diluted with water (70 mL) and extracted with ethyl acetate (2×50 mL). The combined organic layers were washed with brine (30 mL), dried over sodium sulphate and concentrated. The resultant residue was purified by Reveleris C-18 reversed phase column using 58% acetonitrile in aqueous formic acid (0.1%) to afford 2-(2-aminopyrimidin-4-yl)-N-((2-(2,6-dioxopiperidin-3-yl)-1-oxoisoindolin-5-yl)methyl)-2,2-difluoroacetamide (52 mg, 11.6 mmol, 5% yield) as an off white solid. MS (ESI) m/z 445.1 [M+H]+. H NMR (400 MHz, DMSO-d6) δ 10.99 (s, 1H), 9.57 (t, J=6.0 Hz, 1H), 8.46 (d, J=4.8 Hz, 1H), 7.71 (d, J=8.0 Hz, 1H), 7.48 (s, 1H), 7.60 (d, J=7.6 Hz, 1H), 7.07 (s, 1H), 6.86 (d, J=4.8 Hz, 1H), 5.11 (dd, J=13.2, 4.8 Hz, 1H), 4.48 (d, J=5.2 Hz, 2H), 4.46 (d, J=16.9 Hz, 1H), 4.31 (d, J=17.2 Hz, 1H), 2.93-2.89 (m, 1H), 2.67-2.58 (m, 1H), 2.40-2.33 (m, 1H), 2.01-1.98 (m, 1H).

Example 117

N-((2-(2,6-Dioxopiperidin-3-yl)-1-oxoisoindolin-5-yl)methyl)-2,2-difluoro-2-(pyrimidin-4-yl)acetamide

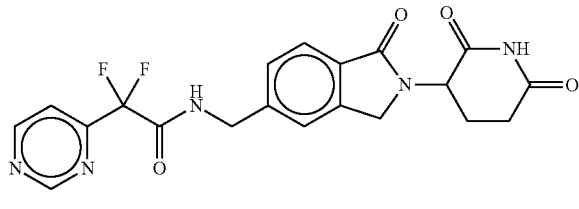

A. Ethyl 2,2-difluoro-2-(2-(methylthio)pyrimidin-4-yl)acetate

To a stirred solution of 4-chloro-2-(methylthio)pyrimidine (5 g, 21.55 mmol) in dimethylsulfoxide (50 mL) was added ethyl 2-bromo-2,2-difluoroacetate (8 mL, 62.2 mmol) followed by copper powder (5.93 g, 93.4 mmol) at RT and stirred at 60° C. for 6 h. The reaction mixture was basified with saturated sodium bicarbonate solution and extracted with ethyl acetate (3×20 mL). The combined organic layers were washed with water (40 mL), brine (40 mL), dried over sodium sulfate, filtered and solvent was concentrated and obtained crude was purified by silica gel column chromatography using 20% ethyl acetate in pet ether to afford ethyl 2,2-difluoro-2-(3-formylphenyl)acetate (3 g, 12.00 mmol, 38%) as a colorless liquid. MS (ESI) m/z 249.66 [M+1]+.

B. Ethyl 2,2-difluoro-2-(pyrimidin-4-yl)acetate

Ethyl 2,2-difluoro-2-(2-(methylthio)pyrimidin-4-yl)acetate (2.8 g, 11.29 mmol) in tetrahydrofuran was added to trimethylsilane (5.3 mL) at 0° C. and added 10% Pd/C (622 mg) then stirred at room temperature for 5 h. The reaction mixture was filtered through celite pad The combined organic layers were washed with brine (10 mL), dried over sodium sulfate, filtered and concentrated. The obtained crude was purified by flash column chromatography (100-200 silica gel, 10% ethyl acetate in pet ether) to afford ethyl 2,2-difluoro-2-(pyrimidin-4-yl)acetate (800 mg, 3.96 mmol, 36% yield) as a colourless liquid MS (ESI) m/z 203.65 [M+1]+.

C. 2,2-Difluoro-2-(pyrimidin-4-yl)acetic acid

To a stirred solution of ethyl 2,2-difluoro-2-(pyrimidin-4-yl)acetate (1 g, 4.95 mmol) in tetrahydrofuran:ethanol:water (15 mL, 1:1:1) was added lithium hydroxide monohydrate (624 mg, 14.85 mmol) and stirred at room temperature for 16 h. The volatiles were removed under reduced pressure and obtained crude was dissolved in water (15 mL) and washed with ethyl acetate (2×10 mL). The aqueous layer was acidified with 1N hydrochloride solution and extracted with ethyl acetate (3×15 mL). The combined organic layers were washed with brine (10 mL), dried over sodium sulfate, filtered and concentrated to 2,2-difluoro-2-(pyrimidin-4-yl)acetic acid (800 mg, 4.59 mmol, 92% yield) as semi-solid compound. MS (ESI) m/z 175 [M+1]+.

D. N-((2-(2,6-Dioxopiperidin-3-yl)-1-oxoisoindolin-5-yl)methyl)-2,2-difluoro-2-(pyrimidin-4-yl)acetamide To an ice cold solution of 2,2-difluoro-2-(pyrimidin-4-yl)acetic acid (203 mg, 1.16 mmol) in pyridine (10 mL) was added phosphorus oxychloride (0.27 mL, 2.91 mmol) drop wise and stirred at 0-5° C. for 1 h and then added 3-(6-(aminomethyl)-1-oxoisoindolin-2-yl)piperidine-2,6-dione hydrochloride (300 mg, 0.97 mmol) and stirred at room temperature for 30 min. The reaction mixture was neutralized with aqueous saturated sodium bicarbonate and extracted with ethyl acetate (3×15 mL). The combined organic layers were washed with water (15 mL), brine (15 mL), dried over sodium sulphate, filtered and concentrated. The resultant residue was purified by Reveleris C-18 reversed phase column chromatography (50-55% acetonitrile in 0.1% aqueous formic acid to afford N-((2-(2,6-dioxopiperidin-3-yl)-1-oxoisoindolin-5-yl)methyl)-2,2-difluoro-2-(pyrimidin-4-yl)acetamide (55 mg, 0.12 mmol, 12% yield) as an off-white solid. MS (ESI) m/z 430.47 [M+1]$^+$. $^1$H NMR (300 MHz, DMSO-d$_6$) δ 10.99 (s, 1H), 9.81 (t, J=6.0 Hz, 1H), 9.41 (s, 1H), 9.12 (d, J=5.1 Hz, 1H) 7.95 (dd, J=5.1, 1.5 Hz, 1H) 7.71 (d, J=7.5 Hz, 1H), 7.52 (s, 1H), 7.44 (d, J=7.5 Hz, 1H), 5.11 (dd, J=13.2, 5.1 Hz, 1H), 4.51 (d, J=6.3 Hz, 2H), 4.47 (d, J=17.6 Hz, 1H), 4.32 (d, J=17.4 Hz, 1H) 2.96-2.88 (m, 1H), 2.63-2.57 (m, 1H), 2.43-2.38 (m, 1H), 2.07-1.98 (m, 1H).

Example 118

N-((2-(2,6-dioxopiperidin-3-yl)-1-oxoisoindolin-5-yl)methyl)-2,2-difluoro-2-(3-(2-(piperidin-1-yl)ethoxy)phenyl)acetamide

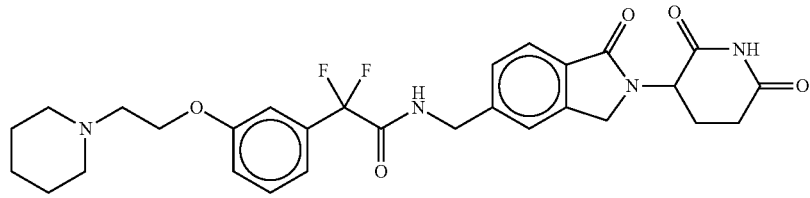

A. Methyl 2,2-difluoro-2-(3-hydroxyphenyl)acetate

To a stirred solution of ethyl 2,2-difluoro-2-(3-(methoxymethoxy)phenyl)acetate (13.0 g, 49.98 mmol) in dichloromethane (130 mL) was added trifluoroacetic acid (65 mL) at 0° C. and stirred at room temperature for 5 h. The reaction mixture was quenched with water (200 mL) and extracted with dichloromethane (3×200 mL). The combined organic layers were washed with water (2×100 mL), brine (100 mL), dried over sodium sulphate and concentrated to afford methyl 2,2-difluoro-2-(3-hydroxyphenyl)acetate (8.0 g, 37.03 mmol, 74% yield). GCMS (m/z) 216.1.

B. 1-(2-Chloroethyl)piperidine

To a stirred solution of 2-(piperidin-1-yl)ethanol (4.0 g, 30.95 mmol) in dichloromethane (40 mL) was added thionyl chloride (7.0 mL, 92.87) at 0° C. and stirred at room temperature for 3 h. The reaction mixture was quenched with water (50 mL) and extracted with dichloromethane (3×50 mL). The combined organic layers were washed with water (2×50 mL), brine (50 mL), dried over sodium sulphate and concentrated to afford 1-(2-chloroethyl)piperidine (1.8 g, 12.24 mmol, 40% yield). GCMS (m/z) 147.1.

C. Ethyl 2,2-difluoro-2-(3-(2-(piperidin-1-yl)ethoxy)phenyl)acetate

To a stirred solution of methyl 2,2-difluoro-2-(3-hydroxyphenyl)acetate (1.0 g, 4.62 mmol) in acetone (15 mL) was added 1-(2-chloroethyl)piperidine (885 mg, 6.01 mmol), potassium carbonate (1.9 g, 13.88 mmol) and stirred at 55° C. for 4 h. The reaction mixture was filtered with celite bed) and wash with ethyl acetate (3×50 mL). The filtrate was dried over sodium sulphate and concentrated to afford ethyl 2,2-difluoro-2-(3-(2-(piperidin-1-yl)ethoxy)phenyl)acetate (1.4 g, 4.28 mmol, 93% yield). LCMS (ESI) m/z 328.0.

D. 2,2-Difluoro-2-(3-(2-(piperidin-1-yl)ethoxy)phenyl)acetic acid

To a cold (0° C.) stirred solution of ethyl 2,2-difluoro-2-(3-(2-(piperidin-1-yl)ethoxy)phenyl)acetate (1.4 g, 4.28 mmol) in methanol-tetrahydrofuran-water mixture (20 mL, 1:1:1) was added lithium hydroxide monohydrate (539 mg, 12.84 mmol) and stirred at room temperature for 2 h. The reaction mixture was concentrated and the residue was neutralized with 10% aqueous potassium bisulphate (20 mL) and extracted with ethyl acetate (2×40 mL). The combined organic layers were washed with brine (20 mL), dried over sodium sulphate and concentrated to afford 2,2-difluoro-2-(3-(2-(piperidin-1-yl)ethoxy)phenyl)acetic acid (700 mg, 2.34 mmol, 55% yield). LCMS (ESI) m/z 300.0.

E. N-((2-(2,6-dioxopiperidin-3-yl)-1-oxoisoindolin-5-yl)methyl)-2,2-difluoro-2-(3-(2-(piperidin-1-yl)ethoxy)phenyl)acetamide To a cold (0° C.) stirred solution of 2,2-difluoro-2-(3-(2-(piperidin-1-yl)ethoxy)phenyl)acetic acid (300 mg, 1.00 mmol) and 3-(5-(aminomethyl)-1-oxoisoindolin-2-yl)piperidine-2,6-dione hydrochloride (310 mg, 1.00 mmol) in N,N-dimethylformamide (20 mL) was added N,N-diisopropylethylamine (389 mg, 3.01 mmol) followed by 1-[Bis(dimethylamino)methylene]-1H-1,2,3-triazolo[4,5-b]pyridinium 3-oxid hexafluorophosphate (572 mg, 1.50 mmol) and stirred at room temperature for 4 h. The reaction mixture was diluted with water (50 mL) and extracted with ethyl acetate (2×40 mL). The combined organic layers were washed with brine (30 mL), dried over sodium sulphate, concentrated and dried under vacuum. The product was purified by Reveleris C-18 reversed phase column using 40% acetonitrile in aqueous formic acid (0.1%) to afford N-((2-(2,6-dioxopiperidin-3-yl)-1-oxoisoindolin-5-yl)methyl)-2,2-difluoro-2-(3-(2-(piperidin-1-yl)ethoxy)phenyl)acetamide (56 mg, 0.09 mmol, 9% yield) as an off-white solid. LCMS (ESI) m/z 555.23 [M+1]$^+$. $^1$H NMR (300 MHz, DMSO-d$_6$) δ (ppm) 10.99 (s, 1H), 9.66 (br t, J=5.9 Hz, 1H), 9.47 (br s, 1H), 7.68 (d, J=7.7 Hz, 1H), 7.51 (t, J=8.1 Hz, 1H), 7.42 (s, 1H), 7.36 (d, J=7.8 Hz, 1H), 7.27-7.12 (m, 3H), 5.11 (br dd, J=5.1, 13.2 Hz, 1H), 4.56-4.21 (m, 6H), 3.61-3.45 (m, 4H), 3.10-2.83 (m, 3H), 2.68-2.55 (m, 1H), 2.44-2.30 (m, 1H), 2.08-1.91 (m, 1H), 1.90-1.60 (m, 5H), 1.50-1.30 (m, 1H).

Example 119

N-((2-(2,6-Dioxopiperidin-3-yl)-1-oxoisoindolin-5-yl)methyl)-2,2-difluoro-2-(3-(2-morpholinoethoxy)phenyl)acetamide

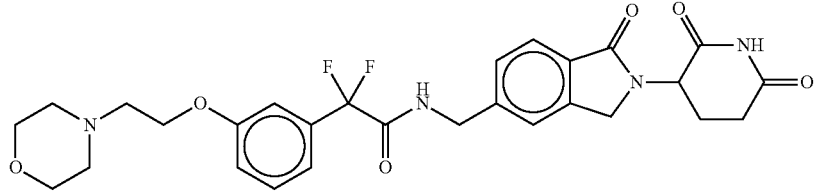

A. Ethyl 2,2-difluoro-2-(3-(2-morpholinoethoxy)phenyl)acetate

To a stirred solution of methyl 2,2-difluoro-2-(3-hydroxyphenyl)acetate (2.0 g, 9.25 mmol) in acetone (25 mL) was added 4-(2-chloroethyl)morpholine hydrochloric acid (2.23 g, 12.03 mmol), potassium carbonate (3.83 g 27.77 mmol) and stirred at 55° C. for 16 h. The reaction mixture was quenched with water (50 mL) and extracted with ethyl acetate (3×50 mL). The combined organic layers were washed with water (2×20 mL), brine (30 mL), dried over sodium sulphate and concentrated to afford ethyl 2,2-difluoro-2-(3-(2-morpholinoethoxy)phenyl)acetate (1.5 g, 4.55 mmol, 49% yield) as brown liquid. LCMS (ESI) m/z 330.0 [M+1]+.

B. 2,2-Difluoro-2-(3-(2-morpholinoethoxy)phenyl)acetic acid

To a cold (0° C.) stirred solution of ethyl 2,2-difluoro-2-(3-(2-morpholinoethoxy)phenyl)acetate (1.5 g, 4.55 mmol) in methanol/tetrahydrofuran/water mixture (20 mL, 1:1:1) was added lithium hydroxide monohydrate (382 mg, 9.11 mmol) and stirred at room temperature for 2 h. The reaction mixture was concentrated and the residue was neutralized with 10% aqueous potassium bisulphate (20 mL) and extracted with ethyl acetate (2×40 mL). The combined organic layers were washed with brine (20 mL), dried over sodium sulphate and concentrated to afford 2,2-difluoro-2-(3-(morpholinoethoxy)phenyl)acetic acid (600 mg, 1.99 mmol, 44% yield) as a brown solid. LCMS (ESI) m/z 302.0 [M+1]+.

C. N-((2-(2,6-Dioxopiperidin-3-yl)-1-oxoisoindolin-5-yl)methyl)-2,2-difluoro-2-(3-(2-morpholinoethoxy)phenyl)acetamide To a cold (0° C.) stirred solution of 2,2-difluoro-2-(3-(morpholinoethoxy)phenyl)acetic acid (513 mg, 1.66 mmol) and 3-(5-(aminomethyl)-1-oxoisoindolin-2-yl)piperidine-2,6-dione hydrochloride (500 mg, 1.66 mmol) in N,N-dimethylformamide (20 mL) was added N,N-diisopropylethylamine (643.8 mg, 4.98 mmol) followed by 1-[Bis(dimethylamino)methylene]-1H-1,2,3-triazolo[4,5-b] pyridinium 3-oxid hexafluorophosphate (946.4 mg, 2.49 mmol) and stirred at room temperature for 4 h. The reaction mixture was diluted with water (50 mL) and extracted with ethyl acetate (2×40 mL). The combined organic layers were washed with brine (30 mL), dried over sodium sulphate, concentrated and dried under vacuum. The product was purified by Reveleris C-18 reversed phase column using 40% acetonitrile in aqueous formic acid (0.1%) to afford N-((2-(2,6-dioxopiperidin-3-yl)-1-oxoisoindolin-5-yl)methyl)-2,2-difluoro-2-(3-(morpholinoethoxy)phenyl)acetamide hydrochloride salt (40 mg, 0.07 mmol, 4.4% yield) as an off-white solid. LCMS (ESI) m/z 557.2 [M+1]+. 1H NMR (400 MHz, DMSO-d6) δ ppm 10.99 (s, 1H), 10.17 (br s, 1H), 9.66 (br t, J=6.1 Hz, 1H), 7.68 (d, J=7.8 Hz, 1H), 7.51 (t, J=8.1 Hz, 1H), 7.42 (s, 1H), 7.36 (d, J=7.8 Hz, 1H), 7.25-7.15 (m, 3H), 5.11 (dd, J=4.9, 13.2 Hz, 1H), 4.48-4.37 (m, 5H), 4.28 (d, J=17.2 Hz, 1H), 3.98 (br d, J=12.2 Hz, 2H), 3.73 (br t, J=11.7 Hz, 2H), 3.64-3.49 (m, 5H), 3.48-3.22 (m, 2H), 2.98-2.84 (m, 1H), 2.68-2.56 (m, 1H), 2.45-2.31 (m, 1H), 2.05-1.95 (m, 1H).

Example 120

2-(3-(2-(4,4-Difluoropiperidin-1-yl)ethoxy)phenyl)-N-((2-(2,6-dioxopiperidin-3-yl)-1-oxoisoindolin-5-yl)methyl)-2,2-difluoroacetamide

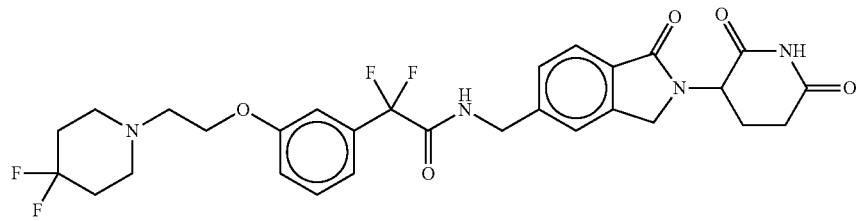

A. Ethyl 2-(4,4-difluoropiperidin-1-yl)acetate

To a stirred solution of 4,4-difluoropiperidine.hydrogenchloride (2 g, 12.048 mmol) in tetrahydrofuran (45 mL) was added ethyl 2-bromoacetate (2.83 g, 18.07 mmol), triethyl amine (6.51 mL, 48.19 mmol) followed by tetrabutylammonium iodide (2.2 g, 6.024 mmol) at room temperature and allowed to stir at the same temperature for 16 h. The reaction was quenched with ice water and extracted with ethyl acetate (3×30 mL). The combined organic layers were washed with brine (30 mL), dried over sodium sulfate, and concentrated to afford ethyl 2-(4,4-difluoropiperidin-1-yl)acetate (1.5 g, 7.2 mmol, 60% yield) as a colourless liquid. GCMS (ESI) m/z 207 [M]$^+$.

B. 2-(4,4-Difluoropiperidin-1-yl)ethanol

To a stirred solution of ethyl 2-(4,4-difluoropiperidin-1-yl)acetate (2 g, 9.66 mmol) in tetrahydrofuran (15 mL) was added lithium alluminiumhydride (9.6 mL, 19.32 mmol) at 0° C. and stirred at room temperature for 3 h. The reaction mixture was cooled to 0° C. and quenched with Celite/sodium sulphate.hydrate (4:1) and stirred at room temperature for 1 h. The white slurry was filtered through a Celite pad and washed with thoroughly dichloromethane (60 mL). The filtrate was dried over sodium sulphate and concentrated to afford 2-(4,4-difluoropiperidin-1-yl)ethanol (1 g, 6.06 mmol, 62% yield) as a colourless liquid. $^1$H NMR (300 MHz, DMSO-d$_6$) δ 4.45 (bs, 1H), 3.50 (t, J=5.6 Hz, 2H), 2.54-2.43 (m, 6H), 2.00-1.87 (m, 4H).

C. 2-(4,4-Difluoropiperidin-1-yl)ethyl methanesulfonate

To a solution of 2-(4,4-difluoropiperidin-1-yl)ethanol (1 g, 4.8 mmol) in tetrahydrofuran was added methane sulphonyl chloride (0.706 mL) at 0° C. and stirred at room temperature for 1 h. The reaction mixture was quenched with aqueous sodium bicarbonate solution and extracted with ethyl acetate (3×10 mL). The combined organic layers were washed with brine (10 mL), dried over sodium sulfate, filtered and concentrated to afford 2-(4,4-difluoropiperidin-1-yl)ethyl methanesulfonate (800 mg, 3.27 mmol, 54% yield) as a colourless liquid. Crude compound was used to the next step without further purification.

D. tert-Butyl(3-iodophenoxy)dimethylsilane

To a stirred solution of 3-iodophenol (5 g, 22.7 mmol) in N,N-dimethylformamide (15 mL, 1:1:1) was added tert-butyldimethyl silyl chloride (8.2 mL, 27.24 mmol) at 0° C. and stirred at room temperature for 16 h. The reaction mixture was poured into ice water (15 mL) and extracted with ethyl acetate (2×10 mL). The combined organic layers were washed with brine (10 mL), dried over sodium sulfate, filtered and concentrated to afford tert-butyl(3-iodophenoxy)dimethylsilane (10 g, 17.96 mmol, 80% yield) as semi-solid compound which was taken to next step without further purification.

E. Ethyl 2,2-difluoro-2-(3-hydroxyphenyl)acetate

To a stirred solution of tert-butyl(3-iodophenoxy)dimethylsilane (10 g, 22.33 mmol) in dimethylsulfoxide (75 mL) was added Copper powder (3.5 g, 55.82 mmol) followed by ethyl 2-bromo-2,2-difluoroacetate (4.3 mL 33.49 mmol) at room temperature and stirred at 55° C. for 16 h. The reaction mixture was poured into water (20 mL) and filtered through a Celite pad. The filtrate was extracted with ethylacetate (3×30 mL) and the combined organic layers were washed with brine (30 mL), dried over sodium sulfate, filtered and concentrated to afford ethyl 2,2-difluoro-2-(3-hydroxyphenyl)acetate (3.5 g, 16.20 mmol, 54% yield) as a colourless liquid. MS (ESI) m/z 215.34[M-1]$^+$.

F. Ethyl 2-(3-(2-(4,4-difluoropiperidin-1-yl)ethoxy)phenyl)-2,2-difluoroacetate To a stirred solution of ethyl 2,2-difluoro-2-(3-hydroxyphenyl)acetate (700 mg, 2.86 mmol) in toluene (20 mL) was added 2-(4,4-difluoropiperidin-1-yl)ethyl methanesulfonate (619 mg, 2.86 mmol) followed by potassium carbonate (1.59 g, 11.47 mmol), tetrabutylammonium iodide (30 mg) at room temperature and allowed to stir at 110° C. for 16 h. The reaction mixture was poured into ice water and extracted with ethylacetate (3×30 mL). The combined organic layers were washed with brine (30 mL), dried over sodium sulfate, filtered and concentrated to afford ethyl 2-(3-(2-(4,4-difluoropiperidin-1-yl)ethoxy)phenyl)-2,2-difluoroacetate (600 mg, 1.65 mmol, 60% yield) as a colourless liquid. MS (ESI) m/z 364.14 [M+1]$^+$.

G. 2-(3-(2-(4,4-Difluoropiperidin-1-yl)ethoxy)phenyl)-2,2-difluoroacetic acid To a stirred solution of ethyl 2-(3-(2-(4,4-difluoropiperidin-1-yl)ethoxy)phenyl)-2,2-difluoroacetate (1 g, 2.75 mmol) in tetrahydrofuran:methanol:water (15 mL, 1:1:1) was added lithium hydroxide monohydrate (348 mg, 8.26 mmol) and stirred at room temperature for 3 h. The volatiles were removed under reduced pressure and obtained crude was dissolved in water (15 mL) and washed with ethyl acetate (2×10 mL). The aqueous layer was acidified with 1N hydrochloride solution and extracted with ethyl acetate (3×15 mL). The combined organic layers were washed with brine (10 mL), dried over sodium sulfate, filtered and concentrated to afford 2-(3-(2-(4,4-difluoropiperidin-1-yl)ethoxy)phenyl)-2,2-difluoroacetic acid (800 mg, 2.38 mmol, 86% yield) as semi-solid compound. MS (ESI) m/z 334.04 [M]$^+$.

H. 2-(3-(2-(4,4-Difluoropiperidin-1-yl)ethoxy)phenyl)-N-((2-(2,6-dioxopiperidin-3-yl)-1-oxoisoindolin-5-yl)methyl)-2,2-difluoroacetamide To a cold (0° C.) stirred solution of 3-(5-(aminomethyl)-1-oxoisoindolin-2-yl)piperidine-2,6-dione hydrochloride (276 mg, 0.895 mmol) and 2-(3-(2-(4,4-difluoropiperidin-1-yl)ethoxy)phenyl)-2,2-difluoroacetic acid (300 mg, 0.895 mmol) in N,N-dimethylformamide (10 mL) was added N,N-diisopropylethylamine (0.3 mL, 1.79 mmol) followed by 1-[Bis(dimethylamino)methylene]-1H-1,2,3-triazolo[4,5-b]pyridinium 3-oxid hexafluorophosphate (408 mg, 1.074 mmol) and stirred at room temperature for 2 h. The reaction mixture was diluted with water (30 mL) and extracted with ethyl acetate (2×40 mL). The combined organic layers were washed with brine (20 mL), dried over sodium sulfate and concentrated. The crude compound was purified by Reveleris C-18 reversed phase column (60% acetonitrile/0.1% aqueous formic acid) to afford 2-(3-(2-(4,4-difluoropiperidin-1-yl)ethoxy)phenyl)-N-((2-(2,6-dioxopiperidin-3-yl)-1-oxoisoindolin-5-yl)methyl)-2,2-difluoroacetamide (45 mg, 0.076 mmol, 8% yield) as an off-white solid. MS (ESI) m/z 591.17. $^1$H NMR (400 MHz, DMSO-d$_6$) δ 10.98 (s, 1H), 9.61 (t, J=5.6 Hz, 1H), 7.67 (d, J=8.0 Hz, 1H), 7.44 (dd, J=8.0, 7.6 Hz, 1H), 7.40 (s, 1H), 7.36 (d, J=7.6 Hz, 1H), 7.16-7.11 (m, 3H), 5.10 (dd, J=13.2, 5.6 Hz, 1H), 4.45 (d, J=6.0 Hz, 2H), 4.42 (d, J=17.8 Hz, 1H), 4.28 (d, J=17.2 Hz, 1H), 4.09 (t, J=5.6 Hz, 2H), 2.95-2.87 (m, 1H), 2.78 (t, J=5.6 Hz, 2H), 2.65-2.59 (m, 5H), 2.45-2.35 (m, 1H), 2.03-1.88 (m, 5H).

Example 121

N-((2-(2,6-Dioxopiperidin-3-yl)-1-oxoisoindolin-5-yl)methyl)-2,2-difluoro-2-(1-methyl-6-oxo-1,6-dihydropyridazin-4-yl)acetamide

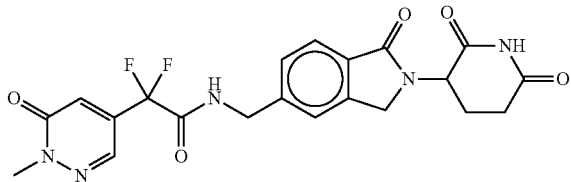

A. 4,5-Dichloro-2-methylpyridazin-3(2H)-one

To a stirred solution of 4,5-dichloropyridazin-3-ol (20 g, 0.121 mol) in N,N-dimethylformamide (100 mL) was added potassium carbonate (42 g, 0.303 mol) followed by methyl iodide (18.9 g, 0.133 mol) and stirred at room temperature for 2 h. The reaction mixture was filtered, to the filtrate was added water (100 mL) and extracted with ethyl acetate (3×100 mL). The combined organic layers were washed with water (100 mL), brine (100 mL), dried over sodium sulphate and concentrated. The resultant residue was purified by column chromatography (100-200 silica) using 10-20% ethyl acetate in hexanes to afford 4,5-dichloro-2-methylpyridazin-3(2H)-one (15 g, 0.0837 mol, 69% yield). MS (ESI) m/z 179.03 [M+1]$^+$.

B. 5-Iodo-2-methylpyridazin-3(2H)-one

To 4,5-dichloro-2-methylpyridazin-3(2H)-one (15 g, 83.79 mmol) was added 47% of aqueous hydroiodic acid (185 mL) and stirred for 24 h at 140° C. To this reaction mixture was added aqueous saturated sodium thiosulphate and extracted with ethyl acetate (3×100 mL). The combined organic layers were washed with water (2×50 mL), brine (50 mL), dried over sodium sulphate and concentrated. The resultant residue was purified by column chromatography (100-200 silica) using 30-40% ethyl acetate in hexanes to afford 5-iodo-2-methylpyridazin-3(2H)-one (8.5 g, 36.016 mmol, 43% yield). MS (ESI) m/z 237.22 [M+1]$^+$.

C. 1-tert-Butyl 3-ethyl 2-(1-methyl-6-oxo-1,6-dihydropyridazin-4-yl)malonate

To a suspension of sodium hydride (2.07 g, 86.44 mmol) in 1,4-dioxane (85 mL) at 10° C. was added drop wise tert-butylethyl malonate (7 g, 37.45 mmol) and allowed to warm to 25° C. over 1 h with stirring. 5-Iodo-2-methylpyridazin-3(2H)-one (8.5 g, 36.016 mmol) was then added portion wise at 25° C. and refluxed for 2 h. The reaction mixture was diluted with ice cold water (100 mL) and extracted with ethyl acetate (3×100 mL). The combined organic layers were washed with water (50 mL), brine (50 mL), dried over sodium sulphate and concentrated. The resultant residue was purified by column chromatography (100-200 silica) using 20-30% ethyl acetate in hexanes to afford 1-tert-butyl 3-ethyl 2-(1-methyl-6-oxo-1,6-dihydropyridazin-4-yl)malonate (7 g, 23.64 mmol, 65% yield). MS (ESI) m/z 296.97 [M+1]$^+$.

D. 1-tert-Butyl 3-ethyl 2-fluoro-2-(1-methyl-6-oxo-1,6-dihydropyridazin-4-yl)malonate To a solution of 1-tert-butyl 3-ethyl 2-(6-chloropyridazin-3-yl)malonate (7 g, 23.64 mmol) in tetrahydrofuran (100 mL) at 0° C. was added sodium hydride (1.2 g, 25.77 mmol). The reaction was stirred for 15 min. A cloudy solution of SelectFluor (9.12 g, 25.77 mmol) in N,N-dimethylformamide (dry 20 mL) was added drop wise at 0° C. over a period of 10 min and allowed stir at room temperature for 2 h. The reaction was quenched with ammonium chloride (50 mL) and extracted with ethyl acetate (3×70 mL). The combined organic layers were washed with water (50 mL), brine (50 mL), dried over sodium sulphate and concentrated. The resultant residue was purified by column chromatography (100-200 silica) using 25-35% ethyl acetate in hexanes to afford 1-tert-butyl 3-ethyl 2-fluoro-2-(1-methyl-6-oxo-1,6-dihydropyridazin-4-yl)malonate (5 g, 15.92 mmol, 67% yield). LCMS (ESI) m/z 315.40 [M+1]$^+$.

E. Ethyl 2-fluoro-2-(1-methyl-6-oxo-1,6-dihydropyridazin-4-yl)acetate

A solution of 1-tert-butyl 3-ethyl 2-fluoro-2-(1-methyl-6-oxo-1,6-dihydropyridazin-4-yl)malonate (5 g, 15.92 mmol) in 25 mL trifluoroacetic acid/dichloromethane (1:1) was stirred at room temperature for 4 h. To this reaction mixture was added aqueous saturated sodium bicarbonate solution and extracted with ethyl acetate (3×70 mL). The combined organic layers were washed with water (50 mL), brine (50 mL), dried over sodium sulphate and concentrated. The resultant residue was purified by column chromatography (100-200 silica) using 25-35% ethyl acetate in hexanes to afford ethyl 2-fluoro-2-(1-methyl-6-oxo-1,6-dihydropyridazin-4-yl)acetate (3 g, 32.71 mmol, 88% yield). LCMS (ESI) m/z 215.13 [M+1]$^+$.

F. Ethyl 2,2-difluoro-2-(1-methyl-6-oxo-1,6-dihydropyridazin-4-yl)acetate

To a solution of ethyl 2-fluoro-2-(1-methyl-6-oxo-1,6-dihydropyridazin-4-yl)acetate (3 g, 32.71 mmol) in dry tetrahydrofuran (30 mL) was added lithium hexamethyldisilylazide (16.8 mL, 39.25 mmol) drop wise at −78° C. over a period of 10 min. After stirring for 15 min at same temperature, a solution of SelectFluor (5.9 g, 16.8 mmol) in dry N,N-dimethylformamide (10 mL) was added drop wise over 10 min. Upon complete addition, the reaction was allowed to warm to room temperature for 30 min with stirring and quenched with saturated ammonium chloride (50 mL). After evaporation of the organic fractions rotary evaporator, the reaction mixture was diluted with ice cold water (50 mL) and extracted with ethyl acetate (5×50 mL). The combined organic layers were washed with water (30 mL), brine (30 mL), dried over sodium sulphate and concentrated. The resultant residue was purified by CombiFlash column chromatography (100-200 silica) using 20-30% ethyl acetate in hexanes to afford ethyl 2,2-difluoro-2-(1-methyl-6-oxo-1,6-dihydropyridazin-4-yl)acetate (1.2 g, 5.17 mmol, 36% yield). LCMS (ESI) m/z 233.39 [M+1]$^+$.

G. 2,2-Difluoro-2-(1-methyl-6-oxo-1,6-dihydropyridazin-4-yl)acetic acid

To a cold (0° C.) stirred solution of ethyl 2,2-difluoro-2-(1-methyl-6-oxo-1,6-dihydropyridazin-4-yl)acetate (1.2 g, 5.17 mmol) in 1,4-dioxane (36 mL) was added 3N aqueous hydrochloric acid solution (24 mL) at 5° C. and stirred at room temperature for 16 h. The reaction mixture was diluted with water (20 mL) and extracted with ethyl acetate (2×30 mL). The combined organic layers were washed with water (20 mL), brine (20 mL), dried over sodium sulphate and concentrated to afford 2,2-difluoro-2-(1-methyl-6-oxo-1,6-dihydropyridazin-4-yl)acetic acid (700 mg, 3.43 mmol, 66% yield) as off white solid. LCMS (ESI) m/z 205.02 [M+1]$^+$.

H. N-((2-(2,6-Dioxopiperidin-3-yl)-1-oxoisoindolin-5-yl)methyl)-2,2-difluoro-2-(1-methyl-6-oxo-1,6-dihydropyridazin-4-yl)acetamide To a cold (0° C.) stirred solution of 2,2-difluoro-2-(1-methyl-6-oxo-1,6-dihydropyridazin-4-yl)acetic acid (197.6 mg, 0.968 mmol) in pyridine was added phosphoryl chloride (0.27 mL, 2.906 mmol) drop wise and stirred at 0-5° C. for 1 h. To this reaction mixture was then added 3-(5-(aminomethyl)-1-oxoisoindolin-2-yl)piperidine-2,6-dione hydrochloride (300 mg, 0.968 mmol) and stirred at room temperature for 30 min. The reaction mixture was neutralized with aqueous saturated sodium bicarbonate (up to pH-8) and extracted with ethyl acetate (3×50 mL). The combined organic layers were washed with water (2×10 mL), brine (10 mL), dried over sodium sulphate and concentrated. The resultant residue was purified by Reveleris C-18 reversed phase column chromatography using 40-60% acetonitrile in aqueous formic acid (0.1%) to afford N-((2-(2,6-dioxopiperidin-3-yl)-1-oxoisoindolin-5-yl)methyl)-2,2-difluoro-2-(1-methyl-6-oxo-1,6-dihydropyridazin-4-yl)acetamide (70 mg, 0.152 mmol, 15% yield) as an off white solid. MS (ESI) m/z 459.16 [M+1]$^+$. $^1$H NMR (300 MHz, DMSO-d$_6$) δ ppm 10.98 (s, 1H) 9.80 (br t, J=5.66 Hz, 1H) 8.06 (d, J=2.19 Hz, 1H) 7.70 (d, J=7.68 Hz, 1H) 7.47 (s, 1H) 7.40 (d, J=8.04 Hz, 1H) 7.15 (s, 1H) 5.11 (dd, J=13.16, 5.12 Hz, 1H) 4.55-4.23 (m, 4H) 3.69 (s, 1H) 3.01-2.82 (m, 1H) 2.68-2.45 (m, 1H) 2.46-2.31 (m, 1H) 2.06-1.93 (m, 1H).

Example 121

N-((2-(2,6-dioxopiperidin-3-yl)-1-oxoisoindolin-5-yl)methyl)-2,2-difluoro-2-(3-(4-methylpiperazin-1-yl)phenyl)acetamide

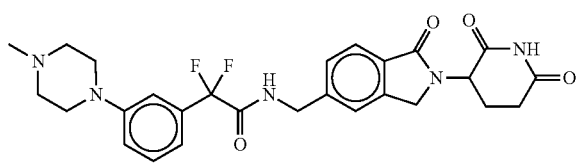

A. Methyl 2-(3-bromophenyl)acetate

To a solution of 2-(3-bromophenyl)acetic acid (25 g, 116.27 mmol) in dichloromethane (60 mL) were added oxalyl chloride (20 mL, 232.25 mmol) followed by N,N-dimethylformamide (1 mL) at 0° C. and stirred at room temperature for 1 h. The reaction mixture was concentrated, to this resulting residue was added methanol (250 mL) and stirred at room temperature for 1 h. The reaction mass was concentrated, the resulting residue was quenched with saturated aqueous sodium bicarbonate (250 mL) and extracted with ethyl acetate (3×200 mL). The combined organic layers were washed with water (2×100 mL), brine (200 mL), dried over sodium sulphate and concentrated methyl 2-(3-bromophenyl)acetate (20 g, 87.71 mmol, 76% yield) as a colorless liquid. LCMS (ESI) m/z 270.29[M+42]$^+$. (ACN adduct).

B. Ethyl 2-(3-(4-methylpiperazin-1-yl)phenyl)acetate

To a degassed solution of methyl 2-(3-bromophenyl)acetate (20 g, 87.71 mmol) in toluene (250 mL) was added 1-methylpiperazine (10.52 g, 105.52 mmol), cesium carbonate (40 g, 122.79 mmol) and degassed for 30 min. To this reaction mixture was then added 2,2'-bis(diphenylphosphino)-1,1'-binaphthalene (818 mg, 1.31 mmol), Palladium (II) acetate (590 mg, 0.877 mmol) and stirred at 110° C. for 16 h. The reaction mixture was filtered through Celite pad, filtrate was concentrated, diluted with water (300 mL) and extracted with ethyl acetate (3×200 mL). The combined organic layers were washed with water (200 mL) and brine (150 mL), dried over sodium sulphate, the organic layer was concentrated under reduced pressure to get crude residue which was purified by CombiFlash column chromatography (100-200 silica) using 21-24% methanol in dichloromethane to afford ethyl 2-(3-(4-methylpiperazin-1-yl)phenyl)acetate (4.0 g, 16.12 mmol, 19% yield) as a brown colour solid. LCMS (ESI) m/z 249.26[M+1]$^+$.

C. Ethyl 2,2-difluoro-2-(3-(4-methylpiperazin-1-yl)phenyl)acetate

To a solution of ethyl 2-(3-(4-methylpiperazin-1-yl)phenyl)acetate (4 g, 16.12 mmol) in dry tetrahydrofuran (80 mL) was added lithium hexamethyldisilamide (1M in tetrahydrofuran) (24 mL, 24.18 mmol) dropwise at −78° C. and stirred for 15 min. To this a solution of N-fluorodibenzenesulfonimide (7.6 g, 24.18 mmol) in dry tetrahydrofuran (20 mL) was added drop wise over a period of 10 min. Upon completion addition, the reaction was allowed to warm to room temperature over a period of 30 min and stirred for 1 h at room temperature. The reaction was quenched with saturated ammonium chloride (50 mL) diluted with ice cold water (100 mL) and extracted with ethyl acetate (2×200 mL). The combined organic layers were washed with brine (100 mL), dried over sodium sulphate and concentrated to afford ethyl 2,2-difluoro-2-(3-(4-methylpiperazin-1-yl)phenyl)acetate (2.2 g, 8.87 mmol) as a light brown color solid. LCMS (ESI) m/z 285.40 [M+1]$^+$.

D. 2,2-Difluoro-2-(3-(4-methylpiperazin-1-yl)phenyl)acetic acid

To a cold (0° C.) stirred solution of ethyl 2,2-difluoro-2-(3-(4-methylpiperazin-1-yl)phenyl)acetate (2.0 g, 7.04 mmol) in tetrahydrofuran:methanol:water mixture (1:1:1, 30 mL) was added lithium hydroxide monohydrate (504 mg, 21.12 mmol) and stirred at room temperature for 2 h. The reaction mixture was concentrated and the residue was diluted with water (50 mL) and washed with diethylether (2×50 mL). Aqueous layer neutralized with 10% aqueous potassium bisulphate (15 mL) and put the lyophilization to give 2,2-difluoro-2-(3-(4-methylpiperazin-1-yl)phenyl)acetic acid (1.2 g, 4.44 mmol). LCMS (ESI) m/z 270.11[M+1]$^+$.

E. N-((2-(2,6-dioxopiperidin-3-yl)-1-oxoisoindolin-5-yl)methyl)-2,2-difluoro-2-(3-(4-methylpiperazin-1-yl)phenyl)acetamide To a cold (0° C.) stirred solution of 2,2-difluoro-2-(3-(4-methylpiperazin-1-yl)phenyl)acetic acid (524 mg, 1.94 mmol) in pyridine (10 mL) was added phosphoryl chloride (0.45 mL, 4.83 mmol) at 0-5° C. and stirred at same temperature for 1 h. Then added 3-(5-(aminomethyl)-1-oxoisoindolin-2-yl)piperidine-2,6-dione hydrochloride (500 mg, 1.61 mmol) and stirred at room temperature for 1 h. The reaction mixture was concentrated. The resultant residue was purified by PREP-HPLC ((Atlantis-T$_3$ column) using acetonitrile—0.1% of ammonium bicarbonate in water as eluent). After lyophilization LCMS indicated 84% of desired m/z, 16% of ring opended m/z was observed, which was further purified by CombiFlash column chromatography using 6-7% methanol in dichloromethane to afford N-((2-(2,6-dioxopiperidin-3-yl)-1-oxoisoindolin-5-yl)methyl)-2,2-difluoro-2-(3-((4-methylpiperazin-1-yl)methyl)phenyl) acetamide (35 mg, 0.067 mmol, 4% yield) as a off-white solid. LCMS (ESI) m/z 526.39 [M+1]$^+$. $^1$H NMR (300 MHz, DMSO-d$_6$) δ=11.00 (s, 1H), 9.59 (br t, J=6.1 Hz, 1H), 7.67 (d, J=7.7 Hz, 1H), 7.45-7.29 (m, 3H), 7.11 (br d, J=8.4 Hz, 1H), 7.04 (s, 1H), 6.97 (br d, J=7.7 Hz, 1H), 5.11 (br dd, J=5.1, 13.2 Hz, 1H), 4.53-4.34 (m, 3H), 4.33-4.21 (m, 1H), 3.42-3.26 (m, 4H), 3.14 (br s, 4H), 3.00-2.84 (m, 1H), 2.66-2.66 (m, 1H), 2.42-2.33 (br dd, J=4.2, 13.0 Hz, 1H), 2.27 (br s, 3H), 2.06-1.92 (m, 1H).

Example 123

Effect of Test Compounds on KG-1 Cell Proliferation

The anti-proliferative activity of the test compound was evaluated on KG-1 cell line (American Type Culture Collection [ATCC]: catalogue number ATCC® CCL-246™) at 72 hours post-treatment. The seeding density for KG-1 was optimized to ensure assay linearity in 384-well plates.

Increasing concentrations of the test compound (0.5 nM to 10 μM) were spotted in a 10-point serial dilution fashion (3-fold dilution) in duplicate via an acoustic dispenser (EDC ATS-100) into an empty 384-well plate. The dimethyl sulfoxide (DMSO) concentration was kept constant for a final assay concentration of 0.1% DMSO. Prior to testing, KG-1 cells were grown in RPMI-1640 (Roswell Park Memorial Institute—1640) medium with 10% FBS (fetal bovine serum: HyClone) and expanded in culture flasks to provide sufficient amounts of starting material. Cells were then diluted to 5000 cells per well, in a 50 μL volume and added directly to the compound-spotted 384-well plates. Cells were allowed to grow for 72 hours in 5% CO$_2$ at 37° C. At the time when exposure of cells to compound began (to), initial viable cell number was assessed via Cell Titer-Glo® Luminescent Cell Viability Assay at a 1 vol:2 vol ratio according to manufacturer's instructions (Promega Corporation, Madison, Wis.) by quantifying the level of luminescence generated by adenosine-5'-triphosphate (ATP) present in viable cells. After 72 hours, cell viability oft-treated cells was assessed via Cell Titer-Glo® and read for luminescence. IC$_{50}$ values for exemplary compounds are provided in Table 1.

In Table 1, IC$_{50}$ values as provided as below:
A: <0.01 μM; B: 0.01 to 0.05 μM; C: >0.05 μM to 0.1 μM; and D: >0.1 μM to 10 μM.

TABLE 1

| Cpd No. | Compound | Name | MH+ | FCA Prolif Cell TiterGlo KG-1 72 h (IC$_{50}$) |
|---|---|---|---|---|
| 1 | 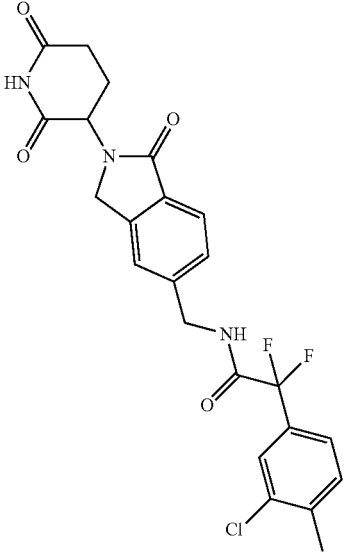 [SMILES: Cc1ccc(C(F)(F)C(=O)NCc2ccc3c(c2)CN(C2CCC(=O)NC2=O)C3=O)cc1Cl] | 2-(3-chloro-4-methylphenyl)-N-((2-(2,6-dioxopiperidin-3-yl)-1-oxoisoindolin-5-yl)methyl)-2,2-difluoroacetamide | 476.2 | B |

TABLE 1-continued
| Cpd No. | Compound | Name | MH+ | FCA Prolif Cell TiterGlo KG-1 72 h (IC$_{50}$) |
|---|---|---|---|---|
| 2 | 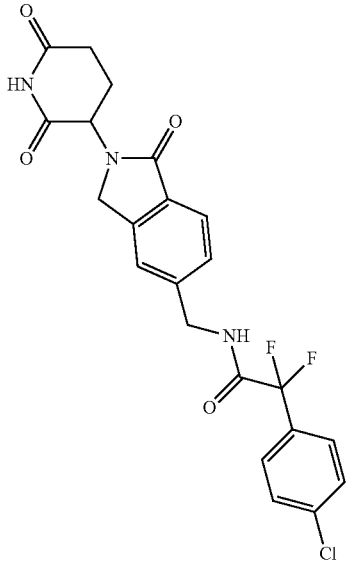 [SMILES: O=C1CCC(N2Cc3cc(CNC(=O)C(F)(F)c4ccc(Cl)cc4)ccc3C2=O)C(=O)N1] | 2-(4-chlorophenyl)-N-((2-(2,6-dioxopiperidin-3-yl)-1-oxoisoindolin-5-yl)methyl)-2,2-difluoroacetamide | 462.0 | B |
| 3 | 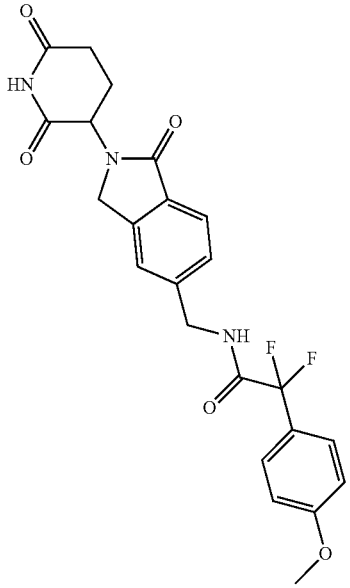 | N-((2-(2,6-dioxopiperidin-3-yl)-1-oxoisoindolin-5-yl)methyl)-2,2-difluoro-2-(4-methoxyphenyl)acetamide | 458.2 | D |

TABLE 1-continued

| Cpd No. | Compound | Name | MH+ | FCA Prolif Cell TiterGlo KG-1 72 h (IC$_{50}$) |
|---|---|---|---|---|
| 4 | | 2-(3-chlorophenyl)-N-((2-(2,6-dioxopiperidin-3-yl)-1-oxoisoindolin-5-yl)methyl)-2,2-difluoroacetamide | 462.2 | B |
| 5 | | N-((2-(2,6-dioxopiperidin-3-yl)-1-oxoisoindolin-5-yl)methyl)-2,2-difluoro-2-(4-fluorophenyl)acetamide | 446.2 | B |
| 6 | | N-((2-(2,6-dioxopiperidin-3-yl)-1-oxoisoindolin-5-yl)methyl)-2,2-difluoro-2-p-tolylacetamide | 442.2 | B |

TABLE 1-continued

| Cpd No. | Compound | Name | MH+ | FCA Prolif Cell TiterGlo KG-1 72 h (IC$_{50}$) |
|---|---|---|---|---|
| 7 | | 2-(3,4-dichlorophenyl)-N-((2-(2,6-dioxopiperidin-3-yl)-1-oxoisoindolin-5-yl)methyl)-2,2-difluoroacetamide | 498.0 | B |
| 8 | | 2-(2-chlorophenyl)-N-((2-(2,6-dioxopiperidin-3-yl)-1-oxoisoindolin-5-yl)methyl)-2,2-difluoroacetamide | 462.0 | D |
| 9 | | N-((2-(2,6-dioxopiperidin-3-yl)-1-oxoisoindolin-5-yl)methyl)-2,2-difluoro-2-(2-(trifluoromethyl)phenyl)acetamide | NA | B |

TABLE 1-continued
| Cpd No. | Compound | Name | MH+ | FCA Prolif Cell TiterGlo KG-1 72 h (IC$_{50}$) |
|---|---|---|---|---|
| 10 | 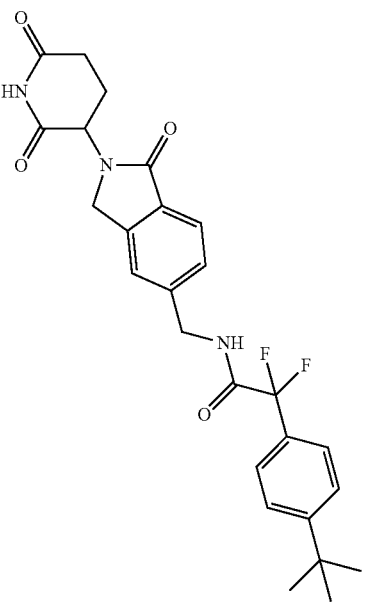 | 2-(4-tert-butylphenyl)-N-((2-(2,6-dioxopiperidin-3-yl)-1-oxoisoindolin-5-yl)methyl)-2,2-difluoroacetamide | 484.0 | A |
| 11 | 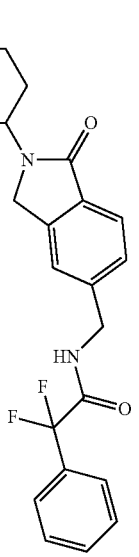 | N-((2-(2,6-dioxopiperidin-3-yl)-1-oxoisoindolin-5-yl)methyl)-2,2-difluoro-2-phenylacetamide | 428.2 | C |

TABLE 1-continued
| Cpd No. | Compound | Name | MH+ | FCA Prolif Cell TiterGlo KG-1 72 h (IC$_{50}$) |
|---|---|---|---|---|
| 12 | 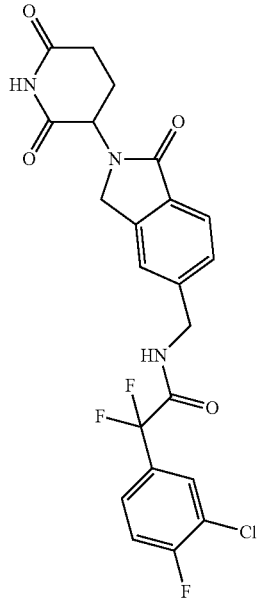 [SMILES: O=C1CCC(N2Cc3cc(CNC(=O)C(F)(F)c4ccc(F)c(Cl)c4)ccc3C2=O)C(=O)N1] | 2-(3-chloro-4-fluorophenyl)-N-((2-(2,6-dioxopiperidin-3-yl)-1-oxoisoindolin-5-yl)methyl)-2,2-difluoroacetamide | 480.0 | B |
| 13 | 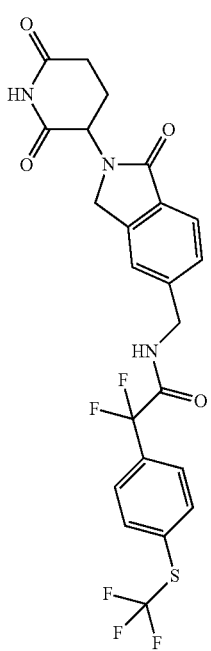 [SMILES: O=C1CCC(N2Cc3cc(CNC(=O)C(F)(F)c4ccc(SC(F)(F)F)cc4)ccc3C2=O)C(=O)N1] | N-((2-(2,6-dioxopiperidin-3-yl)-1-oxoisoindolin-5-yl)methyl)-2,2-difluoro-2-(4-(trifluoromethylthio)phenyl)acetamide | 528.1 | D |

TABLE 1-continued
| Cpd No. | Compound | Name | MH+ | FCA Prolif Cell TiterGlo KG-1 72 h (IC$_{50}$) |
|---|---|---|---|---|
| 14 | 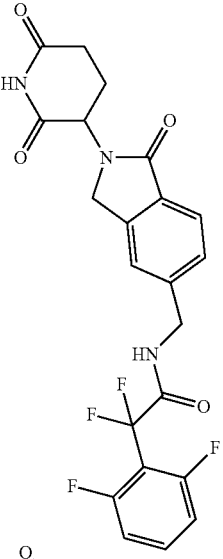 | 2-(2,6-difluorophenyl)-N-((2-(2,6-dioxopiperidin-3-yl)-1-oxoisoindolin-5-yl)methyl)-2,2-difluoroacetamide | 464.2 | D |
| 15 | 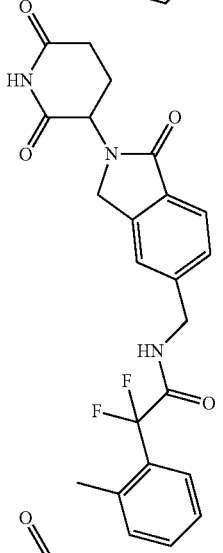 | N-((2-(2,6-dioxopiperidin-3-yl)-1-oxoisoindolin-5-yl)methyl)-2,2-difluoro-2-o-tolylacetamide | 442.2 | B |
| 16 | 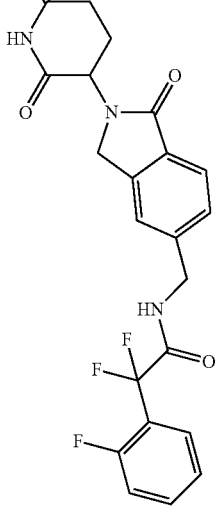 | N-((2-(2,6-dioxopiperidin-3-yl)-1-oxoisoindolin-5-yl)methyl)-2,2-difluoro-2-(2-fluorophenyl)acetamide | 446.2 | C |

TABLE 1-continued
| Cpd No. | Compound | Name | MH+ | FCA Prolif Cell TiterGlo KG-1 72 h (IC$_{50}$) |
|---|---|---|---|---|
| 17 | 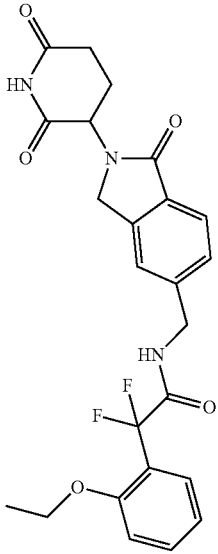 [SMILES: CCOc1ccccc1C(F)(F)C(=O)NCc1ccc2c(c1)CN(C1CCC(=O)NC1=O)C2=O] | N-((2-(2,6-dioxopiperidin-3-yl)-1-oxoisoindolin-5-yl)methyl)-2-(2-ethoxyphenyl)-2,2-difluoroacetamide | 472.2 | B |
| 18 | 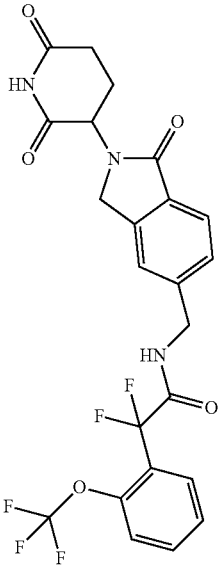 [SMILES: O=C1CCC(N2Cc3cc(CNC(=O)C(F)(F)c4ccccc4OC(F)(F)F)ccc3C2=O)C(=O)N1] | N-((2-(2,6-dioxopiperidin-3-yl)-1-oxoisoindolin-5-yl)methyl)-2,2-difluoro-2-(2-(trifluoromethoxy)phenyl)acetamide | 512.2 | B |

TABLE 1-continued
| Cpd No. | Compound | Name | MH+ | FCA Prolif Cell TiterGlo KG-1 72 h (IC$_{50}$) |
|---|---|---|---|---|
| 19 | 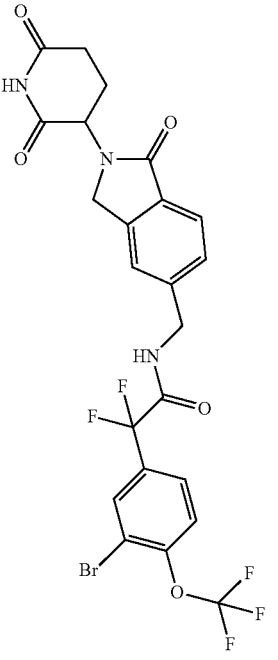 [SMILES: O=C1CCC(N2Cc3cc(CNC(=O)C(F)(F)c4ccc(OC(F)(F)F)c(Br)c4)ccc3C2=O)C(=O)N1] | 2-(3-bromo-4-(trifluoromethoxy)phenyl)-N-((2-(2,6-dioxopiperidin-3-yl)-1-oxoisoindolin-5-yl)methyl)-2,2-difluoroacetamide | 592.0 | B |
| 20 | 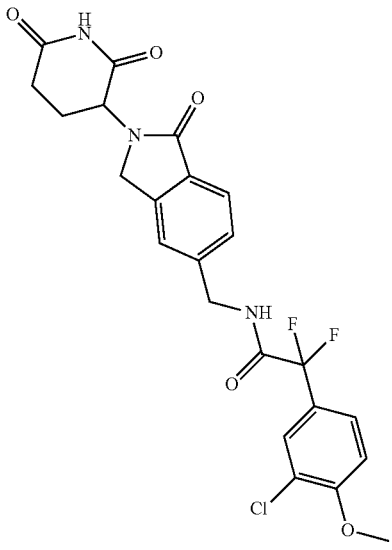 [SMILES: COc1ccc(C(F)(F)C(=O)NCc2ccc3c(c2)CN(C2CCC(=O)NC2=O)C3=O)cc1Cl] | 2-(3-chloro-4-methoxyphenyl)-N-((2-(2,6-dioxopiperidin-3-yl)-1-oxoisoindolin-5-yl)methyl)-2,2-difluoroacetamide | 492.5 | D |

TABLE 1-continued
| Cpd No. | Compound | Name | MH+ | FCA Prolif Cell TiterGlo KG-1 72 h (IC$_{50}$) |
|---|---|---|---|---|
| 21 | 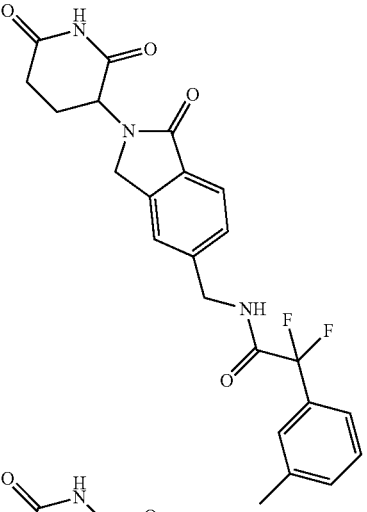 [SMILES: O=C1CCC(N2Cc3cc(CNC(=O)C(F)(F)c4cccc(F)c4)ccc3C2=O)C(=O)N1] | N-((2-(2,6-dioxopiperidin-3-yl)-1-oxoisoindolin-5-yl)methyl)-2,2-difluoro-2-m-tolylacetamide | 442.3 | B |
| 22 | 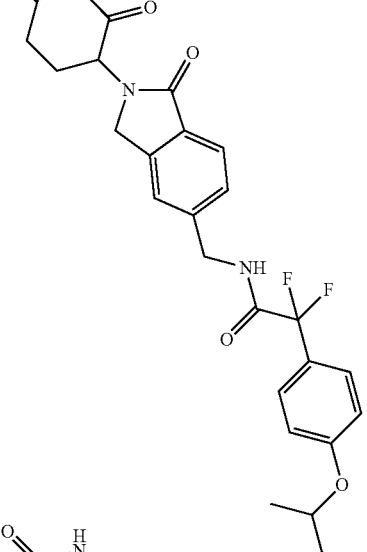 | N-((2-(2,6-dioxopiperidin-3-yl)-1-oxoisoindolin-5-yl)methyl)-2,2-difluoro-2-(4-isopropoxyphenyl)acetamide | 486.1 | B |
| 23 | 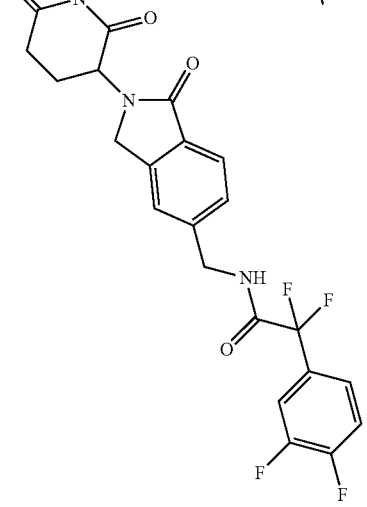 | 2-(3,4-difluorophenyl)-N-((2-(2,6-dioxopiperidin-3-yl)-1-oxoisoindolin-5-yl)methyl)-2,2-difluoroacetamide | 464.0 | D |

TABLE 1-continued

| Cpd No. | Compound | Name | MH+ | FCA Prolif Cell TiterGlo KG-1 72 h (IC$_{50}$) |
|---|---|---|---|---|
| 24 | | N-((2-(2,6-dioxopiperidin-3-yl)-1-oxoisoindolin-5-yl)methyl)-2,2-difluoro-2-(3-fluorophenyl)acetamide | 446.0 | D |
| 25 | | N-((2-(2,6-dioxopiperidin-3-yl)-1-oxoisoindolin-5-yl)methyl)-2,2-difluoro-2-(3-(trifluoromethyl)pyridin-2-yl)acetamide | 497.4 | C |
| 26 | | N-((2-(2,6-dioxopiperidin-3-yl)-1-oxoisoindolin-5-yl)methyl)-2,2-difluoro-2-(4-isopropylphenyl)acetamide | 470.2 | A |

TABLE 1-continued

| Cpd No. | Compound | Name | MH+ | FCA Prolif Cell TiterGlo KG-1 72 h (IC$_{50}$) |
|---|---|---|---|---|
| 27 | | 2-(2,4-dichlorophenyl)-N-((2-(2,6-dioxopiperidin-3-yl)-1-oxoisoindolin-5-yl)methyl)-2,2-difluoroacetamide | 496.0 | C |
| 28 | | N-((2-(2,6-dioxopiperidin-3-yl)-1-oxoisoindolin-5-yl)methyl)-2,2-difluoro-2-(2-methoxyphenyl)acetamide | 458.2 | D |
| 29 | | 2-(4-cyclopropylphenyl)-N-((2-(2,6-dioxopiperidin-3-yl)-1-oxoisoindolin-5-yl)methyl)-2,2-difluoroacetamide | 468.1 | C |

TABLE 1-continued

| Cpd No. | Compound | Name | MH+ | FCA Prolif Cell TiterGlo KG-1 72 h (IC$_{50}$) |
|---|---|---|---|---|
| 30 | | 2-(4-chloro-2-fluorophenyl)-N-((2-(2,6-dioxopiperidin-3-yl)-1-oxoisoindolin-5-yl)methyl)-2,2-difluoroacetamide | 480.1 | A |
| 31 | | 2-(4-chloro-3-fluorophenyl)-N-((2-(2,6-dioxopiperidin-3-yl)-1-oxoisoindolin-5-yl)methyl)-2,2-difluoroacetamide | 480.1 | B |
| 32 | | N-((2-(2,6-dioxopiperidin-3-yl)-1-oxoisoindolin-5-yl)methyl)-2,2-difluoro-2-(3-fluoro-2-methylphenyl)acetamide | 460.1 | B |

TABLE 1-continued

| Cpd No. | Compound | Name | MH+ | FCA Prolif Cell TiterGlo KG-1 72 h (IC$_{50}$) |
|---|---|---|---|---|
| 33 | | 2-(3-chloro-2-methylphenyl)-N-((2-(2,6-dioxopiperidin-3-yl)-1-oxoisoindolin-5-yl)methyl)-2,2-difluoroacetamide | 476.1 | A |
| 34 | | N-((2-(2,6-dioxopiperidin-3-yl)-1-oxoisoindolin-5-yl)methyl)-2,2-difluoro-2-(4-fluoro-2-(trifluoromethyl)phenyl)acetamide | 514.1 | B |
| 35 | | 2-(4-chloro-2-methylphenyl)-N-((2-(2,6-dioxopiperidin-3-yl)-1-oxoisoindolin-5-yl)methyl)-2,2-difluoroacetamide | 476.1 | B |

TABLE 1-continued

| Cpd No. | Compound | Name | MH+ | FCA Prolif Cell TiterGlo KG-1 72 h (IC$_{50}$) |
|---|---|---|---|---|
| 36 | | N-((2-(2,6-dioxopiperidin-3-yl)-1-oxoisoindolin-5-yl)methyl)-2,2-difluoro-2-(4-fluoro-2-methylphenyl)acetamide | 460.1 | B |
| 37 | | 2-(4-chloro-2-(trifluoromethyl)phenyl)-N-((2-(2,6-dioxopiperidin-3-yl)-1-oxoisoindolin-5-yl)methyl)-2,2-difluoroacetamide | 530.1 | B |
| 38 | | 2-cyclohexyl-N-((2-(2,6-dioxopiperidin-3-yl)-1-oxoisoindolin-5-yl)methyl)-2,2-difluoroacetamide | 434.1 | B |

TABLE 1-continued
| Cpd No. | Compound | Name | MH+ | FCA Prolif Cell TiterGlo KG-1 72 h (IC$_{50}$) |
|---|---|---|---|---|
| 39 | 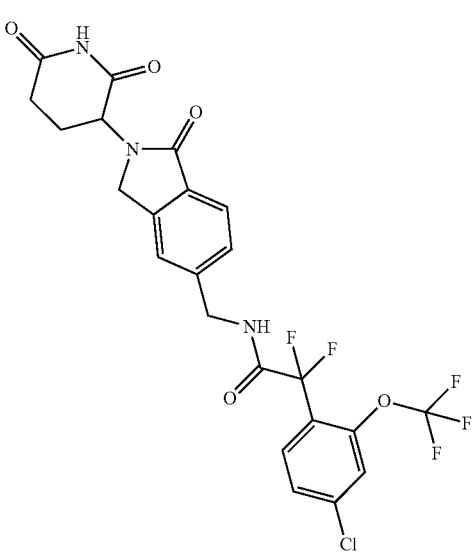 | 2-(4-chloro-2-(trifluoromethoxy)phenyl)-N-((2-(2,6-dioxopiperidin-3-yl)-1-oxoisoindolin-5-yl)methyl)-2,2-difluoroacetamide | 546.0 | A |
| 40 | 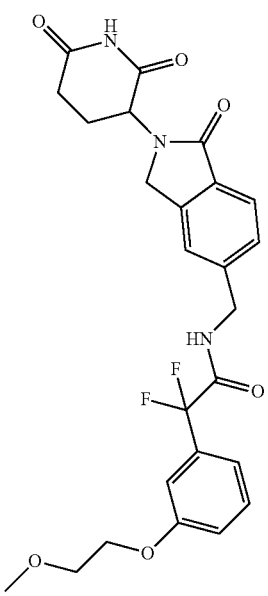 [SMILES: COCCOc1cccc(C(F)(F)C(=O)NCc2ccc3c(c2)CN(C2CCC(=O)NC2=O)C3=O)c1] | N-((2-(2,6-dioxopiperidin-3-yl)-1-oxoisoindolin-5-yl)methyl)-2,2-difluoro-2-(3-(2-methoxyethoxy)phenyl)acetamide | 502.0 | C |

TABLE 1-continued
| Cpd No. | Compound | Name | MH+ | FCA Prolif Cell TiterGlo KG-1 72 h (IC$_{50}$) |
|---|---|---|---|---|
| 41 | 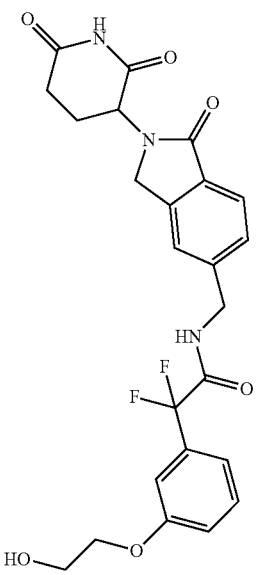 [SMILES: O=C1CCC(N2Cc3cc(CNC(=O)C(F)(F)c4cccc(OCCO)c4)ccc3C2=O)C(=O)N1] | N-((2-(2,6-dioxopiperidin-3-yl)-1-oxoisoindolin-5-yl)methyl)-2,2-difluoro-2-(3-(2-hydroxyethoxy)phenyl)acetamide | 488.1 | D |
| 42 | 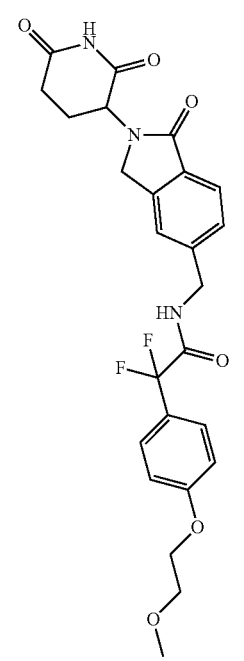 [SMILES: COCCOc1ccc(C(F)(F)C(=O)NCc2ccc3c(c2)CN(C2CCC(=O)NC2=O)C3=O)cc1] | N-((2-(2,6-dioxopiperidin-3-yl)-1-oxoisoindolin-5-yl)methyl)-2,2-difluoro-2-(4-(2-methoxyethoxy)phenyl)acetamide | 502.1 | D |

TABLE 1-continued
| Cpd No. | Compound | Name | MH+ | FCA Prolif Cell TiterGlo KG-1 72 h (IC$_{50}$) |
|---|---|---|---|---|
| 43 | 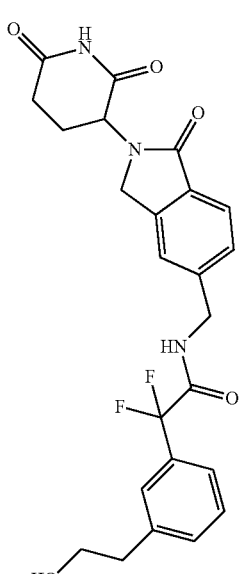 | N-((2-(2,6-dioxopiperidin-3-yl)-1-oxoisoindolin-5-yl)methyl)-2,2-difluoro-2-(3-(2-hydroxyethyl)phenyl)acetamide | 472.1 | D |
| 44 | 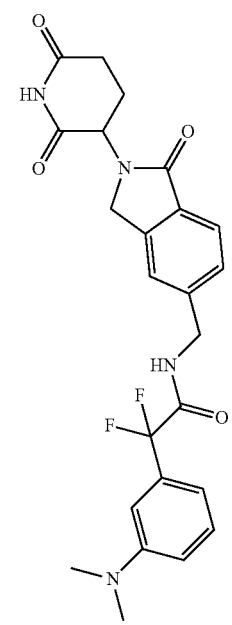 [SMILES: CN(C)c1cccc(C(F)(F)C(=O)NCc2ccc3c(c2)CN(C2CCC(=O)NC2=O)C3=O)c1] | 2-(3-(dimethylamino)phenyl)-N-((2-(2,6-dioxopiperidin-3-yl)-1-oxoisoindolin-5-yl)methyl)-2,2-difluoroacetamide | 470.8 | B |

TABLE 1-continued
| Cpd No. | Compound | Name | MH+ | FCA Prolif Cell TiterGlo KG-1 72 h (IC$_{50}$) |
|---|---|---|---|---|
| 45 | 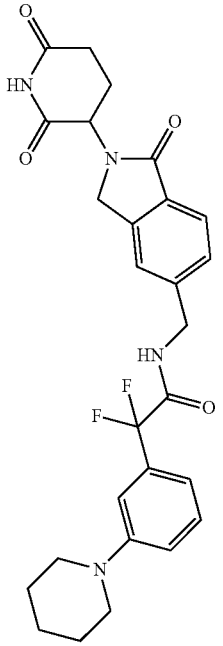 [SMILES: O=C1CCC(N2Cc3cc(CNC(=O)C(F)(F)c4cccc(N5CCCCC5)c4)ccc3C2=O)C(=O)N1] | N-((2-(2,6-dioxopiperidin-3-yl)-1-oxoisoindolin-5-yl)methyl)-2,2-difluoro-2-(3-(piperidin-1-yl)phenyl)acetamide | 510.8 | A |
| 46 | 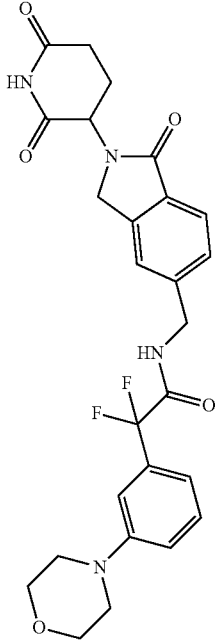 [SMILES: O=C1CCC(N2Cc3cc(CNC(=O)C(F)(F)c4cccc(N5CCOCC5)c4)ccc3C2=O)C(=O)N1] | N-((2-(2,6-dioxopiperidin-3-yl)-1-oxoisoindolin-5-yl)methyl)-2,2-difluoro-2-(3-morpholinophenyl)acetamide | 513.0 | D |

TABLE 1-continued

| Cpd No. | Compound | Name | MH+ | FCA Prolif Cell TiterGlo KG-1 72 h (IC$_{50}$) |
|---|---|---|---|---|
| 47 | | N-((2-(2,6-dioxopiperidin-3-yl)-1-oxoisoindolin-5-yl)methyl)-2,2-difluoro-2-(4-fluoro-2-isopropoxyphenyl)acetamide | 504.0 | A |
| 48 | | N-((2-(2,6-dioxopiperidin-3-yl)-1-oxoisoindolin-5-yl)methyl)-2,2-difluoro-2-(2-(2,2,2-trifluoroethoxy)phenyl)acetamide | 525.9 | B |
| 49 | | N-((2-(2,6-dioxopiperidin-3-yl)-1-oxoisoindolin-5-yl)methyl)-2-(2-ethoxy-4-fluorophenyl)-2,2-difluoroacetamide | 490.0 | B |

TABLE 1-continued
| Cpd No. | Compound | Name | MH+ | FCA Prolif Cell TiterGlo KG-1 72 h (IC$_{50}$) |
|---|---|---|---|---|
| 50 | 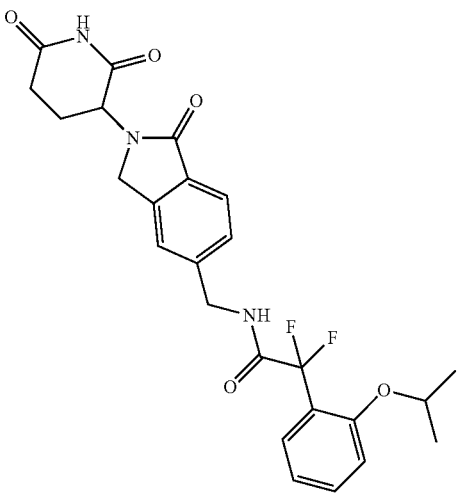 [SMILES: CC(C)Oc1ccccc1C(F)(F)C(=O)NCc1ccc2c(c1)CN(C1CCC(=O)NC1=O)C2=O] | N-((2-(2,6-dioxopiperidin-3-yl)-1-oxoisoindolin-5-yl)methyl)-2,2-difluoro-2-(2-isopropoxyphenyl)acetamide | 486.0 | A |
| 51 | 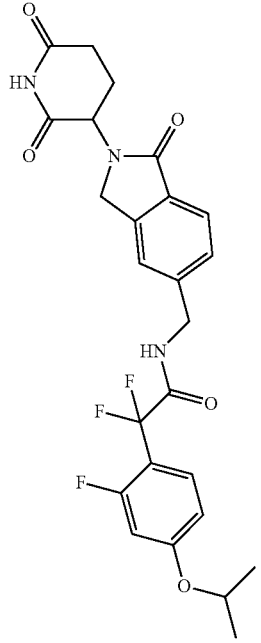 [SMILES: CC(C)Oc1ccc(C(F)(F)C(=O)NCc2ccc3c(c2)CN(C2CCC(=O)NC2=O)C3=O)c(F)c1] | N-((2-(2,6-dioxopiperidin-3-yl)-1-oxoisoindolin-5-yl)methyl)-2,2-difluoro-2-(2-fluoro-4-isopropoxyphenyl)acetamide | 504.0 | B |

TABLE 1-continued
| Cpd No. | Compound | Name | MH+ | FCA Prolif Cell TiterGlo KG-1 72 h ($IC_{50}$) |
|---|---|---|---|---|
| 52 | 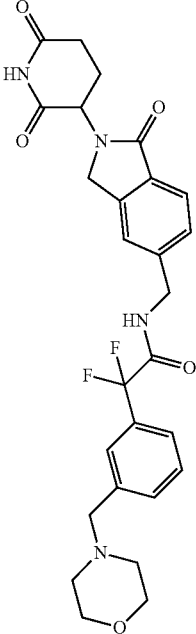 [SMILES: O=C1CCC(N2Cc3cc(CNC(=O)C(F)(F)c4cccc(CN5CCOCC5)c4)ccc3C2=O)C(=O)N1] | N-((2-(2,6-dioxopiperidin-3-yl)-1-oxoisoindolin-5-yl)methyl)-2,2-difluoro-2-(3-(morpholinomethyl)phenyl)acetamide | 527.0 | D |
| 53 | 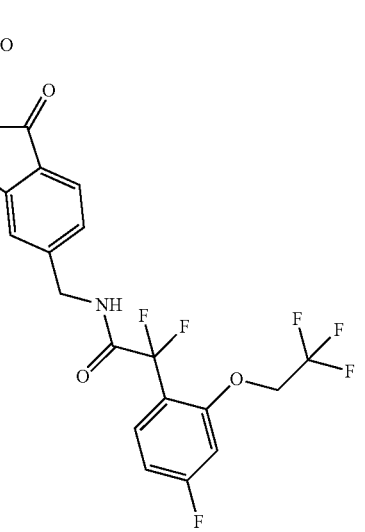 | N-((2-(2,6-dioxopiperidin-3-yl)-1-oxoisoindolin-5-yl)methyl)-2,2-difluoro-2-(4-fluoro-2-(2,2,2-trifluoroethoxy)phenyl)acetamide | 544.0 | A |

| Cpd No. | Compound | Name | MH+ | FCA Prolif Cell TiterGlo KG-1 72 h (IC$_{50}$) |
|---|---|---|---|---|
| 54 | 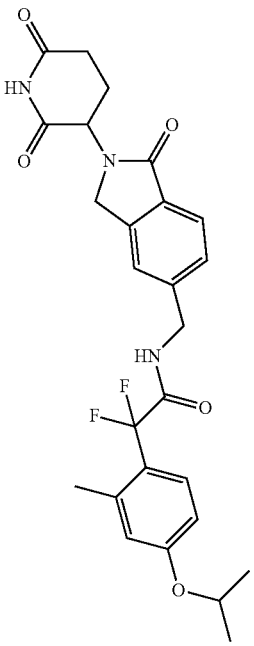 | N-((2-(2,6-dioxopiperidin-3-yl)-1-oxoisoindolin-5-yl)methyl)-2,2-difluoro-2-(4-isopropoxy-2-methylphenyl)acetamide | 500.2 | A |
| 55 | 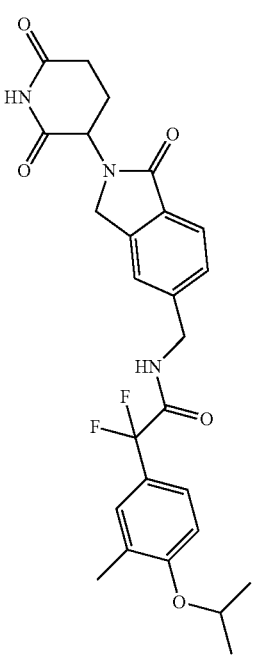 | N-((2-(2,6-dioxopiperidin-3-yl)-1-oxoisoindolin-5-yl)methyl)-2,2-difluoro-2-(4-isopropoxy-3-methylphenyl)acetamide | 500.6 | B |

| Cpd No. | Compound | Name | MH+ | FCA Prolif Cell TiterGlo KG-1 72 h (IC$_{50}$) |
|---|---|---|---|---|
| 56 | 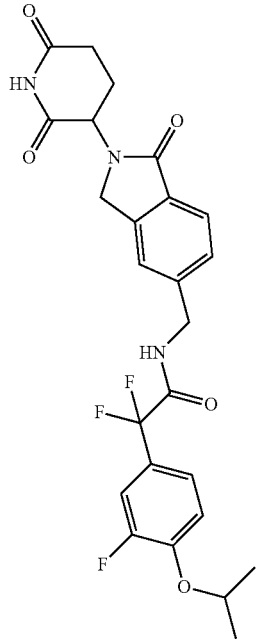 [SMILES: Cc1cc(C(F)(F)C(=O)NCc2ccc3c(c2)CN(C2CCC(=O)NC2=O)C3=O)ccc1OC(C)C] | N-((2-(2,6-dioxopiperidin-3-yl)-1-oxoisoindolin-5-yl)methyl)-2,2-difluoro-2-(3-fluoro-4-isopropoxyphenyl)acetamide | 504.6 | D |
| 57 | 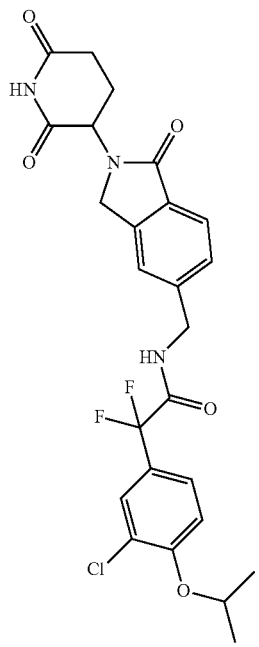 [SMILES: CC(C)Oc1ccc(C(F)(F)C(=O)NCc2ccc3c(c2)CN(C2CCC(=O)NC2=O)C3=O)cc1F] | 2-(3-chloro-4-isopropoxyphenyl)-N-((2-(2,6-dioxopiperidin-3-yl)-1-oxoisoindolin-5-yl)methyl)-2,2-difluoroacetamide | 520.0 | B |

| Cpd No. | Compound | Name | MH+ | FCA Prolif Cell TiterGlo KG-1 72 h (IC$_{50}$) |
|---|---|---|---|---|
| 58 | 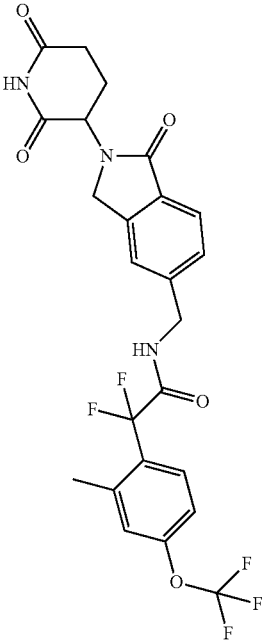 [SMILES: Cc1cc(OC(F)(F)F)ccc1C(F)(F)C(=O)NCc1ccc2c(c1)CN(C1CCC(=O)NC1=O)C2=O] | N-((2-(2,6-dioxopiperidin-3-yl)-1-oxoisoindolin-5-yl)methyl)-2,2-difluoro-2-(2-methyl-4-(trifluoromethoxy)phenyl)acetamide | 526.5 | B |
| 59 | 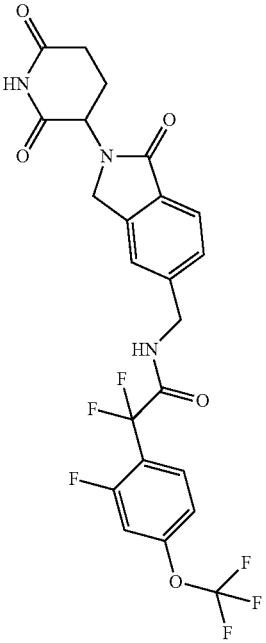 [SMILES: O=C1CCC(N2Cc3cc(CNC(=O)C(F)(F)c4ccc(OC(F)(F)F)cc4F)ccc3C2=O)C(=O)N1] | N-((2-(2,6-dioxopiperidin-3-yl)-1-oxoisoindolin-5-yl)methyl)-2,2-difluoro-2-(2-fluoro-4-(trifluoromethoxy)phenyl)acetamide | 529.6 | D |

TABLE 1-continued
| Cpd No. | Compound | Name | MH+ | FCA Prolif Cell TiterGlo KG-1 72 h (IC$_{50}$) |
|---|---|---|---|---|
| 60 | 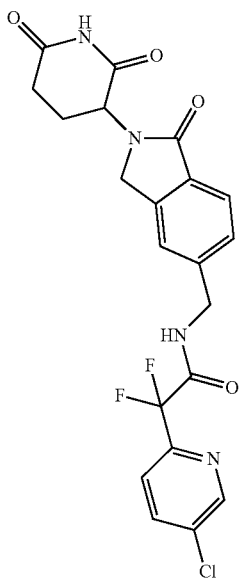 [SMILES: O=C1CCC(N2Cc3cc(CNC(=O)C(F)(F)c4ccc(Cl)cn4)ccc3C2=O)C(=O)N1] | 2-(5-chloropyridin-2-yl)-N-((2-(2,6-dioxopiperidin-3-yl)-1-oxoisoindolin-5-yl)methyl)-2,2-difluoroacetamide | 462.7 | C |
| 61 | 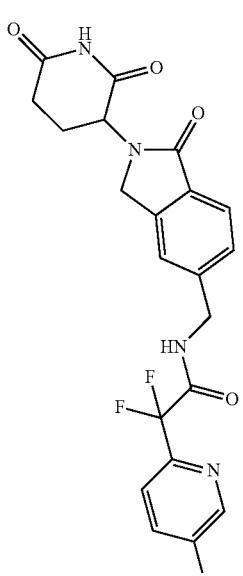 | N-((2-(2,6-dioxopiperidin-3-yl)-1-oxoisoindolin-5-yl)methyl)-2,2-difluoro-2-(5-fluoropyridin-2-yl)acetamide | 446.7 | D |

TABLE 1-continued
| Cpd No. | Compound | Name | MH+ | FCA Prolif Cell TiterGlo KG-1 72 h (IC$_{50}$) |
|---|---|---|---|---|
| 62 | 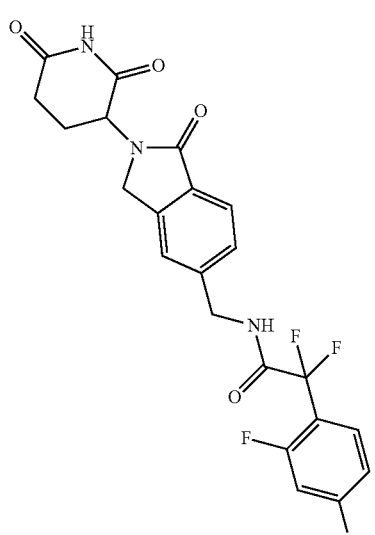 | 2-(2,4-difluorophenyl)-N-((2-(2,6-dioxopiperidin-3-yl)-1-oxoisoindolin-5-yl)methyl)-2,2-difluoroacetamide | 463.7 | B |
| 63 | 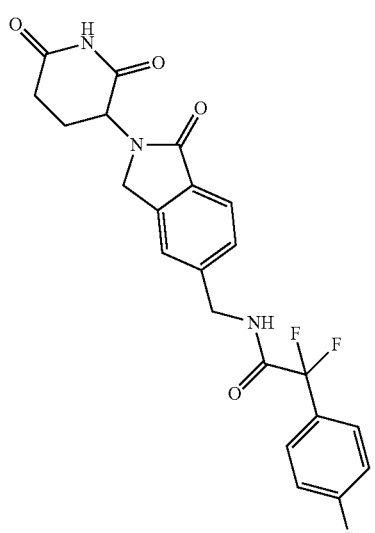 | 2-(4-bromophenyl)-N-((2-(2,6-dioxopiperidin-3-yl)-1-oxoisoindolin-5-yl)methyl)-2,2-difluoroacetamide | 505.6 | C |

TABLE 1-continued

| Cpd No. | Compound | Name | MH+ | FCA Prolif Cell TiterGlo KG-1 72 h (IC$_{50}$) |
|---|---|---|---|---|
| 64 | | N-((2-(2,6-dioxopiperidin-3-yl)-1-oxoisoindolin-5-yl)methyl)-2,2-difluoro-2-(2-(2-methoxyethoxy)phenyl)acetamide | 502.3 | B |
| 65 | | N-((2-(2,6-dioxopiperidin-3-yl)-1-oxoisoindolin-5-yl)methyl)-2,2-difluoro-2-(1-hydroxycyclohexyl)acetamide | 450.2 | B |
| 66 | | N-((2-(2,6-dioxopiperidin-3-yl)-1-oxoisoindolin-5-yl)methyl)-2,2-difluoro-2-(1-hydroxycyclopentyl)acetamide | 436.2 | D |

| Cpd No. | Compound | Name | MH+ | FCA Prolif Cell TiterGlo KG-1 72 h (IC$_{50}$) |
|---|---|---|---|---|
| 67 | 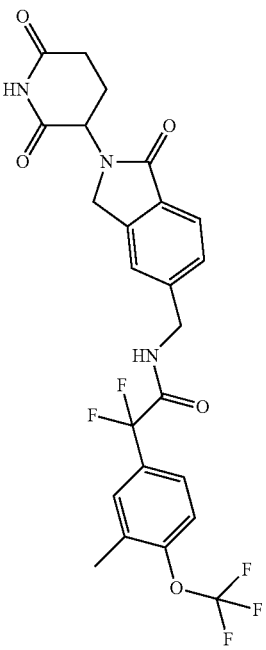 [SMILES: Cc1cc(C(F)(F)C(=O)NCc2ccc3c(c2)CN(C2CCC(=O)NC2=O)C3=O)ccc1OC(F)(F)F] | N-((2-(2,6-dioxopiperidin-3-yl)-1-oxoisoindolin-5-yl)methyl)-2,2-difluoro-2-(3-methyl-4-(trifluoromethoxy)phenyl)acetamide | 526.3 | D |
| 68 | 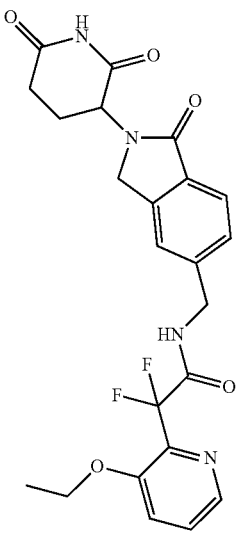 [SMILES: CCOc1cccnc1C(F)(F)C(=O)NCc1ccc2c(c1)CN(C1CCC(=O)NC1=O)C2=O] | N-((2-(2,6-dioxopiperidin-3-yl)-1-oxoisoindolin-5-yl)methyl)-2-(3-ethoxypyridin-2-yl)-2,2-difluoroacetamide | 473.3 | D |

TABLE 1-continued
| Cpd No. | Compound | Name | MH+ | FCA Prolif Cell TiterGlo KG-1 72 h (IC$_{50}$) |
|---|---|---|---|---|
| 69 | | N-((2-(2,6-dioxopiperidin-3-yl)-1-oxoisoindolin-5-yl)methyl)-2,2-difluoro-2-(3-methylpyridin-2-yl)acetamide | 443.3 | B |
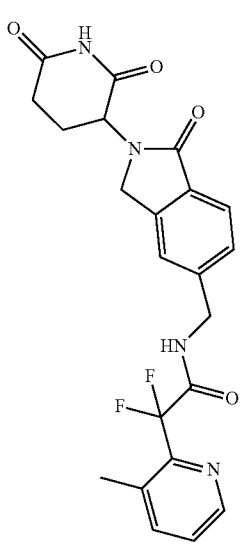 [SMILES: Cc1cccnc1C(F)(F)C(=O)NCc1ccc2c(c1)CN(C1CCC(=O)NC1=O)C2=O]
| 70 | | N-((2-(2,6-dioxopiperidin-3-yl)-1-oxoisoindolin-5-yl)methyl)-2,2-difluoro-2-(5-methylpyridin-2-yl)acetamide | 443.3 | D |
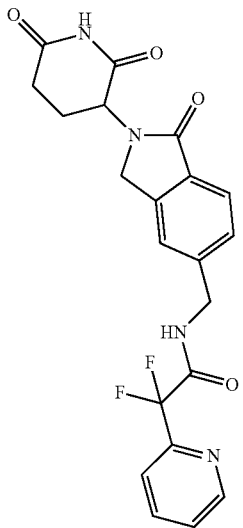

TABLE 1-continued

| Cpd No. | Compound | Name | MH+ | FCA Prolif Cell TiterGlo KG-1 72 h (IC$_{50}$) |
|---|---|---|---|---|
| 71 | | N-((2-(2,6-dioxopiperidin-3-yl)-1-oxoisoindolin-5-yl)methyl)-2-(2-ethoxy-6-fluorophenyl)-2,2-difluoroacetamide | 490.3 | A |
| 72 | | N-((2-(2,6-dioxopiperidin-3-yl)-1-oxoisoindolin-5-yl)methyl)-2,2-difluoro-2-(4'-fluorobiphenyl-4-yl)acetamide | 522.5 | D |
| 73 | | N-((2-(2,6-dioxopiperidin-3-yl)-1-oxoisoindolin-5-yl)methyl)-2-(2-ethoxy-5-fluorophenyl)-2,2-difluoroacetamide | 490.1 | D |

TABLE 1-continued
| Cpd No. | Compound | Name | MH+ | FCA Prolif Cell TiterGlo KG-1 72 h (IC$_{50}$) |
|---|---|---|---|---|
| 74 | 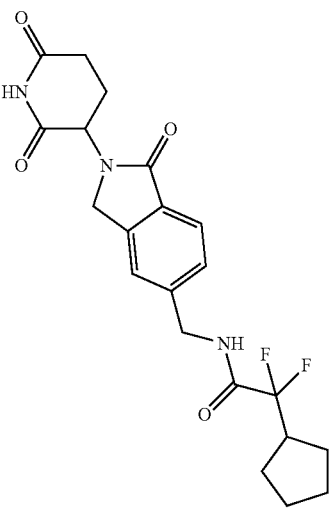 [SMILES: O=C1CCC(N2Cc3cc(CNC(=O)C(F)(F)C4CCCC4)ccc3C2=O)C(=O)N1] | 2-cyclopentyl-N-((2-(2,6-dioxopiperidin-3-yl)-1-oxoisoindolin-5-yl)methyl)-2,2-difluoroacetamide | 420.2 | D |
| 75 | 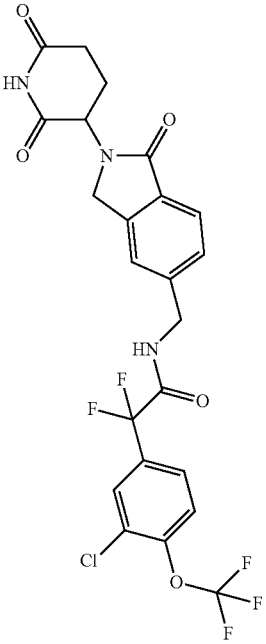 [SMILES: O=C1CCC(N2Cc3cc(CNC(=O)C(F)(F)c4ccc(OC(F)(F)F)c(Cl)c4)ccc3C2=O)C(=O)N1] | 2-(3-chloro-4-(trifluoromethoxy)phenyl)-N-((2-(2,6-dioxopiperidin-3-yl)-1-oxoisoindolin-5-yl)methyl)-2,2-difluoroacetamide | 546.3 | D |

TABLE 1-continued

| Cpd No. | Compound | Name | MH+ | FCA Prolif Cell TiterGlo KG-1 72 h (IC$_{50}$) |
|---|---|---|---|---|
| 76 | | N-((2-(2,6-dioxopiperidin-3-yl)-1-oxoisoindolin-5-yl)methyl)-2,2-difluoro-2-(4-methoxy-2-(trifluoromethyl)phenyl)acetamide | 526.2 | A |
| 77 | | N-((2-(2,6-dioxopiperidin-3-yl)-1-oxoisoindolin-5-yl)methyl)-2,2-difluoro-2-(2-(2-hydroxyethoxy)phenyl)acetamide | 488.1 | D |
| 78 | | 2-(4-chloro-2-ethoxyphenyl)-N-((2-(2,6-dioxopiperidin-3-yl)-1-oxoisoindolin-5-yl)methyl)-2,2-difluoroacetamide | 506.1 | C |

TABLE 1-continued

| Cpd No. | Compound | Name | MH+ | FCA Prolif Cell TiterGlo KG-1 72 h (IC$_{50}$) |
|---|---|---|---|---|
| 79 | | N-((2-(2,6-dioxopiperidin-3-yl)-1-oxoisoindolin-5-yl)methyl)-2,2-difluoro-2-(2-hydroxyphenyl)acetamide | 444.4 | A |
| 80 | | N-((2-(2,6-dioxopiperidin-3-yl)-1-oxoisoindolin-5-yl)methyl)-2,2-difluoro-2-(2-(methylamino)phenyl)acetamide | 457.2 | A |
| 81 | | N-((2-(2,6-dioxopiperidin-3-yl)-1-oxoisoindolin-5-yl)methyl)-2,2-difluoro-2-(4-isopropoxy-2-(trifluoromethyl)phenyl)acetamide | 554.0 | A |

TABLE 1-continued
| Cpd No. | Compound | Name | MH+ | FCA Prolif Cell TiterGlo KG-1 72 h (IC$_{50}$) |
|---|---|---|---|---|
| 82 | 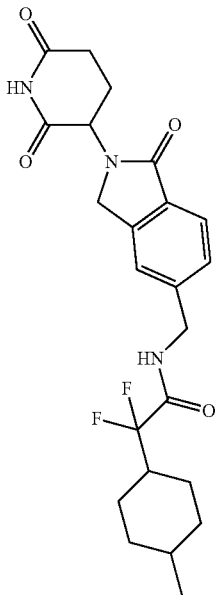 [SMILES: CC1CCC(C(F)(F)C(=O)NCc2ccc3c(c2)CN(C2CCC(=O)NC2=O)C3=O)CC1] | N-((2-(2,6-dioxopiperidin-3-yl)-1-oxoisoindolin-5-yl)methyl)-2,2-difluoro-2-(4-methylcyclohexyl)acetamide | 448.2 | A |
| 83 | 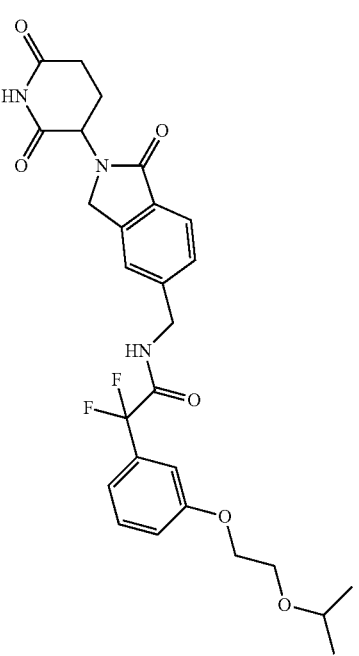 [SMILES: CC(C)OCCOc1cccc(C(F)(F)C(=O)NCc2ccc3c(c2)CN(C2CCC(=O)NC2=O)C3=O)c1] | N-((2-(2,6-dioxopiperidin-3-yl)-1-oxoisoindolin-5-yl)methyl)-2,2-difluoro-2-(3-(2-isopropoxyethoxy)phenyl)acetamide | 529.9 | A |

TABLE 1-continued
| Cpd No. | Compound | Name | MH+ | FCA Prolif Cell TiterGlo KG-1 72 h (IC$_{50}$) |
|---|---|---|---|---|
| 84 | 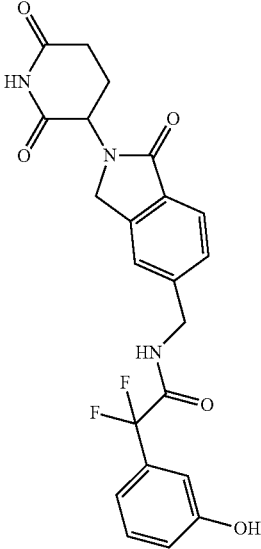 [SMILES: O=C1CCC(N2Cc3cc(CNC(=O)C(F)(F)c4cccc(O)c4)ccc3C2=O)C(=O)N1] | N-((2-(2,6-dioxopiperidin-3-yl)-1-oxoisoindolin-5-yl)methyl)-2,2-difluoro-2-(3-hydroxyphenyl)acetamide | 444.1 | D |
| 85 | 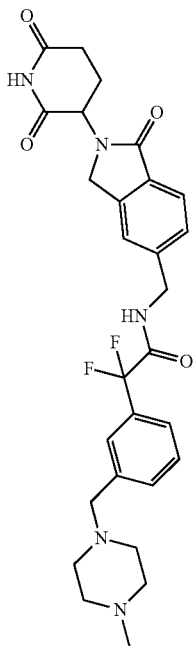 [SMILES: CN1CCN(Cc2cccc(C(F)(F)C(=O)NCc3ccc4c(c3)CN(C3CCC(=O)NC3=O)C4=O)c2)CC1] | N-((2-(2,6-dioxopiperidin-3-yl)-1-oxoisoindolin-5-yl)methyl)-2,2-difluoro-2-(3-((4-methylpiperazin-1-yl)methyl)phenyl)acetamide | 540.4 | D |

TABLE 1-continued
| Cpd No. | Compound | Name | MH+ | FCA Prolif Cell TiterGlo KG-1 72 h (IC$_{50}$) |
|---|---|---|---|---|
| 86 | 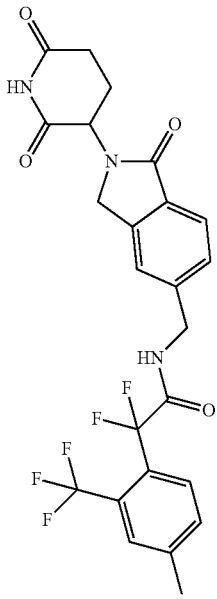 [SMILES: Cc1ccc(C(F)(F)C(=O)NCc2ccc3c(c2)CN(C2CCC(=O)NC2=O)C3=O)c(C(F)(F)F)c1] | N-((2-(2,6-dioxopiperidin-3-yl)-1-oxoisoindolin-5-yl)methyl)-2,2-difluoro-2-(4-methyl-2-(trifluoromethyl)phenyl)acetamide | 510.3 | A |
| 87 | 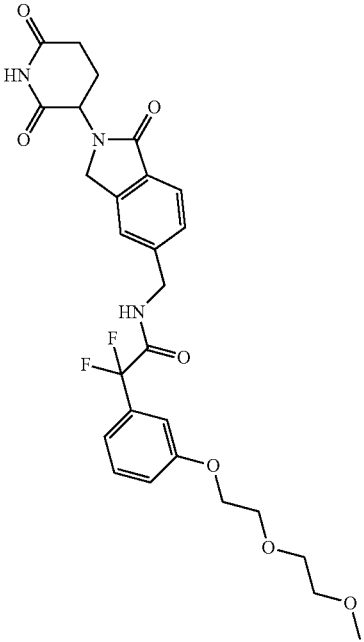 [SMILES: COCCOCCOc1cccc(C(F)(F)C(=O)NCc2ccc3c(c2)CN(C2CCC(=O)NC2=O)C3=O)c1] | N-((2-(2,6-dioxopiperidin-3-yl)-1-oxoisoindolin-5-yl)methyl)-2,2-difluoro-2-(3-(2-(2-methoxyethoxy)ethoxy)phenyl)acetamide | 546.1 | D |

TABLE 1-continued
| Cpd No. | Compound | Name | MH+ | FCA Prolif Cell TiterGlo KG-1 72 h (IC$_{50}$) |
|---|---|---|---|---|
| 88 | 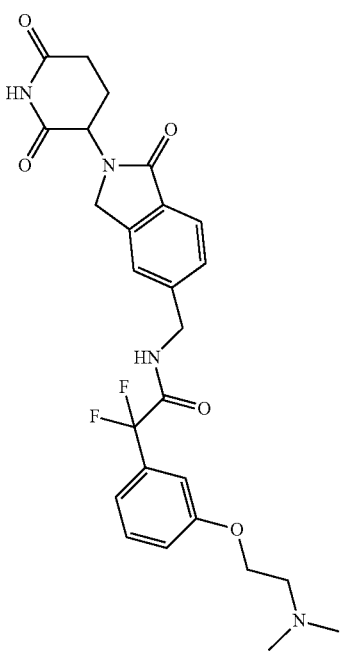 [SMILES: CN(C)CCOc1cccc(C(F)(F)C(=O)NCc2ccc3c(c2)CN(C2CCC(=O)NC2=O)C3=O)c1] | 2-(3-(2-(dimethylamino)ethoxy)phenyl)-N-((2-(2,6-dioxopiperidin-3-yl)-1-oxoisoindolin-5-yl)methyl)-2,2-difluoroacetamide | 515.1 | D |
| 89 | 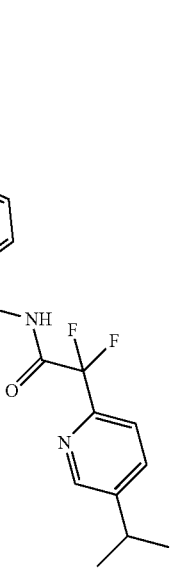 | N-((2-(2,6-dioxopiperidin-3-yl)-1-oxoisoindolin-5-yl)methyl)-2,2-difluoro-2-(5-isopropylpyridin-2-yl)acetamide | 471.1 | C |

TABLE 1-continued
| Cpd No. | Compound | Name | MH+ | FCA Prolif Cell TiterGlo KG-1 72 h (IC$_{50}$) |
|---|---|---|---|---|
| 90 | 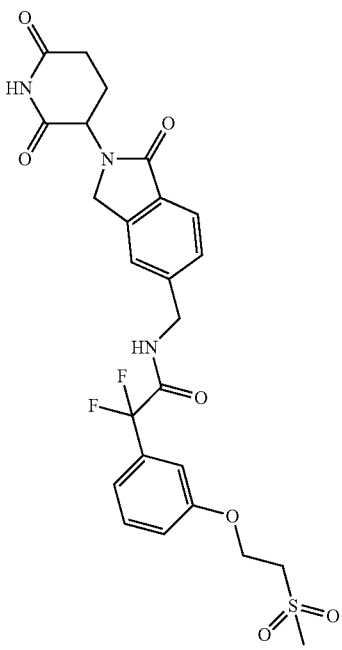 [SMILES: CS(=O)(=O)CCCc1cccc(C(F)(F)C(=O)NCc2ccc3c(c2)CN(C2CCC(=O)NC2=O)C3=O)c1] | N-((2-(2,6-dioxopiperidin-3-yl)-1-oxoisoindolin-5-yl)methyl)-2,2-difluoro-2-(3-(2-(methylsulfonyl)ethoxy)phenyl)acetamide | 549.8 | D |
| 91 | 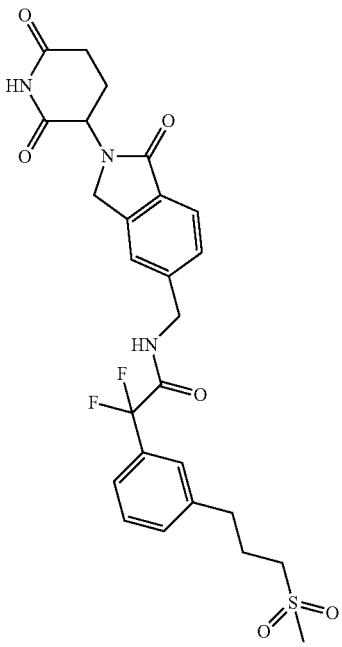 | N-((2-(2,6-dioxopiperidin-3-yl)-1-oxoisoindolin-5-yl)methyl)-2,2-difluoro-2-(3-(3-(methylsulfonyl)propyl)phenyl)acetamide | 548.0 | D |

TABLE 1-continued
| Cpd No. | Compound | Name | MH+ | FCA Prolif Cell TiterGlo KG-1 72 h (IC$_{50}$) |
|---|---|---|---|---|
| 92 | 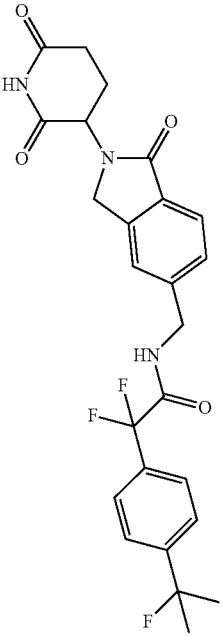 [SMILES: CC(C)(F)c1ccc(C(F)(F)C(=O)NCc2ccc3c(c2)CN(C2CCC(=O)NC2=O)C3=O)cc1] | N-((2-(2,6-dioxopiperidin-3-yl)-1-oxoisoindolin-5-yl)methyl)-2,2-difluoro-2-(4-(2-fluoropropan-2-yl)phenyl)acetamide | 486.2 | C |
| 93 | 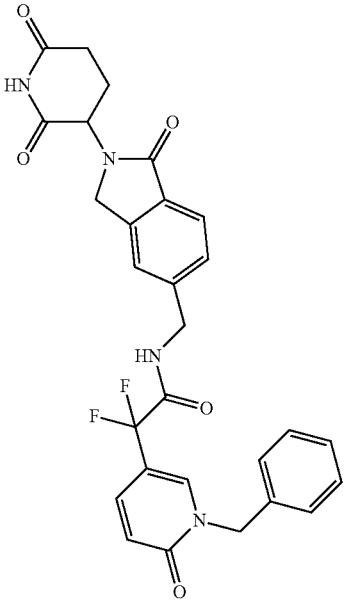 [SMILES: O=C1CCC(N2Cc3cc(CNC(=O)C(F)(F)c4ccc(=O)n(Cc5ccccc5)c4)ccc3C2=O)C(=O)N1] | 2-(1-benzyl-6-oxo-1,6-dihydropyridin-3-yl)-N-((2-(2,6-dioxopiperidin-3-yl)-1-oxoisoindolin-5-yl)methyl)-2,2-difluoroacetamide | 535.1 | D |

TABLE 1-continued
| Cpd No. | Compound | Name | MH+ | FCA Prolif Cell TiterGlo KG-1 72 h (IC$_{50}$) |
|---|---|---|---|---|
| 94 | 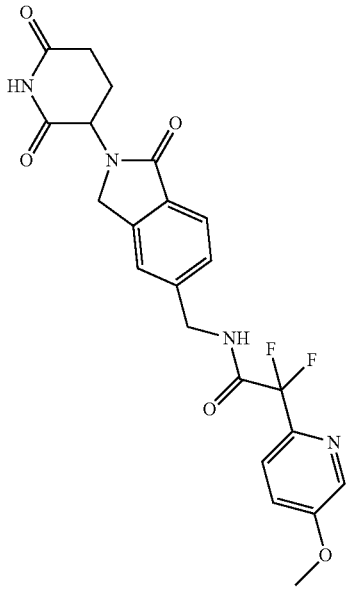 [SMILES: COc1ccc(C(F)(F)C(=O)NCc2ccc3c(c2)CN(C2CCC(=O)NC2=O)C3=O)nc1] | N-((2-(2,6-dioxopiperidin-3-yl)-1-oxoisoindolin-5-yl)methyl)-2,2-difluoro-2-(5-methoxypyridin-2-yl)acetamide | 459.2 | D |
| 95 | 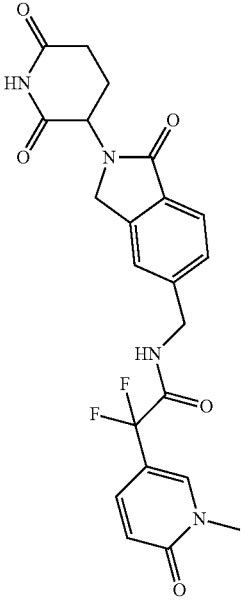 [SMILES: Cn1cc(C(F)(F)C(=O)NCc2ccc3c(c2)CN(C2CCC(=O)NC2=O)C3=O)ccc1=O] | N-((2-(2,6-dioxopiperidin-3-yl)-1-oxoisoindolin-5-yl)methyl)-2,2-difluoro-2-(1-methyl-6-oxo-1,6-dihydropyridin-3-yl)acetamide | 459.2 | D |

TABLE 1-continued
| Cpd No. | Compound | Name | MH+ | FCA Prolif Cell TiterGlo KG-1 72 h (IC$_{50}$) |
|---|---|---|---|---|
| 96 | 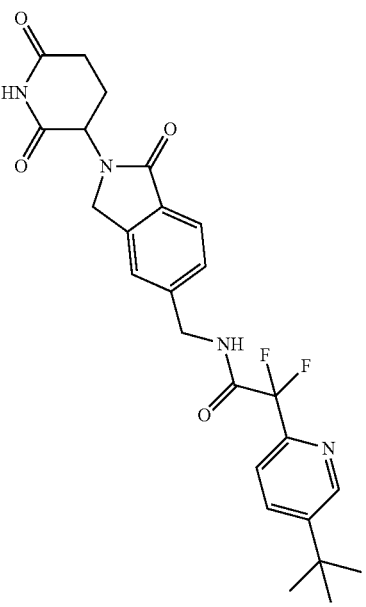 [SMILES: CC(C)(C)c1ccc(C(F)(F)C(=O)NCc2ccc3c(c2)CN(C2CCC(=O)NC2=O)C3=O)nc1] | 2-(5-tert-butylpyridin-2-yl)-N-((2-(2,6-dioxopiperidin-3-yl)-1-oxoisoindolin-5-yl)methyl)-2,2-difluoroacetamide | 485.2 | B |
| 97 | 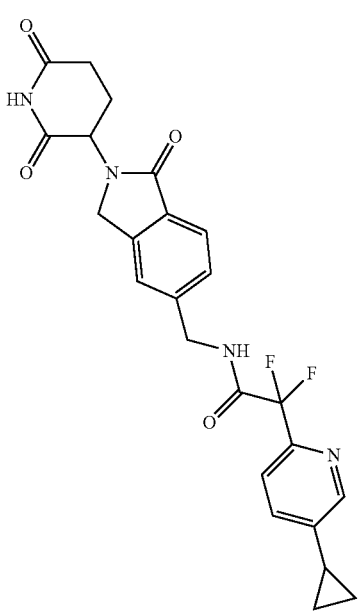 [SMILES: O=C1CCC(N2Cc3cc(CNC(=O)C(F)(F)c4ccc(C5CC5)cn4)ccc3C2=O)C(=O)N1] | 2-(5-cyclopropylpyridin-2-yl)-N-((2-(2,6-dioxopiperidin-3-yl)-1-oxoisoindolin-5-yl)methyl)-2,2-difluoroacetamide | 469.1 | D |

TABLE 1-continued
| Cpd No. | Compound | Name | MH+ | FCA Prolif Cell TiterGlo KG-1 72 h (IC$_{50}$) |
|---|---|---|---|---|
| 98 | 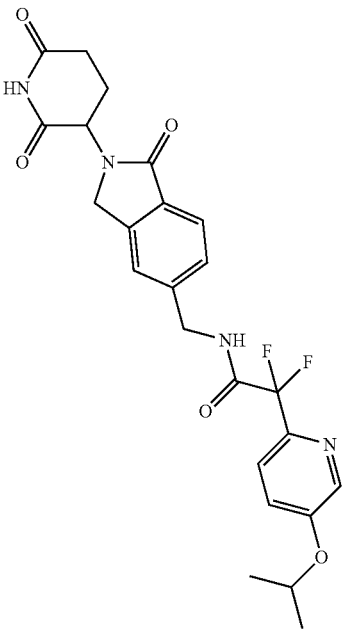 [SMILES: CC(C)Oc1ccc(C(F)(F)C(=O)NCc2ccc3c(c2)CN(C2CCC(=O)NC2=O)C3=O)nc1] | N-((2-(2,6-dioxopiperidin-3-yl)-1-oxoisoindolin-5-yl)methyl)-2,2-difluoro-2-(5-isopropoxypyridin-2-yl)acetamide | 487.2 | D |
| 99 | 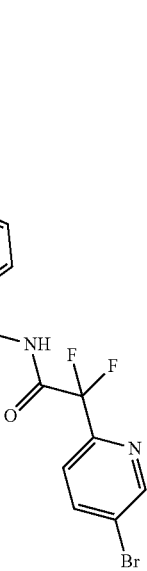 | 2-(5-bromopyridin-2-yl)-N-((2-(2,6-dioxopiperidin-3-yl)-1-oxoisoindolin-5-yl)methyl)-2,2-difluoroacetamide | 507.8 | D |

TABLE 1-continued
| Cpd No. | Compound | Name | MH+ | FCA Prolif Cell TiterGlo KG-1 72 h (IC$_{50}$) |
|---|---|---|---|---|
| 100 | 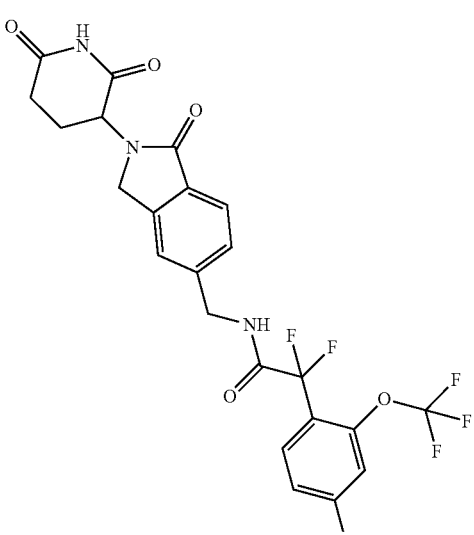 | N-((2-(2,6-dioxopiperidin-3-yl)-1-oxoisoindolin-5-yl)methyl)-2,2-difluoro-2-(4-fluoro-2-(trifluoromethoxy)phenyl)acetamide | 530.1 | C |
| 101 | 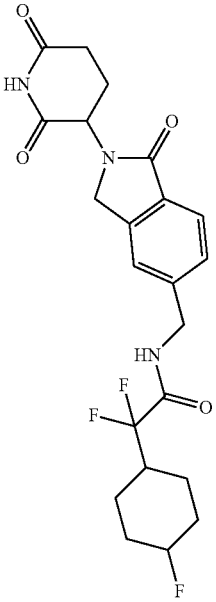 [SMILES: O=C1CCC(N2Cc3cc(CNC(=O)C(F)(F)C4CCC(F)CC4)ccc3C2=O)C(=O)N1] | N-((2-(2,6-dioxopiperidin-3-yl)-1-oxoisoindolin-5-yl)methyl)-2,2-difluoro-2-(4-fluorocyclohexyl)acetamide | 452.2 | D |

TABLE 1-continued
| Cpd No. | Compound | Name | MH+ | FCA Prolif Cell TiterGlo KG-1 72 h (IC$_{50}$) |
|---|---|---|---|---|
| 102 | 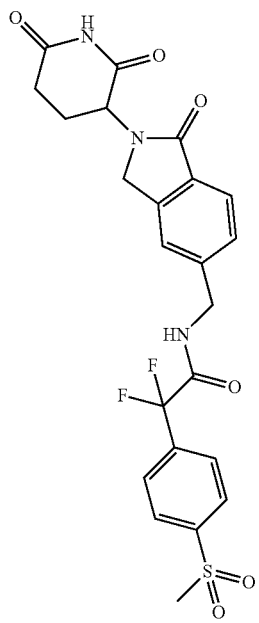 [SMILES: CS(=O)(=O)c1ccc(C(F)(F)C(=O)NCc2ccc3c(c2)CN(C2CCC(=O)NC2=O)C3=O)cc1] | N-((2-(2,6-dioxopiperidin-3-yl)-1-oxoisoindolin-5-yl)methyl)-2,2-difluoro-2-(4-(methylsulfonyl)phenyl)acetamide | 506.1 | D |
| 103 | 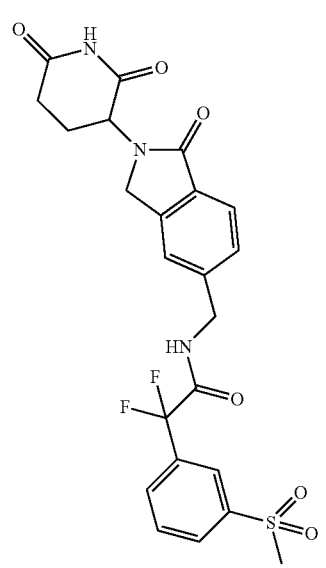 [SMILES: CS(=O)(=O)c1cccc(C(F)(F)C(=O)NCc2ccc3c(c2)CN(C2CCC(=O)NC2=O)C3=O)c1] | N-((2-(2,6-dioxopiperidin-3-yl)-1-oxoisoindolin-5-yl)methyl)-2,2-difluoro-2-(3-(methylsulfonyl)phenyl)acetamide | 506.0 | D |

TABLE 1-continued
| Cpd No. | Compound | Name | MH+ | FCA Prolif Cell TiterGlo KG-1 72 h (IC$_{50}$) |
|---|---|---|---|---|
| 104 | 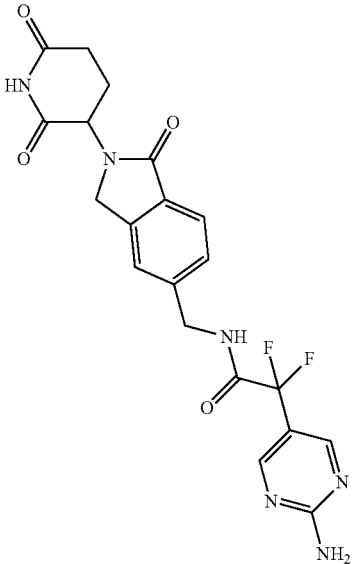 [SMILES: Nc1ncc(C(F)(F)C(=O)NCc2ccc3c(c2)CN(C2CCC(=O)NC2=O)C3=O)cn1] | 2-(2-aminopyrimidin-5-yl)-N-((2-(2,6-dioxopiperidin-3-yl)-1-oxoisoindolin-5-yl)methyl)-2,2-difluoroacetamide | 445.4 | D |
| 105 | 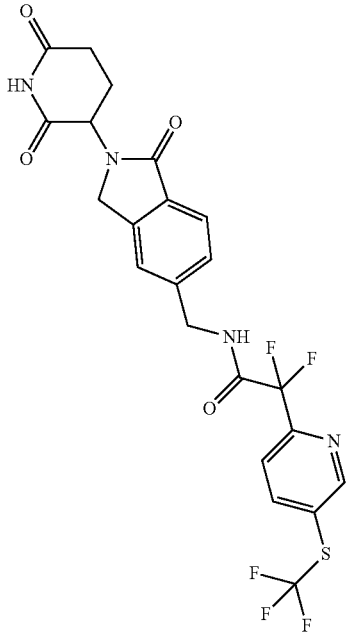 [SMILES: O=C1CCC(N2Cc3cc(CNC(=O)C(F)(F)c4ccc(SC(F)(F)F)cn4)ccc3C2=O)C(=O)N1] | N-((2-(2,6-dioxopiperidin-3-yl)-1-oxoisoindolin-5-yl)methyl)-2,2-difluoro-2-(5-(trifluoromethylthio)pyridin-2-yl)acetamide | 529.0 | D |

TABLE 1-continued
| Cpd No. | Compound | Name | MH+ | FCA Prolif Cell TiterGlo KG-1 72 h (IC$_{50}$) |
|---|---|---|---|---|
| 106 | 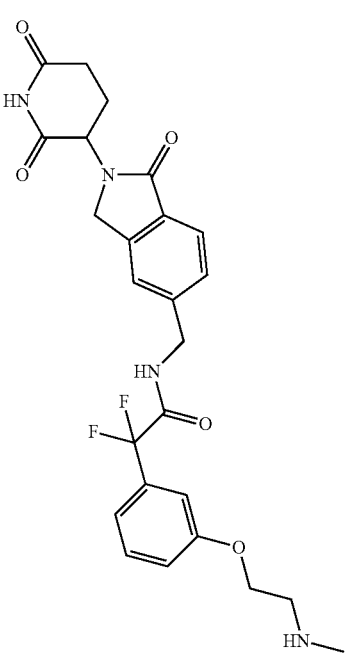 [SMILES: CNCCOc1cccc(C(F)(F)C(=O)NCc2ccc3c(c2)CN(C2CCC(=O)NC2=O)C3=O)c1] | N-((2-(2,6-dioxopiperidin-3-yl)-1-oxoisoindolin-5-yl)methyl)-2,2-difluoro-2-(3-(2-(methylamino)ethoxy)phenyl)acetamide | 501.6 | D |
| 107 | 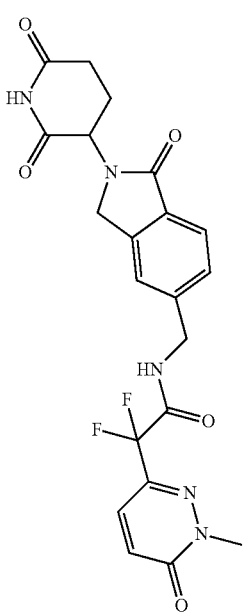 [SMILES: Cn1nc(C(F)(F)C(=O)NCc2ccc3c(c2)CN(C2CCC(=O)NC2=O)C3=O)ccc1=O] | N-((2-(2,6-dioxopiperidin-3-yl)-1-oxoisoindolin-5-yl)methyl)-2,2-difluoro-2-(1-methyl-6-oxo-1,6-dihydropyridazin-3-yl)acetamide | 460.5 | D |

TABLE 1-continued
| Cpd No. | Compound | Name | MH+ | FCA Prolif Cell TiterGlo KG-1 72 h (IC$_{50}$) |
|---|---|---|---|---|
| 108 | 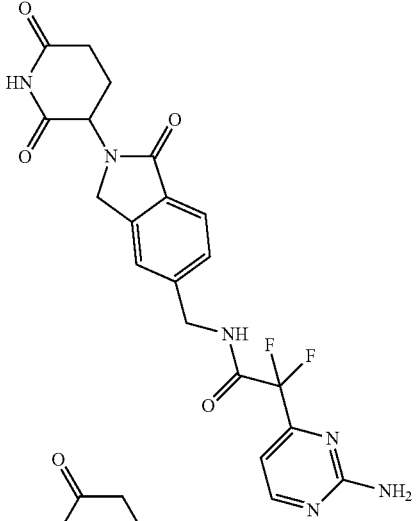 | 2-(2-aminopyrimidin-4-yl)-N-((2-(2,6-dioxopiperidin-3-yl)-1-oxoisoindolin-5-yl)methyl)-2,2-difluoroacetamide | 445.1 | D |
| 109 | 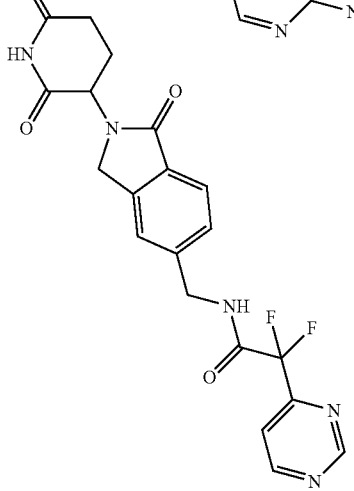 | N-((2-(2,6-dioxopiperidin-3-yl)-1-oxoisoindolin-5-yl)methyl)-2,2-difluoro-2-(pyrimidin-4-yl)acetamide | 430.5 | D |
| 110 | 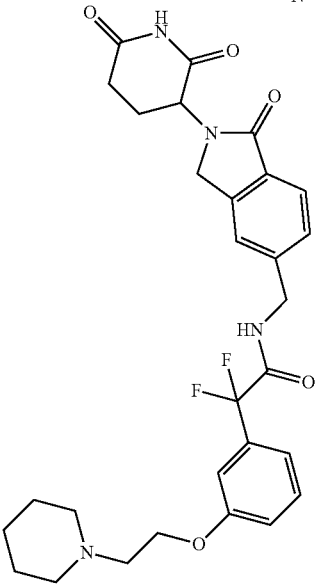 | N-((2-(2,6-dioxopiperidin-3-yl)-1-oxoisoindolin-5-yl)methyl)-2,2-difluoro-2-(3-(2-(piperidin-1-yl)ethoxy)phenyl)acetamide | 555.2 | D |

TABLE 1-continued
| Cpd No. | Compound | Name | MH+ | FCA Prolif Cell TiterGlo KG-1 72 h (IC$_{50}$) |
|---|---|---|---|---|
| 111 | 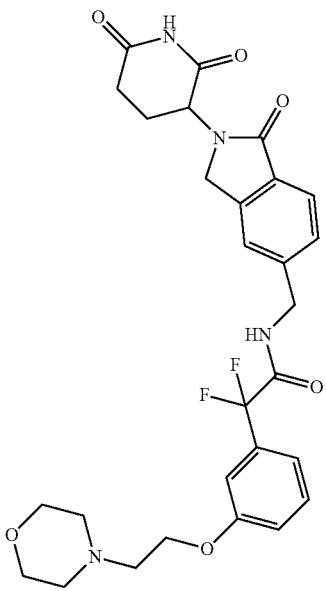 [SMILES: O=C1CCC(N2Cc3cc(CNC(=O)C(F)(F)c4cccc(OCCN5CCOCC5)c4)ccc3C2=O)C(=O)N1] | N-((2-(2,6-dioxopiperidin-3-yl)-1-oxoisoindolin-5-yl)methyl)-2,2-difluoro-2-(3-(2-morpholinoethoxy)phenyl)acetamide | 557.2 | D |
| 112 | 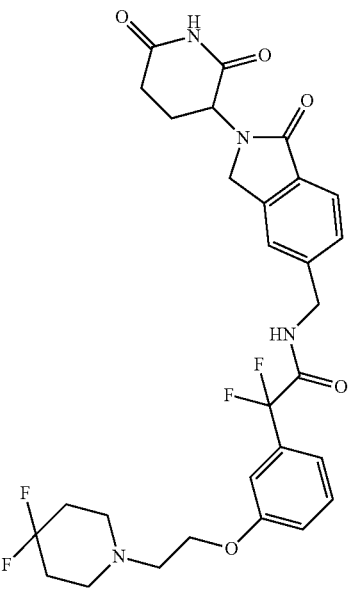 [SMILES: O=C1CCC(N2Cc3cc(CNC(=O)C(F)(F)c4cccc(OCCN5CCC(F)(F)CC5)c4)ccc3C2=O)C(=O)N1] | 2-(3-(2-(4,4-difluoropiperidin-1-yl)ethoxy)phenyl)-N-((2-(2,6-dioxopiperidin-3-yl)-1-oxoisoindolin-5-yl)methyl)-2,2-difluoroacetamide | 591.2 | C |

TABLE 1-continued
| Cpd No. | Compound | Name | MH+ | FCA Prolif Cell TiterGlo KG-1 72 h (IC$_{50}$) |
|---|---|---|---|---|
| 113 | 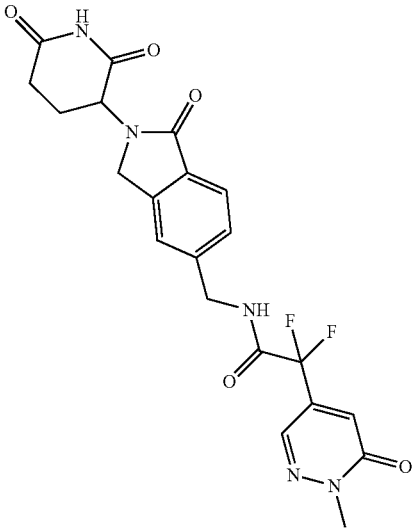 [SMILES: Cn1ncc(C(F)(F)C(=O)NCc2ccc3c(c2)CN(C2CCC(=O)NC2=O)C3=O)cc1=O] | N-((2-(2,6-dioxopiperidin-3-yl)-1-oxoisoindolin-5-yl)methyl)-2,2-difluoro-2-(1-methyl-6-oxo-1,6-dihydropyridazin-4-yl)acetamide | 459.2 | D |
| 114 | 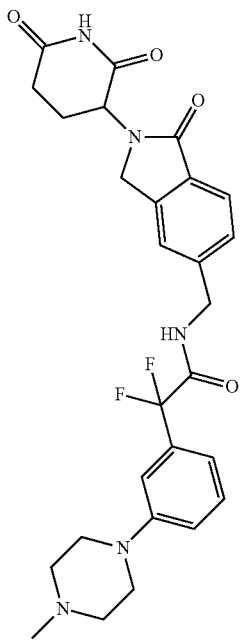 [SMILES: CN1CCN(c2cccc(C(F)(F)C(=O)NCc3ccc4c(c3)CN(C3CCC(=O)NC3=O)C4=O)c2)CC1] | N-((2-(2,6-dioxopiperidin-3-yl)-1-oxoisoindolin-5-yl)methyl)-2,2-difluoro-2-(3-(4-methylpiperazin-1-yl)phenyl)acetamide | 526.4 | D |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

Compounds of the invention are for use in medicine.

Compounds of the invention are for use in the methods of treatment provided herein.

What is claimed is:
1. A compound of Formula I:

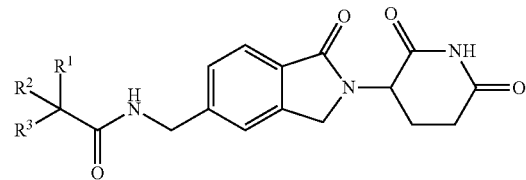

or an enantiomer or a mixture of enantiomers thereof, or a pharmaceutically acceptable salt, solvate, hydrate, co-crystal, clathrate, or polymorph thereof, wherein:
$R^1$ is optionally substituted cycloalkyl, optionally substituted aryl, optionally substituted heteroaryl or optionally substituted heterocyclyl;
$R^2$ and $R^3$ are each halo;
where the substituents on $R^1$, when present, are one to three groups Q, where each Q is independently alkyl, halo, haloalkyl, alkoxyalkyl, oxo, hydroxyl, alkoxy, optionally substituted cycloalkyl, optionally substituted cycloalkylalkyl, optionally substituted heterocyclyl, optionally substituted heterocyclylalkyl, optionally substituted aryl, optionally substituted heteroaryl, —$R^4OR^5$, —$R^4OR^5$—$R^4OR^5$, —$R^4N(R^6)(R^7)$, —$R^4SR^5$, —$R^4OR^4N(R^6)(R^7)$, —$R^4OR^4C(J)N(R^6)(R^7)$, —$C(J)R^9$ or $R^4S(O)_tR^8$;
each $R^4$ is independently alkylene, alkenylene or a direct bond;
each $R^5$ is independently hydrogen, alkyl, haloalkyl, hydroxyalkyl, alkoxyalkyl, cycloalkyl, aryl, heteroaryl, heterocyclyl or heterocyclylalkyl, where alkyl, haloalkyl, hydroxyalkyl, alkoxyalkyl, cycloalkyl, aryl, heteroaryl, heterocyclyl or heterocyclylalkyl groups in $R^5$ are each independently optionally substituted with 1-3 $Q^1$ groups, where each $Q^1$ is independently alkyl, haloalkyl or halo;
$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl;
$R^8$ is alkyl, haloalkyl, or hydroxyalkyl;
$R^9$ is alkyl or aryl;
J is O or S; and
t is 1 or 2.

2. The compound of claim 1, wherein $R^1$ is optionally substituted cycloalkyl, optionally substituted aryl, optionally substituted heteroaryl or optionally substituted heterocyclyl.

3. The compound of claim 1 having Formula II:

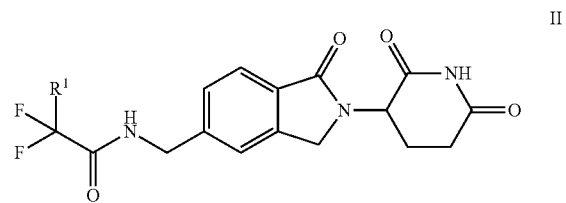

or an enantiomer or a mixture of enantiomers thereof, or a pharmaceutically acceptable salt, solvate, hydrate, co-crystal, clathrate, or polymorph thereof, wherein:
$R^1$ is optionally substituted cycloalkyl, optionally substituted aryl, optionally substituted heteroaryl or optionally substituted heterocyclyl;
where the substituents on $R^1$, when present, are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;
J is O or S;
each $R^4$ is independently alkylene, alkenylene or a direct bond;
each $R^5$ is independently hydrogen, alkyl, haloalkyl or hydroxyalkyl; and
$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl.

4. The compound of claim 1, wherein $R^1$ is optionally substituted aryl;
where the substituents on $R^1$, when present, are one to three groups Q, where each Q is independently alkyl, halo, haloalkyl, hydroxyl, alkoxy, optionally substituted cycloalkyl, optionally substituted cycloalkylalkyl, optionally substituted aryl, —$R^4OR^5$, —$R^4SR^5$, —$R^4N(R^6)(R^7)$, $R^4OR^4N(R^6)(R^7)$ or $R^4OR^4C(J)N(R^6)(R^7)$;
J is O or S;
each $R^4$ is independently alkylene, alkenylene or a direct bond;
each $R^5$ is independently hydrogen, alkyl, haloalkyl or hydroxyalkyl; and
$R^6$ and $R^7$ are selected as follows:
i) $R^6$ and $R^7$ are each independently hydrogen or alkyl; or
ii) $R^6$ and $R^7$ together with the nitrogen atom on which they are substituted form a 5 or 6-membered heterocyclyl or heteroaryl ring, optionally substituted with one or two halo, alkyl or haloalkyl.

5. The compound of claim 1, wherein $R^1$ is optionally substituted phenyl, optionally substituted cyclohexyl, optionally substituted piperidinyl, or optionally substituted pyridyl, where the substituents on $R^1$, when present, are one to three groups Q, where each Q is independently halo, alkyl, —$R^4OR^5$ or —$R^4N(R^6)(R^7)$; each $R^4$ is independently a direct bond or alkylene; each $R^5$ is independently hydrogen, halo, alkyl, alkoxy, haloalkoxy or haloalkyl; and $R^6$ and $R^7$ are selected as follows:

i) R⁶ and R⁷ are each independently hydrogen or alkyl; or ii) R⁶ and R⁷ together with the nitrogen atom on which they are substituted form a 5 or 6-membered heterocyclyl ring.

6. The compound of claim 1, wherein R¹ is optionally substituted phenyl, where the substituents on R¹, when present, are one to three groups Q, where each Q is independently fluoro, chloro, methyl, tert butyl, —R⁴OR⁵, —R⁴SR⁵ or R⁴OR⁴C(J)N(R⁶)(R⁷); each R⁴ is independently a direct bond or methylene; each R⁵ is independently hydrogen, methyl, ethyl or trifluoromethyl; and R⁶ and R⁷ are each independently hydrogen or methyl.

7. The compound of claim 1, wherein the compound has formula III

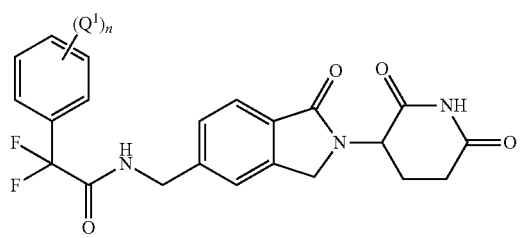

III or an enantiomer or a mixture of enantiomers thereof, or a pharmaceutically acceptable salt, solvate, hydrate, co-crystal, clathrate, or polymorph thereof, wherein:

each Q¹ is independently alkyl, halo, haloalkyl, alkoxyalkyl, hydroxyl, alkoxy, optionally substituted cycloalkyl, optionally substituted cycloalkylalkyl, optionally substituted aryl, —R⁴OR⁵, —R⁴SR⁵, —R⁴N(R⁶)(R⁷), R⁴OR⁴N(R⁶)(R⁷) or R⁴OR⁴C(J)N(R⁶)(R⁷);

J is O or S;

each R⁴ is independently alkylene, alkenylene or a direct bond;

each R⁵ is independently hydrogen, alkyl, halo, alkoxy, haloalkyl or hydroxyalkyl;

R⁶ and R⁷ are selected as follows:

i) R⁶ and R⁷ are each independently hydrogen or alkyl; or ii) R⁶ and R⁷ together with the nitrogen atom on which they are substituted form a 5 or 6-membered heterocyclyl or heteroaryl ring, optionally substituted with one or two halo, alkyl or haloalkyl; and n is 0-3.

8. The compound of claim 1, wherein the compound has formula IV

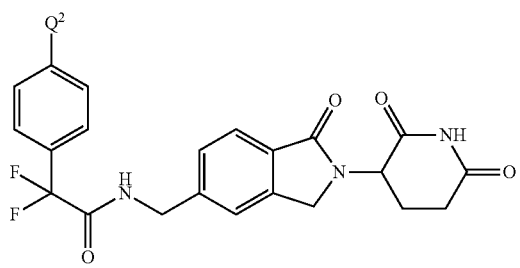

IV or an enantiomer or a mixture of enantiomers thereof, or a pharmaceutically acceptable salt, solvate, hydrate, co-crystal, clathrate, or polymorph thereof, wherein:

Q² is hydrogen, alkyl, halo, haloalkyl, hydroxyl, alkoxy, optionally substituted cycloalkyl, optionally substituted cycloalkylalkyl, optionally substituted aryl, —R⁴OR⁵, —R⁴SR⁵, —R⁴N(R⁶)(R⁷), R⁴OR⁴N(R⁶)(R⁷) or R⁴OR⁴C(J)N(R⁶)(R⁷);

J is O or S;

each R⁴ is independently alkylene, alkenylene or a direct bond;

each R⁵ is independently hydrogen, alkyl, haloalkyl or hydroxyalkyl; and

R⁶ and R⁷ are each independently hydrogen or alkyl.

9. The compound of claim 1, wherein the compound has formula V

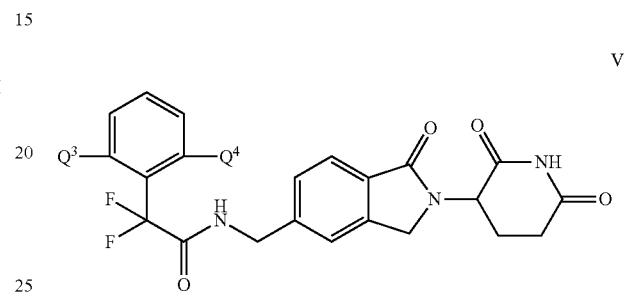

V or an enantiomer or a mixture of enantiomers thereof, or a pharmaceutically acceptable salt, solvate, hydrate, co-crystal, clathrate, or polymorph thereof, wherein:

Q³ and Q⁴ are each independently hydrogen, alkyl, halo, haloalkyl, hydroxyl, alkoxy, optionally substituted cycloalkyl, optionally substituted cycloalkylalkyl, —R⁴OR⁵, —R⁴SR⁵, —R⁴N(R⁶)(R⁷), R⁴OR⁴N(R⁶)(R⁷) or R⁴OR⁴C(J)N(R⁶)(R⁷);

J is O or S;

each R⁴ is independently alkylene, alkenylene or a direct bond;

each R⁵ is independently hydrogen, alkyl, haloalkyl, hydroxyalkyl, or alkoxyalkyl; and R⁶ and R⁷ are each independently hydrogen or alkyl.

10. The compound of claim 1, wherein the compound has formula VI

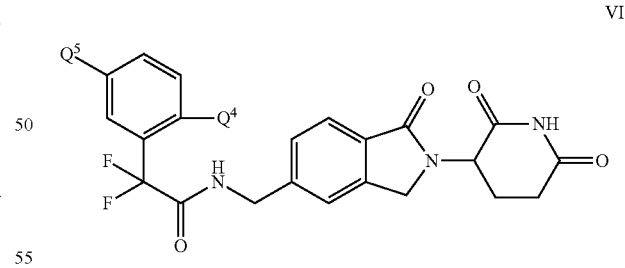

VI or an enantiomer or a mixture of enantiomers thereof, or a pharmaceutically acceptable salt, solvate, hydrate, co-crystal, clathrate, or polymorph thereof, wherein:

Q⁴ and Q⁵ are each independently hydrogen, alkyl, halo, haloalkyl, hydroxyl, alkoxy, optionally substituted cycloalkyl, optionally substituted cycloalkylalkyl, —R⁴OR⁵, —R⁴SR⁵, —R⁴N(R⁶)(R⁷), R⁴OR⁴N(R⁶)(R⁷) or R⁴OR⁴C(J)N(R⁶)(R⁷);

J is O or S;

each R⁴ is independently alkylene, alkenylene or a direct bond;

each R[5] is independently hydrogen, alkyl, haloalkyl, alkoxyalkyl or hydroxyalkyl; and R[6] and R[7] are as follows:
i) R[6] and R[7] are each independently hydrogen or alkyl; or
ii) R[6] and R[7] together with the nitrogen atom on which they are substituted form a 5 or 6-membered heterocyclyl or heteroaryl ring, optionally substituted with one or two halo, alkyl or haloalkyl.

11. The compound of claim 10, wherein Q[4] and Q[5] are each independently hydrogen, halo, alkyl, alkoxyalkyl, —R[4]N(R[6])(R[7]), or —R[4]OR[5]; R[4] is a direct bond or alkylene; R[5] is hydrogen, alkyl or haloalkyl; and R[6] and R[7] together with the nitrogen atom on which they are substituted form a 6-membered heterocyclyl.

12. The compound of claim 1, wherein the compound has formula VII

VII

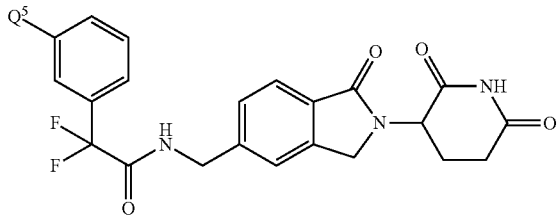

or an enantiomer or a mixture of enantiomers thereof, or a pharmaceutically acceptable salt, solvate, hydrate, co-crystal, clathrate, or polymorph thereof, wherein:
Q[5] is hydrogen, alkyl, halo, haloalkyl, hydroxyl, alkoxy, optionally substituted cycloalkyl, optionally substituted cycloalkylalkyl, —R[4]OR[5], —R[4]SR[5], —R[4]N(R[6])(R[7]), R[4]OR[4]N(R[6])(R[7]) or R[4]OR[4]C(J)N(R[6])(R[7]);
J is O or S;
each R[4] is independently alkylene, alkenylene or a direct bond;
each R[5] is independently hydrogen, alkyl, haloalkyl, alkoxyalkyl or hydroxyalkyl; and
R[6] and R[7] are selected as follows:
i) R[6] and R[7] are each independently hydrogen or alkyl; or
ii) R[6] and R[7] together with the nitrogen atom on which they are substituted form a 5 or 6-membered heterocyclyl or heteroaryl ring, optionally substituted with one or two halo, alkyl or haloalkyl.

13. The compound of claim 12, wherein Q[5] is hydrogen, halo, alkyl, alkoxyalkyl, —R[4]N(R[6])(R[7]) or —R[4]OR[5]; R[4] is a direct bond or alkylene; and R[5] is hydrogen, alkyl or haloalkyl; and R[6] and R[7] together with the nitrogen atom on which they are substituted form a 6-membered heterocyclyl.

14. The compound of claim 1, wherein the compound has formula VIII

VIII

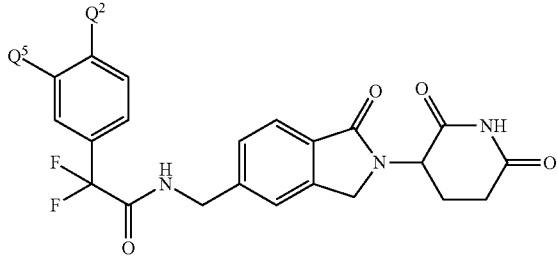

or an enantiomer or a mixture of enantiomers thereof, or a pharmaceutically acceptable salt, solvate, hydrate, co-crystal, clathrate, or polymorph thereof, wherein:

Q[2] and Q[5] are each independently hydrogen, alkyl, halo, haloalkyl, hydroxyl, alkoxy, optionally substituted cycloalkyl, optionally substituted cycloalkylalkyl, optionally substituted aryl, —R[4]OR[5], —R[4]SR[5], —R[4]N(R[6])(R[7]), R[4]OR[4]N(R[6])(R[7]) or R[4]OR[4]C(J)N(R[6])(R[7]);
J is O or S;
each R[4] is independently alkylene, alkenylene or a direct bond;
each R[5] is independently hydrogen, alkyl, haloalkyl or hydroxyalkyl; and
R[6] and R[7] are each independently hydrogen or alkyl, or R[6] and R[7] together with the nitrogen atom on which they are substituted form a 6-membered heterocyclyl.

15. The compound claim 14, wherein Q[2] and Q[5] are each independently hydrogen, halo, alkyl, alkoxyalkyl, optionally substituted aryl, or —R[4]OR[5]; R[4] is a direct bond or alkylene; and R[5] is hydrogen, alkyl or haloalkyl.

16. The compound of claim 1, wherein the compound is selected from
2-(3-chloro-4-methylphenyl)-N-((2-(2,6-dioxopiperidin-3-yl)-1-oxoisoindolin-5-yl)methyl)-2,2-difluoroacetamide;
2-(4-chlorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-methoxyphenyl)acetamide;
2-(3-chlorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-fluorophenyl)acetamide;
N-((2-(2,6-dioxopiperidin-3-yl)-1-oxoisoindolin-5-yl)methyl)-2,2-difluoro-2-p-tolylacetamide;
2-(3,4-dichlorophenyl)-N-((2-(2,6-dioxopiperidin-3-yl)-1-oxoisoindolin-5-yl)methyl)-2,2-difluoroacetamide;
2-(2-chlorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(2-(trifluoromethyl)phenyl)acetamide;
2-(4-tert-butylphenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-phenylacetamide 2-(3-chloro-4-fluorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-(trifluoromethylthio)phenyl)acetamide;
2-(2,6-difluorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-o-tolylacetamide;
N-((2-(2,6-dioxopiperidin-3-yl)-1-oxoisoindolin-5-yl)methyl)-2,2-difluoro-2-(2-fluorophenyl)acetamide;
N-((2-(2,6-dioxopiperidin-3-yl)-1-oxoisoindolin-5-yl)methyl)-2-(2-ethoxyphenyl)-2,2-difluoroacetamide;
N-((2-(2,6-dioxopiperidin-3-yl)-1-oxoisoindolin-5-yl)methyl)-2,2-difluoro-2-(2-(trifluoromethoxy)phenyl)acetamide;
2-(3-bromo-4-(trifluoromethoxy)phenyl)-N-((2-(2,6-dioxopiperidin-3-yl)-1-oxoisoindolin-5-yl)methyl)-2,2-difluoroacetamide;
2-(3-chloro-4-methoxyphenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-m-tolylacetamide;

N-((2-(2,6-dioxopiperidin-3-yl)-1-oxoisoindolin-5-yl)
methyl)-2,2-difluoro-2-(4-isopropoxyphenyl)acet-
amide;
2-(3,4-difluorophenyl)-N-((2-(2,6-dioxopiperidin-3-yl)-
1-oxoisoindolin-5-yl)methyl)-2,2-difluoroacetamide;
N-((2-(2,6-dioxopiperidin-3-yl)-1-oxoisoindolin-5-yl)
methyl)-2,2-difluoro-2-(3-fluorophenyl)acetamide;
N-((2-(2,6-dioxopiperidin-3-yl)-1-oxoisoindolin-5-yl)
methyl)-2,2-difluoro-2-(3-(trifluoromethyl)pyridin-2-
yl)acetamide;
N-((2-(2,6-dioxopiperidin-3-yl)-1-oxoisoindolin-5-yl)
methyl)-2,2-difluoro-2-(4-isopropylphenyl)acetamide;
2-(2,4-dichlorophenyl)-N-((2-(2,6-dioxopiperidin-3-yl)-
1-oxoisoindolin-5-yl)methyl)-2,2-difluoroacetamide;
N-((2-(2,6-dioxopiperidin-3-yl)-1-oxoisoindolin-5-yl)
methyl)-2,2-difluoro-2-(2-methoxyphenyl)acetamide;
2-(4-cyclopropylphenyl)-N-((2-(2,6-dioxopiperidin-3-
yl)-1-oxoisoindolin-5-yl)methyl)-2,2-difluoroacet-
amide;
2-(4-chloro-2-fluorophenyl)-N-((2-(2,6-dioxopiperidin-
3-yl)-1-oxoisoindolin-5-yl)methyl)-2,2-difluoroacet-
amide;
2-(4-chloro-3-fluorophenyl)-N-((2-(2,6-dioxopiperidin-
3-yl)-1-oxoisoindolin-5-yl)methyl)-2,2-difluoroacet-
amide;
N-((2-(2,6-dioxopiperidin-3-yl)-1-oxoisoindolin-5-yl)
methyl)-2,2-difluoro-2-(3-fluoro-2-methylphenyl)acet-
amide;
2-(3-chloro-2-methylphenyl)-N-((2-(2,6-dioxopiperidin-
3-yl)-1-oxoisoindolin-5-yl)methyl)-2,2-difluoroacet-
amide;
N-((2-(2,6-dioxopiperidin-3-yl)-1-oxoisoindolin-5-yl)
methyl)-2,2-difluoro-2-(4-fluoro-2-(trifluoromethyl)
phenyl)acetamide;
2-(4-chloro-2-methylphenyl)-N-((2-(2,6-dioxopiperidin-
3-yl)-1-oxoisoindolin-5-yl)methyl)-2,2-difluoroacet-
amide;
N-((2-(2,6-dioxopiperidin-3-yl)-1-oxoisoindolin-5-yl)
methyl)-2,2-difluoro-2-(4-fluoro-2-methylphenyl)acet-
amide;
2-(4-chloro-2-(trifluoromethyl)phenyl)-N-((2-(2,6-diox-
opiperidin-3-yl)-1-oxoisoindolin-5-yl)methyl)-2,2-dif-
luoroacetamide;
2-cyclohexyl-N-((2-(2,6-dioxopiperidin-3-yl)-1-ox-
oisoindolin-5-yl)methyl)-2,2-difluoroacetamide;
2-(4-chloro-2-(trifluoromethoxy)phenyl)-N-((2-(2,6-di-
oxopiperidin-3-yl)-1-oxoisoindolin-5-yl)methyl)-2,2-
difluoroacetamide;
N-((2-(2,6-dioxopiperidin-3-yl)-1-oxoisoindolin-5-yl)
methyl)-2,2-difluoro-2-(3-(2-methoxyethoxy)phenyl)
acetamide;
N-((2-(2,6-dioxopiperidin-3-yl)-1-oxoisoindolin-5-yl)
methyl)-2,2-difluoro-2-(3-(2-hydroxyethoxy)phenyl)
acetamide;
N-((2-(2,6-dioxopiperidin-3-yl)-1-oxoisoindolin-5-yl)
methyl)-2,2-difluoro-2-(4-(2-methoxyethoxy)phenyl)
acetamide;
N-((2-(2,6-dioxopiperidin-3-yl)-1-oxoisoindolin-5-yl)
methyl)-2,2-difluoro-2-(3-(2-hydroxyethoxy)phenyl)ac-
etamide;
2-(3-(dimethylamino)phenyl)-N-((2-(2,6-dioxopiperidin-
3-yl)-1-oxoisoindolin-5-yl)methyl)-2,2-difluoroacet-
amide;
N-((2-(2,6-dioxopiperidin-3-yl)-1-oxoisoindolin-5-yl)
methyl)-2,2-difluoro-2-(3-(piperidin-1-yl)phenyl)acet-
amide;
N-((2-(2,6-dioxopiperidin-3-yl)-1-oxoisoindolin-5-yl)
methyl)-2,2-difluoro-2-(3-morpholinophenyl)acet-
amide;
N-((2-(2,6-dioxopiperidin-3-yl)-1-oxoisoindolin-5-yl)
methyl)-2,2-difluoro-2-(4-fluoro-2-isopropoxyphenyl)
acetamide;
N-((2-(2,6-dioxopiperidin-3-yl)-1-oxoisoindolin-5-yl)
methyl)-2,2-difluoro-2-(2-(2,2,2-trifluoroethoxy)phe-
nyl)acetamide;
N-((2-(2,6-dioxopiperidin-3-yl)-1-oxoisoindolin-5-yl)
methyl)-2-(ethoxy-4-fluorophenyl)-2,2-difluoroacet-
amide;
N-((2-(2,6-dioxopiperidin-3-yl)-1-oxoisoindolin-5-yl)
methyl)-2,2-difluoro-2-(2-isopropoxyphenyl)acet-
amide;
N-((2-(2,6-dioxopiperidin-3-yl)-1-oxoisoindolin-5-yl)
methyl)-2,2-difluoro-2-(2-fluoro-4-isopropoxyphenyl)
acetamide;
N-((2-(2,6-dioxopiperidin-3-yl)-1-oxoisoindolin-5-yl)
methyl)-2,2-difluoro-2-(3-(morpholinomethyl)phenyl)
acetamide;
N-((2-(2,6-dioxopiperidin-3-yl)-1-oxoisoindolin-5-yl)
methyl)-2,2-difluoro-2-(4-fluoro-2-(2,2,2-trifluoroeth-
oxy)phenyl)acetamide;
N-((2-(2,6-dioxopiperidin-3-yl)-1-oxoisoindolin-5-yl)
methyl)-2,2-difluoro-2-(4-isopropoxy-2-methylphe-
nyl)acetamide;
N-((2-(2,6-dioxopiperidin-3-yl)-1-oxoisoindolin-5-yl)
methyl)-2,2-difluoro-2-(4-isopropoxy-3-methylphe-
nyl)acetamide;
N-((2-(2,6-dioxopiperidin-3-yl)-1-oxoisoindolin-5-yl)
methyl)-2,2-difluoro-2-(3-fluoro-4-isopropoxyphenyl)
acetamide;
2-(3-chloro-4-isopropoxyphenyl)-N-((2-(2,6-dioxopip-
eridin-3-yl)-1-oxoisoindolin-5-yl)methyl)-2,2-difluo-
roacetamide;
N-((2-(2,6-dioxopiperidin-3-yl)-1-oxoisoindolin-5-yl)
methyl)-2,2-difluoro-2-(2-methyl-4-(trifluo-
romethoxy)phenyl)acetamide;
N-((2-(2,6-dioxopiperidin-3-yl)-1-oxoisoindolin-5-yl)
methyl)-2,2-difluoro-2-(2-fluoro-4-(trifluoromethoxy)
phenyl)acetamide;
2-(5-chloropyridin-2-yl)-N-((2-(2,6-dioxopiperidin-3-
yl)-1-oxoisoindolin-5-yl)methyl)-2,2-difluoroacet-
amide;
N-((2-(2,6-dioxopiperidin-3-yl)-1-oxoisoindolin-5-yl)
methyl)-2,2-difluoro-2-(5-fluoropyridin-2-yl)acet-
amide;
2-(2,4-difluorophenyl)-N-((2-(2,6-dioxopiperidin-3-yl)-
1-oxoisoindolin-5-yl)methyl)-2,2-difluoroacetamide;
2-(4-bromophenyl)-N-((2-(2,6-dioxopiperidin-3-yl)-1-
oxoisoindolin-5-yl)methyl)-2,2-difluoroacetamide;
N-((2-(2,6-dioxopiperidin-3-yl)-1-oxoisoindolin-5-yl)
methyl)-2,2-difluoro-2-(2-(2-methoxyethoxy)phenyl)
acetamide;
N-((2-(2,6-dioxopiperidin-3-yl)-1-oxoisoindolin-5-yl)
methyl)-2,2-difluoro-2-(1-hydroxycyclohexyl)acet-
amide;
N-((2-(2,6-dioxopiperidin-3-yl)-1-oxoisoindolin-5-yl)
methyl)-2,2-difluoro-2-(1-hydroxycyclopentyl)acet-
amide;
N-((2-(2,6-dioxopiperidin-3-yl)-1-oxoisoindolin-5-yl)
methyl)-2,2-difluoro-2-(3-methyl-4-(trifluo-
romethoxy)phenyl)acetamide;
N-((2-(2,6-dioxopiperidin-3-yl)-1-oxoisoindolin-5-yl)
methyl)-2-(3-ethoxypyridin-2-yl)-2,2-difluoroacet-
amide;

N-((2-(2,6-dioxopiperidin-3-yl)-1-oxoisoindolin-5-yl) methyl)-2,2-difluoro-2-(3-methylpyridin-2-yl)acetamide;

N-((2-(2,6-dioxopiperidin-3-yl)-1-oxoisoindolin-5-yl) methyl)-2,2-difluoro-2-(5-methylpyridin-2-yl)acetamide;

N-((2-(2,6-dioxopiperidin-3-yl)-1-oxoisoindolin-5-yl) methyl)-2-(2-ethoxy-6-fluorophenyl)-2,2-difluoroacetamide;

N-((2-(2,6-dioxopiperidin-3-yl)-1-oxoisoindolin-5-yl) methyl)-2,2-difluoro-2-(4'-fluorobiphenyl-4-yl)acetamide;

N-((2-(2,6-dioxopiperidin-3-yl)-1-oxoisoindolin-5-yl) methyl)-2-(2-ethoxy-5-fluorophenyl)-2,2-difluoroacetamide;

2-cyclopentyl-N-((2-(2,6-dioxopiperidin-3-yl)-1-oxoisoindolin-5-yl)methyl)-2,2-difluoroacetamide;

2-(3-chloro-4-(trifluoromethoxy)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(4-methoxy-2-(trifluoromethyl)phenyl)acetamide;

N-((2-(2,6-dioxopiperidin-3-yl)-1-oxoisoindolin-5-yl) methyl)-2,2-difluoro-2-(2-(2-hydroxyethoxy)phenyl) acetamide;

2-(4-chloro-2-ethoxyphenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(2-hydroxyphenyl)acetamide;

N-((2-(2,6-dioxopiperidin-3-yl)-1-oxoisoindolin-5-yl) methyl)-2,2-difluoro-2-(2-(methylamino)phenyl)acetamide;

N-((2-(2,6-dioxopiperidin-3-yl)-1-oxoisoindolin-5-yl) methyl)-2,2-difluoro-2-(4-isopropoxy-2-(trifluoromethyl)phenyl)acetamide;

N-((2-(2,6-dioxopiperidin-3-yl)-1-oxoisoindolin-5-yl) methyl)-2,2-difluoro-2-(4-methylcyclohexyl)acetamide;

N-((2-(2,6-dioxopiperidin-3-yl)-1-oxoisoindolin-5-yl) methyl)-2,2-difluoro-2-(3-(2-isopropoxyethoxy)phenyl)acetamide;

N-((2-(2,6-dioxopiperidin-3-yl)-1-oxoisoindolin-5-yl) methyl)-2,2-difluoro-2-(3-hydroxyphenyl)acetamide;

N-((2-(2,6-dioxopiperidin-3-yl)-1-oxoisoindolin-5-yl) methyl)-2,2-difluoro-2-(3-((4-methylpiperazin-1-yl) methyl)phenyl)acetamide;

N-((2-(2,6-dioxopiperidin-3-yl)-1-oxoisoindolin-5-yl) methyl)-2,2-difluoro-2-(4-methyl-2-(trifluoromethyl) phenyl)acetamide;

N-((2-(2,6-dioxopiperidin-3-yl)-1-oxoisoindolin-5-yl) methyl)-2,2-difluoro-2-(3-(2-(2-methoxyethoxy) ethoxy)phenyl)acetamide;

2-(3-(2-(dimethylamino)ethoxy)phenyl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(5-isopropylpyridin-2-yl)acetamide;

N-((2-(2,6-dioxopiperidin-3-yl)-1-oxoisoindolin-5-yl) methyl)-2,2-difluoro-2-(3-(2-(methylsulfonyl)ethoxy) phenyl)acetamide;

N-((2-(2,6-dioxopiperidin-3-yl)-1-oxoisoindolin-5-yl) methyl)-2,2-difluoro-2-(3-(3-(methylsulfonyl)propyl) phenyl)acetamide;

N-((2-(2,6-dioxopiperidin-3-yl)-1-oxoisoindolin-5-yl) methyl)-2,2-difluoro-2-(4-(2-fluoropropan-2-yl)phenyl)acetamide;

2-(1-benzyl-6-oxo-1,6-dihydropyridin-3-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(5-methoxypyridin-2-yl)acetamide;

N-((2-(2,6-dioxopiperidin-3-yl)-1-oxoisoindolin-5-yl) methyl)-2,2-difluoro-2-(1-methyl-6-oxo-1,6-dihydropyridin-3-yl)acetamide;

2-(5-tert-butylpyridin-2-yl)-N-((2-(2,6-dioxopiperidin-3-yl)-1-oxoisoindolin-5-yl)methyl)-2,2-difluoroacetamide;

2-(5-cyclopropylpyridin-2-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(5-isopropoxypyridin-2-yl)acetamide;

2-(5-bromopyridin-2-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(4-fluoro-2-(trifluoromethoxy) phenyl)acetamide;

N-((2-(2,6-dioxopiperidin-3-yl)-1-oxoisoindolin-5-yl) methyl)-2,2-difluoro-2-(4-fluorocyclohexyl)acetamide;

N-((2-(2,6-dioxopiperidin-3-yl)-1-oxoisoindolin-5-yl) methyl)-2,2-difluoro-2-(4-(methyl sulfonyl)phenyl)acetamide;

N-((2-(2,6-dioxopiperidin-3-yl)-1-oxoisoindolin-5-yl) methyl)-2,2-difluoro-2-(3-(methyl sulfonyl)phenyl)acetamide;

2-(2-aminopyrimidin-5-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(5-(trifluoromethylthio)pyridin-2-yl)acetamide;

N-((2-(2,6-dioxopiperidin-3-yl)-1-oxoisoindolin-5-yl) methyl)-2,2-difluoro-2-(3-(2-(methylamino)ethoxy) phenyl)acetamide;

N-((2-(2,6-dioxopiperidin-3-yl)-1-oxoisoindolin-5-yl) methyl)-2,2-difluoro-2-(1-methyl-6-oxo-1,6-dihydropyridazin-3-yl)acetamide;

2-(2-aminopyrimidin-4-yl)-N-((2-(2,6-dioxopiperidin-3-yl)-1-oxoisoindolin-5-yl)methyl)-2,2-difluoroacetamide;

N-((2-(2,6-dioxopiperidin-3-yl)-1-oxoisoindolin-5-yl) methyl)-2,2-difluoro-2-(pyrimidin-4-yl)acetamide;

N-((2-(2,6-dioxopiperidin-3-yl)-1-oxoisoindolin-5-yl) methyl)-2,2-difluoro-2-(3-(2-(piperidin-1-yl)ethoxy) phenyl)acetamide;

N-((2-(2,6-dioxopiperidin-3-yl)-1-oxoisoindolin-5-yl) methyl)-2,2-difluoro-2-(3-(2-morpholinoethoxy)phenyl)acetamide;

2-(3-(2-(4,4-difluoropiperidin-1-yl)ethoxy)phenyl)-N-((2-(2,6-dioxopiperidin-3-yl)-1-oxoisoindolin-5-yl) methyl)-2,2-difluoroacetamide; N-((2-(2,6-dioxopiperidin-3-yl)-1-oxoisoindolin-5-yl)methyl)-2,2-difluoro-2-(1-methyl-6-oxo-1,6-dihydropyridazin-4-yl)acetamide; and N-((2-(2,6-dioxopiperidin-3-yl)-1-oxoisoindolin-5-yl) methyl)-2,2-difluoro-2-(3-(4-methylpiperazin-1-yl) phenyl)acetamide.

17. A method of treating cancer comprising administering to a mammal having cancer a therapeutically effective amount of the compound of claim 1 wherein the cancer is leukemia.

18. A method of treating cancer comprising administering to a mammal having cancer a therapeutically effective amount of the compound of claim 16 wherein the cancer is leukemia.

19. The method of claim 17, wherein the leukemia is chronic lymphocytic leukemia, chronic myelocytic leukemia, acute lymphoblastic leukemia or acute myeloid leukemia.

20. The method of claim 17, wherein the leukemia is an acute myeloid leukemia.

21. The method of claim 17, wherein the leukemia is relapsed, refractory or resistant to conventional therapy.

22. The method of claim 17, further comprising administering a therapeutically effective amount of another second active agent or a support care therapy.

23. The method of claim 22, wherein the other second active agent is a therapeutic antibody that specifically binds to a cancer antigen, hematopoietic growth factor, cytokine, anti-cancer agent, antibiotic, cox-2 inhibitor, immunomodulatory agent, immunosuppressive agent, corticosteroid or a pharmacologically active mutant or derivative thereof.

24. The compound of claim 1, wherein the compound is selected from

N-((2-(2,6-dioxopiperidin-3-yl)-1-oxoisoindolin-5-yl)methyl)-2,2-difluoro-2-(4-methoxyphenyl)acetamide;
2-(4-chlorophenyl)-N-((2-(2,6-dioxopiperidin-3-yl)-1-oxoisoindolin-5-yl)methyl)-2,2-difluoroacetamide;
2-(3-chlorophenyl)-N-((2-(2,6-dioxopiperidin-3-yl)-1-oxoisoindolin-5-yl)methyl)-2,2-difluoroacetamide;
N-((2-(2,6-dioxopiperidin-3-yl)-1-oxoisoindolin-5-yl)methyl)-2,2-difluoro-2-(4-fluorophenyl)acetamide; and
2-(2-chlorophenyl)-N-((2-(2,6-dioxopiperidin-3-yl)-1-oxoisoindolin-5-yl)methyl)-2,2-difluoroacetamide.

25. The compound of claim 1, wherein the compound is N-((2-(2,6-dioxopiperidin-3-yl)-1-oxoisoindolin-5-yl)methyl)-2,2-difluoro-2-(4-methoxyphenyl)acetamide.

26. The compound of claim 1, wherein the compound is 2-(4-chlorophenyl)-N-((2-(2,6-dioxopiperidin-3-yl)-1-oxoisoindolin-5-yl)methyl)-2,2-difluoroacetamide.

27. The compound of claim 1, wherein the compound is 2-(3-chlorophenyl)-N-((2-(2,6-dioxopiperidin-3-yl)-1-oxoisoindolin-5-yl)methyl)-2,2-difluoroacetamide.

28. The compound of claim 1, wherein the compound is N-((2-(2,6-dioxopiperidin-3-yl)-1-oxoisoindolin-5-yl)methyl)-2,2-difluoro-2-(4-fluorophenyl)acetamide.

29. The compound of claim 1, wherein the compound is 2-(2-chlorophenyl)-N-((2-(2,6-dioxopiperidin-3-yl)-1-oxoisoindolin-5-yl)methyl)-2,2-difluoroacetamide.

* * * * *